US010947559B2

(12) United States Patent
Maresca et al.

(10) Patent No.: US 10,947,559 B2
(45) Date of Patent: Mar. 16, 2021

(54) INDUCIBLE MODIFICATION OF A CELL GENOME

(71) Applicant: ASTRAZENECA AB, Södertälje (SE)

(72) Inventors: Marcello Maresca, Södertälje (SE); Mohammad Bohlooly-Yeganeh, Södertälje (SE); Himjyot Jaiswal, Södertälje (SE); Lorenz M. Mayr, Södertälje (SE); Xiufeng Xu, Södertälje (SE)

(73) Assignee: ASTRAZENECA AB, Södertälje (SE)

( * ) Notice: Subject to any disclaimer, the term of this patent is extended or adjusted under 35 U.S.C. 154(b) by 264 days.

(21) Appl. No.: 15/768,482

(22) PCT Filed: Oct. 14, 2016

(86) PCT No.: PCT/IB2016/001902
§ 371 (c)(1),
(2) Date: Apr. 13, 2018

(87) PCT Pub. No.: WO2017/064566
PCT Pub. Date: Apr. 20, 2017

(65) Prior Publication Data

US 2018/0305714 A1 Oct. 25, 2018

Related U.S. Application Data

(60) Provisional application No. 62/242,884, filed on Oct. 16, 2015.

(51) Int. Cl.

| | |
|---|---|
| ***C12N 15/85*** | (2006.01) |
| ***C12N 15/11*** | (2006.01) |
| ***C12N 15/79*** | (2006.01) |
| ***A01K 67/027*** | (2006.01) |
| ***C12N 15/86*** | (2006.01) |
| ***C12N 15/90*** | (2006.01) |

(52) U.S. Cl.
CPC ...... *C12N 15/8509* (2013.01); *A01K 67/0275* (2013.01); *C12N 15/111* (2013.01); *C12N 15/79* (2013.01); *C12N 15/86* (2013.01); *A01K 2217/072* (2013.01); *A01K 2217/075* (2013.01); *A01K 2217/203* (2013.01); *A01K 2217/206* (2013.01); *A01K 2227/105* (2013.01); *A01K 2267/0393* (2013.01); *C12N 15/907* (2013.01); *C12N 2015/8572* (2013.01); *C12N 2310/20* (2017.05)

(58) Field of Classification Search
None
See application file for complete search history.

(56) References Cited

FOREIGN PATENT DOCUMENTS

| | | | |
|---|---|---|---|
| JP | 2015-527889 | A | 9/2015 |
| WO | 2005/123916 | A1 | 12/2005 |
| WO | 2014/018423 | A2 | 1/2014 |
| WO | 2014/093595 | A1 | 6/2014 |

OTHER PUBLICATIONS

Raab et al., "Insulators and promoters: closer than we think" 11 Nature Reviews | Genetics 439-446 (Year: 2010).*
Beerli et al., "Toward controlling gene expression at will: specific regulation of the erbB-2/HER-2 promoter by using polydactyl zinc finger proteins constructed from modular building blocks," Proc Natl Acad Sci USA 95(25):14628-14633 (1998).
Bell et al., "Stopped at the border: boundaries and insulators," Curr Opin Genet Dev 9(2):191-198 (1999).
Bell et al., "Insulators and Boundaries: Versatile Regulatory Elements in the Eukaryotic Genome," Science 291(5503):447-450 (2001).
Bitinate et al., "FokI dimerization is required for DNA cleavage," Proc Natl Acad Sci USA 95:10570-10575 (1998).
Boch et al., "Breaking the Code of DNA Binding Specificity of TAL-Type III Effectors," Science 326(5959):1509-1512 (2009).
Boch, "TALEs of genome targeting," Nat Biotechnol 29(2):135-136 (2011).
Cathomen et al., "Zinc-finger nucleases: the next generation emerges," Mol Ther 16(7):1200-1207 (2008).
Chen et al., "Dynamic imaging of genomic loci in living human cells by an optimized CRISPR/Cas system," Cell 155(7):1479-1491 (2013).
Christian et al., "Targeting DNA Double-Strand Breaks with TAL Effector Nucleases," Genetics 186:757-761 (2010).
Cong et al., "Multiplex Genome Engineering Using CRISPR/Cas Systems," Science 339(6121):819-823 (2013).
Dhar et al., "Architecture of the hin synaptic complex during recombination: the recombinase subunits translocate with the DNA strands," Cell 119(1):33-45 (2004).
Kamtekar et al., "Implications of structures of synaptic tetramers of gamma delta resolvase for the mechanism of recombination," Proc Natl Acad Sci USA 103(28):10642-10647 (2006).
Kiani et al., "Cas9 gRNA engineering for genome editing, activation and repression," Nat Methods 12(11):1051-1054 (2015).
Kim et al., "Hybrid restriction enzymes: Zinc finger fusions to Fok I cleavage domain," Proc Natl Acad Sci USA 93:1156-1160 (1996).
Kim et al., "A guide to genome engineering with programmable nucleases," Nat Rev Genet 15(5):321-334 (2014).
Komor et al., "Programmable editing of a target base in genomic DNA without double-stranded DNA cleavage," Nature 533:420-424 (2016).
Li et al., "Structure of a Synaptic γδ Resolvase Tetramer Covalently Linked to Two Cleaved DNAs," Science 309(5738):1210-1215 (2005).

(Continued)

*Primary Examiner* — Nancy J Leith
(74) *Attorney, Agent, or Firm* — Medler Ferro Woodhouse & Mills, PLLC

(57) ABSTRACT

The present disclosure is directed, in some embodiments, to compositions and methods for inducible modification of a cell genome.

23 Claims, 17 Drawing Sheets

Specification includes a Sequence Listing.

(56) References Cited

OTHER PUBLICATIONS

Liu et al., "A chemical-inducible CRISPR-Cas9 system for rapid control of genome editing," Nat Chem Biol 12(11):980-987 (2016).
Maresca et al., "Obligate ligation-gated recombination (ObLiGaRe): custom-designed nuclease-mediated targeted integration through nonhomologous end joining," Genome Res 23(3):539-546 (2013).
Miller et al., "A TALE nuclease architecture for efficient genome editing," Nat Biotechnol 29(2):143-148 (2011).
Moscou et al., "A Simple Cipher Governs DNA Recognition by TAL Effectors," Science 326(5959):1501 (2009).
Nishida et al., "Targeted nucleotide editing using hybrid prokaryotic and vertebrate adaptive immune systems," Science 353(6305):aaf8729 (2016).
Sander et al., "CRISPR-Cas systems for editing, regulating and targeting genomes," Nature Biotechnol 32(4):347-355 (2014).
Sanders et al., "Stepwise dissection of the Hin-catalyzed recombination reaction from synapsis to resolution," J Mol Biol 340(4):753-766 (2004).
Sarkar et al., "HIV-1 Proviral DNA Excision Using an Evolved Recombinase," 2007.
Schlake et al., "Use of Mutated FLP Recognition Target (FRT) Sites for the Exchange of Expression Cassettes at Defined Chromosomal Loci," Biochemistry 33(43):12746-12751 (1994).
Shen et al., "Efficient genome modification by CRISPR-Cas9 nickase with minimal off-target effects," Nat Methods 11(4):399-402 (2014).
Turan et al., "Multiplexing RMCE: versatile extensions of the Flp-recombinase-mediated cassette-exchange technology," J Mol Biol 402(1):52-69 (2010).
Urrutia, "KRAB-containing zinc-finger repressor proteins," Genome Biol 4(10):231 (2003).
Utomo et al., "Temporal, spatial, and cell type-specific control of Cre-mediated DNA recombination in transgenic mice," Nature Biotechnol 17(11):1091-1096 (1999).
West et al., "Insulators: many functions, many mechanisms," Genes & Dev 16:271-188 (2002).
Zetsche et al., "Cpf1 is a single RNA-guided Endonuclease of a class 2 CRISPR-Cas system," Cell 163(3):759-771 (2015).
Zhu et al., "Cleavage-dependent Ligation by the FLP Recombinase," J Biol Chem 270:23044-23054 (1995).
Zhu et al., "Baculoviral transduction facilitates TALEN-mediated targeted transgene integration and Cre/LoxP cassette exchange in human-induced pluripotent stem cells," Nucleic Acid Res 41(19):e180 (2013).
Ziebarth et al., "CTCFBSDB 2.0: a database for CTCF-binding sites and genome organization," Nucleic Acids Res 41:D188-D194 (2013).
Gossen et al. (1992) "Tight control of gene expression in mammalian cells by tetracycline-responsive promoters." PNAS USA. 89(12):5547-5551.
Gossen et al. (1995) "Transcriptional activation by tetracyclines in mammalian cells." Science. 268(5218):1766-1769.
Sarkar et al. (2007) "HIV-1 proviral DNA excision using an evolved recombinase." Science 316 (5833): 1912-1915.
Notice of Reasons for Rejection dated Nov. 4, 2020 in corresponding Japanese Patent Appl. No. P2018-518522.

* cited by examiner

INDUCIBLE MODIFICATION OF A CELL GENOME

RELATED APPLICATION

This application claims the benefit under 35 U.S.C. § 119(e) of U.S. provisional application No. 62/242,884, filed Oct. 16, 2015, which is incorporated by reference herein in its entirety.

BACKGROUND

Genome editing is a type of genetic engineering in which a genome is modified (e.g., DNA is introduced, removed or replaced) using engineered nucleases. Typically, the nucleases create specific double-stranded break (DSBs) at desired locations in the genome and harness the cell's endogenous mechanisms to repair the induced break by natural processes of homologous recombination (HR) and nonhomologous end joining (NHEJ). There are currently four families of engineered nucleases being used: zinc finger nucleases (ZFNs), transcription activator-like effector nucleases (TALENs), the CRISPR/Cas system, and engineered meganuclease re-engineered homing endonucleases.

SUMMARY

Provided herein, in some embodiments, are engineered nucleic acid constructs ("engineered constructs") useful for cross-species integration and introducing into a genome an inducible genome editing system. In some embodiments, the engineered constructs are introduced into a genome without also introducing vector (plasmid) material. The engineered constructs of the present disclosure, in some embodiments, permit spatially-controlled and temporally-controlled activation of target gene expression following site-specific integration into a genome via the non-homologous end joining (NHEJ) pathway (see, e.g., Maresca et al. *Genome Res.* 2013 March; 23(3):539-46, incorporated herein by reference). Unlike presently-available systems, which typically coordinate targeted modification of a cell genome through the use of at least two independent constructs, the genome editing systems of the present disclosure rely on activation of a single construct that comprises the genetic elements used to express a regulatory protein as well as the inducible genetic elements used to express a target gene. This single-construct configuration results in tightly regulated and substantially non-leaky target gene expression, thereby providing more precise and efficient genome editing capability relative to presently-available systems.

Thus, some embodiments of the present disclosure provide engineered nucleic acid constructs that comprise (a) a promoter operably linked to a nucleic acid encoding a regulatory protein (e.g., an inducer protein or a repressor protein); (b) an inducible promoter operably linked to a nucleic acid encoding an enzyme that cleaves nucleic acid (e.g., Cas9 nuclease, Cpf1 nuclease, or a functional equivalent thereof), a nucleic acid encoding an enzyme that nicks nucleic acid (e.g., Cas9 nickase), or a nucleic acid encoding an enzyme that catalyzes exchange of nucleic acid (e.g., Cre recombinase), wherein activity of the inducible promoter is modulated by the regulatory protein; (c) at least two insulators (e.g., mammalian insulators) located downstream from (a) and upstream from (b); at least one insulator located downstream from (b) and upstream from (a); and (e) at least one deoxyribonucleic acid (DNA)-binding domain recognition sequence located downstream from (b) and upstream from (a). In some embodiments, at least two DNA-binding domain recognition sequence located downstream from (b) and upstream from (a). In some embodiments, the inducible promoter is operably linked to a nucleic acid encoding an enzyme that regulates gene expression (e.g., Cas9 fused to KRAB, Cas9 fused to VP64, Cas9 fused to p300), or a nucleic acid encoding an enzyme that modifies a nucleotide base (e.g., Cas9 dead or nickase fused to AID/ApoBEC domains and to an inhibitor of uracil glycosylase).

The present disclosure further provides, in some embodiments, vectors comprising an engineered nucleic acid construct, cells comprising an engineered nucleic acid construct, or cells comprising vectors containing an engineered nucleic acid construct.

Also provided herein, in some embodiments, are methods of modifying a cell genome. For example, methods of the present disclosure may be used to delete (knockout) a gene of interest, introduce (knockin) a gene of interest, or modify a gene of interest.

In some embodiments, an enzyme is a nuclease, a nickase or a recombinase.

In some embodiments, an inducible promoter is a tissue-specific inducible promoter or a developmental-specific inducible promoter.

In some embodiments, the regulatory protein is a tetracycline-controlled transactivator (tTA) protein, a reverse tetracycline-controlled transactivator (rtTA) protein, or a Lac repressor protein.

In some embodiments, the DNA-binding domain recognition sequence is cleaved by a nuclease having a FokI nuclease domain. Non-limiting examples of such "hybrid nucleases" include zinc finger nucleases (ZFNs), transcription activator-like effector nucleases (TALENs) and hybrid Cas9-FokI nucleases.

In some embodiments, a DNA-binding domain recognition sequence is cleaved by a nuclease not having a FokI nuclease domain. For example, Cpf1 nuclease may be used to cleave a DNA-binding recognition sequence. Other nucleases, similar in structure and function to those nucleases described herein, may be used in the present methods.

Also provided herein is a transgenic mouse comprising in the genome of the mouse an engineered nucleic acid construct (e.g., a TOICas construct) as provided herein. In some embodiments, the engineered nucleic acid construct is integrated in the Rosa26 locus of the mouse genome. It should be understood that while the Rosa26 locus is exemplified in some embodiments, the present disclosure is not limited to genomic integration at the Rosa26 locus. The engineered constructs of the present disclosure may be integrated into any locus in the mouse genome (or the human genome when applicable to the generation of TOIC cell lines, such as TOIC human iPSC lines).

In some embodiments, the mouse is immunocompetent. In some embodiments, expression of the enzyme (e.g., Cas9) is not detectable in the absence of induction of the inducible promoter (e.g., in the absence of Dox administration).

In some embodiments, an engineered nucleic acid of the present disclosure comprises the sequence of SEQ ID NO: 8.

A transgenic mouse (e.g., an immunocompetent mouse) comprising in the genome of the mouse an engineered nucleic acid construct that comprises the sequence of SEQ ID NO: 8 (TOICas9) is also provided herein. In some embodiments, the engineered nucleic acid construct comprising the sequence of SEQ ID NO: 8 is integrated in the Rosa26 locus (or another locus) of the mouse genome.

BRIEF DESCRIPTION OF THE DRAWINGS

The accompanying drawings are not intended to be drawn to scale. For purposes of clarity, not every component may be labeled in every drawing.

DETAILED DESCRIPTION

Figure 1:
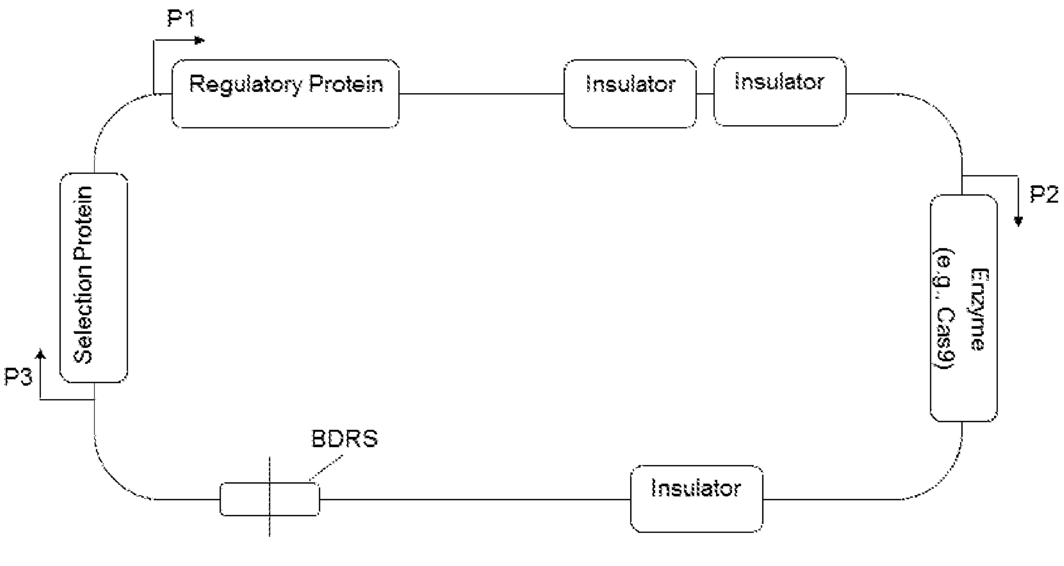
FIG. 1 is a schematic of an example of an engineered nucleic acid construct in accordance with the present disclosure. Promoter P1 is operably linked to a nucleic acid encoding a regulatory protein (e.g., an inducer protein or a repressor protein), which is upstream from two (e.g., at least two) insulators. The insulators are upstream from promoter P2, which is operably linked to a nucleic acid encoding an enzyme that cleaves (e.g., Cas9 nuclease, Cpf1 nuclease, or a functional equivalent thereof) or nicks (e.g., Cas9 nickase) nucleic acid, or catalyzes exchange of nucleic acid (e.g., Cre recombinase). The enzyme is upstream from an additional insulator, which is upstream from a (e.g., at least one) deoxyribonucleic acid (DNA)-binding domain recognition sequence (BDRS). The size of the engineered construct may be, for example, at least 15 kilobases (kb).

The present disclosure provides engineered nucleic acid constructs (e.g., "TOICas constructs") used for cross-species integration and introducing into a genome an inducible genome editing system, in some embodiments, without also introducing vector (plasmid) material. Engineered constructs of the present disclosure facilitate site-specific integration of a linearized form of the construct into a single locus of a genome, into multiple different loci of a genome, or into loci of different genomes (of different species). This direct integration depends on coordinated enzymatic cleavage of the construct and the targeted genomic locus, and ligation of the linearized construct into the genomic locus, for example, via the non-homologous end joining (NHEJ) pathway (see, e.g., Maresca et al. *Genome Res.* 2013 March; 23(3):539-46, incorporated herein by reference).

Custom-designed nucleases, such as Cas9, Cpf1, zinc finger nucleases, Tale nucleases, and functional equivalents thereof contain a DNA cleavage domain and a DNA binding domain assembled from optimized DNA binding modules. In cells, these nucleases generate a double-strand break in the genome at or near a sequence recognized by the DNA binding domain of the nuclease (a "DNA-binding domain recognition sequence") and induce DNA damage repair. The engineered constructs of the present disclosure are based, in part, on results showing that an episomal construct can be ligated into a target genomic locus if the construct and the locus contain the same DNA-binding domain recognition sequence.

In some embodiments, multiple DNA-binding domain recognition sequences are positioned in a construct such that they flank unwanted vector (e.g., bacterial plasmid) DNA. This configuration results in the removal of vector DNA upon integration of the construct into a genome.

The engineered constructs (e.g., "TOICas constructs") of the present disclosure are versatile in that they comprise, in some embodiments, the genetic elements used to induce gene expression in a temporally-controlled and spatially-controlled manner, an array (e.g., two or more) of DNA-binding domain recognition sequences that facilitate site-specific integration of the construct into multiple different loci, and are substantially non-leaky. Thus, the engineered constructs of the present disclosure provide more precise and efficient genome editing capability relative to presently-available genome editing systems.

TOICas Constructs and Transgenic Animals

Engineered constructs are herein referred to, in some embodiments, as TOIC, TOICas or TOICas9 constructs, which include a nucleic acid encoding a Cas9 enzyme. It should be understood that in any of the TOIC, TOICas or TOICas9 constructs, the nucleic acid encoding a Cas9 enzyme may be replaced with another enzyme that cleaves nucleic acid, nicks nucleic acid, catalyzes the exchange of nucleic acid, regulates gene expression, or modifies a nucleotide base. Non-limiting examples of TOIC constructs are depicted in FIGS. 20-28, the nucleic acid sequences of which are represented by SEQ ID NO: 12-20, respectively.

Figure 10:
FIG. 10 shows a schematic of an example of an engineered TOICas construct. Cas9 is fused to GFP by T2A peptide and is flanked by insulators for tight regulation.

TOIC constructs, in some embodiments, include any one of FIGS. 20-28, for example, having a sequence of any one of SEQ ID NO: 12-20, respectively. The TOICas constructs of the present disclosure, as discussed in greater detail below, include a promoter (P1) (e.g., CMV, CAGG, CBh, or EF1alpha, or a tissue-specific promoter) operably linked to a regulatory protein, which is upstream of two insulators positioned in tandem (insulator 1 and insulator 2), which are upstream of a promoter (P2) (e.g., an arrayed sequence bound by the regulator protein) operably lined to an enzyme (e.g., Cas9), which is upstream of an insulator (insulator 3), which is upstream of a DNA-binding domain recognition site (BDRS) (e.g., nuclease, a recombinase, or an integrase), which is optionally upstream of a promoter (P3) operably linked to a nucleic acid encoding a selection protein (e.g., a drug selection protein or a fluorescent marker) (see, e.g., FIG. 1 and FIG. 10).

In some embodiments, a TOIC construct comprises a nucleic acid encoding a guide RNA (gRNA), which may be located, for example, between the enzyme and insulator 3, or between insulator 3 and the BDRS.

Also provided herein are transgenic animals, such as transgenic mouse models, comprising a TOIC construct. While many embodiments described herein refer to transgenic mouse models, is should be understood that the disclosure covers a variety of transgenic animal models (invertebrates and vertebrates), including, but not limited to: *Amphimedon queenslandica, Arbacia punctulata, Aplysia, Branchiostoma floridae, Caenorhabditis elegans, Caledia captiva, Callosobruchus maculatus, Chorthippus parallelus, Ciona intestinalis, Daphnia* spp., *Coelopidae, Diopsidae, Drosophila, Euprymna scolopes, Galleria mellonella, Gryllus bimaculatus, Hydra, Loligo pealei, Macrostomum lignano, Mnemiopsis leidyi, Nematostella vectensis, Oikopleura dioica, Oscarella carmela, Parhyale hawaiensis, Platynereis dumerilii, Podisma* spp., *Pristionchus pacificus, Scathophaga stercoraria, Schmidtea mediterranea, Stomatogastric, Strongylocentrotus purpuratusSymsagittifera roscoffensisTribolium castaneum*, and *Trichoplax adhaerens, Tubifex tubifex* (invertebrates); and *Bombina*, Carolina anole (*Anolis carolinensis*), Cat (*Felis sylvestris catus*), Chicken (*Gallus gallus domesticus*)—Cotton rat (*Sigmodon hispidus*), Dog (*Canis lupus familiaris*), Golden hamster (*Mesocricetus auratus*), Guinea pig (*Cavia porcellus*), Little brown bat (*Myotis lucifugus*), Medaka (*Oryzias latipes*, or Japanese ricefish), Mouse (*Mus musculus*), Naked mole-rat (*Heterocephalus glaber*), *Nothobranchius furzeri*, Pigeon (*Columba livia domestica*), *Poecilia reticulata*, Rat (*Rattus norvegicus*), Rhesus macaque (or rhesus monkey) (*Macaca mulatta*) Sea lamprey (*Petromyzon marinus*), Takifugu (*Takifugu rubripes*, a pufferfish), Three-spined stickleback (*Gasterosteus aculeatus*), *Xenopus tropicalis* and *Xenopus laevis* (African clawed frog), Zebra finch (*Taeniopygia guttata*), and Zebrafish (*Danio rerio*, a freshwater fish).

In some embodiments, the transgenic animal model is selected from a fish, a frog, a bird, a mouse, a rat, a hamster, a cat, a dog, a pig, a sheep and a monkey. some embodiments, the transgenic animal model is a mouse model. In some embodiments, provided herein is an engineered nucleic acid comprising the sequence of SEQ ID NO: 8. Also provided herein is a transgenic animal (e.g., mouse), for example, an immunocompetent animal (e.g., mouse), comprising in the genome of the animal (e.g., mouse) an engineered nucleic acid construct comprising the sequence of SEQ ID NO: 8 integrated, for example, in the Rosa26 locus of the animal (e.g., mouse) genome.

In some embodiments, provided herein is an engineered nucleic acid comprising the sequence of SEQ ID NO: 12. Also provided herein is a transgenic animal (e.g., mouse), for example, an immunocompetent animal (e.g., mouse), comprising in the genome of the animal (e.g., mouse) an engineered nucleic acid construct comprising the sequence of SEQ ID NO: 12 integrated, for example, in the Rosa26 locus of the animal (e.g., mouse) genome.

In some embodiments, provided herein is an engineered nucleic acid comprising the sequence of SEQ ID NO: 13. Also provided herein is a transgenic animal (e.g., mouse), for example, an immunocompetent animal (e.g., mouse), comprising in the genome of the animal (e.g., mouse) an engineered nucleic acid construct comprising the sequence of SEQ ID NO: 13 integrated, for example, in the Rosa26 locus of the animal (e.g., mouse) genome.

In some embodiments, provided herein is an engineered nucleic acid comprising the sequence of SEQ ID NO: 14. Also provided herein is a transgenic animal (e.g., mouse), for example, an immunocompetent animal (e.g., mouse), comprising in the genome of the animal (e.g., mouse) an engineered nucleic acid construct comprising the sequence of SEQ ID NO: 14 integrated, for example, in the Rosa26 locus of the animal (e.g., mouse) genome.

In some embodiments, provided herein is an engineered nucleic acid comprising the sequence of SEQ ID NO: 15. Also provided herein is a transgenic animal (e.g., mouse), for example, an immunocompetent animal (e.g., mouse), comprising in the genome of the animal (e.g., mouse) an engineered nucleic acid construct comprising the sequence of SEQ ID NO: 15 integrated, for example, in the Rosa26 locus of the animal (e.g., mouse) genome.

In some embodiments, provided herein is an engineered nucleic acid comprising the sequence of SEQ ID NO: 16. Also provided herein is a transgenic animal (e.g., mouse), for example, an immunocompetent animal (e.g., mouse), comprising in the genome of the animal (e.g., mouse) an engineered nucleic acid construct comprising the sequence of SEQ ID NO: 16 integrated, for example, in the Rosa26 locus of the animal (e.g., mouse) genome.

In some embodiments, provided herein is an engineered nucleic acid comprising the sequence of SEQ ID NO: 17. Also provided herein is a transgenic animal (e.g., mouse), for example, an immunocompetent animal (e.g., mouse), comprising in the genome of the animal (e.g., mouse) an engineered nucleic acid construct comprising the sequence of SEQ ID NO: 17 integrated, for example, in the Rosa26 locus of the animal (e.g., mouse) genome.

In some embodiments, provided herein is an engineered nucleic acid comprising the sequence of SEQ ID NO: 18. Also provided herein is a transgenic animal (e.g., mouse), for example, an immunocompetent animal (e.g., mouse), comprising in the genome of the animal (e.g., mouse) an engineered nucleic acid construct comprising the sequence of SEQ ID NO: 18 integrated, for example, in the Rosa26 locus of the animal (e.g., mouse) genome.

In some embodiments, provided herein is an engineered nucleic acid comprising the sequence of SEQ ID NO: 19. Also provided herein is a transgenic animal (e.g., mouse), for example, an immunocompetent animal (e.g., mouse), comprising in the genome of the animal (e.g., mouse) an engineered nucleic acid construct comprising the sequence of SEQ ID NO: 19 integrated, for example, in the Rosa26 locus of the animal (e.g., mouse) genome.

In some embodiments, provided herein is an engineered nucleic acid comprising the sequence of SEQ ID NO: 20. Also provided herein is a transgenic animal (e.g., mouse), for example, an immunocompetent animal (e.g., mouse), comprising in the genome of the animal (e.g., mouse) an engineered nucleic acid construct comprising the sequence of SEQ ID NO: 29 integrated, for example, in the Rosa26 locus of the animal (e.g., mouse) genome.

Induction of enzyme (e.g., Cas9) expression in an animal model may be achieved by administering doxycycline or other appropriate induction agent (depending on the particular induction system used in the TOIC construct). In some embodiments, the induction agent (agent that directly or indirectly activates the inducible promoter of the TOIC construct) is administered to an animal via injection (e.g., tail vein injection) or oral gavage.

Transgenic animals, as provided herein, may be used to generate knockout or knockdown alleles, or to overexpress a gene or knock a gene into a particular loci, by homologous recombination or by non-homologous end joining. This may be achieved, for example, by administering to the animal a template DNA (e.g., containing a modification of interest) and a nucleic acid encoding a gRNA targeting a loci and/or gene of interest. Examples of genes of interest include, but are not limited to, oncogenes such as Pik3ca, Kras, Braf, Nras, and tumor suppressor genes such as Pten, p53, Rb, Apc, p16/p19, Brca1, Brca2, Lkb1. Various disease models may be produced by combining TOIC transgenic mice with template DNA and gRNA targeting a gene or genes of interest. Such models include, but are not limited to, lung cancer (e.g., Kras, Lkb, p53 and/or Rb; e.g., targeting MAPK, metabolism), pancreatic cancer (e.g., Kras, p53, p16/p19 and/or Pdx1; e.g., targeting MAPK), prostate cancer (e.g., Pten, Brca1, Brca2 and/or p53; e.g., targeting PI3K, AR, ASO, DDR), breast cancer (e.g., Pik2ca, p53 and/or Pten; e.g., targeting PI3K, SERD), ovarian cancer (e.g., Brca1, Brca2, p53 and/or Rb; e.g., targeting Erk, MEK, Kras, ASO, modp53), melanoma (e.g., Braf and/or Nras; e.g., targeting MAPK) and colorectal cancer (e.g., Pik3ca, Kras and/or Apc; e.g., targeting MAPK, PI3K).

A nucleic acid encoding a gRNA and associated template DNA may be administered to an animal via intratracheal, intravenal, or intraperitoneal transduction using a virus (e.g., adeno-associated virus or adenovirus), for example.

In some embodiments, a nucleic acid encoding a gRNA is integrated into the genome of the transgenic animal model. For example, a tissue-specific gRNA or a constitutively-expressed gRNA may be integrated into the genome of the transgenic animal model.

Also provided herein are organoids (three-dimensional organ-bud grown in vitro) derived from (obtained from) transgenic animals of the present disclosure. Thus, an organoid may comprise any of the TOIC constructs.

Advantageously, TOIC animals (e.g., mice), for example, those described in the Examples, may be immunocompetent (able to produce a normal immune response following exposure to an antigen). Also encompassed herein, however, are immunocompromised (have a weakened immune system) TOIC animals.

Enzymes for Genomic Integration

Engineered constructs (e.g., "TOICas constructs") of the present disclosure are used to facilitate direct, site-specific ligation of a linearized form of the construct into a single locus or multiple different loci of a single genome or multiple different genomes. This direct ligation occurs through the non-homologous end joining (NHEJ) pathway (see, e.g., Maresca et al. *Genome Res.* 2013 March; 23(3): 539-46, incorporated herein by reference). Site-specific integration depends on the presence of hybrid nucleases that contain a DNA binding domain and a DNA cleavage domain (typically a FokI domain) and the presence of nucleic acids that contain at least one DNA-binding domain recognition sequence. A "DNA-binding domain recognition sequence" is a nucleotide sequence to which a nuclease DNA-binding domain binds and a nuclease DNA cleavage domain cleaves.

Engineered constructs contain at least one DNA-binding domain recognition sequence that is recognized and cleaved by a hybrid nuclease. Cleavage of the engineered construct results in a linearized form, which can then be "ligated" into a genome in a site-specific manner.

Engineered constructs (e.g., "TOICas constructs") of the present disclosure, in some embodiments, comprise a single DNA-binding domain recognition sequence (BDRS) or an array (e.g., two or more) of DNA-binding domain recognition sequences, which facilitate site-specific genomic integration of the nucleic acid. Advantageously, an engineered construct of the present disclosure can be used to facilitate site-specific ligation of a linearized form of the construct into multiple different loci of several different genomes, which is useful for cross-species integration of the same construct.

In some embodiments, a DNA-binding domain recognition sequence of an engineered construct corresponds to a sequence located in the Rosa26 locus such that the nucleic acid may be integrated in a mouse genome. In some embodiments, a DNA-binding domain recognition sequence of an engineered construct corresponds to a sequence located in the AAVS1 locus such that the nucleic acid may be integrated in a human genome. Other DNA-binding domain recognition sequence located in other genomic loci are encompassed by the present disclosure.

Examples of hybrid nuclease for use in linearizing an engineered construct include, without limitation, zinc finger nucleases (ZFNs), Tale nucleases (TALENs), dCas9-FokI fusion proteins (catalytically inactive Cas9 fused to FokI), Cas9, Cas9 nickase fused to FokI, and Cas9 variants evolved to generate overhangs.

In some embodiments, the DNA-binding domain recognition sequence is a ZFN DNA binding domain recognition sequence, which is bound by one or more zinc finger(s). The DNA-binding domain of individual ZFNs may contain between three and six individual zinc finger repeats and can each recognize between 9 and 18 base pairs. If the zinc finger domains are specific for their intended target site, then even a pair of 3-finger ZFNs that recognize a total of 18 base pairs can target a single locus in a mammalian genome.

In some embodiments, the DNA-binding domain recognition sequence is a TALEN DNA binding domain recognition sequence, which is bound by one or more TAL effector unit(s). TAL effectors are proteins secreted by *Xanthomonas* bacteria. The DNA binding domain typically contains a repeated highly conserved 33-34 amino acid sequence with the exception of the $12^{th}$ and $13^{th}$ amino acids. These two locations are highly variable (Repeat Variable Diresidue, RVD) and show a strong correlation with specific nucleotide recognition (Boch et al. *Science* 326 (5959): 1509-12, 2009; Moscou et al. *Science* 326 (5959): 1501, 2009, each of which is incorporated by reference herein). In some embodiments, specific DNA-binding domains are engineered by selecting a combination of repeat segments containing the appropriate RVDs (Boch et al. *Nature Biotechnology* 29 (2): 135-6, 2011).

In some embodiments, the DNA-binding domain recognition sequence is a sequence complementary (e.g., 100% complementary) to two co-expressed guide RNAs. In some embodiments, the DNA-binding domain recognition sequence is a sequence that is at least 80%, at least 85%, at least 90%, at least 95% or at least 98% complementary to two co-expressed guide RNAs. In such embodiments, a catalytically inactive Cas9 (dCas9) fused to FokI nuclease may be used to generate double strand breaks in an engineered nucleic acid.

It should be understood that the engineered constructs of the present disclosure may comprise a nucleic acid encoding a nuclease (e.g., Cas9 nuclease, Cpf1 nuclease, or a functional equivalent thereof) and contain a DNA-binding nuclease recognition sequence that is not necessarily recognized by the nuclease of the engineered nucleic acid. For example, an engineered construct for use in genomic editing may encode Cas9 (e.g., wild-type or otherwise catalytically active Cas9 for the purpose of editing the genome of a cell) or Cpf1 nuclease and may also contain a DNA-binding nuclease recognition sequence specific for a zinc finger nuclease or a catalytically inactive Cas9 (dCas) fused to FokI nuclease. If this is the case, it may be necessary to introduce into a cell another nucleic acid encoding the zinc finger nuclease or the dCas9 fused to FokI that specifically recognizes and cleaves the DNA-binding nuclease recognition.

Enzymes for Genomic Editing

Also described herein are nucleic acids that encode enzymes that cleave nucleic acid, nick nucleic acid, or catalyze exchange of nucleic acid. Enzymes that cleave nucleic acids are referred to as nucleases. Enzymes that nick nucleic acids are referred to as nickases. Enzymes that catalyze exchange of nucleic acid are referred to as recombinases.

"Cleavage" refers to the process by which a nuclease cuts (hydrolyzes) each nucleic acid backbone (e.g., sugar-phosphate backbone) of a double-stranded nucleic acid. Thus, the nuclease makes two incisions: one in the backbone between the nucleotide subunits of one strand of the double-stranded nucleic acid, and another in the backbone between the nucleotide subunits of the other strand of the double-stranded nucleic acid. Cleavage of a single nucleic acid molecule typically results in the production of two separate nucleic acid molecules. "Nicking," by contrast, refers to the process by which a nickase cuts only one strand of a double-stranded nucleic acid. "Catalyzing exchange of nucleic acid" refers to the process by which genetic material is broken and joined to other genetic material and encompasses genetic recombination. Recombination is recombining or rearranging genetic material, for example, by crossing over in chromosomes or by joining segments of DNA.

In some embodiments, an engineered nucleic acid encodes a nuclease. Nucleases of the present disclose may be engineered to cut a pre-determined nucleotide sequence, permitting, for example, efficient engineering of genetic information and the creation of a variety of diverse nucleic acid modifications. Examples of engineered nucleases include, without limitation, DNA-guided endonucleases, RNA-guided endonucleases (RGENs) such as Cas9 or Cpf1, zinc finger nucleases (ZFNs) (Kim et al. *Proc Natl Acad Sci USA* 93 (3): 1156-60, 1996; Bitinaite et al. *Proc Natl Acad Sci USA* 95 (18): 10570-5, 1998; and Cathomen et al. *Mol. Ther.* 16 (7): 1200-7, 2008), TAL effector nucleases (TALENs, transcription activator-like effector nucleases) (Boch et al. *Science* 326 (5959): 1509-12, 2009; Christian et al. Genetics 186 (2): 757-61, 2010); and Miller et al. *Nature Biotechnology* 29 (2): 143-8, 2011) (Table 1), and functional equivalents thereof. Nucleases typically comprise a DNA binding domain, which recognizes and binds to a particular DNA sequence, and a DNA cleavage domain, which cleaves the DNA at or near (e.g., within 10 nucleotides of) the DNA binding domain. For example, ZFNs comprise zinc finger domains, which bind DNA, and a Fok I domain, which cleaves the DNA (Kim et al. *Natl Acad Sci USA* 93 (3): 1156-60, 1996). Similarly, TALENs comprise TAL effector units, which bind DNA, and a Fok I domain, which cleaves DNA. The RNA-guided Cas9 nuclease cleaves the DNA, but to do so, it must first be guided to the target cleavage site by a guide RNA, which is complementary to and binds to the DNA cleavage site, as described elsewhere herein.

TABLE 1

Examples of Engineered Nuclease Systems

| Nuclease | DNA binding domain | DNA cleavage domain |
|---|---|---|
| RGEN | Guide RNA that hybridizes to the target DNA (1:1 nucleotide base pairing) | Cas9 protein (contains two nuclease domains); or or Cpf1 protein |
| ZFN | Zinc fingers (each module recognizes 3 bp of target sequence) | Fok I restriction enzyme nuclease domain (requires dimerization for cleavage) |
| TALEN | TAL effector units (each module recognizes 1 bp of target sequence) | Fok I restriction enzyme nuclease domain (requires dimerization for cleavage) |

Cas9 (CRISPR associated protein 9) is an RNA-guided DNA nuclease associated with the CRISPR (Clustered Regularly Interspersed Palindromic Repeats) adaptive immunity system in *Streptococcus pyogenes*, among other bacteria. CRISPR systems for editing, regulating and targeting genomes may comprise at least two distinct components: (1) a guide RNA (gRNA) and (2) Cas9. A gRNA is a single chimeric transcript that combines the targeting specificity of endogenous bacterial CRISPR targeting RNA (crRNA) with the scaffolding properties of trans-activating crRNA (tracrRNA). Typically, a gRNA used for genome editing is transcribed from either a plasmid or a genomic locus within a cell. The gRNA transcript forms a complex with Cas9, and then the gRNA/Cas9 complex is recruited to a target sequence as a result of the base-pairing between the crRNA sequence and its complementary target sequence in genomic DNA, for example.

In a typical synthetic CRISPR/Cas9 genome editing system, a genomic sequence of interest (genomic target sequence) is modified by use of a gRNA complementary to the sequence of interest, which directs the gRNA/Cas9 complex to the target (Sander J D et al., 2014 *Nature Biotechnology* 32, 247-355, incorporated by reference herein). The Cas9 endonuclease cuts the genomic target DNA upstream of a protospacer adjacent motif (PAM), resulting in double-strand breaks. Repair of the double-strand breaks often results in inserts or deletions at the double-strand break site. This CRISPR/Cas9 system is often used to edit the genome of a cell, each iteration requiring the design and introduction of a new gRNA sequence specific to a target sequence of interest.

In some embodiments, an engineered construct of the present disclosure comprises a promoter (e.g., an inducible promoter) operably linked to a nucleic acid encoding a guide RNA (e.g., downstream from a nucleic acid encoding a Cas9 nuclease), which guides the Cas9 nuclease to a genomic target (modification) site. Enzymes that are functionally similar to Cas9 may be used in accordance with the present disclosure.

Cpf1 is a single RNA-guided endonuclease of a class 2 CRISPR-Cas system (Zetsche et al., 2015, *Cell* 163: 1-13, incorporated by reference herein). Cpf1, like Cas9, is a two-component RNA programmable DNA nuclease. Targeted DNA is cleaved as a 5-nt staggered cut distal to a 5' T-rich protospacer adjacent motif (PAM). There are two Cpf1 orthologs that exhibit robust nuclease activity in human cells, either of which may be used as provided herein. Enzymes that are functionally similar to Cpf1 may be used in accordance with the present disclosure.

In other embodiments, a nucleic acid encoding a guide RNA is introduced into a host cell that is modified to express (e.g., stably express) in the cell genome an engineered construct of the present disclosure (e.g., a construct encoding a Cas9 nuclease) and is used to replace any unwanted DNA introduced into the host cell during modification of the host cell genome. For example, a cell, such as a stem cell (e.g., a pluripotent stem cells), may be modified to express (e.g., stably express) in the cell genome an engineered construct comprising (a) a promoter operably linked to a nucleic acid encoding a regulatory protein, (b) an inducible promoter operably linked to a nucleic acid encoding Cas9 or Cpf1, wherein activity of the inducible promoter is modulated by the regulatory protein, (c) at least two insulators located downstream from (a) and upstream from (b), and (d) at least one insulator located downstream from (b). The modification of this host cell may result in the introduction of vector (e.g., bacterial plasmid) DNA in the genome of the cell as well as other unwanted DNA (e.g., sequence encoding a selection marker) following site-specific integration of the construct. This vector DNA and any other unwanted DNA can be removed, for example, by introducing (a) an engineered nucleic acid encoding a guide RNA flanked by DNA-binding domain recognition sequences, (b) an engineered nucleic acid encoding a hybrid nuclease that recognizes and cleaves DNA-binding domain recognition sequences flanking the guide RNA as well as DNA-binding domain recognition sequences flanking unwanted sequence located in the genome of the cells, and (c) and an orthogonal Cas9 (Cas9 obtained from a species different than the species from which the host cell Cas9 was obtained). For example, the host cell may be engineered to express Cas9 obtained from *Streptococcus pyogenes* and the orthogonal Cas9 obtained from *Streptococcus aureus, Streptococcus thermophilis* or *Neisseira meningitis*. Other orthogonal Cas9 nucleases are encompassed by the present disclosure. The hybrid nuclease, the guide RNA and the orthogonal Cas9 may be included on the same construct (e.g., vector) or each on a separate construct. The guide RNA replaces the vector DNA or any unwanted DNA in the genome of the host cell.

In some embodiments, an orthogonal Cas9 is used to replace bacterial plasmid sequence integrated in a host cell genome with a guide RNA of interest and, optionally, a selection marker. In some embodiments, the host cell is a pluripotent stem cell (e.g., a human pluripotent stem cell, such as a human induced pluripotent stem cell) or an embryonic stem cell (e.g., a mouse embryonic stem cell used for the generation of a mouse model system). In these cell types, bacterial plasmid sequence has the potential of inactivating a locus of interest, thus removal of the bacterial plasmid sequence is preferred.

In some embodiments, an orthogonal Cas9 or Cpf1 and a guide RNA are used to delete expression (knockout), reduce expression (knockdown) or increase expression (overexpress) a gene of interest in a differentiated state following a pluripotent state.

In some embodiments vector DNA or any unwanted DNA in the genome of the host cell is removed by using a site-specific recombinase (e.g., Cre, FLP, Dre, Vike or a combination thereof).

The process of introducing an engineered nucleic acid construct into the genome of a cell and removing vector DNA or any unwanted DNA may be performed in a single step (e.g., all constructs are delivered to the host cell(s) simultaneously) or in multiple steps (e.g., each construct is delivered to the host cell(s) sequentially).

The present disclosure also includes the use of catalytically inactive forms of any of the nucleases described herein. For example, in some embodiments, a catalytically inactive form of Cas9 (dCas9) or a catalytically inactive form of Cpf1, which can knockdown gene expression by interfering with transcription, may be used as provided herein. In some embodiments, a dCas9 (or catalytically inactive form of Cpf1 or other nuclease) is fused to a repressor peptide (a peptide that represses transcription, e.g., Cas9-KRAB (Urrutia 2003 *Genome Biol.* 4(10): 231)). In some embodiments, a dCas9 (or catalytically inactive form of Cpf1 or other nuclease) is fused to an activator peptide (a peptide that activates or increase transcription, e.g., Cas9-VP64 (Beerli et al. 1998 *Proc Natl Acad Sci USA.* 95(25):14628-33)). In some embodiments, a dCas9 (or catalytically inactive form of Cpf1 or other nuclease) is fused to an epigenomic regulator (e.g., Cas9-DNMT or Cas9-p500). In some embodiments, a dCas9 (or catalytically inactive form of Cpf1 or other nuclease) is fused to FokI nuclease to generate double strand breaks at sequences homologous to two co-expressed gRNAs.

In some embodiments, an engineered nucleic acid expressing dCas9 (or other catalytically inactive nuclease) is used to image specific sequences in the genome (see, e.g., Chen B., et al. (2013) Cell 155(7): 1479-1491, incorporated herein by reference).

In some embodiments, wild-type or unmodified Cas9 or Cpf1 (or other catalytically inactive nuclease) fused to a repressor peptide (e.g., Cas9-KRAB) or an activator peptide (e.g., Cas9-VP64) is used in combination with a short gRNAs to regulate gene expression (see, e.g., Kiani S, et al. (2015) "Cas9 gRNA engineering for genome editing, activation and repression." *Nature Methods* (2015) [epub ahead of print], incorporated herein by reference).

In some embodiments, an engineered nucleic acid encodes a nickase. A nickase is an enzyme that generates a single-strand break in a double-stranded nucleic acid. In some embodiments, the nickase is Cas9 nickase (Cong et al. 2013 *Science* 339(6121): 819-823; Shen et al. 2014 *Nature Methods* 11, 399-402). Cas9 nickase generates a single-strand DNA break (nick) at a specific location based on a co-expressed gRNA-defined target sequence, rather than a double-strand DNA break (cut) produced by the wild type enzyme. Nicks are preferentially repaired in a cell by homology directed repair (HDR), using the intact strand as the template. HDR has high fidelity and rarely results in errors. Two adjacent, opposite strand nicks can cause a double strand break (DSB) and trigger error-prone non-homologous end joining (NHEJ) repair; however, in the presence of a repair template, the double nicks can be repaired by HDR. Double nicking typically reduces unwanted off-target effects.

In some embodiments, an engineered nucleic acid encodes a recombinase. Recombinases, typically derived from bacteria and fungi, catalyze directionally sensitive DNA exchange reactions between short (e.g., 30-40 nucleotides) target sequences that are specific to each recombinase. These reactions enable four basic functions—excision/insertion, inversion, translocation and cassette exchange—which may be used individually or in combination. Examples of recombinases for use as provided herein include, without limitation, Cre recombinase, FLP recombinase, Hin recombinase (Dhar et al. 2004 *Cell* 119 (1): 33-45; Sanders et al. 2004 *Mol Biol* 340 (4): 753-66; Kamtekar et al. 2006 *Proc Natl Acad Sci USA* 103 (28): 10642-7; Li et al. 2005 *Science* 309 (5738): 1210-5) and Tre recombinase (Sarkar et al. 2007 *Science* 316 (5833): 1912-15).

Cre recombinase is a tyrosine recombinase enzyme derived from the P1 bacteriophage. The enzyme uses a topoisomerase I-like mechanism to carry out site-specific recombination. The enzyme (e.g., 38 kDa) is a member of the integrase family of site-specific recombinase and catalyzes site-specific recombination between two DNA recognition sites (loxP sites). The ~34 base pair (bp) loxP recognition site contains two ~13 bp palindromic sequences that flank an ~8 bp spacer region. The products of Cre-mediated recombination at loxP sites are dependent upon the location and relative orientation of the loxP sites. Two separate DNA species both containing loxP sites can undergo fusion as the result of Cre mediated recombination. DNA sequences found between two loxP sites are said to be "floxed". The products of Cre mediated recombination depends upon the orientation of the loxP sites. DNA found between two loxP sites oriented in the same direction are excised as a circular loop of DNA, while intervening DNA between two loxP sites that are opposingly orientated are inverted. Cre recombinase requires no additional cofactors (such as ATP) or accessory proteins for its function.

Flp-FRT recombination is a site-directed recombination technology analogous to Cre-lox recombination. Flp-FRT recombination involves the recombination of sequences between short flippase recognition target (FRT) sites by the recombinase (Flp) derived from the 2 μm plasmid of baker's yeast *Saccharomyces cerevisiae* (Zhu et al. 1995 *Journal of Biological Chemistry* 270 (39): 23044-54; Schlake et al. 1994 *Biochemistry* 33 (43): 12746-12751; and Turan et al 2010 *J. Mol. Biol.* 402 (1): 52-69).

In some embodiments, an engineered nucleic acid encodes a base editing enzyme. A base editing enzyme is a fusion of a DNA binding protein (e.g., Cas9, TALE, ZF) to a specific effector that induces base exchange (e.g., C to T) in the proximity of a DNA binding site (see, e.g., Komor, A. C., et al. *Nature,* 2016; and Nishida, K., et al. *Science* 353: 6305, 2016).

Control of Gene Expression

Engineered constructs (e.g., "TOICas constructs") of the present disclosure permit spatial control of genomic editing, temporal control of genomic editing, of a combination of spatial and temporal control. Spatial control generally refers to the activation of transcription within specific tissues of an organism. Temporal control generally refers to the activation of transcription at specific times during development. Spatial control and/or temporal control may result from use of a cell-specific or tissue-specific promoter driving nucleic acid expression, from control over the time during which an effector substance is delivered to a cell or organism to induce or repress nucleic acid expression, or from a combination thereof, for example. In some embodiments, a cell-specific or tissue-specific promoter drives expression of a nucleic acid to which it is operably linked only during a particular phase of cell specification or cell differentiation. In some embodiments, an effector substance (e.g., Dox) is delivered to a cell or organism only during a particular phase of cell specification or cell differentiation.

Figure 2:
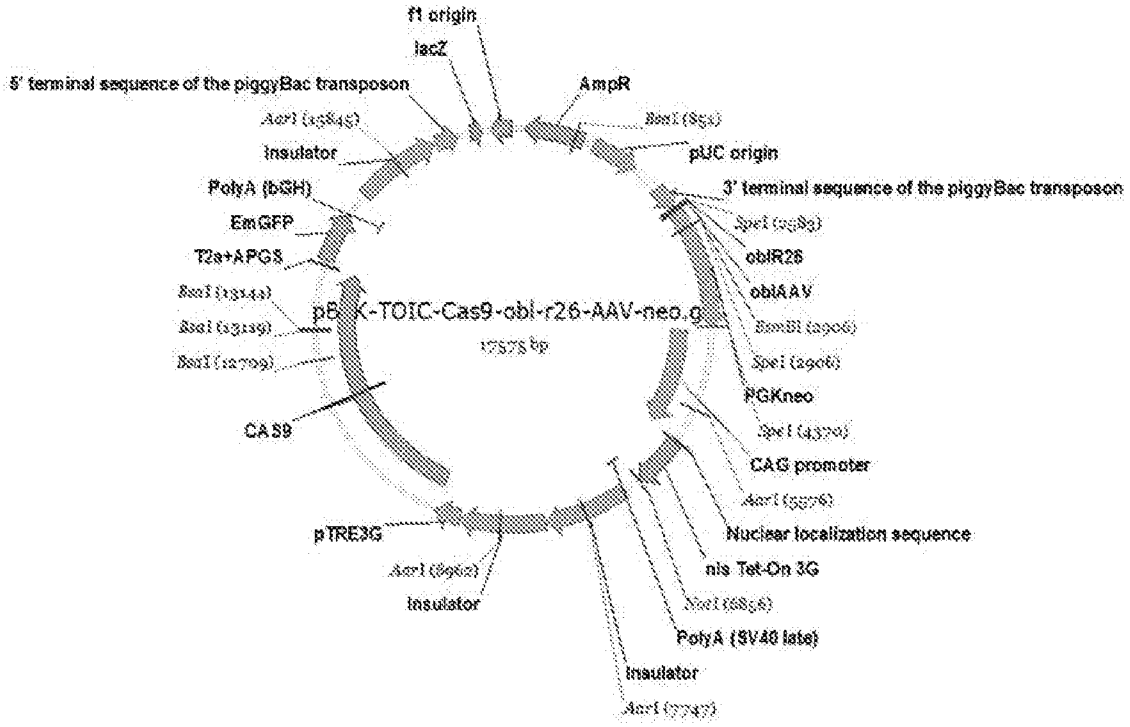
FIG. 2 is a schematic of an example of an engineered nucleic acid construct of the present disclosure used for insertion in the adeno-associated virus integration site 1 (AAVS1) locus (human) or the ROSAβgeo26 (ROSA26) locus (mouse). The size of the engineered construct is 17575 kb.
Figure 3A:
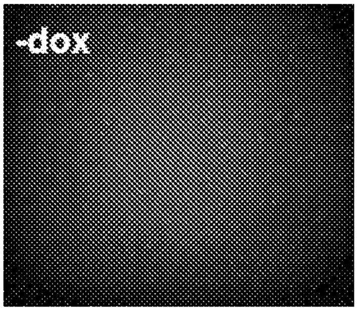
FIGS. 3A-3B show images of induced pluripotent stem cells (iPSCs) containing a doxycycline-inducible system of the present disclosure, as depicted in FIG. 3, in the absence of doxycycline (−dox) (FIG. 3A) and in the presence of doxycycline (+dox). Green fluorescent protein (GFP) is an indicator of activation of nuclease (e.g., Cas9 nuclease, Cpf1 nuclease, or a functional equivalent thereof) or recombinase (e.g., Cre) expression. GFP is expressed only in the presence of doxycycline, indicating no "leakage" of the system (FIG. 3B).
Figure 3B:
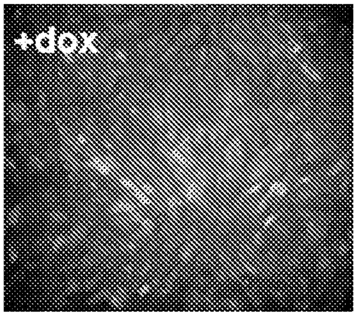
Figure 4:
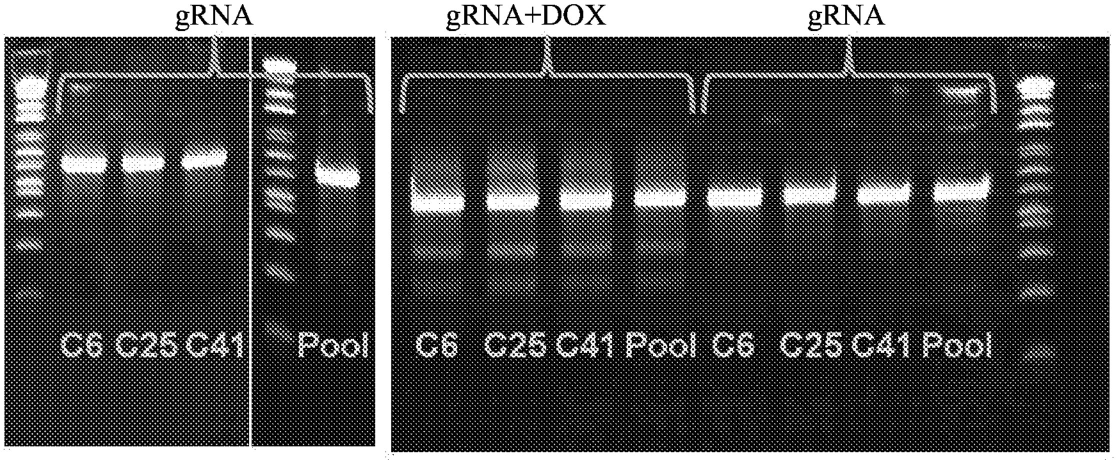
FIG. 4 shows an electrophoretic gel image representative of induction at the level of DNA. A Surveyor assay was used to cut a known human gene, Usp14 (note that this concept is applicable to any sequence, e.g., of the human genome). The assay showed that the inducible system is active in iPSCs only when doxycycline is added to the cell culture medium and a guide RNA (gRNA) is present. Different pools or single clones (C6, C25, C41) of cells were analyzed, each containing an inducible Cas9 system of the present disclosure. Cleavage is indicated by the release of additional lower bands in the electrophoresis gel. The same efficiency of cleavage was observed among all the cells analyzed.
Figure 5:
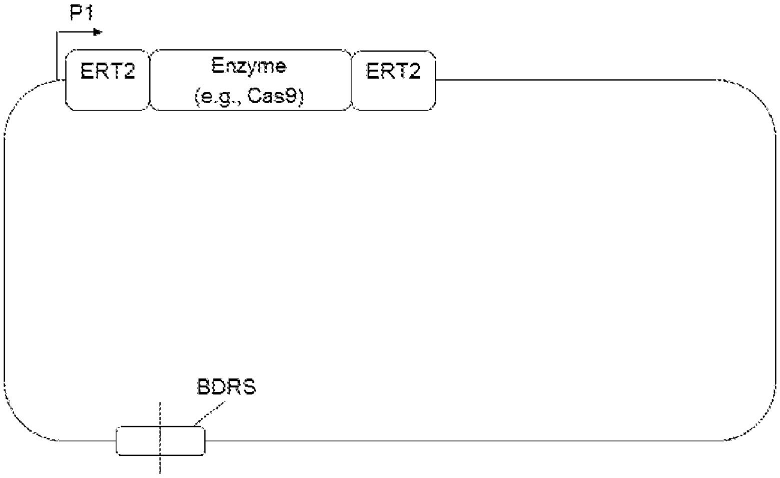
FIG. 5 is a schematic of an example of an engineered nucleic acid construct in accordance with the present disclosure. Promoter P1 is operably linked to a nucleic acid encoding an enzyme that cleaves, a nucleic acid encoding an enzyme that nicks nucleic acid, or a nucleic acid encoding an enzyme that catalyzes exchange of nucleic acid, wherein the nucleic acid encoding the enzyme is flanked by a modified version of estrogen receptor (ERT2) sequences. The enzyme is upstream from a (e.g., at least one) deoxyribonucleic acid (DNA)-binding domain recognition sequence (BDRS).
Figure 6:
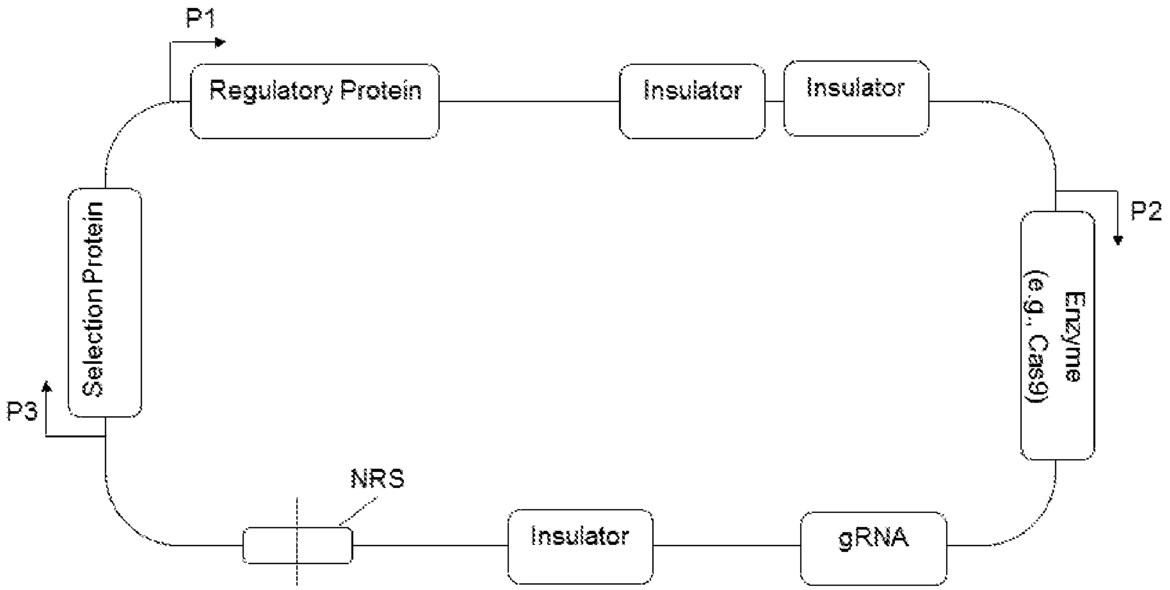
FIG. 6 is a schematic of an example of an engineered construct used to target the MTH1 gene. Promoter P1 is operably linked to a nucleic acid encoding a regulatory protein (e.g., an inducer protein or a repressor protein), which is upstream from two (e.g., at least two) insulators. The insulators are upstream from promoter P2, which is operably linked to a nucleic acid encoding an enzyme that cleaves (e.g., Cas9 nuclease, Cpf1 nuclease, or a functional equivalent thereof), a nucleic acid encoding an enzyme that nicks (e.g., Cas9 nickase) nucleic acid, or a nucleic acid encoding an enzyme that catalyzes exchange of nucleic acid (e.g., Cre recombinase). The enzyme is upstream from a nucleic acid encoding a guide RNA (gRNA), which is upstream from an additional insulator, which is upstream from a (e.g., at least one) deoxyribonucleic acid (DNA)-binding domain recognition sequence (BDRS). In this example, the gRNA is specific for MTH1 gene, is constitutively expressed and will bind Cas9 to form an active complex upon expression of Cas9. The construct in this examples comprises DNA-binding domain recognition sequences that correspond to sequences located in the AAVS1 locus of the human genome. The construct was integrated in the AAVS1 locus by and recombinant clones where selected. The recombinant clones were assayed for cleavage of the endogenous MTH1 locus upon induction.
Figure 7:
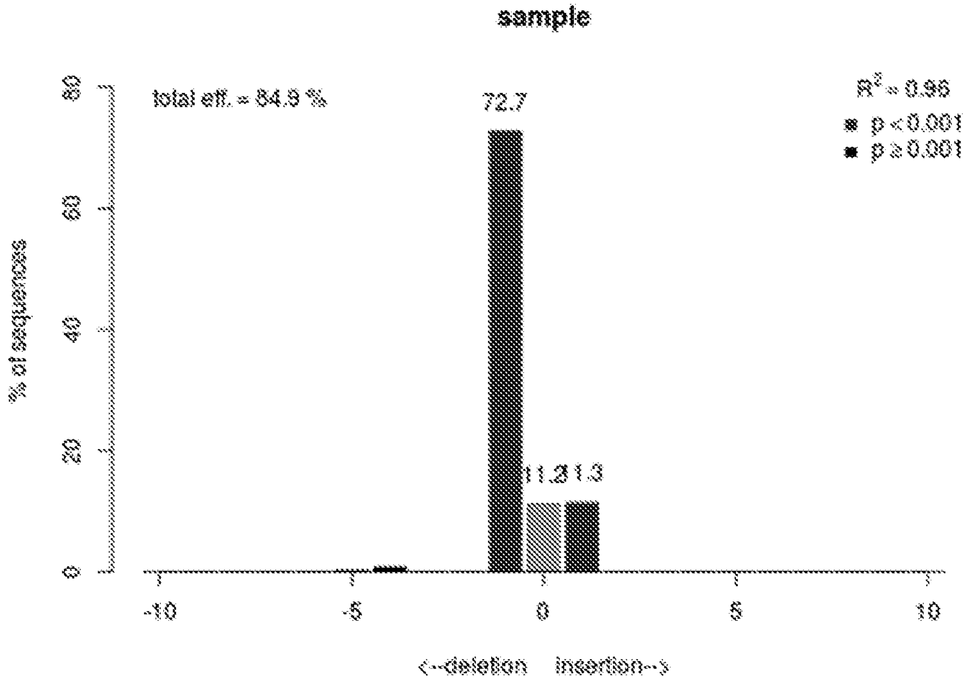
FIG. 7 is a graph showing cleavage efficiency as determined by TIDE software. The analysis shows that 85% of the cells contain a deletion (knockout) in the MTH1 gene, while no deletion was observed in absence of induction. The data from this analysis shows that MTH1 is not lethal when combined with a particular mutation present in the cell line tested.
Figure 8:
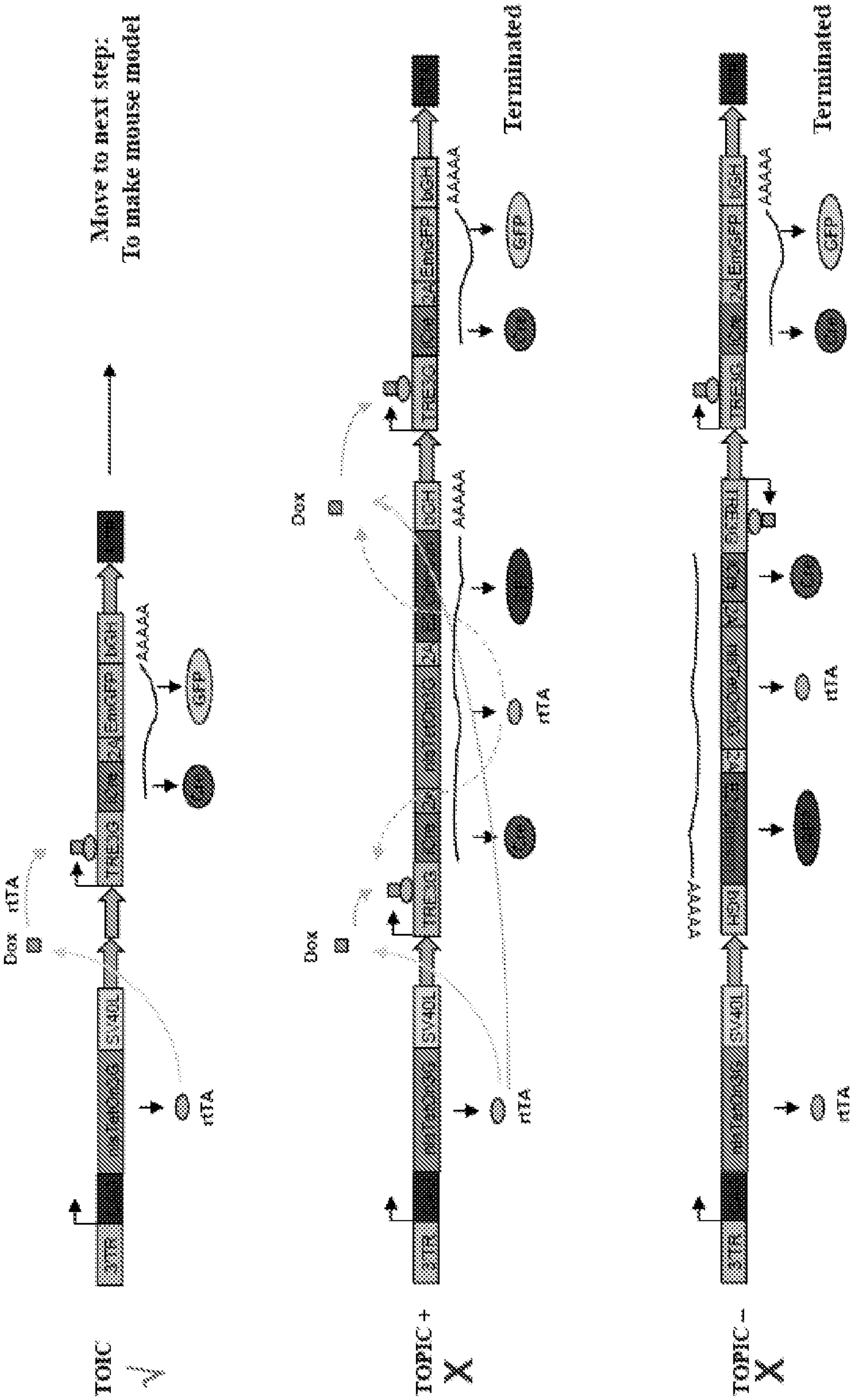
FIG. 8 shows schematics of different engineered nucleic acid constructs, one of which (top panel) expresses GFP upon induction with doxycycline.
Figure 9:
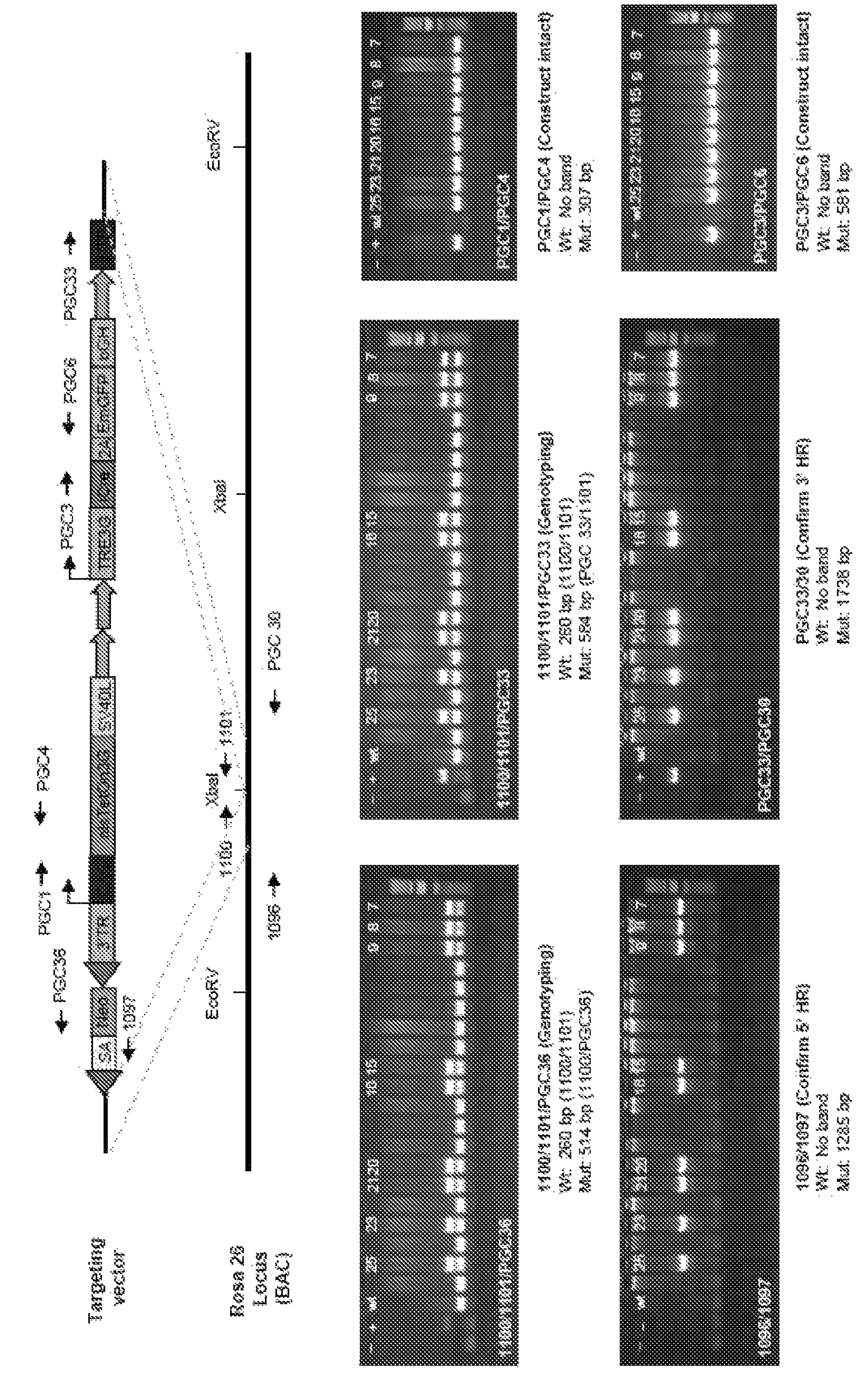
FIG. 9 shows data confirming integration into the Rosa26 locus and germline transmission of the engineered construct depicted in FIG. 8, top panel.

Further, the engineered constructs (e.g., "TOICas constructs") of the present disclosure substantially reduce leaky gene expression. A gene expression system may be considered "leaky" if gene transcription is initiated in the absence of a regulatory protein or in an uncontrolled manner. As described elsewhere herein, regulatory proteins bind to promoters to regulate transcriptional activity. The expression of a gene is considered "leaky" if expression occurs in the absence of the regulatory protein intended to bind the promoter that controls expression of the gene. Expression of a gene is considered "substantially non-leaky" if the level of gene expression in the absence of the regulatory protein is less than 15% (e.g., less than 10%, less than 5%, less than 2%, less than 1%, less than 0.5%) of the level of gene expression in the presence of the regulatory protein. As depicted in FIGS. 1 and 2, for example, at least one insulator (e.g., one, two or more insulators) is positioned between the nucleic acid encoding the regulatory protein and the downstream promoter (P2) (to which the regulatory protein binds) controlling expression of the enzyme (e.g., nuclease or recombinase). An "insulator" is a nucleotide sequence that blocks the interaction between enhancers and promoters. It should be understood that insulator(s) may be positioned, in some embodiments, between any two promoters driving gene expression so as to prevent transcriptional activation of the downstream promoter upon transcriptional activation of the upstream promoter.

Thus, engineered constructs (e.g., "TOICas constructs"), in some embodiments, comprise at least one insulator. In some embodiments, an engineered construct comprises at least 2, at least 3 or at least 4 insulators. In some embodiments, an insulator comprises a mammalian insulator. For example, the insulator may comprise a (at least one) human insulator, such as 5'HS5, DMD/ICR, BEAD-1, apoB (−57 kb), apoB (+43 kb), or DM1site 1 or DM1 site 2 (Table 2). In some embodiments, the insulator may comprise a (at least one) *Mus musculus* insulator, such as BEAD-1, HS2-6 or DMR/ICR. See, e.g., Bell et al., Curr Opin Genet Dev. 1999 April; 9(2):191-8; Science. 2001 Jan. 19; 291(5503):447-50; West et al., Genes Dev. 2002 Feb. 1; 16(3):271-88; and Ziebarth et al., Nucleic Acids Research. 2013; 41(D1): D188-D194, each of which is incorporated herein by reference.

In some embodiments, an insulator comprises a (at least one) non-mammalian insulator. For example, the insulator may comprise a (at least one) *Drosophila melanogaster* insulator, such as scs/scs', gypsy, Fab-7, Fab-8, $fa^{swb}$ or the eve promoter. In some embodiments, the insulator may comprise a *Saccharomyces cerevisiae* insulator, including HMR $tRNA^{Thr}$, Chal UAS, $UAS_{rpg}$ or STAR. In some embodiments, the insulator may comprise a (at least one) *Gallus gallus* insulator, such as Lys 5'A, HS4, or 3'HS. In some embodiments, the insulator may comprise sns, a *Parancentrotus lividus* insulator, UR1, a *Hemicentrotus pulcherrimus* insulator, or RO, a *Xenopus laevis* insulator.

TABLE 2

| | |
|---|---|
| 5'HS5 (*Homo sapiens*) | CATCTTGGACCATTAGCTCCACAGGTATCTTCTTC CCTCTAGTGGTCATAACAGCAGCTTCAGCTACCTC TC (SEQ ID NO: 1) |
| apoB (-57 kb) (*Homo sapiens*) | CAAATTATCCTGCCCCCTAGACATAACCTCCC (SEQ ID NO: 2) |
| BEAD-1 (*Homo sapiens*) | TGCATTGGCTGCCCAGGCCTGCACTGCCGCCTGCC GGCAGGGGTCCAGTCCACGAGACCCAGCTCCCTGC (SEQ ID NO: 3) |
| DM1 site 1 (*Homo sapiens*) | GCCGGCCGCGGACCCGGCCCCTCCCTCCCCGGCCG CTAGGGGGCGGGCCCGGATCACAGGA (SEQ ID NO: 4) |
| DM1 site 2 (*Homo sapiens*) | CATGCACAAGAAAGCTTTGCACTTTGCGAACCAAC GATAGGTGGGGGTGCGTGGAGGATGG (SEQ ID NO: 5) |

"Downstream" and "upstream" refer to the relative position of nucleic acid (e.g., DNA or RNA). Each strand of DNA or RNA has a 5' end and a 3' end, so named for the carbon position on the deoxyribose (or ribose) ring. By convention, upstream and downstream relate to the 5' to 3' direction in which RNA transcription takes place. Upstream is toward the 5' end of the RNA molecule and downstream is toward the 3' end. When considering double-stranded DNA, upstream is toward the 5' end of the coding strand for the gene of interest and downstream is toward the 3' end.

Inducible Gene Editing Systems

Inducible gene editing systems are useful for temporally-controlled, spatially-controlled, and both temporally-controlled and spatially-controlled modification of genes. Some embodiments utilize a Tet-Off or Tet-On inducible system. Other embodiments utilize a tamoxifen-inducible system. Yet other embodiments utilize an isopropyl β-D-1-thiogalactopyranoside (IPTG)-inducible System.

Tetracycline-Inducible System

Tet technology comprises two complementary control circuits, initially described as the tTA dependent (Gossen et al. *Proc Natl Acad Sci USA.* 1992 Jun. 15; 89(12):5547-51) and rtTA dependent (Gossen et al. *Science.* 1995 Jun. 23; 268(5218):1766-9) expression systems. They are now commonly referred to as the Tet-Off system (tTA dependent) and the Tet-On system (rtTA dependent). In each system, a recombinant tetracycline controlled transcription factor (tTA or rtTA) interacts with a tTA/rtTA responsive promoter, Ptet, to drive expression of the gene of interest. Expression is regulated by the effector substance tetracycline (Tc) or one of its derivatives. Tet-On systems respond to doxycycline (Dox). Tetracyclines act at the level of DNA binding of tetracycline-controlled transactivator (tTA) and reverse tetracycline-controlled transactivator (rtTA) transcription factors. rtTA requires a tetracycline ligand for DNA binding and transcription. By contrast, the interaction between tTA and DNA is prevented by tetracycline. Thus, the two versions of the Tet system respond to tetracyclines differently and may be used in a complementary manner.

tTA is a hybrid transcription factor resulting from the fusion of the prokaryotic Tet repressor, TetR, with a eukaryotic transcriptional transactivation domain (e.g., HSV VP16). The TetR moiety confers sequence specific DNA binding, sensitivity to tetracyclines and dimerization to the tTA fusion protein. Accordingly, the response of both TetR and tTA to tetracyclines is similar: binding of the antibiotic lowers their affinity to their common cognate binding sites, the tet operators.

rtTA differs from tTA by a few point mutations within TetR. These, however, result in a complete reversal of tetracycline responsiveness of this transcription factor. rtTA requires tetracyclines for binding to tetO. Specific tetracycline derivatives such as doxycycline (Dox) or anhydrotetracycline (ATc) may be used to exploit the rtTA phenotype.

Ptet is a synthetic promoter responsive to both tTA and rtTA. It is comprised of a minimal RNA polymerase II promoter (transcriptionally silent in the absence of additional transcription factor binding sites) fused to multimerized tetO sequences. This arrangement makes the activity of Ptet dependent on the binding of tTA or rtTA. The design of such synthetic tTA/rtTA responsive promoters is flexible with respect to both the origin of the minimal promoter as well as the exact arrangement of the operators. The original version, for example, which consists of a CMV minimal promoter fused to an array of seven tetO sequences is designated Ptet-1. It is commercially distributed as part of the pTRE vector series (for tetracycline responsive element), somewhat in line with the prevailing eukaryotic nomenclature.

In some embodiments, doxycycline, a tetracycline derivative, is the effector substance used for a Tet-On or a Tet-Off system. Doxycycline binds with high affinity to tTA as well as to rtTA and, thus, is fully effective in a Tet-Off system at concentrations as low as 1-2 ng/ml in the case of tTA, for example. In a Tet-On system, concentrations as low as 80 ng/ml, in the case of rtTA2-syn1, for example, are effective.

In some embodiments of the present disclosure, an engineered construct comprises a promoter (e.g., CAG) operably linked to a nucleic acid (e.g., gene) encoding rtTA, which is located upstream from a Ptet promoter operably linked to a nucleic acid encoding an enzyme that cleaves (e.g., Cas9 nuclease), a nucleic acid encoding an enzyme that nicks (e.g., Cas9 nickase) nucleic acid, or a nucleic acid encoding an enzyme that catalyzes exchange of nucleic acid (e.g., Cre recombinase). Typically, at least one (e.g., one, two or more) insulator is located between the nucleic acid encoding rtTA and the Ptet promoter such that activating transcription of the nucleic acid encoding rtTA does not also activate transcription of the enzyme in the absence of a suitable effector substance, such as doxycycline.

In some embodiments of the present disclosure, an engineered construct comprises a promoter (e.g., CAG) operably linked to a nucleic acid (e.g., gene) encoding tTA, which is located upstream from a Ptet promoter operably linked to a nucleic acid encoding an enzyme that cleaves (e.g., Cas9 nuclease), a nucleic acid encoding an enzyme that nicks (e.g., Cas9 nickase) nucleic acid, or a nucleic acid encoding an enzyme that catalyzes exchange of nucleic acid (e.g., Cre recombinase). Typically, at least one (e.g., one, two or more) insulator is located between the nucleic acid encoding rtTA and the Ptet promoter such that activating transcription of the nucleic acid encoding tTA does not also activate transcription of the enzyme in the absence of a suitable effector substance, such as doxycycline.

IPTG-Inducible System

Some embodiments of the present disclosure utilize a system that relies on the presence of a lactose (lac) repressor protein and a lac operon. The lac repressor is a DNA-binding protein that binds to the lac operon and inhibits expression of a nucleic acid operably linked to the lac operon. The presence of allolactose or an allolactose mimic, such as isopropyl β-D-1-thiogalactopyranoside (IPTG), inhibits the DNA binding ability of the lac repressor protein. This loss of DNA binding by the lac repressor is used for transcriptional activation of the lac operon and expression of any nucleic acid linked to that operon.

The lac operon contains three structural genes, and a promoter, a terminator, regulator, and an operator. The three structural genes are lacZ, lacY, and lacA. lacZ encodes β-galactosidase (LacZ), an intracellular enzyme that cleaves the disaccharide lactose into glucose and galactose; lacY encodes lactose permease (LacY), a transmembrane symporter that pumps β-galactosides into the cell using a proton gradient in the same direction; and lacA encodes galactoside O-acetyltransferase (LacA), an enzyme that transfers an acetyl group from acetyl-CoA to β-galactosides.

In some embodiments of the present disclosure, an engineered construct comprises a promoter (e.g., CAG) operably linked to a nucleic acid (e.g., gene) encoding the lac repressor protein, which is located upstream from a lac operon operably linked to a nucleic acid encoding an enzyme that cleaves (e.g., Cas9 nuclease), a nucleic acid encoding an enzyme that nicks (e.g., Cas9 nickase) nucleic acid, or a nucleic acid encoding an enzyme that catalyzes exchange of nucleic acid (e.g., Cre recombinase). Typically, at least one (e.g., one, two or more) insulator is located between the nucleic acid encoding the lac repressor protein and the lac operon such that activating transcription of the nucleic acid encoding the lac repressor protein does not also activate transcription of the enzyme in the absence of a suitable effector substance, such as IPTG.

Tamoxifen-Inducible System

Also provided herein are engineered constructs comprising (a) a promoter operably linked to a nucleic acid encoding a Cas9 nuclease that does not comprise a nuclear localization signal, wherein the nucleic acid encoding the enzyme is flanked by estrogen receptor (ERT2) sequences, and (b) a deoxyribonucleic acid (DNA)-binding recognition sequence. A nuclear localization signal or sequence (NLS) is an amino acid sequence that 'tags' a protein for import into the cell nucleus by nuclear transport. Typically, this signal contains one or more short sequences of positively charged lysine residues or arginine residues exposed on the protein surface. Different nuclear localized proteins may share the same NLS. An NLS has the opposite function of a nuclear export signal, which targets proteins out of the nucleus. A Cas9 nuclease that does not comprise a nuclear localization signal is a modified Cas9 protein that is not imported into the cell nucleus by nuclear transport.

Cas9 activity can be regulated by fusing the nuclease to a modified fragment of the estrogen receptor (ERT2). In some embodiments, the ERT2 is a modified version of the ER receptor that is highly selective for tamoxifen binding relative to endogenous estrogen. Cas9 fused to a modified fragment is sequestered outside of the nucleus where it cannot direct recombination. In the presence of estrogen receptor antagonists (e.g. tamoxifen), Cas9 can relocate into the nucleus where it is able to function. In some embodiments, an engineered nucleic acid is flanked by ERT2 fragments (comprises an ERT2 fragment on either end of the protein (ERT2Cas9ERT2; SEQ ID NO: 7)). If ERT2Cas9ERT2 expression is driven by (controlled by) tissue specific promoters, genes of interest can be modified in a tissue of interest at any time in their development. Once this information is recorded, the cells can be monitored over the lifetime of the animal. In some embodiments, an engineered construct comprises a nucleic acid that encodes a Cas9 nuclease that does not comprise a nuclear localization signal, wherein the nucleic acid encoding the enzyme is flanked by estrogen receptor (ERT2) sequences (e.g., SEQ ID NO: 7).

Nucleic Acids

An "engineered construct" refers to an artificially constructed segment (linear or circular) of nucleic acid that is used for introduction into a cell. Engineered constructs (e.g., "TOICas constructs") typically contain at least one promoter operably linked to a nucleic acid encoding a protein of interest. Embodiments of the present disclosure provide engineered nucleic acids encoding elements of an inducible nucleic acid expression system. An "engineered nucleic acid" is a nucleic acid (e.g., at least two nucleotides covalently linked together, and in some instances, containing phosphodiester bonds, referred to as a phosphodiester "backbone") that does not occur in nature. Engineered nucleic acids include recombinant nucleic acids and synthetic nucleic acids. A "recombinant nucleic acid" is a molecule that is constructed by joining nucleic acids (e.g., isolated nucleic acids, synthetic nucleic acids or a combination thereof) and, in some embodiments, can replicate in a living cell. A "synthetic nucleic acid" is a molecule that is amplified or chemically, or by other means, synthesized. A synthetic nucleic acid includes those that are chemically modified, or otherwise modified, but can base pair with (also referred to as "binding to," e.g., transiently or stably) naturally-occurring nucleic acid molecules. Recombinant and synthetic nucleic acids also include those molecules that result from the replication of either of the foregoing.

While an engineered nucleic acid, as a whole, is not naturally-occurring, it may include wild-type nucleotide sequences. In some embodiments, an engineered nucleic acid comprises nucleotide sequences obtained from different organisms (e.g., obtained from different species). For example, in some embodiments, an engineered nucleic acid includes a murine nucleotide sequence, a bacterial nucleotide sequence, a human nucleotide sequence, a viral nucleotide sequence, or a combination of any two or more of the foregoing sequences.

In some embodiments, an engineered nucleic acid of the present disclosure may comprise a backbone other than a phosphodiester backbone. For example, an engineered nucleic acid, in some embodiments, may comprise phosphoramide, phosphorothioate, phosphorodithioate, O-methylphophoroamidite linkages, peptide nucleic acids or a combination of any two or more of the foregoing linkages. An engineered nucleic acid may be single-stranded (ss) or double-stranded (ds), as specified, or an engineered nucleic acid may contain portions of both single-stranded and double-stranded sequence. In some embodiments, an engineered nucleic acid contains portions of triple-stranded sequence. An engineered nucleic acid may comprise DNA (e.g., genomic DNA, cDNA or a combination of genomic DNA and cDNA), RNA or a hybrid molecule, for example, where the nucleic acid contains any combination of deoxyribonucleotides and ribonucleotides (e.g., artificial or natural), and any combination of two or more bases, including uracil, adenine, thymine, cytosine, guanine, inosine, xanthine, hypoxanthine, isocytosine and isoguanine.

Engineered nucleic acids of the present disclosure may be produced using standard molecular biology methods (see, e.g., *Green and Sambrook, Molecular Cloning*, A Laboratory Manual, 2012, Cold Spring Harbor Press). In some embodiments, nucleic acids are produced using GIBSON ASSEMBLY® Cloning (see, e.g., Gibson, D. G. et al. *Nature Methods,* 343-345, 2009; and Gibson, D. G. et al. *Nature Methods,* 901-903, 2010, each of which is incorporated by reference herein). GIBSON ASSEMBLY® typically uses three enzymatic activities in a single-tube reaction: 5' exonuclease, the 3' extension activity of a DNA polymerase and DNA ligase activity. The 5' exonuclease activity chews back the 5' end sequences and exposes the complementary sequence for annealing. The polymerase activity then fills in the gaps on the annealed regions. A DNA ligase then seals the nick and covalently links the DNA fragments together. The overlapping sequence of adjoining fragments is much longer than those used in Golden Gate Assembly, and therefore results in a higher percentage of correct assemblies. Other methods of producing engineered nucleic acids are known in the art and may be used in accordance with the present disclosure.

Genetic Elements

Engineered nucleic acids of the present disclosure may include one or more genetic elements. A "genetic element" refers to a sequence of nucleotides that has a role in nucleic acid expression (e.g., promoters, insulators, enhancers, terminators and molecular (e.g., DNA or protein) binding regions) or encodes a product of a nucleic acid (e.g., a sequence of nucleotides encoding a regulatory protein or a sequence of nucleotides encoding an enzyme that cleaves nucleic acid, a nucleic acid encoding an enzyme that nicks nucleic acid, or a nucleic acid encoding an enzyme that catalyzes exchange of nucleic acid).

Expression of engineered nucleic acids is typically driven by a promoter operably linked to the engineered nucleic acid. A "promoter" refers to a control region of a nucleic acid at which initiation and rate of transcription of the remainder of a nucleic acid sequence are controlled. A promoter drives transcription or of the nucleic acid sequence that it regulates, thus, it is typically located at or near the transcriptional start site of a gene. A promoter, in some embodiments, is 100 to 1000 nucleotides in length. A promoter may also contain sub-regions at which regulatory proteins and other molecules may bind, such as RNA polymerase and other transcription factors. Promoters may be constitutive (e.g., CAG promoter, cytomegalovirus (CMV) promoter), inducible (also referred to as activatable), repressible, tissue-specific, developmental stage-specific or any combination of two or more of the foregoing.

A promoter is considered to be "operably linked" when it is in a correct functional location and orientation relative to a sequence of nucleic acid that it regulates (e.g., to control ("drive") transcriptional initiation and/or expression of that sequence).

A promoter, in some embodiments, is naturally associated with a nucleic acid and may be obtained by isolating the 5' non-coding sequence(s) located upstream of the coding region of the given nucleic acid. Such a promoter is referred to as an "endogenous" promoter.

A promoter, in some embodiments, is not naturally associated with a nucleic acid. Such a promoter is referred to as a "heterologous" promoter and includes, for example, promoters that regulate other nucleic acids and promoters obtained from other cells. A heterologous promoter may be synthetic or recombinant. Synthetic heterologous promoters, in some embodiments, contain various elements obtained from known transcriptional regulatory regions. Synthetic heterologous promoters, in some embodiments, contain mutations that alter expression through methods of genetic engineering that are known in the art. Recombinant heterologous promoters, in some embodiments, are produced by recombinant cloning, nucleic acid amplification (e.g., polymerase chain reaction (PCR)), or a combination of recombinant cloning and nucleic acid amplification (see U.S. Pat.

Nos. 4,683,202 and 5,928,906). Other methods of producing synthetic and recombinant heterologous promoters are contemplated herein.

A promoter, in some embodiments, is an inducible promoter. An "inducible promoter" regulates (e.g., activates or inactivates) transcriptional activity of a nucleic acid to which it is operably linked when the promoter is influenced by or contacted by a corresponding regulatory protein.

Thus, a "regulatory protein," as used herein, is a protein that modulates (e.g., activates or inactivates) transcriptional activity from a promoter (e.g., an inducible promoter). In some embodiments, a regulatory protein binds directly to an inducible promoter (e.g., to a sequence of nucleotides within a promoter). In some embodiments, a regulatory binds to a region upstream from an inducible promoter (e.g., within 50 to 100 nucleotides upstream from an inducible promoter). In some embodiments, a regulatory protein binds proximal to (e.g., adjacent to) an inducible promoter. Examples of regulatory proteins include, without limitation, tetracycline-controlled transactivator (tTA) transcription factor, reverse tetracycline-controlled transactivator (rtTA) transcription factor, and Lac repressor protein.

A regulatory protein that modulates transcription may activate or inactivate transcription, depending on the system used. Activation of transcription may involve directly acting on a promoter to drive transcription or indirectly acting on a promoter by inactivation a repressor element (e.g., repressor protein) that is preventing the promoter from driving transcription. Conversely, inactivation of transcription may involve directly acting on a promoter to prevent transcription or indirectly acting on a promoter by activating a repressor element that then acts on the promoter.

Activity of a regulatory protein is often regulated by an effector substance. An "effector substance" is any substance that modulates (e.g., activates or inactivates) activity of a regulatory protein. An effector substance may be an endogenous or exogenous condition (e.g., light or heat), compound (e.g., chemical or non-chemical compound) or other protein that regulates (e.g., directly or indirectly) activity of a regulatory protein.

For example, in the Tet-Off System (also referred to as the tTA-dependent system) and the Tet-On System (also referred to as the PTA-dependent system), a recombinant tetracycline controlled transcription factor (tTA or rtTA) (a "regulatory protein") interacts with a tTA/rtTA inducible promoter, Ptet, to drive expression of the gene operably linked to the promoter. Gene expression is regulated by the effector substance tetracycline or one of its derivatives. Tetracyclines act at the level of DNA binding of tTA and rtTA transcription factors. rtTA requires a tetracycline ligand for DNA binding and hence, transcription. In contrast, the interaction between tTA and DNA is prevented by tetracycline. Thus, the Tet-Off System and the Tet-On System, two versions of the Tet System, respond to tetracyclines (and their derivatives, such as doxycycline) differently.

Typically, the administration or removal of an effector substance results in a switch between activation and inactivation of transcription of the operably linked nucleic acid sequence. Thus, the active state of a promoter operably linked to a nucleic acid sequence refers to the state when the promoter is actively regulating transcription of the nucleic acid sequence (e.g., the linked nucleic acid sequence is expressed). Conversely, the inactive state of a promoter operably linked to a nucleic acid sequence refers to the state when the promoter is not actively regulating transcription of the nucleic acid sequence (e.g., the linked nucleic acid sequence is not expressed).

Examples of effector substances that regulate inducible promoters (e.g., via regulation of a regulatory protein) include, without limitation, physiological conditions, such as changes in light, pH, temperature, radiation, osmotic pressure, saline gradients and cell surface binding. Inducible promoters may also be regulated by varying the concentration of extrinsic or intrinsic effector substances. Examples of extrinsic effector substances include, without limitation, amino acids and amino acid analogs, saccharides and polysaccharides, nucleic acids, protein transcriptional activators and repressors, cytokines, toxins, petroleum-based compounds, metal (e.g., copper) containing compounds, salts, ions, enzyme substrate analogs, hormones or combinations of any two or more of the foregoing. Other effector substances are known in the art and may be used in accordance with the present disclosure.

Examples of inducible promoters include, without limitation, chemically- or biochemically-regulated and physically-regulated promoters, such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells). Other inducible promoters are known in the art and may be used in accordance with the present disclosure.

Enhancers

Engineered nucleic acids, in some embodiments, comprise enhancers. An "enhancer" is a cis-acting regulatory sequence of nucleotides involved in the transcriptional activation of a nucleic acid sequence operably linked to a promoter. The enhancer may be located at any functional location upstream or downstream from the promoter.

Terminators

Engineered nucleic acids, in some embodiments, comprise terminators. A "terminator" is a sequence of nucleotides that causes transcription to stop. A terminator may be unidirectional or bidirectional. A terminator comprises a DNA sequence involved in specific termination of an RNA transcript by an RNA polymerase and prevents transcriptional activation of downstream nucleic acid sequences by upstream promoters.

The most commonly used type of terminator is a forward terminator. When placed downstream of a nucleic acid sequence that is usually transcribed, a forward transcriptional terminator will cause transcription to abort. In some embodiments, bidirectional transcriptional terminators are used, which usually cause transcription to terminate on both the forward and reverse strand. In some embodiments, reverse transcriptional terminators are provided, which usually terminate transcription on the reverse strand only.

Examples of terminators for use in accordance with the present disclosure include, without limitation, termination sequences of genes such as, for example, the bovine growth hormone terminator, and viral termination sequences such as, for example, the T0 terminator, the TE terminator, Lambda T1 and the T1T2 terminator found in bacterial systems. In some embodiments, the termination signal may be a sequence that cannot be transcribed or translated, such as those resulting from a sequence truncation.

Selectable Markers

Engineered constructs (e.g., "TOICas constructs"), in some embodiments, comprise a nucleic acid encoding a selectable marker protein. A selectable marker is a gene introduced into a cell that confers a trait suitable for artificial selection. A selectable marker may be, for example, an antibiotic resistance gene. Non-limiting examples of antibiotic resistance genes include gene encoding resistance to ampicillin, chloroamphenicol, tetracycline or kanamycin. For example, beta-lactamase confers ampicillin resistance to bacterial hosts, the neo gene obtained from Tn5, confers resistance to kanamycin in bacteria and geneticin in eukaryotic cells, the mutant FabI gene (mFabI) obtained from the *Escherichia coli* genome confers triclosan resistance to the host, and URA3, an orotidine-5' phosphate decarboxylase obtained from yeast is a positive and negative selectable marker.

Vectors

Embodiments of the present disclosure provide vectors comprising engineered nucleic acids encoding elements of an inducible nucleic acid expression system. A "vector" refers to a nucleic acid (e.g., DNA) used as a vehicle to carry genetic material (e.g., an engineered nucleic acid) into a cell where, for example, it can be replicated and/or expressed. It should be understood that the term "vector," as used herein, does not encompass lentiviral vectors. Thus, in some embodiments, an engineered nucleic acid of the present disclosure is cloned into a vector, or delivered to a cell via a vector, that is not a lentiviral vector. Vectors for use as provided here are typically engineered and include episomal expression vectors. Examples of episomal expression vectors include, without limitation, plasmids, which are double-stranded generally circular DNA sequences that are capable of automatically replicating in a host cell, and viral vectors, which may be based on sequences from DNA viruses, such as BK virus, bovine papilloma virus 1 and Epstein-Barr virus.

Baculovirus vectors (Kost et al. 2005 *Nat Biotechnol.* 2005 May; 23(5): 567-575) are also provided herein. Baculovirus gene expression systems and gene delivery systems are known (see, e.g., Makela A R et al. *Cold Spring Harb Protoc.* 2010 March; 2010(3), incorporated herein by reference) and may be used in accordance with the present disclosure. In some embodiments, a baculovirus vector is used to deliver TOICas constructs, as provided herein, to cells, such as mammalian cells.

A vector may also be an engineered bacterial artificial chromosome (BAC) (O'Conner M. et al. 1989 *Science* 244 (4910): 1307-1312; Shizuya H. et al. 1992 *Proc Natl Acad Sci USA* 89 (18): 8794-8797; and Shizuya H et al. 2001 *Keio J Med.* 50 (1): 26-30, each of which is incorporated herein by reference) or a yeast artificial chromosome (YAC) (Struhl K et al. 1979 PNAS 76(3): 1035-39, incorporated herein by reference) where, for example, the nucleic acid encoding the regulatory protein, the nucleic acid encoding the nuclease or the nucleic acid encoding the recombinase is placed under an inducible promoter (e.g., a tissue-specific promoter) or a housekeeping-gene promoter. The promoter present in the BAC or YAC may, in some embodiments, regulate a downstream gene.

Vectors comprising engineered nucleic acids (or the engineered nucleic acids themselves), in some embodiments, are larger than typical expression constructs. In some embodiments, engineered nucleic acids (or vectors comprising an engineered nucleic acid) of the present disclosure are at least 12 kilobases (kb). For example, the engineered nucleic acids (or vectors comprising an engineered nucleic acid) may be at least 13 kb, at least 14 kb, at least 15 kb, at least 16 kb, at least 17 kb, at least 18 kb, at least 19 kb or at least 20 kb. In some embodiments, the engineered nucleic acids (or vectors comprising an engineered nucleic acid) are 15 kb to 20 kb, 15 kb to 30 kb, 15 kb to 40 kb, 20 kb to 30 kb, or 20 kb to 40 kb.

Cells

Engineered constructs (e.g., "TOICas constructs") of the present disclosure may be introduced into a variety of different cells. Examples of cells into which an engineered construct may be introduced include, without limitation, mammalian cells, insect cells, bacterial cells and yeast cells. Mammalian cells may be human cells, primate cells (e.g., vero cells), rat cells (e.g., GH3 cells, OC23 cells) or mouse cells (e.g., MC3T3 cells), for example. There are a variety of human cell lines, including, without limitation, HEK cells (e.g., HEK 293 or HEK 293T cells), HeLa cells, cancer cells from the National Cancer Institute's 60 cancer cell lines (NCI60), DU145 (prostate cancer) cells, Lncap (prostate cancer) cells, MCF-7 (breast cancer) cells, MDA-MB-438 (breast cancer) cells, PC3 (prostate cancer) cells, T47D (breast cancer) cells, THP-1 (acute myeloid leukemia) cells, U87 (glioblastoma) cells, SHSYSY human neuroblastoma cells (cloned from a myeloma) and Saos-2 (bone cancer) cells.

In some embodiments, engineered constructs are expressed in stem cells (e.g., human stem cells) such as, for example, pluripotent stem cells (e.g., human pluripotent stem cells including human induced pluripotent stem cells (hiPSCs)). A "stem cell" refers to a cell with the ability to divide for indefinite periods in culture and to give rise to specialized cells. A "pluripotent stem cell" refers to a type of stem cell that is capable of differentiating into all tissues of an organism, but not alone capable of sustaining full organismal development. A "human induced pluripotent stem cell" refers to a somatic (e.g., mature or adult) cell that has been reprogrammed to an embryonic stem cell-like state by being forced to express genes and factors important for maintaining the defining properties of embryonic stem cells (see, e.g., Takahashi and Yamanaka, 2006 *Cell* 126 (4): 663-76, incorporated by reference herein). Human induced pluripotent stem cell express stem cell markers and are capable of generating cells characteristic of all three germ layers (ectoderm, endoderm, mesoderm).

Additional non-limiting examples of cell lines that may be used in accordance with the present disclosure include 293-T, 293-T, 3T3, 4T1, 721, 9L, A-549, A172, A20, A253, A2780, A2780ADR, A2780cis, A431, ALC, B16, B35, BCP-1, BEAS-2B, bEnd.3, BHK-21, BR 293, BxPC3, C2C12, C3H-10T1/2, C6, C6/36, Cal-27, CGR8, CHO, CML T1, CMT, COR-L23, COR-L23/5010, COR-L23/CPR, COR-L23/R23, COS-7, COV-434, CT26, D17, DH82, DU145, DuCaP, E14Tg2a, EL4, EM2, EM3, EMT6/AR1, EMT6/AR10.0, FM3, H1299, H69, HB54, HB55, HCA2, Hepa1c1c7, High Five cells, HL-60, HMEC, HT-29, HUVEC, J558L cells, Jurkat, JY cells, K562 cells, KCL22, KG1, Ku812, KYO1, LNCap, Ma-Mel 1, 2, 3 . . . 48, MC-38, MCF-10A, MCF-7, MDA-MB-231, MDA-MB-435, MDA-MB-468, MDCK II, MG63, MONO-MAC 6, MOR/0.2R, MRCS, MTD-1A, MyEnd, NALM-1, NCI-H69/CPR, NCI-H69/LX10, NCI-H69/LX20, NCI-H69/LX4, NIH-3T3, NW-145, OPCN/OPCT Peer, PNT-1A/PNT 2, PTK2, Raji, RBL cells, RenCa, RIN-5F, RMA/RMAS, S2, Saos-2 cells, Sf21, Sf9, SiHa, SKBR3, SKOV-3, T-47D, T2, T84, THP1, U373, U87, U937, VCaP, WM39, WT-49, X63, YAC-1 and YAR cells.

In some embodiments, engineered constructs of the present disclosure are introduced into human cells, for example, lymphocytes, such as T cells (e.g., $CD8^+$ cells, $CD4^+$ cells), B cells or natural killer cells (NK cells).

Cells of the present disclosure, in some embodiments, are modified. A modified cell is a cell that contains an exogenous nucleic acid or a nucleic acid that does not occur in nature. In some embodiments, a modified cell contains a mutation in a genomic nucleic acid. In some embodiments, a modified cell contains an exogenous independently replicating nucleic acid (e.g., an engineered nucleic acid present on an episomal vector). In some embodiments, a modified cell is produced by introducing a foreign or exogenous nucleic acid into a cell.

An engineered construct may be introduced into a cell by methods, such as, for example, electroporation (see, e.g., Heiser W. C. *Transcription Factor Protocols: Methods in Molecular Biology*™ 2000; 130: 117-134), chemical (e.g., calcium phosphate or lipid), transfection (see, e.g., Lewis W. H., et al., *Somatic Cell Genet.* 1980 May; 6(3): 333-47; Chen C., et al., *Mol Cell Biol.* 1987 August; 7(8): 2745-2752), fusion with bacterial protoplasts containing recombinant plasmids (see, e.g., Schaffner W. *Proc Natl Acad Sci USA.* 1980 April; 77(4): 2163-7), or microinjection of purified DNA directly into the nucleus of the cell (see, e.g., Capecchi M. R. *Cell.* 1980 November; 22(2 Pt 2): 479-88).

Mammalian cells (e.g., human cells) modified to comprise an engineered construct of the present disclosure may be cultured (e.g., maintained in cell culture) using conventional mammalian cell culture methods (see, e.g., Phelan M. C. *Curr Protoc Cell Biol.* 2007 September; Chapter 1: Unit 1.1, incorporated by reference herein). For example, cells may be grown and maintained at an appropriate temperature and gas mixture (e.g., 37° C., 5% $CO_2$ for mammalian cells) in a cell incubator. Culture conditions may vary for each cell type. For example, cell growth media may vary in pH, glucose concentration, growth factors, and the presence of other nutrients. Growth factors used to supplement media are often derived from the serum of animal blood, such as fetal bovine serum (FBS), bovine calf serum, equine serum and/or porcine serum. In some embodiments, culture media used as provided herein may be commercially available and/or well-described (see, e.g., Birch J. R., R. G. Spier (Ed.) Encyclopedia of Cell Technology, Wiley. 411-424, 2000; Keen M. J. *Cytotechnology* 17: 125-132, 1995; Zang, et al. *Bio/Technology.* 13: 389-392, 1995). In some embodiments, chemically defined media is used.

The inducible genome editing systems of the present disclosure permit temporally- and spatially-controlled modification of genome, which is useful for a variety of applications. For example, they may be used to generate animal models, cell lines and induced pluripotent stem cells (iPSCs), where regulation of a target gene during a stage of differentiation must be tightly controlled. Inducible genome editing systems may also be used to generate tissue specific, inducible knockouts or knockins. Other applications include gene therapy.

EXAMPLES

Example 1: Protocol for Insertion of Inducible Cassette

1. Grow cells and split around 500000 cells in a fresh well of a 6-well plate the day before transfection.

2. Transfect cells with ZFNs vectors targeting the Nuclease binding site locus and the TOICas inducible construct using the appropriate transfection reagents (usually Lipofectamine LTX or Fugene HD (most often the ration ZFNs/TOICas is 3:1).
3. 3 days after transfection split the cell in 20 cm well and select with appropriate selection (G418 for dox inducible, puromycine for C9Ert2).
4. 3 weeks after selection, pick clones and check for integration in safe harbor locus.
5. gRNA can be inserted as Lentivirus infection or retargeting the locus with the inducible construct or transient transfected.
6. Induction is performed by adding Doxycycline (10 μgimp or Tamoxifen (0.5 uM) to the medium.
7. Cleavage is assessed 3 days after induction.

Example 2: Generation of Cell Lines Using TOICas Construct

Human induced pluripotent stem cells (hiPSCs) are a valuable tool to study the multistep differentiation processes and for generating cell-based in vitro disease models. They can also be used for chemical screens and cellular therapies. Each of these applications can be significantly enhanced by genome engineering; in particular the inducible knock-in or knock out of genes of interest facilitate the study of its function at different stages of differentiation or disease progression without the use of animal models.

A TOICas construct (FIG. 10) was targeted to the human safe harbor AAVS1 locus in hiPSCs using a tightly-regulated one vector system to achieve doxycycline (Dox) inducible Cas9. In the presence of Dox, the transactivator (3G) binds to responsive element and drives the expression of the protein of interest, Cas9 T2A GFP.

Figure 11:
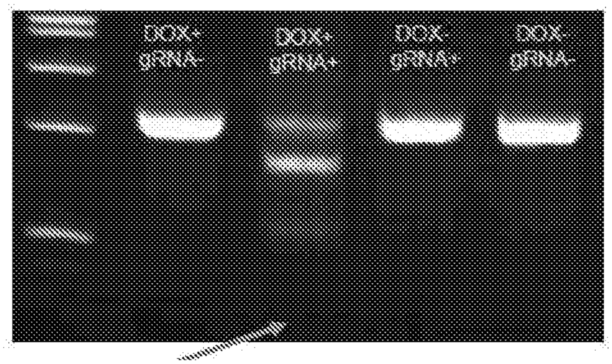
FIG. 11 is an electrophoretic gel image showing efficient cleavage of DNA in the presence of Dox and guide RNA.

The iPSC line generated shows no detectable GFP expression in the absence of Dox, while a clear signal of GFP was detected in the presence of Dox (data not shown). GFP could be detected with as low as 5 ng/ml of Dox, and the signal increased with increasing concentrations (0 ng/ml, 1 ng/ml, 5 ng/ml, 10 ng/ml, 50 ng/ml and 100 ng/ml) over the course of 40 hours, showing that the system can be tuned as required (fluorescent data images not shown). There was no detectable genome cleavage (indicated by indels) on a gRNA target locus in the absence of either Dox or a targeting guide RNA, whereas efficient cleavage is observed in the presence of Dox and guide RNA, showing that the system is efficient with no leaky expression of Cas9 (FIG. 11).

Single or multiple copies of a construct could be inserted using the method of the present disclosure. Higher copy number corresponded with higher protein (e.g., GFP) expression level.

Karyotype is particularly important in cells that are used for differentiation processes, such as induced pluripotent stem cells (iPSC) and mouse embryonic stem cells (mESC). Chromosome analysis of fixed cell suspensions from the human induced pluripotent stem cell line showed an apparently normal make karyotype in 20 cells examined, indicating that the integration method, as provided herein, does not interfere with pluripotency in induced pluripotent stem cells containing the inducible Cas9 system (data not shown).

A time-course of Cas9 induction was also performed following Dox treatment of the cells, showing detectable GFP levels after only 6 hours and persisting for at least 40 hours Maximum expression was observed at 30 hours (data not shown).

An induced pluripotent stem cell (iPSC) line expressing a variant of Cas9 that is enzymatically inactive (Cas9 dead) was also generating using the same the same TOICas system. When compared to Cas9 line in the same TOICas system, toxicity of Cas9 was observed only when the system was overexpressed (100 ng/mL for 2 weeks of expression). The toxicity was indicated by induction of differentiation of the iPSC line, as indicated by morphological changes and by reduction in the expression of pluripotency genes (e.g., Oct4). This indicates that the nuclease activity of Cas9 is associated with toxicity in induced pluripotent stem cells.

Next, gene knockout efficiency was assessed in iPSCs or in cells derived from the iPSCs. Efficient gene knockout was achieved by transfecting synthetic gRNA, synthetic crRNA/tracR and gRNA encoded in an expression plasmid. The efficiency and the precision of deletion increased by using 2 or more gRNA constructs targeting nearby sequences (~10-400 bp apart).

Example 3: Human Endocannabinoid Receptor Deletions

Endocannabinoids (eCBs) play an important role in a diverse range of physiological and pathological processes including neural development, immune function, pain, energy homeostasis, lipid and glucose metabolism. Although endocannabinoids requirement has been extensively studied in mouse little is known about the role of these small signaling lipids in human neuronal development and pathology.

In order to study the need of endocannabinoid signaling in the human system, human induced pluripotent stem cells (hiPSCs) pools were generated using TOICas, in which the human endocannabinoid receptor 1 and 2 genes (CNR1 and CNR2) were targeted, alone or in combination (single and double knock-out, respectively).

Precise deletion was achieved in the CNR1 and 2 genes using synthetic dual guide RNA in presence of Cas9 upon a single DoxA induction in hiPSC (data not shown).

After one week in cell culture, cells were passaged and genomic DNA was extracted. Precise deletion in the CNR1 and CNR2 coding sequence were confirmed by junction PCR, cell assay, and Sanger sequencing (data not shown).

Example 4: TOICAS-KRAB for CRISPR KO and CRISPRi

An iPSC cell line containing a modified version of TOIC was also generated. The normal Cas9 was fused to KRAB domain. A gRNA with a normal/conventional protospacer length or a gRNA with short protospacer length was used to induce respectively CRISPR KO or CRISPRi (see, e.g., methods in Kiani, S., et al. *Nature methods* 12(11): 1051-1054, 2015) This system was also used to target the Oct4 gene and achieved knock out or knock down of the Oct4 gene by using the alternative gRNA indicated above. This system is generally applicable to other modifications, such CRISPRa, base editing and to other orthogonal Cas9 enzymes.

Example 5: Generation of Functional Mouse Model in Immunocompetent Mice Tet-on Inducible Cas9 (iCas9) Mouse for Ex Vivo Primary Cell Modelling CRISPR-Cas9 is a modular and versatile tool for genetic perturbation. It is composed by the ribonucleoprotein endonuclease (Cas9) and a guide RNA (gRNA). Cultured cells are relatively amendable to CRISPR-Cas9 engineering. However, application in living animals cast some major challenge, given the complexity to deliver all the components, precisely and simultaneously, in the tissue of interest. Moreover, conventional knockout strategies affect every cells in an animal, so that its often impossible to distinguish primary and secondary changes in complex phenotype. Finally, any genetic change has potential consequences on mouse development that either preclude or complicate studies on adult animals (e.g., embryonic lethality, abnormalities, metabolic defects, cancer). Therefore, there is a growing necessity of a precise and temporal editing system to use in vivo.

Provided herein is a tight, one component system to achieve doxycycline inducible expression of Cas9 in immunocompetent mice without any other phenotypic consequence. An engineered TOICas construct of the present disclosure (FIG. 10) was inserted in the safe r26 locus in mouse embryonic stem cells (mES). Clones were successfully generated with either single or double copy integration in r26 locus. After doxycycline induction and further confirmation of Cas9 expression, different clones were selected to inject into the blastocyst to produce chimeric mice (data not shown). The expression of Cas9 after dox treatment correlates with the number of copies of the TOICas construct in the r26 locus. Introducing multiple copies into a specific locus is only achievable by using a NHEJ-based method for integration. This is the first animal model generated by this method.

In order to prove the functionality of TOICas in mouse cells, ear fibroblasts were isolated from the founder mice and cultivate ex vivo. The cells were then stimulated with Dox. After imaging under fluorescence microscope, GFP expression was confirmed (data not shown).

Tet-on Inducible Cas9 (iCas9) Mouse for AAV-Mediated In Vivo Genome Editing and Cancer Modeling.

CRISPR-Cas9 moved the boundaries of genome editing towards complex in vivo applications. The promise of a sudden approach of CRISPR to gene therapy is hampered by an increasing demand of more translatable and effective animal models. Mouse molecular genetics has the potential to reproduce human diseases, but conventional knockout strategies are not selective nor versatile enough to be controlled in a spatial or temporal manner. In the recent years, the need for a more flexible in vivo genetic tool is growing fast, especially in the field of complex modelling in adult mice.

Cas9 expression is tightly regulated in the TOICas mouse, and expression of Cas9 was observed in the majority of the tissues only upon doxycycline treatment. The TOICas mouse has an immunocompetent background, therefore can be used for immuno-oncology applications, for example. Here, immunocompetent TOICas mice (6 per cohort) were administered 2 mg/ml of doxycycline (Dox) in drinking water ad libitum for 3 days. After the treatment, a TOICas mouse was euthanized together with an untreated (−Dox) TOICas control mouse (6 per cohort). Six tissues from both mice were immediately isolated and imaged with a epifluorescent stereomicroscope, in order to benchmark Cas9 expression (data not shown). In vivo TOICas activation/GFP expression was observed in the heart, lungs, trachea, liver, spleen, pancreas, and brain after 3 days of Dox induction, while no GFP was detected in tissues from the untreated control mouse (data not shown). Histopathological analysis showed that the mouse tumors resembled human tumors.

Low differentiated adenocarcinoma could be observed in all areas of the lung. The growth pattern included epithelial tumor cells that showed a papillary, trabecular, glandular and compact growth pattern with local invasion in the alveolar spaces and adjacent tissues. Occasionally presence of almost squamous epithelial-like transformation was observed. There was high mitotic activity in tumor tissue as well as few areas of bronchial epithelium with presence of atypical mitoses. There was also presence of highly undifferentiated cells with polyploidy, anisocytosis and anisokaryosis, and a significant increase of alveolar macrophages. There was no evidence of blood vessel infiltrations or metastases. A bronchoalveolar growth pattern was observed as well as areas of trabecular and glandular growth pattern identified by multifocal nodules in alveolar and bronchiolar spaces. High mitotic activity was observed overall, particularly in all tumor nodules (based on an immunohistochemical assay for proliferative marker Ki67) and randomly in bronchial epithelium (data not shown). Surprisingly, what was considered a negative control, the brain (the most difficult organ to reach by drug treatment) also resulted positive to GFP.

Figure 12:
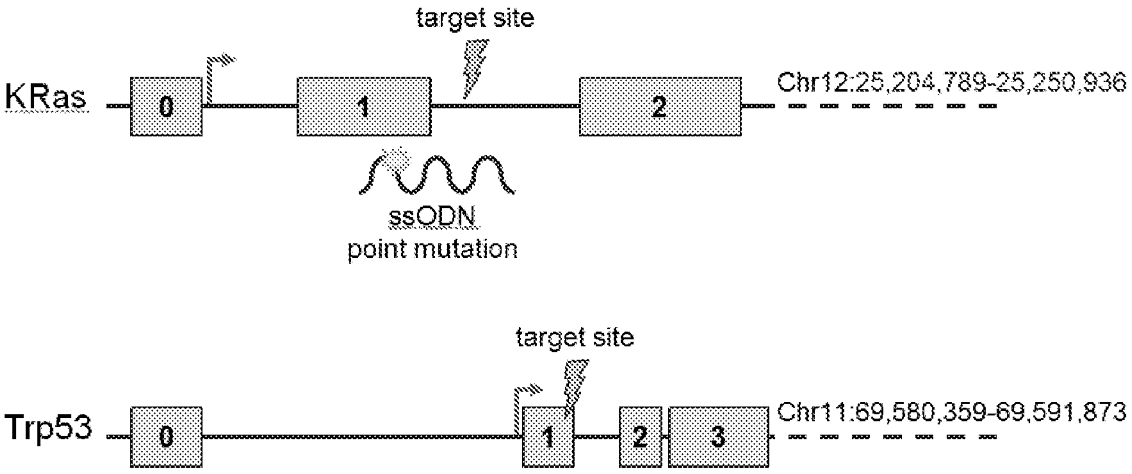
FIG. 12 shows a schematic of a gene target strategy using AAV-U6 gRNA ($p53^{-/-}$/KrasG12D) construct (top panel). A Kras target site is located in an intron to cause less damage possible to the gene in case of failure of HDR ssODN-mediated point-mutation "repair". Trp53 CRISPR follows a "common" strategy (bottom panel).
Figure 13:
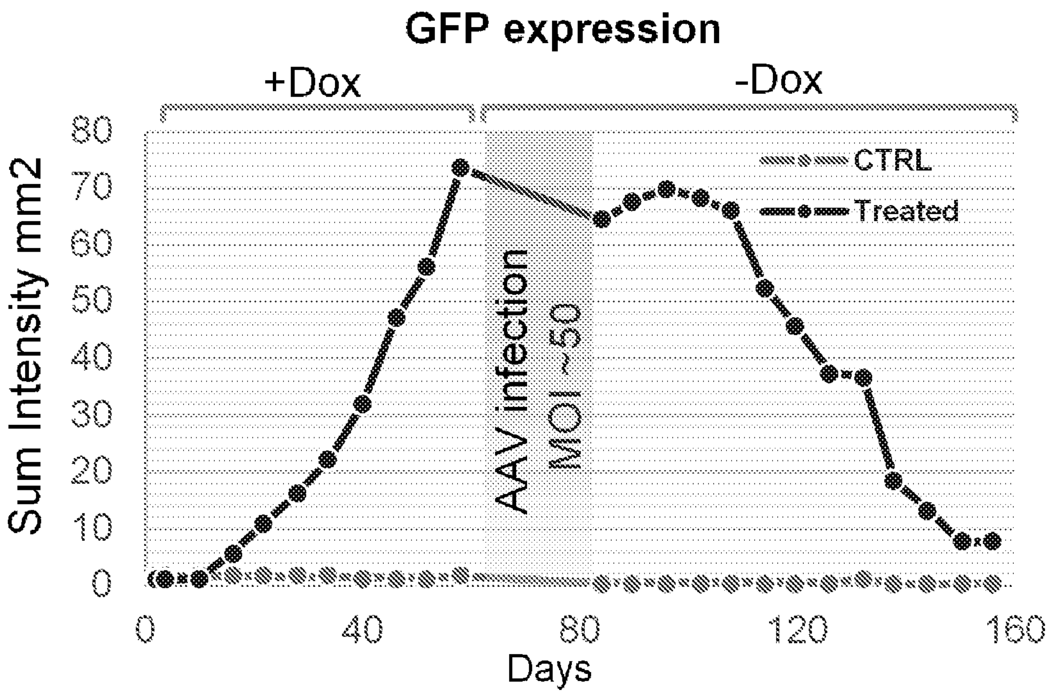
FIG. 13 shows a GFP curve followed over time after Dox stimulation (48 h) and removal (112 h) of cells.
Figure 14:
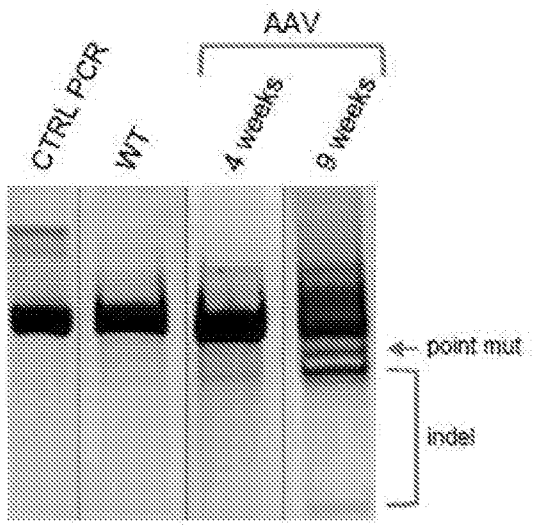
FIG. 14 is an electrophoretic gel image showing results from a surveyor assay on fibroblasts stimulated with Dox and infected with AAV-gRNA-Kras to produce both point mutation and indel.

To generate an in vivo mouse model of cancer, a gRNA against Trp53 and Kras together with a template to introduce KrasG12D mutation were used. Cells were infected with AAV harboring gRNA targeting Kras (FIG. 12, top panel). Cas9 endonuclease activity was assessed by time-course monitoring of GFP expression (FIG. 13). A surveyor assay, performed on genomic DNA collected from cells 4 or 9 weeks after infection, confirmed precise editing represented by the distinct pattern expected from the targeting strategy (indel and point mutation—FIG. 14). Both the knockout (KO) of p53 and kras mutagenesis were confirmed in fibroblast and adult mice.

Figure 15:
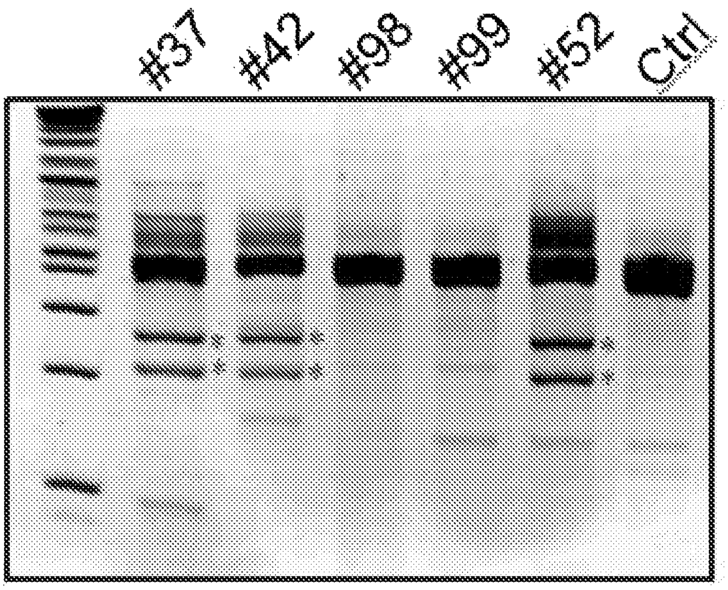
FIG. 15 is an electrophoretic gel image showing results of a surveyor nuclease assay demonstrating the precise cut in Trp53 gene (red asterisks) in the lungs of mice administered intra-tracheal with AAV-gRNA-Trp53 (#37, #42, #52), validating the function of TOICas.
Figure 16:
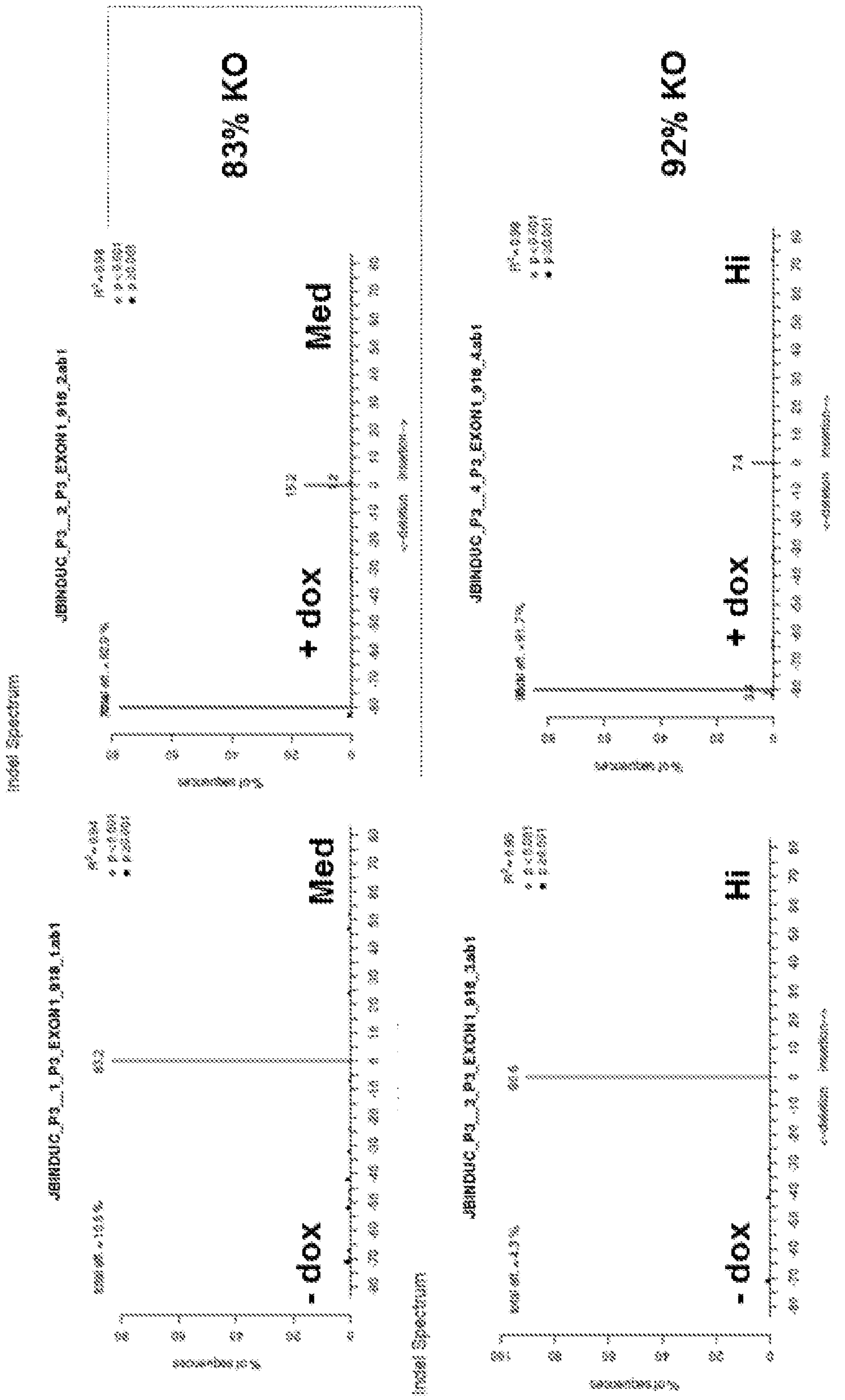
FIG. 16 shows data from a Sanger sequencing analysis demonstrating that TOICas9 (inducible Cas9) cleavage is not observed in the absence of Dox.
Figure 17:
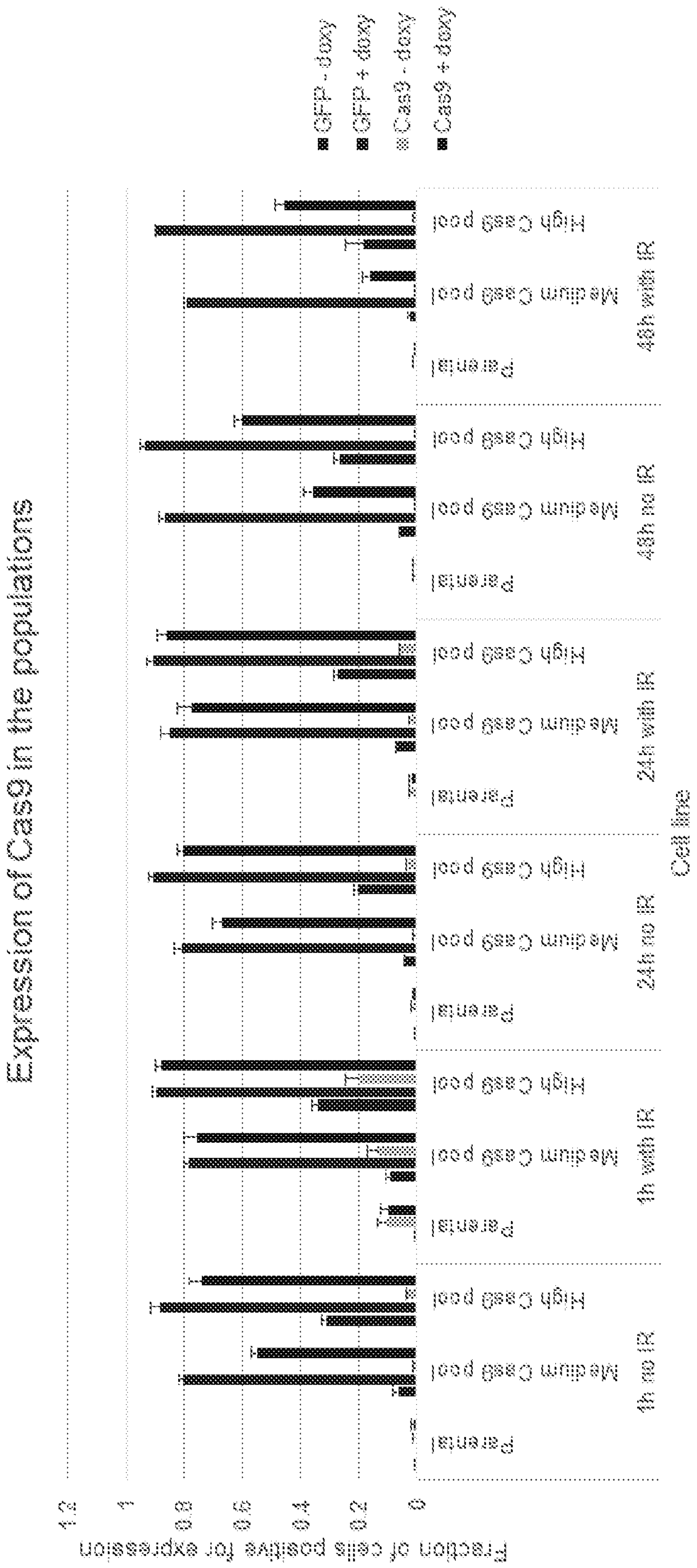
FIG. 17 is a graph showing GFP expression and Cas9 expression as a proportion of the parental population and the stable pools.
Figure 18:
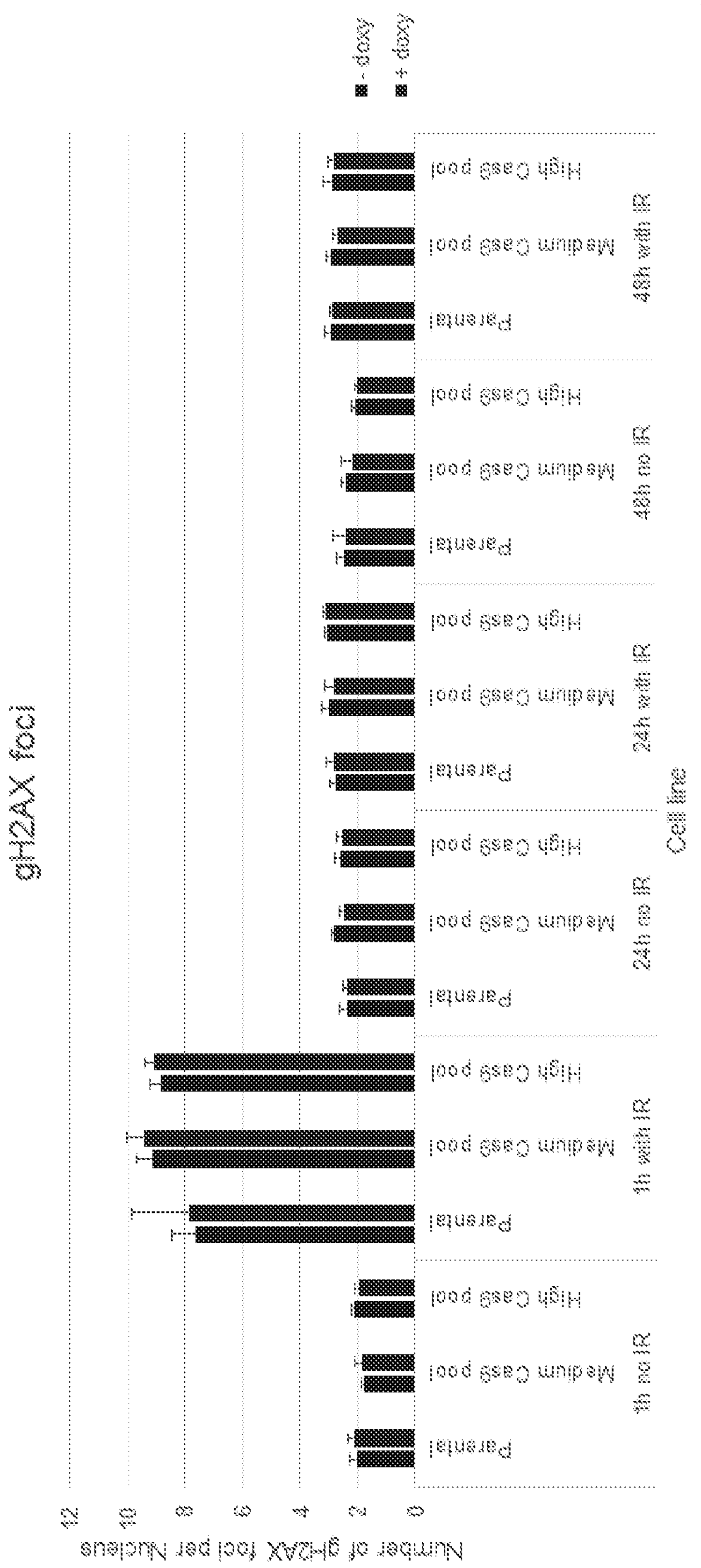
FIG. 18 is a graph showing the effect of Cas9 expression on acute DNA damage (gH2AX foci formation).
Figure 19:
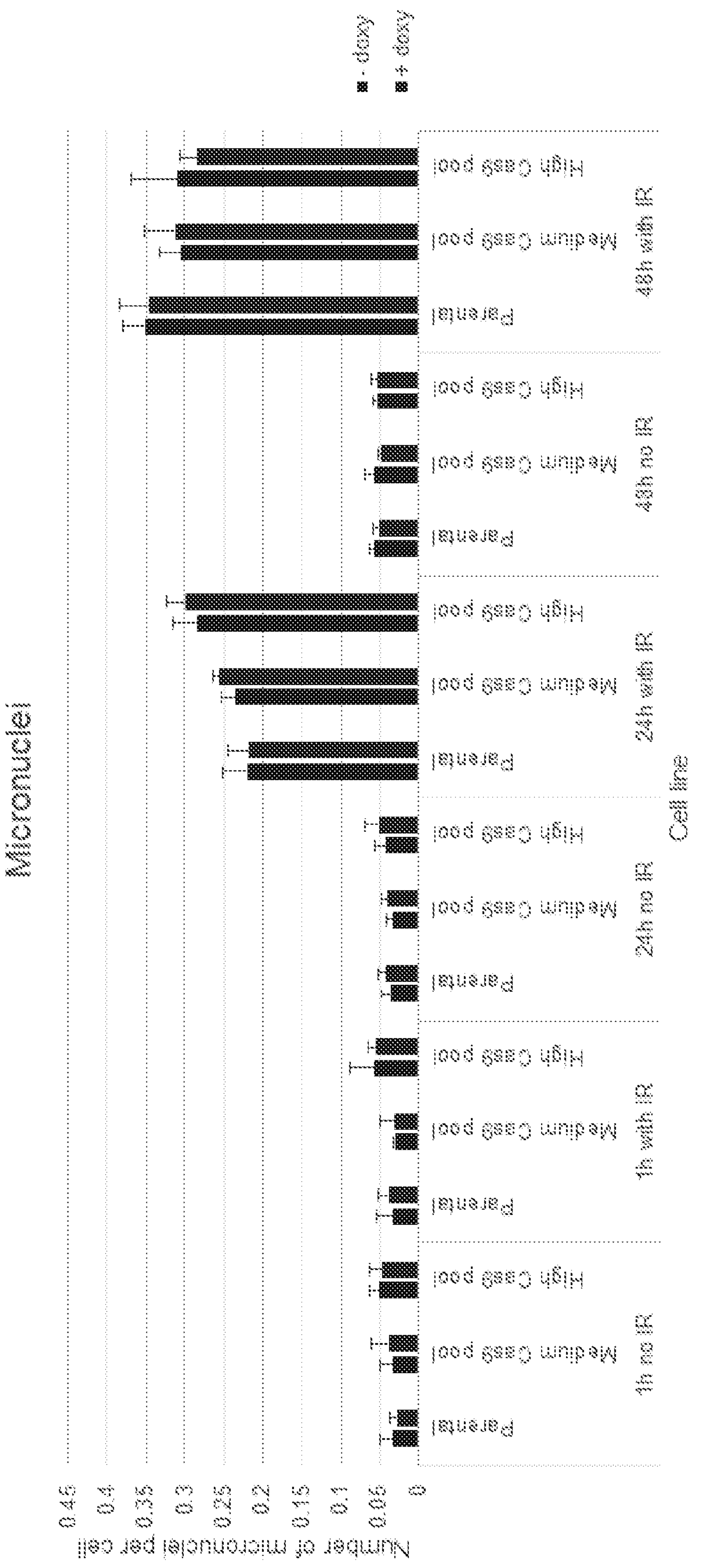
FIG. 19 is a graph showing the effect of Cas9 expression on persistent DNA damage (micronuclei formation).
Figure 20:
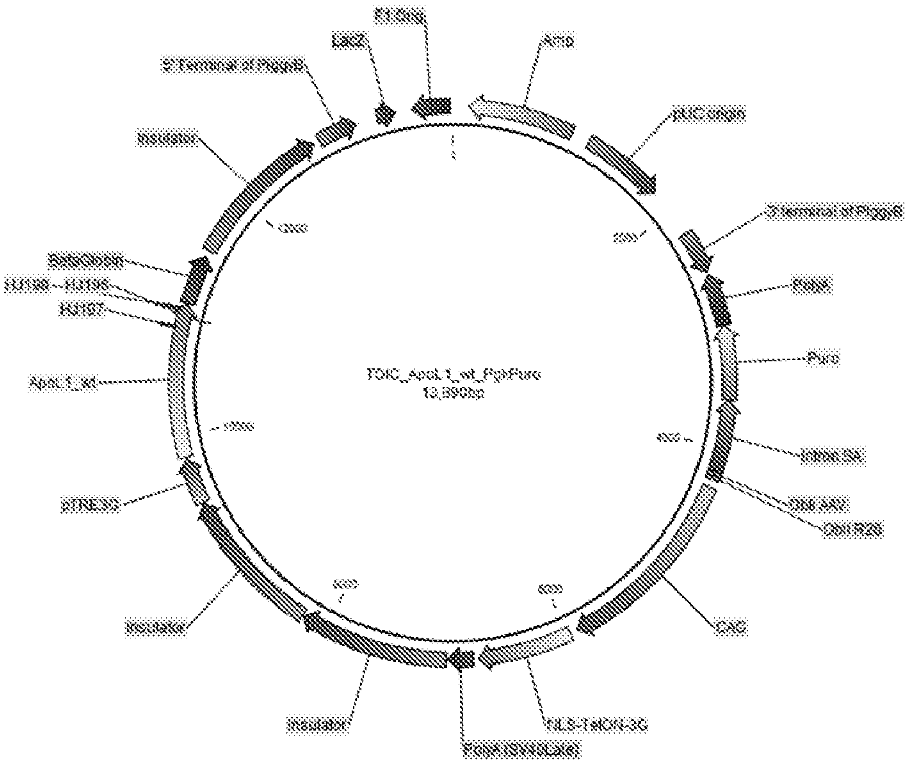
FIGS. 20-28 show plasmid maps of examples of TOICas constructs encompassed by the present disclosure. The sequences of FIGS. 20-28 correspond respectively to SEQ ID NO: 12-20.
Figure 21:
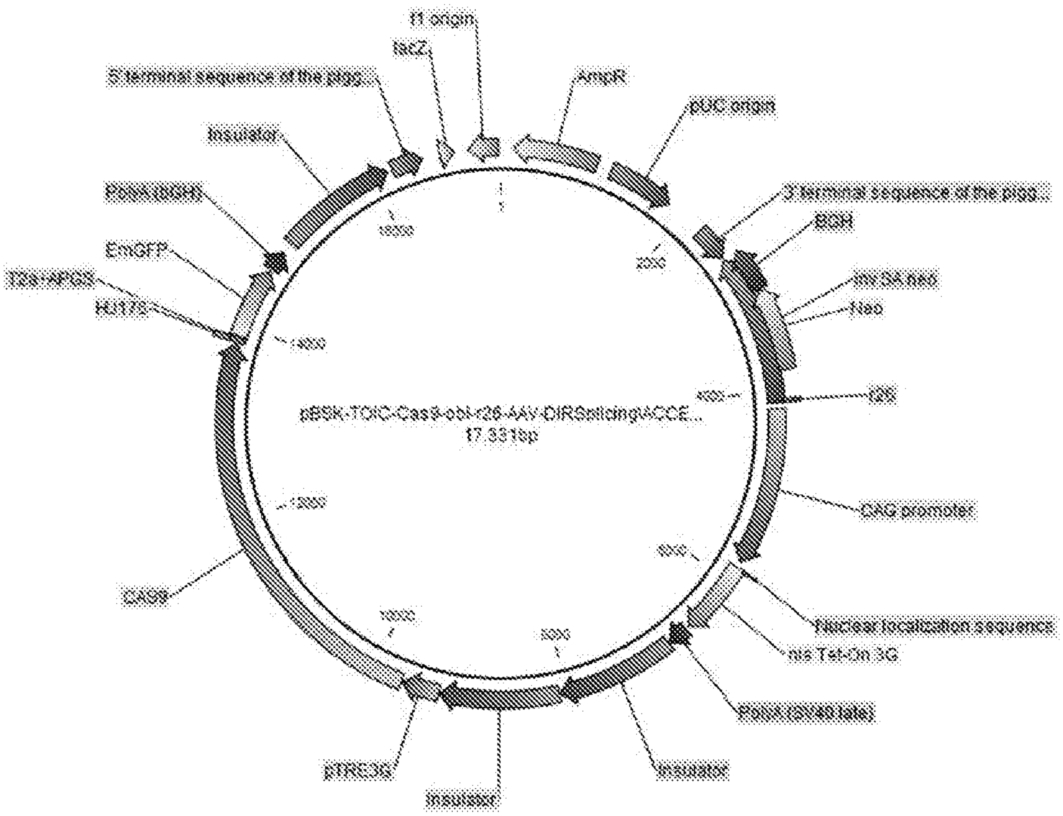
Figure 22:
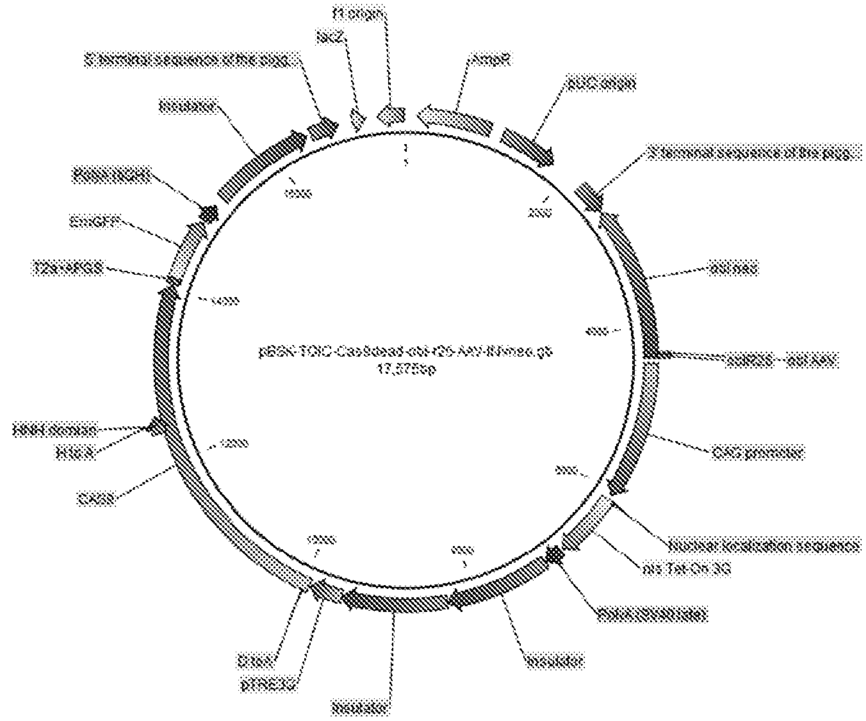
Figure 23:
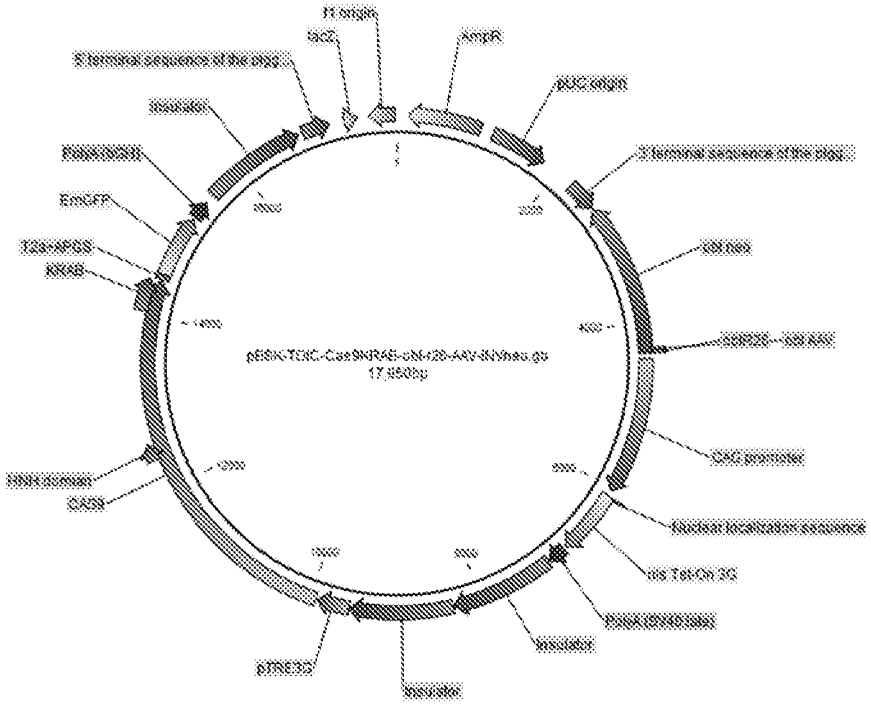
Figure 24:
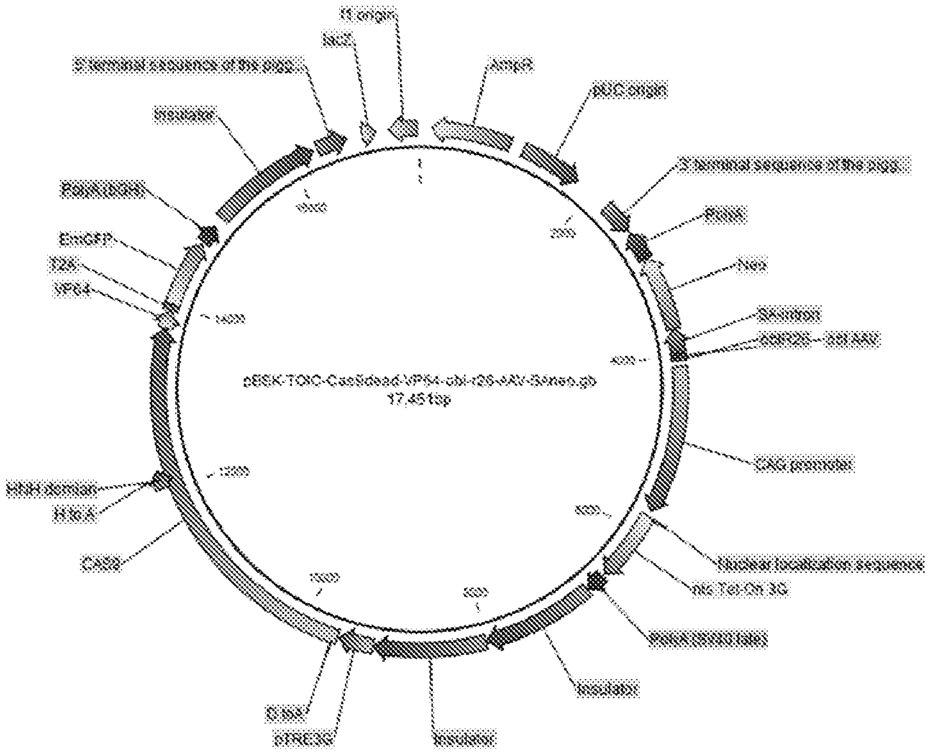
Figure 25:
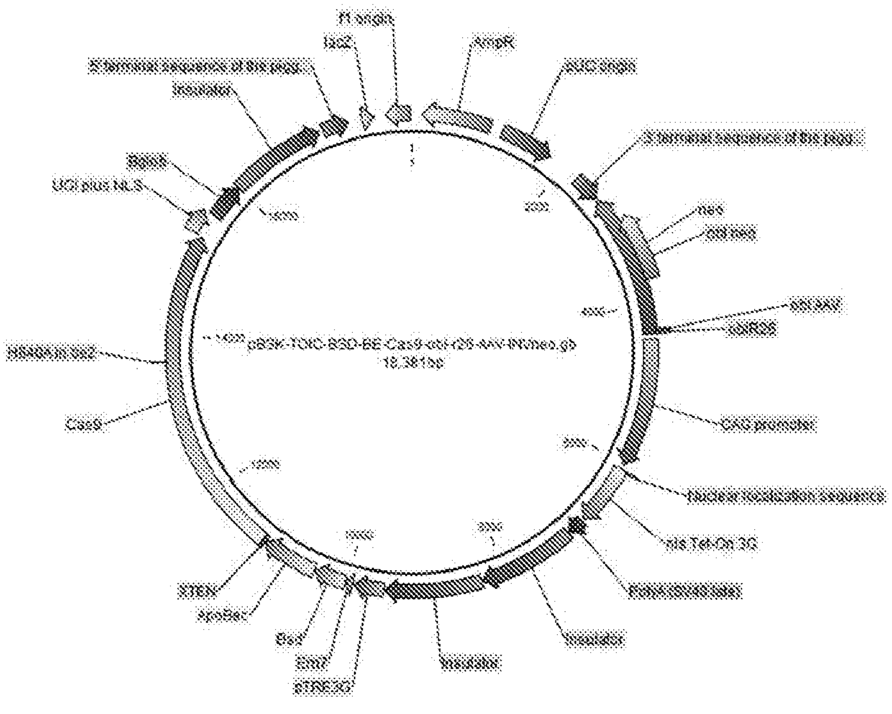
Figure 26:
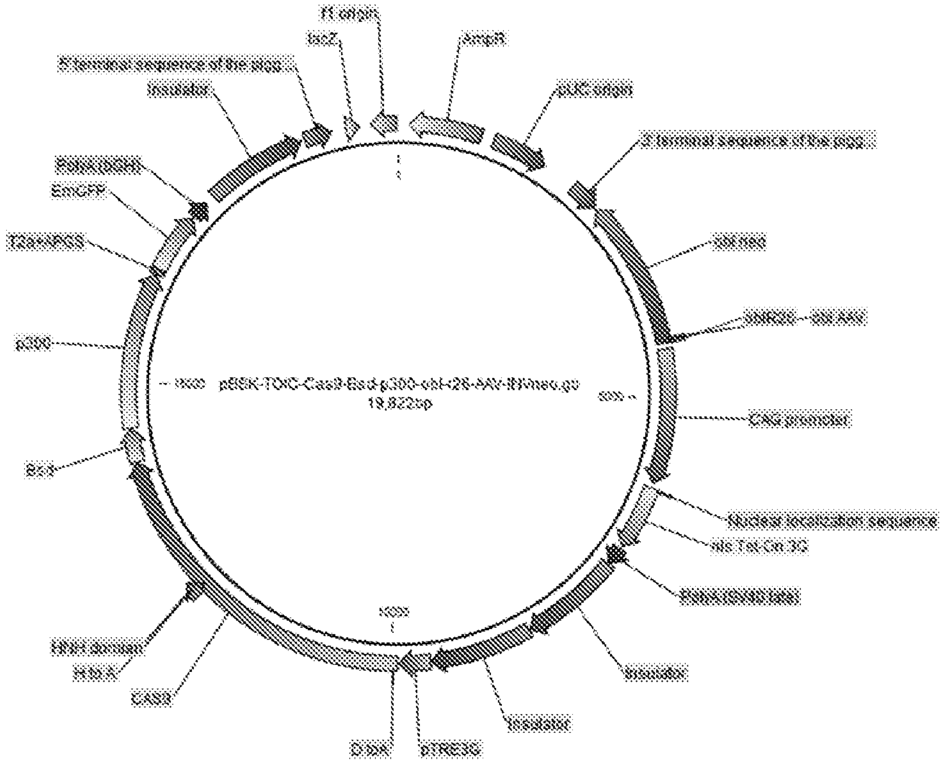
Figure 27:
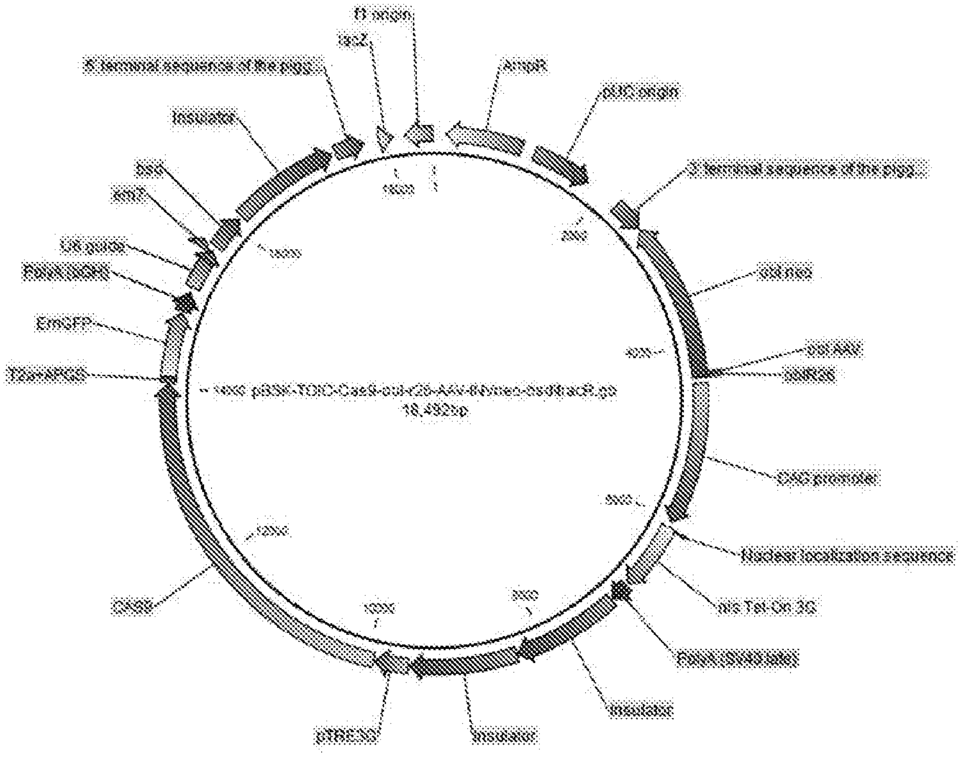
Figure 28:
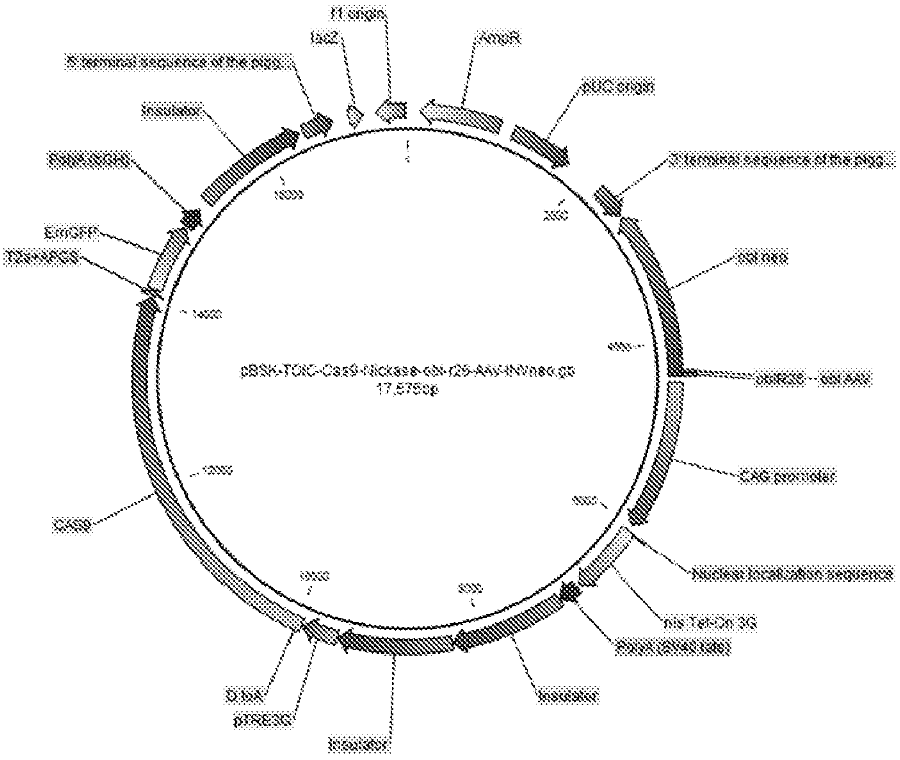

Next, TOICas mice were infected with AAV harboring the guide RNA targeting Trp53 gene (FIG. 12, bottom panel) via intratracheal injection. 24 hours before infection, Cas9 was activate by Dox in mice #37, #42 and #52, while mice #98 and #99 were left untreated (−Dox). Four weeks after infection, lungs were collected from all mice and genomic DNA was extracted to perform surveyor nuclease assay. The presence of precise mutation in Trp53 gene was then confirmed in the treated and infected mice as shown in FIG. 15.

Example 6: Tissue-Specific Knockout

Several strategies were developed for spatial and temporal regulation of CRISPR in the TOICas system of the present disclosure. One strategy is to drive the expression of the rtTA under a tissue-specific promoter. Aalpha myosin heavy chain (aMHC) was used to drive the expression of rtTA and consequently the regulation of Cas9; this strategy is generally applicable using any other tissue promoter and induces the expression of Cas9 only in a particular tissue.

An alternative strategy is to introduce the gRNA cassette in a tissue-specific transcript driven by a polII promoter (e.g., tissue specific). The gRNA is integrated in an intron and may have rybozyme or other RNA processing sequence to be subsequently cleaved by the original transcript.

Yet another strategy is based on the activation of gRNA upon induction of a tissue-specific recombinase or a tissue-specific orthogonal Cas9/CRISPR. In this case, the expression of the gRNA is prevented by the presence of a stop cassette present between the promoter and the functional part of the gRNA. The presence of orthogonal Cas9/CRISPR or a site-specific recombinase induces the removal of the stop cassette, therefore enabling the expression of the gRNA only in the tissue where the orthogonal Cas9/CRISPR or site specific recombinase are expressed.

The examples described above enable the spatial and temporal regulation of the Cas9/CRISPR system, therefore it is possible to generate tissue-specific Knock Out, Knock Down, and Base Editing in adult animals as well as in differentiated cells, starting from embryonic stem cells or induced pluripotent stem cells.

One of the application of the TOICas system is the inducible ablation of tissues or cells of interest to study the function of a cell/tissue or to mimic disease status. In this case, the temporal expression of Cas9 in TOICas system (regulated by Dox) is combined with a tissue-specific expression of a gRNA targeting multiple repeats in the target genome. Two non-limiting examples of repeats as target sites are the repeats B1 in the murine genome (CTCACTATGTAGACCAGGC (SEQ ID NO: 10)) and the repeats AluI in the human genome (CCTGTAATCCCAGCACTTTCACTTTGGGAGGCCGAGGCGAGTCTCGC TCTGTCGCCC (SEQ ID NO: 11)). The tissue-specific and temporal activation of the system promotes the cleavage in multiple sites and, therefore, the degradation of the target genome only in the tissue where the TOICas system is expressed and only upon Dox treatment.

Example 7: gRNA Cloning Methods

Three main strategies were developed to clone the gRNA for a particular gene in a cell or a plasmid expressing Cas9. T The first strategy was to use recombineering to insert a cassette containing a site-specific gRNA plus a bacterial selection marker and a polIII promoter driving the expression of the gRNA. The gRNA can be inserted in a high throughput way by selecting in bacteria for cells that received the gRNA and the selection marker.

The second strategy was to use Cas9 from *Neisseria Meningitis* to target the neo gene in cells containing the TOICas construct and introduce a gRNA plus a mammalian selection marker within the neo selection marker. This strategy is not restricted to the neo selection marker and to the Cas9NM since any other orthogonal Cas9 and insertion point can be used for gRNA integration.

The third strategy was to use Cas9 RiboNucleoProtein to deliver the gRNA by homologous recombination method or NHEJ based method in a precise locus. Alternative methods are insertions by lentivirus and transposons.

Example 8: Further Analysis of TOICas System

As shown in FIGS. 16-19, although there is the occasional cell expressing Cas9 in the absence of doxycycline, Cas9 induction is very clean. Maximal amount of Cas9 is expressed after just 24 hours of doxycycline exposure. Further, induction of Cas9 expression in A549 cells does not appear to effect: cell growth, incidence of DNA damage (as measured by gH2AX foci), or persistence of DNA damage (as measured by micronuclei formation). Generally, Cas9 expression does not appear to increase sensitivity to IR or increase DNA damage caused by IR.

SEQUENCES

Additional example of a mammalian insulator sequence for use in accordance with the present disclosure:

(SEQ ID NO: 6)
CTAGAGGGACAGCCCCCCCCCAAAGCCCCCAGGGATGTAATTACGTCCCTCCCCCGCTAGGGGCA
GCAGCGAGCCGCCCGGGGCTCCGCTCCGGTCCGGCGCTCCCCCCGCATCCCCGAGCCGGCAGCGT
GCGGGGACAGCCCGGGCACGGGGAAGGTGGCACGGGATCGCTTTCCTCTGAACGCTTCTCGCTGC
TCTTTGAGCCTGCAGACACCTGGGGGGATACGGGGAAAAAGCTTTAGGCTGAAAGAGAGATTTAG
AATGACAGAATCATAGAACGGCCTGGGTTGCAAAGGAGCACAGTGCTCATCCAGATCCAACCCCC
TGCTATGTGCAGGGTCATCAACCAGCAGCCCAGGCTGCCCAGAGCCACATCCAGCCTGGCCTTGA
ATGCCTGCAGGGATGGGGCATCCACAGCCTCCTTGGGCAACCTGTTCAGTGCGTCACCACCCTCTG
GGGGAAAAACTGCCTCCTCATATCCAACCCAAACCTCCCCTGTCTCAGTGTAAAGCCATTCCCCCT
TGTCCTATCAAGGGGGAGTTTGCTGTGACATTGTTGGTCTGGGGTGACACATGTTTGCCAATTCAG
TGCATCACGGAGAGGCAGATCTTGGGGATAAGGAAGTGCAGGACAGCATGGACGTGGGACATGC
AGGTGTTGAGGGCTCTGGGACACTCTCCAAGTCACAGCGTTCAGAACAGCCTTAAGGATAAGAAG
ATAGGATAGAAGGACAAAGAGCAAGTTAAAACCCAGCATGGAGAGGAGCACAAAAAGGCCACAG
ACACTGCTGGTCCCTGTGTCTGAGCCTGCATGTTTGATGGTGTCTGGATGCAAGCAGAAGGGGTGG
AAGAGCTTGCCTGGAGAGATACAGCTGGGTCAGTAGGACTGGGACAGGCAGCTGGAGAATTGCCA
TGTAGATGTTCATACAATCGTCAAATCATGAAGGCTGGAAAAGCCCTCCAAGATCCCCAAGACCA
ACCCCAACCCACCCACCGTGCCCACTGGCCATGTCCCTCAGTGCCACATCCCCACAGTTCTTCATC
ACCTCCAGGGACGGTGACCCCCCCACCTCCGTGGGCAGCTGTGCCACTGCAGCACCGCTCTTTGGA
GAAGGTAAATCTTGCTAAATCCAGCCCGACCCTCCCCTGGCACAACGTAAGGCCATTATCTCTCAT
CCAACTCCAGGACGGAGTCAGTGAGGATGGGGCT

Cas9 ERT2:

(SEQ ID NO: 7)
ATGGCTCTCGAGCCATCTGCTGGAGACATGAGAGCTGCCAACCTTTGGCCAAGCCCGCTCATGATC
AAACGCTCTAAGAAGAACAGCCTGGCCTTGTCCCTGACGGCCGACCAGATGGTCAGTGCCTTGTTG
GATGCTGAGCCCCCCATACTCTATTCCGAGTATGATCCTACCAGACCCTTCAGTGAAGCTTCGATG
ATGGGCTTACTGACCAACCTGGCAGACAGGGAGCTGGTTCACATGATCAACTGGGCGAAGAGGGT
GCCAGGCTTTGTGGATTTGACCCTCCATGATCAGGTCCACCTTCTGGAATGTGCCTGGCTAGAGAT
CCTGATGATTGGTCTCGTCTGGCGCTCTATGGAGCACCCAGTGAAGCTACTGTTTGCTCCTAACTTG
CTCTTGGACAGGAACCAGGGAAAATGTGTAGAGGGCATGGTGGAGATCTTCGACATGCTGCTGGC
TACATCATCTCGGTTCCGCATGATGAATCTGCAGGGAGAGGAGTTTGTGTGCCTCAAATCTATTAT
TTTGCTTAATTCTGGAGTGTACACATTTCTGTCCAGCACCCTGAAGTCTCTGGAAGAGAAGGACCA
TATCCACCGAGTCCTGGACAAGATCACAGACACTTTGATCCACCTGATGGCCAAGGCAGGCCTGA
CCCTGCAGCAGCAGCACCAGCGGCTGGCCCAGCTCCTCCTCATCCTCTCCCACATCAGGCACATGA
GTAACAAAGGCATGGAGCATCTGTACAGCATGAAGTGCAAGAACGTGGTGCCCCTCTATGACCTG
CTGCTGGAGGCGGCGGACGCCCACCGCCTACATGCGCCCACTAGCCGTGGAGGGGCATCCGTGGA
GGAGACGGACCAAAGCCACTTGGCCACTGCGGGCTCTACTTCATCGCATTCCTTGCAAAAGTATTA
CATCACGGGGGAGGCAGAGGGTTTCCCTGCCACAGCTGACAAGAAATACTCAATCGGGCTGGACA
TCGGAACTAACTCAGTGGGGTGGGCAGTCATTACTGACGAGTACAAAGTGCCAAGCAAGAAATTT
AAGGTCCTGGGCAACACCGATAGGCACTCCATCAAGAAAAATCTGATTGGGGCCCTGCTGTTCGA
CTCTGGAGAGACAGCTGAAGCAACTAGACTGAAAAGGACTGCTAGAAGGCGCTATACCCGGCGAA
AGAATCGCATCTGCTACCTGCAGGAGATTTTCTCTAACGAAATGGCCAAGGTGGACGATAGTTTCT
TTCATCGGCTGGAGGAATCATTCCTGGTCGAGGAAGATAAGAAACACGAGAGACATCCTATCTTT

-continued

GGAAACATTGTGGACGAGGTCGCTTATCACGAAAAATACCCCACCATCTATCATCTGCGCAAGAA

ACTGGTGGACTCTACAGATAAAGCAGACCTGCGGCTGATCTATCTGGCCCTGGCTCACATGATTAA

GTTCAGAGGCCATTTTCTGATCGAGGGAGATCTGAACCCAGACAATAGCGATGTGGACAAGCTGT

TCATCCAGCTGGTCCAGACATACAATCAGCTGTTTGAGGAAAACCCTATTAATGCATCTGGCGTGG

ACGCAAAAGCCATCCTGAGTGCCAGGCTGTCTAAGAGTAGAAGGCTGGAGAACCTGATCGCTCAG

CTGCCAGGCGAAAAGAAAAACGGCCTGTTTGGAAATCTGATTGCACTGTCACTGGGACTGACACC

TAACTTCAAGAGCAATTTTGATCTGGCCGAGGACGCTAAACTGCAGCTGAGCAAGGACACTTATG

ACGATGACCTGGATAACCTGCTGGCTCAGATCGGAGATCAGTACGCAGACCTGTTCCTGGCCGCTA

AGAATCTGTCTGACGCTATCCTGCTGAGTGATATTCTGCGGGTGAACACCGAGATTACAAAAGCCC

CTCTGTCAGCTAGCATGATCAAGAGATATGACGAGCACCATCAGGATCTGACCCTGCTGAAGGCA

CTGGTGCGCCAGCAGCTGCCCGAGAAGTACAAGGAAATCTTCTTTGATCAGAGTAAGAACGGGTA

CGCCGGTTATATTGACGGCGGAGCTTCACAGGAGGAATTCTACAAGTTTATCAAACCTATTCTGGA

GAAGATGGACGGCACCGAGGAACTGCTGGTGAAACTGAATCGCGAGGACCTGCTGCGCAAGCAG

CGGACATTTGATAACGGCTCCATCCCCCACCAGATTCATCTGGGAGAGCTGCACGCAATCCTGCGA

CGACAGGAAGACTTCTACCCATTTCTGAAGGATAACCGCGAGAAGATCGAAAAAATTCTGACCTT

CCGGATCCCTTACTATGTGGGGCCCCTGGCAAGGGGTAATTCCCGCTTTGCCTGGATGACACGGAA

ATCTGAGGAAACAATCACTCCTTGGAACTTCGAGGAAGTGGTCGATAAGGGAGCTTCCGCACAGT

CTTTCATCGAGAGAATGACAAACTTCGACAAAAACCTGCCAAATGAGAAAGTGCTGCCTAAGCAC

AGTCTGCTGTACGAGTATTTCACAGTCTATAACGAACTGACTAAGGTGAAATACGTCACCGAGGG

GATGAGGAAGCCCGCCTTCCTGAGCGGTGAACAGAAGAAAGCTATCGTGGACCTGCTGTTTAAAA

CCAATCGCAAGGTGACAGTCAAGCAGCTGAAGGAGGACTACTTCAAGAAAATTGAATGTTTCGAT

TCTGTGGAGATCAGTGGCGTCGAAGACAGATTTAACGCTTCTCTGGGAACCTACCACGATCTGCTG

AAGATCATTAAGGATAAAGACTTCCTGGACAACGAGGAAAATGAGGATATCCTGGAAGACATTGT

GCTGACCCTGACACTGTTTGAGGATCGCGAAATGATCGAGGAACGGCTGAAAACTTATGCCCATCT

GTTCGATGACAAGGTGATGAAACAGCTGAAGCGAAGAAGGTACACCGGCTGGGGACGACTGAGC

AGAAAGCTGATCAACGGCATTCGGGACAAACAGAGTGGAAAGACTATCCTGGACTTTCTGAAATC

AGATGGCTTCGCTAACAGAAATTTTATGCAGCTGATTCACGATGACAGCCTGACCTTCAAAGAGGA

TATCCAGAAGGCACAGGTGTCCGGGCAGGGTGACTCTCTGCACGAGCATATCGCAAACCTGGCCG

GGTCCCCCGCCATCAAGAAAGGTATTCTGCAGACCGTGAAGGTGGTCGATGAGCTGGTGAAAGTC

ATGGGCAGGCATAAGCCAGAAAACATCGTGATTGAGATGGCCCGCGAAAATCAGACCACACAGA

AAGGACAGAAGAACAGCCGCGAGCGGATGAAAAGGATCGAGGAAGGCATTAAGGAACTGGGATC

CCAGATCCTGAAAGAGCACCCTGTGGAAAACACTCAGCTGCAGAATGAGAAGCTGTATCTGTACT

ATCTGCAGAATGGGCGGGATATGTACGTGGACCAGGAGCTGGATATTAACCGACTGTCTGATTAC

GACGTGGATCATATCGTCCCACAGTCATTCCTGAAAGATGACAGCATTGACAATAAGGTGCTGACC

CGGAGTGACAAAAACCGAGGAAAGAGTGATAATGTCCCTTCAGAGGAAGTGGTCAAGAAAATGA

AGAACTACTGGAGACAGCTGCTGAATGCCAAACTGATCACACAGCGAAAGTTTGATAACCTGACT

AAAGCTGAGAGAGGGGGTCTGTCAGAACTGGACAAAGCAGGCTTCATCAAGCGACAGCTGGTGG

AGACCAGACAGATCACAAAGCACGTCGCTCAGATTCTGGATAGCAGGATGAACACAAAGTACGAT

GAGAATGACAAACTGATCCGCGAAGTGAAGGTCATTACTCTGAAGTCAAAACTTGTGAGCGACTT

CAGAAAGGATTTCCAGTTCTACAAAGTCAGGGAGATCAACAATTATCACCATGCTCATGACGCAT

ACCTGAACGCAGTGGTCGGGACCGCCCTGATTAAGAAATACCCCAAACTGGAGAGCGAATTCGTG

-continued

```
TACGGTGACTATAAGGTGTACGATGTCAGAAAAATGATCGCCAAGAGTGAGCAGGAAATTGGAAA

AGCCACCGCTAAGTATTTCTTTTACTCAAACATCATGAATTTCTTTAAGACTGAGATCACCCTGGCA

AATGGGGAAATCCGAAAGAGACCACTGATTGAGACTAACGGCGAGACCGGAGAAATCGTGTGGG

ACAAGGGTAGGGATTTTGCCACAGTGCGCAAGGTCCTGTCCATGCCTCAAGTGAATATTGTCAAGA

AAACAGAGGTGCAGACTGGCGGATTCAGTAAGGAATCAATTCTGCCCAAACGGAACTCTGATAAG

CTGATCGCCCGAAAGAAAGACTGGGATCCCAAGAAATATGGGGGTTTCGACTCCCCAACAGTGGC

TTACTCTGTCCTGGTGGTCGCAAAGGTGGAGAAGGGGAAAAGCAAGAAACTGAAATCCGTCAAGG

AGCTGCTGGGTATCACTATTATGGAGAGGAGCTCCTTCGAGAAGAACCCCATCGATTTTCTGGAGG

CTAAAGGCTATAAGGAAGTGAAGAAAGACCTGATCATTAAACTGCCAAAGTACAGCCTGTTTGAG

CTGGAAAACGGAAGGAAGCGAATGCTGGCATCCGCAGGAGAGCTGCAGAAGGGTAATGAACTGG

CCCTGCCTTCTAAGTACGTGAACTTCCTGTATCTGGCTAGCCACTACGAGAAGCTGAAAGGCTCCC

CCGAGGATAACGAACAGAAACAGCTGTTTGTGGAGCAGCACAAGCATTATCTGGACGAGATCATT

GAACAGATTAGCGAGTTCTCCAAAAGAGTGATCCTGGCTGACGCAAATCTGGATAAGGTCCTGAG

CGCATACAACAAACACAGAGATAAGCCAATCAGGGAGCAGGCCGAAAATATCATTCATCTGTTCA

CTCTGACCAACCTGGGAGCCCCTGCAGCCTTCAAGTATTTTGACACTACCATCGATCGGAAACGAT

ACACATCCACTAAGGAGGTGCTGGACGCTACCCTGATTCACCAGAGCATTACCGGCCTGTATGAA

ACAAGGATTGACCTGTCTCAGCTGGGGGGCGACCTCGAGCCATCTGCTGGAGACATGAGAGCTGC

CAACCTTTGGCCAAGCCCGCTCATGATCAAACGCTCTAAGAAGAACAGCCTGGCCTTGTCCCTGAC

GGCCGACCAGATGGTCAGTGCCTTGTTGGATGCTGAGCCCCCCATACTCTATTCCGAGTATGATCC

TACCAGACCCTTCAGTGAAGCTTCGATGATGGGCTTACTGACCAACCTGGCAGACAGGGAGCTGG

TTCACATGATCAACTGGGCGAAGAGGGTGCCAGGCTTTGTGGATTTGACCCTCCATGATCAGGTCC

ACCTTCTGGAATGTGCCTGGCTAGAGATCCTGATGATTGGTCTCGTCTGGCGCTCTATGGAGCACC

CAGTGAAGCTACTGTTTGCTCCTAACTTGCTCTTGGACAGGAACCAGGGAAAATGTGTAGAGGGC

ATGGTGGAGATCTTCGACATGCTGCTGGCTACATCATCTCGGTTCCGCATGATGAATCTGCAGGGA

GAGGAGTTTGTGTGCCTCAAATCTATTATTTTGCTTAATTCTGGAGTGTACACATTTCTGTCCAGCA

CCCTGAAGTCTCTGGAAGAGAAGGACCATATCCACCGAGTCCTGGACAAGATCACAGACACTTTG

ATCCACCTGATGGCCAAGGCAGGCCTGACCCTGCAGCAGCAGCACCAGCGGCTGGCCCAGCTCCT

CCTCATCCTCTCCCACATCAGGCACATGAGTAACAAAGGCATGGAGCATCTGTACAGCATGAAGT

GCAAGAACGTGGTGCCCCTCTATGACCTGCTGCTGGAGGCGGCGGACGCCCACCGCCTACATGCG

CCCACTAGCCGTGGAGGGGCATCCGTGGAGGAGACGGACCAAAGCCACTTGGCCACTGCGGGCTC

TACTTCATCGCATTCCTTGCAAAAGTATTACATCACGGGGGAGGCAGAGGGTTTCCCTGCCACAGC

TTGA
```

Sequence of TOIC construct depicted in FIG. 2

(SEQ ID NO: 8)

```
GTGGCACTTTTCGGGGAAATGTGCGCGGAACCCCTATTTGTTTATTTTTCTAAATACATTCAAATAT

GTATCCGCTCATGAGACAATAACCCTGATAAATGCTTCAATAATATTGAAAAAGGAAGAGTATGA

GTATTCAACATTTCCGTGTCGCCCTTATTCCCTTTTTTGCGGCATTTTGCCTTCCTGTTTTTGCTCAC

CCAGAAACGCTGGTGAAAGTAAAAGATGCTGAAGATCAGTTGGGTGCACGAGTGGGTTACATCGA

ACTGGATCTCAACAGCGGTAAGATCCTTGAGAGTTTTCGCCCCGAAGAACGTTTTCCAATGATGAG

CACTTTTAAAGTTCTGCTATGTGGCGCGGTATTATCCCGTATTGACGCCGGGCAAGAGCAACTCGG

TCGCCGCATACACTATTCTCAGAATGACTTGGTTGAGTACTCACCAGTCACAGAAAAGCATCTTAC

GGATGGCATGACAGTAAGAGAATTATGCAGTGCTGCCATAACCATGAGTGATAACACTGCGGCCA
```

-continued

ACTTACTTCTGACAACGATCGGAGGACCGAAGGAGCTAACCGCTTTTTTGCACAACATGGGGGATC

ATGTAACTCGCCTTGATCGTTGGGAACCGGAGCTGAATGAAGCCATACCAAACGACGAGCGTGAC

ACCACGATGCCTGTAGCAATGGCAACAACGTTGCGCAAACTATTAACTGGCGAACTACTTACTCTA

GCTTCCCGGCAACAATTAATAGACTGGATGGAGGCGGATAAAGTTGCAGGACCACTTCTGCGCTC

GGCCCTTCCGGCTGGCTGGTTTATTGCTGATAAATCTGGAGCCGGTGAGCGTGGGTCTCGCGGTAT

CATTGCAGCACTGGGGCCAGATGGTAAGCCCTCCCGTATCGTAGTTATCTACACGACGGGGAGTCA

GGCAACTATGGATGAACGAAATAGACAGATCGCTGAGATAGGTGCCTCACTGATTAAGCATTGGT

AACTGTCAGACCAAGTTTACTCATATATACTTTAGATTGATTTAAAACTTCATTTTTAATTTAAAAG

GATCTAGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGTAATC

TGCTGCTTGCAAACAAAAAAACCACCGCTACCAGCGGTGGTTTGTTTGCCGGATCAAGAGCTACCA

ACTCTTTTTCCGAAGGTAACTGGCTTCAGCAGAGCGCAGATACCAAATACTGTTCTTCTAGTGTAG

CCGTAGTTAGGCCACCACTTCAAGAACTCTGTAGCACCGCCTACATACCTCGCTCTGCTAATCCTG

TTACCAGTGGCTGCTGCCAGTGGCGATAAGTCGTGTCTTACCGGGTTGGACTCAAGACGATAGTTA

CCGGATAAGGCGCAGCGGTCGGGCTGAACGGGGGGTTCGTGCACACAGCCCAGCTTGGAGCGAAC

GACCTACACCGAACTGAGATACCTACAGCGTGAGCTATGAGAAAGCGCCACGCTTCCCGAAGGGA

GAAAGGCGGACAGGTATCCGGTAAGCGGCAGGGTCGGAACAGGAGAGCGCACGAGGGAGCTTCC

AGGGGGAAACGCCTGGTATCTTTATAGTCCTGTCGGGTTTCGCCACCTCTGACTTGAGCGTCGATT

TTTGTGATGCTCGTCAGGGGGGCGGAGCCTATGGAAAAACGCCAGCAACGCGGCCTTTTTACGGTT

CCTGGCCTTTTGCTGGCCTTTTGCTCACATGTTCTTTCCTGCGTTATCCCCTGATTCTGTGGATAACC

GTATTACCGCCTTTGAGTGAGCTGATACCGCTCGCCGCAGCCGAACGACCGAGCGCAGCGAGTCA

GTGAGCGAGGAAGCGGAAGAGCGCCCAATACGCAAACCGCCTCTCCCCGCGCGTTGGCCGATTCA

TTAATGCAGCTGGCACGACAGGTTTCCCGACTGGAAAGCGGGCAGTGAGCGCAACGCAATTAATG

TGAGTTAGCTCACTCATTAGGCACCCCAGGCTTTACACTTTATGCTTCCGGCTCGTATGTTGTGTGG

AATTGTGAGCGGATAACAATTTCACACAGGAAACAGCTATGACCATGATTACGCCAAGCGCGCAA

TTAACCCTCACTAAAGGGAACCTCCCCTAGCTTAATTAACCCTAGAAAGATAATCATATTGTGACG

TACGTTAAAGATAATCATGCGTAAAATTGACGCATGTGTTTTATCGATCTGTATATCGAGGTTTATT

TATTAATTTGAATAGATATTAAGTTTTATTATATTTACACTTACATACTAATAATAAATTCAACAAA

CAATTTATTTATGTTTATTTATTTATTAAAAAAAAACAAAAACTCAAAATTTCTTCTATAAAGTAAC

AAAACTTTTAAACATTCTCTCTTTTACAAAAATAAACTTATTTTGTACTTTAAAAACAGTCATGTTG

TATTATAAAATAAGTAATTAGCTTAACTTATACATAATAGAAACAAATTATACTTATTAATCGCAT

TGATTATTGACTAGTCGTATTAAGGGTTCCGGATCAGCTTGATTCGAGCCCCAGCTGGTTCTTTCCG

CCTCAGAAGCCATAGAGCCCACCGCATCCCCAGCATGCCTGCTATTGTCTTCCCAATCCTCCCCCTT

GCTGTCCTGCCCCACCCCACCCCCCAGAATAGAATGACACCTACTCAGACAATGCGATGCAATTTC

CTCATTTTATTAGGAAAGGACAGTGGGAGTGGCACCTTCCAGGGTCAAGGAAGGCACGGGGGAGG

GGCAAACAACAGATGGCTGGCAACTAGAAGGCACAGTCGAGGCTGATCAGCGAGCTCTAGAGAA

TTGATCCCCTCAGAAGAACTCGTCAAGAAGGCGATAGAAGGCGATGCGCTGCGAATCGGGAGCGG

CGATACCGTAAAGCACGAGGAAGCGGTCAGCCCATTCGCCGCCAAGCTCTTCAGCAATATCACGG

GTAGCCAACGCTATGTCCTGATAGCGGTCCGCCACACCCAGCCGGCCACAGTCGATGAATCCAGA

AAAGCGGCCATTTTCCACCATGATATTCGGCAAGCAGGCATCGCCATGGGTCACGACGAGATCCTC

GCCGTCGGGCATGCGCGCCTTGAGCCTGGCGAACAGTTCGGCTGGCGCGAGCCCCTGATGCTCTTC

-continued

GTCCAGATCATCCTGATCGACAAGACCGGCTTCCATCCGAGTACGTGCTCGCTCGATGCGATGTTT

CGCTTGGTGGTCGAATGGGCAGGTAGCCGGATCAAGCGTATGCAGCCGCCGCATTGCATCAGCCA

TGATGGATACTTTCTCGGCAGGAGCAAGGTGAGATGACAGGAGATCCTGCCCCGGCACTTCGCCC

AATAGCAGCCAGTCCCTTCCCGCTTCAGTGACAACGTCGAGCACAGCTGCGCAAGGAACGCCCGT

CGTGGCCAGCCACGATAGCCGCGCTGCCTCGTCCTGCAGTTCATTCAGGGCACCGGACAGGTCGGT

CTTGACAAAAAGAACCGGGCGCCCCTGCGCTGACAGCCGGAACACGGCGGCATCAGAGCAGCCG

ATTGTCTGTTGTGCCCAGTCATAGCCGAATAGCCTCTCCACCCAAGCGGCCGGAGAACCTGCGTGC

AATCCATCTTGTTCAATGGCCGATCCCATGGTTTAGTTCCTCACCTTGTCGTATTATACTATGCCGA

TATACTATGCCGATGATTAATTGTCAACACGTGCTGCTGCAGGTCGAAAGGCCCGGAGATGAGGA

AGAGGAGAACAGCGCGGCAGACGTGCGCTTTTGAAGCGTGCAGAATGCCGGGCCTCCGGAGGACC

TTCGGGCGCCCGCCCCGCCCCTGAGCCCGCCCCTGAGCCCGCCCCCGGACCCACCCCTTCCCAGCC

TCTGAGCCCAGAAAGCGAAGGAGCAAAGCTGCTATTGGCCGCTGCCCCAAAGGCCTACCCGCTTC

CATTGCTCAGCGGTGCTGTCCATCTGCACGAGACTAGTGAGACGTGCTACTTCCATTTGTCACGTC

CTGCACGACGCGAGCTGCGGGGCGGGGGGAACTTCCTGACTAGGGGAGGAGTAGAAGGTGGCG

CGAAGGGGCCACCAAAGAACGGAGCCGGTTGGCGCCTACCGGTGGATGTGGAATGTGTGCGAGCC

AGAGGCCACTTGTGTAGCGCCAAGTGCCCAGCGGGGCTGCTAAAGCGCATGCTCCAGACTGCCTT

GGGAAAAGCGCCTCCCCTACCCGGTAGACACCCCACAGTGGGTGGCCTAGGGACAGGATTGCAAC

TCCAGTCTTTCTTCTTCTTGGGCGGGAGTCACTAGTTATTAATAGTAATCAATTACGGGGTCATTAG

TTCATAGCCCATATATGGAGTTCCGCGTTACATAACTTACGGTAAATGGCCCGCCTGGCTGACCGC

CCAACGACCCCCGCCCATTGACGTCAATAATGACGTATGTTCCCATAGTAACGCCAATAGGGACTT

TCCATTGACGTCAATGGGTGGACTATTTACGGTAAACTGCCCACTTGGCAGTACATCAAGTGTATC

ATATGCCAAGTACGCCCCCTATTGACGTCAATGACGGTAAATGGCCCGCCTGGCATTATGCCCAGT

ACATGACCTTATGGGACTTTCCTACTTGGCAGTACATCTACGTATTAGTCATCGCTATTACCATGGG

TCGAGGTGAGCCCCACGTTCTGCTTCACTCTCCCCATCTCCCCCCCCTCCCCACCCCCAATTTTGTA

TTTATTTATTTTTTAATTATTTTGTGCAGCGATGGGGGCGGGGGGGGGGGGGGCGCGCGCCAGGCG

GGGCGGGGCGGGGCGAGGGGCGGGGCGGGGCGAGGCGGAGAGGTGCGGCGGCAGCCAATCAGA

GCGGCGCGCTCCGAAAGTTTCCTTTTATGGCGAGGCGGCGGCGGCGGCGGCCCTATAAAAAGCGA

AGCGCGCGGCGGGCGGGAGTCGCTGCGTTGCCTTCGCCCCGTGCCCCGCTCCGCGCCGCCTCGCGC

CGCCCGCCCCGGCTCTGACTGACCGCGTTACTCCCACAGGTGAGCGGGCGGGACGGCCCTTCTCCT

CCGGGCTGTAATTAGCGCTTGGTTTAATGACGGCTCGTTTCTTTTCTGTGGCTGCGTGAAAGCCTTA

AAGGGCTCCGGGAGGGCCCTTTGTGCGGGGGGGAGCGGCTCGGGGGGTGCGTGCGTGTGTGTGTG

CGTGGGGAGCGCCGCGTGCGGCCCGCGCTGCCCGGCGGCTGTGAGCGCTGCGGGCGCGGCGCGGG

GCTTTGTGCGCTCCGCGTGTGCGCGAGGGGAGCGCGGCCGGGGGCGGTGCCCCGCGGTGCGGGGG

GGCTGCGAGGGGAACAAAGGCTGCGTGCGGGGTGTGTGCGTGGGGGGGTGAGCAGGGGGTGTGG

GCGCGGCGGTCGGGCTGTAACCCCCCCCTGCACCCCCCTCCCCGAGTTGCTGAGCACGGCCCGGCT

TCGGGTGCGGGGCTCCGTGCGGGGCGTGGCGCGGGGCTCGCCGTGCCGGGCGGGGGGTGGCGGCA

GGTGGGGGTGCCGGGCGGGGCGGGGCCGCCTCGGGCCGGGGAGGGCTCGGGGGAGGGGCGCGGC

GGCCCCGGAGCGCCGGCGGCTGTCGAGGCGCGGCGAGCCGCAGCCATTGCCTTTTATGGTAATCG

TGCGAGAGGGCGCAGGGACTTCCTTTGTCCCAAATCTGGCGGAGCCGAAATCTGGGAGGCGCCGC

CGCACCCCCTCTAGCGGGCGCGGGCGAAGCGGTGCGGCGCCGGCAGGAAGGAAATGGGCGGGGA

GGGCCTTCGTGCGTCGCCGCGCCGCCGTCCCCTTCTCCATCTCCAGCCTCGGGGCTGCCGCAGGGG

-continued

GACGGCTGCCTTCGGGGGGGACGGGGCAGGGCGGGGTTCGGCTTCTGGCGTGTGACCGGCGGCTC

TAGAGCCTCTGCTAACCATGTTCATGCCTTCTTCTTTTTCCTACAGCTCCTGGGCAACGTGCTGGTT

ATTGTGCTGTCTCATCATTTTGGCAAAGAATTCGCCACCATGGTGCCCAAGAAGAAGAGGAAAGTC

TCTAGACTGGACAAGAGCAAAGTCATAAACTCTGCTCTGGAATTACTCAATGGAGTCGGTATCGA

AGGCCTGACGACAAGGAAACTCGCTCAAAAGCTGGGAGTTGAGCAGCCTACCCTGTACTGGCACG

TGAAGAACAAGCGGGCCCTGCTCGATGCCCTGCCAATCGAGATGCTGGACAGGCATCATACCCAC

TCCTGCCCCCTGGAAGGCGAGTCATGGCAAGACTTTCTGCGGAACAACGCCAAGTCATACCGCTGT

GCTCTCCTCTCACATCGCGACGGGGCTAAAGTGCATCTCGGCACCCGCCCAACAGAGAAACAGTA

CGAAACCCTGGAAAATCAGCTCGCGTTCCTGTGTCAGCAAGGCTTCTCCCTGGAGAACGCACTGTA

CGCTCTGTCCGCCGTGGGCCACTTTACACTGGGCTGCGTATTGGAGGAACAGGAGCATCAAGTAGC

AAAAGAGGAAAGAGAGACACCTACCACCGATTCTATGCCCCCACTTCTGAAACAAGCAATTGAGC

TGTTCGACCGGCAGGGAGCCGAACCTGCCTTCCTTTTCGGCCTGGAACTAATCATATGTGGCCTGG

AGAAACAGCTAAAGTGCGAAAGCGGCGGGCCGACCGACGCCCTTGACGATTTTGACTTAGACATG

CTCCCAGCCGATGCCCTTGACGACTTTGACCTTGATATGCTGCCTGCTGACGCTCTTGACGATTTTG

ACCTTGACATGCTCCCCGGGTAAAGCGGCCGCGACTCTAGATCATAATCAGCCATACCACATTTGT

AGAGGTTTTACTTGCTTTAAAAAACCTCCCACACCTCCCCCTGAACCTGAAACATAAAATGAATGC

AATTGTTGTTGTTAACTTGTTTATTGCAGCTTATAATGGTTACAAATAAAGCAATAGCATCACAAA

TTTCACAAATAAAGCATTTTTTTCACTGCATTCTAGTTGTGGTTTGTCCAAACTCATCAATGTATCT

TAAGGGATCCCTAGAGGGACAGCCCCCCCCCAAAGCCCCCAGGGATGTAATTACGTCCCTCCCCC

GCTAGGGGCAGCAGCGAGCCGCCCGGGGCTCCGCTCCGGTCCGGCGCTCCCCCCGCATCCCCGAG

CCGGCAGCGTGCGGGGACAGCCCGGGCACGGGGAAGGTGGCACGGGATCGCTTTCCTCTGAACGC

TTCTCGCTGCTCTTTGAGCCTGCAGACACCTGGGGGGATACGGGGAAAAAGCTTTAGGCTGAAAG

AGAGATTTAGAATGACAGAATCATAGAACGGCCTGGGTTGCAAAGGAGCACAGTGCTCATCCAGA

TCCAACCCCCTGCTATGTGCAGGGTCATCAACCAGCAGCCCAGGCTGCCCAGAGCCACATCCAGCC

TGGCCTTGAATGCCTGCAGGGATGGGGCATCCACAGCCTCCTTGGGCAACCTGTTCAGTGCGTCAC

CACCCTCTGGGGGAAAAACTGCCTCCTCATATCCAACCCAAACCTCCCCTGTCTCAGTGTAAAGCC

ATTCCCCCTTGTCCTATCAAGGGGGAGTTTGCTGTGACATTGTTGGTCTGGGGTGACACATGTTTGC

CAATTCAGTGCATCACGGAGAGGCAGATCTTGGGGATAAGGAAGTGCAGGACAGCATGGACGTGG

GACATGCAGGTGTTGAGGGCTCTGGGACACTCTCCAAGTCACAGCGTTCAGAACAGCCTTAAGGA

TAAGAAGATAGGATAGAAGGACAAAGAGCAAGTTAAAACCCAGCATGGAGAGGAGCACAAAAAG

GCCACAGACACTGCTGGTCCCTGTGTCTGAGCCTGCATGTTTGATGGTGTCTGGATGCAAGCAGAA

GGGGTGGAAGAGCTTGCCTGGAGAGATACAGCTGGGTCAGTAGGACTGGGACAGGCAGCTGGAG

AATTGCCATGTAGATGTTCATACAATCGTCAAATCATGAAGGCTGGAAAAGCCCTCCAAGATCCCC

AAGACCAACCCCAACCCACCCACCGTGCCCACTGGCCATGTCCCTCAGTGCCACATCCCCACAGTT

CTTCATCACCTCCAGGGACGGTGACCCCCCCACCTCCGTGGGCAGCTGTGCCACTGCAGCACCGCT

CTTTGGAGAAGGTAAATCTTGCTAAATCCAGCCCGACCCTCCCCTGGCACAACGTAAGGCCATTAT

CTCTCATCCAACTCCAGGACGGAGTCAGTGAGGATGGGGCTGTCGACCTAGAGGGACAGCCCCCC

CCCAAAGCCCCCAGGGATGTAATTACGTCCCTCCCCCGCTAGGGGCAGCAGCGAGCCGCCCGGGG

CTCCGCTCCGGTCCGGCGCTCCCCCCGCATCCCCGAGCCGGCAGCGTGCGGGGACAGCCCGGGCA

CGGGGAAGGTGGCACGGGATCGCTTTCCTCTGAACGCTTCTCGCTGCTCTTTGAGCCTGCAGACAC

CTGGGGGGATACGGGGAAAAAGCTTTAGGCTGAAAGAGAGATTTAGAATGACAGAATCATAGAA

-continued

CGGCCTGGGTTGCAAAGGAGCACAGTGCTCATCCAGATCCAACCCCCTGCTATGTGCAGGGTCATC

AACCAGCAGCCCAGGCTGCCCAGAGCCACATCCAGCCTGGCCTTGAATGCCTGCAGGGATGGGGC

ATCCACAGCCTCCTTGGGCAACCTGTTCAGTGCGTCACCACCCTCTGGGGGAAAAACTGCCTCCTC

ATATCCAACCCAAACCTCCCCTGTCTCAGTGTAAAGCCATTCCCCCTTGTCCTATCAAGGGGGAGT

TTGCTGTGACATTGTTGGTCTGGGGTGACACATGTTTGCCAATTCAGTGCATCACGGAGAGGCAGA

TCTTGGGGATAAGGAAGTGCAGGACAGCATGGACGTGGGACATGCAGGTGTTGAGGGCTCTGGGA

CACTCTCCAAGTCACAGCGTTCAGAACAGCCTTAAGGATAAGAAGATAGGATAGAAGGACAAAGA

GCAAGTTAAAACCCAGCATGGAGAGGAGCACAAAAAGGCCACAGACACTGCTGGTCCCTGTGTCT

GAGCCTGCATGTTTGATGGTGTCTGGATGCAAGCAGAAGGGGTGGAAGAGCTTGCCTGGAGAGAT

ACAGCTGGGTCAGTAGGACTGGGACAGGCAGCTGGAGAATTGCCATGTAGATGTTCATACAATCG

TCAAATCATGAAGGCTGGAAAAGCCCTCCAAGATCCCCAAGACCAACCCCAACCCACCCACCGTG

CCCACTGGCCATGTCCCTCAGTGCCACATCCCCACAGTTCTTCATCACCTCCAGGGACGGTGACCC

CCCCACCTCCGTGGGCAGCTGTGCCACTGCAGCACCGCTCTTTGGAGAAGGTAAATCTTGCTAAAT

CCAGCCCGACCCTCCCCTGGCACAACGTAAGGCCATTATCTCTCATCCAACTCCAGGACGGAGTCA

GTGAGGATGGGGCTCAATTGTTTACTCCCTATCAGTGATAGAGAACGTATGAAGAGTTTACTCCCT

ATCAGTGATAGAGAACGTATGCAGACTTTACTCCCTATCAGTGATAGAGAACGTATAAGGAGTTTA

CTCCCTATCAGTGATAGAGAACGTATGACCAGTTTACTCCCTATCAGTGATAGAGAACGTATCTAC

AGTTTACTCCCTATCAGTGATAGAGAACGTATATCCAGTTTACTCCCTATCAGTGATAGAGAACGT

ATAAGCTTTAGGCGTGTACGGTGGGCGCCTATAAAAGCAGAGCTCGTTTAGTGAACCGTCAGATC

GCCTGGAGCAATTCCACAACACTTTTGTCTTATACCAACTTTCCGTACCACTTCCTACCCTCGTAAA

AAGCTTGTCCACCATGGCTCCTAAGAAAAAGCGGAAGGTGGACAAGAAATACTCAATCGGGCTGG

ACATCGGAACTAACTCAGTGGGGTGGGCAGTCATTACTGACGAGTACAAAGTGCCAAGCAAGAAA

TTTAAGGTCCTGGGCAACACCGATAGGCACTCCATCAAGAAAAATCTGATTGGGGCCCTGCTGTTC

GACTCTGGAGAGACAGCTGAAGCAACTAGACTGAAAAGGACTGCTAGAAGGCGCTATACCCGGCG

AAAGAATCGCATCTGCTACCTGCAGGAGATTTTCTCTAACGAAATGGCCAAGGTGGACGATAGTTT

CTTTCATCGGCTGGAGGAATCATTCCTGGTCGAGGAAGATAAGAAACACGAGAGACATCCTATCTT

TGGAAACATTGTGGACGAGGTCGCTTATCACGAAAAATACCCCACCATCTATCATCTGCGCAAGA

AACTGGTGGACTCTACAGATAAAGCAGACCTGCGGCTGATCTATCTGGCCCTGGCTCACATGATTA

AGTTCAGAGGCCATTTTCTGATCGAGGGAGATCTGAACCCAGACAATAGCGATGTGGACAAGCTG

TTCATCCAGCTGGTCCAGACATACAATCAGCTGTTTGAGGAAAACCCTATTAATGCATCTGGCGTG

GACGCAAAAGCCATCCTGAGTGCCAGGCTGTCTAAGAGTAGAAGGCTGGAGAACCTGATCGCTCA

GCTGCCAGGCGAAAAGAAAAACGGCCTGTTTGGAAATCTGATTGCACTGTCACTGGGACTGACAC

CTAACTTCAAGAGCAATTTTGATCTGGCCGAGGACGCTAAACTGCAGCTGAGCAAGGACACTTAT

GACGATGACCTGGATAACCTGCTGGCTCAGATCGGAGATCAGTACGCAGACCTGTTCCTGGCCGCT

AAGAATCTGTCTGACGCTATCCTGCTGAGTGATATTCTGCGGGTGAACACCGAGATTACAAAAGCC

CCTCTGTCAGCTAGCATGATCAAGAGATATGACGAGCACCATCAGGATCTGACCCTGCTGAAGGC

ACTGGTGCGCCAGCAGCTGCCCGAGAAGTACAAGGAAATCTTCTTTGATCAGAGTAAGAACGGGT

ACGCCGGTTATATTGACGGCGGAGCTTCACAGGAGGAATTCTACAAGTTTATCAAACCTATTCTGG

AGAAGATGGACGGCACCGAGGAACTGCTGGTGAAACTGAATCGCGAGGACCTGCTGCGCAAGCA

GCGGACATTTGATAACGGCTCCATCCCCCACCAGATTCATCTGGGAGAGCTGCACGCAATCCTGCG

ACGACAGGAAGACTTCTACCCATTTCTGAAGGATAACCGCGAGAAGATCGAAAAAATTCTGACCT

-continuede

TCCGGATCCCTTACTATGTGGGGCCCCTGGCAAGGGGTAATTCCCGCTTTGCCTGGATGACACGGA

AATCTGAGGAAACAATCACTCCTTGGAACTTCGAGGAAGTGGTCGATAAGGGAGCTTCCGCACAG

TCTTTCATCGAGAGAATGACAAACTTCGACAAAAACCTGCCAAATGAGAAAGTGCTGCCTAAGCA

CAGTCTGCTGTACGAGTATTTCACAGTCTATAACGAACTGACTAAGGTGAAATACGTCACCGAGGG

GATGAGGAAGCCCGCCTTCCTGAGCGGTGAACAGAAGAAAGCTATCGTGGACCTGCTGTTTAAAA

CCAATCGCAAGGTGACAGTCAAGCAGCTGAAGGAGGACTACTTCAAGAAAATTGAATGTTTCGAT

TCTGTGGAGATCAGTGGCGTCGAAGACAGATTTAACGCTTCTCTGGGAACCTACCACGATCTGCTG

AAGATCATTAAGGATAAAGACTTCCTGGACAACGAGGAAAATGAGGATATCCTGGAAGACATTGT

GCTGACCCTGACACTGTTTGAGGATCGCGAAATGATCGAGGAACGGCTGAAAACTTATGCCCATCT

GTTCGATGACAAGGTGATGAAACAGCTGAAGCGAAGAAGGTACACCGGCTGGGGACGACTGAGC

AGAAAGCTGATCAACGGCATTCGGGACAAACAGAGTGGAAAGACTATCCTGGACTTTCTGAAATC

AGATGGCTTCGCTAACAGAAATTTTATGCAGCTGATTCACGATGACAGCCTGACCTTCAAAGAGGA

TATCCAGAAGGCACAGGTGTCCGGGCAGGGTGACTCTCTGCACGAGCATATCGCAAACCTGGCCG

GGTCCCCCGCCATCAAGAAAGGTATTCTGCAGACCGTGAAGGTGGTCGATGAGCTGGTGAAAGTC

ATGGGCAGGCATAAGCCAGAAAACATCGTGATTGAGATGGCCCGCGAAAATCAGACCACACAGA

AAGGACAGAAGAACAGCCGCGAGCGGATGAAAAGGATCGAGGAAGGCATTAAGGAACTGGGATC

CCAGATCCTGAAAGAGCACCCTGTGGAAAACACTCAGCTGCAGAATGAGAAGCTGTATCTGTACT

ATCTGCAGAATGGGCGGGATATGTACGTGGACCAGGAGCTGGATATTAACCGACTGTCTGATTAC

GACGTGGATCATATCGTCCCACAGTCATTCCTGAAAGATGACAGCATTGACAATAAGGTGCTGACC

CGGAGTGACAAAAACCGAGGAAAGAGTGATAATGTCCCTTCAGAGGAAGTGGTCAAGAAAATGA

AGAACTACTGGAGACAGCTGCTGAATGCCAAACTGATCACACAGCGAAAGTTTGATAACCTGACT

AAAGCTGAGAGAGGGGGTCTGTCAGAACTGGACAAAGCAGGCTTCATCAAGCGACAGCTGGTGG

AGACCAGACAGATCACAAAGCACGTCGCTCAGATTCTGGATAGCAGGATGAACACAAAGTACGAT

GAGAATGACAAACTGATCCGCGAAGTGAAGGTCATTACTCTGAAGTCAAAACTTGTGAGCGACTT

CAGAAAGGATTTCCAGTTCTACAAAGTCAGGGAGATCAACAATTATCACCATGCTCATGACGCAT

ACCTGAACGCAGTGGTCGGGACCGCCCTGATTAAGAAATACCCCAAACTGGAGAGCGAATTCGTG

TACGGTGACTATAAGGTGTACGATGTCAGAAAAATGATCGCCAAGAGTGAGCAGGAAATTGGAAA

AGCCACCGCTAAGTATTTCTTTTACTCAAACATCATGAATTTCTTTAAGACTGAGATCACCCTGGCA

AATGGGGAAATCCGAAAGAGACCACTGATTGAGACTAACGGCGAGACCGGAGAAATCGTGTGGG

ACAAGGGTAGGGATTTTGCCACAGTGCGCAAGGTCCTGTCCATGCCTCAAGTGAATATTGTCAAGA

AAACAGAGGTGCAGACTGGCGGATTCAGTAAGGAATCAATTCTGCCCAAACGGAACTCTGATAAG

CTGATCGCCCGAAAGAAAGACTGGGATCCCAAGAAATATGGGGGTTTCGACTCCCCAACAGTGGC

TTACTCTGTCCTGGTGGTCGCAAAGGTGGAGAAGGGGAAAAGCAAGAAACTGAAATCCGTCAAGG

AGCTGCTGGGTATCACTATTATGGAGAGGAGCTCCTTCGAGAAGAACCCCATCGATTTTCTGGAGG

CTAAAGGCTATAAGGAAGTGAAGAAAGACCTGATCATTAAACTGCCAAAGTACAGCCTGTTTGAG

CTGGAAAACGGAAGGAAGCGAATGCTGGCATCCGCAGGAGAGCTGCAGAAGGGTAATGAACTGG

CCCTGCCTTCTAAGTACGTGAACTTCCTGTATCTGGCTAGCCACTACGAGAAGCTGAAAGGCTCCC

CCGAGGATAACGAACAGAAACAGCTGTTTGTGGAGCAGCACAAGCATTATCTGGACGAGATCATT

GAACAGATTAGCGAGTTCTCCAAAAGAGTGATCCTGGCTGACGCAAATCTGGATAAGGTCCTGAG

CGCATACAACAAACACAGAGATAAGCCAATCAGGGAGCAGGCCGAAAATATCATTCATCTGTTCA

CTCTGACCAACCTGGGAGCCCCTGCAGCCTTCAAGTATTTTGACACTACCATCGATCGGAAACGAT

-continuede

ACACATCCACTAAGGAGGTGCTGGACGCTACCCTGATTCACCAGAGCATTACCGGCCTGTATGAA

ACAAGGATTGACCTGTCTCAGCTGGGGGGCGACCTCGAGGGAAGCGGAGAGGGCAGAGGAAGTC

TGCTAACATGCGGTGACGTCGAGGAGAATCCTGGCCCAGCACCGGGATCCATGGTGAGCAAGGGC

GAGGAGCTGTTCACCGGGGTGGTGCCCATCCTGGTCGAGCTGGACGGCGACGTAAACGGCCACAA

GTTCAGCGTGTCCGGCGAGGGCGAGGGCGATGCCACCTACGGCAAGCTGACCCTGAAGTTCATCT

GCACCACCGGCAAGCTGCCCGTGCCCTGGCCCACCCTCGTGACCACCTTCACCTACGGCGTGCAGT

GCTTCGCCCGCTACCCCGACCACATGAAGCAGCACGACTTCTTCAAGTCCGCCATGCCCGAAGGCT

ACGTCCAGGAGCGCACCATCTTCTTCAAGGACGACGGCAACTACAAGACCCGCGCCGAGGTGAAG

TTCGAGGGCGACACCCTGGTGAACCGCATCGAGCTGAAGGGCATCGACTTCAAGGAGGACGGCAA

CATCCTGGGGCACAAGCTGGAGTACAACTACAACAGCCACAAGGTCTATATCACCGCCGACAAGC

AGAAGAACGGCATCAAGGTGAACTTCAAGACCCGCCACAACATCGAGGACGGCAGCGTGCAGCTC

GCCGACCACTACCAGCAGAACACCCCCATCGGCGACGGCCCCGTGCTGCTGCCCGACAACCACTA

CCTGAGCACCCAGTCCGCCCTGAGCAAAGACCCCAACGAGAAGCGCGATCACATGGTCCTGCTGG

AGTTCGTGACCGCCGCCGGGATCACTCTCGGCATGGACGAGCTGTACAAGTAAACCTAATCTAGC

AGCTCGCTGATCAGCCTCGACTGTGCCTTCTAGTTGCCAGCCATCTGTTGTTTGCCCCTCCCCCGTG

CCTTCCTTGACCCTGGAAGGTGCCACTCCCACTGTCCTTTCCTAATAAAATGAGGAAATTGCATCG

CATTGTCTGAGTAGGTGTCATTCTATTCTGGGGGGTGGGGTGGGGCAGGACAGCAAGGGGGAGGA

TTGGGAAGACAATAGCAGGCATGCTGGGGATGCGGTGGGCTCTATGGCTTCTGAGGCGGAAAGAA

CCAGCTGGGGCTCGATCCTCTAGTTGGCGCGTCATGGTCCATATGAATATCCTCCTTAGTTCCTATT

CCGCTAGCCTAGAGGGACAGCCCCCCCCCAAAGCCCCCAGGGATGTAATTACGTCCCTCCCCCGCT

AGGGGCAGCAGCGAGCCGCCCGGGGCTCCGCTCCGGTCCGGCGCTCCCCCCGCATCCCCGAGCCG

GCAGCGTGCGGGGACAGCCCGGGCACGGGGAAGGTGGCACGGGATCGCTTTCCTCTGAACGCTTC

TCGCTGCTCTTTGAGCCTGCAGACACCTGGGGGGATACGGGGAAAAAGCTTTAGGCTGAAAGAGA

GATTTAGAATGACAGAATCATAGAACGGCCTGGGTTGCAAAGGAGCACAGTGCTCATCCAGATCC

AACCCCCTGCTATGTGCAGGGTCATCAACCAGCAGCCCAGGCTGCCCAGAGCCACATCCAGCCTG

GCCTTGAATGCCTGCAGGGATGGGGCATCCACAGCCTCCTTGGGCAACCTGTTCAGTGCGTCACCA

CCCTCTGGGGGAAAAACTGCCTCCTCATATCCAACCCAAACCTCCCCTGTCTCAGTGTAAAGCCAT

TCCCCCTTGTCCTATCAAGGGGGAGTTTGCTGTGACATTGTTGGTCTGGGGTGACACATGTTTGCCA

ATTCAGTGCATCACGGAGAGGCAGATCTTGGGGATAAGGAAGTGCAGGACAGCATGGACGTGGG

ACATGCAGGTGTTGAGGGCTCTGGGACACTCTCCAAGTCACAGCGTTCAGAACAGCCTTAAGGAT

AAGAAGATAGGATAGAAGGACAAAGAGCAAGTTAAAACCCAGCATGGAGAGGAGCACAAAAAG

GCCACAGACACTGCTGGTCCCTGTGTCTGAGCCTGCATGTTTGATGGTGTCTGGATGCAAGCAGAA

GGGGTGGAAGAGCTTGCCTGGAGAGATACAGCTGGGTCAGTAGGACTGGGACAGGCAGCTGGAG

AATTGCCATGTAGATGTTCATACAATCGTCAAATCATGAAGGCTGGAAAAGCCCTCCAAGATCCCC

AAGACCAACCCCAACCCACCCACCGTGCCCACTGGCCATGTCCCTCAGTGCCACATCCCCACAGTT

CTTCATCACCTCCAGGGACGGTGACCCCCCCACCTCCGTGGGCAGCTGTGCCACTGCAGCACCGCT

CTTTGGAGAAGGTAAATCTTGCTAAATCCAGCCCGACCCTCCCCTGGCACAACGTAAGGCCATTAT

CTCTCATCCAACTCCAGGACGGAGTCAGTGAGGATGGGGCTGGATCCGAAGCAGCTCCAGCCTAC

ACAATCGCTCAAGACGTGTAATGCTTTTATTATATATTAGTCACGATATCTATAACAAGAAAATAT

ATATATAATAAGTTATCACGTAAGTAGAACATGAAATAACAATATAATTATCGTATGAGTTAAATC

TTAAAAGTCACGTAAAAGATAATCATGCGTCATTTTGACTCACGCGGTCGTTATAGTTCAAAATCA

-continuede

GTGACACTTACCGCATTGACAAGCACGCCTCACGGGAGCTCCAAGCGGCGACTGAGATGTCCTAA

ATGCACAGCGACGGATTCGCGCTATTTAGAAAGAGAGAGCAATATTTCAAGAATGCATGCGTCAA

TTTTACGCAGACTATCTTTCTAGGGTTAAAAAAGATTTGCGCTTTACTCGACCTAAACTTTAAACAC

GTCATAGAATCTTCGTTTGACAAAAACCACATTGTGGGGTACCGAGCTCTTAATTAAGGCGCGCCG

GGGAGGTTCCCTTTAGTGAGGGTTAATTGCGGGTCGCCCTATAGTGAGTCGTATTACAATTCACTG

GCCGTCGTTTTACAACGTCGTGACTGGGAAAACCCTGGCGTTACCCAACTTAATCGCCTTGCAGCA

CATCCCCCTTTCGCCAGCTGGCGTAATAGCGAAGAGGCCCGCACCGATCGCCCTTCCCAACAGTTG

CGCAGCCTGAATGGCGAATGGCAAATTGTAAGCGTTAATATTTTGTTAAAATTCGCGTTAAATTTT

TGTTAAATCAGCTCATTTTTTAACCAATAGGCCGAAATCGGCAAAATCCCTTATAAATCAAAAGAA

TAGACCGAGATAGGGTTGAGTGTTGTTCCAGTTTGGAACAAGAGTCCACTATTAAAGAACGTGGA

CTCCAACGTCAAAGGGCGAAAAACCGTCTATCAGGGCGATGGCCCACTACGTGAACCATCACCCT

AATCAAGTTTTTTGGGGTCGAGGTGCCGTAAAGCACTAAATCGGAACCCTAAAGGGAGCCCCCGA

TTTAGAGCTTGACGGGGAAAGCCGGCGAACGTGGCGAGAAAGGAAGGGAAGAAAGCGAAAGGAG

CGGGCGCTAGGGCGCTGGCAAGTGTAGCGGTCACGCTGCGCGTAACCACCACACCCGCCGCGCTT

AATGCGCCGCTACAGGGCGCGTCAG

AAV gRNA Sequence (SEQ ID NO: 9)

CCTGCAGGCAGCTGCGCGCTCGCTCGCTCACTGAGGCCGCCCGGGCAAAGCCCGGGCGTCGGGCG

ACCTTTGGTCGCCCGGCCTCAGTGAGCGAGCGAGCGCGCAGAGAGGGAGTGGCCAACTCCATCAC

TAGGGGTTCCTGCGGCCGCACGCGTGAGGGCCTATTTCCCATGATTCCTTCATATTTGCATATACG

ATACAAGGCTGTTAGAGAGATAATTGGAATTAATTTGACTGTAAACACAAAGATATTAGTACAAA

ATACGTGACGTAGAAAGTAATAATTTCTTGGGTAGTTTGCAGTTTTAAAATTATGTTTTAAAATGG

ACTATCATATGCTTACCGTAACTTGAAAGTATTTCGATTTCTTGGCTTTATATATCTTGTGGAAAGG

ACGAAACACCGCAGCGTTACCTCTATCGTAGTTTTAGAGCTAGAAATAGCAAGTTAAAATAAGGC

TAGTCCGTTATCAACTTGAAAAAGTGGCACCGAGTCGGTGCTTTTTTGGATCCGAGGGCCTATTTC

CCATGATTCCTTCATATTTGCATATACGATACAAGGCTGTTAGAGAGATAATTGGAATTAATTTGA

CTGTAAACACAAAGATATTAGTACAAAATACGTGACGTAGAAAGTAATAATTTCTTGGGTAGTTTG

CAGTTTTAAAATTATGTTTTAAAATGGACTATCATATGCTTACCGTAACTTGAAAGTATTTCGATTT

CTTGGCTTTATATATCTTGTGGAAAGGACGAAACACCGTGTAATAGCTCCTGCATGGGTTTTAGAG

CTAGAAATAGCAAGTTAAAATAAGGCTAGTCCGTTATCAACTTGAAAAAGTGGCACCGAGTCGGT

GCTTTTTTTCTAGAAGGTACCAGGTCTTGAAAGGAGTGGGAATTGGCTCCGGTGCCCGTCAGTGGG

CAGAGCGCACATCGCCCACAGTCCCCGAGAAGTTGGGGGGAGGGGTCGGCAATTGAACCGGTGCC

TAGAGAAGGTGGCGCGGGGTAAACTGGGAAAGTGATGTCGTGTACTGGCTCCGCCTTTTTCCCGA

GGGTGGGGGAGAACCGTATATAAGTGCAGTAGTCGCCGTGAACGTTCTTTTTCGCAACGGGTTTGC

CGCCAGAACACAGGCGTACGGCCACCATGACTTCGAAAGTTTATGATCCAGAACAAAGGAAACGG

ATGATAACTGGTCCGCAGTGGTGGGCCAGATGTAAACAAATGAATGTTCTTGATTCATTTATTAAT

TATTATGATTCAGAAAAACATGCAGAAAATGCTGTTATTTTTTTACATGGTAACGCGGCCTCTTCTT

ATTTATGGCGACATGTTGTGCCACATATTGAGCCAGTAGCGCGGTGTATTATACCAGACCTTATTG

GTATGGGCAAATCAGGCAAATCTGGTAATGGTTCTTATAGGTTACTTGATCATTACAAATATCTTA

CTGCATGGTTTGAACTTCTTAATTTACCAAAGAAGATCATTTTTGTCGGCCATGATTGGGGTGCTTG

TTTGGCATTTCATTATAGCTATGAGCATCAAGATAAGATCAAAGCAATAGTTCACGCTGAAAGTGT

AGTAGATGTGATTGAATCATGGGATGAATGGCCTGATATTGAAGAAGATATTGCGTTGATCAAATC

-continuede

TGAAGAAGGAGAAAAAAATGGTTTTGGAGAATAACTTCTTCGTGGAAACCATGTTGCCATCAAAAA

TCATGAGAAAGTTAGAACCAGAAGAATTTGCAGCATATCTTGAACCATTCAAAGAGAAAGGTGAA

GTTCGTCGTCCAACATTATCATGGCCTCGTGAAATCCCGTTAGTAAAAGGTGGTAAACCTGACGTT

GTACAAATTGTTAGGAATTATAATGCTTATCTACGTGCAAGTGATGATTTACCAAAAATGTTTATT

GAATCGGACCCAGGATTCTTTTCCAATGCTATTGTTGAAGGTGCCAAGAAGTTTCCTAATACTGAA

TTTGTCAAAGTAAAAGGTCTTCATTTTTCGCAAGAAGATGCACCTGATGAAATGGGAAAATATATC

AAATCGTTCGTTGAGCGAGTTCTCAAAAATGAACAATAAAGCGCTAATAAAAGATCTTTATTTTCA

TTAGATCTGTGTGTTGGTTTTTTGTGTAAGCTTTGGCTCCAACACAGATGTTCTTAGGCTACCTAAC

TTCTAACTTTTAATATCCAGTCAACAAAGAATACCGCAAGGGTAGGTGTTGGGATAGCTGTCGACA

AGCTCATGCGGGTGTGTCCACAGGGTATAGCGTACTATGCAGAATATTTGTACTGAGTGAAGTCAT

GATACATTCCTTTGAGAGCCATTAGCTGCTACAAAACAGTAATCTGGCTGTTTAGATCAACAAGCT

AAATGATAGAAGATGAAAGTACTGGTTTCCATGTATTTTTATTAAGTGTTGATGAGAAAGTTGTAA

GTGACTTACAGGTTACTCTGTACATCTGTAGTCACTGAATTCGGAATATCTTAGAGTTTTACACACA

AAGGTGAGTGTTAAAATATTGATAAAGTTTTTGATAATCTTGTGTGAGACATGTTCTAATTTAGTTG

TATTTTATTATTTTTATTGTAAGGCCTGCTGAAAATGACTGAGTATAAACTTGTGGTCGTGGGCGCC

GACGGCGTGGGCAAGAGCGCTTTGACGATACAGCTAATTCAGAATCACTTTGTGGATGAGTATGA

TCCAACCATCGAGGTAACGCTGCTCTACAGTCTGCGTGCGCTTGTAAAGGACGGCAGCCAGCCGCT

TTGAAAAAGATATCATTTTTATATTTATTAGAAAATTATATTGAAAGTTATTTCAGTTATATGTGAT

GTCCTTTAGTTCCAAGGCTTTAAACTGGGTGTTAGGGAACCATAGGTGCAAGAAAGTCCACTTCTC

ATGAGAGCTCACCACAGAGAAAGAAAGTCCACTTCTCAGGTAACCACGTGCGGACCGAGCGGCCG

CAGGAACCCCTAGTGATGGAGTTGGCCACTCCCTCTCTGCGCGCTCGCTCGCTCACTGAGGCCGGG

CGACCAAAGGTCGCCCGACGCCCGGGCTTTGCCCGGGCGGCCTCAGTGAGCGAGCGAGCGCGCAG

CTGCCTGCAGGTATTTTCTCCTTACGCATCTGTGCGGTATTTCACACCGCATACGTCAAAGCAACCA

TAGTACGCGCCCTGTAGCGGCGCATTAAGCGCGGCGGGTGTGGTGGTTACGCGCAGCGTGACCGC

TACACTTGCCAGCGCCCTAGCGCCCGCTCCTTTCGCTTTCTTCCCTTCCTTTCTCGCCACGTTCGCCG

GCTTTCCCCGTCAAGCTCTAAATCGGGGGCTCCCTTTAGGGTTCCGATTTAGTGCTTTACGGCACCT

CGACCCCAAAAAACTTGATTTGGGTGATGGTTCACGTAGTGGGCCATCGCCCTGATAGACGGTTTT

TCGCCCTTTGACGTTGGAGTCCACGTTCTTTAATAGTGGACTCTTGTTCCAAACTGGAACAACACTC

AACCCTATCTCGGGCTATTCTTTTGATTTATAAGGGATTTTGCCGATTTCGGCCTATTGGTTAAAAA

ATGAGCTGATTTAACAAAAATTTAACGCGAATTTTAACAAAATATTAACGTTTACAATTTTATGGT

GCACTCTCAGTACAATCTGCTCTGATGCCGCATAGTTAAGCCAGCCCCGACACCCGCCAACACCCG

CTGACGCGCCCTGACGGGCTTGTCTGCTCCCGGCATCCGCTTACAGACAAGCTGTGACCGTCTCCG

GGAGCTGCATGTGTCAGAGGTTTTCACCGTCATCACCGAAACGCGCGAGACGAAAGGGCCTCGTG

ATACGCCTATTTTTATAGGTTAATGTCATGATAATAATGGTTTCTTAGACGTCAGGTGGCACTTTTC

GGGGAAATGTGCGCGGAACCCCTATTTGTTTATTTTTCTAAATACATTCAAATATGTATCCGCTCAT

GAGACAATAACCCTGATAAATGCTTCAATAATATTGAAAAAGGAAGAGTATGAGTATTCAACATT

TCCGTGTCGCCCTTATTCCCTTTTTTGCGGCATTTTGCCTTCCTGTTTTTGCTCACCCAGAAACGCTG

GTGAAAGTAAAAGATGCTGAAGATCAGTTGGGTGCACGAGTGGGTTACATCGAACTGGATCTCAA

CAGCGGTAAGATCCTTGAGAGTTTTCGCCCCGAAGAACGTTTTCCAATGATGAGCACTTTTAAAGT

TCTGCTATGTGGCGCGGTATTATCCCGTATTGACGCCGGGCAAGAGCAACTCGGTCGCCGCATACA

CTATTCTCAGAATGACTTGGTTGAGTACTCACCAGTCACAGAAAAGCATCTTACGGATGGCATGAC

-continuede

AGTAAGAGAATTATGCAGTGCTGCCATAACCATGAGTGATAACACTGCGGCCAACTTACTTCTGAC

AACGATCGGAGGACCGAAGGAGCTAACCGCTTTTTTGCACAACATGGGGGATCATGTAACTCGCC

TTGATCGTTGGGAACCGGAGCTGAATGAAGCCATACCAAACGACGAGCGTGACACCACGATGCCT

GTAGCAATGGCAACAACGTTGCGCAAACTATTAACTGGCGAACTACTTACTCTAGCTTCCCGGCAA

CAATTAATAGACTGGATGGAGGCGGATAAAGTTGCAGGACCACTTCTGCGCTCGGCCCTTCCGGCT

GGCTGGTTTATTGCTGATAAATCTGGAGCCGGTGAGCGTGGGTCTCGCGGTATCATTGCAGCACTG

GGGCCAGATGGTAAGCCCTCCCGTATCGTAGTTATCTACACGACGGGGAGTCAGGCAACTATGGA

TGAACGAAATAGACAGATCGCTGAGATAGGTGCCTCACTGATTAAGCATTGGTAACTGTCAGACC

AAGTTTACTCATATATACTTTAGATTGATTTAAAACTTCATTTTTAATTTAAAAGGATCTAGGTGAA

GATCCTTTTTGATAATCTCATGACCAAAATCCCTTAACGTGAGTTTTCGTTCCACTGAGCGTCAGAC

CCCGTAGAAAAGATCAAAGGATCTTCTTGAGATCCTTTTTTTCTGCGCGTAATCTGCTGCTTGCAAA

CAAAAAAACCACCGCTACCAGCGGTGGTTTGTTTGCCGGATCAAGAGCTACCAACTCTTTTTCCGA

AGGTAACTGGCTTCAGCAGAGCGCAGATACCAAATACTGTCCTTCTAGTGTAGCCGTAGTTAGGCC

ACCACTTCAAGAACTCTGTAGCACCGCCTACATACCTCGCTCTGCTAATCCTGTTACCAGTGGCTG

CTGCCAGTGGCGATAAGTCGTGTCTTACCGGGTTGGACTCAAGACGATAGTTACCGGATAAGGCG

CAGCGGTCGGGCTGAACGGGGGGTTCGTGCACACAGCCCAGCTTGGAGCGAACGACCTACACCGA

ACTGAGATACCTACAGCGTGAGCTATGAGAAAGCGCCACGCTTCCCGAAGGGAGAAAGGCGGAC

AGGTATCCGGTAAGCGGCAGGGTCGGAACAGGAGAGCGCACGAGGGAGCTTCCAGGGGGAAACG

CCTGGTATCTTTATAGTCCTGTCGGGTTTCGCCACCTCTGACTTGAGCGTCGATTTTTGTGATGCTC

GTCAGGGGGGCGGAGCCTATGGAAAAACGCCAGCAACGCGGCCTTTTTACGGTTCCTGGCCTTTTG

CTGGCCTTTTGCTCACATGT.

TOIC_ApoL1_wt_PgkPuro (SEQ ID NO: 12)

SequenceGTGGCACTTTTCGGGGAAATGTGCGCGGAACCCCTATTTGTTTATTTTTCTAAATACATT

CAAATATGTATCCGCTCATGAGACAATAACCCTGATAAATGCTTCAATAATATTGAAAAAGGAAG

AGTATGAGTATTCAACATTTCCGTGTCGCCCTTATTCCCTTTTTTGCGGCATTTTGCCTTCCTGTTTT

TGCTCACCCAGAAACGCTGGTGAAAGTAAAAGATGCTGAAGATCAGTTGGGTGCACGAGTGGGTT

ACATCGAACTGGATCTCAACAGCGGTAAGATCCTTGAGAGTTTTCGCCCCGAAGAACGTTTTCCAA

TGATGAGCACTTTTAAAGTTCTGCTATGTGGCGCGGTATTATCCCGTATTGACGCCGGGCAAGAGC

AACTCGGTCGCCGCATACACTATTCTCAGAATGACTTGGTTGAGTACTCACCAGTCACAGAAAAGC

ATCTTACGGATGGCATGACAGTAAGAGAATTATGCAGTGCTGCCATAACCATGAGTGATAACACT

GCGGCCAACTTACTTCTGACAACGATCGGAGGACCGAAGGAGCTAACCGCTTTTTTGCACAACATG

GGGGATCATGTAACTCGCCTTGATCGTTGGGAACCGGAGCTGAATGAAGCCATACCAAACGACGA

GCGTGACACCACGATGCCTGTAGCAATGGCAACAACGTTGCGCAAACTATTAACTGGCGAACTAC

TTACTCTAGCTTCCCGGCAACAATTAATAGACTGGATGGAGGCGGATAAAGTTGCAGGACCACTTC

TGCGCTCGGCCCTTCCGGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTAGTTATCTACACGACGG

GGAGTCAGGCAACTATGGATGAACGAAATAGACAGATCGCTGAGATAGGTGCCTCACTGATTAAG

CATTGGTAACTGTCAGACCAAGTTTACTCATATATACTTTAGATTGATTTAAAACTTCATTTTTAAT

TTAAAAGGATCTAGGTGAAGATCCTTTTTGATAATCTCATGACCAAAATCCCTTAACGTGAGTTTT

CGTTCCACTGAGCGTCAGACCCCGTAGAAAAGATCAAAGGATCTTCTTGAGATCCTTTTTTTCTGC

-continuede

GCGTAATCTGCTGCTTGCAAACAAAAAAACCACCGCTACCAGCGGTGGTTTGTTTGCCGGATCAAG

AGCTACCAACTCTTTTTCCGAAGGTAACTGGCTTCAGCAGAGCGCAGATACCAAATACTGTTCTTC

TAGTGTAGCCGTAGTTAGGCCACCACTTCAAGAACTCTGTAGCACCGCCTACATACCTCGCTCTGC

TAATCCTGTTACCAGTGGCTGCTGCCAGTGGCGATAAGTCGTGTCTTACCGGGTTGGACTCAAGAC

GATAGTTACCGGATAAGGCGCAGCGGTCGGGCTGAACGGGGGGTTCGTGCACACAGCCCAGCTTG

GAGCGAACGACCTACACCGAACTGAGATACCTACAGCGTGAGCTATGAGAAAGCGCCACGCTTCC

CGAAGGGAGAAAGGCGGACAGGTATCCGGTAAGCGGCAGGGTCGGAACAGGAGAGCGCACGAGG

GAGCTTCCAGGGGGAAACGCCTGGTATCTTTATAGTCCTGTCGGGTTTCGCCACCTCTGACTTGAG

CGTCGATTTTTGTGATGCTCGTCAGGGGGGCGGAGCCTATGGAAAAACGCCAGCAACGCGGCCTTT

TTACGGTTCCTGGCCTTTTGCTGGCCTTTTGCTCACATGTTCTTTCCTGCGTTATCCCCTGATTCTGT

GGATAACCGTATTACCGCCTTTGAGTGAGCTGATACCGCTCGCCGCAGCCGAACGACCGAGCGCA

GCGAGTCAGTGAGCGAGGAAGCGGAAGAGCGCCCAATACGCAAACCGCCTCTCCCCGCGCGTTGG

CCGATTCATTAATGCAGCTGGCACGACAGGTTTCCCGACTGGAAAGCGGGCAGTGAGCGCAACGC

AATTAATGTGAGTTAGCTCACTCATTAGGCACCCCAGGCTTTACACTTTATGCTTCCGGCTCGTATG

TTGTGTGGAATTGTGAGCGGATAACAATTTCACACAGGAAACAGCTATGACCATGATTACGCCAA

GCGCGCAATTAACCCTCACTAAAGGGAACCTCCCCTAGCTTAATTAACCCTAGAAAGATAATCATA

TTGTGACGTACGTTAAAGATAATCATGCGTAAAATTGACGCATGTGTTTTATCGATCTGTATATCG

AGGTTTATTTATTAATTTGAATAGATATTAAGTTTTATTATATTTACACTTACATACTAATAATAAA

TTCAACAAACAATTTATTTATGTTTATTTATTTATTAAAAAAAAACAAAAACTCAAAATTTCTTCTA

TAAAGTAACAAAACTTTTAAACATTCTCTCTTTTACAAAAATAAACTTATTTTGTACTTTAAAAACA

GTCATGTTGTATTATAAAATAAGTAATTAGCTTAACTTATACATAATAGAAACAAATTATACTTAT

TAATCGCATTGATTATTGACTAGTCGTATTAAGGGTTCCGGATCAGCTTGATTCGAGCCCCAGCTG

GTTCTTTCCGCCTCAGAAGCCATAGAGCCCACCGCATCCCCAGCATGCCTGCTATTGTCTTCCCAAT

CCTCCCCCTTGCTGTCCTGCCCCACCCCACCCCCCAGAATAGAATGACACCTACTCAGACAATGCG

ATGCAATTTCCTCATTTTATTAGGAAAGGACAGTGGGAGTGGCACCTTCCAGGGTCAAGGAAGGC

ACGGGGGAGGGGCAAACAACAGATGGCTGGCAACTAGAAGGCACAGTCGAGGCTGATCAGCGAG

CTCTAGAGAATTGATCCCCTCAGAAGAACTCGTCAAGAAGGCGATAGAAGGCGATGCGCTGCGAA

TCGGGAGCGGCGATACCGTAAAGCACGAGGAAGCGGTCAGCCCATTCGCCGCCtcaggcaccgggc ttgcgggtcatgcaccaggtgcgcggtccttcgggcacctcgacgtcggcggtgacggtgaagccga gccgctcgtagaaggggaggttgcggggcgcggaggtctccaggaaggcgggcaccccggcgcgct cggccgcctccactccggggagcacgacggcgctgcccagacccttgccctggtggtcgggcgagacg ccgacggtggccaggaaccacgcgggctccttgggccggtgcggcgccaggaggccttccatagtt gagcgcggccagccgggaaccgctcaactcggccatgcgcgggccgatctcggcgaacaccgcccc cgcttcgacgctctccggcgtggtccagaccgccaccgcggcgccgtcgtccgcgacccacacctt gccgatgtcgagcccgacgcgcgtgaggaagagttcttgcagctcggtgacccgctcgatgtggcg gtccgggtcgacggtgtggcgcgtggcggggtagtcggcgaacgcggcggcgagggtgcgtacggcc cgggggacgtcgtcgcgggtggcgaggcgcaccgtgggcttgtactcggtcatGGTTTAGTTCCTCAC

CTTGTCGTATTATACTATGCCGATATACTATGCCGATGATTAATTGTCAACACGTGCTGCTGCAGGTC

GAAAGGCCCGGAGATGAGGAAGAGGAGAACAGCGCGGCAGACGTGCGCTTTTGAAGCGTGCAGAATG

CCGGGCCTCCGGAGGACCTTCGGGCGCCCGCCCCGCCCCTGAGCCCGCCCCTGAGCCCGCCCCCGG

ACCCACCCCTTCCCAGCCTCTGAGCCCAGAAAGCGAAGGAGCAAAGCTGCTATTGGCCGCTGCCC

-continuede

CAAAGGCCTACCCGCTTCCATTGCTCAGCGGTGCTGTCCATCTGCACGAGACTAGTGAGACGTGCT

ACTTCCATTTGTCACGTCCTGCACGACGCGAGCTGCGGGGCGGGGGGGAACTTCCTGACTAGGGG

AGGAGTAGAAGGTGGCGCGAAGGGGCCACCAAAGAACGGAGCCGGTTGGCGCCTACCGGTGGAT

GTGGAATGTGTGCGAGCCAGAGGCCACTTGTGTAGCGCCAAGTGCCCAGCGGGGCTGCTAAAGCG

CATGCTCCAGACTGCCTTGGGAAAAGCGCCTCCCCTACCCGGTAGACACCCCACAGTGGGTGGCCT

AGGGACAGGATTGCAACTCCAGTCTTTCTTCTTCTTGGGCGGGAGTCACTAGTTATTAATAGTAAT

CAATTACGGGGTCATTAGTTCATAGCCCATATATGGAGTTCCGCGTTACATAACTTACGGTAAATG

GCCCGCCTGGCTGACCGCCCAACGACCCCCGCCCATTGACGTCAATAATGACGTATGTTCCCATAG

TAACGCCAATAGGGACTTTCCATTGACGTCAATGGGTGGACTATTTACGGTAAACTGCCCACTTGG

CAGTACATCAAGTGTATCATATGCCAAGTACGCCCCCTATTGACGTCAATGACGGTAAATGGCCCG

CCTGGCATTATGCCCAGTACATGACCTTATGGGACTTTCCTACTTGGCAGTACATCTACGTATTAGT

CATCGCTATTACCATGGGTCGAGGTGAGCCCCACGTTCTGCTTCACTCTCCCCATCTCCCCCCCCTC

CCCACCCCCAATTTTGTATTTATTTATTTTTTAATTATTTTGTGCAGCGATGGGGGCGGGGGGGGGG

GGGGCGCGCGCCAGGCGGGGCGGGGCGGGGCGAGGGGCGGGGCGGGGCGAGGCGGAGAGGTGC

GGCGGCAGCCAATCAGAGCGGCGCGCTCCGAAAGTTTCCTTTTATGGCGAGGCGGCGGCGGCGGC

GGCCCTATAAAAAGCGAAGCGCGCGGCGGGCGGGAGTCGCTGCGTTGCCTTCGCCCCGTGCCCCG

CTCCGCGCCGCCTCGCGCCGCCCGCCCCGGCTCTGACTGACCGCGTTACTCCCACAGGTGAGCGGG

CGGGACGGCCCTTCTCCTCCGGGCTGTAATTAGCGCTTGGTTTAATGACGGCTCGTTTCTTTTCTGT

GGCTGCGTGAAAGCCTTAAAGGGCTCCGGGAGGGCCCTTTGTGCGGGGGGGAGCGGCTCGGGGGG

TGCGTGCGTGTGTGTGTGCGTGGGGAGCGCCGCGTGCGGCCCGCGCTGCCCGGCGGCTGTGAGCG

CTGCGGGCGCGGCGCGGGGCTTTGTGCGCTCCGCGTGTGCGCGAGGGGAGCGCGGCCGGGGGCGG

TGCCCCGCGGTGCGGGGGGGCTGCGAGGGGAACAAAGGCTGCGTGCGGGGTGTGTGCGTGGGGG

GGTGAGCAGGGGGTGTGGGCGCGGCGGTCGGGCTGTAACCCCCCCCTGCACCCCCCTCCCCGAGT

TGCTGAGCACGGCCCGGCTTCGGGTGCGGGGCTCCGTGCGGGGCGTGGCGCGGGGCTCGCCGTGC

CGGGCGGGGGGTGGCGGCAGGTGGGGGTGCCGGGCGGGGCGGGGCCGCCTCGGGCCGGGGAGGG

CTCGGGGGAGGGGCGCGGCGGCCCCGGAGCGCCGGCGGCTGTCGAGGCGCGGCGAGCCGCAGCC

ATTGCCTTTTATGGTAATCGTGCGAGAGGGCGCAGGGACTTCCTTTGTCCCAAATCTGGCGGAGCC

GAAATCTGGGAGGCGCCGCCGCACCCCCTCTAGCGGGCGCGGGCGAAGCGGTGCGGCGCCGGCAG

GAAGGAAATGGGCGGGGAGGGCCTTCGTGCGTCGCCGCGCCGCCGTCCCCTTCTCCATCTCCAGCC

TCGGGGCTGCCGCAGGGGGACGGCTGCCTTCGGGGGGGACGGGGCAGGGCGGGGTTCGGCTTCTG

GCGTGTGACCGGCGGCTCTAGAGCCTCTGCTAACCATGTTCATGCCTTCTTCTTTTTCCTACAGCTC

CTGGGCAACGTGCTGGTTATTGTGCTGTCTCATCATTTTGGCAAAGAATTCGCCACCATGGTGCCC

AAGAAGAAGAGGAAAGTCTCTAGACTGGACAAGAGCAAAGTCATAAACTCTGCTCTGGAATTACT

CAATGGAGTCGGTATCGAAGGCCTGACGACAAGGAAACTCGCTCAAAAGCTGGGAGTTGAGCAGC

CTACCCTGTACTGGCACGTGAAGAACAAGCGGGCCCTGCTCGATGCCCTGCCAATCGAGATGCTG

GACAGGCATCATACCCACTCCTGCCCCCTGGAAGGCGAGTCATGGCAAGACTTTCTGCGGAACAA

CGCCAAGTCATACCGCTGTGCTCTCCTCTCACATCGCGACGGGGCTAAAGTGCATCTCGGCACCCG

CCCAACAGAGAAACAGTACGAAACCCTGGAAAATCAGCTCGCGTTCCTGTGTCAGCAAGGCTTCT

CCCTGGAGAACGCACTGTACGCTCTGTCCGCCGTGGGCCACTTTACACTGGGCTGCGTATTGGAGG

AACAGGAGCATCAAGTAGCAAAAGAGGAAAGAGAGACACCTACCACCGATTCTATGCCCCCACTT

-continuede

CTGAAACAAGCAATTGAGCTGTTCGACCGGCAGGGAGCCGAACCTGCCTTCCTTTTCGGCCTGGAA

CTAATCATATGTGGCCTGGAGAAACAGCTAAAGTGCGAAAGCGGCGGGCCGACCGACGCCCTTGA

CGATTTTGACTTAGACATGCTCCCAGCCGATGCCCTTGACGACTTTGACCTTGATATGCTGCCTGCT

GACGCTCTTGACGATTTTGACCTTGACATGCTCCCCGGGTAAAGCGGCCGCGACTCTAGATCATAA

TCAGCCATACCACATTTGTAGAGGTTTTACTTGCTTTAAAAAACCTCCCACACCTCCCCCTGAACCT

GAAACATAAAATGAATGCAATTGTTGTTGTTAACTTGTTTATTGCAGCTTATAATGGTTACAAATA

AAGCAATAGCATCACAAATTTCACAAATAAAGCATTTTTTTCACTGCATTCTAGTTGTGGTTTGTCC

AAACTCATCAATGTATCTTAAGGGATCCCTAGAGGGACAGCCCCCCCCCAAAGCCCCCAGGGATG

TAATTACGTCCCTCCCCCGCTAGGGGCAGCAGCGAGCCGCCCGGGGCTCCGCTCCGGTCCGGCGCT

CCCCCCGCATCCCCGAGCCGGCAGCGTGCGGGGACAGCCCGGGCACGGGGAAGGTGGCACGGGA

TCGCTTTCCTCTGAACGCTTCTCGCTGCTCTTTGAGCCTGCAGACACCTGGGGGGATACGGGGAAA

AAGCTTTAGGCTGAAAGAGAGATTTAGAATGACAGAATCATAGAACGGCCTGGGTTGCAAAGGAG

CACAGTGCTCATCCAGATCCAACCCCCTGCTATGTGCAGGGTCATCAACCAGCAGCCCAGGCTGCC

CAGAGCCACATCCAGCCTGGCCTTGAATGCCTGCAGGGATGGGGCATCCACAGCCTCCTTGGGCA

ACCTGTTCAGTGCGTCACCACCCTCTGGGGGAAAAACTGCCTCCTCATATCCAACCCAAACCTCCC

CTGTCTCAGTGTAAAGCCATTCCCCCTTGTCCTATCAAGGGGGAGTTTGCTGTGACATTGTTGGTCT

GGGGTGACACATGTTTGCCAATTCAGTGCATCACGGAGAGGCAGATCTTGGGGATAAGGAAGTGC

AGGACAGCATGGACGTGGGACATGCAGGTGTTGAGGGCTCTGGGACACTCTCCAAGTCACAGCGT

TCAGAACAGCCTTAAGGATAAGAAGATAGGATAGAAGGACAAAGAGCAAGTTAAAACCCAGCAT

GGAGAGGAGCACAAAAAGGCCACAGACACTGCTGGTCCCTGTGTCTGAGCCTGCATGTTTGATGG

TGTCTGGATGCAAGCAGAAGGGGTGGAAGAGCTTGCCTGGAGAGATACAGCTGGGTCAGTAGGAC

TGGGACAGGCAGCTGGAGAATTGCCATGTAGATGTTCATACAATCGTCAAATCATGAAGGCTGGA

AAAGCCCTCCAAGATCCCCAAGACCAACCCCAACCCACCCACCGTGCCCACTGGCCATGTCCCTCA

GTGCCACATCCCCACAGTTCTTCATCACCTCCAGGGACGGTGACCCCCCCACCTCCGTGGGCAGCT

GTGCCACTGCAGCACCGCTCTTTGGAGAAGGTAAATCTTGCTAAATCCAGCCCGACCCTCCCCTGG

CACAACGTAAGGCCATTATCTCTCATCCAACTCCAGGACGGAGTCAGTGAGGATGGGGCTGTCGA

CCTAGAGGGACAGCCCCCCCCCAAAGCCCCCAGGGATGTAATTACGTCCCTCCCCCGCTAGGGGC

AGCAGCGAGCCGCCCGGGGCTCCGCTCCGGTCCGGCGCTCCCCCCGCATCCCCGAGCCGGCAGCG

TGCGGGGACAGCCCGGGCACGGGGAAGGTGGCACGGGATCGCTTTCCTCTGAACGCTTCTCGCTG

CTCTTTGAGCCTGCAGACACCTGGGGGGATACGGGGAAAAAGCTTTAGGCTGAAAGAGAGATTTA

GAATGACAGAATCATAGAACGGCCTGGGTTGCAAAGGAGCACAGTGCTCATCCAGATCCAACCCC

CTGCTATGTGCAGGGTCATCAACCAGCAGCCCAGGCTGCCCAGAGCCACATCCAGCCTGGCCTTGA

ATGCCTGCAGGGATGGGGCATCCACAGCCTCCTTGGGCAACCTGTTCAGTGCGTCACCACCCTCTG

GGGGAAAAACTGCCTCCTCATATCCAACCCAAACCTCCCCTGTCTCAGTGTAAAGCCATTCCCCCT

TGTCCTATCAAGGGGGAGTTTGCTGTGACATTGTTGGTCTGGGGTGACACATGTTTGCCAATTCAG

TGCATCACGGAGAGGCAGATCTTGGGGATAAGGAAGTGCAGGACAGCATGGACGTGGGACATGC

AGGTGTTGAGGGCTCTGGGACACTCTCCAAGTCACAGCGTTCAGAACAGCCTTAAGGATAAGAAG

ATAGGATAGAAGGACAAAGAGCAAGTTAAAACCCAGCATGGAGAGGAGCACAAAAAGGCCACAG

ACACTGCTGGTCCCTGTGTCTGAGCCTGCATGTTTGATGGTGTCTGGATGCAAGCAGAAGGGGTGG

AAGAGCTTGCCTGGAGAGATACAGCTGGGTCAGTAGGACTGGGACAGGCAGCTGGAGAATTGCCA

TGTAGATGTTCATACAATCGTCAAATCATGAAGGCTGGAAAAGCCCTCCAAGATCCCCAAGACCA

-continuede
ACCCCAACCCACCCACCGTGCCCACTGGCCATGTCCCTCAGTGCCACATCCCCACAGTTCTTCATC

ACCTCCAGGGACGGTGACCCCCCCACCTCCGTGGGCAGCTGTGCCACTGCAGCACCGCTCTTTGGA

GAAGGTAAATCTTGCTAAATCCAGCCCGACCCTCCCCTGGCACAACGTAAGGCCATTATCTCTCAT

CCAACTCCAGGACGGAGTCAGTGAGGATGGGGCTCAATTGTTTACTCCCTATCAGTGATAGAGAA

CGTATGAAGAGTTTACTCCCTATCAGTGATAGAGAACGTATGCAGACTTTACTCCCTATCAGTGAT

AGAGAACGTATAAGGAGTTTACTCCCTATCAGTGATAGAGAACGTATGACCAGTTTACTCCCTATC

AGTGATAGAGAACGTATCTACAGTTTACTCCCTATCAGTGATAGAGAACGTATATCCAGTTTACTC

CCTATCAGTGATAGAGAACGTATAAGCTTTAGGCGTGTACGGTGGGCGCCTATAAAAGCAGAGCT

CGTTTAGTGAACCGTCAGATCGCCTGGAGCAATTCCACAACACTTTTGTCTTATACCAACTTTCCGT

ACCACTTCCTACCCTCGTAAAAAGCTTGTCCACCATGAGATTCAAAAGCCACACTGTGGAATTGAG

GAGGCCCTGCAGCGACATGGAGGGAGCTGCTTTGCTGAGAGTCTCTGTCCTCTGCATCTGGATGAG

TGCACTTTTCCTTGGTGTGGGAGTGAGGGCAGAGGAAGCTGGAGCGAGGGTGCAACAAAACGTTC

CAAGTGGGACAGATACTGGAGATCCTCAAAGTAAGCCCCTCGGTGACTGGGCTGCTGGCACCATG

GACCCAGAGAGCAGTATCTTTATTGAGGATGCCATTAAGTATTTCAAGGAAAAAGTGAGCACACA

GAATCTGCTACTCCTGCTGACTGATAATGAGGCCTGGAACGGATTCGTGGCTGCTGCTGAACTGCC

CAGGAATGAGGCAGATGAGCTCCGTAAAGCTCTGGACAACCTTGCAAGACAAATGATCATGAAAG

ACAAAAACTGGCACGATAAAGGCCAGCAGTACAGAAACTGGTTTCTGAAAGAGTTTCCTCGGTTG

AAAAGTGAGCTTGAGGATAACATAAGAAGGCTCCGTGCCCTTGCAGATGGGGTTCAGAAGGTCCA

CAAAGGCACCACCATCGCCAATGTGGTGTCTGGCTCTCTCAGCATTTCCTCTGGCATCCTGACCCTC

GTCGGCATGGGTCTGGCACCCTTCACAGAGGGAGGCAGCCTTGTACTCTTGGAACCTGGGATGGA

GTTGGGAATCACAGCCGCTTTGACCGGGATTACCAGCAGTACCATGGACTACGGAAAGAAGTGGT

GGACACAAGCCCAAGCCCACGACCTGGTCATCAAAAGCCTTGACAAATTGAAGGAGGTGAGGGA

GTTTTTGGGTGAGAACATATCCAACTTTCTTTCCTTAGCTGGCAATACTTACCAACTCACACGAGGC

ATTGGGAAGGACATCCGTGCCCTCAGACGAGCCAGAGCCAATCTTCAGTCAGTACCGCATGCCTC

AGCCTCACGCCCACGAGTCACTGAGCCAATCTCAGCTGAAAGCGGTGAACAGGTGGAGAGGGTTA

ATGAACCCAGCATCCTGGAAATGAGCAGAGGAGTCAAGCTCACGGATGTGGCCCCTGTAAGCTTC

TTTCTTGTGCTGGATGTAGTCTACCTCGTGTACGAATCAAAGCACTTACATGAGGGGGCAAAGTCA

GAGACAGCTGAGGAGCTGAAGAAGGTGGCTCAGGAGCTGGAGGAGAAGCTAAACATTCTCAACA

ATAATTATAAGATTCTGCAGGCGGACCAAGAACTGTGAAATTCTAAAATACAGCATAGCAAAACT

TTAACCTCCAAATCAAGCCTCTACTTGAATCCTTTTCTGAGGGATGAATAAGGCATAGGCATCAGG

GGCTGTTGCCAATGTGCATTAGCTGTTTGCAGCCTCACCTTCTTTCATGGAGTTTAAGATATAGTGT

ATTTTCCCAAGGTTTGAACTAGCTCTTCATTTCTTTATGTTTTAAATGCACTGACCTCCCACATTCCC

TTTTTAGTAAAATATTCAGAAATAATTTAAATACATCATTGCAATGAAAATAAATGTTTTTTATTAG

GCAGAATCCAGATGCTCAAGGCCCTTCATAATATCCCCCAGTTTAGTAGTTGGACTTAGGGAACAA

AGGAACCTTTAATAGAAATTGGACAGCAAGAAAGCGAGCTTCTAGCTCGAGATGGTCCATATGAA

TATCCTCCTTAGTTCCTATTCCGCTAGCCTAGAGGGACAGCCCCCCCCCAAAGCCCCCAGGGATGT

AATTACGTCCCTCCCCCGCTAGGGGCAGCAGCGAGCCGCCCGGGGCTCCGCTCCGGTCCGGCGCTC

CCCCCGCATCCCCGAGCCGGCAGCGTGCGGGGACAGCCCGGGCACGGGGAAGGTGGCACGGGAT

CGCTTTCCTCTGAACGCTTCTCGCTGCTCTTTGAGCCTGCAGACACCTGGGGGGATACGGGGAAAA

AGCTTTAGGCTGAAAGAGAGATTTAGAATGACAGAATCATAGAACGGCCTGGGTTGCAAAGGAGC

ACAGTGCTCATCCAGATCCAACCCCCTGCTATGTGCAGGGTCATCAACCAGCAGCCCAGGCTGCCC

-continuede

AGAGCCACATCCAGCCTGGCCTTGAATGCCTGCAGGGATGGGGCATCCACAGCCTCCTTGGGCAA

CCTGTTCAGTGCGTCACCACCCTCTGGGGGAAAAACTGCCTCCTCATATCCAACCCAAACCTCCCC

TGTCTCAGTGTAAAGCCATTCCCCCTTGTCCTATCAAGGGGGAGTTTGCTGTGACATTGTTGGTCTG

GGGTGACACATGTTTGCCAATTCAGTGCATCACGGAGAGGCAGATCTTGGGGATAAGGAAGTGCA

GGACAGCATGGACGTGGGACATGCAGGTGTTGAGGGCTCTGGGACACTCTCCAAGTCACAGCGTT

CAGAACAGCCTTAAGGATAAGAAGATAGGATAGAAGGACAAAGAGCAAGTTAAAACCCAGCATG

GAGAGGAGCACAAAAAGGCCACAGACACTGCTGGTCCCTGTGTCTGAGCCTGCATGTTTGATGGT

GTCTGGATGCAAGCAGAAGGGGTGGAAGAGCTTGCCTGGAGAGATACAGCTGGGTCAGTAGGACT

GGGACAGGCAGCTGGAGAATTGCCATGTAGATGTTCATACAATCGTCAAATCATGAAGGCTGGAA

AAGCCCTCCAAGATCCCCAAGACCAACCCCAACCCACCCACCGTGCCCACTGGCCATGTCCCTCAG

TGCCACATCCCCACAGTTCTTCATCACCTCCAGGGACGGTGACCCCCCCACCTCCGTGGGCAGCTG

TGCCACTGCAGCACCGCTCTTTGGAGAAGGTAAATCTTGCTAAATCCAGCCCGACCCTCCCCTGGC

ACAACGTAAGGCCATTATCTCTCATCCAACTCCAGGACGGAGTCAGTGAGGATGGGGCTGGATCC

GAAGCAGCTCCAGCCTACACAATCGCTCAAGACGTGTAATGCTTTTATTATATATTAGTCACGATA

TCTATAACAAGAAAATATATATATAATAAGTTATCACGTAAGTAGAACATGAAATAACAATATAA

TTATCGTATGAGTTAAATCTTAAAAGTCACGTAAAAGATAATCATGCGTCATTTTGACTCACGCGG

TCGTTATAGTTCAAAATCAGTGACACTTACCGCATTGACAAGCACGCCTCACGGGAGCTCCAAGCG

GCGACTGAGATGTCCTAAATGCACAGCGACGGATTCGCGCTATTTAGAAAGAGAGAGCAATATTT

CAAGAATGCATGCGTCAATTTTACGCAGACTATCTTTCTAGGGTTAAAAAAGATTTGCGCTTTACT

CGACCTAAACTTTAAACACGTCATAGAATCTTCGTTTGACAAAAACCACATTGTGGGGTACCGAGC

TCTTAATTAAGGCGCGCCGGGGAGGTTCCCTTTAGTGAGGGTTAATTGCGGGTCGCCCTATAGTGA

GTCGTATTACAATTCACTGGCCGTCGTTTTACAACGTCGTGACTGGGAAAACCCTGGCGTTACCCA

ACTTAATCGCCTTGCAGCACATCCCCCTTTCGCCAGCTGGCGTAATAGCGAAGAGGCCCGCACCGA

TCGCCCTTCCCAACAGTTGCGCAGCCTGAATGGCGAATGGCAAATTGTAAGCGTTAATATTTTGTT

AAAATTCGCGTTAAATTTTTGTTAAATCAGCTCATTTTTTAACCAATAGGCCGAAATCGGCAAAAT

CCCTTATAAATCAAAAGAATAGACCGAGATAGGGTTGAGTGTTGTTCCAGTTTGGAACAAGAGTC

CACTATTAAAGAACGTGGACTCCAACGTCAAAGGGCGAAAAACCGTCTATCAGGGCGATGGCCCA

CTACGTGAACCATCACCCTAATCAAGTTTTTTGGGGTCGAGGTGCCGTAAAGCACTAAATCGGAAC

CCTAAAGGGAGCCCCCGATTTAGAGCTTGACGGGGAAAGCCGGCGAACGTGGCGAGAAAGGAAG

GGAAGAAAGCGAAAGGAGCGGGCGCTAGGGCGCTGGCAAGTGTAGCGGTCACGCTGCGCGTAAC

CACCACACCCGCCGCGCTTAATGCGCCGCTACAGGGCGCGTCAG

TOIC-Cas9_obl_r26_AAVS_SANeo (SEQ ID NO: 13)

GTGGCACTTTTCGGGGAAATGTGCGCGGAACCCCTATTTGTTTATTTTTCTAAATACATTCAAATAT

GTATCCGCTCATGAGACAATAACCCTGATAAATGCTTCAATAATATTGAAAAAGGAAGAGTATGA

GTATTCAACATTTCCGTGTCGCCCTTATTCCCTTTTTTGCGGCATTTTGCCTTCCTGTTTTTGCTCAC

CCAGAAACGCTGGTGAAAGTAAAAGATGCTGAAGATCAGTTGGGTGCACGAGTGGGTTACATCGA

ACTGGATCTCAACAGCGGTAAGATCCTTGAGAGTTTTCGCCCCGAAGAACGTTTTCCAATGATGAG

CACTTTTAAAGTTCTGCTATGTGGCGCGGTATTATCCCGTATTGACGCCGGGCAAGAGCAACTCGG

TCGCCGCATACACTATTCTCAGAATGACTTGGTTGAGTACTCACCAGTCACAGAAAAGCATCTTAC

GGATGGCATGACAGTAAGAGAATTATGCAGTGCTGCCATAACCATGAGTGATAACACTGCGGCCA

ACTTACTTCTGACAACGATCGGAGGACCGAAGGAGCTAACCGCTTTTTTGCACAACATGGGGGATC

-continuede

ATGTAACTCGCCTTGATCGTTGGGAACCGGAGCTGAATGAAGCCATACCAAACGACGAGCGTGAC

ACCACGATGCCTGTAGCAATGGCAACAACGTTGCGCAAACTATTAACTGGCGAACTACTTACTCTA

GCTTCCCGGCAACAATTAATAGACTGGATGGAGGCGGATAAAGTTGCAGGACCACTTCTGCGCTC

GGCCCTTCCGGCTGGCTGGTTTATTGCTGATAAATCTGGAGCCGGTGAGCGTGGGTCTCGCGGTAT

CATTGCAGCACTGGGGCCAGATGGTAAGCCCTCCCGTATCGTAGTTATCTACACGACGGGGAGTCA

GGCAACTATGGATGAACGAAATAGACAGATCGCTGAGATAGGTGCCTCACTGATTAAGCATTGGT

AACTGTCAGACCAAGTTTACTCATATATACTTTAGATTGATTTAAAACTTCATTTTTAATTTAAAAG

GATCTAGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGTAATC

TGCTGCTTGCAAACAAAAAAACCACCGCTACCAGCGGTGGTTTGTTTGCCGGATCAAGAGCTACCA

ACTCTTTTTCCGAAGGTAACTGGCTTCAGCAGAGCGCAGATACCAAATACTGTTCTTCTAGTGTAG

CCGTAGTTAGGCCACCACTTCAAGAACTCTGTAGCACCGCCTACATACCTCGCTCTGCTAATCCTG

TTACCAGTGGCTGCTGCCAGTGGCGATAAGTCGTGTCTTACCGGGTTGGACTCAAGACGATAGTTA

CCGGATAAGGCGCAGCGGTCGGGCTGAACGGGGGGTTCGTGCACACAGCCCAGCTTGGAGCGAAC

GACCTACACCGAACTGAGATACCTACAGCGTGAGCTATGAGAAAGCGCCACGCTTCCCGAAGGGA

GAAAGGCGGACAGGTATCCGGTAAGCGGCAGGGTCGGAACAGGAGAGCGCACGAGGGAGCTTCC

AGGGGGAAACGCCTGGTATCTTTATAGTCCTGTCGGGTTTCGCCACCTCTGACTTGAGCGTCGATT

TTTGTGATGCTCGTCAGGGGGGCGGAGCCTATGGAAAAACGCCAGCAACGCGGCCTTTTTACGGTT

CCTGGCCTTTTGCTGGCCTTTTGCTCACATGTTCTTTCCTGCGTTATCCCCTGATTCTGTGGATAACC

GTATTACCGCCTTTGAGTGAGCTGATACCGCTCGCCGCAGCCGAACGACCGAGCGCAGCGAGTCA

GTGAGCGAGGAAGCGGAAGAGCGCCCAATACGCAAACCGCCTCTCCCCGCGCGTTGGCCGATTCA

TTAATGCAGCTGGCACGACAGGTTTCCCGACTGGAAAGCGGGCAGTGAGCGCAACGCAATTAATG

TGAGTTAGCTCACTCATTAGGCACCCCAGGCTTTACACTTTATGCTTCCGGCTCGTATGTTGTGTGG

AATTGTGAGCGGATAACAATTTCACACAGGAAACAGCTATGACCATGATTACGCCAAGCGCGCAA

TTAACCCTCACTAAAGGGAACCTCCCCTAGCTTAATTAACCCTAGAAAGATAATCATATTGTGACG

TACGTTAAAGATAATCATGCGTAAAATTGACGCATGTGTTTTATCGATCTGTATATCGAGGTTTATT

TATTAATTTGAATAGATATTAAGTTTTATTATATTTACACTTACATACTAATAATAAATTCAACAAA

CAATTTATTTATGTTTATTTATTTATTAAAAAAAAACAAAAACTCAAAATTTCTTCTATAAAGTAAC

AAAACTTTTAAACATTCTCTCTTTTACAAAAATAAACTTATTTTGTACTTTAAAAACAGTCATGTTG

TATTATAAAATAAGTAATTAGCTTAACTTATACATAATAGAAACAAATTATACTTATTAATCGCAT

TGATTATTGACTAGTCACAATATGATTATCTTTCTAGGGTTAATTAAGATATCTGAAGTTCCTATAC

TTTCTAGAGAATAGGAACTTCGGAATAGGAACTTCAAAGCAAGCTAGAGACCATTAAGGGTTCCG

GATCAGCTTGATTCGAGCCCCAGCTGGTTCTTTCCGCCTCAGAAGCCATAGAGCCCACCGCATCCC

CAGCATGCCTGCTATTGTCTTCCCAATCCTCCCCCTTGCTGTCCTGCCCCACCCCACCCCCCCAGAAT

AGAATGACACCTACTCAGACAATGCGATGCAATTTCCTCATTTTATTAGGAAAGGACAGTGGGAGT

GGCACCTTCCAGGGTCAAGGAAGGCACGGGGGAGGGGCAAACAACAGATGGCTGGCAACTAGAA

GGCACAGTCGAGGCTGATCAGCGAGCTCTAGAGAATTGATCCCCTCAGAAGAACTCGTCAAGAAG

GCGATAGAAGGCGATGCGCTGCGAATCGGGAGCGGCGATACCGTAAAGCACGAGGAAGCGGTCA

GCCCATTCGCCGCCAAGCTCTTCAGCAATATCACGGGTAGCCAACGCTATGTCCTGATAGCGGTCC

GCCACACCCAGCCGGCCACAGTCGATGAATCCAGAAAAGCGGCCATTTTCCACCATGATATTCGG

CAAGCAGGCATCGCCATGGGTCACGACGAGATCCTCGCCGTCGGGCATGCGCGCCTTGAGCCTGG

-continuede

CGAACAGTTCGGCTGGCGCGAGCCCCTGATGCTCTTCGTCCAGATCATCCTGATCGACAAGACCGG

CTTCCATCCGAGTACGTGCTCGCTCGATGCGATGTTTCGCTTGGTGGTCGAATGGGCAGGTAGCCG

GATCAAGCGTATGCAGCCGCCGCATTGCATCAGCCATGATGGATACTTTCTCGGCAGGAGCAAGG

TGAGATGACAGGAGATCCTGCCCCGGCACTTCGCCCAATAGCAGCCAGTCCCTTCCCGCTTCAGTG

ACAACGTCGAGCACAGCTGCGCAAGGAACGCCCGTCGTGGCCAGCCACGATAGCCGCGCTGCCTC

GTCCTGCAGTTCATTCAGGGCACCGGACAGGTCGGTCTTGACAAAAAGAACCGGGCGCCCCTGCG

CTGACAGCCGGAACACGGCGGCATCAGAGCAGCCGATTGTCTGTTGTGCCCAGTCATAGCCGAAT

AGCCTCTCCACCCAAGCGGCCGGAGAACCTGCGTGCAATCCATCTTGTTCAATGGCCGATCCCATG

GCGGTATCGATAAGCTAGCTTGGGCTGCAGGTCGAGGGACCTAATTAAGGGTTCCGGATCCACTA

GTTCTAGAGCGGCCTCGACTCTACGATACCGTCGATCCCCACTGGAAAGACCGCGAAGAGTTTGTC

CTCAACCGCGAGCTGTGGAAAAAAAAGGGACAGGATAAGTATGACATCATCAAGGAAACCCTGG

ACTACTGCGCCCTACAGATCCCTGAAGTTCCTATACTTTCTAGAGAATAGGAACTTCGGAATAGGA

ACTTCAAAGATGCAACTCCAGTCTTTCTTCTTCTTGGGCGGGAGTCTACTAGTTATTAATAGTAATC

AATTACGGGGTCATTAGTTCATAGCCCATATATGGAGTTCCGCGTTACATAACTTACGGTAAATGG

CCCGCCTGGCTGACCGCCCAACGACCCCCGCCCATTGACGTCAATAATGACGTATGTTCCCATAGT

AACGCCAATAGGGACTTTCCATTGACGTCAATGGGTGGACTATTTACGGTAAACTGCCCACTTGGC

AGTACATCAAGTGTATCATATGCCAAGTACGCCCCCTATTGACGTCAATGACGGTAAATGGCCCGC

CTGGCATTATGCCCAGTACATGACCTTATGGGACTTTCCTACTTGGCAGTACATCTACGTATTAGTC

ATCGCTATTACCATGGGTCGAGGTGAGCCCCACGTTCTGCTTCACTCTCCCCATCTCCCCCCCCTCC

CCACCCCCAATTTTGTATTTATTTATTTTTTAATTATTTTGTGCAGCGATGGGGGCGGGGGGGGGGG

GGGCGCGCGCCAGGCGGGGCGGGGCGGGGCGAGGGGCGGGGCGGGGCGAGGCGGAGAGGTGCG

GCGGCAGCCAATCAGAGCGGCGCGCTCCGAAAGTTTCCTTTTATGGCGAGGCGGCGGCGGCGGCG

GCCCTATAAAAAGCGAAGCGCGCGGCGGGCGGGAGTCGCTGCGTTGCCTTCGCCCCGTGCCCCGC

TCCGCGCCGCCTCGCGCCGCCCGCCCCGGCTCTGACTGACCGCGTTACTCCCACAGGTGAGCGGGC

GGGACGGCCCTTCTCCTCCGGGCTGTAATTAGCGCTTGGTTTAATGACGGCTCGTTTCTTTTCTGTG

GCTGCGTGAAAGCCTTAAAGGGCTCCGGGAGGGCCCTTTGTGCGGGGGGGAGCGGCTCGGGGGGT

GCGTGCGTGTGTGTGTGCGTGGGGAGCGCCGCGTGCGGCCCGCGCTGCCCGGCGGCTGTGAGCGC

TGCGGGCGCGGCGCGGGGCTTTGTGCGCTCCGCGTGTGCGCGAGGGGAGCGCGGCCGGGGGCGGT

GCCCCGCGGTGCGGGGGGGCTGCGAGGGGAACAAAGGCTGCGTGCGGGGTGTGTGCGTGGGGGG

GTGAGCAGGGGGTGTGGGCGCGGCGGTCGGGCTGTAACCCCCCCCTGCACCCCCCTCCCCGAGTT

GCTGAGCACGGCCCGGCTTCGGGTGCGGGGCTCCGTGCGGGGCGTGGCGCGGGGCTCGCCGTGCC

GGGCGGGGGGTGGCGGCAGGTGGGGGTGCCGGGCGGGGCGGGGCCGCCTCGGGCCGGGGAGGGC

TCGGGGGAGGGGCGCGGCGGCCCCGGAGCGCCGGCGGCTGTCGAGGCGCGGCGAGCCGCAGCCA

TTGCCTTTTATGGTAATCGTGCGAGAGGGCGCAGGGACTTCCTTTGTCCCAAATCTGGCGGAGCCG

AAATCTGGGAGGCGCCGCCGCACCCCCTCTAGCGGGCGCGGGCGAAGCGGTGCGGCGCCGGCAGG

AAGGAAATGGGCGGGGAGGGCCTTCGTGCGTCGCCGCGCCGCCGTCCCCTTCTCCATCTCCAGCCT

CGGGGCTGCCGCAGGGGGACGGCTGCCTTCGGGGGGGACGGGGCAGGGCGGGGTTCGGCTTCTGG

CGTGTGACCGGCGGCTCTAGAGCCTCTGCTAACCATGTTCATGCCTTCTTCTTTTTCCTACAGCTCC

TGGGCAACGTGCTGGTTATTGTGCTGTCTCATCATTTTGGCAAAGAATTCGCCACCATGGTGCCCA

AGAAGAAGAGGAAAGTCTCTAGACTGGACAAGAGCAAAGTCATAAACTCTGCTCTGGAATTACTC

AATGGAGTCGGTATCGAAGGCCTGACGACAAGGAAACTCGCTCAAAAGCTGGGAGTTGAGCAGCC

-continuede

TACCCTGTACTGGCACGTGAAGAACAAGCGGGCCCTGCTCGATGCCCTGCCAATCGAGATGCTGG

ACAGGCATCATACCCACTCCTGCCCCCTGGAAGGCGAGTCATGGCAAGACTTTCTGCGGAACAAC

GCCAAGTCATACCGCTGTGCTCTCCTCTCACATCGCGACGGGGCTAAAGTGCATCTCGGCACCCGC

CCAACAGAGAAACAGTACGAAACCCTGGAAAATCAGCTCGCGTTCCTGTGTCAGCAAGGCTTCTC

CCTGGAGAACGCACTGTACGCTCTGTCCGCCGTGGGCCACTTTACACTGGGCTGCGTATTGGAGGA

ACAGGAGCATCAAGTAGCAAAAGAGGAAAGAGAGACACCTACCACCGATTCTATGCCCCCACTTC

TGAAACAAGCAATTGAGCTGTTCGACCGGCAGGGAGCCGAACCTGCCTTCCTTTTCGGCCTGGAAC

TAATCATATGTGGCCTGGAGAAACAGCTAAAGTGCGAAAGCGGCGGGCCGACCGACGCCCTTGAC

GATTTTGACTTAGACATGCTCCCAGCCGATGCCCTTGACGACTTTGACCTTGATATGCTGCCTGCTG

ACGCTCTTGACGATTTTGACCTTGACATGCTCCCCGGGTAAAGCGGCCGCGACTCTAGATCATAAT

CAGCCATACCACATTTGTAGAGGTTTTACTTGCTTTAAAAAACCTCCCACACCTCCCCCTGAACCTG

AAACATAAAATGAATGCAATTGTTGTTGTTAACTTGTTTATTGCAGCTTATAATGGTTACAAATAA

AGCAATAGCATCACAAATTTCACAAATAAAGCATTTTTTTCACTGCATTCTAGTTGTGGTTTGTCCA

AACTCATCAATGTATCTTAAGGGATCCCTAGAGGGACAGCCCCCCCCCAAAGCCCCCAGGGATGT

AATTACGTCCCTCCCCCGCTAGGGGCAGCAGCGAGCCGCCCGGGGCTCCGCTCCGGTCCGGCGCTC

CCCCCGCATCCCCGAGCCGGCAGCGTGCGGGGACAGCCCGGGCACGGGGAAGGTGGCACGGGAT

CGCTTTCCTCTGAACGCTTCTCGCTGCTCTTTGAGCCTGCAGACACCTGGGGGGATACGGGGAAAA

AGCTTTAGGCTGAAAGAGAGATTTAGAATGACAGAATCATAGAACGGCCTGGGTTGCAAAGGAGC

ACAGTGCTCATCCAGATCCAACCCCCTGCTATGTGCAGGGTCATCAACCAGCAGCCCAGGCTGCCC

AGAGCCACATCCAGCCTGGCCTTGAATGCCTGCAGGGATGGGGCATCCACAGCCTCCTTGGGCAA

CCTGTTCAGTGCGTCACCACCCTCTGGGGGAAAAACTGCCTCCTCATATCCAACCCAAACCTCCCC

TGTCTCAGTGTAAAGCCATTCCCCCTTGTCCTATCAAGGGGGAGTTTGCTGTGACATTGTTGGTCTG

GGGTGACACATGTTTGCCAATTCAGTGCATCACGGAGAGGCAGATCTTGGGGATAAGGAAGTGCA

GGACAGCATGGACGTGGGACATGCAGGTGTTGAGGGCTCTGGGACACTCTCCAAGTCACAGCGTT

CAGAACAGCCTTAAGGATAAGAAGATAGGATAGAAGGACAAAGAGCAAGTTAAAACCCAGCATG

GAGAGGAGCACAAAAAGGCCACAGACACTGCTGGTCCCTGTGTCTGAGCCTGCATGTTTGATGGT

GTCTGGATGCAAGCAGAAGGGGTGGAAGAGCTTGCCTGGAGAGATACAGCTGGGTCAGTAGGACT

GGGACAGGCAGCTGGAGAATTGCCATGTAGATGTTCATACAATCGTCAAATCATGAAGGCTGGAA

AAGCCCTCCAAGATCCCCAAGACCAACCCCAACCCACCCACCGTGCCCACTGGCCATGTCCCTCAG

TGCCACATCCCCACAGTTCTTCATCACCTCCAGGGACGGTGACCCCCCCACCTCCGTGGGCAGCTG

TGCCACTGCAGCACCGCTCTTTGGAGAAGGTAAATCTTGCTAAATCCAGCCCGACCCTCCCCTGGC

ACAACGTAAGGCCATTATCTCTCATCCAACTCCAGGACGGAGTCAGTGAGGATGGGGCTGTCGAC

CTAGAGGGACAGCCCCCCCCCAAAGCCCCCAGGGATGTAATTACGTCCCTCCCCCGCTAGGGGCA

GCAGCGAGCCGCCCGGGGCTCCGCTCCGGTCCGGCGCTCCCCCCGCATCCCCGAGCCGGCAGCGT

GCGGGGACAGCCCGGGCACGGGGAAGGTGGCACGGGATCGCTTTCCTCTGAACGCTTCTCGCTGC

TCTTTGAGCCTGCAGACACCTGGGGGGATACGGGGAAAAAGCTTTAGGCTGAAAGAGAGATTTAG

AATGACAGAATCATAGAACGGCCTGGGTTGCAAAGGAGCACAGTGCTCATCCAGATCCAACCCCC

TGCTATGTGCAGGGTCATCAACCAGCAGCCCAGGCTGCCCAGAGCCACATCCAGCCTGGCCTTGA

ATGCCTGCAGGGATGGGGCATCCACAGCCTCCTTGGGCAACCTGTTCAGTGCGTCACCACCCTCTG

GGGGAAAAACTGCCTCCTCATATCCAACCCAAACCTCCCCTGTCTCAGTGTAAAGCCATTCCCCCT

TGTCCTATCAAGGGGGAGTTTGCTGTGACATTGTTGGTCTGGGGTGACACATGTTTGCCAATTCAG

-continued

TGCATCACGGAGAGGCAGATCTTGGGGATAAGGAAGTGCAGGACAGCATGGACGTGGGACATGC

AGGTGTTGAGGGCTCTGGGACACTCTCCAAGTCACAGCGTTCAGAACAGCCTTAAGGATAAGAAG

ATAGGATAGAAGGACAAAGAGCAAGTTAAAACCCAGCATGGAGAGGAGCACAAAAAGGCCACAG

ACACTGCTGGTCCCTGTGTCTGAGCCTGCATGTTTGATGGTGTCTGGATGCAAGCAGAAGGGGTGG

AAGAGCTTGCCTGGAGAGATACAGCTGGGTCAGTAGGACTGGGACAGGCAGCTGGAGAATTGCCA

TGTAGATGTTCATACAATCGTCAAATCATGAAGGCTGGAAAAGCCCTCCAAGATCCCCAAGACCA

ACCCCAACCCACCCACCGTGCCCACTGGCCATGTCCCTCAGTGCCACATCCCCACAGTTCTTCATC

ACCTCCAGGGACGGTGACCCCCCCACCTCCGTGGGCAGCTGTGCCACTGCAGCACCGCTCTTTGGA

GAAGGTAAATCTTGCTAAATCCAGCCCGACCCTCCCCTGGCACAACGTAAGGCCATTATCTCTCAT

CCAACTCCAGGACGGAGTCAGTGAGGATGGGGCTCAATTGTTTACTCCCTATCAGTGATAGAGAA

CGTATGAAGAGTTTACTCCCTATCAGTGATAGAGAACGTATGCAGACTTTACTCCCTATCAGTGAT

AGAGAACGTATAAGGAGTTTACTCCCTATCAGTGATAGAGAACGTATGACCAGTTTACTCCCTATC

AGTGATAGAGAACGTATCTACAGTTTACTCCCTATCAGTGATAGAGAACGTATATCCAGTTTACTC

CCTATCAGTGATAGAGAACGTATAAGCTTTAGGCGTGTACGGTGGGCGCCTATAAAAGCAGAGCT

CGTTTAGTGAACCGTCAGATCGCCTGGAGCAATTCCACAACACTTTTGTCTTATACCAACTTTCCGT

ACCACTTCCTACCCTCGTAAAAAGCTTGTCCACCATGGCTCCTAAGAAAAAGCGGAAGGTGGACA

AGAAATACTCAATCGGGCTGGACATCGGAACTAACTCAGTGGGGTGGGCAGTCATTACTGACGAG

TACAAAGTGCCAAGCAAGAAATTTAAGGTCCTGGGCAACACCGATAGGCACTCCATCAAGAAAAA

TCTGATTGGGGCCCTGCTGTTCGACTCTGGAGAGACAGCTGAAGCAACTAGACTGAAAAGGACTG

CTAGAAGGCGCTATACCCGGCGAAAGAATCGCATCTGCTACCTGCAGGAGATTTTCTCTAACGAA

ATGGCCAAGGTGGACGATAGTTTCTTTCATCGGCTGGAGGAATCATTCCTGGTCGAGGAAGATAA

GAAACACGAGAGACATCCTATCTTTGGAAACATTGTGGACGAGGTCGCTTATCACGAAAAATACC

CCACCATCTATCATCTGCGCAAGAAACTGGTGGACTCTACAGATAAAGCAGACCTGCGGCTGATCT

ATCTGGCCCTGGCTCACATGATTAAGTTCAGAGGCCATTTTCTGATCGAGGGAGATCTGAACCCAG

ACAATAGCGATGTGGACAAGCTGTTCATCCAGCTGGTCCAGACATACAATCAGCTGTTTGAGGAA

AACCCTATTAATGCATCTGGCGTGGACGCAAAAGCCATCCTGAGTGCCAGGCTGTCTAAGAGTAG

AAGGCTGGAGAACCTGATCGCTCAGCTGCCAGGCGAAAAGAAAAACGGCCTGTTTGGAAATCTGA

TTGCACTGTCACTGGGACTGACACCTAACTTCAAGAGCAATTTTGATCTGGCCGAGGACGCTAAAC

TGCAGCTGAGCAAGGACACTTATGACGATGACCTGGATAACCTGCTGGCTCAGATCGGAGATCAG

TACGCAGACCTGTTCCTGGCCGCTAAGAATCTGTCTGACGCTATCCTGCTGAGTGATATTCTGCGG

GTGAACACCGAGATTACAAAAGCCCCTCTGTCAGCTAGCATGATCAAGAGATATGACGAGCACCA

TCAGGATCTGACCCTGCTGAAGGCACTGGTGCGCCAGCAGCTGCCCGAGAAGTACAAGGAAATCT

TCTTTGATCAGAGTAAGAACGGGTACGCCGGTTATATTGACGGCGGAGCTTCACAGGAGGAATTCT

ACAAGTTTATCAAACCTATTCTGGAGAAGATGGACGGCACCGAGGAACTGCTGGTGAAACTGAAT

CGCGAGGACCTGCTGCGCAAGCAGCGGACATTTGATAACGGCTCCATCCCCCACCAGATTCATCTG

GGAGAGCTGCACGCAATCCTGCGACGACAGGAAGACTTCTACCCATTTCTGAAGGATAACCGCGA

GAAGATCGAAAAAATTCTGACCTTCCGGATCCCTTACTATGTGGGGCCCCTGGCAAGGGGTAATTC

CCGCTTTGCCTGGATGACACGGAAATCTGAGGAAACAATCACTCCTTGGAACTTCGAGGAAGTGG

TCGATAAGGGAGCTTCCGCACAGTCTTTCATCGAGAGAATGACAAACTTCGACAAAAACCTGCCA

AATGAGAAAGTGCTGCCTAAGCACAGTCTGCTGTACGAGTATTTCACAGTCTATAACGAACTGACT

AAGGTGAAATACGTCACCGAGGGGATGAGGAAGCCCGCCTTCCTGAGCGGTGAACAGAAGAAAG

-continuede

CTATCGTGGACCTGCTGTTTAAAACCAATCGCAAGGTGACAGTCAAGCAGCTGAAGGAGGACTAC

TTCAAGAAAATTGAATGTTTCGATTCTGTGGAGATCAGTGGCGTCGAAGACAGATTTAACGCTTCT

CTGGGAACCTACCACGATCTGCTGAAGATCATTAAGGATAAAGACTTCCTGGACAACGAGGAAAA

TGAGGATATCCTGGAAGACATTGTGCTGACCCTGACACTGTTTGAGGATCGCGAAATGATCGAGG

AACGGCTGAAAACTTATGCCCATCTGTTCGATGACAAGGTGATGAAACAGCTGAAGCGAAGAAGG

TACACCGGCTGGGGACGACTGAGCAGAAAGCTGATCAACGGCATTCGGGACAAACAGAGTGGAA

AGACTATCCTGGACTTTCTGAAATCAGATGGCTTCGCTAACAGAAATTTTATGCAGCTGATTCACG

ATGACAGCCTGACCTTCAAAGAGGATATCCAGAAGGCACAGGTGTCCGGGCAGGGTGACTCTCTG

CACGAGCATATCGCAAACCTGGCCGGGTCCCCCGCCATCAAGAAAGGTATTCTGCAGACCGTGAA

GGTGGTCGATGAGCTGGTGAAAGTCATGGGCAGGCATAAGCCAGAAAACATCGTGATTGAGATGG

CCCGCGAAAATCAGACCACACAGAAAGGACAGAAGAACAGCCGCGAGCGGATGAAAAGGATCGA

GGAAGGCATTAAGGAACTGGGATCCCAGATCCTGAAAGAGCACCCTGTGGAAAACACTCAGCTGC

AGAATGAGAAGCTGTATCTGTACTATCTGCAGAATGGGCGGGATATGTACGTGGACCAGGAGCTG

GATATTAACCGACTGTCTGATTACGACGTGGATCATATCGTCCCACAGTCATTCCTGAAAGATGAC

AGCATTGACAATAAGGTGCTGACCCGGAGTGACAAAAACCGAGGAAAGAGTGATAATGTCCCTTC

AGAGGAAGTGGTCAAGAAAATGAAGAACTACTGGAGACAGCTGCTGAATGCCAAACTGATCACA

CAGCGAAAGTTTGATAACCTGACTAAAGCTGAGAGAGGGGGTCTGTCAGAACTGGACAAAGCAGG

CTTCATCAAGCGACAGCTGGTGGAGACCAGACAGATCACAAAGCACGTCGCTCAGATTCTGGATA

GCAGGATGAACACAAAGTACGATGAGAATGACAAACTGATCCGCGAAGTGAAGGTCATTACTCTG

AAGTCAAAACTTGTGAGCGACTTCAGAAAGGATTTCCAGTTCTACAAAGTCAGGGAGATCAACAA

TTATCACCATGCTCATGACGCATACCTGAACGCAGTGGTCGGGACCGCCCTGATTAAGAAATACCC

CAAACTGGAGAGCGAATTCGTGTACGGTGACTATAAGGTGTACGATGTCAGAAAAATGATCGCCA

AGAGTGAGCAGGAAATTGGAAAAGCCACCGCTAAGTATTTCTTTTACTCAAACATCATGAATTTCT

TTAAGACTGAGATCACCCTGGCAAATGGGGAAATCCGAAAGAGACCACTGATTGAGACTAACGGC

GAGACCGGAGAAATCGTGTGGGACAAGGGTAGGGATTTTGCCACAGTGCGCAAGGTCCTGTCCAT

GCCTCAAGTGAATATTGTCAAGAAAACAGAGGTGCAGACTGGCGGATTCAGTAAGGAATCAATTC

TGCCCAAACGGAACTCTGATAAGCTGATCGCCCGAAAGAAAGACTGGGATCCCAAGAAATATGGG

GGTTTCGACTCCCCAACAGTGGCTTACTCTGTCCTGGTGGTCGCAAAGGTGGAGAAGGGGAAAAG

CAAGAAACTGAAATCCGTCAAGGAGCTGCTGGGTATCACTATTATGGAGAGGAGCTCCTTCGAGA

AGAACCCCATCGATTTTCTGGAGGCTAAAGGCTATAAGGAAGTGAAGAAAGACCTGATCATTAAA

CTGCCAAAGTACAGCCTGTTTGAGCTGGAAAACGGAAGGAAGCGAATGCTGGCATCCGCAGGAGA

GCTGCAGAAGGGTAATGAACTGGCCCTGCCTTCTAAGTACGTGAACTTCCTGTATCTGGCTAGCCA

CTACGAGAAGCTGAAAGGCTCCCCCGAGGATAACGAACAGAAACAGCTGTTTGTGGAGCAGCACA

AGCATTATCTGGACGAGATCATTGAACAGATTAGCGAGTTCTCCAAAAGAGTGATCCTGGCTGAC

GCAAATCTGGATAAGGTCCTGAGCGCATACAACAAACACAGAGATAAGCCAATCAGGGAGCAGG

CCGAAAATATCATTCATCTGTTCACTCTGACCAACCTGGGAGCCCCTGCAGCCTTCAAGTATTTTG

ACACTACCATCGATCGGAAACGATACACATCCACTAAGGAGGTGCTGGACGCTACCCTGATTCAC

CAGAGCATTACCGGCCTGTATGAAACAAGGATTGACCTGTCTCAGCTGGGGGGCGACCTCGAGGG

AAGCGGAGAGGGCAGAGGAAGTCTGCTAACATGCGGTGACGTCGAGGAGAATCCTGGCCCAGCA

CCGGGATCCATGGTGAGCAAGGGCGAGGAGCTGTTCACCGGGGTGGTGCCCATCCTGGTCGAGCT

GGACGGCGACGTAAACGGCCACAAGTTCAGCGTGTCCGGCGAGGGCGAGGGCGATGCCACCTACG

-continued

GCAAGCTGACCCTGAAGTTCATCTGCACCACCGGCAAGCTGCCCGTGCCCTGGCCCACCCTCGTGA
CCACCTTCACCTACGGCGTGCAGTGCTTCGCCCGCTACCCCGACCACATGAAGCAGCACGACTTCT
TCAAGTCCGCCATGCCCGAAGGCTACGTCCAGGAGCGCACCATCTTCTTCAAGGACGACGGCAAC
TACAAGACCCGCGCCGAGGTGAAGTTCGAGGGCGACACCCTGGTGAACCGCATCGAGCTGAAGGG
CATCGACTTCAAGGAGGACGGCAACATCCTGGGGCACAAGCTGGAGTACAACTACAACAGCCACA
AGGTCTATATCACCGCCGACAAGCAGAAGAACGGCATCAAGGTGAACTTCAAGACCCGCCACAAC
ATCGAGGACGGCAGCGTGCAGCTCGCCGACCACTACCAGCAGAACACCCCCATCGGCGACGGCCC
CGTGCTGCTGCCCGACAACCACTACCTGAGCACCCAGTCCGCCCTGAGCAAAGACCCCAACGAGA
AGCGCGATCACATGGTCCTGCTGGAGTTCGTGACCGCCGCCGGGATCACTCTCGGCATGGACGAG
CTGTACAAGTAAACCTAATCTAGCAGCTCGCTGATCAGCCTCGACTGTGCCTTCTAGTTGCCAGCC
ATCTGTTGTTTGCCCCTCCCCCGTGCCTTCCTTGACCCTGGAAGGTGCCACTCCCACTGTCCTTTCCT
AATAAAATGAGGAAATTGCATCGCATTGTCTGAGTAGGTGTCATTCTATTCTGGGGGGTGGGGTGG
GGCAGGACAGCAAGGGGGAGGATTGGGAAGACAATAGCAGGCATGCTGGGGATGCGGTGGGCTC
TATGGCTTCTGAGGCGGAAAGAACCAGCTGGGGCTCGATCCTCTAGTTGGCGCGTCATGGTCCATA
TGAATATCCTCCTTAGTTCCTATTCCGCTAGCCTAGAGGGACAGCCCCCCCCCAAAGCCCCCAGGG
ATGTAATTACGTCCCTCCCCCGCTAGGGGCAGCAGCGAGCCGCCCGGGGCTCCGCTCCGGTCCGGC
GCTCCCCCCGCATCCCCGAGCCGGCAGCGTGCGGGGACAGCCCGGGCACGGGGAAGGTGGCACGG
GATCGCTTTCCTCTGAACGCTTCTCGCTGCTCTTTGAGCCTGCAGACACCTGGGGGGATACGGGGA
AAAAGCTTTAGGCTGAAAGAGAGATTTAGAATGACAGAATCATAGAACGGCCTGGGTTGCAAAGG
AGCACAGTGCTCATCCAGATCCAACCCCCTGCTATGTGCAGGGTCATCAACCAGCAGCCCAGGCTG
CCCAGAGCCACATCCAGCCTGGCCTTGAATGCCTGCAGGGATGGGGCATCCACAGCCTCCTTGGGC
AACCTGTTCAGTGCGTCACCACCCTCTGGGGGAAAAACTGCCTCCTCATATCCAACCCAAACCTCC
CCTGTCTCAGTGTAAAGCCATTCCCCCTTGTCCTATCAAGGGGGAGTTTGCTGTGACATTGTTGGTC
TGGGGTGACACATGTTTGCCAATTCAGTGCATCACGGAGAGGCAGATCTTGGGGATAAGGAAGTG
CAGGACAGCATGGACGTGGGACATGCAGGTGTTGAGGGCTCTGGGACACTCTCCAAGTCACAGCG
TTCAGAACAGCCTTAAGGATAAGAAGATAGGATAGAAGGACAAAGAGCAAGTTAAAACCCAGCA
TGGAGAGGAGCACAAAAAGGCCACAGACACTGCTGGTCCCTGTGTCTGAGCCTGCATGTTTGATG
GTGTCTGGATGCAAGCAGAAGGGGTGGAAGAGCTTGCCTGGAGAGATACAGCTGGGTCAGTAGGA
CTGGGACAGGCAGCTGGAGAATTGCCATGTAGATGTTCATACAATCGTCAAATCATGAAGGCTGG
AAAAGCCCTCCAAGATCCCCAAGACCAACCCCAACCCACCCACCGTGCCCACTGGCCATGTCCCTC
AGTGCCACATCCCCACAGTTCTTCATCACCTCCAGGGACGGTGACCCCCCCACCTCCGTGGGCAGC
TGTGCCACTGCAGCACCGCTCTTTGGAGAAGGTAAATCTTGCTAAATCCAGCCCGACCCTCCCCTG
GCACAACGTAAGGCCATTATCTCTCATCCAACTCCAGGACGGAGTCAGTGAGGATGGGGCTGGAT
CCGAAGCAGCTCCAGCCTACACAATCGCTCAAGACGTGTAATGCTTTTATTATATATTAGTCACGA
TATCTATAACAAGAAAATATATATATAATAAGTTATCACGTAAGTAGAACATGAAATAACAATAT
AATTATCGTATGAGTTAAATCTTAAAAGTCACGTAAAAGATAATCATGCGTCATTTTGACTCACGC
GGTCGTTATAGTTCAAAATCAGTGACACTTACCGCATTGACAAGCACGCCTCACGGGAGCTCCAAG
CGGCGACTGAGATGTCCTAAATGCACAGCGACGGATTCGCGCTATTTAGAAAGAGAGAGCAATAT
TTCAAGAATGCATGCGTCAATTTTACGCAGACTATCTTTCTAGGGTTAAAAAAGATTTGCGCTTTA
CTCGACCTAAACTTTAAACACGTCATAGAATCTTCGTTTGACAAAAACCACATTGTGGGGTACCGA
GCTCTTAATTAAGGCGCGCCGGGGAGGTTCCCTTTAGTGAGGGTTAATTGCGGGTCGCCCTATAGT

-continuede

GAGTCGTATTACAATTCACTGGCCGTCGTTTTACAACGTCGTGACTGGGAAAACCCTGGCGTTACC

CAACTTAATCGCCTTGCAGCACATCCCCCTTTCGCCAGCTGGCGTAATAGCGAAGAGGCCCGCACC

GATCGCCCTTCCCAACAGTTGCGCAGCCTGAATGGCGAATGGCAAATTGTAAGCGTTAATATTTTG

TTAAAATTCGCGTTAAATTTTTGTTAAATCAGCTCATTTTTTAACCAATAGGCCGAAATCGGCAAA

ATCCCTTATAAATCAAAAGAATAGACCGAGATAGGGTTGAGTGTTGTTCCAGTTTGGAACAAGAG

TCCACTATTAAAGAACGTGGACTCCAACGTCAAAGGGCGAAAAACCGTCTATCAGGGCGATGGCC

CACTACGTGAACCATCACCCTAATCAAGTTTTTTGGGGTCGAGGTGCCGTAAAGCACTAAATCGGA

ACCCTAAAGGGAGCCCCCGATTTAGAGCTTGACGGGGAAAGCCGGCGAACGTGGCGAGAAAGGA

AGGGAAGAAAGCGAAAGGAGCGGGCGCTAGGGCGCTGGCAAGTGTAGCGGTCACGCTGCGCGTA

ACCACCACACCCGCCGCGCTTAATGCGCCGCTACAGGGCGCGTCAG

TOIC_Cas9Dead_obl_r26_AAV_PgkNeo (SEQ ID NO: 14)

GTGGCACTTTTCGGGGAAATGTGCGCGGAACCCCTATTTGTTTATTTTTCTAAATACATTCAAATAT

GTATCCGCTCATGAGACAATAACCCTGATAAATGCTTCAATAATATTGAAAAAGGAAGAGTATGA

GTATTCAACATTTCCGTGTCGCCCTTATTCCCTTTTTTGCGGCATTTTGCCTTCCTGTTTTTGCTCAC

CCAGAAACGCTGGTGAAAGTAAAAGATGCTGAAGATCAGTTGGGTGCACGAGTGGGTTACATCGA

ACTGGATCTCAACAGCGGTAAGATCCTTGAGAGTTTTCGCCCCGAAGAACGTTTTCCAATGATGAG

CACTTTTAAAGTTCTGCTATGTGGCGCGGTATTATCCCGTATTGACGCCGGGCAAGAGCAACTCGG

TCGCCGCATACACTATTCTCAGAATGACTTGGTTGAGTACTCACCAGTCACAGAAAAGCATCTTAC

GGATGGCATGACAGTAAGAGAATTATGCAGTGCTGCCATAACCATGAGTGATAACACTGCGGCCA

ACTTACTTCTGACAACGATCGGAGGACCGAAGGAGCTAACCGCTTTTTTGCACAACATGGGGGATC

ATGTAACTCGCCTTGATCGTTGGGAACCGGAGCTGAATGAAGCCATACCAAACGACGAGCGTGAC

ACCACGATGCCTGTAGCAATGGCAACAACGTTGCGCAAACTATTAACTGGCGAACTACTTACTCTA

GCTTCCCGGCAACAATTAATAGACTGGATGGAGGCGGATAAAGTTGCAGGACCACTTCTGCGCTC

GGCCCTTCCGGCTGGCTGGTTTATTGCTGATAAATCTGGAGCCGGTGAGCGTGGGTCTCGCGGTAT

CATTGCAGCACTGGGGCCAGATGGTAAGCCCTCCCGTATCGTAGTTATCTACACGACGGGGAGTCA

GGCAACTATGGATGAACGAAATAGACAGATCGCTGAGATAGGTGCCTCACTGATTAAGCATTGGT

AACTGTCAGACCAAGTTTACTCATATATACTTTAGATTGATTTAAAACTTCATTTTTAATTTAAAAG

GATCTAGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGTAATC

TGCTGCTTGCAAACAAAAAAACCACCGCTACCAGCGGTGGTTTGTTTGCCGGATCAAGAGCTACCA

ACTCTTTTTCCGAAGGTAACTGGCTTCAGCAGAGCGCAGATACCAAATACTGTTCTTCTAGTGTAG

CCGTAGTTAGGCCACCACTTCAAGAACTCTGTAGCACCGCCTACATACCTCGCTCTGCTAATCCTG

TTACCAGTGGCTGCTGCCAGTGGCGATAAGTCGTGTCTTACCGGGTTGGACTCAAGACGATAGTTA

CCGGATAAGGCGCAGCGGTCGGGCTGAACGGGGGGTTCGTGCACACAGCCCAGCTTGGAGCGAAC

GACCTACACCGAACTGAGATACCTACAGCGTGAGCTATGAGAAAGCGCCACGCTTCCCGAAGGGA

GAAAGGCGGACAGGTATCCGGTAAGCGGCAGGGTCGGAACAGGAGAGCGCACGAGGGAGCTTCC

AGGGGGAAACGCCTGGTATCTTTATAGTCCTGTCGGGTTTCGCCACCTCTGACTTGAGCGTCGATT

TTTGTGATGCTCGTCAGGGGGGCGGAGCCTATGGAAAAACGCCAGCAACGCGGCCTTTTTACGGTT

CCTGGCCTTTTGCTGGCCTTTTGCTCACATGTTCTTTCCTGCGTTATCCCCTGATTCTGTGGATAACC

GTATTACCGCCTTTGAGTGAGCTGATACCGCTCGCCGCAGCCGAACGACCGAGCGCAGCGAGTCA

GTGAGCGAGGAAGCGGAAGAGCGCCCAATACGCAAACCGCCTCTCCCCGCGCGTTGGCCGATTCA

-continuede

TTAATGCAGCTGGCACGACAGGTTTCCCGACTGGAAAGCGGGCAGTGAGCGCAACGCAATTAATG

TGAGTTAGCTCACTCATTAGGCACCCCAGGCTTTACACTTTATGCTTCCGGCTCGTATGTTGTGTGG

AATTGTGAGCGGATAACAATTTCACACAGGAAACAGCTATGACCATGATTACGCCAAGCGCGCAA

TTAACCCTCACTAAAGGGAACCTCCCCTAGCTTAATTAACCCTAGAAAGATAATCATATTGTGACG

TACGTTAAAGATAATCATGCGTAAAATTGACGCATGTGTTTTATCGATCTGTATATCGAGGTTTATT

TATTAATTTGAATAGATATTAAGTTTTATTATATTTACACTTACATACTAATAATAAATTCAACAAA

CAATTTATTTATGTTTATTTATTTATTAAAAAAAAACAAAAACTCAAAATTTCTTCTATAAAGTAAC

AAAACTTTTAAACATTCTCTCTTTTACAAAAATAAACTTATTTTGTACTTTAAAAACAGTCATGTTG

TATTATAAAATAAGTAATTAGCTTAACTTATACATAATAGAAACAAATTATACTTATTAATCGCAT

TGATTATTGACTAGTCGTATTAAGGGTTCCGGATCAGCTTGATTCGAGCCCCAGCTGGTTCTTTCCG

CCTCAGAAGCCATAGAGCCCACCGCATCCCCAGCATGCCTGCTATTGTCTTCCCAATCCTCCCCCTT

GCTGTCCTGCCCCACCCCACCCCCCAGAATAGAATGACACCTACTCAGACAATGCGATGCAATTTC

CTCATTTTATTAGGAAAGGACAGTGGGAGTGGCACCTTCCAGGGTCAAGGAAGGCACGGGGGAGG

GGCAAACAACAGATGGCTGGCAACTAGAAGGCACAGTCGAGGCTGATCAGCGAGCTCTAGAGAA

TTGATCCCCTCAGAAGAACTCGTCAAGAAGGCGATAGAAGGCGATGCGCTGCGAATCGGGAGCGG

CGATACCGTAAAGCACGAGGAAGCGGTCAGCCCATTCGCCGCCAAGCTCTTCAGCAATATCACGG

GTAGCCAACGCTATGTCCTGATAGCGGTCCGCCACACCCAGCCGGCCACAGTCGATGAATCCAGA

AAAGCGGCCATTTTCCACCATGATATTCGGCAAGCAGGCATCGCCATGGGTCACGACGAGATCCTC

GCCGTCGGGCATGCGCGCCTTGAGCCTGGCGAACAGTTCGGCTGGCGCGAGCCCCTGATGCTCTTC

GTCCAGATCATCCTGATCGACAAGACCGGCTTCCATCCGAGTACGTGCTCGCTCGATGCGATGTTT

CGCTTGGTGGTCGAATGGGCAGGTAGCCGGATCAAGCGTATGCAGCCGCCGCATTGCATCAGCCA

TGATGGATACTTTCTCGGCAGGAGCAAGGTGAGATGACAGGAGATCCTGCCCCGGCACTTCGCCC

AATAGCAGCCAGTCCCTTCCCGCTTCAGTGACAACGTCGAGCACAGCTGCGCAAGGAACGCCCGT

CGTGGCCAGCCACGATAGCCGCGCTGCCTCGTCCTGCAGTTCATTCAGGGCACCGGACAGGTCGGT

CTTGACAAAAAGAACCGGGCGCCCCTGCGCTGACAGCCGGAACACGGCGGCATCAGAGCAGCCG

ATTGTCTGTTGTGCCCAGTCATAGCCGAATAGCCTCTCCACCCAAGCGGCCGGAGAACCTGCGTGC

AATCCATCTTGTTCAATGGCCGATCCCATGGTTTAGTTCCTCACCTTGTCGTATTATACTATGCCGA

TATACTATGCCGATGATTAATTGTCAACACGTGCTGCTGCAGGTCGAAAGGCCCGGAGATGAGGA

AGAGGAGAACAGCGCGGCAGACGTGCGCTTTTGAAGCGTGCAGAATGCCGGGCCTCCGGAGGACC

TTCGGGCGCCCGCCCCGCCCCTGAGCCCGCCCCTGAGCCCGCCCCCGGACCCACCCCTTCCCAGCC

TCTGAGCCCAGAAAGCGAAGGAGCAAAGCTGCTATTGGCCGCTGCCCCAAAGGCCTACCCGCTTC

CATTGCTCAGCGGTGCTGTCCATCTGCACGAGACTAGTGAGACGTGCTACTTCCATTTGTCACGTC

CTGCACGACGCGAGCTGCGGGGCGGGGGGGAACTTCCTGACTAGGGGAGGAGTAGAAGGTGGCG

CGAAGGGGCCACCAAAGAACGGAGCCGGTTGGCGCCTACCGGTGGATGTGGAATGTGTGCGAGCC

AGAGGCCACTTGTGTAGCGCCAAGTGCCCAGCGGGGCTGCTAAAGCGCATGCTCCAGACTGCCTT

GGGAAAAGCGCCTCCCCTACCCGGTAGACACCCCACAGTGGGTGGCCTAGGGACAGGATTGCAAC

TCCAGTCTTTCTTCTTCTTGGGCGGGAGTCACTAGTTATTAATAGTAATCAATTACGGGGTCATTAG

TTCATAGCCCATATATGGAGTTCCGCGTTACATAACTTACGGTAAATGGCCCGCCTGGCTGACCGC

CCAACGACCCCCGCCCATTGACGTCAATAATGACGTATGTTCCCATAGTAACGCCAATAGGGACTT

TCCATTGACGTCAATGGGTGGACTATTTACGGTAAACTGCCCACTTGGCAGTACATCAAGTGTATC

ATATGCCAAGTACGCCCCCTATTGACGTCAATGACGGTAAATGGCCCGCCTGGCATTATGCCCAGT

-continuede

ACATGACCTTATGGGACTTTCCTACTTGGCAGTACATCTACGTATTAGTCATCGCTATTACCATGGG

TCGAGGTGAGCCCCACGTTCTGCTTCACTCTCCCCATCTCCCCCCCCTCCCCACCCCCAATTTTGTA

TTTATTTATTTTTTAATTATTTTGTGCAGCGATGGGGGCGGGGGGGGGGGGGGCGCGCGCCAGGCG

GGGCGGGGCGGGGCGAGGGGCGGGGCGGGGCGAGGCGGAGAGGTGCGGCGGCAGCCAATCAGA

GCGGCGCGCTCCGAAAGTTTCCTTTTATGGCGAGGCGGCGGCGGCGGCGGCCCTATAAAAAGCGA

AGCGCGCGGCGGGCGGGAGTCGCTGCGTTGCCTTCGCCCCGTGCCCCGCTCCGCGCCGCCTCGCGC

CGCCCGCCCCGGCTCTGACTGACCGCGTTACTCCCACAGGTGAGCGGGCGGGACGGCCCTTCTCCT

CCGGGCTGTAATTAGCGCTTGGTTTAATGACGGCTCGTTTCTTTTCTGTGGCTGCGTGAAAGCCTTA

AAGGGCTCCGGGAGGGCCCTTTGTGCGGGGGGGAGCGGCTCGGGGGGTGCGTGCGTGTGTGTGTG

CGTGGGGAGCGCCGCGTGCGGCCCGCGCTGCCCGGCGGCTGTGAGCGCTGCGGGCGCGGCGCGGG

GCTTTGTGCGCTCCGCGTGTGCGCGAGGGGAGCGCGGCCGGGGGCGGTGCCCCGCGGTGCGGGGG

GGCTGCGAGGGGAACAAAGGCTGCGTGCGGGGTGTGTGCGTGGGGGGGTGAGCAGGGGGTGTGG

GCGCGGCGGTCGGGCTGTAACCCCCCCCTGCACCCCCCTCCCCGAGTTGCTGAGCACGGCCCGGCT

TCGGGTGCGGGGCTCCGTGCGGGGCGTGGCGCGGGGCTCGCCGTGCCGGGCGGGGGGTGGCGGCA

GGTGGGGGTGCCGGGCGGGGCGGGGCCGCCTCGGGCCGGGGAGGGCTCGGGGGAGGGGCGCGGC

GGCCCCGGAGCGCCGGCGGCTGTCGAGGCGCGGCGAGCCGCAGCCATTGCCTTTTATGGTAATCG

TGCGAGAGGGCGCAGGGACTTCCTTTGTCCCAAATCTGGCGGAGCCGAAATCTGGGAGGCGCCGC

CGCACCCCCTCTAGCGGGCGCGGGCGAAGCGGTGCGGCGCCGGCAGGAAGGAAATGGGCGGGGA

GGGCCTTCGTGCGTCGCCGCGCCGCCGTCCCCTTCTCCATCTCCAGCCTCGGGGCTGCCGCAGGGG

GACGGCTGCCTTCGGGGGGGACGGGGCAGGGCGGGGTTCGGCTTCTGGCGTGTGACCGGCGGCTC

TAGAGCCTCTGCTAACCATGTTCATGCCTTCTTCTTTTTCCTACAGCTCCTGGGCAACGTGCTGGTT

ATTGTGCTGTCTCATCATTTTGGCAAAGAATTCGCCACCATGGTGCCCAAGAAGAAGAGGAAAGTC

TCTAGACTGGACAAGAGCAAAGTCATAAACTCTGCTCTGGAATTACTCAATGGAGTCGGTATCGA

AGGCCTGACGACAAGGAAACTCGCTCAAAAGCTGGGAGTTGAGCAGCCTACCCTGTACTGGCACG

TGAAGAACAAGCGGGCCCTGCTCGATGCCCTGCCAATCGAGATGCTGGACAGGCATCATACCCAC

TCCTGCCCCCTGGAAGGCGAGTCATGGCAAGACTTTCTGCGGAACAACGCCAAGTCATACCGCTGT

GCTCTCCTCTCACATCGCGACGGGGCTAAAGTGCATCTCGGCACCCGCCCAACAGAGAAACAGTA

CGAAACCCTGGAAAATCAGCTCGCGTTCCTGTGTCAGCAAGGCTTCTCCCTGGAGAACGCACTGTA

CGCTCTGTCCGCCGTGGGCCACTTTACACTGGGCTGCGTATTGGAGGAACAGGAGCATCAAGTAGC

AAAAGAGGAAAGAGAGACACCTACCACCGATTCTATGCCCCCACTTCTGAAACAAGCAATTGAGC

TGTTCGACCGGCAGGGAGCCGAACCTGCCTTCCTTTTCGGCCTGGAACTAATCATATGTGGCCTGG

AGAAACAGCTAAAGTGCGAAAGCGGCGGGCCGACCGACGCCCTTGACGATTTTGACTTAGACATG

CTCCCAGCCGATGCCCTTGACGACTTTGACCTTGATATGCTGCCTGCTGACGCTCTTGACGATTTTG

ACCTTGACATGCTCCCCGGGTAAAGCGGCCGCGACTCTAGATCATAATCAGCCATACCACATTTGT

AGAGGTTTTACTTGCTTTAAAAAACCTCCCACACCTCCCCCTGAACCTGAAACATAAAATGAATGC

AATTGTTGTTGTTAACTTGTTTATTGCAGCTTATAATGGTTACAAATAAAGCAATAGCATCACAAA

TTTCACAAATAAAGCATTTTTTTCACTGCATTCTAGTTGTGGTTTGTCCAAACTCATCAATGTATCT

TAAGGGATCCCTAGAGGGACAGCCCCCCCCCAAAGCCCCCAGGGATGTAATTACGTCCCTCCCCC

GCTAGGGGCAGCAGCGAGCCGCCCGGGGCTCCGCTCCGGTCCGGCGCTCCCCCCGCATCCCCGAG

CCGGCAGCGTGCGGGGACAGCCCGGGCACGGGGAAGGTGGCACGGGATCGCTTTCCTCTGAACGC

TTCTCGCTGCTCTTTGAGCCTGCAGACACCTGGGGGGATACGGGGAAAAAGCTTTAGGCTGAAAG

-continuede

AGAGATTTAGAATGACAGAATCATAGAACGGCCTGGGTTGCAAAGGAGCACAGTGCTCATCCAGA

TCCAACCCCCTGCTATGTGCAGGGTCATCAACCAGCAGCCCAGGCTGCCCAGAGCCACATCCAGCC

TGGCCTTGAATGCCTGCAGGGATGGGGCATCCACAGCCTCCTTGGGCAACCTGTTCAGTGCGTCAC

CACCCTCTGGGGGAAAAACTGCCTCCTCATATCCAACCCAAACCTCCCCTGTCTCAGTGTAAAGCC

ATTCCCCCTTGTCCTATCAAGGGGGAGTTTGCTGTGACATTGTTGGTCTGGGGTGACACATGTTTGC

CAATTCAGTGCATCACGGAGAGGCAGATCTTGGGGATAAGGAAGTGCAGGACAGCATGGACGTGG

GACATGCAGGTGTTGAGGGCTCTGGGACACTCTCCAAGTCACAGCGTTCAGAACAGCCTTAAGGA

TAAGAAGATAGGATAGAAGGACAAAGAGCAAGTTAAAACCCAGCATGGAGAGGAGCACAAAAAG

GCCACAGACACTGCTGGTCCCTGTGTCTGAGCCTGCATGTTTGATGGTGTCTGGATGCAAGCAGAA

GGGGTGGAAGAGCTTGCCTGGAGAGATACAGCTGGGTCAGTAGGACTGGGACAGGCAGCTGGAG

AATTGCCATGTAGATGTTCATACAATCGTCAAATCATGAAGGCTGGAAAAGCCCTCCAAGATCCCC

AAGACCAACCCCAACCCACCCACCGTGCCCACTGGCCATGTCCCTCAGTGCCACATCCCCACAGTT

CTTCATCACCTCCAGGGACGGTGACCCCCCCACCTCCGTGGGCAGCTGTGCCACTGCAGCACCGCT

CTTTGGAGAAGGTAAATCTTGCTAAATCCAGCCCGACCCTCCCCTGGCACAACGTAAGGCCATTAT

CTCTCATCCAACTCCAGGACGGAGTCAGTGAGGATGGGGCTGTCGACCTAGAGGGACAGCCCCCC

CCCAAAGCCCCCAGGGATGTAATTACGTCCCTCCCCCGCTAGGGGCAGCAGCGAGCCGCCCGGGG

CTCCGCTCCGGTCCGGCGCTCCCCCCGCATCCCCGAGCCGGCAGCGTGCGGGGACAGCCCGGGCA

CGGGGAAGGTGGCACGGGATCGCTTTCCTCTGAACGCTTCTCGCTGCTCTTTGAGCCTGCAGACAC

CTGGGGGGATACGGGGAAAAAGCTTTAGGCTGAAAGAGAGATTTAGAATGACAGAATCATAGAA

CGGCCTGGGTTGCAAAGGAGCACAGTGCTCATCCAGATCCAACCCCCTGCTATGTGCAGGGTCATC

AACCAGCAGCCCAGGCTGCCCAGAGCCACATCCAGCCTGGCCTTGAATGCCTGCAGGGATGGGGC

ATCCACAGCCTCCTTGGGCAACCTGTTCAGTGCGTCACCACCCTCTGGGGGAAAAACTGCCTCCTC

ATATCCAACCCAAACCTCCCCTGTCTCAGTGTAAAGCCATTCCCCCTTGTCCTATCAAGGGGGAGT

TTGCTGTGACATTGTTGGTCTGGGGTGACACATGTTTGCCAATTCAGTGCATCACGGAGAGGCAGA

TCTTGGGGATAAGGAAGTGCAGGACAGCATGGACGTGGGACATGCAGGTGTTGAGGGCTCTGGGA

CACTCTCCAAGTCACAGCGTTCAGAACAGCCTTAAGGATAAGAAGATAGGATAGAAGGACAAAGA

GCAAGTTAAAACCCAGCATGGAGAGGAGCACAAAAAGGCCACAGACACTGCTGGTCCCTGTGTCT

GAGCCTGCATGTTTGATGGTGTCTGGATGCAAGCAGAAGGGGTGGAAGAGCTTGCCTGGAGAGAT

ACAGCTGGGTCAGTAGGACTGGGACAGGCAGCTGGAGAATTGCCATGTAGATGTTCATACAATCG

TCAAATCATGAAGGCTGGAAAAGCCCTCCAAGATCCCCAAGACCAACCCCAACCCACCCACCGTG

CCCACTGGCCATGTCCCTCAGTGCCACATCCCCACAGTTCTTCATCACCTCCAGGGACGGTGACCC

CCCCACCTCCGTGGGCAGCTGTGCCACTGCAGCACCGCTCTTTGGAGAAGGTAAATCTTGCTAAAT

CCAGCCCGACCCTCCCCTGGCACAACGTAAGGCCATTATCTCTCATCCAACTCCAGGACGGAGTCA

GTGAGGATGGGGCTCAATTGTTTACTCCCTATCAGTGATAGAGAACGTATGAAGAGTTTACTCCCT

ATCAGTGATAGAGAACGTATGCAGACTTTACTCCCTATCAGTGATAGAGAACGTATAAGGAGTTTA

CTCCCTATCAGTGATAGAGAACGTATGACCAGTTTACTCCCTATCAGTGATAGAGAACGTATCTAC

AGTTTACTCCCTATCAGTGATAGAGAACGTATATCCAGTTTACTCCCTATCAGTGATAGAGAACGT

ATAAGCTTTAGGCGTGTACGGTGGGCGCCTATAAAAGCAGAGCTCGTTTAGTGAACCGTCAGATC

GCCTGGAGCAATTCCACAACACTTTTGTCTTATACCAACTTTCCGTACCACTTCCTACCCTCGTAAA

AAGCTTGTCCACCATGGCTCCTAAGAAAAAGCGGAAGGTGGACAAGAAATACTCAATCGGGCTGG

CCATCGGAACTAACTCAGTGGGGTGGGCAGTCATTACTGACGAGTACAAAGTGCCAAGCAAGAAA

-continued
TTTAAGGTCCTGGGCAACACCGATAGGCACTCCATCAAGAAAAATCTGATTGGGGCCCTGCTGTTC
GACTCTGGAGAGACAGCTGAAGCAACTAGACTGAAAAGGACTGCTAGAAGGCGCTATACCCGGCG
AAAGAATCGCATCTGCTACCTGCAGGAGATTTTCTCTAACGAAATGGCCAAGGTGGACGATAGTTT
CTTTCATCGGCTGGAGGAATCATTCCTGGTCGAGGAAGATAAGAAACACGAGAGACATCCTATCTT
TGGAAACATTGTGGACGAGGTCGCTTATCACGAAAAATACCCCACCATCTATCATCTGCGCAAGA
AACTGGTGGACTCTACAGATAAAGCAGACCTGCGGCTGATCTATCTGGCCCTGGCTCACATGATTA
AGTTCAGAGGCCATTTTCTGATCGAGGGAGATCTGAACCCAGACAATAGCGATGTGGACAAGCTG
TTCATCCAGCTGGTCCAGACATACAATCAGCTGTTTGAGGAAAACCCTATTAATGCATCTGGCGTG
GACGCAAAAGCCATCCTGAGTGCCAGGCTGTCTAAGAGTAGAAGGCTGGAGAACCTGATCGCTCA
GCTGCCAGGCGAAAAGAAAAACGGCCTGTTTGGAAATCTGATTGCACTGTCACTGGGACTGACAC
CTAACTTCAAGAGCAATTTTGATCTGGCCGAGGACGCTAAACTGCAGCTGAGCAAGGACACTTAT
GACGATGACCTGGATAACCTGCTGGCTCAGATCGGAGATCAGTACGCAGACCTGTTCCTGGCCGCT
AAGAATCTGTCTGACGCTATCCTGCTGAGTGATATTCTGCGGGTGAACACCGAGATTACAAAAGCC
CCTCTGTCAGCTAGCATGATCAAGAGATATGACGAGCACCATCAGGATCTGACCCTGCTGAAGGC
ACTGGTGCGCCAGCAGCTGCCCGAGAAGTACAAGGAAATCTTCTTTGATCAGAGTAAGAACGGGT
ACGCCGGTTATATTGACGGCGGAGCTTCACAGGAGGAATTCTACAAGTTTATCAAACCTATTCTGG
AGAAGATGGACGGCACCGAGGAACTGCTGGTGAAACTGAATCGCGAGGACCTGCTGCGCAAGCA
GCGGACATTTGATAACGGCTCCATCCCCCACCAGATTCATCTGGGAGAGCTGCACGCAATCCTGCG
ACGACAGGAAGACTTCTACCCATTTCTGAAGGATAACCGCGAGAAGATCGAAAAAATTCTGACCT
TCCGGATCCCTTACTATGTGGGGCCCCTGGCAAGGGGTAATTCCCGCTTTGCCTGGATGACACGGA
AATCTGAGGAAACAATCACTCCTTGGAACTTCGAGGAAGTGGTCGATAAGGGAGCTTCCGCACAG
TCTTTCATCGAGAGAATGACAAACTTCGACAAAAACCTGCCAAATGAGAAAGTGCTGCCTAAGCA
CAGTCTGCTGTACGAGTATTTCACAGTCTATAACGAACTGACTAAGGTGAAATACGTCACCGAGGG
GATGAGGAAGCCCGCCTTCCTGAGCGGTGAACAGAAGAAAGCTATCGTGGACCTGCTGTTTAAAA
CCAATCGCAAGGTGACAGTCAAGCAGCTGAAGGAGGACTACTTCAAGAAAATTGAATGTTTCGAT
TCTGTGGAGATCAGTGGCGTCGAAGACAGATTTAACGCTTCTCTGGGAACCTACCACGATCTGCTG
AAGATCATTAAGGATAAAGACTTCCTGGACAACGAGGAAAATGAGGATATCCTGGAAGACATTGT
GCTGACCCTGACACTGTTTGAGGATCGCGAAATGATCGAGGAACGGCTGAAAACTTATGCCCATCT
GTTCGATGACAAGGTGATGAAACAGCTGAAGCGAAGAAGGTACACCGGCTGGGGACGACTGAGC
AGAAAGCTGATCAACGGCATTCGGGACAAACAGAGTGGAAAGACTATCCTGGACTTTCTGAAATC
AGATGGCTTCGCTAACAGAAATTTTATGCAGCTGATTCACGATGACAGCCTGACCTTCAAAGAGGA
TATCCAGAAGGCACAGGTGTCCGGGCAGGGTGACTCTCTGCACGAGCATATCGCAAACCTGGCCG
GGTCCCCCGCCATCAAGAAAGGTATTCTGCAGACCGTGAAGGTGGTCGATGAGCTGGTGAAAGTC
ATGGGCAGGCATAAGCCAGAAAACATCGTGATTGAGATGGCCCGCGAAAATCAGACCACACAGA
AAGGACAGAAGAACAGCCGCGAGCGGATGAAAAGGATCGAGGAAGGCATTAAGGAACTGGGATC
CCAGATCCTGAAAGAGCACCCTGTGGAAAACACTCAGCTGCAGAATGAGAAGCTGTATCTGTACT
ATCTGCAGAATGGGCGGGATATGTACGTGGACCAGGAGCTGGATATTAACCGACTGTCTGATTAC
GACGTGGATGCCATCGTCCCACAGTCATTCCTGAAAGATGACAGCATTGACAATAAGGTGCTGAC
CCGGAGTGACAAAAACCGAGGAAAGAGTGATAATGTCCCTTCAGAGGAAGTGGTCAAGAAAATG
AAGAACTACTGGAGACAGCTGCTGAATGCCAAACTGATCACACAGCGAAAGTTTGATAACCTGAC
TAAAGCTGAGAGAGGGGGTCTGTCAGAACTGGACAAAGCAGGCTTCATCAAGCGACAGCTGGTGG -continuede

AGACCAGACAGATCACAAAGCACGTCGCTCAGATTCTGGATAGCAGGATGAACACAAAGTACGAT

GAGAATGACAAACTGATCCGCGAAGTGAAGGTCATTACTCTGAAGTCAAAACTTGTGAGCGACTT

CAGAAAGGATTTCCAGTTCTACAAAGTCAGGGAGATCAACAATTATCACCATGCTCATGACGCAT

ACCTGAACGCAGTGGTCGGGACCGCCCTGATTAAGAAATACCCCAAACTGGAGAGCGAATTCGTG

TACGGTGACTATAAGGTGTACGATGTCAGAAAAATGATCGCCAAGAGTGAGCAGGAAATTGGAAA

AGCCACCGCTAAGTATTTCTTTTACTCAAACATCATGAATTTCTTTAAGACTGAGATCACCCTGGCA

AATGGGGAAATCCGAAAGAGACCACTGATTGAGACTAACGGCGAGACCGGAGAAATCGTGTGGG

ACAAGGGTAGGGATTTTGCCACAGTGCGCAAGGTCCTGTCCATGCCTCAAGTGAATATTGTCAAGA

AAACAGAGGTGCAGACTGGCGGATTCAGTAAGGAATCAATTCTGCCCAAACGGAACTCTGATAAG

CTGATCGCCCGAAAGAAAGACTGGGATCCCAAGAAATATGGGGGTTTCGACTCCCCAACAGTGGC

TTACTCTGTCCTGGTGGTCGCAAAGGTGGAGAAGGGGAAAAGCAAGAAACTGAAATCCGTCAAGG

AGCTGCTGGGTATCACTATTATGGAGAGGAGCTCCTTCGAGAAGAACCCCATCGATTTTCTGGAGG

CTAAAGGCTATAAGGAAGTGAAGAAAGACCTGATCATTAAACTGCCAAAGTACAGCCTGTTTGAG

CTGGAAAACGGAAGGAAGCGAATGCTGGCATCCGCAGGAGAGCTGCAGAAGGGTAATGAACTGG

CCCTGCCTTCTAAGTACGTGAACTTCCTGTATCTGGCTAGCCACTACGAGAAGCTGAAAGGCTCCC

CCGAGGATAACGAACAGAAACAGCTGTTTGTGGAGCAGCACAAGCATTATCTGGACGAGATCATT

GAACAGATTAGCGAGTTCTCCAAAAGAGTGATCCTGGCTGACGCAAATCTGGATAAGGTCCTGAG

CGCATACAACAAACACAGAGATAAGCCAATCAGGGAGCAGGCCGAAAATATCATTCATCTGTTCA

CTCTGACCAACCTGGGAGCCCCTGCAGCCTTCAAGTATTTTGACACTACCATCGATCGGAAACGAT

ACACATCCACTAAGGAGGTGCTGGACGCTACCCTGATTCACCAGAGCATTACCGGCCTGTATGAA

ACAAGGATTGACCTGTCTCAGCTGGGGGGCGACCTCGAGGGAAGCGGAGAGGGCAGAGGAAGTC

TGCTAACATGCGGTGACGTCGAGGAGAATCCTGGCCCAGCACCGGGATCCATGGTGAGCAAGGGC

GAGGAGCTGTTCACCGGGGTGGTGCCCATCCTGGTCGAGCTGGACGGCGACGTAAACGGCCACAA

GTTCAGCGTGTCCGGCGAGGGCGAGGGCGATGCCACCTACGGCAAGCTGACCCTGAAGTTCATCT

GCACCACCGGCAAGCTGCCCGTGCCCTGGCCCACCCTCGTGACCACCTTCACCTACGGCGTGCAGT

GCTTCGCCCGCTACCCCGACCACATGAAGCAGCACGACTTCTTCAAGTCCGCCATGCCCGAAGGCT

ACGTCCAGGAGCGCACCATCTTCTTCAAGGACGACGGCAACTACAAGACCCGCGCCGAGGTGAAG

TTCGAGGGCGACACCCTGGTGAACCGCATCGAGCTGAAGGGCATCGACTTCAAGGAGGACGGCAA

CATCCTGGGGCACAAGCTGGAGTACAACTACAACAGCCACAAGGTCTATATCACCGCCGACAAGC

AGAAGAACGGCATCAAGGTGAACTTCAAGACCCGCCACAACATCGAGGACGGCAGCGTGCAGCTC

GCCGACCACTACCAGCAGAACACCCCCATCGGCGACGGCCCCGTGCTGCTGCCCGACAACCACTA

CCTGAGCACCCAGTCCGCCCTGAGCAAAGACCCCAACGAGAAGCGCGATCACATGGTCCTGCTGG

AGTTCGTGACCGCCGCCGGGATCACTCTCGGCATGGACGAGCTGTACAAGTAAACCTAATCTAGC

AGCTCGCTGATCAGCCTCGACTGTGCCTTCTAGTTGCCAGCCATCTGTTGTTTGCCCCTCCCCCGTG

CCTTCCTTGACCCTGGAAGGTGCCACTCCCACTGTCCTTTCCTAATAAAATGAGGAAATTGCATCG

CATTGTCTGAGTAGGTGTCATTCTATTCTGGGGGGTGGGGTGGGGCAGGACAGCAAGGGGGAGGA

TTGGGAAGACAATAGCAGGCATGCTGGGGATGCGGTGGGCTCTATGGCTTCTGAGGCGGAAAGAA

CCAGCTGGGGCTCGATCCTCTAGTTGGCGCGTCATGGTCCATATGAATATCCTCCTTAGTTCCTATT

CCGCTAGCCTAGAGGGACAGCCCCCCCCCAAAGCCCCCAGGGATGTAATTACGTCCCTCCCCCGCT

AGGGGCAGCAGCGAGCCGCCCGGGGCTCCGCTCCGGTCCGGCGCTCCCCCCGCATCCCCGAGCCG

GCAGCGTGCGGGGACAGCCCGGGCACGGGGAAGGTGGCACGGGATCGCTTTCCTCTGAACGCTTC

-continuede

TCGCTGCTCTTTGAGCCTGCAGACACCTGGGGGGATACGGGGAAAAAGCTTTAGGCTGAAAGAGA

GATTTAGAATGACAGAATCATAGAACGGCCTGGGTTGCAAAGGAGCACAGTGCTCATCCAGATCC

AACCCCCTGCTATGTGCAGGGTCATCAACCAGCAGCCCAGGCTGCCCAGAGCCACATCCAGCCTG

GCCTTGAATGCCTGCAGGGATGGGGCATCCACAGCCTCCTTGGGCAACCTGTTCAGTGCGTCACCA

CCCTCTGGGGGAAAAACTGCCTCCTCATATCCAACCCAAACCTCCCCTGTCTCAGTGTAAAGCCAT

TCCCCCTTGTCCTATCAAGGGGGAGTTTGCTGTGACATTGTTGGTCTGGGGTGACACATGTTTGCCA

ATTCAGTGCATCACGGAGAGGCAGATCTTGGGGATAAGGAAGTGCAGGACAGCATGGACGTGGG

ACATGCAGGTGTTGAGGGCTCTGGGACACTCTCCAAGTCACAGCGTTCAGAACAGCCTTAAGGAT

AAGAAGATAGGATAGAAGGACAAAGAGCAAGTTAAAACCCAGCATGGAGAGGAGCACAAAAAG

GCCACAGACACTGCTGGTCCCTGTGTCTGAGCCTGCATGTTTGATGGTGTCTGGATGCAAGCAGAA

GGGGTGGAAGAGCTTGCCTGGAGAGATACAGCTGGGTCAGTAGGACTGGGACAGGCAGCTGGAG

AATTGCCATGTAGATGTTCATACAATCGTCAAATCATGAAGGCTGGAAAAGCCCTCCAAGATCCCC

AAGACCAACCCCAACCCACCCACCGTGCCCACTGGCCATGTCCCTCAGTGCCACATCCCCACAGTT

CTTCATCACCTCCAGGGACGGTGACCCCCCCACCTCCGTGGGCAGCTGTGCCACTGCAGCACCGCT

CTTTGGAGAAGGTAAATCTTGCTAAATCCAGCCCGACCCTCCCCTGGCACAACGTAAGGCCATTAT

CTCTCATCCAACTCCAGGACGGAGTCAGTGAGGATGGGGCTGGATCCGAAGCAGCTCCAGCCTAC

ACAATCGCTCAAGACGTGTAATGCTTTTATTATATATTAGTCACGATATCTATAACAAGAAAATAT

ATATATAATAAGTTATCACGTAAGTAGAACATGAAATAACAATATAATTATCGTATGAGTTAAATC

TTAAAAGTCACGTAAAAGATAATCATGCGTCATTTTGACTCACGCGGTCGTTATAGTTCAAAATCA

GTGACACTTACCGCATTGACAAGCACGCCTCACGGGAGCTCCAAGCGGCGACTGAGATGTCCTAA

ATGCACAGCGACGGATTCGCGCTATTTAGAAAGAGAGAGCAATATTTCAAGAATGCATGCGTCAA

TTTTACGCAGACTATCTTTCTAGGGTTAAAAAAGATTTGCGCTTTACTCGACCTAAACTTTAAACAC

GTCATAGAATCTTCGTTTGACAAAAACCACATTGTGGGGTACCGAGCTCTTAATTAAGGCGCGCCG

GGGAGGTTCCCTTTAGTGAGGGTTAATTGCGGGTCGCCCTATAGTGAGTCGTATTACAATTCACTG

GCCGTCGTTTTACAACGTCGTGACTGGGAAAACCCTGGCGTTACCCAACTTAATCGCCTTGCAGCA

CATCCCCCTTTCGCCAGCTGGCGTAATAGCGAAGAGGCCCGCACCGATCGCCCTTCCCAACAGTTG

CGCAGCCTGAATGGCGAATGGCAAATTGTAAGCGTTAATATTTTGTTAAAATTCGCGTTAAATTTT

TGTTAAATCAGCTCATTTTTTAACCAATAGGCCGAAATCGGCAAAATCCCTTATAAATCAAAAGAA

TAGACCGAGATAGGGTTGAGTGTTGTTCCAGTTTGGAACAAGAGTCCACTATTAAAGAACGTGGA

CTCCAACGTCAAAGGGCGAAAAACCGTCTATCAGGGCGATGGCCCACTACGTGAACCATCACCCT

AATCAAGTTTTTTGGGGTCGAGGTGCCGTAAAGCACTAAATCGGAACCCTAAAGGGAGCCCCCGA

TTTAGAGCTTGACGGGGAAAGCCGGCGAACGTGGCGAGAAAGGAAGGGAAGAAAGCGAAAGGAG

CGGGCGCTAGGGCGCTGGCAAGTGTAGCGGTCACGCTGCGCGTAACCACCACACCCGCCGCGCTT

AATGCGCCGCTACAGGGCGCGTCAG

TOIC_Cas9_KRAB_obl_r26_AAVS_PGKNeo (SEQ ID NO: 15)

GTGGCACTTTTCGGGGAAATGTGCGCGGAACCCCTATTTGTTTATTTTTCTAAATACATTCAAATAT

GTATCCGCTCATGAGACAATAACCCTGATAAATGCTTCAATAATATTGAAAAAGGAAGAGTATGA

GTATTCAACATTTCCGTGTCGCCCTTATTCCCTTTTTTGCGGCATTTTGCCTTCCTGTTTTTGCTCAC

CCAGAAACGCTGGTGAAAGTAAAAGATGCTGAAGATCAGTTGGGTGCACGAGTGGGTTACATCGA

ACTGGATCTCAACAGCGGTAAGATCCTTGAGAGTTTTCGCCCCGAAGAACGTTTTCCAATGATGAG

CACTTTTAAAGTTCTGCTATGTGGCGCGGTATTATCCCGTATTGACGCCGGGCAAGAGCAACTCGG

-continuede

TCGCCGCATACACTATTCTCAGAATGACTTGGTTGAGTACTCACCAGTCACAGAAAAGCATCTTAC

GGATGGCATGACAGTAAGAGAATTATGCAGTGCTGCCATAACCATGAGTGATAACACTGCGGCCA

ACTTACTTCTGACAACGATCGGAGGACCGAAGGAGCTAACCGCTTTTTTGCACAACATGGGGGATC

ATGTAACTCGCCTTGATCGTTGGGAACCGGAGCTGAATGAAGCCATACCAAACGACGAGCGTGAC

ACCACGATGCCTGTAGCAATGGCAACAACGTTGCGCAAACTATTAACTGGCGAACTACTTACTCTA

GCTTCCCGGCAACAATTAATAGACTGGATGGAGGCGGATAAAGTTGCAGGACCACTTCTGCGCTC

GGCCCTTCCGGCTGGCTGGTTTATTGCTGATAAATCTGGAGCCGGTGAGCGTGGGTCTCGCGGTAT

CATTGCAGCACTGGGGCCAGATGGTAAGCCCTCCCGTATCGTAGTTATCTACACGACGGGGAGTCA

GGCAACTATGGATGAACGAAATAGACAGATCGCTGAGATAGGTGCCTCACTGATTAAGCATTGGT

AACTGTCAGACCAAGTTTACTCATATATACTTTAGATTGATTTAAAACTTCATTTTTAATTTAAAAG

GATCTAGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGTAATC

TGCTGCTTGCAAACAAAAAAACCACCGCTACCAGCGGTGGTTTGTTTGCCGGATCAAGAGCTACCA

ACTCTTTTTCCGAAGGTAACTGGCTTCAGCAGAGCGCAGATACCAAATACTGTTCTTCTAGTGTAG

CCGTAGTTAGGCCACCACTTCAAGAACTCTGTAGCACCGCCTACATACCTCGCTCTGCTAATCCTG

TTACCAGTGGCTGCTGCCAGTGGCGATAAGTCGTGTCTTACCGGGTTGGACTCAAGACGATAGTTA

CCGGATAAGGCGCAGCGGTCGGGCTGAACGGGGGGTTCGTGCACACAGCCCAGCTTGGAGCGAAC

GACCTACACCGAACTGAGATACCTACAGCGTGAGCTATGAGAAAGCGCCACGCTTCCCGAAGGGA

GAAAGGCGGACAGGTATCCGGTAAGCGGCAGGGTCGGAACAGGAGAGCGCACGAGGGAGCTTCC

AGGGGGAAACGCCTGGTATCTTTATAGTCCTGTCGGGTTTCGCCACCTCTGACTTGAGCGTCGATT

TTTGTGATGCTCGTCAGGGGGGCGGAGCCTATGGAAAAACGCCAGCAACGCGGCCTTTTTACGGTT

CCTGGCCTTTTGCTGGCCTTTTGCTCACATGTTCTTTCCTGCGTTATCCCCTGATTCTGTGGATAACC

GTATTACCGCCTTTGAGTGAGCTGATACCGCTCGCCGCAGCCGAACGACCGAGCGCAGCGAGTCA

GTGAGCGAGGAAGCGGAAGAGCGCCCAATACGCAAACCGCCTCTCCCCGCGCGTTGGCCGATTCA

TTAATGCAGCTGGCACGACAGGTTTCCCGACTGGAAAGCGGGCAGTGAGCGCAACGCAATTAATG

TGAGTTAGCTCACTCATTAGGCACCCCAGGCTTTACACTTTATGCTTCCGGCTCGTATGTTGTGTGG

AATTGTGAGCGGATAACAATTTCACACAGGAAACAGCTATGACCATGATTACGCCAAGCGCGCAA

TTAACCCTCACTAAAGGGAACCTCCCCTAGCTTAATTAACCCTAGAAAGATAATCATATTGTGACG

TACGTTAAAGATAATCATGCGTAAAATTGACGCATGTGTTTTATCGATCTGTATATCGAGGTTTATT

TATTAATTTGAATAGATATTAAGTTTTATTATATTTACACTTACATACTAATAATAAATTCAACAAA

CAATTTATTTATGTTTATTTATTTATTAAAAAAAAACAAAAACTCAAAATTTCTTCTATAAAGTAAC

AAAACTTTTAAACATTCTCTCTTTTACAAAAATAAACTTATTTTGTACTTTAAAAACAGTCATGTTG

TATTATAAAATAAGTAATTAGCTTAACTTATACATAATAGAAACAAATTATACTTATTAATCGCAT

TGATTATTGACTAGTCGTATTAAGGGTTCCGGATCAGCTTGATTCGAGCCCCAGCTGGTTCTTTCCG

CCTCAGAAGCCATAGAGCCCACCGCATCCCCAGCATGCCTGCTATTGTCTTCCCAATCCTCCCCCTT

GCTGTCCTGCCCCACCCCACCCCCCAGAATAGAATGACACCTACTCAGACAATGCGATGCAATTTC

CTCATTTTATTAGGAAAGGACAGTGGGAGTGGCACCTTCCAGGGTCAAGGAAGGCACGGGGGAGG

GGCAAACAACAGATGGCTGGCAACTAGAAGGCACAGTCGAGGCTGATCAGCGAGCTCTAGAGAA

TTGATCCCCTCAGAAGAACTCGTCAAGAAGGCGATAGAAGGCGATGCGCTGCGAATCGGGAGCGG

CGATACCGTAAAGCACGAGGAAGCGGTCAGCCCATTCGCCGCCAAGCTCTTCAGCAATATCACGG

GTAGCCAACGCTATGTCCTGATAGCGGTCCGCCACACCCAGCCGGCCACAGTCGATGAATCCAGA

-continuede

AAAGCGGCCATTTTCCACCATGATATTCGGCAAGCAGGCATCGCCATGGGTCACGACGAGATCCTC

GCCGTCGGGCATGCGCGCCTTGAGCCTGGCGAACAGTTCGGCTGGCGCGAGCCCCTGATGCTCTTC

GTCCAGATCATCCTGATCGACAAGACCGGCTTCCATCCGAGTACGTGCTCGCTCGATGCGATGTTT

CGCTTGGTGGTCGAATGGGCAGGTAGCCGGATCAAGCGTATGCAGCCGCCGCATTGCATCAGCCA

TGATGGATACTTTCTCGGCAGGAGCAAGGTGAGATGACAGGAGATCCTGCCCCGGCACTTCGCCC

AATAGCAGCCAGTCCCTTCCCGCTTCAGTGACAACGTCGAGCACAGCTGCGCAAGGAACGCCCGT

CGTGGCCAGCCACGATAGCCGCGCTGCCTCGTCCTGCAGTTCATTCAGGGCACCGGACAGGTCGGT

CTTGACAAAAAGAACCGGGCGCCCCTGCGCTGACAGCCGGAACACGGCGGCATCAGAGCAGCCG

ATTGTCTGTTGTGCCCAGTCATAGCCGAATAGCCTCTCCACCCAAGCGGCCGGAGAACCTGCGTGC

AATCCATCTTGTTCAATGGCCGATCCCATGGTTTAGTTCCTCACCTTGTCGTATTATACTATGCCGA

TATACTATGCCGATGATTAATTGTCAACACGTGCTGCTGCAGGTCGAAAGGCCCGGAGATGAGGA

AGAGGAGAACAGCGCGGCAGACGTGCGCTTTTGAAGCGTGCAGAATGCCGGGCCTCCGGAGGACC

TTCGGGCGCCCGCCCCGCCCCTGAGCCCGCCCCTGAGCCCGCCCCCGGACCCACCCCTTCCCAGCC

TCTGAGCCCAGAAAGCGAAGGAGCAAAGCTGCTATTGGCCGCTGCCCCAAAGGCCTACCCGCTTC

CATTGCTCAGCGGTGCTGTCCATCTGCACGAGACTAGTGAGACGTGCTACTTCCATTTGTCACGTC

CTGCACGACGCGAGCTGCGGGGCGGGGGGGAACTTCCTGACTAGGGGAGGAGTAGAAGGTGGCG

CGAAGGGGCCACCAAAGAACGGAGCCGGTTGGCGCCTACCGGTGGATGTGGAATGTGTGCGAGCC

AGAGGCCACTTGTGTAGCGCCAAGTGCCCAGCGGGGCTGCTAAAGCGCATGCTCCAGACTGCCTT

GGGAAAAGCGCCTCCCCTACCCGGTAGACACCCCACAGTGGGTGGCCTAGGGACAGGATTGCAAC

TCCAGTCTTTCTTCTTCTTGGGCGGGAGTCACTAGTTATTAATAGTAATCAATTACGGGGTCATTAG

TTCATAGCCCATATATGGAGTTCCGCGTTACATAACTTACGGTAAATGGCCCGCCTGGCTGACCGC

CCAACGACCCCCGCCCATTGACGTCAATAATGACGTATGTTCCCATAGTAACGCCAATAGGGACTT

TCCATTGACGTCAATGGGTGGACTATTTACGGTAAACTGCCCACTTGGCAGTACATCAAGTGTATC

ATATGCCAAGTACGCCCCCTATTGACGTCAATGACGGTAAATGGCCCGCCTGGCATTATGCCCAGT

ACATGACCTTATGGGACTTTCCTACTTGGCAGTACATCTACGTATTAGTCATCGCTATTACCATGGG

TCGAGGTGAGCCCCACGTTCTGCTTCACTCTCCCCATCTCCCCCCCCTCCCCACCCCCAATTTTGTA

TTTATTTATTTTTTAATTATTTTGTGCAGCGATGGGGGCGGGGGGGGGGGGGGCGCGCGCCAGGCG

GGGCGGGGCGGGGCGAGGGGCGGGGCGGGGCGAGGCGGAGAGGTGCGGCGGCAGCCAATCAGA

GCGGCGCGCTCCGAAAGTTTCCTTTTATGGCGAGGCGGCGGCGGCGGCGGCCCTATAAAAAGCGA

AGCGCGCGGCGGGCGGGAGTCGCTGCGTTGCCTTCGCCCCGTGCCCCGCTCCGCGCCGCCTCGCGC

CGCCCGCCCCGGCTCTGACTGACCGCGTTACTCCCACAGGTGAGCGGGCGGGACGGCCCTTCTCCT

CCGGGCTGTAATTAGCGCTTGGTTTAATGACGGCTCGTTTCTTTTCTGTGGCTGCGTGAAAGCCTTA

AAGGGCTCCGGGAGGGCCCTTTGTGCGGGGGGGAGCGGCTCGGGGGGTGCGTGCGTGTGTGTGTG

CGTGGGGAGCGCCGCGTGCGGCCCGCGCTGCCCGGCGGCTGTGAGCGCTGCGGGCGCGGCGCGGG

GCTTTGTGCGCTCCGCGTGTGCGCGAGGGGAGCGCGGCCGGGGGCGGTGCCCCGCGGTGCGGGGG

GGCTGCGAGGGGAACAAAGGCTGCGTGCGGGGTGTGTGCGTGGGGGGGTGAGCAGGGGGTGTGG

GCGCGGCGGTCGGGCTGTAACCCCCCCCTGCACCCCCCTCCCCGAGTTGCTGAGCACGGCCCGGCT

TCGGGTGCGGGGCTCCGTGCGGGGCGTGGCGCGGGGCTCGCCGTGCCGGGCGGGGGGTGGCGGCA

GGTGGGGGTGCCGGGCGGGGCGGGGCCGCCTCGGGCCGGGGAGGGCTCGGGGGAGGGGCGCGGC

GGCCCCGGAGCGCCGGCGGCTGTCGAGGCGCGGCGAGCCGCAGCCATTGCCTTTTATGGTAATCG

TGCGAGAGGGCGCAGGGACTTCCTTTGTCCCAAATCTGGCGGAGCCGAAATCTGGGAGGCGCCGC

-continued

CGCACCCCCTCTAGCGGGCGCGGGCGAAGCGGTGCGGCGCCGGCAGGAAGGAAATGGGCGGGGA

GGGCCTTCGTGCGTCGCCGCGCCGCCGTCCCCTTCTCCATCTCCAGCCTCGGGGCTGCCGCAGGGG

GACGGCTGCCTTCGGGGGGGACGGGGCAGGGCGGGGTTCGGCTTCTGGCGTGTGACCGGCGGCTC

TAGAGCCTCTGCTAACCATGTTCATGCCTTCTTCTTTTTCCTACAGCTCCTGGGCAACGTGCTGGTT

ATTGTGCTGTCTCATCATTTTGGCAAAGAATTCGCCACCATGGTGCCCAAGAAGAAGAGGAAAGTC

TCTAGACTGGACAAGAGCAAAGTCATAAACTCTGCTCTGGAATTACTCAATGGAGTCGGTATCGA

AGGCCTGACGACAAGGAAACTCGCTCAAAAGCTGGGAGTTGAGCAGCCTACCCTGTACTGGCACG

TGAAGAACAAGCGGGCCCTGCTCGATGCCCTGCCAATCGAGATGCTGGACAGGCATCATACCCAC

TCCTGCCCCCTGGAAGGCGAGTCATGGCAAGACTTTCTGCGGAACAACGCCAAGTCATACCGCTGT

GCTCTCCTCTCACATCGCGACGGGGCTAAAGTGCATCTCGGCACCCGCCCAACAGAGAAACAGTA

CGAAACCCTGGAAAATCAGCTCGCGTTCCTGTGTCAGCAAGGCTTCTCCCTGGAGAACGCACTGTA

CGCTCTGTCCGCCGTGGGCCACTTTACACTGGGCTGCGTATTGGAGGAACAGGAGCATCAAGTAGC

AAAAGAGGAAAGAGAGACACCTACCACCGATTCTATGCCCCCACTTCTGAAACAAGCAATTGAGC

TGTTCGACCGGCAGGGAGCCGAACCTGCCTTCCTTTTCGGCCTGGAACTAATCATATGTGGCCTGG

AGAAACAGCTAAAGTGCGAAAGCGGCGGGCCGACCGACGCCCTTGACGATTTTGACTTAGACATG

CTCCCAGCCGATGCCCTTGACGACTTTGACCTTGATATGCTGCCTGCTGACGCTCTTGACGATTTTG

ACCTTGACATGCTCCCCGGGTAAAGCGGCCGCGACTCTAGATCATAATCAGCCATACCACATTTGT

AGAGGTTTTACTTGCTTTAAAAAACCTCCCACACCTCCCCCTGAACCTGAAACATAAAATGAATGC

AATTGTTGTTGTTAACTTGTTTATTGCAGCTTATAATGGTTACAAATAAAGCAATAGCATCACAAA

TTTCACAAATAAAGCATTTTTTTCACTGCATTCTAGTTGTGGTTTGTCCAAACTCATCAATGTATCT

TAAGGGATCCCTAGAGGGACAGCCCCCCCCCAAAGCCCCCAGGGATGTAATTACGTCCCTCCCCC

GCTAGGGGCAGCAGCGAGCCGCCCGGGGCTCCGCTCCGGTCCGGCGCTCCCCCCGCATCCCCGAG

CCGGCAGCGTGCGGGGACAGCCCGGGCACGGGGAAGGTGGCACGGGATCGCTTTCCTCTGAACGC

TTCTCGCTGCTCTTTGAGCCTGCAGACACCTGGGGGGATACGGGGAAAAAGCTTTAGGCTGAAAG

AGAGATTTAGAATGACAGAATCATAGAACGGCCTGGGTTGCAAAGGAGCACAGTGCTCATCCAGA

TCCAACCCCCTGCTATGTGCAGGGTCATCAACCAGCAGCCCAGGCTGCCCAGAGCCACATCCAGCC

TGGCCTTGAATGCCTGCAGGGATGGGGCATCCACAGCCTCCTTGGGCAACCTGTTCAGTGCGTCAC

CACCCTCTGGGGGAAAAACTGCCTCCTCATATCCAACCCAAACCTCCCCTGTCTCAGTGTAAAGCC

ATTCCCCCTTGTCCTATCAAGGGGGAGTTTGCTGTGACATTGTTGGTCTGGGGTGACACATGTTTGC

CAATTCAGTGCATCACGGAGAGGCAGATCTTGGGGATAAGGAAGTGCAGGACAGCATGGACGTGG

GACATGCAGGTGTTGAGGGCTCTGGGACACTCTCCAAGTCACAGCGTTCAGAACAGCCTTAAGGA

TAAGAAGATAGGATAGAAGGACAAAGAGCAAGTTAAAACCCAGCATGGAGAGGAGCACAAAAAG

GCCACAGACACTGCTGGTCCCTGTGTCTGAGCCTGCATGTTTGATGGTGTCTGGATGCAAGCAGAA

GGGGTGGAAGAGCTTGCCTGGAGAGATACAGCTGGGTCAGTAGGACTGGGACAGGCAGCTGGAG

AATTGCCATGTAGATGTTCATACAATCGTCAAATCATGAAGGCTGGAAAAGCCCTCCAAGATCCCC

AAGACCAACCCCAACCCACCCACCGTGCCCACTGGCCATGTCCCTCAGTGCCACATCCCCACAGTT

CTTCATCACCTCCAGGGACGGTGACCCCCCCACCTCCGTGGGCAGCTGTGCCACTGCAGCACCGCT

CTTTGGAGAAGGTAAATCTTGCTAAATCCAGCCCGACCCTCCCCTGGCACAACGTAAGGCCATTAT

CTCTCATCCAACTCCAGGACGGAGTCAGTGAGGATGGGGCTGTCGACCTAGAGGGACAGCCCCCC

CCCAAAGCCCCCAGGGATGTAATTACGTCCCTCCCCCGCTAGGGGCAGCAGCGAGCCGCCCGGGG

CTCCGCTCCGGTCCGGCGCTCCCCCCGCATCCCCGAGCCGGCAGCGTGCGGGGACAGCCCGGGCA

-continuede

CGGGGAAGGTGGCACGGGATCGCTTTCCTCTGAACGCTTCTCGCTGCTCTTTGAGCCTGCAGACAC

CTGGGGGGATACGGGGAAAAAGCTTTAGGCTGAAAGAGAGATTTAGAATGACAGAATCATAGAA

CGGCCTGGGTTGCAAAGGAGCACAGTGCTCATCCAGATCCAACCCCCTGCTATGTGCAGGGTCATC

AACCAGCAGCCCAGGCTGCCCAGAGCCACATCCAGCCTGGCCTTGAATGCCTGCAGGGATGGGGC

ATCCACAGCCTCCTTGGGCAACCTGTTCAGTGCGTCACCACCCTCTGGGGGAAAAACTGCCTCCTC

ATATCCAACCCAAACCTCCCCTGTCTCAGTGTAAAGCCATTCCCCCTTGTCCTATCAAGGGGGAGT

TTGCTGTGACATTGTTGGTCTGGGGTGACACATGTTTGCCAATTCAGTGCATCACGGAGAGGCAGA

TCTTGGGGATAAGGAAGTGCAGGACAGCATGGACGTGGGACATGCAGGTGTTGAGGGCTCTGGGA

CACTCTCCAAGTCACAGCGTTCAGAACAGCCTTAAGGATAAGAAGATAGGATAGAAGGACAAAGA

GCAAGTTAAAACCCAGCATGGAGAGGAGCACAAAAAGGCCACAGACACTGCTGGTCCCTGTGTCT

GAGCCTGCATGTTTGATGGTGTCTGGATGCAAGCAGAAGGGGTGGAAGAGCTTGCCTGGAGAGAT

ACAGCTGGGTCAGTAGGACTGGGACAGGCAGCTGGAGAATTGCCATGTAGATGTTCATACAATCG

TCAAATCATGAAGGCTGGAAAAGCCCTCCAAGATCCCCAAGACCAACCCCAACCCACCCACCGTG

CCCACTGGCCATGTCCCTCAGTGCCACATCCCCACAGTTCTTCATCACCTCCAGGGACGGTGACCC

CCCCACCTCCGTGGGCAGCTGTGCCACTGCAGCACCGCTCTTTGGAGAAGGTAAATCTTGCTAAAT

CCAGCCCGACCCTCCCCTGGCACAACGTAAGGCCATTATCTCTCATCCAACTCCAGGACGGAGTCA

GTGAGGATGGGGCTCAATTGTTTACTCCCTATCAGTGATAGAGAACGTATGAAGAGTTTACTCCCT

ATCAGTGATAGAGAACGTATGCAGACTTTACTCCCTATCAGTGATAGAGAACGTATAAGGAGTTTA

CTCCCTATCAGTGATAGAGAACGTATGACCAGTTTACTCCCTATCAGTGATAGAGAACGTATCTAC

AGTTTACTCCCTATCAGTGATAGAGAACGTATATCCAGTTTACTCCCTATCAGTGATAGAGAACGT

ATAAGCTTTAGGCGTGTACGGTGGGCGCCTATAAAAGCAGAGCTCGTTTAGTGAACCGTCAGATC

GCCTGGAGCAATTCCACAACACTTTTGTCTTATACCAACTTTCCGTACCACTTCCTACCCTCGTAAA

AAGCTTGTCCACCATGGCTCCTAAGAAAAAGCGGAAGGTGGACAAGAAATACTCAATCGGGCTGG

ACATCGGAACTAACTCAGTGGGGTGGGCAGTCATTACTGACGAGTACAAAGTGCCAAGCAAGAAA

TTTAAGGTCCTGGGCAACACCGATAGGCACTCCATCAAGAAAAATCTGATTGGGGCCCTGCTGTTC

GACTCTGGAGAGACAGCTGAAGCAACTAGACTGAAAAGGACTGCTAGAAGGCGCTATACCCGGCG

AAAGAATCGCATCTGCTACCTGCAGGAGATTTTCTCTAACGAAATGGCCAAGGTGGACGATAGTTT

CTTTCATCGGCTGGAGGAATCATTCCTGGTCGAGGAAGATAAGAAACACGAGAGACATCCTATCTT

TGGAAACATTGTGGACGAGGTCGCTTATCACGAAAAATACCCCACCATCTATCATCTGCGCAAGA

AACTGGTGGACTCTACAGATAAAGCAGACCTGCGGCTGATCTATCTGGCCCTGGCTCACATGATTA

AGTTCAGAGGCCATTTTCTGATCGAGGGAGATCTGAACCCAGACAATAGCGATGTGGACAAGCTG

TTCATCCAGCTGGTCCAGACATACAATCAGCTGTTTGAGGAAAACCCTATTAATGCATCTGGCGTG

GACGCAAAAGCCATCCTGAGTGCCAGGCTGTCTAAGAGTAGAAGGCTGGAGAACCTGATCGCTCA

GCTGCCAGGCGAAAAGAAAAACGGCCTGTTTGGAAATCTGATTGCACTGTCACTGGGACTGACAC

CTAACTTCAAGAGCAATTTTGATCTGGCCGAGGACGCTAAACTGCAGCTGAGCAAGGACACTTAT

GACGATGACCTGGATAACCTGCTGGCTCAGATCGGAGATCAGTACGCAGACCTGTTCCTGGCCGCT

AAGAATCTGTCTGACGCTATCCTGCTGAGTGATATTCTGCGGGTGAACACCGAGATTACAAAAGCC

CCTCTGTCAGCTAGCATGATCAAGAGATATGACGAGCACCATCAGGATCTGACCCTGCTGAAGGC

ACTGGTGCGCCAGCAGCTGCCCGAGAAGTACAAGGAAATCTTCTTTGATCAGAGTAAGAACGGGT

ACGCCGGTTATATTGACGGCGGAGCTTCACAGGAGGAATTCTACAAGTTTATCAAACCTATTCTGG

AGAAGATGGACGGCACCGAGGAACTGCTGGTGAAACTGAATCGCGAGGACCTGCTGCGCAAGCA

-continuede

GCGGACATTTGATAACGGCTCCATCCCCCACCAGATTCATCTGGGAGAGCTGCACGCAATCCTGCG

ACGACAGGAAGACTTCTACCCATTTCTGAAGGATAACCGCGAGAAGATCGAAAAAATTCTGACCT

TCCGGATCCCTTACTATGTGGGGCCCCTGGCAAGGGGTAATTCCCGCTTTGCCTGGATGACACGGA

AATCTGAGGAAACAATCACTCCTTGGAACTTCGAGGAAGTGGTCGATAAGGGAGCTTCCGCACAG

TCTTTCATCGAGAGAATGACAAACTTCGACAAAAACCTGCCAAATGAGAAAGTGCTGCCTAAGCA

CAGTCTGCTGTACGAGTATTTCACAGTCTATAACGAACTGACTAAGGTGAAATACGTCACCGAGGG

GATGAGGAAGCCCGCCTTCCTGAGCGGTGAACAGAAGAAAGCTATCGTGGACCTGCTGTTTAAAA

CCAATCGCAAGGTGACAGTCAAGCAGCTGAAGGAGGACTACTTCAAGAAAATTGAATGTTTCGAT

TCTGTGGAGATCAGTGGCGTCGAAGACAGATTTAACGCTTCTCTGGGAACCTACCACGATCTGCTG

AAGATCATTAAGGATAAAGACTTCCTGGACAACGAGGAAAATGAGGATATCCTGGAAGACATTGT

GCTGACCCTGACACTGTTTGAGGATCGCGAAATGATCGAGGAACGGCTGAAAACTTATGCCCATCT

GTTCGATGACAAGGTGATGAAACAGCTGAAGCGAAGAAGGTACACCGGCTGGGGACGACTGAGC

AGAAAGCTGATCAACGGCATTCGGGACAAACAGAGTGGAAAGACTATCCTGGACTTTCTGAAATC

AGATGGCTTCGCTAACAGAAATTTTATGCAGCTGATTCACGATGACAGCCTGACCTTCAAAGAGGA

TATCCAGAAGGCACAGGTGTCCGGGCAGGGTGACTCTCTGCACGAGCATATCGCAAACCTGGCCG

GGTCCCCCGCCATCAAGAAAGGTATTCTGCAGACCGTGAAGGTGGTCGATGAGCTGGTGAAAGTC

ATGGGCAGGCATAAGCCAGAAAACATCGTGATTGAGATGGCCCGCGAAAATCAGACCACACAGA

AAGGACAGAAGAACAGCCGCGAGCGGATGAAAAGGATCGAGGAAGGCATTAAGGAACTGGGATC

CCAGATCCTGAAAGAGCACCCTGTGGAAAACACTCAGCTGCAGAATGAGAAGCTGTATCTGTACT

ATCTGCAGAATGGGCGGGATATGTACGTGGACCAGGAGCTGGATATTAACCGACTGTCTGATTAC

GACGTGGATCATATCGTCCCACAGTCATTCCTGAAAGATGACAGCATTGACAATAAGGTGCTGACC

CGGAGTGACAAAAACCGAGGAAAGAGTGATAATGTCCCTTCAGAGGAAGTGGTCAAGAAAATGA

AGAACTACTGGAGACAGCTGCTGAATGCCAAACTGATCACACAGCGAAAGTTTGATAACCTGACT

AAAGCTGAGAGAGGGGGTCTGTCAGAACTGGACAAAGCAGGCTTCATCAAGCGACAGCTGGTGG

AGACCAGACAGATCACAAAGCACGTCGCTCAGATTCTGGATAGCAGGATGAACACAAAGTACGAT

GAGAATGACAAACTGATCCGCGAAGTGAAGGTCATTACTCTGAAGTCAAAACTTGTGAGCGACTT

CAGAAAGGATTTCCAGTTCTACAAAGTCAGGGAGATCAACAATTATCACCATGCTCATGACGCAT

ACCTGAACGCAGTGGTCGGGACCGCCCTGATTAAGAAATACCCCAAACTGGAGAGCGAATTCGTG

TACGGTGACTATAAGGTGTACGATGTCAGAAAAATGATCGCCAAGAGTGAGCAGGAAATTGGAAA

AGCCACCGCTAAGTATTTCTTTTACTCAAACATCATGAATTTCTTTAAGACTGAGATCACCCTGGCA

AATGGGGAAATCCGAAAGAGACCACTGATTGAGACTAACGGCGAGACCGGAGAAATCGTGTGGG

ACAAGGGTAGGGATTTTGCCACAGTGCGCAAGGTCCTGTCCATGCCTCAAGTGAATATTGTCAAGA

AAACAGAGGTGCAGACTGGCGGATTCAGTAAGGAATCAATTCTGCCCAAACGGAACTCTGATAAG

CTGATCGCCCGAAAGAAAGACTGGGATCCCAAGAAATATGGGGGTTTCGACTCCCCAACAGTGGC

TTACTCTGTCCTGGTGGTCGCAAAGGTGGAGAAGGGGAAAAGCAAGAAACTGAAATCCGTCAAGG

AGCTGCTGGGTATCACTATTATGGAGAGGAGCTCCTTCGAGAAGAACCCCATCGATTTTCTGGAGG

CTAAAGGCTATAAGGAAGTGAAGAAAGACCTGATCATTAAACTGCCAAAGTACAGCCTGTTTGAG

CTGGAAAACGGAAGGAAGCGAATGCTGGCATCCGCAGGAGAGCTGCAGAAGGGTAATGAACTGG

CCCTGCCTTCTAAGTACGTGAACTTCCTGTATCTGGCTAGCCACTACGAGAAGCTGAAAGGCTCCC

CCGAGGATAACGAACAGAAACAGCTGTTTGTGGAGCAGCACAAGCATTATCTGGACGAGATCATT

GAACAGATTAGCGAGTTCTCCAAAAGAGTGATCCTGGCTGACGCAAATCTGGATAAGGTCCTGAG

-continuede

CGCATACAACAAACACAGAGATAAGCCAATCAGGGAGCAGGCCGAAAATATCATTCATCTGTTCA

CTCTGACCAACCTGGGAGCCCCTGCAGCCTTCAAGTATTTTGACACTACCATCGATCGGAAACGAT

ACACATCCACTAAGGAGGTGCTGGACGCTACCCTGATTCACCAGAGCATTACCGGCCTGTATGAA

ACAAGGATTGACCTGTCTCAGCTGGGGGGCGACCTCGAGGATGGCGGTGGCGCGCTGTCCCCGCA

GCACTCCGCCGTGACCCAGGGGAGTATAATCAAAAACAAAGAGGGCATGGATGCTAAGAGCCTTA

CCGCCTGGTCCCGAACACTGGTCACGTTTAAGGATGTGTTCGTCGATTTTACCCGGGAGGAGTGGA

AACTGCTCGACACCGCGCAGCAGATCGTGTACCGGAATGTCATGCTCGAAAATTACAAAAACTTG

GTCAGCCTCGGGTACCAATTGACCAAACCAGATGTCATACTGCGACTGGAAAAAGGAGAGGAACC

CTGGCTCGTCGAGCGCGAAATTCATCAAGAAACACACCCGGATTCTGAAACCGCCTTCGAGATTA

AGAGCAGTGTGCCTAGGCTCGAGGGAAGCGGAGAGGGCAGAGGAAGTCTGCTAACATGCGGTGA

CGTCGAGGAGAATCCTGGCCCAGCACCGGGATCCATGGTGAGCAAGGGCGAGGAGCTGTTCACCG

GGGTGGTGCCCATCCTGGTCGAGCTGGACGGCGACGTAAACGGCCACAAGTTCAGCGTGTCCGGC

GAGGGCGAGGGCGATGCCACCTACGGCAAGCTGACCCTGAAGTTCATCTGCACCACCGGCAAGCT

GCCCGTGCCCTGGCCCACCCTCGTGACCACCTTCACCTACGGCGTGCAGTGCTTCGCCCGCTACCC

CGACCACATGAAGCAGCACGACTTCTTCAAGTCCGCCATGCCCGAAGGCTACGTCCAGGAGCGCA

CCATCTTCTTCAAGGACGACGGCAACTACAAGACCCGCGCCGAGGTGAAGTTCGAGGGCGACACC

CTGGTGAACCGCATCGAGCTGAAGGGCATCGACTTCAAGGAGGACGGCAACATCCTGGGGCACAA

GCTGGAGTACAACTACAACAGCCACAAGGTCTATATCACCGCCGACAAGCAGAAGAACGGCATCA

AGGTGAACTTCAAGACCCGCCACAACATCGAGGACGGCAGCGTGCAGCTCGCCGACCACTACCAG

CAGAACACCCCCATCGGCGACGGCCCCGTGCTGCTGCCCGACAACCACTACCTGAGCACCCAGTC

CGCCCTGAGCAAAGACCCCAACGAGAAGCGCGATCACATGGTCCTGCTGGAGTTCGTGACCGCCG

CCGGGATCACTCTCGGCATGGACGAGCTGTACAAGTAAACCTAATCTAGCAGCTCGCTGATCAGCC

TCGACTGTGCCTTCTAGTTGCCAGCCATCTGTTGTTTGCCCCTCCCCCGTGCCTTCCTTGACCCTGG

AAGGTGCCACTCCCACTGTCCTTTCCTAATAAAATGAGGAAATTGCATCGCATTGTCTGAGTAGGT

GTCATTCTATTCTGGGGGGTGGGGTGGGGCAGGACAGCAAGGGGGAGGATTGGGAAGACAATAG

CAGGCATGCTGGGGATGCGGTGGGCTCTATGGCTTCTGAGGCGGAAAGAACCAGCTGGGGCTCGA

TCCTCTAGTTGGCGCGTCATGGTCCATATGAATATCCTCCTTAGTTCCTATTCCGCTAGCCTAGAGG

GACAGCCCCCCCCCAAAGCCCCCAGGGATGTAATTACGTCCCTCCCCCGCTAGGGGCAGCAGCGA

GCCGCCCGGGGCTCCGCTCCGGTCCGGCGCTCCCCCCGCATCCCCGAGCCGGCAGCGTGCGGGGA

CAGCCCGGGCACGGGGAAGGTGGCACGGGATCGCTTTCCTCTGAACGCTTCTCGCTGCTCTTTGAG

CCTGCAGACACCTGGGGGGATACGGGGAAAAAGCTTTAGGCTGAAAGAGAGATTTAGAATGACA

GAATCATAGAACGGCCTGGGTTGCAAAGGAGCACAGTGCTCATCCAGATCCAACCCCCTGCTATG

TGCAGGGTCATCAACCAGCAGCCCAGGCTGCCCAGAGCCACATCCAGCCTGGCCTTGAATGCCTG

CAGGGATGGGGCATCCACAGCCTCCTTGGGCAACCTGTTCAGTGCGTCACCACCCTCTGGGGGAA

AAACTGCCTCCTCATATCCAACCCAAACCTCCCCTGTCTCAGTGTAAAGCCATTCCCCCTTGTCCTA

TCAAGGGGGAGTTTGCTGTGACATTGTTGGTCTGGGGTGACACATGTTTGCCAATTCAGTGCATCA

CGGAGAGGCAGATCTTGGGGATAAGGAAGTGCAGGACAGCATGGACGTGGGACATGCAGGTGTT

GAGGGCTCTGGGACACTCTCCAAGTCACAGCGTTCAGAACAGCCTTAAGGATAAGAAGATAGGAT

AGAAGGACAAAGAGCAAGTTAAAACCCAGCATGGAGAGGAGCACAAAAAGGCCACAGACACTGC

TGGTCCCTGTGTCTGAGCCTGCATGTTTGATGGTGTCTGGATGCAAGCAGAAGGGGTGGAAGAGCT

TGCCTGGAGAGATACAGCTGGGTCAGTAGGACTGGGACAGGCAGCTGGAGAATTGCCATGTAGAT

-continuede

GTTCATACAATCGTCAAATCATGAAGGCTGGAAAAGCCCTCCAAGATCCCCAAGACCAACCCCAA

CCCACCCACCGTGCCCACTGGCCATGTCCCTCAGTGCCACATCCCCACAGTTCTTCATCACCTCCAG

GGACGGTGACCCCCCCACCTCCGTGGGCAGCTGTGCCACTGCAGCACCGCTCTTTGGAGAAGGTA

AATCTTGCTAAATCCAGCCCGACCCTCCCCTGGCACAACGTAAGGCCATTATCTCTCATCCAACTC

CAGGACGGAGTCAGTGAGGATGGGGCTGGATCCGAAGCAGCTCCAGCCTACACAATCGCTCAAGA

CGTGTAATGCTTTTATTATATATTAGTCACGATATCTATAACAAGAAAATATATATATAATAAGTT

ATCACGTAAGTAGAACATGAAATAACAATATAATTATCGTATGAGTTAAATCTTAAAAGTCACGTA

AAAGATAATCATGCGTCATTTTGACTCACGCGGTCGTTATAGTTCAAAATCAGTGACACTTACCGC

ATTGACAAGCACGCCTCACGGGAGCTCCAAGCGGCGACTGAGATGTCCTAAATGCACAGCGACGG

ATTCGCGCTATTTAGAAAGAGAGAGCAATATTTCAAGAATGCATGCGTCAATTTTACGCAGACTAT

CTTTCTAGGGTTAAAAAAGATTTGCGCTTTACTCGACCTAAACTTTAAACACGTCATAGAATCTTC

GTTTGACAAAAACCACATTGTGGGGTACCGAGCTCTTAATTAAGGCGCGCCGGGGAGGTTCCCTTT

AGTGAGGGTTAATTGCGGGTCGCCCTATAGTGAGTCGTATTACAATTCACTGGCCGTCGTTTTACA

ACGTCGTGACTGGGAAAACCCTGGCGTTACCCAACTTAATCGCCTTGCAGCACATCCCCCTTTCGC

CAGCTGGCGTAATAGCGAAGAGGCCCGCACCGATCGCCCTTCCCAACAGTTGCGCAGCCTGAATG

GCGAATGGCAAATTGTAAGCGTTAATATTTTGTTAAAATTCGCGTTAAATTTTTGTTAAATCAGCTC

ATTTTTTAACCAATAGGCCGAAATCGGCAAAATCCCTTATAAATCAAAAGAATAGACCGAGATAG

GGTTGAGTGTTGTTCCAGTTTGGAACAAGAGTCCACTATTAAAGAACGTGGACTCCAACGTCAAAG

GGCGAAAAACCGTCTATCAGGGCGATGGCCCACTACGTGAACCATCACCCTAATCAAGTTTTTTGG

GGTCGAGGTGCCGTAAAGCACTAAATCGGAACCCTAAAGGGAGCCCCCGATTTAGAGCTTGACGG

GGAAAGCCGGCGAACGTGGCGAGAAAGGAAGGGAAGAAAGCGAAAGGAGCGGGCGCTAGGGCG

CTGGCAAGTGTAGCGGTCACGCTGCGCGTAACCACCACACCCGCCGCGCTTAATGCGCCGCTACA

GGGCGCGTCAG

TOIC_Cas9_Dead_VP64_obl_r26_AAVS_SANeo (SEQ ID NO: 16)

GTGGCACTTTTCGGGGAAATGTGCGCGGAACCCCTATTTGTTTATTTTTCTAAATACATTCAAATAT

GTATCCGCTCATGAGACAATAACCCTGATAAATGCTTCAATAATATTGAAAAAGGAAGAGTATGA

GTATTCAACATTTCCGTGTCGCCCTTATTCCCTTTTTTGCGGCATTTTGCCTTCCTGTTTTTGCTCAC

CCAGAAACGCTGGTGAAAGTAAAAGATGCTGAAGATCAGTTGGGTGCACGAGTGGGTTACATCGA

ACTGGATCTCAACAGCGGTAAGATCCTTGAGAGTTTTCGCCCCGAAGAACGTTTTCCAATGATGAG

CACTTTTAAAGTTCTGCTATGTGGCGCGGTATTATCCCGTATTGACGCCGGGCAAGAGCAACTCGG

TCGCCGCATACACTATTCTCAGAATGACTTGGTTGAGTACTCACCAGTCACAGAAAAGCATCTTAC

GGATGGCATGACAGTAAGAGAATTATGCAGTGCTGCCATAACCATGAGTGATAACACTGCGGCCA

ACTTACTTCTGACAACGATCGGAGGACCGAAGGAGCTAACCGCTTTTTTGCACAACATGGGGGATC

ATGTAACTCGCCTTGATCGTTGGGAACCGGAGCTGAATGAAGCCATACCAAACGACGAGCGTGAC

ACCACGATGCCTGTAGCAATGGCAACAACGTTGCGCAAACTATTAACTGGCGAACTACTTACTCTA

GCTTCCCGGCAACAATTAATAGACTGGATGGAGGCGGATAAAGTTGCAGGACCACTTCTGCGCTC

GGCCCTTCCGGCTGGCTGGTTTATTGCTGATAAATCTGGAGCCGGTGAGCGTGGGTCTCGCGGTAT

CATTGCAGCACTGGGGCCAGATGGTAAGCCCTCCCGTATCGTAGTTATCTACACGACGGGGAGTCA

GGCAACTATGGATGAACGAAATAGACAGATCGCTGAGATAGGTGCCTCACTGATTAAGCATTGGT

AACTGTCAGACCAAGTTTACTCATATATACTTTAGATTGATTTAAAACTTCATTTTTAATTTAAAAG

GATCTAGGTGAAGATCCTTTTTGATAATCTCATGACCAAAATCCCTTAACGTGAGTTTTCGTTCCAC

-continuede

TGAGCGTCAGACCCCGTAGAAAAGATCAAAGGATCTTCTTGAGATCCTTTTTTTCTGCGCGTAATC

TGCTGCTTGCAAACAAAAAAACCACCGCTACCAGCGGTGGTTTGTTTGCCGGATCAAGAGCTACCA

ACTCTTTTTCCGAAGGTAACTGGCTTCAGCAGAGCGCAGATACCAAATACTGTTCTTCTAGTGTAG

CCGTAGTTAGGCCACCACTTCAAGAACTCTGTAGCACCGCCTACATACCTCGCTCTGCTAATCCTG

TTACCAGTGGCTGCTGCCAGTGGCGATAAGTCGTGTCTTACCGGGTTGGACTCAAGACGATAGTTA

CCGGATAAGGCGCAGCGGTCGGGCTGAACGGGGGGTTCGTGCACACAGCCCAGCTTGGAGCGAAC

GACCTACACCGAACTGAGATACCTACAGCGTGAGCTATGAGAAAGCGCCACGCTTCCCGAAGGGA

GAAAGGCGGACAGGTATCCGGTAAGCGGCAGGGTCGGAACAGGAGAGCGCACGAGGGAGCTTCC

AGGGGGAAACGCCTGGTATCTTTATAGTCCTGTCGGGTTTCGCCACCTCTGACTTGAGCGTCGATT

TTTGTGATGCTCGTCAGGGGGGCGGAGCCTATGGAAAAACGCCAGCAACGCGGCCTTTTTACGGTT

CCTGGCCTTTTGCTGGCCTTTTGCTCACATGTTCTTTCCTGCGTTATCCCCTGATTCTGTGGATAACC

GTATTACCGCCTTTGAGTGAGCTGATACCGCTCGCCGCAGCCGAACGACCGAGCGCAGCGAGTCA

GTGAGCGAGGAAGCGGAAGAGCGCCCAATACGCAAACCGCCTCTCCCCGCGCGTTGGCCGATTCA

TTAATGCAGCTGGCACGACAGGTTTCCCGACTGGAAAGCGGGCAGTGAGCGCAACGCAATTAATG

TGAGTTAGCTCACTCATTAGGCACCCCAGGCTTTACACTTTATGCTTCCGGCTCGTATGTTGTGTGG

AATTGTGAGCGGATAACAATTTCACACAGGAAACAGCTATGACCATGATTACGCCAAGCGCGCAA

TTAACCCTCACTAAAGGGAACCTCCCCTAGCTTAATTAACCCTAGAAAGATAATCATATTGTGACG

TACGTTAAAGATAATCATGCGTAAAATTGACGCATGTGTTTTATCGATCTGTATATCGAGGTTTATT

TATTAATTTGAATAGATATTAAGTTTTATTATATTTACACTTACATACTAATAATAAATTCAACAAA

CAATTTATTTATGTTTATTTATTTATTAAAAAAAAACAAAAACTCAAAATTTCTTCTATAAAGTAAC

AAAACTTTTAAACATTCTCTCTTTTACAAAAATAAACTTATTTTGTACTTTAAAAACAGTCATGTTG

TATTATAAAATAAGTAATTAGCTTAACTTATACATAATAGAAACAAATTATACTTATTAATCGCAT

TGATTATTGACTAGTCGTATTAAGGGTTCCGGATCAGCTTGATTCGAGCCCCAGCTGGTTCTTTCCG

CCTCAGAAGCCATAGAGCCCACCGCATCCCCAGCATGCCTGCTATTGTCTTCCCAATCCTCCCCCTT

GCTGTCCTGCCCCACCCCACCCCCCAGAATAGAATGACACCTACTCAGACAATGCGATGCAATTTC

CTCATTTTATTAGGAAAGGACAGTGGGAGTGGCACCTTCCAGGGTCAAGGAAGGCACGGGGGAGG

GGCAAACAACAGATGGCTGGCAACTAGAAGGCACAGTCGAGGCTGATCAGCGAGCTCTAGAGAA

TTGATCCCCTCAGAAGAACTCGTCAAGAAGGCGATAGAAGGCGATGCGCTGCGAATCGGGAGCGG

CGATACCGTAAAGCACGAGGAAGCGGTCAGCCCATTCGCCGCCAAGCTCTTCAGCAATATCACGG

GTAGCCAACGCTATGTCCTGATAGCGGTCCGCCACACCCAGCCGGCCACAGTCGATGAATCCAGA

AAAGCGGCCATTTTCCACCATGATATTCGGCAAGCAGGCATCGCCATGGGTCACGACGAGATCCTC

GCCGTCGGGCATGCGCGCCTTGAGCCTGGCGAACAGTTCGGCTGGCGCGAGCCCCTGATGCTCTTC

GTCCAGATCATCCTGATCGACAAGACCGGCTTCCATCCGAGTACGTGCTCGCTCGATGCGATGTTT

CGCTTGGTGGTCGAATGGGCAGGTAGCCGGATCAAGCGTATGCAGCCGCCGCATTGCATCAGCCA

TGATGGATACTTTCTCGGCAGGAGCAAGGTGAGATGACAGGAGATCCTGCCCCGGCACTTCGCCC

AATAGCAGCCAGTCCCTTCCCGCTTCAGTGACAACGTCGAGCACAGCTGCGCAAGGAACGCCCGT

CGTGGCCAGCCACGATAGCCGCGCTGCCTCGTCCTGCAGTTCATTCAGGGCACCGGACAGGTCGGT

CTTGACAAAAAGAACCGGGCGCCCCTGCGCTGACAGCCGGAACACGGCGGCATCAGAGCAGCCG

ATTGTCTGTTGTGCCCAGTCATAGCCGAATAGCCTCTCCACCCAAGCGGCCGGAGAACCTGCGTGC

AATCCATCTTGTTCAATGGCCGATCCCATGGCGGTATCGATAAGCTAGCTTGGGCTGCAGGTCGAG

GGACCTAATTAAGGGTTCCGGATCCACTAGTTCTAGAGCGGCCTCGACTCTACGATACCGTCGATC

-continuede

CCCACTGGAAAGACCGCGAAGAGTTTGTCCTCAACCGCGAGCTGTGGAAAAAAAAGGGACAGGAT

AAGTATGACATCATCAAGGAAACCCTGGACTACTGCGCCCTACAGATCCCTGAAGTTCCTATACTT

TCTAGAGAATAGGAACTTCGGAATAGGAACTTCAAAGAACGCGTACCCCACAGTGGGTGGCCTAG

GGACAGGATTGCAACTCCAGTCTTTCTTCTTCTTGGGCGGGAGTCACTAGTTATTAATAGTAATCA

ATTACGGGGTCATTAGTTCATAGCCCATATATGGAGTTCCGCGTTACATAACTTACGGTAAATGGC

CCGCCTGGCTGACCGCCCAACGACCCCCGCCCATTGACGTCAATAATGACGTATGTTCCCATAGTA

ACGCCAATAGGGACTTTCCATTGACGTCAATGGGTGGACTATTTACGGTAAACTGCCCACTTGGCA

GTACATCAAGTGTATCATATGCCAAGTACGCCCCCTATTGACGTCAATGACGGTAAATGGCCCGCC

TGGCATTATGCCCAGTACATGACCTTATGGGACTTTCCTACTTGGCAGTACATCTACGTATTAGTCA

TCGCTATTACCATGGGTCGAGGTGAGCCCCACGTTCTGCTTCACTCTCCCCATCTCCCCCCCCTCCC

CACCCCCAATTTTGTATTTATTTATTTTTTAATTATTTTGTGCAGCGATGGGGGCGGGGGGGGGGG

GGCGCGCGCCAGGCGGGGCGGGGCGGGGCGAGGGGCGGGGCGGGGCGAGGCGGAGAGGTGCGG

CGGCAGCCAATCAGAGCGGCGCGCTCCGAAAGTTTCCTTTTATGGCGAGGCGGCGGCGGCGG

CCCTATAAAAAGCGAAGCGCGCGGCGGGCGGGAGTCGCTGCGTTGCCTTCGCCCCGTGCCCCGCT

CCGCGCCGCCTCGCGCCGCCCGCCCCGGCTCTGACTGACCGCGTTACTCCCACAGGTGAGCGGGCG

GGACGGCCCTTCTCCTCCGGGCTGTAATTAGCGCTTGGTTTAATGACGGCTCGTTTCTTTTCTGTGG

CTGCGTGAAAGCCTTAAAGGGCTCCGGGAGGGCCCTTTGTGCGGGGGGGAGCGGCTCGGGGGGTG

CGTGCGTGTGTGTGTGCGTGGGGAGCGCCGCGTGCGGCCCGCGCTGCCCGGCGGCTGTGAGCGCT

GCGGGCGCGGCGCGGGGCTTTGTGCGCTCCGCGTGTGCGCGAGGGGAGCGCGGCCGGGGGCGGTG

CCCCGCGGTGCGGGGGGGCTGCGAGGGGAACAAAGGCTGCGTGCGGGGTGTGTGCGTGGGGGGG

TGAGCAGGGGGTGTGGGCGCGGCGGTCGGGCTGTAACCCCCCCCTGCACCCCCCTCCCCGAGTTGC

TGAGCACGGCCCGGCTTCGGGTGCGGGGCTCCGTGCGGGGCGTGGCGCGGGGCTCGCCGTGCCGG

GCGGGGGGTGGCGGCAGGTGGGGGTGCCGGGCGGGGCGGGGCCGCCTCGGGCCGGGGAGGGCTC

GGGGGAGGGGCGCGGCGGCCCCGGAGCGCCGGCGGCTGTCGAGGCGCGGCGAGCCGCAGCCATT

GCCTTTTATGGTAATCGTGCGAGAGGGCGCAGGGACTTCCTTTGTCCCAAATCTGGCGGAGCCGAA

ATCTGGGAGGCGCCGCCGCACCCCCTCTAGCGGGCGCGGGCGAAGCGGTGCGGCGCCGGCAGGAA

GGAAATGGGCGGGGAGGGCCTTCGTGCGTCGCCGCGCCGCCGTCCCCTTCTCCATCTCCAGCCTCG

GGGCTGCCGCAGGGGGACGGCTGCCTTCGGGGGGGACGGGGCAGGGCGGGGTTCGGCTTCTGGCG

TGTGACCGGCGGCTCTAGAGCCTCTGCTAACCATGTTCATGCCTTCTTCTTTTTCCTACAGCTCCTG

GGCAACGTGCTGGTTATTGTGCTGTCTCATCATTTTGGCAAAGAATTCGCCACCATGGTGCCCAAG

AAGAAGAGGAAAGTCTCTAGACTGGACAAGAGCAAAGTCATAAACTCTGCTCTGGAATTACTCAA

TGGAGTCGGTATCGAAGGCCTGACGACAAGGAAACTCGCTCAAAAGCTGGGAGTTGAGCAGCCTA

CCCTGTACTGGCACGTGAAGAACAAGCGGGCCCTGCTCGATGCCCTGCCAATCGAGATGCTGGAC

AGGCATCATACCCACTCCTGCCCCCTGGAAGGCGAGTCATGGCAAGACTTTCTGCGGAACAACGC

CAAGTCATACCGCTGTGCTCTCCTCTCACATCGCGACGGGGCTAAAGTGCATCTCGGCACCCGCCC

AACAGAGAAACAGTACGAAACCCTGGAAAATCAGCTCGCGTTCCTGTGTCAGCAAGGCTTCTCCC

TGGAGAACGCACTGTACGCTCTGTCCGCCGTGGGCCACTTTACACTGGGCTGCGTATTGGAGGAAC

AGGAGCATCAAGTAGCAAAAGAGGAAAGAGAGACACCTACCACCGATTCTATGCCCCCACTTCTG

AAACAAGCAATTGAGCTGTTCGACCGGCAGGGAGCCGAACCTGCCTTCCTTTTCGGCCTGGAACTA

ATCATATGTGGCCTGGAGAAACAGCTAAAGTGCGAAAGCGGCGGGCCGACCGACGCCCTTGACGA

TTTTGACTTAGACATGCTCCCAGCCGATGCCCTTGACGACTTTGACCTTGATATGCTGCCTGCTGAC

-continuede

GCTCTTGACGATTTTGACCTTGACATGCTCCCCGGGTAAAGCGGCCGCGACTCTAGATCATAATCA

GCCATACCACATTTGTAGAGGTTTTACTTGCTTTAAAAAACCTCCCACACCTCCCCCTGAACCTGA

AACATAAAATGAATGCAATTGTTGTTGTTAACTTGTTTATTGCAGCTTATAATGGTTACAAATAAA

GCAATAGCATCACAAATTTCACAAATAAAGCATTTTTTTCACTGCATTCTAGTTGTGGTTTGTCCAA

ACTCATCAATGTATCTTAAGGGATCCCTAGAGGGACAGCCCCCCCCCAAAGCCCCCAGGGATGTA

ATTACGTCCCTCCCCCGCTAGGGGCAGCAGCGAGCCGCCCGGGGCTCCGCTCCGGTCCGGCGCTCC

CCCCGCATCCCCGAGCCGGCAGCGTGCGGGGACAGCCCGGGCACGGGGAAGGTGGCACGGGATC

GCTTTCCTCTGAACGCTTCTCGCTGCTCTTTGAGCCTGCAGACACCTGGGGGGATACGGGGAAAAA

GCTTTAGGCTGAAAGAGAGATTTAGAATGACAGAATCATAGAACGGCCTGGGTTGCAAAGGAGCA

CAGTGCTCATCCAGATCCAACCCCCTGCTATGTGCAGGGTCATCAACCAGCAGCCCAGGCTGCCCA

GAGCCACATCCAGCCTGGCCTTGAATGCCTGCAGGGATGGGGCATCCACAGCCTCCTTGGGCAAC

CTGTTCAGTGCGTCACCACCCTCTGGGGGAAAAACTGCCTCCTCATATCCAACCCAAACCTCCCCT

GTCTCAGTGTAAAGCCATTCCCCCTTGTCCTATCAAGGGGGAGTTTGCTGTGACATTGTTGGTCTGG

GGTGACACATGTTTGCCAATTCAGTGCATCACGGAGAGGCAGATCTTGGGGATAAGGAAGTGCAG

GACAGCATGGACGTGGGACATGCAGGTGTTGAGGGCTCTGGGACACTCTCCAAGTCACAGCGTTC

AGAACAGCCTTAAGGATAAGAAGATAGGATAGAAGGACAAAGAGCAAGTTAAAACCCAGCATGG

AGAGGAGCACAAAAAGGCCACAGACACTGCTGGTCCCTGTGTCTGAGCCTGCATGTTTGATGGTG

TCTGGATGCAAGCAGAAGGGGTGGAAGAGCTTGCCTGGAGAGATACAGCTGGGTCAGTAGGACTG

GGACAGGCAGCTGGAGAATTGCCATGTAGATGTTCATACAATCGTCAAATCATGAAGGCTGGAAA

AGCCCTCCAAGATCCCCAAGACCAACCCCAACCCACCCACCGTGCCCACTGGCCATGTCCCTCAGT

GCCACATCCCCACAGTTCTTCATCACCTCCAGGGACGGTGACCCCCCCACCTCCGTGGGCAGCTGT

GCCACTGCAGCACCGCTCTTTGGAGAAGGTAAATCTTGCTAAATCCAGCCCGACCCTCCCCTGGCA

CAACGTAAGGCCATTATCTCTCATCCAACTCCAGGACGGAGTCAGTGAGGATGGGGCTGTCGACCT

AGAGGGACAGCCCCCCCCCAAAGCCCCCAGGGATGTAATTACGTCCCTCCCCCGCTAGGGGCAGC

AGCGAGCCGCCCGGGGCTCCGCTCCGGTCCGGCGCTCCCCCCGCATCCCCGAGCCGGCAGCGTGC

GGGGACAGCCCGGGCACGGGGAAGGTGGCACGGGATCGCTTTCCTCTGAACGCTTCTCGCTGCTCT

TTGAGCCTGCAGACACCTGGGGGGATACGGGGAAAAAGCTTTAGGCTGAAAGAGAGATTTAGAAT

GACAGAATCATAGAACGGCCTGGGTTGCAAAGGAGCACAGTGCTCATCCAGATCCAACCCCCTGC

TATGTGCAGGGTCATCAACCAGCAGCCCAGGCTGCCCAGAGCCACATCCAGCCTGGCCTTGAATG

CCTGCAGGGATGGGGCATCCACAGCCTCCTTGGGCAACCTGTTCAGTGCGTCACCACCCTCTGGGG

GAAAAACTGCCTCCTCATATCCAACCCAAACCTCCCCTGTCTCAGTGTAAAGCCATTCCCCCTTGTC

CTATCAAGGGGGAGTTTGCTGTGACATTGTTGGTCTGGGGTGACACATGTTTGCCAATTCAGTGCA

TCACGGAGAGGCAGATCTTGGGGATAAGGAAGTGCAGGACAGCATGGACGTGGGACATGCAGGT

GTTGAGGGCTCTGGGACACTCTCCAAGTCACAGCGTTCAGAACAGCCTTAAGGATAAGAAGATAG

GATAGAAGGACAAAGAGCAAGTTAAAACCCAGCATGGAGAGGAGCACAAAAAGGCCACAGACAC

TGCTGGTCCCTGTGTCTGAGCCTGCATGTTTGATGGTGTCTGGATGCAAGCAGAAGGGGTGGAAGA

GCTTGCCTGGAGAGATACAGCTGGGTCAGTAGGACTGGGACAGGCAGCTGGAGAATTGCCATGTA

GATGTTCATACAATCGTCAAATCATGAAGGCTGGAAAAGCCCTCCAAGATCCCCAAGACCAACCC

CAACCCACCCACCGTGCCCACTGGCCATGTCCCTCAGTGCCACATCCCCACAGTTCTTCATCACCTC

CAGGGACGGTGACCCCCCCACCTCCGTGGGCAGCTGTGCCACTGCAGCACCGCTCTTTGGAGAAG

GTAAATCTTGCTAAATCCAGCCCGACCCTCCCCTGGCACAACGTAAGGCCATTATCTCTCATCCAA

-continuede

CTCCAGGACGGAGTCAGTGAGGATGGGGCTCAATTGTTTACTCCCTATCAGTGATAGAGAACGTAT

GAAGAGTTTACTCCCTATCAGTGATAGAGAACGTATGCAGACTTTACTCCCTATCAGTGATAGAGA

ACGTATAAGGAGTTTACTCCCTATCAGTGATAGAGAACGTATGACCAGTTTACTCCCTATCAGTGA

TAGAGAACGTATCTACAGTTTACTCCCTATCAGTGATAGAGAACGTATATCCAGTTTACTCCCTAT

CAGTGATAGAGAACGTATAAGCTTTAGGCGTGTACGGTGGGCGCCTATAAAAGCAGAGCTCGTTT

AGTGAACCGTCAGATCGCCTGGAGCAATTCCACAACACTTTTGTCTTATACCAACTTTCCGTACCA

CTTCCTACCCTCGTAAAAAGCTTGTCCACCATGGCTCCTAAGAAAAAGCGGAAGGTGGACAAGAA

ATACTCAATCGGGCTGGCCATCGGAACTAACTCAGTGGGGTGGGCAGTCATTACTGACGAGTACA

AAGTGCCAAGCAAGAAATTTAAGGTCCTGGGCAACACCGATAGGCACTCCATCAAGAAAAATCTG

ATTGGGGCCCTGCTGTTCGACTCTGGAGAGACAGCTGAAGCAACTAGACTGAAAAGGACTGCTAG

AAGGCGCTATACCCGGCGAAAGAATCGCATCTGCTACCTGCAGGAGATTTTCTCTAACGAAATGG

CCAAGGTGGACGATAGTTTCTTTCATCGGCTGGAGGAATCATTCCTGGTCGAGGAAGATAAGAAA

CACGAGAGACATCCTATCTTTGGAAACATTGTGGACGAGGTCGCTTATCACGAAAAATACCCCACC

ATCTATCATCTGCGCAAGAAACTGGTGGACTCTACAGATAAAGCAGACCTGCGGCTGATCTATCTG

GCCCTGGCTCACATGATTAAGTTCAGAGGCCATTTTCTGATCGAGGGAGATCTGAACCCAGACAAT

AGCGATGTGGACAAGCTGTTCATCCAGCTGGTCCAGACATACAATCAGCTGTTTGAGGAAAACCCT

ATTAATGCATCTGGCGTGGACGCAAAAGCCATCCTGAGTGCCAGGCTGTCTAAGAGTAGAAGGCT

GGAGAACCTGATCGCTCAGCTGCCAGGCGAAAAGAAAAACGGCCTGTTTGGAAATCTGATTGCAC

TGTCACTGGGACTGACACCTAACTTCAAGAGCAATTTTGATCTGGCCGAGGACGCTAAACTGCAGC

TGAGCAAGGACACTTATGACGATGACCTGGATAACCTGCTGGCTCAGATCGGAGATCAGTACGCA

GACCTGTTCCTGGCCGCTAAGAATCTGTCTGACGCTATCCTGCTGAGTGATATTCTGCGGGTGAAC

ACCGAGATTACAAAAGCCCCTCTGTCAGCTAGCATGATCAAGAGATATGACGAGCACCATCAGGA

TCTGACCCTGCTGAAGGCACTGGTGCGCCAGCAGCTGCCCGAGAAGTACAAGGAAATCTTCTTTGA

TCAGAGTAAGAACGGGTACGCCGGTTATATTGACGGCGGAGCTTCACAGGAGGAATTCTACAAGT

TTATCAAACCTATTCTGGAGAAGATGGACGGCACCGAGGAACTGCTGGTGAAACTGAATCGCGAG

GACCTGCTGCGCAAGCAGCGGACATTTGATAACGGCTCCATCCCCCACCAGATTCATCTGGGAGA

GCTGCACGCAATCCTGCGACGACAGGAAGACTTCTACCCATTTCTGAAGGATAACCGCGAGAAGA

TCGAAAAAATTCTGACCTTCCGGATCCCTTACTATGTGGGGCCCCTGGCAAGGGGTAATTCCCGCT

TTGCCTGGATGACACGGAAATCTGAGGAAACAATCACTCCTTGGAACTTCGAGGAAGTGGTCGAT

AAGGGAGCTTCCGCACAGTCTTTCATCGAGAGAATGACAAACTTCGACAAAAACCTGCCAAATGA

GAAAGTGCTGCCTAAGCACAGTCTGCTGTACGAGTATTTCACAGTCTATAACGAACTGACTAAGGT

GAAATACGTCACCGAGGGGATGAGGAAGCCCGCCTTCCTGAGCGGTGAACAGAAGAAAGCTATCG

TGGACCTGCTGTTTAAAACCAATCGCAAGGTGACAGTCAAGCAGCTGAAGGAGGACTACTTCAAG

AAAATTGAATGTTTCGATTCTGTGGAGATCAGTGGCGTCGAAGACAGATTTAACGCTTCTCTGGGA

ACCTACCACGATCTGCTGAAGATCATTAAGGATAAAGACTTCCTGGACAACGAGGAAAATGAGGA

TATCCTGGAAGACATTGTGCTGACCCTGACACTGTTTGAGGATCGCGAAATGATCGAGGAACGGCT

GAAAACTTATGCCCATCTGTTCGATGACAAGGTGATGAAACAGCTGAAGCGAAGAAGGTACACCG

GCTGGGGACGACTGAGCAGAAAGCTGATCAACGGCATTCGGGACAAACAGAGTGGAAAGACTAT

CCTGGACTTTCTGAAATCAGATGGCTTCGCTAACAGAAATTTTATGCAGCTGATTCACGATGACAG

CCTGACCTTCAAAGAGGATATCCAGAAGGCACAGGTGTCCGGGCAGGGTGACTCTCTGCACGAGC

ATATCGCAAACCTGGCCGGGTCCCCCGCCATCAAGAAAGGTATTCTGCAGACCGTGAAGGTGGTC

-continuede

GATGAGCTGGTGAAAGTCATGGGCAGGCATAAGCCAGAAAACATCGTGATTGAGATGGCCCGCGA

AAATCAGACCACACAGAAAGGACAGAAGAACAGCCGCGAGCGGATGAAAAGGATCGAGGAAGG

CATTAAGGAACTGGGATCCCAGATCCTGAAAGAGCACCCTGTGGAAAACACTCAGCTGCAGAATG

AGAAGCTGTATCTGTACTATCTGCAGAATGGGCGGGATATGTACGTGGACCAGGAGCTGGATATT

AACCGACTGTCTGATTACGACGTGGATGCCATCGTCCCACAGTCATTCCTGAAAGATGACAGCATT

GACAATAAGGTGCTGACCCGGAGTGACAAAAACCGAGGAAAGAGTGATAATGTCCCTTCAGAGG

AAGTGGTCAAGAAAATGAAGAACTACTGGAGACAGCTGCTGAATGCCAAACTGATCACACAGCGA

AAGTTTGATAACCTGACTAAAGCTGAGAGAGGGGGTCTGTCAGAACTGGACAAAGCAGGCTTCAT

CAAGCGACAGCTGGTGGAGACCAGACAGATCACAAAGCACGTCGCTCAGATTCTGGATAGCAGGA

TGAACACAAAGTACGATGAGAATGACAAACTGATCCGCGAAGTGAAGGTCATTACTCTGAAGTCA

AAACTTGTGAGCGACTTCAGAAAGGATTTCCAGTTCTACAAAGTCAGGGAGATCAACAATTATCA

CCATGCTCATGACGCATACCTGAACGCAGTGGTCGGGACCGCCCTGATTAAGAAATACCCCAAAC

TGGAGAGCGAATTCGTGTACGGTGACTATAAGGTGTACGATGTCAGAAAAATGATCGCCAAGAGT

GAGCAGGAAATTGGAAAAGCCACCGCTAAGTATTTCTTTTACTCAAACATCATGAATTTCTTTAAG

ACTGAGATCACCCTGGCAAATGGGGAAATCCGAAAGAGACCACTGATTGAGACTAACGGCGAGAC

CGGAGAAATCGTGTGGGACAAGGGTAGGGATTTTGCCACAGTGCGCAAGGTCCTGTCCATGCCTC

AAGTGAATATTGTCAAGAAAACAGAGGTGCAGACTGGCGGATTCAGTAAGGAATCAATTCTGCCC

AAACGGAACTCTGATAAGCTGATCGCCCGAAAGAAAGACTGGGATCCCAAGAAATATGGGGGTTT

CGACTCCCCAACAGTGGCTTACTCTGTCCTGGTGGTCGCAAAGGTGGAGAAGGGGAAAAGCAAGA

AACTGAAATCCGTCAAGGAGCTGCTGGGTATCACTATTATGGAGAGGAGCTCCTTCGAGAAGAAC

CCCATCGATTTTCTGGAGGCTAAAGGCTATAAGGAAGTGAAGAAAGACCTGATCATTAAACTGCC

AAAGTACAGCCTGTTTGAGCTGGAAAACGGAAGGAAGCGAATGCTGGCATCCGCAGGAGAGCTGC

AGAAGGGTAATGAACTGGCCCTGCCTTCTAAGTACGTGAACTTCCTGTATCTGGCTAGCCACTACG

AGAAGCTGAAAGGCTCCCCCGAGGATAACGAACAGAAACAGCTGTTTGTGGAGCAGCACAAGCAT

TATCTGGACGAGATCATTGAACAGATTAGCGAGTTCTCCAAAAGAGTGATCCTGGCTGACGCAAA

TCTGGATAAGGTCCTGAGCGCATACAACAAACACAGAGATAAGCCAATCAGGGAGCAGGCCGAA

AATATCATTCATCTGTTCACTCTGACCAACCTGGGAGCCCCTGCAGCCTTCAAGTATTTTGACACTA

CCATCGATCGGAAACGATACACATCCACTAAGGAGGTGCTGGACGCTACCCTGATTCACCAGAGC

ATTACCGGCCTGTATGAAACAAGGATTGACCTGTCTCAGCTGGGGGGCGACCTCGAGCCGAAAAA

GAAACGCAAAGTTGGGCGCGCCGACGCGCTGGACGATTTCGATCTCGACATGCTGGGCAGCGACG

CCCTGGATGACTTCGACCTGGATATGCTGGGCTCTGATGCCCTGGACGACTTTGACTTGGACATGT

TGGGATCCGACGCTCTCGATGATTTTGACCTTGACATGCTGATCAACGGCAGCGGCGAGGGCAGA

GGCAGCCTGCTAACATGCGGTGACGTCGAGGAGAATCCTGGCCCAGCACCGGGATCCATGGTGAG

CAAGGGCGAGGAGCTGTTCACCGGGGTGGTGCCCATCCTGGTCGAGCTGGACGGCGACGTAAACG

GCCACAAGTTCAGCGTGTCCGGCGAGGGCGAGGGCGATGCCACCTACGGCAAGCTGACCCTGAAG

TTCATCTGCACCACCGGCAAGCTGCCCGTGCCCTGGCCCACCCTCGTGACCACCTTCACCTACGGC

GTGCAGTGCTTCGCCCGCTACCCCGACCACATGAAGCAGCACGACTTCTTCAAGTCCGCCATGCCC

GAAGGCTACGTCCAGGAGCGCACCATCTTCTTCAAGGACGACGGCAACTACAAGACCCGCGCCGA

GGTGAAGTTCGAGGGCGACACCCTGGTGAACCGCATCGAGCTGAAGGGCATCGACTTCAAGGAGG

ACGGCAACATCCTGGGGCACAAGCTGGAGTACAACTACAACAGCCACAAGGTCTATATCACCGCC

GACAAGCAGAAGAACGGCATCAAGGTGAACTTCAAGACCCGCCACAACATCGAGGACGGCAGCG

-continuede
TGCAGCTCGCCGACCACTACCAGCAGAACACCCCCATCGGCGACGGCCCCGTGCTGCTGCCCGAC

AACCACTACCTGAGCACCCAGTCCGCCCTGAGCAAAGACCCCAACGAGAAGCGCGATCACATGGT

CCTGCTGGAGTTCGTGACCGCCGCCGGGATCACTCTCGGCATGGACGAGCTGTACAAGTAAACCTA

ATCTAGCAGCTCGCTGATCAGCCTCGACTGTGCCTTCTAGTTGCCAGCCATCTGTTGTTTGCCCCTC

CCCCGTGCCTTCCTTGACCCTGGAAGGTGCCACTCCCACTGTCCTTTCCTAATAAAATGAGGAAAT

TGCATCGCATTGTCTGAGTAGGTGTCATTCTATTCTGGGGGGTGGGGTGGGGCAGGACAGCAAGG

GGGAGGATTGGGAAGACAATAGCAGGCATGCTGGGGATGCGGTGGGCTCTATGGCTTCTGAGGCG

GAAAGAACCAGCTGGGGCTCGATCCTCTAGTTGGCGCGTCATGGTCCATATGAATATCCTCCTTAG

TTCCTATTCCGCTAGCCTAGAGGGACAGCCCCCCCCCAAAGCCCCCAGGGATGTAATTACGTCCCT

CCCCCGCTAGGGGCAGCAGCGAGCCGCCCGGGGCTCCGCTCCGGTCCGGCGCTCCCCCCGCATCCC

CGAGCCGGCAGCGTGCGGGGACAGCCCGGGCACGGGGAAGGTGGCACGGGATCGCTTTCCTCTGA

ACGCTTCTCGCTGCTCTTTGAGCCTGCAGACACCTGGGGGGATACGGGGAAAAAGCTTTAGGCTGA

AAGAGAGATTTAGAATGACAGAATCATAGAACGGCCTGGGTTGCAAAGGAGCACAGTGCTCATCC

AGATCCAACCCCCTGCTATGTGCAGGGTCATCAACCAGCAGCCCAGGCTGCCCAGAGCCACATCC

AGCCTGGCCTTGAATGCCTGCAGGGATGGGGCATCCACAGCCTCCTTGGGCAACCTGTTCAGTGCG

TCACCACCCTCTGGGGGAAAAACTGCCTCCTCATATCCAACCCAAACCTCCCCTGTCTCAGTGTAA

AGCCATTCCCCCTTGTCCTATCAAGGGGGAGTTTGCTGTGACATTGTTGGTCTGGGGTGACACATG

TTTGCCAATTCAGTGCATCACGGAGAGGCAGATCTTGGGGATAAGGAAGTGCAGGACAGCATGGA

CGTGGGACATGCAGGTGTTGAGGGCTCTGGGACACTCTCCAAGTCACAGCGTTCAGAACAGCCTT

AAGGATAAGAAGATAGGATAGAAGGACAAAGAGCAAGTTAAAACCCAGCATGGAGAGGAGCACA

AAAAGGCCACAGACACTGCTGGTCCCTGTGTCTGAGCCTGCATGTTTGATGGTGTCTGGATGCAAG

CAGAAGGGGTGGAAGAGCTTGCCTGGAGAGATACAGCTGGGTCAGTAGGACTGGGACAGGCAGC

TGGAGAATTGCCATGTAGATGTTCATACAATCGTCAAATCATGAAGGCTGGAAAAGCCCTCCAAG

ATCCCCAAGACCAACCCCAACCCACCCACCGTGCCCACTGGCCATGTCCCTCAGTGCCACATCCCC

ACAGTTCTTCATCACCTCCAGGGACGGTGACCCCCCCACCTCCGTGGGCAGCTGTGCCACTGCAGC

ACCGCTCTTTGGAGAAGGTAAATCTTGCTAAATCCAGCCCGACCCTCCCCTGGCACAACGTAAGGC

CATTATCTCTCATCCAACTCCAGGACGGAGTCAGTGAGGATGGGGCTGGATCCGAAGCAGCTCCA

GCCTACACAATCGCTCAAGACGTGTAATGCTTTTATTATATATTAGTCACGATATCTATAACAAGA

AAATATATATATAATAAGTTATCACGTAAGTAGAACATGAAATAACAATATAATTATCGTATGAGT

TAAATCTTAAAAGTCACGTAAAAGATAATCATGCGTCATTTTGACTCACGCGGTCGTTATAGTTCA

AAATCAGTGACACTTACCGCATTGACAAGCACGCCTCACGGGAGCTCCAAGCGGCGACTGAGATG

TCCTAAATGCACAGCGACGGATTCGCGCTATTTAGAAAGAGAGAGCAATATTTCAAGAATGCATG

CGTCAATTTTACGCAGACTATCTTTCTAGGGTTAAAAAAGATTTGCGCTTTACTCGACCTAAACTTT

AAACACGTCATAGAATCTTCGTTTGACAAAAACCACATTGTGGGGTACCGAGCTCTTAATTAAGGC

GCGCCGGGGAGGTTCCCTTTAGTGAGGGTTAATTGCGGGTCGCCCTATAGTGAGTCGTATTACAAT

TCACTGGCCGTCGTTTTACAACGTCGTGACTGGGAAAACCCTGGCGTTACCCAACTTAATCGCCTT

GCAGCACATCCCCCTTTCGCCAGCTGGCGTAATAGCGAAGAGGCCCGCACCGATCGCCCTTCCCAA

CAGTTGCGCAGCCTGAATGGCGAATGGCAAATTGTAAGCGTTAATATTTTGTTAAAATTCGCGTTA

AATTTTTGTTAAATCAGCTCATTTTTTAACCAATAGGCCGAAATCGGCAAAATCCCTTATAAATCA

AAAGAATAGACCGAGATAGGGTTGAGTGTTGTTCCAGTTTGGAACAAGAGTCCACTATTAAAGAA

CGTGGACTCCAACGTCAAAGGGCGAAAAACCGTCTATCAGGGCGATGGCCCACTACGTGAACCAT

-continuede

CACCCTAATCAAGTTTTTTGGGGTCGAGGTGCCGTAAAGCACTAAATCGGAACCCTAAAGGGAGC

CCCCGATTTAGAGCTTGACGGGGAAAGCCGGCGAACGTGGCGAGAAAGGAAGGGAAGAAAGCGA

AAGGAGCGGGCGCTAGGGCGCTGGCAAGTGTAGCGGTCACGCTGCGCGTAACCACCACACCCGCC

GCGCTTAATGCGCCGCTACAGGGCGCGTCAG

TOIC_Bsd_BE_Cas9_obl_r26_AAVS_PgkNeo (SEQ ID NO: 17)

GTGGCACTTTTCGGGGAAATGTGCGCGGAACCCCTATTTGTTTATTTTTCTAAATACATTCAAATAT

GTATCCGCTCATGAGACAATAACCCTGATAAATGCTTCAATAATATTGAAAAAGGAAGAGTATGA

GTATTCAACATTTCCGTGTCGCCCTTATTCCCTTTTTTGCGGCATTTTGCCTTCCTGTTTTTGCTCAC

CCAGAAACGCTGGTGAAAGTAAAAGATGCTGAAGATCAGTTGGGTGCACGAGTGGGTTACATCGA

ACTGGATCTCAACAGCGGTAAGATCCTTGAGAGTTTTCGCCCCGAAGAACGTTTTCCAATGATGAG

CACTTTTAAAGTTCTGCTATGTGGCGCGGTATTATCCCGTATTGACGCCGGGCAAGAGCAACTCGG

TCGCCGCATACACTATTCTCAGAATGACTTGGTTGAGTACTCACCAGTCACAGAAAAGCATCTTAC

GGATGGCATGACAGTAAGAGAATTATGCAGTGCTGCCATAACCATGAGTGATAACACTGCGGCCA

ACTTACTTCTGACAACGATCGGAGGACCGAAGGAGCTAACCGCTTTTTTGCACAACATGGGGGATC

ATGTAACTCGCCTTGATCGTTGGGAACCGGAGCTGAATGAAGCCATACCAAACGACGAGCGTGAC

ACCACGATGCCTGTAGCAATGGCAACAACGTTGCGCAAACTATTAACTGGCGAACTACTTACTCTA

GCTTCCCGGCAACAATTAATAGACTGGATGGAGGCGGATAAAGTTGCAGGACCACTTCTGCGCTC

GGCCCTTCCGGCTGGCTGGTTTATTGCTGATAAATCTGGAGCCGGTGAGCGTGGGTCTCGCGGTAT

CATTGCAGCACTGGGGCCAGATGGTAAGCCCTCCCGTATCGTAGTTATCTACACGACGGGGAGTCA

GGCAACTATGGATGAACGAAATAGACAGATCGCTGAGATAGGTGCCTCACTGATTAAGCATTGGT

AACTGTCAGACCAAGTTTACTCATATATACTTTAGATTGATTTAAAACTTCATTTTTAATTTAAAAG

GATCTAGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGTAATC

TGCTGCTTGCAAACAAAAAAACCACCGCTACCAGCGGTGGTTTGTTTGCCGGATCAAGAGCTACCA

ACTCTTTTTCCGAAGGTAACTGGCTTCAGCAGAGCGCAGATACCAAATACTGTTCTTCTAGTGTAG

CCGTAGTTAGGCCACCACTTCAAGAACTCTGTAGCACCGCCTACATACCTCGCTCTGCTAATCCTG

TTACCAGTGGCTGCTGCCAGTGGCGATAAGTCGTGTCTTACCGGGTTGGACTCAAGACGATAGTTA

CCGGATAAGGCGCAGCGGTCGGGCTGAACGGGGGGTTCGTGCACACAGCCCAGCTTGGAGCGAAC

GACCTACACCGAACTGAGATACCTACAGCGTGAGCTATGAGAAAGCGCCACGCTTCCCGAAGGGA

GAAAGGCGGACAGGTATCCGGTAAGCGGCAGGGTCGGAACAGGAGAGCGCACGAGGGAGCTTCC

AGGGGGAAACGCCTGGTATCTTTATAGTCCTGTCGGGTTTCGCCACCTCTGACTTGAGCGTCGATT

TTTGTGATGCTCGTCAGGGGGGCGGAGCCTATGGAAAAACGCCAGCAACGCGGCCTTTTTACGGTT

CCTGGCCTTTTGCTGGCCTTTTGCTCACATGTTCTTTCCTGCGTTATCCCCTGATTCTGTGGATAACC

GTATTACCGCCTTTGAGTGAGCTGATACCGCTCGCCGCAGCCGAACGACCGAGCGCAGCGAGTCA

GTGAGCGAGGAAGCGGAAGAGCGCCCAATACGCAAACCGCCTCTCCCCGCGCGTTGGCCGATTCA

TTAATGCAGCTGGCACGACAGGTTTCCCGACTGGAAAGCGGGCAGTGAGCGCAACGCAATTAATG

TGAGTTAGCTCACTCATTAGGCACCCCAGGCTTTACACTTTATGCTTCCGGCTCGTATGTTGTGTGG

AATTGTGAGCGGATAACAATTTCACACAGGAAACAGCTATGACCATGATTACGCCAAGCGCGCAA

TTAACCCTCACTAAAGGGAACCTCCCCTAGCTTAATTAACCCTAGAAAGATAATCATATTGTGACG

TACGTTAAAGATAATCATGCGTAAAATTGACGCATGTGTTTTATCGATCTGTATATCGAGGTTTATT

TATTAATTTGAATAGATATTAAGTTTTATTATATTTACACTTACATACTAATAATAAATTCAACAAA

-continuede

CAATTTATTTATGTTTATTTATTTATTAAAAAAAAACAAAAACTCAAAATTTCTTCTATAAAGTAAC

AAAACTTTTAAACATTCTCTCTTTTACAAAAATAAACTTATTTTGTACTTTAAAAACAGTCATGTTG

TATTATAAAATAAGTAATTAGCTTAACTTATACATAATAGAAACAAATTATACTTATTAATCGCAT

TGATTATTGACTAGTCGTATTAAGGGTTCCGGATCAGCTTGATTCGAGCCCCAGCTGGTTCTTTCCG

CCTCAGAAGCCATAGAGCCCACCGCATCCCCAGCATGCCTGCTATTGTCTTCCCAATCCTCCCCCTT

GCTGTCCTGCCCCACCCCACCCCCCAGAATAGAATGACACCTACTCAGACAATGCGATGCAATTTC

CTCATTTTATTAGGAAAGGACAGTGGGAGTGGCACCTTCCAGGGTCAAGGAAGGCACGGGGGAGG

GGCAAACAACAGATGGCTGGCAACTAGAAGGCACAGTCGAGGCTGATCAGCGAGCTCTAGAGAA

TTGATCCCCTCAGAAGAACTCGTCAAGAAGGCGATAGAAGGCGATGCGCTGCGAATCGGGAGCGG

CGATACCGTAAAGCACGAGGAAGCGGTCAGCCCATTCGCCGCCAAGCTCTTCAGCAATATCACGG

GTAGCCAACGCTATGTCCTGATAGCGGTCCGCCACACCCAGCCGGCCACAGTCGATGAATCCAGA

AAAGCGGCCATTTTCCACCATGATATTCGGCAAGCAGGCATCGCCATGGGTCACGACGAGATCCTC

GCCGTCGGGCATGCGCGCCTTGAGCCTGGCGAACAGTTCGGCTGGCGCGAGCCCCTGATGCTCTTC

GTCCAGATCATCCTGATCGACAAGACCGGCTTCCATCCGAGTACGTGCTCGCTCGATGCGATGTTT

CGCTTGGTGGTCGAATGGGCAGGTAGCCGGATCAAGCGTATGCAGCCGCCGCATTGCATCAGCCA

TGATGGATACTTTCTCGGCAGGAGCAAGGTGAGATGACAGGAGATCCTGCCCCGGCACTTCGCCC

AATAGCAGCCAGTCCCTTCCCGCTTCAGTGACAACGTCGAGCACAGCTGCGCAAGGAACGCCCGT

CGTGGCCAGCCACGATAGCCGCGCTGCCTCGTCCTGCAGTTCATTCAGGGCACCGGACAGGTCGGT

CTTGACAAAAAGAACCGGGCGCCCCTGCGCTGACAGCCGGAACACGGCGGCATCAGAGCAGCCG

ATTGTCTGTTGTGCCCAGTCATAGCCGAATAGCCTCTCCACCCAAGCGGCCGGAGAACCTGCGTGC

AATCCATCTTGTTCAATGGCCGATCCCATGGTTTAGTTCCTCACCTTGTCGTATTATACTATGCCGA

TATACTATGCCGATGATTAATTGTCAACACGTGCTGCTGCAGGTCGAAAGGCCCGGAGATGAGGA

AGAGGAGAACAGCGCGGCAGACGTGCGCTTTTGAAGCGTGCAGAATGCCGGGCCTCCGGAGGACC

TTCGGGCGCCCGCCCCGCCCCTGAGCCCGCCCCTGAGCCCGCCCCCGGACCCACCCCTTCCCAGCC

TCTGAGCCCAGAAAGCGAAGGAGCAAAGCTGCTATTGGCCGCTGCCCCAAAGGCCTACCCGCTTC

CATTGCTCAGCGGTGCTGTCCATCTGCACGAGACTAGTGAGACGTGCTACTTCCATTTGTCACGTC

CTGCACGACGCGAGCTGCGGGGCGGGGGGAACTTCCTGACTAGGGGAGGAGTAGAAGGTGGCG

CGAAGGGGCCACCAAAGAACGGAGCCGGTTGGCGCCTACCGGTGGATGTGGAATGTGTGCGAGCC

AGAGGCCACTTGTGTAGCGCCAAGTGCCCAGCGGGGCTGCTAAAGCGCATGCTCCAGACTGCCTT

GGGAAAAGCGCCTCCCCTACCCGGTAGACACCCCACAGTGGGTGGCCTAGGGACAGGATTGCAAC

TCCAGTCTTTCTTCTTCTTGGGCGGGAGTCACTAGTTATTAATAGTAATCAATTACGGGGTCATTAG

TTCATAGCCCATATATGGAGTTCCGCGTTACATAACTTACGGTAAATGGCCCGCCTGGCTGACCGC

CCAACGACCCCCGCCCATTGACGTCAATAATGACGTATGTTCCCATAGTAACGCCAATAGGGACTT

TCCATTGACGTCAATGGGTGGACTATTTACGGTAAACTGCCCACTTGGCAGTACATCAAGTGTATC

ATATGCCAAGTACGCCCCCTATTGACGTCAATGACGGTAAATGGCCCGCCTGGCATTATGCCCAGT

ACATGACCTTATGGGACTTTCCTACTTGGCAGTACATCTACGTATTAGTCATCGCTATTACCATGGG

TCGAGGTGAGCCCCACGTTCTGCTTCACTCTCCCCATCTCCCCCCCCTCCCCACCCCCAATTTTGTA

TTTATTTATTTTTTAATTATTTTGTGCAGCGATGGGGGCGGGGGGGGGGGGGGCGCGCGCCAGGCG

GGGCGGGGCGGGGCGAGGGGCGGGGCGGGGCGAGGCGGAGAGGTGCGGCGGCAGCCAATCAGA

GCGGCGCGCTCCGAAAGTTTCCTTTTATGGCGAGGCGGCGGCGGCGGCGGCCCTATAAAAAGCGA

AGCGCGCGGCGGGCGGGAGTCGCTGCGTTGCCTTCGCCCCGTGCCCCGCTCCGCGCCGCCTCGCGC

-continuede

CGCCCGCCCCGGCTCTGACTGACCGCGTTACTCCCACAGGTGAGCGGGCGGGACGGCCCTTCTCCT

CCGGGCTGTAATTAGCGCTTGGTTTAATGACGGCTCGTTTCTTTTCTGTGGCTGCGTGAAAGCCTTA

AAGGGCTCCGGGAGGGCCCTTTGTGCGGGGGGGAGCGGCTCGGGGGGTGCGTGCGTGTGTGTGTG

CGTGGGGAGCGCCGCGTGCGGCCCGCGCTGCCCGGCGGCTGTGAGCGCTGCGGGCGCGGCGCGGG

GCTTTGTGCGCTCCGCGTGTGCGCGAGGGGAGCGCGGCCGGGGGCGGTGCCCCGCGGTGCGGGGG

GGCTGCGAGGGGAACAAAGGCTGCGTGCGGGGTGTGTGCGTGGGGGGGTGAGCAGGGGGTGTGG

GCGCGGCGGTCGGGCTGTAACCCCCCCCTGCACCCCCCTCCCCGAGTTGCTGAGCACGGCCCGGCT

TCGGGTGCGGGGCTCCGTGCGGGGCGTGGCGCGGGGCTCGCCGTGCCGGGCGGGGGGTGGCGGCA

GGTGGGGGTGCCGGGCGGGGCGGGGCCGCCTCGGGCCGGGGAGGGCTCGGGGGAGGGGCGCGGC

GGCCCCGGAGCGCCGGCGGCTGTCGAGGCGCGGCGAGCCGCAGCCATTGCCTTTTATGGTAATCG

TGCGAGAGGGCGCAGGGACTTCCTTTGTCCCAAATCTGGCGGAGCCGAAATCTGGGAGGCGCCGC

CGCACCCCCTCTAGCGGGCGCGGGCGAAGCGGTGCGGCGCCGGCAGGAAGGAAATGGGCGGGGA

GGGCCTTCGTGCGTCGCCGCGCCGCCGTCCCCTTCTCCATCTCCAGCCTCGGGGCTGCCGCAGGGG

GACGGCTGCCTTCGGGGGGGACGGGGCAGGGCGGGGTTCGGCTTCTGGCGTGTGACCGGCGGCTC

TAGAGCCTCTGCTAACCATGTTCATGCCTTCTTCTTTTTCCTACAGCTCCTGGGCAACGTGCTGGTT

ATTGTGCTGTCTCATCATTTTGGCAAAGAATTCGCCACCATGGTGCCCAAGAAGAAGAGGAAAGTC

TCTAGACTGGACAAGAGCAAAGTCATAAACTCTGCTCTGGAATTACTCAATGGAGTCGGTATCGA

AGGCCTGACGACAAGGAAACTCGCTCAAAAGCTGGGAGTTGAGCAGCCTACCCTGTACTGGCACG

TGAAGAACAAGCGGGCCCTGCTCGATGCCCTGCCAATCGAGATGCTGGACAGGCATCATACCCAC

TCCTGCCCCCTGGAAGGCGAGTCATGGCAAGACTTTCTGCGGAACAACGCCAAGTCATACCGCTGT

GCTCTCCTCTCACATCGCGACGGGGCTAAAGTGCATCTCGGCACCCGCCCAACAGAGAAACAGTA

CGAAACCCTGGAAAATCAGCTCGCGTTCCTGTGTCAGCAAGGCTTCTCCCTGGAGAACGCACTGTA

CGCTCTGTCCGCCGTGGGCCACTTTACACTGGGCTGCGTATTGGAGGAACAGGAGCATCAAGTAGC

AAAAGAGGAAAGAGAGACACCTACCACCGATTCTATGCCCCCACTTCTGAAACAAGCAATTGAGC

TGTTCGACCGGCAGGGAGCCGAACCTGCCTTCCTTTTCGGCCTGGAACTAATCATATGTGGCCTGG

AGAAACAGCTAAAGTGCGAAAGCGGCGGGCCGACCGACGCCCTTGACGATTTTGACTTAGACATG

CTCCCAGCCGATGCCCTTGACGACTTTGACCTTGATATGCTGCCTGCTGACGCTCTTGACGATTTTG

ACCTTGACATGCTCCCCGGGTAAAGCGGCCGCGACTCTAGATCATAATCAGCCATACCACATTTGT

AGAGGTTTTACTTGCTTTAAAAAACCTCCCACACCTCCCCCTGAACCTGAAACATAAAATGAATGC

AATTGTTGTTGTTAACTTGTTTATTGCAGCTTATAATGGTTACAAATAAAGCAATAGCATCACAAA

TTTCACAAATAAAGCATTTTTTTCACTGCATTCTAGTTGTGGTTTGTCCAAACTCATCAATGTATCT

TAAGGGATCCCTAGAGGGACAGCCCCCCCCCAAAGCCCCCAGGGATGTAATTACGTCCCTCCCCC

GCTAGGGGCAGCAGCGAGCCGCCCGGGGCTCCGCTCCGGTCCGGCGCTCCCCCCGCATCCCCGAG

CCGGCAGCGTGCGGGGACAGCCCGGGCACGGGGAAGGTGGCACGGGATCGCTTTCCTCTGAACGC

TTCTCGCTGCTCTTTGAGCCTGCAGACACCTGGGGGGATACGGGGAAAAAGCTTTAGGCTGAAAG

AGAGATTTAGAATGACAGAATCATAGAACGGCCTGGGTTGCAAAGGAGCACAGTGCTCATCCAGA

TCCAACCCCCTGCTATGTGCAGGGTCATCAACCAGCAGCCCAGGCTGCCCAGAGCCACATCCAGCC

TGGCCTTGAATGCCTGCAGGGATGGGGCATCCACAGCCTCCTTGGGCAACCTGTTCAGTGCGTCAC

CACCCTCTGGGGGAAAAACTGCCTCCTCATATCCAACCCAAACCTCCCCTGTCTCAGTGTAAAGCC

ATTCCCCCTTGTCCTATCAAGGGGGAGTTTGCTGTGACATTGTTGGTCTGGGGTGACACATGTTTGC

CAATTCAGTGCATCACGGAGAGGCAGATCTTGGGGATAAGGAAGTGCAGGACAGCATGGACGTGG

-continuede

GACATGCAGGTGTTGAGGGCTCTGGGACACTCTCCAAGTCACAGCGTTCAGAACAGCCTTAAGGA

TAAGAAGATAGGATAGAAGGACAAAGAGCAAGTTAAAACCCAGCATGGAGAGGAGCACAAAAAG

GCCACAGACACTGCTGGTCCCTGTGTCTGAGCCTGCATGTTTGATGGTGTCTGGATGCAAGCAGAA

GGGGTGGAAGAGCTTGCCTGGAGAGATACAGCTGGGTCAGTAGGACTGGGACAGGCAGCTGGAG

AATTGCCATGTAGATGTTCATACAATCGTCAAATCATGAAGGCTGGAAAAGCCCTCCAAGATCCCC

AAGACCAACCCCAACCCACCCACCGTGCCCACTGGCCATGTCCCTCAGTGCCACATCCCCACAGTT

CTTCATCACCTCCAGGGACGGTGACCCCCCCACCTCCGTGGGCAGCTGTGCCACTGCAGCACCGCT

CTTTGGAGAAGGTAAATCTTGCTAAATCCAGCCCGACCCTCCCCTGGCACAACGTAAGGCCATTAT

CTCTCATCCAACTCCAGGACGGAGTCAGTGAGGATGGGGCTGTCGACCTAGAGGGACAGCCCCCC

CCCAAAGCCCCCAGGGATGTAATTACGTCCCTCCCCCGCTAGGGGCAGCAGCGAGCCGCCCGGGG

CTCCGCTCCGGTCCGGCGCTCCCCCCGCATCCCCGAGCCGGCAGCGTGCGGGGACAGCCCGGGCA

CGGGGAAGGTGGCACGGGATCGCTTTCCTCTGAACGCTTCTCGCTGCTCTTTGAGCCTGCAGACAC

CTGGGGGGATACGGGGAAAAAGCTTTAGGCTGAAAGAGAGATTTAGAATGACAGAATCATAGAA

CGGCCTGGGTTGCAAAGGAGCACAGTGCTCATCCAGATCCAACCCCCTGCTATGTGCAGGGTCATC

AACCAGCAGCCCAGGCTGCCCAGAGCCACATCCAGCCTGGCCTTGAATGCCTGCAGGGATGGGGC

ATCCACAGCCTCCTTGGGCAACCTGTTCAGTGCGTCACCACCCTCTGGGGGAAAAACTGCCTCCTC

ATATCCAACCCAAACCTCCCCTGTCTCAGTGTAAAGCCATTCCCCCTTGTCCTATCAAGGGGGAGT

TTGCTGTGACATTGTTGGTCTGGGGTGACACATGTTTGCCAATTCAGTGCATCACGGAGAGGCAGA

TCTTGGGGATAAGGAAGTGCAGGACAGCATGGACGTGGGACATGCAGGTGTTGAGGGCTCTGGGA

CACTCTCCAAGTCACAGCGTTCAGAACAGCCTTAAGGATAAGAAGATAGGATAGAAGGACAAAGA

GCAAGTTAAAACCCAGCATGGAGAGGAGCACAAAAAGGCCACAGACACTGCTGGTCCCTGTGTCT

GAGCCTGCATGTTTGATGGTGTCTGGATGCAAGCAGAAGGGGTGGAAGAGCTTGCCTGGAGAGAT

ACAGCTGGGTCAGTAGGACTGGGACAGGCAGCTGGAGAATTGCCATGTAGATGTTCATACAATCG

TCAAATCATGAAGGCTGGAAAAGCCCTCCAAGATCCCCAAGACCAACCCCAACCCACCCACCGTG

CCCACTGGCCATGTCCCTCAGTGCCACATCCCCACAGTTCTTCATCACCTCCAGGGACGGTGACCC

CCCCACCTCCGTGGGCAGCTGTGCCACTGCAGCACCGCTCTTTGGAGAAGGTAAATCTTGCTAAAT

CCAGCCCGACCCTCCCCTGGCACAACGTAAGGCCATTATCTCTCATCCAACTCCAGGACGGAGTCA

GTGAGGATGGGGCTCAATTGTTTACTCCCTATCAGTGATAGAGAACGTATGAAGAGTTTACTCCCT

ATCAGTGATAGAGAACGTATGCAGACTTTACTCCCTATCAGTGATAGAGAACGTATAAGGAGTTTA

CTCCCTATCAGTGATAGAGAACGTATGACCAGTTTACTCCCTATCAGTGATAGAGAACGTATCTAC

AGTTTACTCCCTATCAGTGATAGAGAACGTATATCCAGTTTACTCCCTATCAGTGATAGAGAACGT

ATAAGCTTTAGGCGTGTACGGTGGGCGCCTATAAAAGCAGAGCTCGTTTAGTGAACCGTCAGATC

GCCTGGAGCAATTCCACAACACTTTTGTCTTATACCAACTTTCCGTACCACTTCCTACCCTCGTAAA

AAGCTTGTCCACTCGAGATTCTCTAGACATCATTAATTCCTAATTTTTGTTGACACTCTATCATTGA

TAGAGTTATTTTACCACTCCCTATCAGTGATAGAGAAAAGTGAAATGGCCAAGCCTTTGTCTCAAG

AAGAATCCACCCTCATTGAAAGAGCAACGGCTACAATCAACAGCATCCCCATCTCTGAAGACTAC

AGCGTCGCCAGCGCAGCTCTCTCTAGCGACGGCCGCATCTTCACTGGTGTCAATGTATATCATTTT

ACTGGGGGACCTTGTGCAGAACTCGTGGTGCTGGGCACTGCTGCTGCTGCGGCAGCTGGCAACCTG

ACTTGTATCGTCGCGATCGGAAATGAGAACAGGGGCATCTTGAGCCCCTGCGGACGGTGTCGACA

GGTGCTTCTCGATCTGCATCCTGGGATCAAAGCGATAGTGAAGGACAGTGATGGACAGCCGACGG

CAGTTGGGATTCGTGAATTGCTGCCCTCTGGTTATGTGTGGGAGGGCTAACTCGAGATGAGCTCAG

-continuede

AGACTGGCCCAGTGGCTGTGGACCCCACATTGAGACGGCGGATCGAGCCCCATGAGTTTGAGGTA

TTCTTCGATCCGAGAGAGCTCCGCAAGGAGACCTGCCTGCTTTACGAAATTAATTGGGGGGGCCGG

CACTCCATTTGGCGACATACATCACAGAACACTAACAAGCACGTCGAAGTCAACTTCATCGAGAA

GTTCACGACAGAAAGATATTTCTGTCCGAACACAAGGTGCAGCATTACCTGGTTTCTCAGCTGGAG

CCCATGCGGCGAATGTAGTAGGGCCATCACTGAATTCCTGTCAAGGTATCCCCACGTCACTCTGTT

TATTTACATCGCAAGGCTGTACCACCACGCTGACCCCCGCAATCGACAAGGCCTGCGGGATTTGAT

CTCTTCAGGTGTGACTATCCAAATTATGACTGAGCAGGAGTCAGGATACTGCTGGAGAAACTTTGT

GAATTATAGCCCGAGTAATGAAGCCCACTGGCCTAGGTATCCCCATCTGTGGGTACGACTGTACGT

TCTTGAACTGTACTGCATCATACTGGGCCTGCCTCCTTGTCTCAACATTCTGAGAAGGAAGCAGCC

ACAGCTGACATTCTTTACCATCGCTCTTCAGTCTTGTCATTACCAGCGACTGCCCCCACACATTCTC

TGGGCCACCGGGTTGAAAAGCGGCAGCGAGACTCCCGGGACCTCAGAGTCCGCCACACCCGAAAG

TGATAAAAAGTATTCTATTGGTTTAGCCATCGGCACTAATTCCGTTGGATGGGCTGTCATAACCGA

TGAATACAAAGTACCTTCAAAGAAATTTAAGGTGTTGGGGAACACAGACCGTCATTCGATTAAAA

AGAATCTTATCGGTGCCCTCCTATTCGATAGTGGCGAAACGGCAGAGGCGACTCGCCTGAAACGA

ACCGCTCGGAGAAGGTATACACGTCGCAAGAACCGAATATGTTACTTACAAGAAATTTTTAGCAA

TGAGATGGCCAAAGTTGACGATTCTTTCTTTCACCGTTTGGAAGAGTCCTTCCTTGTCGAAGAGGA

CAAGAAACATGAACGGCACCCCATCTTTGGAAACATAGTAGATGAGGTGGCATATCATGAAAAGT

ACCCAACGATTTATCACCTCAGAAAAAAGCTAGTTGACTCAACTGATAAAGCGGACCTGAGGTTA

ATCTACTTGGCTCTTGCCCATATGATAAAGTTCCGTGGGCACTTTCTCATTGAGGGTGATCTAAATC

CGGACAACTCGGATGTCGACAAACTGTTCATCCAGTTAGTACAAACCTATAATCAGTTGTTTGAAG

AGAACCCTATAAATGCAAGTGGCGTGGATGCGAAGGCTATTCTTAGCGCCCGCCTCTCTAAATCCC

GACGGCTAGAAAACCTGATCGCACAATTACCCGGAGAGAAGAAAAATGGGTTGTTCGGTAACCTT

ATAGCGCTCTCACTAGGCCTGACACCAAATTTTAAGTCGAACTTCGACTTAGCTGAAGATGCCAAA

TTGCAGCTTAGTAAGGACACGTACGATGACGATCTCGACAATCTACTGGCACAAATTGGAGATCA

GTATGCGGACTTATTTTTGGCTGCCAAAAACCTTAGCGATGCAATCCTCCTATCTGACATACTGAG

AGTTAATACTGAGATTACCAAGGCGCCGTTATCCGCTTCAATGATCAAAAGGTACGATGAACATCA

CCAAGACTTGACACTTCTCAAGGCCCTAGTCCGTCAGCAACTGCCTGAGAAATATAAGGAAATATT

CTTTGATCAGTCGAAAAACGGGTACGCAGGTTATATTGACGGCGGAGCGAGTCAAGAGGAATTCT

ACAAGTTTATCAAACCCATATTAGAGAAGATGGATGGGACGGAAGAGTTGCTTGTAAAACTCAAT

CGCGAAGATCTACTGCGAAAGCAGCGGACTTTCGACAACGGTAGCATTCCACATCAAATCCACTT

AGGCGAATTGCATGCTATACTTAGAAGGCAGGAGGATTTTTATCCGTTCCTCAAAGACAATCGTGA

AAAGATTGAGAAAATCCTAACCTTTCGCATACCTTACTATGTGGGACCCCTGGCCCGAGGGAACTC

TCGGTTCGCATGGATGACAAGAAAGTCCGAAGAAACGATTACTCCATGGAATTTTGAGGAAGTTG

TCGATAAAGGTGCGTCAGCTCAATCGTTCATCGAGAGGATGACCAACTTTGACAAGAATTTACCGA

ACGAAAAAGTATTGCCTAAGCACAGTTTACTTTACGAGTATTTCACAGTGTACAATGAACTCACGA

AAGTTAAGTATGTCACTGAGGGCATGCGTAAACCCGCCTTTCTAAGCGGAGAACAGAAGAAAGCA

ATAGTAGATCTGTTATTCAAGACCAACCGCAAAGTGACAGTTAAGCAATTGAAAGAGGACTACTT

TAAGAAAATTGAATGCTTCGATTCTGTCGAGATCTCCGGGGTAGAAGATCGATTTAATGCGTCACT

TGGTACGTATCATGACCTCCTAAAGATAATTAAAGATAAGGACTTCCTGGATAACGAAGAGAATG

AAGATATCTTAGAAGATATAGTGTTGACTCTTACCCTCTTTGAAGATCGGGAAATGATTGAGGAAA

GACTAAAAACATACGCTCACCTGTTCGACGATAAGGTTATGAAACAGTTAAAGAGGCGTCGCTAT

-continuede

ACGGGCTGGGGACGATTGTCGCGGAAACTTATCAACGGGATAAGAGACAAGCAAAGTGGTAAAA

CTATTCTCGATTTTCTAAAGAGCGACGGCTTCGCCAATAGGAACTTTATGCAGCTGATCCATGATG

ACTCTTTAACCTTCAAAGAGGATATACAAAAGGCACAGGTTTCCGGACAAGGGGACTCATTGCAC

GAACATATTGCGAATCTTGCTGGTTCGCCAGCCATCAAAAAGGGCATACTCCAGACAGTCAAAGT

AGTGGATGAGCTAGTTAAGGTCATGGGACGTCACAAACCGGAAAACATTGTAATCGAGATGGCAC

GCGAAAATCAAACGACTCAGAAGGGGCAAAAAAACAGTCGAGAGCGGATGAAGAGAATAGAAG

AGGGTATTAAAGAACTGGGCAGCCAGATCTTAAAGGAGCATCCTGTGGAAAATACCCAATTGCAG

AACGAGAAACTTTACCTCTATTACCTACAAAATGGAAGGGACATGTATGTTGATCAGGAACTGGA

CATAAACCGTTTATCTGATTACGACGTCGATCACATTGTACCCCAATCCTTTTTGAAGGACGATTCA

ATCGACAATAAAGTGCTTACACGCTCGGATAAGAACCGAGGGAAAAGTGACAATGTTCCAAGCGA

GGAAGTCGTAAAGAAAATGAAGAACTATTGGCGGCAGCTCCTAAATGCGAAACTGATAACGCAAA

GAAAGTTCGATAACTTAACTAAAGCTGAGAGGGGTGGCTTGTCTGAACTTGACAAGGCCGGATTT

ATTAAACGTCAGCTCGTGGAAACCCGCCAAATCACAAAGCATGTTGCACAGATACTAGATTCCCG

AATGAATACGAAATACGACGAGAACGATAAGCTGATTCGGGAAGTCAAAGTAATCACTTTAAAGT

CAAAATTGGTGTCGGACTTCAGAAAGGATTTTCAATTCTATAAAGTTAGGGAGATAAATAACTACC

ACCATGCGCACGACGCTTATCTTAATGCCGTCGTAGGGACCGCACTCATTAAGAAATACCCGAAGC

TAGAAAGTGAGTTTGTGTATGGTGATTACAAAGTTTATGACGTCCGTAAGATGATCGCGAAAAGC

GAACAGGAGATAGGCAAGGCTACAGCCAAATACTTCTTTTATTCTAACATTATGAATTTCTTTAAG

ACGGAAATCACTCTGGCAAACGGAGAGATACGCAAACGACCTTTAATTGAAACCAATGGGGAGAC

AGGTGAAATCGTATGGGATAAGGGCCGGGACTTCGCGACGGTGAGAAAAGTTTTGTCCATGCCCC

AAGTCAACATAGTAAAGAAAACTGAGGTGCAGACCGGAGGGTTTTCAAAGGAATCGATTCTTCCA

AAAAGGAATAGTGATAAGCTCATCGCTCGTAAAAAGGACTGGGACCCGAAAAAGTACGGTGGCTT

CGATAGCCCTACAGTTGCCTATTCTGTCCTAGTAGTGGCAAAAGTTGAGAAGGGAAAATCCAAGA

AACTGAAGTCAGTCAAAGAATTATTGGGGATAACGATTATGGAGCGCTCGTCTTTTGAAAAGAAC

CCCATCGACTTCCTTGAGGCGAAAGGTTACAAGGAAGTAAAAAAGGATCTCATAATTAAACTACC

AAAGTATAGTCTGTTTGAGTTAGAAAATGGCCGAAAACGGATGTTGGCTAGCGCCGGAGAGCTTC

AAAAGGGGAACGAACTCGCACTACCGTCTAAATACGTGAATTTCCTGTATTTAGCGTCCCATTACG

AGAAGTTGAAAGGTTCACCTGAAGATAACGAACAGAAGCAACTTTTTGTTGAGCAGCACAAACAT

TATCTCGACGAAATCATAGAGCAAATTTCGGAATTCAGTAAGAGAGTCATCCTAGCTGATGCCAAT

CTGGACAAAGTATTAAGCGCATACAACAAGCACAGGGATAAACCCATACGTGAGCAGGCGGAAA

ATATTATCCATTTGTTTACTCTTACCAACCTCGGCGCTCCAGCCGCATTCAAGTATTTTGACACAAC

GATAGATCGCAAACGATACACTTCTACCAAGGAGGTGCTAGACGCGACACTGATTCACCAATCCA

TCACGGGATTATATGAAACTCGGATAGATTTGTCACAGCTTGGGGGTGACTCTGGTGGTTCTACTA

ATCTGTCAGATATTATTGAAAAGGAGACCGGTAAGCAACTGGTTATCCAGGAATCCATCCTCATGC

TCCCAGAGGAGGTGGAAGAAGTCATTGGGAACAAGCCGGAAAGCGATATACTCGTGCACACCGCC

TACGACGAGAGCACCGACGAGAATGTCATGCTTCTGACTAGCGACGCCCCTGAATACAAGCCTTG

GGCTCTGGTCATACAGGATAGCAACGGTGAGAACAAGATTAAGATGCTCTCTGGTGGTTCTCCCAA

GAAGAAGAGGAAAGTCTAAAAATTCTAAAATACAGCATAGCAAAACTTTAACCTCCAAATCAAGC

CTCTACTTGAATCCTTTTCTGAGGGATGAATAAGGCATAGGCATCAGGGGCTGTTGCCAATGTGCA

TTAGCTGTTTGCAGCCTCACCTTCTTTCATGGAGTTTAAGATATAGTGTATTTTCCCAAGGTTTGAA

CTAGCTCTTCATTTCTTTATGTTTTAAATGCACTGACCTCCCACATTCCCTTTTTAGTAAAATATTCA

-continuede

GAAATAATTTAAATACATCATTGCAATGAAAATAAATGTTTTTTATTAGGCAGAATCCAGATGCTC

AAGGCCCTTCATAATATCCCCCAGTTTAGTAGTTGGACTTAGGGAACAAAGGAACCTTTAATAGAA

ATTGGACAGCAAGAAAGCGAGCTTCTAGATGGTCCATATGAATATCCTCCTTAGTTCCTATTCCGC

TAGCCTAGAGGGACAGCCCCCCCCCAAAGCCCCCAGGGATGTAATTACGTCCCTCCCCCGCTAGG

GGCAGCAGCGAGCCGCCCGGGGCTCCGCTCCGGTCCGGCGCTCCCCCCGCATCCCCGAGCCGGCA

GCGTGCGGGGACAGCCCGGGCACGGGGAAGGTGGCACGGGATCGCTTTCCTCTGAACGCTTCTCG

CTGCTCTTTGAGCCTGCAGACACCTGGGGGGATACGGGGAAAAAGCTTTAGGCTGAAAGAGAGAT

TTAGAATGACAGAATCATAGAACGGCCTGGGTTGCAAAGGAGCACAGTGCTCATCCAGATCCAAC

CCCCTGCTATGTGCAGGGTCATCAACCAGCAGCCCAGGCTGCCCAGAGCCACATCCAGCCTGGCCT

TGAATGCCTGCAGGGATGGGGCATCCACAGCCTCCTTGGGCAACCTGTTCAGTGCGTCACCACCCT

CTGGGGGAAAAACTGCCTCCTCATATCCAACCCAAACCTCCCCTGTCTCAGTGTAAAGCCATTCCC

CCTTGTCCTATCAAGGGGGAGTTTGCTGTGACATTGTTGGTCTGGGGTGACACATGTTTGCCAATTC

AGTGCATCACGGAGAGGCAGATCTTGGGGATAAGGAAGTGCAGGACAGCATGGACGTGGGACAT

GCAGGTGTTGAGGGCTCTGGGACACTCTCCAAGTCACAGCGTTCAGAACAGCCTTAAGGATAAGA

AGATAGGATAGAAGGACAAAGAGCAAGTTAAAACCCAGCATGGAGAGGAGCACAAAAAGGCCAC

AGACACTGCTGGTCCCTGTGTCTGAGCCTGCATGTTTGATGGTGTCTGGATGCAAGCAGAAGGGGT

GGAAGAGCTTGCCTGGAGAGATACAGCTGGGTCAGTAGGACTGGGACAGGCAGCTGGAGAATTGC

CATGTAGATGTTCATACAATCGTCAAATCATGAAGGCTGGAAAAGCCCTCCAAGATCCCCAAGAC

CAACCCCAACCCACCCACCGTGCCCACTGGCCATGTCCCTCAGTGCCACATCCCCACAGTTCTTCA

TCACCTCCAGGGACGGTGACCCCCCCACCTCCGTGGGCAGCTGTGCCACTGCAGCACCGCTCTTTG

GAGAAGGTAAATCTTGCTAAATCCAGCCCGACCCTCCCCTGGCACAACGTAAGGCCATTATCTCTC

ATCCAACTCCAGGACGGAGTCAGTGAGGATGGGGCTGGATCCGAAGCAGCTCCAGCCTACACAAT

CGCTCAAGACGTGTAATGCTTTTATTATATATTAGTCACGATATCTATAACAAGAAAATATATATA

TAATAAGTTATCACGTAAGTAGAACATGAAATAACAATATAATTATCGTATGAGTTAAATCTTAAA

AGTCACGTAAAAGATAATCATGCGTCATTTTGACTCACGCGGTCGTTATAGTTCAAAATCAGTGAC

ACTTACCGCATTGACAAGCACGCCTCACGGGAGCTCCAAGCGGCGACTGAGATGTCCTAAATGCA

CAGCGACGGATTCGCGCTATTTAGAAAGAGAGAGCAATATTTCAAGAATGCATGCGTCAATTTTAC

GCAGACTATCTTTCTAGGGTTAAAAAAGATTTGCGCTTTACTCGACCTAAACTTTAAACACGTCAT

AGAATCTTCGTTTGACAAAAACCACATTGTGGGGTACCGAGCTCTTAATTAAGGCGCGCCGGGGA

GGTTCCCTTTAGTGAGGGTTAATTGCGGGTCGCCCTATAGTGAGTCGTATTACAATTCACTGGCCG

TCGTTTTACAACGTCGTGACTGGGAAAACCCTGGCGTTACCCAACTTAATCGCCTTGCAGCACATC

CCCCTTTCGCCAGCTGGCGTAATAGCGAAGAGGCCCGCACCGATCGCCCTTCCCAACAGTTGCGCA

GCCTGAATGGCGAATGGCAAATTGTAAGCGTTAATATTTTGTTAAAATTCGCGTTAAATTTTTGTTA

AATCAGCTCATTTTTTAACCAATAGGCCGAAATCGGCAAAATCCCTTATAAATCAAAAGAATAGAC

CGAGATAGGGTTGAGTGTTGTTCCAGTTTGGAACAAGAGTCCACTATTAAAGAACGTGGACTCCA

ACGTCAAAGGGCGAAAAACCGTCTATCAGGGCGATGGCCCACTACGTGAACCATCACCCTAATCA

AGTTTTTTGGGGTCGAGGTGCCGTAAAGCACTAAATCGGAACCCTAAAGGGAGCCCCCGATTTAG

AGCTTGACGGGGAAAGCCGGCGAACGTGGCGAGAAAGGAAGGGAAGAAAGCGAAAGGAGCGGG

CGCTAGGGCGCTGGCAAGTGTAGCGGTCACGCTGCGCGTAACCACCACACCCGCCGCGCTTAATG

CGCCGCTACAGGGCGCGTCAG

-continuede

TOIC_Cas9_Bsd_p300_obl_r26_AAVS_PgkNeo (SEQ ID NO: 18)

GTGGCACTTTTCGGGGAAATGTGCGCGGAACCCCTATTTGTTTATTTTTCTAAATACATTCAAATAT

GTATCCGCTCATGAGACAATAACCCTGATAAATGCTTCAATAATATTGAAAAAGGAAGAGTATGA

GTATTCAACATTTCCGTGTCGCCCTTATTCCCTTTTTTGCGGCATTTTGCCTTCCTGTTTTTGCTCAC

CCAGAAACGCTGGTGAAAGTAAAAGATGCTGAAGATCAGTTGGGTGCACGAGTGGGTTACATCGA

ACTGGATCTCAACAGCGGTAAGATCCTTGAGAGTTTTCGCCCCGAAGAACGTTTTCCAATGATGAG

CACTTTTAAAGTTCTGCTATGTGGCGCGGTATTATCCCGTATTGACGCCGGGCAAGAGCAACTCGG

TCGCCGCATACACTATTCTCAGAATGACTTGGTTGAGTACTCACCAGTCACAGAAAAGCATCTTAC

GGATGGCATGACAGTAAGAGAATTATGCAGTGCTGCCATAACCATGAGTGATAACACTGCGGCCA

ACTTACTTCTGACAACGATCGGAGGACCGAAGGAGCTAACCGCTTTTTTGCACAACATGGGGGATC

ATGTAACTCGCCTTGATCGTTGGGAACCGGAGCTGAATGAAGCCATACCAAACGACGAGCGTGAC

ACCACGATGCCTGTAGCAATGGCAACAACGTTGCGCAAACTATTAACTGGCGAACTACTTACTCTA

GCTTCCCGGCAACAATTAATAGACTGGATGGAGGCGGATAAAGTTGCAGGACCACTTCTGCGCTC

GGCCCTTCCGGCTGGCTGGTTTATTGCTGATAAATCTGGAGCCGGTGAGCGTGGGTCTCGCGGTAT

CATTGCAGCACTGGGGCCAGATGGTAAGCCCTCCCGTATCGTAGTTATCTACACGACGGGGAGTCA

GGCAACTATGGATGAACGAAATAGACAGATCGCTGAGATAGGTGCCTCACTGATTAAGCATTGGT

AACTGTCAGACCAAGTTTACTCATATATACTTTAGATTGATTTAAAACTTCATTTTTAATTTAAAAG

GATCTAGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGTAATC

TGCTGCTTGCAAACAAAAAAACCACCGCTACCAGCGGTGGTTTGTTTGCCGGATCAAGAGCTACCA

ACTCTTTTTCCGAAGGTAACTGGCTTCAGCAGAGCGCAGATACCAAATACTGTTCTTCTAGTGTAG

CCGTAGTTAGGCCACCACTTCAAGAACTCTGTAGCACCGCCTACATACCTCGCTCTGCTAATCCTG

TTACCAGTGGCTGCTGCCAGTGGCGATAAGTCGTGTCTTACCGGGTTGGACTCAAGACGATAGTTA

CCGGATAAGGCGCAGCGGTCGGGCTGAACGGGGGGTTCGTGCACACAGCCCAGCTTGGAGCGAAC

GACCTACACCGAACTGAGATACCTACAGCGTGAGCTATGAGAAAGCGCCACGCTTCCCGAAGGGA

GAAAGGCGGACAGGTATCCGGTAAGCGGCAGGGTCGGAACAGGAGAGCGCACGAGGGAGCTTCC

AGGGGGAAACGCCTGGTATCTTTATAGTCCTGTCGGGTTTCGCCACCTCTGACTTGAGCGTCGATT

TTTGTGATGCTCGTCAGGGGGGCGGAGCCTATGGAAAAACGCCAGCAACGCGGCCTTTTTACGGTT

CCTGGCCTTTTGCTGGCCTTTTGCTCACATGTTCTTTCCTGCGTTATCCCCTGATTCTGTGGATAACC

GTATTACCGCCTTTGAGTGAGCTGATACCGCTCGCCGCAGCCGAACGACCGAGCGCAGCGAGTCA

GTGAGCGAGGAAGCGGAAGAGCGCCCAATACGCAAACCGCCTCTCCCCGCGCGTTGGCCGATTCA

TTAATGCAGCTGGCACGACAGGTTTCCCGACTGGAAAGCGGGCAGTGAGCGCAACGCAATTAATG

TGAGTTAGCTCACTCATTAGGCACCCCAGGCTTTACACTTTATGCTTCCGGCTCGTATGTTGTGTGG

AATTGTGAGCGGATAACAATTTCACACAGGAAACAGCTATGACCATGATTACGCCAAGCGCGCAA

TTAACCCTCACTAAAGGGAACCTCCCCTAGCTTAATTAACCCTAGAAAGATAATCATATTGTGACG

TACGTTAAAGATAATCATGCGTAAAATTGACGCATGTGTTTTATCGATCTGTATATCGAGGTTTATT

TATTAATTTGAATAGATATTAAGTTTTATTATATTTACACTTACATACTAATAATAAATTCAACAAA

CAATTTATTTATGTTTATTTATTTATTAAAAAAAAACAAAAACTCAAAATTTCTTCTATAAAGTAAC

AAAACTTTTAAACATTCTCTCTTTTACAAAAATAAACTTATTTTGTACTTTAAAAACAGTCATGTTG

TATTATAAAATAAGTAATTAGCTTAACTTATACATAATAGAAACAAATTATACTTATTAATCGCAT

TGATTATTGACTAGTCGTATTAAGGGTTCCGGATCAGCTTGATTCGAGCCCCAGCTGGTTCTTTCCG

-continuede

CCTCAGAAGCCATAGAGCCCACCGCATCCCCAGCATGCCTGCTATTGTCTTCCCAATCCTCCCCCTT

GCTGTCCTGCCCCACCCCACCCCCCAGAATAGAATGACACCTACTCAGACAATGCGATGCAATTTC

CTCATTTTATTAGGAAAGGACAGTGGGAGTGGCACCTTCCAGGGTCAAGGAAGGCACGGGGGAGG

GGCAAACAACAGATGGCTGGCAACTAGAAGGCACAGTCGAGGCTGATCAGCGAGCTCTAGAGAA

TTGATCCCCTCAGAAGAACTCGTCAAGAAGGCGATAGAAGGCGATGCGCTGCGAATCGGGAGCGG

CGATACCGTAAAGCACGAGGAAGCGGTCAGCCCATTCGCCGCCAAGCTCTTCAGCAATATCACGG

GTAGCCAACGCTATGTCCTGATAGCGGTCCGCCACACCCAGCCGGCCACAGTCGATGAATCCAGA

AAAGCGGCCATTTTCCACCATGATATTCGGCAAGCAGGCATCGCCATGGGTCACGACGAGATCCTC

GCCGTCGGGCATGCGCGCCTTGAGCCTGGCGAACAGTTCGGCTGGCGCGAGCCCCTGATGCTCTTC

GTCCAGATCATCCTGATCGACAAGACCGGCTTCCATCCGAGTACGTGCTCGCTCGATGCGATGTTT

CGCTTGGTGGTCGAATGGGCAGGTAGCCGGATCAAGCGTATGCAGCCGCCGCATTGCATCAGCCA

TGATGGATACTTTCTCGGCAGGAGCAAGGTGAGATGACAGGAGATCCTGCCCCGGCACTTCGCCC

AATAGCAGCCAGTCCCTTCCCGCTTCAGTGACAACGTCGAGCACAGCTGCGCAAGGAACGCCCGT

CGTGGCCAGCCACGATAGCCGCGCTGCCTCGTCCTGCAGTTCATTCAGGGCACCGGACAGGTCGGT

CTTGACAAAAAGAACCGGGCGCCCCTGCGCTGACAGCCGGAACACGGCGGCATCAGAGCAGCCG

ATTGTCTGTTGTGCCCAGTCATAGCCGAATAGCCTCTCCACCCAAGCGGCCGGAGAACCTGCGTGC

AATCCATCTTGTTCAATGGCCGATCCCATGGTTTAGTTCCTCACCTTGTCGTATTATACTATGCCGA

TATACTATGCCGATGATTAATTGTCAACACGTGCTGCTGCAGGTCGAAAGGCCCGGAGATGAGGA

AGAGGAGAACAGCGCGGCAGACGTGCGCTTTTGAAGCGTGCAGAATGCCGGGCCTCCGGAGGACC

TTCGGGCGCCCGCCCCGCCCCTGAGCCCGCCCCTGAGCCCGCCCCCGGACCCACCCCTTCCCAGCC

TCTGAGCCCAGAAAGCGAAGGAGCAAAGCTGCTATTGGCCGCTGCCCCAAAGGCCTACCCGCTTC

CATTGCTCAGCGGTGCTGTCCATCTGCACGAGACTAGTGAGACGTGCTACTTCCATTTGTCACGTC

CTGCACGACGCGAGCTGCGGGGCGGGGGGGAACTTCCTGACTAGGGGAGGAGTAGAAGGTGGCG

CGAAGGGGCCACCAAAGAACGGAGCCGGTTGGCGCCTACCGGTGGATGTGGAATGTGTGCGAGCC

AGAGGCCACTTGTGTAGCGCCAAGTGCCCAGCGGGGCTGCTAAAGCGCATGCTCCAGACTGCCTT

GGGAAAAGCGCCTCCCCTACCCGGTAGACACCCCACAGTGGGTGGCCTAGGGACAGGATTGCAAC

TCCAGTCTTTCTTCTTCTTGGGCGGGAGTCACTAGTTATTAATAGTAATCAATTACGGGGTCATTAG

TTCATAGCCCATATATGGAGTTCCGCGTTACATAACTTACGGTAAATGGCCCGCCTGGCTGACCGC

CCAACGACCCCCGCCCATTGACGTCAATAATGACGTATGTTCCCATAGTAACGCCAATAGGGACTT

TCCATTGACGTCAATGGGTGGACTATTTACGGTAAACTGCCCACTTGGCAGTACATCAAGTGTATC

ATATGCCAAGTACGCCCCCTATTGACGTCAATGACGGTAAATGGCCCGCCTGGCATTATGCCCAGT

ACATGACCTTATGGGACTTTCCTACTTGGCAGTACATCTACGTATTAGTCATCGCTATTACCATGGG

TCGAGGTGAGCCCCACGTTCTGCTTCACTCTCCCCATCTCCCCCCCCTCCCCACCCCCAATTTTGTA

TTTATTTATTTTTTAATTATTTTGTGCAGCGATGGGGGCGGGGGGGGGGGGGGCGCGCGCCAGGCG

GGGCGGGGCGGGGCGAGGGGCGGGGCGGGGCGAGGCGGAGAGGTGCGGCGGCAGCCAATCAGA

GCGGCGCGCTCCGAAAGTTTCCTTTTATGGCGAGGCGGCGGCGGCGGCGGCCCTATAAAAAGCGA

AGCGCGCGGCGGGCGGGAGTCGCTGCGTTGCCTTCGCCCCGTGCCCCGCTCCGCGCCGCCTCGCGC

CGCCCGCCCCGGCTCTGACTGACCGCGTTACTCCCACAGGTGAGCGGGCGGGACGGCCCTTCTCCT

CCGGGCTGTAATTAGCGCTTGGTTTAATGACGGCTCGTTTCTTTTCTGTGGCTGCGTGAAAGCCTTA

AAGGGCTCCGGGAGGGCCCTTTGTGCGGGGGGGAGCGGCTCGGGGGGTGCGTGCGTGTGTGTGTG

CGTGGGGAGCGCCGCGTGCGGCCCGCGCTGCCCGGCGGCTGTGAGCGCTGCGGGCGCGGCGCGGG

-continuede

GCTTTGTGCGCTCCGCGTGTGCGCGAGGGGAGCGCGGCCGGGGGCGGTGCCCCGCGGTGCGGGGG

GGCTGCGAGGGGAACAAAGGCTGCGTGCGGGGTGTGTGCGTGGGGGGGTGAGCAGGGGGTGTGG

GCGCGGCGGTCGGGCTGTAACCCCCCCCTGCACCCCCCTCCCCGAGTTGCTGAGCACGGCCCGGCT

TCGGGTGCGGGGCTCCGTGCGGGGCGTGGCGCGGGGCTCGCCGTGCCGGGCGGGGGGTGGCGGCA

GGTGGGGGTGCCGGGCGGGGCGGGGCCGCCTCGGGCCGGGGAGGGCTCGGGGGAGGGGCGCGGC

GGCCCCGGAGCGCCGGCGGCTGTCGAGGCGCGGCGAGCCGCAGCCATTGCCTTTTATGGTAATCG

TGCGAGAGGGCGCAGGGACTTCCTTTGTCCCAAATCTGGCGGAGCCGAAATCTGGGAGGCGCCGC

CGCACCCCCTCTAGCGGGCGCGGGCGAAGCGGTGCGGCGCCGGCAGGAAGGAAATGGGCGGGGA

GGGCCTTCGTGCGTCGCCGCGCCGCCGTCCCCTTCTCCATCTCCAGCCTCGGGGCTGCCGCAGGGG

GACGGCTGCCTTCGGGGGGGACGGGGCAGGGCGGGGTTCGGCTTCTGGCGTGTGACCGGCGGCTC

TAGAGCCTCTGCTAACCATGTTCATGCCTTCTTCTTTTTCCTACAGCTCCTGGGCAACGTGCTGGTT

ATTGTGCTGTCTCATCATTTTGGCAAAGAATTCGCCACCATGGTGCCCAAGAAGAAGAGGAAAGTC

TCTAGACTGGACAAGAGCAAAGTCATAAACTCTGCTCTGGAATTACTCAATGGAGTCGGTATCGA

AGGCCTGACGACAAGGAAACTCGCTCAAAAGCTGGGAGTTGAGCAGCCTACCCTGTACTGGCACG

TGAAGAACAAGCGGGCCCTGCTCGATGCCCTGCCAATCGAGATGCTGGACAGGCATCATACCCAC

TCCTGCCCCCTGGAAGGCGAGTCATGGCAAGACTTTCTGCGGAACAACGCCAAGTCATACCGCTGT

GCTCTCCTCTCACATCGCGACGGGGCTAAAGTGCATCTCGGCACCCGCCCAACAGAGAAACAGTA

CGAAACCCTGGAAAATCAGCTCGCGTTCCTGTGTCAGCAAGGCTTCTCCCTGGAGAACGCACTGTA

CGCTCTGTCCGCCGTGGGCCACTTTACACTGGGCTGCGTATTGGAGGAACAGGAGCATCAAGTAGC

AAAAGAGGAAAGAGAGACACCTACCACCGATTCTATGCCCCCACTTCTGAAACAAGCAATTGAGC

TGTTCGACCGGCAGGGAGCCGAACCTGCCTTCCTTTTCGGCCTGGAACTAATCATATGTGGCCTGG

AGAAACAGCTAAAGTGCGAAAGCGGCGGGCCGACCGACGCCCTTGACGATTTTGACTTAGACATG

CTCCCAGCCGATGCCCTTGACGACTTTGACCTTGATATGCTGCCTGCTGACGCTCTTGACGATTTTG

ACCTTGACATGCTCCCCGGGTAAAGCGGCCGCGACTCTAGATCATAATCAGCCATACCACATTTGT

AGAGGTTTTACTTGCTTTAAAAAACCTCCCACACCTCCCCCTGAACCTGAAACATAAAATGAATGC

AATTGTTGTTGTTAACTTGTTTATTGCAGCTTATAATGGTTACAAATAAAGCAATAGCATCACAAA

TTTCACAAATAAAGCATTTTTTTCACTGCATTCTAGTTGTGGTTTGTCCAAACTCATCAATGTATCT

TAAGGGATCCCTAGAGGGACAGCCCCCCCCCAAAGCCCCCAGGGATGTAATTACGTCCCTCCCCC

GCTAGGGGCAGCAGCGAGCCGCCCGGGGCTCCGCTCCGGTCCGGCGCTCCCCCCGCATCCCCGAG

CCGGCAGCGTGCGGGGACAGCCCGGGCACGGGGAAGGTGGCACGGGATCGCTTTCCTCTGAACGC

TTCTCGCTGCTCTTTGAGCCTGCAGACACCTGGGGGGATACGGGGAAAAAGCTTTAGGCTGAAAG

AGAGATTTAGAATGACAGAATCATAGAACGGCCTGGGTTGCAAAGGAGCACAGTGCTCATCCAGA

TCCAACCCCCTGCTATGTGCAGGGTCATCAACCAGCAGCCCAGGCTGCCCAGAGCCACATCCAGCC

TGGCCTTGAATGCCTGCAGGGATGGGGCATCCACAGCCTCCTTGGGCAACCTGTTCAGTGCGTCAC

CACCCTCTGGGGGAAAAACTGCCTCCTCATATCCAACCCAAACCTCCCCTGTCTCAGTGTAAAGCC

ATTCCCCCTTGTCCTATCAAGGGGGAGTTTGCTGTGACATTGTTGGTCTGGGGTGACACATGTTTGC

CAATTCAGTGCATCACGGAGAGGCAGATCTTGGGGATAAGGAAGTGCAGGACAGCATGGACGTGG

GACATGCAGGTGTTGAGGGCTCTGGGACACTCTCCAAGTCACAGCGTTCAGAACAGCCTTAAGGA

TAAGAAGATAGGATAGAAGGACAAAGAGCAAGTTAAAACCCAGCATGGAGAGGAGCACAAAAAG

GCCACAGACACTGCTGGTCCCTGTGTCTGAGCCTGCATGTTTGATGGTGTCTGGATGCAAGCAGAA

GGGGTGGAAGAGCTTGCCTGGAGAGATACAGCTGGGTCAGTAGGACTGGGACAGGCAGCTGGAG

-continuede

AATTGCCATGTAGATGTTCATACAATCGTCAAATCATGAAGGCTGGAAAAGCCCTCCAAGATCCCC

AAGACCAACCCCAACCCACCCACCGTGCCCACTGGCCATGTCCCTCAGTGCCACATCCCCACAGTT

CTTCATCACCTCCAGGGACGGTGACCCCCCCACCTCCGTGGGCAGCTGTGCCACTGCAGCACCGCT

CTTTGGAGAAGGTAAATCTTGCTAAATCCAGCCCGACCCTCCCCTGGCACAACGTAAGGCCATTAT

CTCTCATCCAACTCCAGGACGGAGTCAGTGAGGATGGGGCTGTCGACCTAGAGGGACAGCCCCCC

CCCAAAGCCCCCAGGGATGTAATTACGTCCCTCCCCCGCTAGGGGCAGCAGCGAGCCGCCCGGGG

CTCCGCTCCGGTCCGGCGCTCCCCCCGCATCCCCGAGCCGGCAGCGTGCGGGGACAGCCCGGGCA

CGGGGAAGGTGGCACGGGATCGCTTTCCTCTGAACGCTTCTCGCTGCTCTTTGAGCCTGCAGACAC

CTGGGGGGATACGGGGAAAAAGCTTTAGGCTGAAAGAGAGATTTAGAATGACAGAATCATAGAA

CGGCCTGGGTTGCAAAGGAGCACAGTGCTCATCCAGATCCAACCCCCTGCTATGTGCAGGGTCATC

AACCAGCAGCCCAGGCTGCCCAGAGCCACATCCAGCCTGGCCTTGAATGCCTGCAGGGATGGGGC

ATCCACAGCCTCCTTGGGCAACCTGTTCAGTGCGTCACCACCCTCTGGGGGAAAAACTGCCTCCTC

ATATCCAACCCAAACCTCCCCTGTCTCAGTGTAAAGCCATTCCCCCTTGTCCTATCAAGGGGGAGT

TTGCTGTGACATTGTTGGTCTGGGGTGACACATGTTTGCCAATTCAGTGCATCACGGAGAGGCAGA

TCTTGGGGATAAGGAAGTGCAGGACAGCATGGACGTGGGACATGCAGGTGTTGAGGGCTCTGGGA

CACTCTCCAAGTCACAGCGTTCAGAACAGCCTTAAGGATAAGAAGATAGGATAGAAGGACAAAGA

GCAAGTTAAAACCCAGCATGGAGAGGAGCACAAAAAGGCCACAGACACTGCTGGTCCCTGTGTCT

GAGCCTGCATGTTTGATGGTGTCTGGATGCAAGCAGAAGGGGTGGAAGAGCTTGCCTGGAGAGAT

ACAGCTGGGTCAGTAGGACTGGGACAGGCAGCTGGAGAATTGCCATGTAGATGTTCATACAATCG

TCAAATCATGAAGGCTGGAAAAGCCCTCCAAGATCCCCAAGACCAACCCCAACCCACCCACCGTG

CCCACTGGCCATGTCCCTCAGTGCCACATCCCCACAGTTCTTCATCACCTCCAGGGACGGTGACCC

CCCCACCTCCGTGGGCAGCTGTGCCACTGCAGCACCGCTCTTTGGAGAAGGTAAATCTTGCTAAAT

CCAGCCCGACCCTCCCCTGGCACAACGTAAGGCCATTATCTCTCATCCAACTCCAGGACGGAGTCA

GTGAGGATGGGGCTCAATTGTTTACTCCCTATCAGTGATAGAGAACGTATGAAGAGTTTACTCCCT

ATCAGTGATAGAGAACGTATGCAGACTTTACTCCCTATCAGTGATAGAGAACGTATAAGGAGTTTA

CTCCCTATCAGTGATAGAGAACGTATGACCAGTTTACTCCCTATCAGTGATAGAGAACGTATCTAC

AGTTTACTCCCTATCAGTGATAGAGAACGTATATCCAGTTTACTCCCTATCAGTGATAGAGAACGT

ATAAGCTTTAGGCGTGTACGGTGGGCGCCTATAAAAGCAGAGCTCGTTTAGTGAACCGTCAGATC

GCCTGGAGCAATTCCACAACACTTTTGTCTTATACCAACTTTCCGTACCACTTCCTACCCTCGTAAA

AAGCTTGTCCACCATGGCTCCTAAGAAAAAGCGGAAGGTGGACAAGAAATACTCAATCGGGCTGG

CCATCGGAACTAACTCAGTGGGGTGGGCAGTCATTACTGACGAGTACAAAGTGCCAAGCAAGAAA

TTTAAGGTCCTGGGCAACACCGATAGGCACTCCATCAAGAAAAATCTGATTGGGGCCCTGCTGTTC

GACTCTGGAGAGACAGCTGAAGCAACTAGACTGAAAAGGACTGCTAGAAGGCGCTATACCCGGCG

AAAGAATCGCATCTGCTACCTGCAGGAGATTTTCTCTAACGAAATGGCCAAGGTGGACGATAGTTT

CTTTCATCGGCTGGAGGAATCATTCCTGGTCGAGGAAGATAAGAAACACGAGAGACATCCTATCTT

TGGAAACATTGTGGACGAGGTCGCTTATCACGAAAAATACCCCACCATCTATCATCTGCGCAAGA

AACTGGTGGACTCTACAGATAAAGCAGACCTGCGGCTGATCTATCTGGCCCTGGCTCACATGATTA

AGTTCAGAGGCCATTTTCTGATCGAGGGAGATCTGAACCCAGACAATAGCGATGTGGACAAGCTG

TTCATCCAGCTGGTCCAGACATACAATCAGCTGTTTGAGGAAAACCCTATTAATGCATCTGGCGTG

GACGCAAAAGCCATCCTGAGTGCCAGGCTGTCTAAGAGTAGAAGGCTGGAGAACCTGATCGCTCA

GCTGCCAGGCGAAAAGAAAAACGGCCTGTTTGGAAATCTGATTGCACTGTCACTGGGACTGACAC

-continuede

CTAACTTCAAGAGCAATTTTGATCTGGCCGAGGACGCTAAACTGCAGCTGAGCAAGGACACTTAT

GACGATGACCTGGATAACCTGCTGGCTCAGATCGGAGATCAGTACGCAGACCTGTTCCTGGCCGCT

AAGAATCTGTCTGACGCTATCCTGCTGAGTGATATTCTGCGGGTGAACACCGAGATTACAAAAGCC

CCTCTGTCAGCTAGCATGATCAAGAGATATGACGAGCACCATCAGGATCTGACCCTGCTGAAGGC

ACTGGTGCGCCAGCAGCTGCCCGAGAAGTACAAGGAAATCTTCTTTGATCAGAGTAAGAACGGGT

ACGCCGGTTATATTGACGGCGGAGCTTCACAGGAGGAATTCTACAAGTTTATCAAACCTATTCTGG

AGAAGATGGACGGCACCGAGGAACTGCTGGTGAAACTGAATCGCGAGGACCTGCTGCGCAAGCA

GCGGACATTTGATAACGGCTCCATCCCCCACCAGATTCATCTGGGAGAGCTGCACGCAATCCTGCG

ACGACAGGAAGACTTCTACCCATTTCTGAAGGATAACCGCGAGAAGATCGAAAAAATTCTGACCT

TCCGGATCCCTTACTATGTGGGGCCCCTGGCAAGGGGTAATTCCCGCTTTGCCTGGATGACACGGA

AATCTGAGGAAACAATCACTCCTTGGAACTTCGAGGAAGTGGTCGATAAGGGAGCTTCCGCACAG

TCTTTCATCGAGAGAATGACAAACTTCGACAAAAACCTGCCAAATGAGAAAGTGCTGCCTAAGCA

CAGTCTGCTGTACGAGTATTTCACAGTCTATAACGAACTGACTAAGGTGAAATACGTCACCGAGGG

GATGAGGAAGCCCGCCTTCCTGAGCGGTGAACAGAAGAAAGCTATCGTGGACCTGCTGTTTAAAA

CCAATCGCAAGGTGACAGTCAAGCAGCTGAAGGAGGACTACTTCAAGAAAATTGAATGTTTCGAT

TCTGTGGAGATCAGTGGCGTCGAAGACAGATTTAACGCTTCTCTGGGAACCTACCACGATCTGCTG

AAGATCATTAAGGATAAAGACTTCCTGGACAACGAGGAAAATGAGGATATCCTGGAAGACATTGT

GCTGACCCTGACACTGTTTGAGGATCGCGAAATGATCGAGGAACGGCTGAAAACTTATGCCCATCT

GTTCGATGACAAGGTGATGAAACAGCTGAAGCGAAGAAGGTACACCGGCTGGGGACGACTGAGC

AGAAAGCTGATCAACGGCATTCGGGACAAACAGAGTGGAAAGACTATCCTGGACTTTCTGAAATC

AGATGGCTTCGCTAACAGAAATTTTATGCAGCTGATTCACGATGACAGCCTGACCTTCAAAGAGGA

TATCCAGAAGGCACAGGTGTCCGGGCAGGGTGACTCTCTGCACGAGCATATCGCAAACCTGGCCG

GGTCCCCCGCCATCAAGAAAGGTATTCTGCAGACCGTGAAGGTGGTCGATGAGCTGGTGAAAGTC

ATGGGCAGGCATAAGCCAGAAAACATCGTGATTGAGATGGCCCGCGAAAATCAGACCACACAGA

AAGGACAGAAGAACAGCCGCGAGCGGATGAAAAGGATCGAGGAAGGCATTAAGGAACTGGGATC

CCAGATCCTGAAAGAGCACCCTGTGGAAAACACTCAGCTGCAGAATGAGAAGCTGTATCTGTACT

ATCTGCAGAATGGGCGGGATATGTACGTGGACCAGGAGCTGGATATTAACCGACTGTCTGATTAC

GACGTGGATGCCATCGTCCCACAGTCATTCCTGAAAGATGACAGCATTGACAATAAGGTGCTGAC

CCGGAGTGACAAAAACCGAGGAAAGAGTGATAATGTCCCTTCAGAGGAAGTGGTCAAGAAAATG

AAGAACTACTGGAGACAGCTGCTGAATGCCAAACTGATCACACAGCGAAAGTTTGATAACCTGAC

TAAAGCTGAGAGAGGGGGTCTGTCAGAACTGGACAAAGCAGGCTTCATCAAGCGACAGCTGGTGG

AGACCAGACAGATCACAAAGCACGTCGCTCAGATTCTGGATAGCAGGATGAACACAAAGTACGAT

GAGAATGACAAACTGATCCGCGAAGTGAAGGTCATTACTCTGAAGTCAAAACTTGTGAGCGACTT

CAGAAAGGATTTCCAGTTCTACAAAGTCAGGGAGATCAACAATTATCACCATGCTCATGACGCAT

ACCTGAACGCAGTGGTCGGGACCGCCCTGATTAAGAAATACCCCAAACTGGAGAGCGAATTCGTG

TACGGTGACTATAAGGTGTACGATGTCAGAAAAATGATCGCCAAGAGTGAGCAGGAAATTGGAAA

AGCCACCGCTAAGTATTTCTTTTACTCAAACATCATGAATTTCTTTAAGACTGAGATCACCCTGGCA

AATGGGGAAATCCGAAAGAGACCACTGATTGAGACTAACGGCGAGACCGGAGAAATCGTGTGGG

ACAAGGGTAGGGATTTTGCCACAGTGCGCAAGGTCCTGTCCATGCCTCAAGTGAATATTGTCAAGA

AAACAGAGGTGCAGACTGGCGGATTCAGTAAGGAATCAATTCTGCCCAAACGGAACTCTGATAAG

CTGATCGCCCGAAAGAAAGACTGGGATCCCAAGAAATATGGGGGTTTCGACTCCCCAACAGTGGC

-continuede

TTACTCTGTCCTGGTGGTCGCAAAGGTGGAGAAGGGGAAAAGCAAGAAACTGAAATCCGTCAAGG

AGCTGCTGGGTATCACTATTATGGAGAGGAGCTCCTTCGAGAAGAACCCCATCGATTTTCTGGAGG

CTAAAGGCTATAAGGAAGTGAAGAAAGACCTGATCATTAAACTGCCAAAGTACAGCCTGTTTGAG

CTGGAAAACGGAAGGAAGCGAATGCTGGCATCCGCAGGAGAGCTGCAGAAGGGTAATGAACTGG

CCCTGCCTTCTAAGTACGTGAACTTCCTGTATCTGGCTAGCCACTACGAGAAGCTGAAAGGCTCCC

CCGAGGATAACGAACAGAAACAGCTGTTTGTGGAGCAGCACAAGCATTATCTGGACGAGATCATT

GAACAGATTAGCGAGTTCTCCAAAAGAGTGATCCTGGCTGACGCAAATCTGGATAAGGTCCTGAG

CGCATACAACAAACACAGAGATAAGCCAATCAGGGAGCAGGCCGAAAATATCATTCATCTGTTCA

CTCTGACCAACCTGGGAGCCCCTGCAGCCTTCAAGTATTTTGACACTACCATCGATCGGAAACGAT

ACACATCCACTAAGGAGGTGCTGGACGCTACCCTGATTCACCAGAGCATTACCGGCCTGTATGAA

ACAAGGATTGACCTGTCTCAGCTGGGGGGCGACCTCGAGATGGCCAAGCCCCTGAGCCAAGAGGA

AAGCACCCTGATCGAGCGGGCCACCGCCACCATCAACAGCATCCCCATCAGCGAGGACTACAGCG

TGGCCTCTGCCGCCCTGAGCAGCGACGGCAGAATCTTCACCGGCGTGAACGTGTACCACTTCACAG

GCGGCCCTTGCGCCGAGCTGGTGGTGCTGGGAACAGCTGCCGCCGCTGCCGCTGGCAACCTGACCT

GTATCGTGGCCATCGGCAACGAGAACCGGGGCATCCTGAGCCCCTGCGGCAGATGCAGACAGGTG

CTGCTGGACCTGCACCCCGGCATCAAGGCCATCGTGAAGGACAGCGACGGCCAGCCCACCGCCGT

GGGCATTAGAGAGCTGCTGCCCAGCGGCTACGTGTGGGAGGGCTGACTCGAGATTTTCAAACCAG

AAGAACTACGACAGGCACTGATGCCCACCCTGGAAGCCCTGTACCGGCAGGACCCCGAGAGCCTG

CCCTTCAGACAGCCCGTGGATCCCCAGCTGCTGGGCATCCCCGACTACTTCGACATCGTGAAGTCC

CCCATGGACCTGAGCACCATCAAGCGGAAGCTGGACACCGGCCAGTACCAAGAGCCCTGGCAGTA

CGTGGACGACATCTGGCTGATGTTCAACAACGCCTGGCTGTACAACAGAAAGACCAGCCGGGTGT

ACAAGTACTGCAGCAAGCTGAGCGAGGTGTTCGAGCAAGAGATCGACCCCGTGATGCAGAGCCTG

GGCTACTGCTGCGGCAGAAAGCTGGAATTCAGCCCCCAGACCCTGTGCTGCTACGGCAAGCAGCT

GTGCACCATCCCCCGGGACGCCACCTACTACAGCTACCAGAACAGATACCACTTCTGCGAGAAGT

GCTTCAACGAGATCCAGGGCGAGAGCGTGTCCCTGGGCGACGACCCTAGCCAGCCCCAGACCACA

ATCAACAAAGAGCAGTTCAGCAAGCGGAAGAACGACACCCTGGACCCCGAGCTGTTCGTGGAATG

CACCGAGTGCGGCCGGAAGATGCACCAGATCTGCGTGCTGCACCACGAGATCATCTGGCCTGCCG

GCTTCGTGTGCGACGGCTGCCTGAAGAAGTCCGCCCGGACCCGGAAAGAGAACAAGTTCAGCGCC

AAGCGGCTGCCCTCTACCCGGCTGGGCACCTTCCTGGAAAACAGAGTGAACGACTTCCTGCGGCG

GCAGAACCACCCCGAGTCCGGCGAAGTGACAGTGCGGGTGGTGCACGCCAGCGACAAGACCGTG

GAAGTGAAGCCTGGCATGAAGGCCAGATTCGTGGACAGCGGCGAGATGGCCGAGAGCTTCCCCTA

CCGGACCAAGGCCCTGTTCGCCTTCGAAGAGATCGATGGCGTGGACCTGTGCTTCTTCGGCATGCA

CGTGCAAGAGTACGGCAGCGACTGCCCCCCACCCAACCAGCGGCGGGTGTACATCAGCTACCTGG

ACAGCGTGCACTTCTTCCGGCCCAAGTGCCTGCGGACCGCCGTGTATCACGAGATCCTGATCGGCT

ACCTGGAATACGTGAAGAAGCTGGGCTACACCACCGGCCACATCTGGGCCTGTCCTCCCAGCGAG

GGCGACGACTACATCTTCCACTGCCACCCCCCCGACCAGAAGATCCCCAAGCCCAAGAGACTGCA

AGAGTGGTACAAGAAGATGCTGGACAAGGCCGTGTCCGAGCGGATCGTGCACGACTACAAGGAC

ATCTTCAAGCAGGCCACCGAGGACCGGCTGACCAGCGCCAAAGAGCTGCCCTACTTCGAGGGCGA

CTTCTGGCCCAACGTGCTGGAAGAGAGCATCAAAGAGCTGGAACAAGAGGAAGAGGAACGCAAG

CGGGAAGAGAACACCAGCAACGAGAGCACCGACGTGACCAAGGGCGACAGCAAGAACGCCAAGA

AGAAGAACAACAAGAAAACCAGCAAGAACAAGAGCAGCCTGAGCCGGGGAAACAAGAAAAAGC

-continuede

CCGGCATGCCCAACGTGTCCAACGACCTGAGCCAGAAACTGTACGCCACCATGGAAAAGCACAAA

GAGGTGTTCTTCGTCATCCGGCTGATCGCCGGACCTGCCGCCAACAGCCTGCCCCCCATCGTGGAC

CCCGACCCCCTGATCCCCTGCGACCTGATGGACGGCAGGGACGCCTTCCTGACCCTGGCCCGGGAC

AAGCACCTGGAATTCTCCAGCCTGCGGAGAGCCCAGTGGTCCACCATGTGCATGCTGGTGGAACT

GCACACCCAGAGCCAGGACGAGGGCAGAGGAAGTCTGCTAACATGCGGTGACGTCGAGGAGAAT

CCTGGCCCAGCACCGGGATCCATGGTGAGCAAGGGCGAGGAGCTGTTCACCGGGGTGGTGCCCAT

CCTGGTCGAGCTGGACGGCGACGTAAACGGCCACAAGTTCAGCGTGTCCGGCGAGGGCGAGGGCG

ATGCCACCTACGGCAAGCTGACCCTGAAGTTCATCTGCACCACCGGCAAGCTGCCCGTGCCCTGGC

CCACCCTCGTGACCACCTTCACCTACGGCGTGCAGTGCTTCGCCCGCTACCCCGACCACATGAAGC

AGCACGACTTCTTCAAGTCCGCCATGCCCGAAGGCTACGTCCAGGAGCGCACCATCTTCTTCAAGG

ACGACGGCAACTACAAGACCCGCGCCGAGGTGAAGTTCGAGGGCGACACCCTGGTGAACCGCATC

GAGCTGAAGGGCATCGACTTCAAGGAGGACGGCAACATCCTGGGGCACAAGCTGGAGTACAACTA

CAACAGCCACAAGGTCTATATCACCGCCGACAAGCAGAAGAACGGCATCAAGGTGAACTTCAAGA

CCCGCCACAACATCGAGGACGGCAGCGTGCAGCTCGCCGACCACTACCAGCAGAACACCCCCATC

GGCGACGGCCCCGTGCTGCTGCCCGACAACCACTACCTGAGCACCCAGTCCGCCCTGAGCAAAGA

CCCCAACGAGAAGCGCGATCACATGGTCCTGCTGGAGTTCGTGACCGCCGCCGGGATCACTCTCG

GCATGGACGAGCTGTACAAGTAAACCTAATCTAGCAGCTCGCTGATCAGCCTCGACTGTGCCTTCT

AGTTGCCAGCCATCTGTTGTTTGCCCCTCCCCCGTGCCTTCCTTGACCCTGGAAGGTGCCACTCCCA

CTGTCCTTTCCTAATAAAATGAGGAAATTGCATCGCATTGTCTGAGTAGGTGTCATTCTATTCTGGG

GGGTGGGGTGGGGCAGGACAGCAAGGGGGAGGATTGGGAAGACAATAGCAGGCATGCTGGGGAT

GCGGTGGGCTCTATGGCTTCTGAGGCGGAAAGAACCAGCTGGGGCTCGATCCTCTAGTTGGCGCGT

CATGGTCCATATGAATATCCTCCTTAGTTCCTATTCCGCTAGCCTAGAGGGACAGCCCCCCCCCAA

AGCCCCCAGGGATGTAATTACGTCCCTCCCCCGCTAGGGGCAGCAGCGAGCCGCCCGGGGCTCCG

CTCCGGTCCGGCGCTCCCCCCGCATCCCCGAGCCGGCAGCGTGCGGGGACAGCCCGGGCACGGGG

AAGGTGGCACGGGATCGCTTTCCTCTGAACGCTTCTCGCTGCTCTTTGAGCCTGCAGACACCTGGG

GGGATACGGGGAAAAAGCTTTAGGCTGAAAGAGAGATTTAGAATGACAGAATCATAGAACGGCC

TGGGTTGCAAAGGAGCACAGTGCTCATCCAGATCCAACCCCCTGCTATGTGCAGGGTCATCAACCA

GCAGCCCAGGCTGCCCAGAGCCACATCCAGCCTGGCCTTGAATGCCTGCAGGGATGGGGCATCCA

CAGCCTCCTTGGGCAACCTGTTCAGTGCGTCACCACCCTCTGGGGGAAAAACTGCCTCCTCATATC

CAACCCAAACCTCCCCTGTCTCAGTGTAAAGCCATTCCCCCTTGTCCTATCAAGGGGGAGTTTGCT

GTGACATTGTTGGTCTGGGGTGACACATGTTTGCCAATTCAGTGCATCACGGAGAGGCAGATCTTG

GGGATAAGGAAGTGCAGGACAGCATGGACGTGGGACATGCAGGTGTTGAGGGCTCTGGGACACTC

TCCAAGTCACAGCGTTCAGAACAGCCTTAAGGATAAGAAGATAGGATAGAAGGACAAAGAGCAA

GTTAAAACCCAGCATGGAGAGGAGCACAAAAAGGCCACAGACACTGCTGGTCCCTGTGTCTGAGC

CTGCATGTTTGATGGTGTCTGGATGCAAGCAGAAGGGGTGGAAGAGCTTGCCTGGAGAGATACAG

CTGGGTCAGTAGGACTGGGACAGGCAGCTGGAGAATTGCCATGTAGATGTTCATACAATCGTCAA

ATCATGAAGGCTGGAAAAGCCCTCCAAGATCCCCAAGACCAACCCCAACCCACCCACCGTGCCCA

CTGGCCATGTCCCTCAGTGCCACATCCCCACAGTTCTTCATCACCTCCAGGGACGGTGACCCCCCC

ACCTCCGTGGGCAGCTGTGCCACTGCAGCACCGCTCTTTGGAGAAGGTAAATCTTGCTAAATCCAG

CCCGACCCTCCCCTGGCACAACGTAAGGCCATTATCTCTCATCCAACTCCAGGACGGAGTCAGTGA

GGATGGGGCTGGATCCGAAGCAGCTCCAGCCTACACAATCGCTCAAGACGTGTAATGCTTTTATTA

-continuede

TATATTAGTCACGATATCTATAACAAGAAAATATATATATAATAAGTTATCACGTAAGTAGAACAT

GAAATAACAATATAATTATCGTATGAGTTAAATCTTAAAAGTCACGTAAAAGATAATCATGCGTCA

TTTTGACTCACGCGGTCGTTATAGTTCAAAATCAGTGACACTTACCGCATTGACAAGCACGCCTCA

CGGGAGCTCCAAGCGGCGACTGAGATGTCCTAAATGCACAGCGACGGATTCGCGCTATTTAGAAA

GAGAGAGCAATATTTCAAGAATGCATGCGTCAATTTTACGCAGACTATCTTTCTAGGGTTAAAAAA

GATTTGCGCTTTACTCGACCTAAACTTTAAACACGTCATAGAATCTTCGTTTGACAAAAACCACAT

TGTGGGGTACCGAGCTCTTAATTAAGGCGCGCCGGGGAGGTTCCCTTTAGTGAGGGTTAATTGCGG

GTCGCCCTATAGTGAGTCGTATTACAATTCACTGGCCGTCGTTTTACAACGTCGTGACTGGGAAAA

CCCTGGCGTTACCCAACTTAATCGCCTTGCAGCACATCCCCCTTTCGCCAGCTGGCGTAATAGCGA

AGAGGCCCGCACCGATCGCCCTTCCCAACAGTTGCGCAGCCTGAATGGCGAATGGCAAATTGTAA

GCGTTAATATTTTGTTAAAATTCGCGTTAAATTTTTGTTAAATCAGCTCATTTTTTAACCAATAGGC

CGAAATCGGCAAAATCCCTTATAAATCAAAAGAATAGACCGAGATAGGGTTGAGTGTTGTTCCAG

TTTGGAACAAGAGTCCACTATTAAAGAACGTGGACTCCAACGTCAAAGGGCGAAAAACCGTCTAT

CAGGGCGATGGCCCACTACGTGAACCATCACCCTAATCAAGTTTTTTGGGGTCGAGGTGCCGTAAA

GCACTAAATCGGAACCCTAAAGGGAGCCCCCGATTTAGAGCTTGACGGGGAAAGCCGGCGAACGT

GGCGAGAAAGGAAGGGAAGAAAGCGAAAGGAGCGGGCGCTAGGGCGCTGGCAAGTGTAGCGGTC

ACGCTGCGCGTAACCACCACACCCGCCGCGCTTAATGCGCCGCTACAGGGCGCGTCAG

TOIC_Cas9_obl_r26_AAVS_PgkNeo_Bsd_tracR (SEQ ID NO: 19)

GTGGCACTTTTCGGGGAAATGTGCGCGGAACCCCTATTTGTTTATTTTTCTAAATACATTCAAATAT

GTATCCGCTCATGAGACAATAACCCTGATAAATGCTTCAATAATATTGAAAAAGGAAGAGTATGA

GTATTCAACATTTCCGTGTCGCCCTTATTCCCTTTTTTGCGGCATTTTGCCTTCCTGTTTTTGCTCAC

CCAGAAACGCTGGTGAAAGTAAAAGATGCTGAAGATCAGTTGGGTGCACGAGTGGGTTACATCGA

ACTGGATCTCAACAGCGGTAAGATCCTTGAGAGTTTTCGCCCCGAAGAACGTTTTCCAATGATGAG

CACTTTTAAAGTTCTGCTATGTGGCGCGGTATTATCCCGTATTGACGCCGGGCAAGAGCAACTCGG

TCGCCGCATACACTATTCTCAGAATGACTTGGTTGAGTACTCACCAGTCACAGAAAAGCATCTTAC

GGATGGCATGACAGTAAGAGAATTATGCAGTGCTGCCATAACCATGAGTGATAACACTGCGGCCA

ACTTACTTCTGACAACGATCGGAGGACCGAAGGAGCTAACCGCTTTTTTGCACAACATGGGGGATC

ATGTAACTCGCCTTGATCGTTGGGAACCGGAGCTGAATGAAGCCATACCAAACGACGAGCGTGAC

ACCACGATGCCTGTAGCAATGGCAACAACGTTGCGCAAACTATTAACTGGCGAACTACTTACTCTA

GCTTCCCGGCAACAATTAATAGACTGGATGGAGGCGGATAAAGTTGCAGGACCACTTCTGCGCTC

GGCCCTTCCGGCTGGCTGGTTTATTGCTGATAAATCTGGAGCCGGTGAGCGTGGGTCTCGCGGTAT

CATTGCAGCACTGGGGCCAGATGGTAAGCCCTCCCGTATCGTAGTTATCTACACGACGGGGAGTCA

GGCAACTATGGATGAACGAAATAGACAGATCGCTGAGATAGGTGCCTCACTGATTAAGCATTGGT

AACTGTCAGACCAAGTTTACTCATATATACTTTAGATTGATTTAAAACTTCATTTTTAATTTAAAAG

GATCTAGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGTAATC

TGCTGCTTGCAAACAAAAAAACCACCGCTACCAGCGGTGGTTTGTTTGCCGGATCAAGAGCTACCA

ACTCTTTTTCCGAAGGTAACTGGCTTCAGCAGAGCGCAGATACCAAATACTGTTCTTCTAGTGTAG

CCGTAGTTAGGCCACCACTTCAAGAACTCTGTAGCACCGCCTACATACCTCGCTCTGCTAATCCTG

TTACCAGTGGCTGCTGCCAGTGGCGATAAGTCGTGTCTTACCGGGTTGGACTCAAGACGATAGTTA

CCGGATAAGGCGCAGCGGTCGGGCTGAACGGGGGGTTCGTGCACACAGCCCAGCTTGGAGCGAAC

-continuede

GACCTACACCGAACTGAGATACCTACAGCGTGAGCTATGAGAAAGCGCCACGCTTCCCGAAGGGA

GAAAGGCGGACAGGTATCCGGTAAGCGGCAGGGTCGGAACAGGAGAGCGCACGAGGGAGCTTCC

AGGGGGAAACGCCTGGTATCTTTATAGTCCTGTCGGGTTTCGCCACCTCTGACTTGAGCGTCGATT

TTTGTGATGCTCGTCAGGGGGGCGGAGCCTATGGAAAAACGCCAGCAACGCGGCCTTTTTACGGTT

CCTGGCCTTTTGCTGGCCTTTTGCTCACATGTTCTTTCCTGCGTTATCCCCTGATTCTGTGGATAACC

GTATTACCGCCTTTGAGTGAGCTGATACCGCTCGCCGCAGCCGAACGACCGAGCGCAGCGAGTCA

GTGAGCGAGGAAGCGGAAGAGCGCCCAATACGCAAACCGCCTCTCCCCGCGCGTTGGCCGATTCA

TTAATGCAGCTGGCACGACAGGTTTCCCGACTGGAAAGCGGGCAGTGAGCGCAACGCAATTAATG

TGAGTTAGCTCACTCATTAGGCACCCCAGGCTTTACACTTTATGCTTCCGGCTCGTATGTTGTGTGG

AATTGTGAGCGGATAACAATTTCACACAGGAAACAGCTATGACCATGATTACGCCAAGCGCGCAA

TTAACCCTCACTAAAGGGAACCTCCCCTAGCTTAATTAACCCTAGAAAGATAATCATATTGTGACG

TACGTTAAAGATAATCATGCGTAAAATTGACGCATGTGTTTTATCGATCTGTATATCGAGGTTTATT

TATTAATTTGAATAGATATTAAGTTTTATTATATTTACACTTACATACTAATAATAAATTCAACAAA

CAATTTATTTATGTTTATTTATTTATTAAAAAAAAACAAAAACTCAAAATTTCTTCTATAAAGTAAC

AAAACTTTTAAACATTCTCTCTTTTACAAAAATAAACTTATTTTGTACTTTAAAAACAGTCATGTTG

TATTATAAAATAAGTAATTAGCTTAACTTATACATAATAGAAACAAATTATACTTATTAATCGCAT

TGATTATTGACTAGTCGTATTAAGGGTTCCGGATCAGCTTGATTCGAGCCCCAGCTGGTTCTTTCCG

CCTCAGAAGCCATAGAGCCCACCGCATCCCCAGCATGCCTGCTATTGTCTTCCCAATCCTCCCCCTT

GCTGTCCTGCCCCACCCCACCCCCCAGAATAGAATGACACCTACTCAGACAATGCGATGCAATTTC

CTCATTTTATTAGGAAAGGACAGTGGGAGTGGCACCTTCCAGGGTCAAGGAAGGCACGGGGGAGG

GGCAAACAACAGATGGCTGGCAACTAGAAGGCACAGTCGAGGCTGATCAGCGAGCTCTAGAGAA

TTGATCCCCTCAGAAGAACTCGTCAAGAAGGCGATAGAAGGCGATGCGCTGCGAATCGGGAGCGG

CGATACCGTAAAGCACGAGGAAGCGGTCAGCCCATTCGCCGCCAAGCTCTTCAGCAATATCACGG

GTAGCCAACGCTATGTCCTGATAGCGGTCCGCCACACCCAGCCGGCCACAGTCGATGAATCCAGA

AAAGCGGCCATTTTCCACCATGATATTCGGCAAGCAGGCATCGCCATGGGTCACGACGAGATCCTC

GCCGTCGGGCATGCGCGCCTTGAGCCTGGCGAACAGTTCGGCTGGCGCGAGCCCCTGATGCTCTTC

GTCCAGATCATCCTGATCGACAAGACCGGCTTCCATCCGAGTACGTGCTCGCTCGATGCGATGTTT

CGCTTGGTGGTCGAATGGGCAGGTAGCCGGATCAAGCGTATGCAGCCGCCGCATTGCATCAGCCA

TGATGGATACTTTCTCGGCAGGAGCAAGGTGAGATGACAGGAGATCCTGCCCCGGCACTTCGCCC

AATAGCAGCCAGTCCCTTCCCGCTTCAGTGACAACGTCGAGCACAGCTGCGCAAGGAACGCCCGT

CGTGGCCAGCCACGATAGCCGCGCTGCCTCGTCCTGCAGTTCATTCAGGGCACCGGACAGGTCGGT

CTTGACAAAAAGAACCGGGCGCCCCTGCGCTGACAGCCGGAACACGGCGGCATCAGAGCAGCCG

ATTGTCTGTTGTGCCCAGTCATAGCCGAATAGCCTCTCCACCCAAGCGGCCGGAGAACCTGCGTGC

AATCCATCTTGTTCAATGGCCGATCCCATGGTTTAGTTCCTCACCTTGTCGTATTATACTATGCCGA

TATACTATGCCGATGATTAATTGTCAACACGTGCTGCTGCAGGTCGAAAGGCCCGGAGATGAGGA

AGAGGAGAACAGCGCGGCAGACGTGCGCTTTTGAAGCGTGCAGAATGCCGGGCCTCCGGAGGACC

TTCGGGCGCCCGCCCCGCCCCTGAGCCCGCCCCTGAGCCCGCCCCCGGACCCACCCCTTCCCAGCC

TCTGAGCCCAGAAAGCGAAGGAGCAAAGCTGCTATTGGCCGCTGCCCCAAAGGCCTACCCGCTTC

CATTGCTCAGCGGTGCTGTCCATCTGCACGAGACTAGTGAGACGTGCTACTTCCATTTGTCACGTC

CTGCACGACGCGAGCTGCGGGGCGGGGGGGAACTTCCTGACTAGGGGAGGAGTAGAAGGTGGCG

CGAAGGGGCCACCAAAGAACGGAGCCGGTTGGCGCCTACCGGTGGATGTGGAATGTGTGCGAGCC

-continuede

AGAGGCCACTTGTGTAGCGCCAAGTGCCCAGCGGGGCTGCTAAAGCGCATGCTCCAGACTGCCTT

GGGAAAAGCGCCTCCCCTACCCGGTAGACACCCCACAGTGGGTGGCCTAGGGACAGGATTGCAAC

TCCAGTCTTTCTTCTTCTTGGGCGGGAGTCACTAGTTATTAATAGTAATCAATTACGGGGTCATTAG

TTCATAGCCCATATATGGAGTTCCGCGTTACATAACTTACGGTAAATGGCCCGCCTGGCTGACCGC

CCAACGACCCCCGCCCATTGACGTCAATAATGACGTATGTTCCCATAGTAACGCCAATAGGGACTT

TCCATTGACGTCAATGGGTGGACTATTTACGGTAAACTGCCCACTTGGCAGTACATCAAGTGTATC

ATATGCCAAGTACGCCCCCTATTGACGTCAATGACGGTAAATGGCCCGCCTGGCATTATGCCCAGT

ACATGACCTTATGGGACTTTCCTACTTGGCAGTACATCTACGTATTAGTCATCGCTATTACCATGGG

TCGAGGTGAGCCCCACGTTCTGCTTCACTCTCCCCATCTCCCCCCCCTCCCCACCCCCAATTTTGTA

TTTATTTATTTTTTAATTATTTTGTGCAGCGATGGGGGCGGGGGGGGGGGGGCGCGCGCCAGGCG

GGGCGGGGCGGGGCGAGGGGCGGGGCGGGGCGAGGCGGAGAGGTGCGGCGGCAGCCAATCAGA

GCGGCGCGCTCCGAAAGTTTCCTTTTATGGCGAGGCGGCGGCGGCGGCGGCCCTATAAAAAGCGA

AGCGCGCGGCGGGCGGGAGTCGCTGCGTTGCCTTCGCCCCGTGCCCCGCTCCGCGCCGCCTCGCGC

CGCCCGCCCCGGCTCTGACTGACCGCGTTACTCCCACAGGTGAGCGGGCGGGACGGCCCTTCTCCT

CCGGGCTGTAATTAGCGCTTGGTTTAATGACGGCTCGTTTCTTTTCTGTGGCTGCGTGAAAGCCTTA

AAGGGCTCCGGGAGGGCCCTTTGTGCGGGGGGGAGCGGCTCGGGGGGTGCGTGCGTGTGTGTGTG

CGTGGGGAGCGCCGCGTGCGGCCCGCGCTGCCCGGCGGCTGTGAGCGCTGCGGGCGCGGCGCGGG

GCTTTGTGCGCTCCGCGTGTGCGCGAGGGGAGCGCGGCCGGGGGCGGTGCCCCGCGGTGCGGGGG

GGCTGCGAGGGGAACAAAGGCTGCGTGCGGGGTGTGTGCGTGGGGGGGTGAGCAGGGGGTGTGG

GCGCGGCGGTCGGGCTGTAACCCCCCCCTGCACCCCCCTCCCCGAGTTGCTGAGCACGGCCCGGCT

TCGGGTGCGGGGCTCCGTGCGGGGCGTGGCGCGGGGCTCGCCGTGCCGGGCGGGGGGTGGCGGCA

GGTGGGGGTGCCGGGCGGGGCGGGGCCGCCTCGGGCCGGGGAGGGCTCGGGGGAGGGGCGCGGC

GGCCCCGGAGCGCCGGCGGCTGTCGAGGCGCGGCGAGCCGCAGCCATTGCCTTTTATGGTAATCG

TGCGAGAGGGCGCAGGGACTTCCTTTGTCCCAAATCTGGCGGAGCCGAAATCTGGGAGGCGCCGC

CGCACCCCCTCTAGCGGGCGCGGGCGAAGCGGTGCGGCGCCGGCAGGAAGGAAATGGGCGGGGA

GGGCCTTCGTGCGTCGCCGCGCCGCCGTCCCCTTCTCCATCTCCAGCCTCGGGGCTGCCGCAGGGG

GACGGCTGCCTTCGGGGGGGACGGGGCAGGGCGGGGTTCGGCTTCTGGCGTGTGACCGGCGGCTC

TAGAGCCTCTGCTAACCATGTTCATGCCTTCTTCTTTTTCCTACAGCTCCTGGGCAACGTGCTGGTT

ATTGTGCTGTCTCATCATTTTGGCAAAGAATTCGCCACCATGGTGCCCAAGAAGAAGAGGAAAGTC

TCTAGACTGGACAAGAGCAAAGTCATAAACTCTGCTCTGGAATTACTCAATGGAGTCGGTATCGA

AGGCCTGACGACAAGGAAACTCGCTCAAAAGCTGGGAGTTGAGCAGCCTACCCTGTACTGGCACG

TGAAGAACAAGCGGGCCCTGCTCGATGCCCTGCCAATCGAGATGCTGGACAGGCATCATACCCAC

TCCTGCCCCCTGGAAGGCGAGTCATGGCAAGACTTTCTGCGGAACAACGCCAAGTCATACCGCTGT

GCTCTCCTCTCACATCGCGACGGGGCTAAAGTGCATCTCGGCACCCGCCCAACAGAGAAACAGTA

CGAAACCCTGGAAAATCAGCTCGCGTTCCTGTGTCAGCAAGGCTTCTCCCTGGAGAACGCACTGTA

CGCTCTGTCCGCCGTGGGCCACTTTACACTGGGCTGCGTATTGGAGGAACAGGAGCATCAAGTAGC

AAAAGAGGAAAGAGAGACACCTACCACCGATTCTATGCCCCCACTTCTGAAACAAGCAATTGAGC

TGTTCGACCGGCAGGGAGCCGAACCTGCCTTCCTTTTCGGCCTGGAACTAATCATATGTGGCCTGG

AGAAACAGCTAAAGTGCGAAAGCGGCGGGCCGACCGACGCCCTTGACGATTTTGACTTAGACATG

CTCCCAGCCGATGCCCTTGACGACTTTGACCTTGATATGCTGCCTGCTGACGCTCTTGACGATTTTG

ACCTTGACATGCTCCCCGGGTAAAGCGGCCGCGACTCTAGATCATAATCAGCCATACCACATTTGT

-continuede

AGAGGTTTTACTTGCTTTAAAAAACCTCCCACACCTCCCCCTGAACCTGAAACATAAAATGAATGC

AATTGTTGTTGTTAACTTGTTTATTGCAGCTTATAATGGTTACAAATAAAGCAATAGCATCACAAA

TTTCACAAATAAAGCATTTTTTTCACTGCATTCTAGTTGTGGTTTGTCCAAACTCATCAATGTATCT

TAAGGGATCCCTAGAGGGACAGCCCCCCCCCAAAGCCCCCAGGGATGTAATTACGTCCCTCCCCC

GCTAGGGGCAGCAGCGAGCCGCCCGGGGCTCCGCTCCGGTCCGGCGCTCCCCCCGCATCCCCGAG

CCGGCAGCGTGCGGGGACAGCCCGGGCACGGGGAAGGTGGCACGGGATCGCTTTCCTCTGAACGC

TTCTCGCTGCTCTTTGAGCCTGCAGACACCTGGGGGGATACGGGGAAAAAGCTTTAGGCTGAAAG

AGAGATTTAGAATGACAGAATCATAGAACGGCCTGGGTTGCAAAGGAGCACAGTGCTCATCCAGA

TCCAACCCCCTGCTATGTGCAGGGTCATCAACCAGCAGCCCAGGCTGCCCAGAGCCACATCCAGCC

TGGCCTTGAATGCCTGCAGGGATGGGGCATCCACAGCCTCCTTGGGCAACCTGTTCAGTGCGTCAC

CACCCTCTGGGGGAAAAACTGCCTCCTCATATCCAACCCAAACCTCCCCTGTCTCAGTGTAAAGCC

ATTCCCCCTTGTCCTATCAAGGGGGAGTTTGCTGTGACATTGTTGGTCTGGGGTGACACATGTTTGC

CAATTCAGTGCATCACGGAGAGGCAGATCTTGGGGATAAGGAAGTGCAGGACAGCATGGACGTGG

GACATGCAGGTGTTGAGGGCTCTGGGACACTCTCCAAGTCACAGCGTTCAGAACAGCCTTAAGGA

TAAGAAGATAGGATAGAAGGACAAAGAGCAAGTTAAAACCCAGCATGGAGAGGAGCACAAAAAG

GCCACAGACACTGCTGGTCCCTGTGTCTGAGCCTGCATGTTTGATGGTGTCTGGATGCAAGCAGAA

GGGGTGGAAGAGCTTGCCTGGAGAGATACAGCTGGGTCAGTAGGACTGGGACAGGCAGCTGGAG

AATTGCCATGTAGATGTTCATACAATCGTCAAATCATGAAGGCTGGAAAAGCCCTCCAAGATCCCC

AAGACCAACCCCAACCCACCCACCGTGCCCACTGGCCATGTCCCTCAGTGCCACATCCCCACAGTT

CTTCATCACCTCCAGGGACGGTGACCCCCCCACCTCCGTGGGCAGCTGTGCCACTGCAGCACCGCT

CTTTGGAGAAGGTAAATCTTGCTAAATCCAGCCCGACCCTCCCCTGGCACAACGTAAGGCCATTAT

CTCTCATCCAACTCCAGGACGGAGTCAGTGAGGATGGGGCTGTCGACCTAGAGGGACAGCCCCCC

CCCAAAGCCCCCAGGGATGTAATTACGTCCCTCCCCCGCTAGGGGCAGCAGCGAGCCGCCCGGGG

CTCCGCTCCGGTCCGGCGCTCCCCCCGCATCCCCGAGCCGGCAGCGTGCGGGGACAGCCCGGGCA

CGGGGAAGGTGGCACGGGATCGCTTTCCTCTGAACGCTTCTCGCTGCTCTTTGAGCCTGCAGACAC

CTGGGGGGATACGGGGAAAAAGCTTTAGGCTGAAAGAGAGATTTAGAATGACAGAATCATAGAA

CGGCCTGGGTTGCAAAGGAGCACAGTGCTCATCCAGATCCAACCCCCTGCTATGTGCAGGGTCATC

AACCAGCAGCCCAGGCTGCCCAGAGCCACATCCAGCCTGGCCTTGAATGCCTGCAGGGATGGGGC

ATCCACAGCCTCCTTGGGCAACCTGTTCAGTGCGTCACCACCCTCTGGGGGAAAAACTGCCTCCTC

ATATCCAACCCAAACCTCCCCTGTCTCAGTGTAAAGCCATTCCCCCTTGTCCTATCAAGGGGGAGT

TTGCTGTGACATTGTTGGTCTGGGGTGACACATGTTTGCCAATTCAGTGCATCACGGAGAGGCAGA

TCTTGGGGATAAGGAAGTGCAGGACAGCATGGACGTGGGACATGCAGGTGTTGAGGGCTCTGGGA

CACTCTCCAAGTCACAGCGTTCAGAACAGCCTTAAGGATAAGAAGATAGGATAGAAGGACAAAGA

GCAAGTTAAAACCCAGCATGGAGAGGAGCACAAAAAGGCCACAGACACTGCTGGTCCCTGTGTCT

GAGCCTGCATGTTTGATGGTGTCTGGATGCAAGCAGAAGGGGTGGAAGAGCTTGCCTGGAGAGAT

ACAGCTGGGTCAGTAGGACTGGGACAGGCAGCTGGAGAATTGCCATGTAGATGTTCATACAATCG

TCAAATCATGAAGGCTGGAAAAGCCCTCCAAGATCCCCAAGACCAACCCCAACCCACCCACCGTG

CCCACTGGCCATGTCCCTCAGTGCCACATCCCCACAGTTCTTCATCACCTCCAGGGACGGTGACCC

CCCCACCTCCGTGGGCAGCTGTGCCACTGCAGCACCGCTCTTTGGAGAAGGTAAATCTTGCTAAAT

CCAGCCCGACCCTCCCCTGGCACAACGTAAGGCCATTATCTCTCATCCAACTCCAGGACGGAGTCA

GTGAGGATGGGGCTCAATTGTTTACTCCCTATCAGTGATAGAGAACGTATGAAGAGTTTACTCCCT

-continuede

ATCAGTGATAGAGAACGTATGCAGACTTTACTCCCTATCAGTGATAGAGAACGTATAAGGAGTTTA

CTCCCTATCAGTGATAGAGAACGTATGACCAGTTTACTCCCTATCAGTGATAGAGAACGTATCTAC

AGTTTACTCCCTATCAGTGATAGAGAACGTATATCCAGTTTACTCCCTATCAGTGATAGAGAACGT

ATAAGCTTTAGGCGTGTACGGTGGGCGCCTATAAAAGCAGAGCTCGTTTAGTGAACCGTCAGATC

GCCTGGAGCAATTCCACAACACTTTTGTCTTATACCAACTTTCCGTACCACTTCCTACCCTCGTAAA

AAGCTTGTCCACCATGGCTCCTAAGAAAAAGCGGAAGGTGGACAAGAAATACTCAATCGGGCTGG

ACATCGGAACTAACTCAGTGGGGTGGGCAGTCATTACTGACGAGTACAAAGTGCCAAGCAAGAAA

TTTAAGGTCCTGGGCAACACCGATAGGCACTCCATCAAGAAAAATCTGATTGGGGCCCTGCTGTTC

GACTCTGGAGAGACAGCTGAAGCAACTAGACTGAAAAGGACTGCTAGAAGGCGCTATACCCGGCG

AAAGAATCGCATCTGCTACCTGCAGGAGATTTTCTCTAACGAAATGGCCAAGGTGGACGATAGTTT

CTTTCATCGGCTGGAGGAATCATTCCTGGTCGAGGAAGATAAGAAACACGAGAGACATCCTATCTT

TGGAAACATTGTGGACGAGGTCGCTTATCACGAAAAATACCCCACCATCTATCATCTGCGCAAGA

AACTGGTGGACTCTACAGATAAAGCAGACCTGCGGCTGATCTATCTGGCCCTGGCTCACATGATTA

AGTTCAGAGGCCATTTTCTGATCGAGGGAGATCTGAACCCAGACAATAGCGATGTGGACAAGCTG

TTCATCCAGCTGGTCCAGACATACAATCAGCTGTTTGAGGAAAACCCTATTAATGCATCTGGCGTG

GACGCAAAAGCCATCCTGAGTGCCAGGCTGTCTAAGAGTAGAAGGCTGGAGAACCTGATCGCTCA

GCTGCCAGGCGAAAAGAAAAACGGCCTGTTTGGAAATCTGATTGCACTGTCACTGGGACTGACAC

CTAACTTCAAGAGCAATTTTGATCTGGCCGAGGACGCTAAACTGCAGCTGAGCAAGGACACTTAT

GACGATGACCTGGATAACCTGCTGGCTCAGATCGGAGATCAGTACGCAGACCTGTTCCTGGCCGCT

AAGAATCTGTCTGACGCTATCCTGCTGAGTGATATTCTGCGGGTGAACACCGAGATTACAAAAGCC

CCTCTGTCAGCTAGCATGATCAAGAGATATGACGAGCACCATCAGGATCTGACCCTGCTGAAGGC

ACTGGTGCGCCAGCAGCTGCCCGAGAAGTACAAGGAAATCTTCTTTGATCAGAGTAAGAACGGGT

ACGCCGGTTATATTGACGGCGGAGCTTCACAGGAGGAATTCTACAAGTTTATCAAACCTATTCTGG

AGAAGATGGACGGCACCGAGGAACTGCTGGTGAAACTGAATCGCGAGGACCTGCTGCGCAAGCA

GCGGACATTTGATAACGGCTCCATCCCCCACCAGATTCATCTGGGAGAGCTGCACGCAATCCTGCG

ACGACAGGAAGACTTCTACCCATTTCTGAAGGATAACCGCGAGAAGATCGAAAAAATTCTGACCT

TCCGGATCCCTTACTATGTGGGGCCCCTGGCAAGGGGTAATTCCCGCTTTGCCTGGATGACACGGA

AATCTGAGGAAACAATCACTCCTTGGAACTTCGAGGAAGTGGTCGATAAGGGAGCTTCCGCACAG

TCTTTCATCGAGAGAATGACAAACTTCGACAAAAACCTGCCAAATGAGAAAGTGCTGCCTAAGCA

CAGTCTGCTGTACGAGTATTTCACAGTCTATAACGAACTGACTAAGGTGAAATACGTCACCGAGGG

GATGAGGAAGCCCGCCTTCCTGAGCGGTGAACAGAAGAAAGCTATCGTGGACCTGCTGTTTAAAA

CCAATCGCAAGGTGACAGTCAAGCAGCTGAAGGAGGACTACTTCAAGAAAATTGAATGTTTCGAT

TCTGTGGAGATCAGTGGCGTCGAAGACAGATTTAACGCTTCTCTGGGAACCTACCACGATCTGCTG

AAGATCATTAAGGATAAAGACTTCCTGGACAACGAGGAAAATGAGGATATCCTGGAAGACATTGT

GCTGACCCTGACACTGTTTGAGGATCGCGAAATGATCGAGGAACGGCTGAAAACTTATGCCCATCT

GTTCGATGACAAGGTGATGAAACAGCTGAAGCGAAGAAGGTACACCGGCTGGGGACGACTGAGC

AGAAAGCTGATCAACGGCATTCGGGACAAACAGAGTGGAAAGACTATCCTGGACTTTCTGAAATC

AGATGGCTTCGCTAACAGAAATTTTATGCAGCTGATTCACGATGACAGCCTGACCTTCAAAGAGGA

TATCCAGAAGGCACAGGTGTCCGGGCAGGGTGACTCTCTGCACGAGCATATCGCAAACCTGGCCG

GGTCCCCCGCCATCAAGAAAGGTATTCTGCAGACCGTGAAGGTGGTCGATGAGCTGGTGAAAGTC

ATGGGCAGGCATAAGCCAGAAAACATCGTGATTGAGATGGCCCGCGAAAATCAGACCACACAGA

-continuede

AAGGACAGAAGAACAGCCGCGAGCGGATGAAAAGGATCGAGGAAGGCATTAAGGAACTGGGATC

CCAGATCCTGAAAGAGCACCCTGTGGAAAACACTCAGCTGCAGAATGAGAAGCTGTATCTGTACT

ATCTGCAGAATGGGCGGGATATGTACGTGGACCAGGAGCTGGATATTAACCGACTGTCTGATTAC

GACGTGGATCATATCGTCCCACAGTCATTCCTGAAAGATGACAGCATTGACAATAAGGTGCTGACC

CGGAGTGACAAAAACCGAGGAAAGAGTGATAATGTCCCTTCAGAGGAAGTGGTCAAGAAAATGA

AGAACTACTGGAGACAGCTGCTGAATGCCAAACTGATCACACAGCGAAAGTTTGATAACCTGACT

AAAGCTGAGAGAGGGGGTCTGTCAGAACTGGACAAAGCAGGCTTCATCAAGCGACAGCTGGTGG

AGACCAGACAGATCACAAAGCACGTCGCTCAGATTCTGGATAGCAGGATGAACACAAAGTACGAT

GAGAATGACAAACTGATCCGCGAAGTGAAGGTCATTACTCTGAAGTCAAAACTTGTGAGCGACTT

CAGAAAGGATTTCCAGTTCTACAAAGTCAGGGAGATCAACAATTATCACCATGCTCATGACGCAT

ACCTGAACGCAGTGGTCGGGACCGCCCTGATTAAGAAATACCCCAAACTGGAGAGCGAATTCGTG

TACGGTGACTATAAGGTGTACGATGTCAGAAAAATGATCGCCAAGAGTGAGCAGGAAATTGGAAA

AGCCACCGCTAAGTATTTCTTTTACTCAAACATCATGAATTTCTTTAAGACTGAGATCACCCTGGCA

AATGGGGAAATCCGAAAGAGACCACTGATTGAGACTAACGGCGAGACCGGAGAAATCGTGTGGG

ACAAGGGTAGGGATTTTGCCACAGTGCGCAAGGTCCTGTCCATGCCTCAAGTGAATATTGTCAAGA

AAACAGAGGTGCAGACTGGCGGATTCAGTAAGGAATCAATTCTGCCCAAACGGAACTCTGATAAG

CTGATCGCCCGAAAGAAAGACTGGGATCCCAAGAAATATGGGGGTTTCGACTCCCCAACAGTGGC

TTACTCTGTCCTGGTGGTCGCAAAGGTGGAGAAGGGGAAAAGCAAGAAACTGAAATCCGTCAAGG

AGCTGCTGGGTATCACTATTATGGAGAGGAGCTCCTTCGAGAAGAACCCCATCGATTTTCTGGAGG

CTAAAGGCTATAAGGAAGTGAAGAAAGACCTGATCATTAAACTGCCAAAGTACAGCCTGTTTGAG

CTGGAAAACGGAAGGAAGCGAATGCTGGCATCCGCAGGAGAGCTGCAGAAGGGTAATGAACTGG

CCCTGCCTTCTAAGTACGTGAACTTCCTGTATCTGGCTAGCCACTACGAGAAGCTGAAAGGCTCCC

CCGAGGATAACGAACAGAAACAGCTGTTTGTGGAGCAGCACAAGCATTATCTGGACGAGATCATT

GAACAGATTAGCGAGTTCTCCAAAAGAGTGATCCTGGCTGACGCAAATCTGGATAAGGTCCTGAG

CGCATACAACAAACACAGAGATAAGCCAATCAGGGAGCAGGCCGAAAATATCATTCATCTGTTCA

CTCTGACCAACCTGGGAGCCCCTGCAGCCTTCAAGTATTTTGACACTACCATCGATCGGAAACGAT

ACACATCCACTAAGGAGGTGCTGGACGCTACCCTGATTCACCAGAGCATTACCGGCCTGTATGAA

ACAAGGATTGACCTGTCTCAGCTGGGGGGCGACCTCGAGGGAAGCGGAGAGGGCAGAGGAAGTC

TGCTAACATGCGGTGACGTCGAGGAGAATCCTGGCCCAGCACCGGGATCCATGGTGAGCAAGGGC

GAGGAGCTGTTCACCGGGGTGGTGCCCATCCTGGTCGAGCTGGACGGCGACGTAAACGGCCACAA

GTTCAGCGTGTCCGGCGAGGGCGAGGGCGATGCCACCTACGGCAAGCTGACCCTGAAGTTCATCT

GCACCACCGGCAAGCTGCCCGTGCCCTGGCCCACCCTCGTGACCACCTTCACCTACGGCGTGCAGT

GCTTCGCCCGCTACCCCGACCACATGAAGCAGCACGACTTCTTCAAGTCCGCCATGCCCGAAGGCT

ACGTCCAGGAGCGCACCATCTTCTTCAAGGACGACGGCAACTACAAGACCCGCGCCGAGGTGAAG

TTCGAGGGCGACACCCTGGTGAACCGCATCGAGCTGAAGGGCATCGACTTCAAGGAGGACGGCAA

CATCCTGGGGCACAAGCTGGAGTACAACTACAACAGCCACAAGGTCTATATCACCGCCGACAAGC

AGAAGAACGGCATCAAGGTGAACTTCAAGACCCGCCACAACATCGAGGACGGCAGCGTGCAGCTC

GCCGACCACTACCAGCAGAACACCCCCATCGGCGACGGCCCCGTGCTGCTGCCCGACAACCACTA

CCTGAGCACCCAGTCCGCCCTGAGCAAAGACCCCAACGAGAAGCGCGATCACATGGTCCTGCTGG

AGTTCGTGACCGCCGCCGGGATCACTCTCGGCATGGACGAGCTGTACAAGTAAACCTAATCTAGC

AGCTCGCTGATCAGCCTCGACTGTGCCTTCTAGTTGCCAGCCATCTGTTGTTTGCCCCTCCCCCGTG

-continuede

CCTTCCTTGACCCTGGAAGGTGCCACTCCCACTGTCCTTTCCTAATAAAATGAGGAAATTGCATCG

CATTGTCTGAGTAGGTGTCATTCTATTCTGGGGGGTGGGGTGGGGCAGGACAGCAAGGGGGAGGA

TTGGGAAGACAATAGCAGGCATGCTGGGGATGCGGTGGGCTCTATGGCTTCTGAGGCGGAAAGAA

CCAGCTGGGGCTCGATCCTCTAGTTGGCGCGTCTGTACAAAAAAGCAGGCTTTAAAGGAACCAATT

CAGTCGACTGGATCCGGTACCAAGGTCGGGCAGGAAGAGGGCCTATTTCCCATGATTCCTTCATAT

TTGCATATACGATACAAGGCTGTTAGAGAGATAATTAGAATTAATTTGACTGTAAACACAAAGAT

ATTAGTACAAAATACGTGACGTAGAAAGTAATAATTTCTTGGGTAGTTTGCAGTTTTAAAATTATG

TTTTAAAATGGACTATCATATGCTTACCGTAACTTGAAAGTATTTCGATTTCTTGGCTTTATATATC

TTGTGGAAAGGACGAAACACCGAGCATAGCAAGTTAAAATAAGGCTAGTCCGTTATCAACTTGAA

AAAGTGGCACCGAGTCGGTGCTTTTTTTCTAGACCCAGCTTTCTTGTACAAAGTTGGCATTAATTCT

CTAGACATCATTAATTCCTAATTTTTGTTGACACTCTATCATTGATAGAGTTATTTTACCACTCCCT

ATCAGTGATAGAGAAAAGTGAAATGGCCAAGCCTTTGTCTCAAGAAGAATCCACCCTCATTGAAA

GAGCAACGGCTACAATCAACAGCATCCCCATCTCTGAAGACTACAGCGTCGCCAGCGCAGCTCTCT

CTAGCGACGGCCGCATCTTCACTGGTGTCAATGTATATCATTTTACTGGGGGACCTTGTGCAGAAC

TCGTGGTGCTGGGCACTGCTGCTGCTGCGGCAGCTGGCAACCTGACTTGTATCGTCGCGATCGGAA

ATGAGAACAGGGGCATCTTGAGCCCCTGCGGACGGTGTCGACAGGTGCTTCTCGATCTGCATCCTG

GGATCAAAGCGATAGTGAAGGACAGTGATGGACAGCCGACGGCAGTTGGGATTCGTGAATTGCTG

CCCTCTGGTTATGTGTGGGAGGGCTAAATGGTCCATATGAATATCCTCCTTAGTTCCTATTCCGCTA

GCCTAGAGGGACAGCCCCCCCCCAAAGCCCCCAGGGATGTAATTACGTCCCTCCCCCGCTAGGGG

CAGCAGCGAGCCGCCCGGGGCTCCGCTCCGGTCCGGCGCTCCCCCCGCATCCCCGAGCCGGCAGC

GTGCGGGGACAGCCCGGGCACGGGGAAGGTGGCACGGGATCGCTTTCCTCTGAACGCTTCTCGCT

GCTCTTTGAGCCTGCAGACACCTGGGGGGATACGGGGAAAAAGCTTTAGGCTGAAAGAGAGATTT

AGAATGACAGAATCATAGAACGGCCTGGGTTGCAAAGGAGCACAGTGCTCATCCAGATCCAACCC

CCTGCTATGTGCAGGGTCATCAACCAGCAGCCCAGGCTGCCCAGAGCCACATCCAGCCTGGCCTTG

AATGCCTGCAGGGATGGGGCATCCACAGCCTCCTTGGGCAACCTGTTCAGTGCGTCACCACCCTCT

GGGGGAAAAACTGCCTCCTCATATCCAACCCAAACCTCCCCTGTCTCAGTGTAAAGCCATTCCCCC

TTGTCCTATCAAGGGGGAGTTTGCTGTGACATTGTTGGTCTGGGGTGACACATGTTTGCCAATTCA

GTGCATCACGGAGAGGCAGATCTTGGGGATAAGGAAGTGCAGGACAGCATGGACGTGGGACATG

CAGGTGTTGAGGGCTCTGGGACACTCTCCAAGTCACAGCGTTCAGAACAGCCTTAAGGATAAGAA

GATAGGATAGAAGGACAAAGAGCAAGTTAAAACCCAGCATGGAGAGGAGCACAAAAAGGCCACA

GACACTGCTGGTCCCTGTGTCTGAGCCTGCATGTTTGATGGTGTCTGGATGCAAGCAGAAGGGGTG

GAAGAGCTTGCCTGGAGAGATACAGCTGGGTCAGTAGGACTGGGACAGGCAGCTGGAGAATTGCC

ATGTAGATGTTCATACAATCGTCAAATCATGAAGGCTGGAAAAGCCCTCCAAGATCCCCAAGACC

AACCCCAACCCACCCACCGTGCCCACTGGCCATGTCCCTCAGTGCCACATCCCCACAGTTCTTCAT

CACCTCCAGGGACGGTGACCCCCCCACCTCCGTGGGCAGCTGTGCCACTGCAGCACCGCTCTTTGG

AGAAGGTAAATCTTGCTAAATCCAGCCCGACCCTCCCCTGGCACAACGTAAGGCCATTATCTCTCA

TCCAACTCCAGGACGGAGTCAGTGAGGATGGGGCTGGATCCGAAGCAGCTCCAGCCTACACAATC

GCTCAAGACGTGTAATGCTTTTATTATATATTAGTCACGATATCTATAACAAGAAAATATATATAT

AATAAGTTATCACGTAAGTAGAACATGAAATAACAATATAATTATCGTATGAGTTAAATCTTAAAA

GTCACGTAAAAGATAATCATGCGTCATTTTGACTCACGCGGTCGTTATAGTTCAAAATCAGTGACA

CTTACCGCATTGACAAGCACGCCTCACGGGAGCTCCAAGCGGCGACTGAGATGTCCTAAATGCAC

-continuede
AGCGACGGATTCGCGCTATTTAGAAAGAGAGAGCAATATTTCAAGAATGCATGCGTCAATTTTAC
GCAGACTATCTTTCTAGGGTTAAAAAAGATTTGCGCTTTACTCGACCTAAACTTTAAACACGTCAT
AGAATCTTCGTTTGACAAAAACCACATTGTGGGGTACCGAGCTCTTAATTAAGGCGCGCCGGGGA
GGTTCCCTTTAGTGAGGGTTAATTGCGGGTCGCCCTATAGTGAGTCGTATTACAATTCACTGGCCG
TCGTTTTACAACGTCGTGACTGGGAAAACCCTGGCGTTACCCAACTTAATCGCCTTGCAGCACATC
CCCCTTTCGCCAGCTGGCGTAATAGCGAAGAGGCCCGCACCGATCGCCCTTCCCAACAGTTGCGCA
GCCTGAATGGCGAATGGCAAATTGTAAGCGTTAATATTTTGTTAAAATTCGCGTTAAATTTTTGTTA
AATCAGCTCATTTTTTAACCAATAGGCCGAAATCGGCAAAATCCCTTATAAATCAAAAGAATAGAC
CGAGATAGGGTTGAGTGTTGTTCCAGTTTGGAACAAGAGTCCACTATTAAAGAACGTGGACTCCA
ACGTCAAAGGGCGAAAAACCGTCTATCAGGGCGATGGCCCACTACGTGAACCATCACCCTAATCA
AGTTTTTTGGGGTCGAGGTGCCGTAAAGCACTAAATCGGAACCCTAAAGGGAGCCCCCGATTTAG
AGCTTGACGGGGAAAGCCGGCGAACGTGGCGAGAAAGGAAGGGAAGAAAGCGAAAGGAGCGGG
CGCTAGGGCGCTGGCAAGTGTAGCGGTCACGCTGCGCGTAACCACCACACCCGCCGCGCTTAATG
CGCCGCTACAGGGCGCGTCAG TOIC_Cas9_Nickase_obl_r26_AAVS_PgkNeo
(SEQ ID NO: 20)
GTGGCACTTTTCGGGGAAATGTGCGCGGAACCCCTATTTGTTTATTTTTCTAAATACATTCAAATAT
GTATCCGCTCATGAGACAATAACCCTGATAAATGCTTCAATAATATTGAAAAAGGAAGAGTATGA
GTATTCAACATTTCCGTGTCGCCCTTATTCCCTTTTTTGCGGCATTTTGCCTTCCTGTTTTTGCTCAC
CCAGAAACGCTGGTGAAAGTAAAAGATGCTGAAGATCAGTTGGGTGCACGAGTGGGTTACATCGA
ACTGGATCTCAACAGCGGTAAGATCCTTGAGAGTTTTCGCCCCGAAGAACGTTTTCCAATGATGAG
CACTTTTAAAGTTCTGCTATGTGGCGCGGTATTATCCCGTATTGACGCCGGGCAAGAGCAACTCGG
TCGCCGCATACACTATTCTCAGAATGACTTGGTTGAGTACTCACCAGTCACAGAAAAGCATCTTAC
GGATGGCATGACAGTAAGAGAATTATGCAGTGCTGCCATAACCATGAGTGATAACACTGCGGCCA
ACTTACTTCTGACAACGATCGGAGGACCGAAGGAGCTAACCGCTTTTTTGCACAACATGGGGGATC
ATGTAACTCGCCTTGATCGTTGGGAACCGGAGCTGAATGAAGCCATACCAAACGACGAGCGTGAC
ACCACGATGCCTGTAGCAATGGCAACAACGTTGCGCAAACTATTAACTGGCGAACTACTTACTCTA
GCTTCCCGGCAACAATTAATAGACTGGATGGAGGCGGATAAAGTTGCAGGACCACTTCTGCGCTC
GGCCCTTCCGGCTGGCTGGTTTATTGCTGATAAATCTGGAGCCGGTGAGCGTGGGTCTCGCGGTAT
CATTGCAGCACTGGGGCCAGATGGTAAGCCCTCCCGTATCGTAGTTATCTACACGACGGGGAGTCA
GGCAACTATGGATGAACGAAATAGACAGATCGCTGAGATAGGTGCCTCACTGATTAAGCATTGGT
AACTGTCAGACCAAGTTTACTCATATATACTTTAGATTGATTTAAAACTTCATTTTTAATTTAAAAG
GATCTAGGTGAAGATCCTTTTTGATAATCTCATGACCAAAATCCCTTAACGTGAGTTTTCGTTCCAC
TGAGCGTCAGACCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATCAAGAGCTACCA
ACTCTTTTTCCGAAGGTAACTGGCTTCAGCAGAGCGCAGATACCAAATACTGTTCTTCTAGTGTAG
CCGTAGTTAGGCCACCACTTCAAGAACTCTGTAGCACCGCCTACATACCTCGCTCTGCTAATCCTG
TTACCAGTGGCTGCTGCCAGTGGCGATAAGTCGTGTCTTACCGGGTTGGACTCAAGACGATAGTTA
CCGGATAAGGCGCAGCGGTCGGGCTGAACGGGGGGTTCGTGCACACAGCCCAGCTTGGAGCGAAC
GACCTACACCGAACTGAGATACCTACAGCGTGAGCTATGAGAAAGCGCCACGCTTCCCGAAGGGA
GAAAGGCGGACAGGTATCCGGTAAGCGGCAGGGTCGGAACAGGAGAGCGCACGAGGGAGCTTCC
AGGGGGAAACGCCTGGTATCTTTATAGTCCTGTCGGGTTTCGCCACCTCTGACTTGAGCGTCGATT -continuede

TTTGTGATGCTCGTCAGGGGGGCGGAGCCTATGGAAAAACGCCAGCAACGCGGCCTTTTTACGGTT

CCTGGCCTTTTGCTGGCCTTTTGCTCACATGTTCTTTCCTGCGTTATCCCCTGATTCTGTGGATAACC

GTATTACCGCCTTTGAGTGAGCTGATACCGCTCGCCGCAGCCGAACGACCGAGCGCAGCGAGTCA

GTGAGCGAGGAAGCGGAAGAGCGCCCAATACGCAAACCGCCTCTCCCCGCGCGTTGGCCGATTCA

TTAATGCAGCTGGCACGACAGGTTTCCCGACTGGAAAGCGGGCAGTGAGCGCAACGCAATTAATG

TGAGTTAGCTCACTCATTAGGCACCCCAGGCTTTACACTTTATGCTTCCGGCTCGTATGTTGTGTGG

AATTGTGAGCGGATAACAATTTCACACAGGAAACAGCTATGACCATGATTACGCCAAGCGCGCAA

TTAACCCTCACTAAAGGGAACCTCCCCTAGCTTAATTAACCCTAGAAAGATAATCATATTGTGACG

TACGTTAAAGATAATCATGCGTAAAATTGACGCATGTGTTTTATCGATCTGTATATCGAGGTTTATT

TATTAATTTGAATAGATATTAAGTTTTATTATATTTACACTTACATACTAATAATAAATTCAACAAA

CAATTTATTTATGTTTATTTATTTATTAAAAAAAAACAAAAACTCAAAATTTCTTCTATAAAGTAAC

AAAACTTTTAAACATTCTCTCTTTTACAAAAATAAACTTATTTTGTACTTTAAAAACAGTCATGTTG

TATTATAAAATAAGTAATTAGCTTAACTTATACATAATAGAAACAAATTATACTTATTAATCGCAT

TGATTATTGACTAGTCGTATTAAGGGTTCCGGATCAGCTTGATTCGAGCCCCAGCTGGTTCTTTCCG

CCTCAGAAGCCATAGAGCCCACCGCATCCCCAGCATGCCTGCTATTGTCTTCCCAATCCTCCCCCTT

GCTGTCCTGCCCCACCCCACCCCCCAGAATAGAATGACACCTACTCAGACAATGCGATGCAATTTC

CTCATTTTATTAGGAAAGGACAGTGGGAGTGGCACCTTCCAGGGTCAAGGAAGGCACGGGGGAGG

GGCAAACAACAGATGGCTGGCAACTAGAAGGCACAGTCGAGGCTGATCAGCGAGCTCTAGAGAA

TTGATCCCCTCAGAAGAACTCGTCAAGAAGGCGATAGAAGGCGATGCGCTGCGAATCGGGAGCGG

CGATACCGTAAAGCACGAGGAAGCGGTCAGCCCATTCGCCGCCAAGCTCTTCAGCAATATCACGG

GTAGCCAACGCTATGTCCTGATAGCGGTCCGCCACACCCAGCCGGCCACAGTCGATGAATCCAGA

AAAGCGGCCATTTTCCACCATGATATTCGGCAAGCAGGCATCGCCATGGGTCACGACGAGATCCTC

GCCGTCGGGCATGCGCGCCTTGAGCCTGGCGAACAGTTCGGCTGGCGCGAGCCCCTGATGCTCTTC

GTCCAGATCATCCTGATCGACAAGACCGGCTTCCATCCGAGTACGTGCTCGCTCGATGCGATGTTT

CGCTTGGTGGTCGAATGGGCAGGTAGCCGGATCAAGCGTATGCAGCCGCCGCATTGCATCAGCCA

TGATGGATACTTTCTCGGCAGGAGCAAGGTGAGATGACAGGAGATCCTGCCCCGGCACTTCGCCC

AATAGCAGCCAGTCCCTTCCCGCTTCAGTGACAACGTCGAGCACAGCTGCGCAAGGAACGCCCGT

CGTGGCCAGCCACGATAGCCGCGCTGCCTCGTCCTGCAGTTCATTCAGGGCACCGGACAGGTCGGT

CTTGACAAAAAGAACCGGGCGCCCCTGCGCTGACAGCCGGAACACGGCGGCATCAGAGCAGCCG

ATTGTCTGTTGTGCCCAGTCATAGCCGAATAGCCTCTCCACCCAAGCGGCCGGAGAACCTGCGTGC

AATCCATCTTGTTCAATGGCCGATCCCATGGTTTAGTTCCTCACCTTGTCGTATTATACTATGCCGA

TATACTATGCCGATGATTAATTGTCAACACGTGCTGCTGCAGGTCGAAAGGCCCGGAGATGAGGA

AGAGGAGAACAGCGCGGCAGACGTGCGCTTTTGAAGCGTGCAGAATGCCGGGCCTCCGGAGGACC

TTCGGGCGCCCGCCCCGCCCCTGAGCCCGCCCCTGAGCCCGCCCCCGGACCCACCCCTTCCCAGCC

TCTGAGCCCAGAAAGCGAAGGAGCAAAGCTGCTATTGGCCGCTGCCCCAAAGGCCTACCCGCTTC

CATTGCTCAGCGGTGCTGTCCATCTGCACGAGACTAGTGAGACGTGCTACTTCCATTTGTCACGTC

CTGCACGACGCGAGCTGCGGGGCGGGGGGGAACTTCCTGACTAGGGGAGGAGTAGAAGGTGGCG

CGAAGGGGCCACCAAAGAACGGAGCCGGTTGGCGCCTACCGGTGGATGTGGAATGTGTGCGAGCC

AGAGGCCACTTGTGTAGCGCCAAGTGCCCAGCGGGGCTGCTAAAGCGCATGCTCCAGACTGCCTT

GGGAAAAGCGCCTCCCCTACCCGGTAGACACCCCACAGTGGGTGGCCTAGGGACAGGATTGCAAC

TCCAGTCTTTCTTCTTCTTGGGCGGGAGTCACTAGTTATTAATAGTAATCAATTACGGGGTCATTAG

-continuede

TTCATAGCCCATATATGGAGTTCCGCGTTACATAACTTACGGTAAATGGCCCGCCTGGCTGACCGC

CCAACGACCCCCGCCCATTGACGTCAATAATGACGTATGTTCCCATAGTAACGCCAATAGGGACTT

TCCATTGACGTCAATGGGTGGACTATTTACGGTAAACTGCCCACTTGGCAGTACATCAAGTGTATC

ATATGCCAAGTACGCCCCCTATTGACGTCAATGACGGTAAATGGCCCGCCTGGCATTATGCCCAGT

ACATGACCTTATGGGACTTTCCTACTTGGCAGTACATCTACGTATTAGTCATCGCTATTACCATGGG

TCGAGGTGAGCCCCACGTTCTGCTTCACTCTCCCCATCTCCCCCCCCTCCCCACCCCCAATTTTGTA

TTTATTTATTTTTTAATTATTTTGTGCAGCGATGGGGGCGGGGGGGGGGGGGGCGCGCGCCAGGCG

GGGCGGGGCGGGGCGAGGGGCGGGGCGGGGCGAGGCGGAGAGGTGCGGCGGCAGCCAATCAGA

GCGGCGCGCTCCGAAAGTTTCCTTTTATGGCGAGGCGGCGGCGGCGGCGGCCCTATAAAAAGCGA

AGCGCGCGGCGGGCGGGAGTCGCTGCGTTGCCTTCGCCCCGTGCCCCGCTCCGCGCCGCCTCGCGC

CGCCCGCCCCGGCTCTGACTGACCGCGTTACTCCCACAGGTGAGCGGGCGGGACGGCCCTTCTCCT

CCGGGCTGTAATTAGCGCTTGGTTTAATGACGGCTCGTTTCTTTTCTGTGGCTGCGTGAAAGCCTTA

AAGGGCTCCGGGAGGGCCCTTTGTGCGGGGGGGAGCGGCTCGGGGGGTGCGTGCGTGTGTGTGTG

CGTGGGGAGCGCCGCGTGCGGCCCGCGCTGCCCGGCGGCTGTGAGCGCTGCGGGCGCGGCGCGGG

GCTTTGTGCGCTCCGCGTGTGCGCGAGGGGAGCGCGGCCGGGGGCGGTGCCCCGCGGTGCGGGGG

GGCTGCGAGGGGAACAAAGGCTGCGTGCGGGGTGTGTGCGTGGGGGGGTGAGCAGGGGGTGTGG

GCGCGGCGGTCGGGCTGTAACCCCCCCCTGCACCCCCCTCCCCGAGTTGCTGAGCACGGCCCGGCT

TCGGGTGCGGGGCTCCGTGCGGGGCGTGGCGCGGGGCTCGCCGTGCCGGGCGGGGGGTGGCGGCA

GGTGGGGGTGCCGGGCGGGGCGGGGCCGCCTCGGGCCGGGGAGGGCTCGGGGGAGGGGCGCGGC

GGCCCCGGAGCGCCGGCGGCTGTCGAGGCGCGGCGAGCCGCAGCCATTGCCTTTTATGGTAATCG

TGCGAGAGGGCGCAGGGACTTCCTTTGTCCCAAATCTGGCGGAGCCGAAATCTGGGAGGCGCCGC

CGCACCCCCTCTAGCGGGCGCGGGCGAAGCGGTGCGGCGCCGGCAGGAAGGAAATGGGCGGGGA

GGGCCTTCGTGCGTCGCCGCGCCGCCGTCCCCTTCTCCATCTCCAGCCTCGGGGCTGCCGCAGGGG

GACGGCTGCCTTCGGGGGGGACGGGGCAGGGCGGGGTTCGGCTTCTGGCGTGTGACCGGCGGCTC

TAGAGCCTCTGCTAACCATGTTCATGCCTTCTTCTTTTTCCTACAGCTCCTGGGCAACGTGCTGGTT

ATTGTGCTGTCTCATCATTTTGGCAAAGAATTCGCCACCATGGTGCCCAAGAAGAAGAGGAAAGTC

TCTAGACTGGACAAGAGCAAAGTCATAAACTCTGCTCTGGAATTACTCAATGGAGTCGGTATCGA

AGGCCTGACGACAAGGAAACTCGCTCAAAAGCTGGGAGTTGAGCAGCCTACCCTGTACTGGCACG

TGAAGAACAAGCGGGCCCTGCTCGATGCCCTGCCAATCGAGATGCTGGACAGGCATCATACCCAC

TCCTGCCCCCTGGAAGGCGAGTCATGGCAAGACTTTCTGCGGAACAACGCCAAGTCATACCGCTGT

GCTCTCCTCTCACATCGCGACGGGGCTAAAGTGCATCTCGGCACCCGCCCAACAGAGAAACAGTA

CGAAACCCTGGAAAATCAGCTCGCGTTCCTGTGTCAGCAAGGCTTCTCCCTGGAGAACGCACTGTA

CGCTCTGTCCGCCGTGGGCCACTTTACACTGGGCTGCGTATTGGAGGAACAGGAGCATCAAGTAGC

AAAAGAGGAAAGAGAGACACCTACCACCGATTCTATGCCCCCACTTCTGAAACAAGCAATTGAGC

TGTTCGACCGGCAGGGAGCCGAACCTGCCTTCCTTTTCGGCCTGGAACTAATCATATGTGGCCTGG

AGAAACAGCTAAAGTGCGAAAGCGGCGGGCCGACCGACGCCCTTGACGATTTTGACTTAGACATG

CTCCCAGCCGATGCCCTTGACGACTTTGACCTTGATATGCTGCCTGCTGACGCTCTTGACGATTTTG

ACCTTGACATGCTCCCCGGGTAAAGCGGCCGCGACTCTAGATCATAATCAGCCATACCACATTTGT

AGAGGTTTTACTTGCTTTAAAAAACCTCCCACACCTCCCCCTGAACCTGAAACATAAAATGAATGC

AATTGTTGTTGTTAACTTGTTTATTGCAGCTTATAATGGTTACAAATAAAGCAATAGCATCACAAA

TTTCACAAATAAAGCATTTTTTTCACTGCATTCTAGTTGTGGTTTGTCCAAACTCATCAATGTATCT

-continuede

TAAGGGATCCCTAGAGGGACAGCCCCCCCCCAAAGCCCCCAGGGATGTAATTACGTCCCTCCCCC

GCTAGGGGCAGCAGCGAGCCGCCCGGGGCTCCGCTCCGGTCCGGCGCTCCCCCCGCATCCCCGAG

CCGGCAGCGTGCGGGGACAGCCCGGGCACGGGGAAGGTGGCACGGGATCGCTTTCCTCTGAACGC

TTCTCGCTGCTCTTTGAGCCTGCAGACACCTGGGGGGATACGGGGAAAAAGCTTTAGGCTGAAAG

AGAGATTTAGAATGACAGAATCATAGAACGGCCTGGGTTGCAAAGGAGCACAGTGCTCATCCAGA

TCCAACCCCCTGCTATGTGCAGGGTCATCAACCAGCAGCCCAGGCTGCCCAGAGCCACATCCAGCC

TGGCCTTGAATGCCTGCAGGGATGGGGCATCCACAGCCTCCTTGGGCAACCTGTTCAGTGCGTCAC

CACCCTCTGGGGGAAAAACTGCCTCCTCATATCCAACCCAAACCTCCCCTGTCTCAGTGTAAAGCC

ATTCCCCCTTGTCCTATCAAGGGGGAGTTTGCTGTGACATTGTTGGTCTGGGGTGACACATGTTTGC

CAATTCAGTGCATCACGGAGAGGCAGATCTTGGGGATAAGGAAGTGCAGGACAGCATGGACGTGG

GACATGCAGGTGTTGAGGGCTCTGGGACACTCTCCAAGTCACAGCGTTCAGAACAGCCTTAAGGA

TAAGAAGATAGGATAGAAGGACAAAGAGCAAGTTAAAACCCAGCATGGAGAGGAGCACAAAAAG

GCCACAGACACTGCTGGTCCCTGTGTCTGAGCCTGCATGTTTGATGGTGTCTGGATGCAAGCAGAA

GGGGTGGAAGAGCTTGCCTGGAGAGATACAGCTGGGTCAGTAGGACTGGGACAGGCAGCTGGAG

AATTGCCATGTAGATGTTCATACAATCGTCAAATCATGAAGGCTGGAAAAGCCCTCCAAGATCCCC

AAGACCAACCCCAACCCACCCACCGTGCCCACTGGCCATGTCCCTCAGTGCCACATCCCCACAGTT

CTTCATCACCTCCAGGGACGGTGACCCCCCCACCTCCGTGGGCAGCTGTGCCACTGCAGCACCGCT

CTTTGGAGAAGGTAAATCTTGCTAAATCCAGCCCGACCCTCCCCTGGCACAACGTAAGGCCATTAT

CTCTCATCCAACTCCAGGACGGAGTCAGTGAGGATGGGGCTGTCGACCTAGAGGGACAGCCCCCC

CCCAAAGCCCCCAGGGATGTAATTACGTCCCTCCCCCGCTAGGGGCAGCAGCGAGCCGCCCGGGG

CTCCGCTCCGGTCCGGCGCTCCCCCCGCATCCCCGAGCCGGCAGCGTGCGGGGACAGCCCGGGCA

CGGGGAAGGTGGCACGGGATCGCTTTCCTCTGAACGCTTCTCGCTGCTCTTTGAGCCTGCAGACAC

CTGGGGGGATACGGGGAAAAAGCTTTAGGCTGAAAGAGAGATTTAGAATGACAGAATCATAGAA

CGGCCTGGGTTGCAAAGGAGCACAGTGCTCATCCAGATCCAACCCCCTGCTATGTGCAGGGTCATC

AACCAGCAGCCCAGGCTGCCCAGAGCCACATCCAGCCTGGCCTTGAATGCCTGCAGGGATGGGGC

ATCCACAGCCTCCTTGGGCAACCTGTTCAGTGCGTCACCACCCTCTGGGGGAAAAACTGCCTCCTC

ATATCCAACCCAAACCTCCCCTGTCTCAGTGTAAAGCCATTCCCCCTTGTCCTATCAAGGGGGAGT

TTGCTGTGACATTGTTGGTCTGGGGTGACACATGTTTGCCAATTCAGTGCATCACGGAGAGGCAGA

TCTTGGGGATAAGGAAGTGCAGGACAGCATGGACGTGGGACATGCAGGTGTTGAGGGCTCTGGGA

CACTCTCCAAGTCACAGCGTTCAGAACAGCCTTAAGGATAAGAAGATAGGATAGAAGGACAAAGA

GCAAGTTAAAACCCAGCATGGAGAGGAGCACAAAAAGGCCACAGACACTGCTGGTCCCTGTGTCT

GAGCCTGCATGTTTGATGGTGTCTGGATGCAAGCAGAAGGGGTGGAAGAGCTTGCCTGGAGAGAT

ACAGCTGGGTCAGTAGGACTGGGACAGGCAGCTGGAGAATTGCCATGTAGATGTTCATACAATCG

TCAAATCATGAAGGCTGGAAAAGCCCTCCAAGATCCCCAAGACCAACCCCAACCCACCCACCGTG

CCCACTGGCCATGTCCCTCAGTGCCACATCCCCACAGTTCTTCATCACCTCCAGGGACGGTGACCC

CCCCACCTCCGTGGGCAGCTGTGCCACTGCAGCACCGCTCTTTGGAGAAGGTAAATCTTGCTAAAT

CCAGCCCGACCCTCCCCTGGCACAACGTAAGGCCATTATCTCTCATCCAACTCCAGGACGGAGTCA

GTGAGGATGGGGCTCAATTGTTTACTCCCTATCAGTGATAGAGAACGTATGAAGAGTTTACTCCCT

ATCAGTGATAGAGAACGTATGCAGACTTTACTCCCTATCAGTGATAGAGAACGTATAAGGAGTTTA

CTCCCTATCAGTGATAGAGAACGTATGACCAGTTTACTCCCTATCAGTGATAGAGAACGTATCTAC

AGTTTACTCCCTATCAGTGATAGAGAACGTATATCCAGTTTACTCCCTATCAGTGATAGAGAACGT

-continuede

ATAAGCTTTAGGCGTGTACGGTGGGCGCCTATAAAAGCAGAGCTCGTTTAGTGAACCGTCAGATC

GCCTGGAGCAATTCCACAACACTTTTGTCTTATACCAACTTTCCGTACCACTTCCTACCCTCGTAAA

AAGCTTGTCCACCATGGCTCCTAAGAAAAAGCGGAAGGTGGACAAGAAATACTCAATCGGGCTGG

CCATCGGAACTAACTCAGTGGGGTGGGCAGTCATTACTGACGAGTACAAAGTGCCAAGCAAGAAA

TTTAAGGTCCTGGGCAACACCGATAGGCACTCCATCAAGAAAAATCTGATTGGGGCCCTGCTGTTC

GACTCTGGAGAGACAGCTGAAGCAACTAGACTGAAAAGGACTGCTAGAAGGCGCTATACCCGGCG

AAAGAATCGCATCTGCTACCTGCAGGAGATTTTCTCTAACGAAATGGCCAAGGTGGACGATAGTTT

CTTTCATCGGCTGGAGGAATCATTCCTGGTCGAGGAAGATAAGAAACACGAGAGACATCCTATCTT

TGGAAACATTGTGGACGAGGTCGCTTATCACGAAAAATACCCCACCATCTATCATCTGCGCAAGA

AACTGGTGGACTCTACAGATAAAGCAGACCTGCGGCTGATCTATCTGGCCCTGGCTCACATGATTA

AGTTCAGAGGCCATTTTCTGATCGAGGGAGATCTGAACCCAGACAATAGCGATGTGGACAAGCTG

TTCATCCAGCTGGTCCAGACATACAATCAGCTGTTTGAGGAAAACCCTATTAATGCATCTGGCGTG

GACGCAAAAGCCATCCTGAGTGCCAGGCTGTCTAAGAGTAGAAGGCTGGAGAACCTGATCGCTCA

GCTGCCAGGCGAAAAGAAAAACGGCCTGTTTGGAAATCTGATTGCACTGTCACTGGGACTGACAC

CTAACTTCAAGAGCAATTTTGATCTGGCCGAGGACGCTAAACTGCAGCTGAGCAAGGACACTTAT

GACGATGACCTGGATAACCTGCTGGCTCAGATCGGAGATCAGTACGCAGACCTGTTCCTGGCCGCT

AAGAATCTGTCTGACGCTATCCTGCTGAGTGATATTCTGCGGGTGAACACCGAGATTACAAAAGCC

CCTCTGTCAGCTAGCATGATCAAGAGATATGACGAGCACCATCAGGATCTGACCCTGCTGAAGGC

ACTGGTGCGCCAGCAGCTGCCCGAGAAGTACAAGGAAATCTTCTTTGATCAGAGTAAGAACGGGT

ACGCCGGTTATATTGACGGCGGAGCTTCACAGGAGGAATTCTACAAGTTTATCAAACCTATTCTGG

AGAAGATGGACGGCACCGAGGAACTGCTGGTGAAACTGAATCGCGAGGACCTGCTGCGCAAGCA

GCGGACATTTGATAACGGCTCCATCCCCCACCAGATTCATCTGGGAGAGCTGCACGCAATCCTGCG

ACGACAGGAAGACTTCTACCCATTTCTGAAGGATAACCGCGAGAAGATCGAAAAAATTCTGACCT

TCCGGATCCCTTACTATGTGGGGCCCCTGGCAAGGGGTAATTCCCGCTTTGCCTGGATGACACGGA

AATCTGAGGAAACAATCACTCCTTGGAACTTCGAGGAAGTGGTCGATAAGGGAGCTTCCGCACAG

TCTTTCATCGAGAGAATGACAAACTTCGACAAAAACCTGCCAAATGAGAAAGTGCTGCCTAAGCA

CAGTCTGCTGTACGAGTATTTCACAGTCTATAACGAACTGACTAAGGTGAAATACGTCACCGAGGG

GATGAGGAAGCCCGCCTTCCTGAGCGGTGAACAGAAGAAAGCTATCGTGGACCTGCTGTTTAAAA

CCAATCGCAAGGTGACAGTCAAGCAGCTGAAGGAGGACTACTTCAAGAAAATTGAATGTTTCGAT

TCTGTGGAGATCAGTGGCGTCGAAGACAGATTTAACGCTTCTCTGGGAACCTACCACGATCTGCTG

AAGATCATTAAGGATAAAGACTTCCTGGACAACGAGGAAAATGAGGATATCCTGGAAGACATTGT

GCTGACCCTGACACTGTTTGAGGATCGCGAAATGATCGAGGAACGGCTGAAAACTTATGCCCATCT

GTTCGATGACAAGGTGATGAAACAGCTGAAGCGAAGAAGGTACACCGGCTGGGGACGACTGAGC

AGAAAGCTGATCAACGGCATTCGGGACAAACAGAGTGGAAAGACTATCCTGGACTTTCTGAAATC

AGATGGCTTCGCTAACAGAAATTTTATGCAGCTGATTCACGATGACAGCCTGACCTTCAAAGAGGA

TATCCAGAAGGCACAGGTGTCCGGGCAGGGTGACTCTCTGCACGAGCATATCGCAAACCTGGCCG

GGTCCCCCGCCATCAAGAAAGGTATTCTGCAGACCGTGAAGGTGGTCGATGAGCTGGTGAAAGTC

ATGGGCAGGCATAAGCCAGAAAACATCGTGATTGAGATGGCCCGCGAAAATCAGACCACACAGA

AAGGACAGAAGAACAGCCGCGAGCGGATGAAAAGGATCGAGGAAGGCATTAAGGAACTGGGATC

CCAGATCCTGAAAGAGCACCCTGTGGAAAACACTCAGCTGCAGAATGAGAAGCTGTATCTGTACT

ATCTGCAGAATGGGCGGGATATGTACGTGGACCAGGAGCTGGATATTAACCGACTGTCTGATTAC

-continuede

GACGTGGATCATATCGTCCCACAGTCATTCCTGAAAGATGACAGCATTGACAATAAGGTGCTGACC

CGGAGTGACAAAAACCGAGGAAAGAGTGATAATGTCCCTTCAGAGGAAGTGGTCAAGAAAATGA

AGAACTACTGGAGACAGCTGCTGAATGCCAAACTGATCACACAGCGAAAGTTTGATAACCTGACT

AAAGCTGAGAGAGGGGGTCTGTCAGAACTGGACAAAGCAGGCTTCATCAAGCGACAGCTGGTGG

AGACCAGACAGATCACAAAGCACGTCGCTCAGATTCTGGATAGCAGGATGAACACAAAGTACGAT

GAGAATGACAAACTGATCCGCGAAGTGAAGGTCATTACTCTGAAGTCAAAACTTGTGAGCGACTT

CAGAAAGGATTTCCAGTTCTACAAAGTCAGGGAGATCAACAATTATCACCATGCTCATGACGCAT

ACCTGAACGCAGTGGTCGGGACCGCCCTGATTAAGAAATACCCCAAACTGGAGAGCGAATTCGTG

TACGGTGACTATAAGGTGTACGATGTCAGAAAAATGATCGCCAAGAGTGAGCAGGAAATTGGAAA

AGCCACCGCTAAGTATTTCTTTTACTCAAACATCATGAATTTCTTTAAGACTGAGATCACCCTGGCA

AATGGGGAAATCCGAAAGAGACCACTGATTGAGACTAACGGCGAGACCGGAGAAATCGTGTGGG

ACAAGGGTAGGGATTTTGCCACAGTGCGCAAGGTCCTGTCCATGCCTCAAGTGAATATTGTCAAGA

AAACAGAGGTGCAGACTGGCGGATTCAGTAAGGAATCAATTCTGCCCAAACGGAACTCTGATAAG

CTGATCGCCCGAAAGAAAGACTGGGATCCCAAGAAATATGGGGGTTTCGACTCCCCAACAGTGGC

TTACTCTGTCCTGGTGGTCGCAAAGGTGGAGAAGGGGAAAAGCAAGAAACTGAAATCCGTCAAGG

AGCTGCTGGGTATCACTATTATGGAGAGGAGCTCCTTCGAGAAGAACCCCATCGATTTTCTGGAGG

CTAAAGGCTATAAGGAAGTGAAGAAAGACCTGATCATTAAACTGCCAAAGTACAGCCTGTTTGAG

CTGGAAAACGGAAGGAAGCGAATGCTGGCATCCGCAGGAGAGCTGCAGAAGGGTAATGAACTGG

CCCTGCCTTCTAAGTACGTGAACTTCCTGTATCTGGCTAGCCACTACGAGAAGCTGAAAGGCTCCC

CCGAGGATAACGAACAGAAACAGCTGTTTGTGGAGCAGCACAAGCATTATCTGGACGAGATCATT

GAACAGATTAGCGAGTTCTCCAAAAGAGTGATCCTGGCTGACGCAAATCTGGATAAGGTCCTGAG

CGCATACAACAAACACAGAGATAAGCCAATCAGGGAGCAGGCCGAAAATATCATTCATCTGTTCA

CTCTGACCAACCTGGGAGCCCCTGCAGCCTTCAAGTATTTTGACACTACCATCGATCGGAAACGAT

ACACATCCACTAAGGAGGTGCTGGACGCTACCCTGATTCACCAGAGCATTACCGGCCTGTATGAA

ACAAGGATTGACCTGTCTCAGCTGGGGGGCGACCTCGAGGGAAGCGGAGAGGGCAGAGGAAGTC

TGCTAACATGCGGTGACGTCGAGGAGAATCCTGGCCCAGCACCGGGATCCATGGTGAGCAAGGGC

GAGGAGCTGTTCACCGGGGTGGTGCCCATCCTGGTCGAGCTGGACGGCGACGTAAACGGCCACAA

GTTCAGCGTGTCCGGCGAGGGCGAGGGCGATGCCACCTACGGCAAGCTGACCCTGAAGTTCATCT

GCACCACCGGCAAGCTGCCCGTGCCCTGGCCCACCCTCGTGACCACCTTCACCTACGGCGTGCAGT

GCTTCGCCCGCTACCCCGACCACATGAAGCAGCACGACTTCTTCAAGTCCGCCATGCCCGAAGGCT

ACGTCCAGGAGCGCACCATCTTCTTCAAGGACGACGGCAACTACAAGACCCGCGCCGAGGTGAAG

TTCGAGGGCGACACCCTGGTGAACCGCATCGAGCTGAAGGGCATCGACTTCAAGGAGGACGGCAA

CATCCTGGGGCACAAGCTGGAGTACAACTACAACAGCCACAAGGTCTATATCACCGCCGACAAGC

AGAAGAACGGCATCAAGGTGAACTTCAAGACCCGCCACAACATCGAGGACGGCAGCGTGCAGCTC

GCCGACCACTACCAGCAGAACACCCCCATCGGCGACGGCCCCGTGCTGCTGCCCGACAACCACTA

CCTGAGCACCCAGTCCGCCCTGAGCAAAGACCCCAACGAGAAGCGCGATCACATGGTCCTGCTGG

AGTTCGTGACCGCCGCCGGGATCACTCTCGGCATGGACGAGCTGTACAAGTAAACCTAATCTAGC

AGCTCGCTGATCAGCCTCGACTGTGCCTTCTAGTTGCCAGCCATCTGTTGTTTGCCCCTCCCCCGTG

CCTTCCTTGACCCTGGAAGGTGCCACTCCCACTGTCCTTTCCTAATAAAATGAGGAAATTGCATCG

CATTGTCTGAGTAGGTGTCATTCTATTCTGGGGGGTGGGGTGGGGCAGGACAGCAAGGGGGAGGA

TTGGGAAGACAATAGCAGGCATGCTGGGGATGCGGTGGGCTCTATGGCTTCTGAGGCGGAAAGAA

-continuede

CCAGCTGGGGCTCGATCCTCTAGTTGGCGCGTCATGGTCCATATGAATATCCTCCTTAGTTCCTATT

CCGCTAGCCTAGAGGGACAGCCCCCCCCCAAAGCCCCCAGGGATGTAATTACGTCCCTCCCCCGCT

AGGGGCAGCAGCGAGCCGCCCGGGGCTCCGCTCCGGTCCGGCGCTCCCCCCGCATCCCCGAGCCG

GCAGCGTGCGGGGACAGCCCGGGCACGGGGAAGGTGGCACGGGATCGCTTTCCTCTGAACGCTTC

TCGCTGCTCTTTGAGCCTGCAGACACCTGGGGGGATACGGGGAAAAAGCTTTAGGCTGAAAGAGA

GATTTAGAATGACAGAATCATAGAACGGCCTGGGTTGCAAAGGAGCACAGTGCTCATCCAGATCC

AACCCCCTGCTATGTGCAGGGTCATCAACCAGCAGCCCAGGCTGCCCAGAGCCACATCCAGCCTG

GCCTTGAATGCCTGCAGGGATGGGGCATCCACAGCCTCCTTGGGCAACCTGTTCAGTGCGTCACCA

CCCTCTGGGGGAAAAACTGCCTCCTCATATCCAACCCAAACCTCCCCTGTCTCAGTGTAAAGCCAT

TCCCCCTTGTCCTATCAAGGGGGAGTTTGCTGTGACATTGTTGGTCTGGGGTGACACATGTTTGCCA

ATTCAGTGCATCACGGAGAGGCAGATCTTGGGGATAAGGAAGTGCAGGACAGCATGGACGTGGG

ACATGCAGGTGTTGAGGGCTCTGGGACACTCTCCAAGTCACAGCGTTCAGAACAGCCTTAAGGAT

AAGAAGATAGGATAGAAGGACAAAGAGCAAGTTAAAACCCAGCATGGAGAGGAGCACAAAAAG

GCCACAGACACTGCTGGTCCCTGTGTCTGAGCCTGCATGTTTGATGGTGTCTGGATGCAAGCAGAA

GGGGTGGAAGAGCTTGCCTGGAGAGATACAGCTGGGTCAGTAGGACTGGGACAGGCAGCTGGAG

AATTGCCATGTAGATGTTCATACAATCGTCAAATCATGAAGGCTGGAAAAGCCCTCCAAGATCCCC

AAGACCAACCCCAACCCACCCACCGTGCCCACTGGCCATGTCCCTCAGTGCCACATCCCCACAGTT

CTTCATCACCTCCAGGGACGGTGACCCCCCCACCTCCGTGGGCAGCTGTGCCACTGCAGCACCGCT

CTTTGGAGAAGGTAAATCTTGCTAAATCCAGCCCGACCCTCCCCTGGCACAACGTAAGGCCATTAT

CTCTCATCCAACTCCAGGACGGAGTCAGTGAGGATGGGGCTGGATCCGAAGCAGCTCCAGCCTAC

ACAATCGCTCAAGACGTGTAATGCTTTTATTATATATTAGTCACGATATCTATAACAAGAAAATAT

ATATATAATAAGTTATCACGTAAGTAGAACATGAAATAACAATATAATTATCGTATGAGTTAAATC

TTAAAAGTCACGTAAAAGATAATCATGCGTCATTTTGACTCACGCGGTCGTTATAGTTCAAAATCA

GTGACACTTACCGCATTGACAAGCACGCCTCACGGGAGCTCCAAGCGGCGACTGAGATGTCCTAA

ATGCACAGCGACGGATTCGCGCTATTTAGAAAGAGAGAGCAATATTTCAAGAATGCATGCGTCAA

TTTTACGCAGACTATCTTTCTAGGGTTAAAAAAGATTTGCGCTTTACTCGACCTAAACTTTAAACAC

GTCATAGAATCTTCGTTTGACAAAAACCACATTGTGGGGTACCGAGCTCTTAATTAAGGCGCGCCG

GGGAGGTTCCCTTTAGTGAGGGTTAATTGCGGGTCGCCCTATAGTGAGTCGTATTACAATTCACTG

GCCGTCGTTTTACAACGTCGTGACTGGGAAAACCCTGGCGTTACCCAACTTAATCGCCTTGCAGCA

CATCCCCCTTTCGCCAGCTGGCGTAATAGCGAAGAGGCCCGCACCGATCGCCCTTCCCAACAGTTG

CGCAGCCTGAATGGCGAATGGCAAATTGTAAGCGTTAATATTTTGTTAAAATTCGCGTTAAATTTT

TGTTAAATCAGCTCATTTTTTAACCAATAGGCCGAAATCGGCAAAATCCCTTATAAATCAAAAGAA

TAGACCGAGATAGGGTTGAGTGTTGTTCCAGTTTGGAACAAGAGTCCACTATTAAAGAACGTGGA

CTCCAACGTCAAAGGGCGAAAAACCGTCTATCAGGGCGATGGCCCACTACGTGAACCATCACCCT

AATCAAGTTTTTTGGGGTCGAGGTGCCGTAAAGCACTAAATCGGAACCCTAAAGGGAGCCCCCGA

TTTAGAGCTTGACGGGGAAAGCCGGCGAACGTGGCGAGAAAGGAAGGGAAGAAAGCGAAAGGAG

CGGGCGCTAGGGCGCTGGCAAGTGTAGCGGTCACGCTGCGCGTAACCACCACACCCGCCGCGCTT

AATGCGCCGCTACAGGGCGCGTCAG

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A circular engineered nucleic acid construct comprising:

(a) a promoter operably linked to a nucleic acid encoding a regulatory protein;

(b) an inducible promoter operably linked to a nucleic acid encoding an enzyme that cleaves nucleic acid, a nucleic acid encoding an enzyme that nicks nucleic acid, or a nucleic acid encoding an enzyme that catalyzes exchange of nucleic acid, wherein activity of the inducible promoter is modulated by the regulatory protein;

(c) at least two insulators located downstream from (a) and upstream from (b);

(d) at least one insulator located downstream from (b) and upstream from (a); and (e) at least one deoxyribonucleic acid (DNA)-binding domain recognition sequence located downstream from (b) and upstream from (a).

2. The engineered nucleic acid construct of claim 1, comprising at least two DNA-binding domain recognition sequences.

3. The engineered nucleic acid construct of claim 2, wherein at least one of the DNA-binding domain recognition sequences comprises a nucleotide sequence that is identical to a nucleotide sequence located in a AAVS1 locus of a human genome such that a nuclease can generate a double-strand break in the genome at or near the DNA-binding domain recognition sequence and the nucleic acid construct may be integrated into the human genome in the AAVS1 locus.

4. The engineered nucleic acid construct of claim 2, wherein at least one of the DNA-binding domain recognition sequences comprises a nucleotide sequence that is identical to a nucleotide sequence located in a Rosa26 locus of a mouse genome such that a nuclease can generate a double-strand break in the genome at or near the DNA-binding domain recognition sequence and the nucleic acid construct may be integrated into the mouse genome in the Rosa26 locus.

5. The engineered nucleic acid construct of claim 2, wherein at least one DNA-binding domain recognition sequence is located upstream of (a), and wherein at least one DNA-binding domain recognition sequence is located downstream of (b).

6. The engineered nucleic acid construct of claim 1, further comprising a promoter operably linked to a nucleic acid encoding a selectable marker protein.

7. The engineered nucleic acid construct of claim 1, wherein the enzyme is a nuclease, a nickase or a recombinase.

8. The engineered nucleic acid construct of claim 7, wherein the enzyme is a nuclease.

9. The engineered nucleic acid construct of claim 8, wherein the nuclease is a Cas9 nuclease.

10. The engineered nucleic acid construct of claim 9 wherein the Cas9 nuclease is a catalytically inactive Cas9 nuclease.

11. The engineered nucleic acid construct of claim 10, wherein the catalytically inactive Cas9 nuclease is fused to a transcriptional activator peptide, transcriptional repressor peptide, or an epigenomic regulator peptide.

12. The engineered nucleic acid construct of claim 8, wherein the nuclease is a Cpf1 nuclease.

13. The engineered nucleic acid construct of claim 7, wherein the enzyme is a recombinase.

14. The engineered nucleic acid construct of claim 13, wherein the recombinase is Cre recombinase.

15. The engineered nucleic acid construct of claim 1, wherein the construct further comprises a nucleic acid encoding a guide RNA.

16. The engineered nucleic acid construct of claim 9, wherein the nuclease is fused to a FokI nuclease domain.

17. A vector comprising the engineered nucleic acid construct of claim 1.

18. An isolated cell comprising the vector of claim 17.

19. The isolated cell of claim 18, wherein the cell is an induced pluripotent stem cell (iPSC).

20. An isolated cell comprising the engineered nucleic acid construct of claim 1.

21. A method of modifying a cell genome, comprising:

introducing into a cell a circular engineered nucleic acid construct comprising (a) a promoter operably linked to a nucleic acid encoding a regulatory protein;

(b) an inducible promoter operably linked to a nucleic acid encoding an enzyme that cleaves nucleic acid, a nucleic acid encoding an enzyme that nicks nucleic acid, or a nucleic acid encoding an enzyme that catalyzes exchange of nucleic acid, wherein activity of the inducible promoter is modulated by the regulatory protein;

(c) at least two insulators located downstream from (a) and upstream from (b);

(d) at least one insulator located downstream from (b) and upstream from (a); and (e) at least one deoxyribonucleic acid (DNA)-binding domain recognition sequence located downstream from (b) and upstream from (a);

introducing into the cell an engineered nucleic acid comprising a promoter operably linked to a nucleic acid encoding a guide RNA (gRNA) that targets a genomic region of the cell;

introducing into the cell an engineered nucleic acid comprising a promoter operably linked to a nucleic acid encoding a hybrid nuclease that binds to the at least one DNA-binding domain recognition sequence; and incubating the cell in the presence of an effector substance that modulates activity of the regulatory protein under conditions that result in modification of the cell genome.

22. A method of modifying a cell genome, comprising:

introducing into a cell a circular engineered nucleic acid construct comprising (a) a promoter operably linked to a nucleic acid encoding a regulatory protein;

(b) an inducible promoter operably linked to a nucleic acid encoding an enzyme that cleaves nucleic acid, nicks nucleic acid, or catalyzes exchange of nucleic acid, wherein activity of the inducible promoter is modulated by the regulatory protein;

(c) at least two insulators located downstream from (a) and upstream from (b);

(d) at least one insulator located downstream from (b) and upstream from (a);

(e) a promoter operably linked to a nucleic acid encoding a guide RNA (gRNA) that targets a genomic region of the cell; and (f) at least one deoxyribonucleic acid (DNA)-binding domain recognition sequence located downstream from (b) and upstream from (a);

introducing into the cell an engineered nucleic acid comprising a promoter operably linked to a nucleic acid encoding a hybrid nuclease that binds to the at least one DNA-binding domain recognition sequence; and incubating the cell in the presence of an effector substance that modulates activity of the regulatory protein under conditions that result in modification of the cell genome.

23. An engineered nucleic acid comprising the sequence of any one of SEQ ID NO: 8 or 12-20.

* * * * *

SEQUENCE LISTING

```
<160> NUMBER OF SEQ ID NOS: 20

<210> SEQ ID NO 1
<211> LENGTH: 72
<212> TYPE: DNA
<213> ORGANISM: Homo sapiens

<400> SEQUENCE: 1

catcttggac cattagctcc acaggtatct tcttccctct agtggtcata acagcagctt    60

cagctacctc tc                                                        72

<210> SEQ ID NO 2
<211> LENGTH: 32
<212> TYPE: DNA
<213> ORGANISM: Homo sapiens

<400> SEQUENCE: 2

caaattatcc tgccccctag acataacctc cc                                  32

<210> SEQ ID NO 3
<211> LENGTH: 70
<212> TYPE: DNA
<213> ORGANISM: Homo sapiens

<400> SEQUENCE: 3

tgcattggct gcccaggcct gcactgccgc ctgccggcag gggtccagtc cacgagaccc    60

agctccctgc                                                           70

<210> SEQ ID NO 4
<211> LENGTH: 61
<212> TYPE: DNA
<213> ORGANISM: Homo sapiens

<400> SEQUENCE: 4

gccggccgcg gacccggccc ctccctcccc ggccgctagg gggcgggccc ggatcacagg    60

a                                                                    61

<210> SEQ ID NO 5
<211> LENGTH: 61
<212> TYPE: DNA
<213> ORGANISM: Homo sapiens

<400> SEQUENCE: 5

catgcacaag aaagctttgc actttgcgaa ccaacgatag gtgggggtgc gtggaggatg    60

g                                                                    61

<210> SEQ ID NO 6
<211> LENGTH: 1209
<212> TYPE: DNA
```

<213> ORGANISM: Artificial Sequence
<220> FEATURE:
<223> OTHER INFORMATION: Synthetic Polynucleotide

<400> SEQUENCE: 6
ctagagggac agccccccccc caaagccccc agggatgtaa ttacgtccct cccccgctag 60
gggcagcagc gagccgcccg gggctccgct ccggtccggc gctccccccg catccccgag 120
ccggcagcgt gcggggacag cccgggcacg gggaaggtgg cacgggatcg ctttcctctg 180
aacgcttctc gctgctcttt gagcctgcag acacctgggg ggatacgggg aaaaagcttt 240
aggctgaaag agagatttag aatgacagaa tcatagaacg gcctgggttg caaaggagca 300
cagtgctcat ccagatccaa ccccctgcta tgtgcagggt catcaaccag cagcccaggc 360
tgcccagagc cacatccagc ctggccttga atgcctgcag ggatggggca tccacagcct 420
ccttgggcaa cctgttcagt gcgtcaccac cctctggggg aaaaactgcc tcctcatatc 480
caacccaaac ctcccctgtc tcagtgtaaa gccattcccc cttgtcctat caagggggag 540
tttgctgtga cattgttggt ctggggtgac acatgtttgc caattcagtg catcacggag 600
aggcagatct tggggataag gaagtgcagg acagcatgga cgtgggacat gcaggtgttg 660
agggctctgg gacactctcc aagtcacagc gttcagaaca gccttaagga taagaagata 720
ggatagaagg acaaagagca agttaaaacc cagcatggag aggagcacaa aaaggccaca 780
gacactgctg gtccctgtgt ctgagcctgc atgtttgatg gtgtctggat gcaagcagaa 840
ggggtggaag agcttgcctg gagagataca gctgggtcag taggactggg acaggcagct 900
ggagaattgc catgtagatg ttcatacaat cgtcaaatca tgaaggctgg aaaagccctc 960
caagatcccc aagaccaacc ccaacccacc caccgtgccc actggccatg tccctcagtg 1020
ccacatcccc acagttcttc atcacctcca gggacggtga cccccccacc tccgtgggca 1080
gctgtgccac tgcagcaccg ctctttggag aaggtaaatc ttgctaaatc cagcccgacc 1140
ctcccctggc acaacgtaag gccattatct ctcatccaac tccaggacgg agtcagtgag 1200
gatggggct 1209

<210> SEQ ID NO 7
<211> LENGTH: 6012
<212> TYPE: DNA
<213> ORGANISM: Artificial Sequence
<220> FEATURE:
<223> OTHER INFORMATION: Synthetic Polynucleotide

<400> SEQUENCE: 7
atggctctcg agccatctgc tggagacatg agagctgcca acctttggcc aagcccgctc 60
atgatcaaac gctctaagaa gaacagcctg gccttgtccc tgacggccga ccagatggtc 120
agtgccttgt tggatgctga gccccccata ctctattccg agtatgatcc taccagaccc 180
ttcagtgaag cttcgatgat gggcttactg accaacctgg cagacaggga gctggttcac 240
atgatcaact gggcgaagag ggtgccaggc tttgtggatt tgaccctcca tgatcaggtc 300
caccttctgg aatgtgcctg gctagagatc ctgatgattg gtctcgtctg gcgctctatg 360
gagcacccag tgaagctact gtttgctcct aacttgctct tggacaggaa ccagggaaaa 420
tgtgtagagg gcatggtgga gatcttcgac atgctgctgg ctacatcatc tcggttccgc 480
atgatgaatc tgcagggaga ggagtttgtg tgcctcaaat ctattatttt gcttaattct 540
ggagtgtaca catttctgtc cagcaccctg aagtctctgg aagagaagga ccatatccac 600
cgagtcctgg acaagatcac agacactttg atccacctga tggccaaggc aggcctgacc 660

```
ctgcagcagc agcaccagcg gctggcccag ctcctcctca tcctctccca catcaggcac    720
atgagtaaca aaggcatgga gcatctgtac agcatgaagt gcaagaacgt ggtgcccctc    780
tatgacctgc tgctggaggc ggcggacgcc caccgcctac atgcgcccac tagccgtgga    840
ggggcatccg tggaggagac ggaccaaagc cacttggcca ctgcgggctc tacttcatcg    900
cattccttgc aaaagtatta catcacgggg gaggcagagg gtttccctgc cacagctgac    960
aagaaatact caatcgggct ggacatcgga actaactcag tggggtgggc agtcattact   1020
gacgagtaca aagtgccaag caagaaattt aaggtcctgg gcaacaccga taggcactcc   1080
atcaagaaaa atctgattgg ggccctgctg ttcgactctg gagagacagc tgaagcaact   1140
agactgaaaa ggactgctag aaggcgctat acccggcgaa agaatcgcat ctgctacctg   1200
caggagattt tctctaacga aatggccaag gtggacgata gtttctttca tcggctggag   1260
gaatcattcc tggtcgagga agataagaaa cacgagagac atcctatctt tggaaacatt   1320
gtggacgagg tcgcttatca cgaaaaatac cccaccatct atcatctgcg caagaaactg   1380
gtggactcta cagataaagc agacctgcgg ctgatctatc tggccctggc tcacatgatt   1440
aagttcagag gccatttttct gatcgaggga gatctgaacc cagacaatag cgatgtggac   1500
aagctgttca tccagctggt ccagacatac aatcagctgt ttgaggaaaa ccctattaat   1560
gcatctggcg tggacgcaaa agccatcctg agtgccaggc tgtctaagag tagaaggctg   1620
gagaacctga tcgctcagct gccaggcgaa aagaaaaacg gcctgtttgg aaatctgatt   1680
gcactgtcac tgggactgac acctaacttc aagagcaatt ttgatctggc cgaggacgct   1740
aaactgcagc tgagcaagga cacttatgac gatgacctgg ataacctgct ggctcagatc   1800
ggagatcagt acgcagacct gttcctggcc gctaagaatc tgtctgacgc tatcctgctg   1860
agtgatattc tgcgggtgaa caccgagatt acaaaagccc ctctgtcagc tagcatgatc   1920
aagagatatg acgagcacca tcaggatctg accctgctga aggcactggt gcgccagcag   1980
ctgcccgaga agtacaagga aatcttcttt gatcagagta agaacgggta cgccggttat   2040
attgacggcg gagcttcaca ggaggaattc tacaagttta tcaaacctat tctggagaag   2100
atggacggca ccgaggaact gctggtgaaa ctgaatcgcg aggacctgct gcgcaagcag   2160
cggacatttg ataacggctc catcccccac cagattcatc tgggagagct gcacgcaatc   2220
ctgcgacgac aggaagactt ctacccattt ctgaaggata accgcgagaa gatcgaaaaa   2280
attctgacct tccggatccc ttactatgtg ggccccctgg caaggggtaa ttcccgcttt   2340
gcctggatga cacggaaatc tgaggaaaca atcactcctt ggaacttcga ggaagtggtc   2400
gataagggag cttccgcaca gtctttcatc gagagaatga caaacttcga caaaaacctg   2460
ccaaatgaga aagtgctgcc taagcacagt ctgctgtacg agtatttcac agtctataac   2520
gaactgacta aggtgaaata cgtcaccgag gggatgagga agcccgcctt cctgagcggt   2580
gaacagaaga aagctatcgt ggacctgctg tttaaaacca atcgcaaggt gacagtcaag   2640
cagctgaagg aggactactt caagaaaatt gaatgtttcg attctgtgga gatcagtggc   2700
gtcgaagaca gatttaacgc ttctctggga acctaccacg atctgctgaa gatcattaag   2760
gataaagact tcctggacaa cgaggaaaat gaggatatcc tggaagacat tgtgctgacc   2820
ctgacactgt ttgaggatcg cgaaatgatc gaggaacggc tgaaaactta tgcccatctg   2880
ttcgatgaca aggtgatgaa acagctgaag cgaagaaggt acaccggctg gggacgactg   2940
agcagaaagc tgatcaacgg cattcgggac aaacagagtg gaaagactat cctggacttt   3000
```

-continued ctgaaatcag atggcttcgc taacagaaat tttatgcagc tgattcacga tgacagcctg 3060
accttcaaag aggatatcca gaaggcacag gtgtccgggc agggtgactc tctgcacgag 3120
catatcgcaa acctggccgg gtcccccgcc atcaagaaag gtattctgca gaccgtgaag 3180
gtggtcgatg agctggtgaa agtcatgggc aggcataagc cagaaaacat cgtgattgag 3240
atggcccgcg aaaatcagac cacacagaaa ggacagaaga acagccgcga gcggatgaaa 3300
aggatcgagg aaggcattaa ggaactggga tcccagatcc tgaaagagca ccctgtggaa 3360
aacactcagc tgcagaatga gaagctgtat ctgtactatc tgcagaatgg gcgggatatg 3420
tacgtggacc aggagctgga tattaaccga ctgtctgatt acgacgtgga tcatatcgtc 3480
ccacagtcat tcctgaaaga tgacagcatt gacaataagg tgctgacccg gagtgacaaa 3540
aaccgaggaa agagtgataa tgtcccttca gaggaagtgg tcaagaaaat gaagaactac 3600
tggagacagc tgctgaatgc caaactgatc acacagcgaa agtttgataa cctgactaaa 3660
gctgagagag gggtctgtc agaactggac aaagcaggct tcatcaagcg acagctggtg 3720
gagaccagac agatcacaaa gcacgtcgct cagattctgg atagcaggat gaacacaaag 3780
tacgatgaga atgacaaact gatccgcgaa gtgaaggtca ttactctgaa gtcaaaactt 3840
gtgagcgact tcagaaagga tttccagttc tacaaagtca gggagatcaa caattatcac 3900
catgctcatg acgcatacct gaacgcagtg gtcgggaccg ccctgattaa gaaatacccc 3960
aaactggaga gcgaattcgt gtacggtgac tataaggtgt acgatgtcag aaaaatgatc 4020
gccaagagtg agcaggaaat tggaaaagcc accgctaagt atttctttta ctcaaacatc 4080
atgaatttct ttaagactga gatcaccctg gcaaatgggg aaatccgaaa gagaccactg 4140
attgagacta acggcgagac cggagaaatc gtgtgggaca agggtaggga ttttgccaca 4200
gtgcgcaagg tcctgtccat gcctcaagtg aatattgtca agaaaacaga ggtgcagact 4260
ggcggattca gtaaggaatc aattctgccc aaacggaact ctgataagct gatcgcccga 4320
aagaaagact gggatcccaa gaaatatggg ggtttcgact ccccaacagt ggcttactct 4380
gtcctggtgg tcgcaaaggt ggagaagggg aaaagcaaga aactgaaatc cgtcaaggag 4440
ctgctgggta tcactattat ggagaggagc tccttcgaga agaaccccat cgattttctg 4500
gaggctaaag gctataagga agtgaagaaa gacctgatca ttaaactgcc aaagtacagc 4560
ctgtttgagc tggaaaacgg aaggaagcga atgctggcat ccgcaggaga gctgcagaag 4620
ggtaatgaac tggccctgcc ttctaagtac gtgaacttcc tgtatctggc tagccactac 4680
gagaagctga aaggctcccc cgaggataac gaacagaaac agctgtttgt ggagcagcac 4740
aagcattatc tggacgagat cattgaacag attagcgagt tctccaaaag agtgatcctg 4800
gctgacgcaa atctggataa ggtcctgagc gcatacaaca aacacagaga taagccaatc 4860
agggagcagg ccgaaaatat cattcatctg ttcactctga ccaacctggg agcccctgca 4920
gccttcaagt attttgacac taccatcgat cggaaacgat acacatccac taaggaggtg 4980
ctggacgcta ccctgattca ccagagcatt accggcctgt atgaaacaag gattgacctg 5040
tctcagctgg ggggcgacct cgagccatct gctggagaca tgagagctgc caacctttgg 5100
ccaagcccgc tcatgatcaa acgctctaag aagaacagcc tggccttgtc cctgacggcc 5160
gaccagatgg tcagtgcctt gttggatgct gagcccccca tactctattc cgagtatgat 5220
cctaccagac ccttcagtga agcttcgatg atgggcttac tgaccaacct ggcagacagg 5280
gagctggttc acatgatcaa ctgggcgaag agggtgccag gctttgtgga tttgaccctc 5340
catgatcagg tccaccttct ggaatgtgcc tggctagaga tcctgatgat tggtctcgtc 5400
tggcgctcta tggagcaccc agtgaagcta ctgtttgctc ctaacttgct cttggacagg 5460
aaccagggaa aatgtgtaga gggcatggtg gagatcttcg acatgctgct ggctacatca 5520
tctcggttcc gcatgatgaa tctgcaggga gaggagtttg tgtgcctcaa atctattatt 5580
ttgcttaatt ctggagtgta cacatttctg tccagcaccc tgaagtctct ggaagagaag 5640
gaccatatcc accgagtcct ggacaagatc acagacactt tgatccacct gatggccaag 5700
gcaggcctga ccctgcagca gcagcaccag cggctggccc agctcctcct catcctctcc 5760
cacatcaggc acatgagtaa caaaggcatg gagcatctgt acagcatgaa gtgcaagaac 5820
gtggtgcccc tctatgacct gctgctggag gcggcggacg cccaccgcct acatgcgccc 5880
actagccgtg gaggggcatc cgtggaggag acggaccaaa gccacttggc cactgcgggc 5940
tctacttcat cgcattcctt gcaaaagtat tacatcacgg gggaggcaga gggtttccct 6000
gccacagctt ga 6012

<210> SEQ ID NO 8
<211> LENGTH: 17575
<212> TYPE: DNA
<213> ORGANISM: Artificial Sequence
<220> FEATURE:
<223> OTHER INFORMATION: Synthetic Polynucleotide

<400> SEQUENCE: 8
gtggcacttt tcggggaaat gtgcgcggaa cccctatttg tttatttttc taaatacatt 60
caaatatgta tccgctcatg agacaataac cctgataaat gcttcaataa tattgaaaaa 120
ggaagagtat gagtattcaa catttccgtg tcgcccttat tccctttttt gcggcatttt 180
gccttcctgt ttttgctcac ccagaaacgc tggtgaaagt aaaagatgct gaagatcagt 240
tgggtgcacg agtgggttac atcgaactgg atctcaacag cggtaagatc cttgagagtt 300
ttcgccccga agaacgtttt ccaatgatga gcacttttaa agttctgcta tgtggcgcgg 360
tattatcccg tattgacgcc gggcaagagc aactcggtcg ccgcatacac tattctcaga 420
atgacttggt tgagtactca ccagtcacag aaaagcatct tacggatggc atgacagtaa 480
gagaattatg cagtgctgcc ataaccatga gtgataacac tgcggccaac ttacttctga 540
caacgatcgg aggaccgaag gagctaaccg cttttttgca caacatgggg gatcatgtaa 600
ctcgccttga tcgttgggaa ccggagctga atgaagccat accaaacgac gagcgtgaca 660
ccacgatgcc tgtagcaatg gcaacaacgt tgcgcaaact attaactggc gaactactta 720
ctctagcttc ccggcaacaa ttaatagact ggatggaggc ggataaagtt gcaggaccac 780
ttctgcgctc ggcccttccg gctggctggt ttattgctga taaatctgga gccggtgagc 840
gtgggtctcg cggtatcatt gcagcactgg ggccagatgg taagccctcc cgtatcgtag 900
ttatctacac gacggggagt caggcaacta tggatgaacg aaatagacag atcgctgaga 960
taggtgcctc actgattaag cattggtaac tgtcagacca agtttactca tatatacttt 1020
agattgattt aaaacttcat ttttaattta aaaggatcta ggtgaagatc ctttttgata 1080
atctcatgac caaaatccct taacgtgagt tttcgttcca ctgagcgtca gaccccgtag 1140
aaaagatcaa aggatcttct tgagatcctt tttttctgcg cgtaatctgc tgcttgcaaa 1200
caaaaaaacc accgctacca gcggtggttt gtttgccgga tcaagagcta ccaactcttt 1260
ttccgaaggt aactggcttc agcagagcgc agataccaaa tactgttctt ctagtgtagc 1320
cgtagttagg ccaccacttc aagaactctg tagcaccgcc tacatacctc gctctgctaa 1380

-continued

```
tcctgttacc agtggctgct gccagtggcg ataagtcgtg tcttaccggg ttggactcaa   1440
gacgatagtt accggataag gcgcagcggt cgggctgaac ggggggttcg tgcacacagc   1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740
tatggaaaaa cgccagcaac gcggcctttt tacggttcct ggccttttgc tggccttttg   1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacctcccct agcttaatta accctagaaa   2220
gataatcata ttgtgacgta cgttaaagat aatcatgcgt aaaattgacg catgtgtttt   2280
atcgatctgt atatcgaggt ttatttatta atttgaatag atattaagtt ttattatatt   2340
tacacttaca tactaataat aaattcaaca aacaatttat ttatgtttat ttatttatta   2400
aaaaaaaaca aaaactcaaa atttcttcta taaagtaaca aaacttttaa acattctctc   2460
ttttacaaaa ataaacttat tttgtacttt aaaaacagtc atgttgtatt ataaaataag   2520
taattagctt aacttataca taatagaaac aaattatact tattaatcgc attgattatt   2580
gactagtcgt attaagggtt ccggatcagc ttgattcgag ccccagctgg ttctttccgc   2640
ctcagaagcc atagagccca ccgcatcccc agcatgcctg ctattgtctt cccaatcctc   2700
ccccttgctg tcctgcccca ccccaccccc cagaatagaa tgacacctac tcagacaatg   2760
cgatgcaatt tcctcatttt attaggaaag gacagtggga gtggcacctt ccagggtcaa   2820
ggaaggcacg gggggagggc aaacaacaga tggctggcaa ctagaaggca cagtcgaggc   2880
tgatcagcga gctctagaga attgatcccc tcagaagaac tcgtcaagaa ggcgatagaa   2940
ggcgatgcgc tgcgaatcgg gagcggcgat accgtaaagc acgaggaagc ggtcagccca   3000
ttcgccgcca agctcttcag caatatcacg ggtagccaac gctatgtcct gatagcggtc   3060
cgccacaccc agccggccac agtcgatgaa tccagaaaag cggccatttt ccaccatgat   3120
attcggcaag caggcatcgc catgggtcac gacgagatcc tcgccgtcgg gcatgcgcgc   3180
cttgagcctg gcgaacagtt cggctggcgc gagcccctga tgctcttcgt ccagatcatc   3240
ctgatcgaca agaccggctt ccatccgagt acgtgctcgc tcgatgcgat gtttcgcttg   3300
gtggtcgaat gggcaggtag ccggatcaag cgtatgcagc cgccgcattg catcagccat   3360
gatggatact ttctcggcag gagcaaggtg agatgacagg agatcctgcc ccggcacttc   3420
gcccaatagc agccagtccc ttcccgcttc agtgacaacg tcgagcacag ctgcgcaagg   3480
aacgcccgtc gtggccagcc acgatagccg cgctgcctcg tcctgcagtt cattcagggc   3540
accggacagg tcggtcttga caaaaagaac cgggcgcccc tgcgctgaca gccggaacac   3600
ggcggcatca gagcagccga ttgtctgttg tgcccagtca tagccgaata gcctctccac   3660
ccaagcggcc ggagaacctg cgtgcaatcc atcttgttca atggccgatc ccatggttta   3720
gttcctcacc ttgtcgtatt atactatgcc gatatactat gccgatgatt aattgtcaac   3780
```

acgtgctgct gcaggtcgaa aggcccggag atgaggaaga ggagaacagc gcggcagacg 3840
tgcgcttttg aagcgtgcag aatgccgggc ctccggagga ccttcgggcg cccgccccgc 3900
ccctgagccc gcccctgagc ccgcccccgg acccacccct tcccagcctc tgagcccaga 3960
aagcgaagga gcaaagctgc tattggccgc tgccccaaag gcctacccgc ttccattgct 4020
cagcggtgct gtccatctgc acgagactag tgagacgtgc tacttccatt tgtcacgtcc 4080
tgcacgacgc gagctgcggg gcggggggga acttcctgac taggggagga gtagaaggtg 4140
gcgcgaaggg gccaccaaag aacggagccg gttggcgcct accggtggat gtggaatgtg 4200
tgcgagccag aggccacttg tgtagcgcca agtgcccagc ggggctgcta aagcgcatgc 4260
tccagactgc cttgggaaaa gcgcctcccc tacccggtag acaccccaca gtgggtggcc 4320
tagggacagg attgcaactc cagtctttct tcttcttggg cgggagtcac tagttattaa 4380
tagtaatcaa ttacggggtc attagttcat agcccatata tggagttccg cgttacataa 4440
cttacggtaa atggcccgcc tggctgaccg cccaacgacc cccgcccatt gacgtcaata 4500
atgacgtatg ttcccatagt aacgccaata gggactttcc attgacgtca atgggtggac 4560
tatttacggt aaactgccca cttggcagta catcaagtgt atcatatgcc aagtacgccc 4620
cctattgacg tcaatgacgg taaatggccc gcctggcatt atgcccagta catgacctta 4680
tgggactttc ctacttggca gtacatctac gtattagtca tcgctattac catgggtcga 4740
ggtgagcccc acgttctgct tcactctccc catctccccc ccctccccac ccccaatttt 4800
gtatttattt atttttaat tattttgtgc agcgatgggg gcgggggggg ggggggcgcg 4860
cgccaggcgg ggcggggcgg ggcgaggggc ggggcggggc gaggcggaga ggtgcggcgg 4920
cagccaatca gagcggcgcg ctccgaaagt ttccttttat ggcgaggcgg cggcggcggc 4980
ggccctataa aaagcgaagc gcgcggcggg cgggagtcgc tgcgttgcct tcgccccgtg 5040
ccccgctccg cgccgcctcg cgccgcccgc cccggctctg actgaccgcg ttactcccac 5100
aggtgagcgg gcgggacggc ccttctcctc cgggctgtaa ttagcgcttg gtttaatgac 5160
ggctcgtttc ttttctgtgg ctgcgtgaaa gccttaaagg gctccgggag ggccctttgt 5220
gcggggggga gcggctcggg gggtgcgtgc gtgtgtgtgt gcgtggggag cgccgcgtgc 5280
ggcccgcgct gcccggcggc tgtgagcgct gcgggcgcgg cgcggggctt tgtgcgctcc 5340
gcgtgtgcgc gaggggagcg cggccggggg cggtgccccg cggtgcgggg gggctgcgag 5400
gggaacaaag gctgcgtgcg gggtgtgtgc gtgggggggt gagcaggggg tgtgggcgcg 5460
gcggtcgggc tgtaaccccc ccctgcaccc ccctccccga gttgctgagc acggcccggc 5520
ttcgggtgcg gggctccgtg cggggcgtgg cgcggggctc gccgtgccgg gcggggggtg 5580
gcggcaggtg ggggtgccgg gcggggcggg gccgcctcgg gccggggagg gctcggggga 5640
ggggcgcggc ggcccccgga gcgccggcgg ctgtcgaggcg cggcgagccg cagccattgc 5700
cttttatggt aatcgtgcga gagggcgcag ggacttcctt tgtcccaaat ctggcggagc 5760
cgaaatctgg gaggcgccgc cgcacccccct ctagcgggcg cgggcgaagc ggtgcggcgc 5820
cggcaggaag gaaatgggcg gggagggcct tcgtgcgtcg ccgcgccgcc gtccccttct 5880
ccatctccag cctcggggct gccgcagggg gacggctgcc ttcggggggg acggggcagg 5940
gcggggttcg gcttctggcg tgtgaccggc ggctctagag cctctgctaa ccatgttcat 6000
gccttcttct ttttcctaca gctcctgggc aacgtgctgg ttattgtgct gtctcatcat 6060
tttggcaaag aattcgccac catggtgccc aagaagaaga ggaaagtctc tagactggac 6120

```
aagagcaaag tcataaactc tgctctggaa ttactcaatg gagtcggtat cgaaggcctg   6180
acgacaagga aactcgctca aaagctggga gttgagcagc ctaccctgta ctggcacgtg   6240
aagaacaagc gggccctgct cgatgccctg ccaatcgaga tgctggacag gcatcatacc   6300
cactcctgcc ccctggaagg cgagtcatgg caagactttc tgcggaacaa cgccaagtca   6360
taccgctgtg ctctcctctc acatcgcgac ggggctaaag tgcatctcgg cacccgccca   6420
acagagaaac agtacgaaac cctggaaaat cagctcgcgt tcctgtgtca gcaaggcttc   6480
tccctggaga acgcactgta cgctctgtcc gccgtgggcc actttacact gggctgcgta   6540
ttggaggaac aggagcatca agtagcaaaa gaggaaagag agacacctac caccgattct   6600
atgcccccac ttctgaaaca agcaattgag ctgttcgacc ggcagggagc cgaacctgcc   6660
ttccttttcg gcctggaact aatcatatgt ggcctggaga aacagctaaa gtgcgaaagc   6720
ggcgggccga ccgacgccct tgacgatttt gacttagaca tgctcccagc cgatgccctt   6780
gacgactttg accttgatat gctgcctgct gacgctcttg acgattttga ccttgacatg   6840
ctccccgggt aaagcggccg cgactctaga tcataatcag ccataccaca tttgtagagg   6900
ttttacttgc tttaaaaaac ctcccacacc tcccccctgaa cctgaaacat aaaatgaatg   6960
caattgttgt tgttaacttg tttattgcag cttataatgg ttacaaataa agcaatagca   7020
tcacaaattt cacaaataaa gcattttttt cactgcattc tagttgtggt ttgtccaaac   7080
tcatcaatgt atcttaaggg atccctagag ggacagcccc cccccaaagc cccagggat   7140
gtaattacgt ccctcccccg ctaggggcag cagcgagccg cccggggctc cgctccggtc   7200
cggcgctccc cccgcatccc cgagccggca gcgtgcgggg acagcccggg cacggggaag   7260
gtggcacggg atcgctttcc tctgaacgct tctcgctgct ctttgagcct gcagacacct   7320
ggggggatac ggggaaaaag ctttaggctg aaagagagat ttagaatgac agaatcatag   7380
aacggcctgg gttgcaaagg agcacagtgc tcatccagat ccaacccccct gctatgtgca   7440
gggtcatcaa ccagcagccc aggctgccca gagccacatc cagcctggcc ttgaatgcct   7500
gcagggatgg ggcatccaca gcctccttgg gcaacctgtt cagtgcgtca ccaccctctg   7560
ggggaaaaac tgcctcctca tatccaaccc aaacctcccc tgtctcagtg taaagccatt   7620
ccccccttgtc ctatcaaggg ggagtttgct gtgacattgt tggtctgggg tgacacatgt   7680
ttgccaattc agtgcatcac ggagaggcag atcttgggga taaggaagtg caggacagca   7740
tggacgtggg acatgcaggt gttgagggct ctgggacact ctccaagtca cagcgttcag   7800
aacagcctta aggataagaa gataggatag aaggacaaag agcaagttaa aacccagcat   7860
ggagaggagc acaaaaaggc cacagacact gctggtccct gtgtctgagc ctgcatgttt   7920
gatggtgtct ggatgcaagc agaaggggtg gaagagcttg cctggagaga tacagctggg   7980
tcagtaggac tgggacaggc agctggagaa ttgccatgta gatgttcata caatcgtcaa   8040
atcatgaagg ctggaaaagc cctccaagat ccccaagacc aaccccaacc cacccaccgt   8100
gcccactggc catgtccctc agtgccacat ccccacagtt cttcatcacc tccagggacg   8160
gtgacccccc cacctccgtg ggcagctgtg ccactgcagc accgctcttt ggagaaggta   8220
aatcttgcta aatccagccc gaccctcccc tggcacaacg taaggccatt atctctcatc   8280
caactccagg acggagtcag tgaggatggg gctgtcgacc tagagggaca gcccccccccc   8340
aaagccccca gggatgtaat tacgtccctc ccccgctagg ggcagcagcg agccgcccgg   8400
ggctccgctc cggtccggcg ctccccccgc atccccgagc cggcagcgtg cggggacagc   8460
ccgggcacgg ggaaggtggc acgggatcgc tttcctctga acgcttctcg ctgctctttg   8520
```

```
agcctgcaga cacctggggg gatacgggga aaaagcttta ggctgaaaga gagatttaga   8580
atgacagaat catagaacgg cctgggttgc aaaggagcac agtgctcatc cagatccaac   8640
cccctgctat gtgcagggtc atcaaccagc agcccaggct gcccagagcc acatccagcc   8700
tggccttgaa tgcctgcagg gatggggcat ccacagcctc cttgggcaac ctgttcagtg   8760
cgtcaccacc ctctgggggga aaaactgcct cctcatatcc aacccaaacc tcccctgtct   8820
cagtgtaaag ccattccccc ttgtcctatc aagggggagt ttgctgtgac attgttggtc   8880
tggggtgaca catgtttgcc aattcagtgc atcacggaga ggcagatctt ggggataagg   8940
aagtgcagga cagcatggac gtgggacatg caggtgttga gggctctggg acactctcca   9000
agtcacagcg ttcagaacag ccttaaggat aagaagatag gatagaagga caaagagcaa   9060
gttaaaaccc agcatggaga ggagcacaaa aaggccacag acactgctgg tccctgtgtc   9120
tgagcctgca tgtttgatgg tgtctggatg caagcagaag ggtggaaga gcttgcctgg   9180
agagatacag ctgggtcagt aggactggga caggcagctg gagaattgcc atgtagatgt   9240
tcatacaatc gtcaaatcat gaaggctgga aaagccctcc aagatcccca agaccaaccc   9300
caacccaccc accgtgccca ctggccatgt ccctcagtgc cacatcccca cagttcttca   9360
tcacctccag ggacggtgac ccccccacct ccgtgggcag ctgtgccact gcagcaccgc   9420
tctttggaga aggtaaatct tgctaaatcc agcccgaccc tcccctggca caacgtaagg   9480
ccattatctc tcatccaact ccaggacgga gtcagtgagg atggggctca attgtttact   9540
ccctatcagt gatagagaac gtatgaagag tttactccct atcagtgata gagaacgtat   9600
gcagacttta ctccctatca gtgatagaga acgtataagg agtttactcc ctatcagtga   9660
tagagaacgt atgaccagtt tactccctat cagtgataga gaacgtatct acagtttact   9720
ccctatcagt gatagagaac gtatatccag tttactccct atcagtgata gagaacgtat   9780
aagctttagg cgtgtacggt gggcgcctat aaaagcagag ctcgtttagt gaaccgtcag   9840
atcgcctgga gcaattccac aacacttttg tcttatacca actttccgta ccacttccta   9900
ccctcgtaaa aagcttgtcc accatggctc ctaagaaaaa gcggaaggtg gacaagaaat   9960
actcaatcgg gctggacatc ggaactaact cagtggggtg ggcagtcatt actgacgagt  10020
acaaagtgcc aagcaagaaa tttaaggtcc tgggcaacac cgataggcac tccatcaaga  10080
aaaatctgat tggggccctg ctgttcgact ctggagagac agctgaagca actagactga  10140
aaaggactgc tagaaggcgc tatacccggc gaaagaatcg catctgctac ctgcaggaga  10200
ttttctctaa cgaaatggcc aaggtggacg atagtttctt tcatcggctg gaggaatcat  10260
tcctggtcga ggaagataag aaacacgaga gacatcctat ctttggaaac attgtggacg  10320
aggtcgctta tcacgaaaaa taccccacca tctatcatct gcgcaagaaa ctggtggact  10380
ctacagataa agcagacctg cggctgatct atctggccct ggctcacatg attaagttca  10440
gaggccattt tctgatcgag ggagatctga acccagacaa tagcgatgtg gacaagctgt  10500
tcatccagct ggtccagaca tacaatcagc tgtttgagga aaaccctatt aatgcatctg  10560
gcgtggacgc aaaagccatc ctgagtgcca ggctgtctaa gagtagaagg ctggagaacc  10620
tgatcgctca gctgccaggc gaaaagaaaa acggcctgtt tggaaatctg attgcactgt  10680
cactgggact gacacctaac ttcaagagca attttgatct ggccgaggac gctaaactgc  10740
agctgagcaa ggacacttat gacgatgacc tggataacct gctggctcag atcggagatc  10800
agtacgcaga cctgttcctg gccgctaaga atctgtctga cgctatcctg ctgagtgata  10860
```

-continued ttctgcgggt gaacaccgag attacaaaag cccctctgtc agctagcatg atcaagagat 10920
atgacgagca ccatcaggat ctgaccctgc tgaaggcact ggtgcgccag cagctgcccg 10980
agaagtacaa ggaaatcttc tttgatcaga gtaagaacgg gtacgccggt tatattgacg 11040
gcggagcttc acaggaggaa ttctacaagt ttatcaaacc tattctggag aagatggacg 11100
gcaccgagga actgctggtg aaactgaatc gcgaggacct gctgcgcaag cagcggacat 11160
ttgataacgg ctccatcccc caccagattc atctgggaga gctgcacgca atcctgcgac 11220
gacaggaaga cttctaccca tttctgaagg ataaccgcga gaagatcgaa aaaattctga 11280
ccttccggat cccttactat gtggggcccc tggcaagggg taattcccgc tttgcctgga 11340
tgacacggaa atctgaggaa acaatcactc cttggaactt cgaggaagtg gtcgataagg 11400
gagcttccgc acagtctttc atcgagagaa tgacaaactt cgacaaaaac ctgccaaatg 11460
agaaagtgct gcctaagcac agtctgctgt acgagtattt cacagtctat aacgaactga 11520
ctaaggtgaa atacgtcacc gaggggatga ggaagcccgc cttcctgagc ggtgaacaga 11580
agaaagctat cgtggacctg ctgtttaaaa ccaatcgcaa ggtgacagtc aagcagctga 11640
aggaggacta cttcaagaaa attgaatgtt tcgattctgt ggagatcagt ggcgtcgaag 11700
acagatttaa cgcttctctg ggaacctacc acgatctgct gaagatcatt aaggataaag 11760
acttcctgga caacgaggaa aatgaggata tcctggaaga cattgtgctg accctgacac 11820
tgtttgagga tcgcgaaatg atcgaggaac ggctgaaaac ttatgcccat ctgttcgatg 11880
acaaggtgat gaaacagctg aagcgaagaa ggtacaccgg ctggggacga ctgagcagaa 11940
agctgatcaa cggcattcgg gacaaacaga gtggaaagac tatcctggac tttctgaaat 12000
cagatggctt cgctaacaga aattttatgc agctgattca cgatgacagc ctgaccttca 12060
aagaggatat ccagaaggca caggtgtccg ggcagggtga ctctctgcac gagcatatcg 12120
caaacctggc cgggtccccc gccatcaaga aaggtattct gcagaccgtg aaggtggtcg 12180
atgagctggt gaaagtcatg ggcaggcata agccagaaaa catcgtgatt gagatggccc 12240
gcgaaaatca gaccacacag aaaggacaga agaacagccg cgagcggatg aaaaggatcg 12300
aggaaggcat taaggaactg ggatcccaga tcctgaaaga gcaccctgtg gaaaacactc 12360
agctgcagaa tgagaagctg tatctgtact atctgcagaa tgggcgggat atgtacgtgg 12420
accaggagct ggatattaac cgactgtctg attacgacgt ggatcatatc gtcccacagt 12480
cattcctgaa agatgacagc attgacaata aggtgctgac ccggagtgac aaaaaccgag 12540
gaaagagtga taatgtccct tcagaggaag tggtcaagaa aatgaagaac tactggagac 12600
agctgctgaa tgccaaactg atcacacagc gaaagtttga taacctgact aaagctgaga 12660
gaggggggtct gtcagaactg gacaaagcag gcttcatcaa gcgacagctg gtggagacca 12720
gacagatcac aaagcacgtc gctcagattc tggatagcag gatgaacaca aagtacgatg 12780
agaatgacaa actgatccgc gaagtgaagg tcattactct gaagtcaaaa cttgtgagcg 12840
acttcagaaa ggatttccag ttctacaaag tcagggagat caacaattat caccatgctc 12900
atgacgcata cctgaacgca gtggtcggga ccgccctgat taagaaatac cccaaactgg 12960
agagcgaatt cgtgtacggt gactataagg tgtacgatgt cagaaaaatg atcgccaaga 13020
gtgagcagga aattggaaaa gccaccgcta agtatttctt ttactcaaac atcatgaatt 13080
tctttaagac tgagatcacc ctggcaaatg gggaaatccg aaagagacca ctgattgaga 13140
ctaacggcga gaccggagaa atcgtgtggg acaagggtag ggattttgcc acagtgcgca 13200
aggtcctgtc catgcctcaa gtgaatattg tcaagaaaac agaggtgcag actggcggat 13260

```
tcagtaagga atcaattctg cccaaacgga actctgataa gctgatcgcc cgaaagaaag  13320
actgggatcc caagaaatat gggggtttcg actccccaac agtggcttac tctgtcctgg  13380
tggtcgcaaa ggtggagaag gggaaaagca agaaactgaa atccgtcaag gagctgctgg  13440
gtatcactat tatggagagg agctccttcg agaagaaccc catcgatttt ctggaggcta  13500
aaggctataa ggaagtgaag aaagacctga tcattaaact gccaaagtac agcctgtttg  13560
agctggaaaa cggaaggaag cgaatgctgg catccgcagg agagctgcag aagggtaatg  13620
aactggccct gccttctaag tacgtgaact tcctgtatct ggctagccac tacgagaagc  13680
tgaaaggctc ccccgaggat aacgaacaga aacagctgtt tgtggagcag cacaagcatt  13740
atctggacga gatcattgaa cagattagcg agttctccaa aagagtgatc ctggctgacg  13800
caaatctgga taaggtcctg agcgcataca acaaacacag agataagcca atcagggagc  13860
aggccgaaaa tatcattcat ctgttcactc tgaccaacct gggagcccct gcagccttca  13920
agtattttga cactaccatc gatcggaaac gatacacatc cactaaggag gtgctggacg  13980
ctaccctgat tcaccagagc attaccggcc tgtatgaaac aaggattgac ctgtctcagc  14040
tgggggggcga cctcgaggga agcggagagg gcagaggaag tctgctaaca tgcggtgacg  14100
tcgaggagaa tcctggccca gcaccgggat ccatggtgag caagggcgag gagctgttca  14160
ccggggtggt gcccatcctg gtcgagctgg acggcgacgt aaacggccac aagttcagcg  14220
tgtccggcga gggcgagggc gatgccacct acggcaagct gaccctgaag ttcatctgca  14280
ccaccggcaa gctgcccgtg ccctggccca ccctcgtgac caccttcacc tacggcgtgc  14340
agtgcttcgc ccgctacccc gaccacatga agcagcacga cttcttcaag tccgccatgc  14400
ccgaaggcta cgtccaggag cgcaccatct tcttcaagga cgacggcaac tacaagaccc  14460
gcgccgaggt gaagttcgag ggcgacaccc tggtgaaccg catcgagctg aagggcatcg  14520
acttcaagga ggacggcaac atcctggggc acaagctgga gtacaactac aacagccaca  14580
aggtctatat caccgccgac aagcagaaga acggcatcaa ggtgaacttc aagacccgcc  14640
acaacatcga ggacggcagc gtgcagctcg ccgaccacta ccagcagaac acccccatcg  14700
gcgacggccc cgtgctgctg cccgacaacc actacctgag cacccagtcc gccctgagca  14760
aagaccccaa cgagaagcgc gatcacatgg tcctgctgga gttcgtgacc gccgccggga  14820
tcactctcgg catggacgag ctgtacaagt aaacctaatc tagcagctcg ctgatcagcc  14880
tcgactgtgc cttctagttg ccagccatct gttgtttgcc cctcccccgt gccttccttg  14940
accctggaag gtgccactcc cactgtcctt tcctaataaa atgaggaaat tgcatcgcat  15000
tgtctgagta ggtgtcattc tattctgggg ggtggggtgg ggcaggacag caagggggag  15060
gattgggaag acaatagcag gcatgctggg gatgcggtgg gctctatggc ttctgaggcg  15120
gaaagaacca gctggggctc gatcctctag ttggcgcgtc atggtccata tgaatatcct  15180
ccttagttcc tattccgcta gcctagaggg acagcccccc cccaaagccc ccagggatgt  15240
aattacgtcc ctcccccgct aggggcagca gcgagccgcc cggggctccg ctccggtccg  15300
gcgctccccc cgcatccccg agccggcagc gtgcggggac agcccgggca cggggaaggt  15360
ggcacgggat cgctttcctc tgaacgcttc tcgctgctct ttgagcctgc agacacctgg  15420
ggggatacgg ggaaaaagct ttaggctgaa agagagattt agaatgacag aatcatagaa  15480
cggcctgggt tgcaaaggag cacagtgctc atccagatcc aacccccctgc tatgtgcagg  15540
gtcatcaacc agcagcccag gctgcccaga gccacatcca gcctggcctt gaatgcctgc  15600
```

agggatgggg catccacagc ctccttgggc aacctgttca gtgcgtcacc accctctggg 15660
ggaaaaactg cctcctcata tccaacccaa acctcccctg tctcagtgta aagccattcc 15720
cccttgtcct atcaaggggg agtttgctgt gacattgttg gtctggggtg acacatgttt 15780
gccaattcag tgcatcacgg agaggcagat cttggggata aggaagtgca ggacagcatg 15840
gacgtgggac atgcaggtgt tgagggctct gggacactct ccaagtcaca gcgttcagaa 15900
cagccttaag gataagaaga taggatagaa ggacaaagag caagttaaaa cccagcatgg 15960
agaggagcac aaaaaggcca cagacactgc tggtccctgt gtctgagcct gcatgtttga 16020
tggtgtctgg atgcaagcag aaggggtgga agagcttgcc tggagagata cagctgggtc 16080
agtaggactg ggacaggcag ctggagaatt gccatgtaga tgttcataca atcgtcaaat 16140
catgaaggct ggaaaagccc tccaagatcc ccaagaccaa ccccaaccca cccaccgtgc 16200
ccactggcca tgtccctcag tgccacatcc ccacagttct tcatcacctc cagggacggt 16260 gacccccca cctccgtggg cagctgtgcc actgcagcac cgctctttgg agaaggtaaa 16320
tcttgctaaa tccagcccga ccctcccctg gcacaacgta aggccattat ctctcatcca 16380
actccaggac ggagtcagtg aggatggggc tggatccgaa gcagctccag cctacacaat 16440
cgctcaagac gtgtaatgct tttattatat attagtcacg atatctataa caagaaaata 16500
tatatataat aagttatcac gtaagtagaa catgaaataa caatataatt atcgtatgag 16560
ttaaatctta aaagtcacgt aaaagataat catgcgtcat tttgactcac gcggtcgtta 16620
tagttcaaaa tcagtgacac ttaccgcatt gacaagcacg cctcacggga gctccaagcg 16680
gcgactgaga tgtcctaaat gcacagcgac ggattcgcgc tatttagaaa gagagagcaa 16740
tatttcaaga atgcatgcgt caattttacg cagactatct ttctagggtt aaaaaagatt 16800
tgcgctttac tcgacctaaa ctttaaacac gtcatagaat cttcgtttga caaaaaccac 16860
attgtggggt accgagctct taattaaggc gcgccgggga ggttcccttt agtgagggtt 16920
aattgcgggt cgccctatag tgagtcgtat tacaattcac tggccgtcgt tttacaacgt 16980
cgtgactggg aaaaccctgg cgttacccaa cttaatcgcc ttgcagcaca tccccctttc 17040
gccagctggc gtaatagcga agaggcccgc accgatcgcc cttcccaaca gttgcgcagc 17100
ctgaatggcg aatggcaaat tgtaagcgtt aatattttgt taaaattcgc gttaaatttt 17160
tgttaaatca gctcattttt taaccaatag gccgaaatcg gcaaaatccc ttataaatca 17220
aaagaataga ccgagatagg gttgagtgtt gttccagttt ggaacaagag tccactatta 17280
aagaacgtgg actccaacgt caaagggcga aaaaccgtct atcagggcga tggcccacta 17340
cgtgaaccat caccctaatc aagttttttg gggtcgaggt gccgtaaagc actaaatcgg 17400
aaccctaaag ggagcccccg atttagagct tgacggggaa agccggcgaa cgtggcgaga 17460
aaggaaggga agaaagcgaa aggagcgggc gctagggcgc tggcaagtgt agcggtcacg 17520
ctgcgcgtaa ccaccacacc cgccgcgctt aatgcgccgc tacagggcgc gtcag 17575

<210> SEQ ID NO 9
<211> LENGTH: 5692
<212> TYPE: DNA
<213> ORGANISM: Artificial Sequence
<220> FEATURE:
<223> OTHER INFORMATION: Synthetic Polynucleotide

<400> SEQUENCE: 9
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccgca cgcgtgaggg cctatttccc atgattcctt 180
catatttgca tatacgatac aaggctgtta gagagataat tggaattaat ttgactgtaa 240
acacaaagat attagtacaa aatacgtgac gtagaaagta ataatttctt gggtagtttg 300
cagttttaaa attatgtttt aaaatggact atcatatgct taccgtaact tgaaagtatt 360
tcgatttctt ggctttatat atcttgtgga aaggacgaaa caccgcagcg ttacctctat 420
cgtagtttta gagctagaaa tagcaagtta aaataaggct agtccgttat caacttgaaa 480
aagtggcacc gagtcggtgc tttttggat ccgagggcct atttcccatg attccttcat 540
atttgcatat acgatacaag gctgttagag agataattgg aattaatttg actgtaaaca 600
caaagatatt agtacaaaat acgtgacgta gaaagtaata atttcttggg tagtttgcag 660
ttttaaaatt atgttttaaa atggactatc atatgcttac cgtaacttga aagtatttcg 720
atttcttggc tttatatatc ttgtggaaag gacgaaacac cgtgtaatag ctcctgcatg 780
ggttttagag ctagaaatag caagttaaaa taaggctagt ccgttatcaa cttgaaaaag 840
tggcaccgag tcggtgcttt ttttctagaa ggtaccaggt cttgaaagga gtgggaattg 900
gctccggtgc ccgtcagtgg gcagagcgca catcgcccac agtccccgag aagttggggg 960
gaggggtcgg caattgaacc ggtgcctaga gaaggtggcg cggggtaaac tgggaaagtg 1020
atgtcgtgta ctggctccgc ctttttcccg agggtggggg agaaccgtat ataagtgcag 1080
tagtcgccgt gaacgttctt tttcgcaacg ggtttgccgc cagaacacag gcgtacggcc 1140
accatgactt cgaaagttta tgatccagaa caaaggaaac ggatgataac tggtccgcag 1200
tggtgggcca gatgtaaaca aatgaatgtt cttgattcat ttattaatta ttatgattca 1260
gaaaaacatg cagaaaatgc tgttattttt ttacatggta acgcggcctc ttcttattta 1320
tggcgacatg ttgtgccaca tattgagcca gtagcgcggt gtattatacc agaccttatt 1380
ggtatgggca aatcaggcaa atctggtaat ggttcttata ggttacttga tcattacaaa 1440
tatcttactg catggtttga acttcttaat ttaccaaaga agatcatttt tgtcggccat 1500
gattggggtg cttgtttggc atttcattat agctatgagc atcaagataa gatcaaagca 1560
atagttcacg ctgaaagtgt agtagatgtg attgaatcat gggatgaatg gcctgatatt 1620
gaagaagata ttgcgttgat caaatctgaa gaaggagaaa aaatggtttt ggagaataac 1680
ttcttcgtgg aaaccatgtt gccatcaaaa atcatgagaa agttagaacc agaagaattt 1740
gcagcatatc ttgaaccatt caaagagaaa ggtgaagttc gtcgtccaac attatcatgg 1800
cctcgtgaaa tcccgttagt aaaaggtggt aaacctgacg ttgtacaaat tgttaggaat 1860
tataatgctt atctacgtgc aagtgatgat ttaccaaaaa tgtttattga atcggaccca 1920
ggattctttt ccaatgctat tgttgaaggt gccaagaagt ttcctaatac tgaatttgtc 1980
aaagtaaaag gtcttcattt ttcgcaagaa gatgcacctg atgaaatggg aaaatatatc 2040
aaatcgttcg ttgagcgagt tctcaaaaat gaacaataaa gcgctaataa aagatcttta 2100
ttttcattag atctgtgtgt tggttttttg tgtaagcttt ggctccaaca cagatgttct 2160
taggctacct aacttctaac ttttaatatc cagtcaacaa agaataccgc aagggtaggt 2220
gttgggatag ctgtcgacaa gctcatgcgg gtgtgtccac agggtatagc gtactatgca 2280
gaatatttgt actgagtgaa gtcatgatac attcctttga gagccattag ctgctacaaa 2340
acagtaatct ggctgtttag atcaacaagc taaatgatag aagatgaaag tactggtttc 2400
catgtatttt tattaagtgt tgatgagaaa gttgtaagtg acttacaggt tactctgtac 2460
atctgtagtc actgaattcg gaatatctta gagttttaca cacaaaggtg agtgttaaaa 2520
tattgataaa gtttttgata atcttgtgtg agacatgttc taatttagtt gtattttatt 2580
atttttattg taaggcctgc tgaaaatgac tgagtataaa cttgtggtcg tgggcgccga 2640
cggcgtgggc aagagcgctt tgacgataca gctaattcag aatcactttg tggatgagta 2700
tgatccaacc atcgaggtaa cgctgctcta cagtctgcgt gcgcttgtaa aggacggcag 2760
ccagccgctt tgaaaaagat atcattttta tatttattag aaaattatat tgaaagttat 2820
ttcagttata tgtgatgtcc tttagttcca aggctttaaa ctgggtgtta gggaaccata 2880
ggtgcaagaa agtccacttc tcatgagagc tcaccacaga gaaagaaagt ccacttctca 2940
ggtaaccacg tgcggaccga gcggccgcag gaacccctag tgatggagtt ggccactccc 3000
tctctgcgcg ctcgctcgct cactgaggcc gggcgaccaa aggtcgcccg acgcccgggc 3060
tttgcccggg cggcctcagt gagcgagcga gcgcgcagct gcctgcaggt attttctcct 3120
tacgcatctg tgcggtattt cacaccgcat acgtcaaagc aaccatagta cgcgccctgt 3180
agcggcgcat taagcgcggc gggtgtggtg gttacgcgca gcgtgaccgc tacacttgcc 3240
agcgccctag cgcccgctcc tttcgctttc ttcccttcct ttctcgccac gttcgccggc 3300
tttccccgtc aagctctaaa tcgggggctc cctttagggt tccgatttag tgctttacgg 3360
cacctcgacc ccaaaaaact tgatttgggt gatggttcac gtagtgggcc atcgccctga 3420
tagacggttt ttcgcccttt gacgttggag tccacgttct ttaatagtgg actcttgttc 3480
caaactggaa caacactcaa ccctatctcg ggctattctt ttgatttata agggattttg 3540
ccgatttcgg cctattggtt aaaaaatgag ctgatttaac aaaaatttaa cgcgaatttt 3600
aacaaaatat taacgtttac aattttatgg tgcactctca gtacaatctg ctctgatgcc 3660
gcatagttaa gccagccccg acacccgcca acacccgctg acgcgccctg acgggcttgt 3720
ctgctcccgg catccgctta cagacaagct gtgaccgtct ccgggagctg catgtgtcag 3780
aggttttcac cgtcatcacc gaaacgcgcg agacgaaagg gcctcgtgat acgcctattt 3840
ttataggtta atgtcatgat aataatggtt tcttagacgt caggtggcac ttttcgggga 3900
aatgtgcgcg gaacccctat ttgtttattt ttctaaatac attcaaatat gtatccgctc 3960
atgagacaat aaccctgata aatgcttcaa taatattgaa aaaggaagag tatgagtatt 4020
caacatttcc gtgtcgccct tattcccttt tttgcggcat tttgccttcc tgtttttgct 4080
cacccagaaa cgctggtgaa agtaaaagat gctgaagatc agttgggtgc acgagtgggt 4140
tacatcgaac tggatctcaa cagcggtaag atccttgaga gttttcgccc cgaagaacgt 4200
tttccaatga tgagcacttt taaagttctg ctatgtggcg cggtattatc ccgtattgac 4260
gccgggcaag agcaactcgg tcgccgcata cactattctc agaatgactt ggttgagtac 4320
tcaccagtca cagaaaagca tcttacggat ggcatgacag taagagaatt atgcagtgct 4380
gccataacca tgagtgataa cactgcggcc aacttacttc tgacaacgat cggaggaccg 4440
aaggagctaa ccgctttttt gcacaacatg ggggatcatg taactcgcct tgatcgttgg 4500
gaaccggagc tgaatgaagc cataccaaac gacgagcgtg acaccacgat gcctgtagca 4560
atggcaacaa cgttgcgcaa actattaact ggcgaactac ttactctagc ttcccggcaa 4620
caattaatag actggatgga ggcggataaa gttgcaggac cacttctgcg ctcggccctt 4680
ccggctggct ggtttattgc tgataaatct ggagccggtg agcgtgggtc tcgcggtatc 4740
attgcagcac tggggccaga tggtaagccc tcccgtatcg tagttatcta cacgacgggg 4800
agtcaggcaa ctatggatga acgaaataga cagatcgctg agataggtgc ctcactgatt 4860

```
aagcattggt aactgtcaga ccaagtttac tcatatatac tttagattga tttaaaactt   4920

catttttaat ttaaaaggat ctaggtgaag atcctttttg ataatctcat gaccaaaatc   4980

ccttaacgtg agttttcgtt ccactgagcg tcagaccccg tagaaaagat caaaggatct   5040

tcttgagatc ctttttttct gcgcgtaatc tgctgcttgc aaacaaaaaa accaccgcta   5100

ccagcggtgg tttgtttgcc ggatcaagag ctaccaactc tttttccgaa ggtaactggc   5160

ttcagcagag cgcagatacc aaatactgtc cttctagtgt agccgtagtt aggccaccac   5220

ttcaagaact ctgtagcacc gcctacatac ctcgctctgc taatcctgtt accagtggct   5280

gctgccagtg gcgataagtc gtgtcttacc gggttggact caagacgata gttaccggat   5340

aaggcgcagc ggtcgggctg aacggggggt tcgtgcacac agcccagctt ggagcgaacg   5400

acctacaccg aactgagata cctacagcgt gagctatgag aaagcgccac gcttcccgaa   5460

gggagaaagg cggacaggta tccggtaagc ggcagggtcg gaacaggaga gcgcacgagg   5520

gagcttccag ggggaaacgc ctggtatctt tatagtcctg tcgggtttcg ccacctctga   5580

cttgagcgtc gatttttgtg atgctcgtca ggggggcgga gcctatggaa aaacgccagc   5640

aacgcggcct ttttacggtt cctggccttt tgctggcctt ttgctcacat gt           5692
```

<210> SEQ ID NO 10
<211> LENGTH: 19
<212> TYPE: DNA
<213> ORGANISM: Nannospalax galili

<400> SEQUENCE: 10

```
ctcactatgt agaccaggc                                                  19
```

<210> SEQ ID NO 11
<211> LENGTH: 57
<212> TYPE: DNA
<213> ORGANISM: Homo sapiens

<400> SEQUENCE: 11

```
cctgtaatcc cagcactttc actttgggag gccgaggcga gtctcgctct gtcgccc        57
```

<210> SEQ ID NO 12
<211> LENGTH: 13890
<212> TYPE: DNA
<213> ORGANISM: Artificial Sequence
<220> FEATURE:
<223> OTHER INFORMATION: Synthetic Polynucleotide

<400> SEQUENCE: 12

```
gtggcacttt tcggggaaat gtgcgcggaa cccctatttg tttatttttc taaatacatt     60

caaatatgta tccgctcatg agacaataac cctgataaat gcttcaataa tattgaaaaa    120

ggaagagtat gagtattcaa catttccgtg tcgcccttat tccctttttt gcggcatttt    180

gccttcctgt ttttgctcac ccagaaacgc tggtgaaagt aaaagatgct gaagatcagt    240

tgggtgcacg agtgggttac atcgaactgg atctcaacag cggtaagatc cttgagagtt    300

ttcgccccga agaacgtttt ccaatgatga gcacttttaa agttctgcta tgtggcgcgg    360

tattatcccg tattgacgcc gggcaagagc aactcggtcg ccgcatacac tattctcaga    420

atgacttggt tgagtactca ccagtcacag aaaagcatct tacggatggc atgacagtaa    480

gagaattatg cagtgctgcc ataaccatga gtgataacac tgcggccaac ttacttctga    540

caacgatcgg aggaccgaag gagctaaccg cttttttgca caacatgggg gatcatgtaa    600
```

```
ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc ctttttgata   1080
atctcatgac caaaatccct taacgtgagt tttcgttcca ctgagcgtca gaccccgtag   1140
aaaagatcaa aggatcttct tgagatcctt tttttctgcg cgtaatctgc tgcttgcaaa   1200
caaaaaaacc accgctacca gcggtggttt gtttgccgga tcaagagcta ccaactcttt   1260
ttccgaaggt aactggcttc agcagagcgc agataccaaa tactgttctt ctagtgtagc   1320
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag gcgcagcggt cgggctgaac ggggggttcg tgcacacagc   1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740
tatggaaaaa cgccagcaac gcggcctttt tacggttcct ggccttttgc tggccttttg   1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacctcccct agcttaatta accctagaaa   2220
gataatcata ttgtgacgta cgttaaagat aatcatgcgt aaaattgacg catgtgtttt   2280
atcgatctgt atatcgaggt ttatttatta atttgaatag atattaagtt ttattatatt   2340
tacacttaca tactaataat aaattcaaca aacaatttat ttatgtttat ttatttatta   2400
aaaaaaaaca aaaactcaaa atttcttcta taaagtaaca aaacttttaa acattctctc   2460
ttttacaaaa ataaacttat tttgtacttt aaaaacagtc atgttgtatt ataaaataag   2520
taattagctt aacttataca taatagaaac aaattatact tattaatcgc attgattatt   2580
gactagtcgt attaagggtt ccggatcagc ttgattcgag ccccagctgg ttctttccgc   2640
ctcagaagcc atagagccca ccgcatcccc agcatgcctg ctattgtctt cccaatcctc   2700
ccccttgctg tcctgcccca ccccaccccc cagaatagaa tgacacctac tcagacaatg   2760
cgatgcaatt tcctcatttt attaggaaag gacagtggga gtggcacctt ccagggtcaa   2820
ggaaggcacg gggggagggc aaacaacaga tggctggcaa ctagaaggca cagtcgaggc   2880
tgatcagcga gctctagaga attgatcccc tcagaagaac tcgtcaagaa ggcgatagaa   2940
ggcgatgcgc tgcgaatcgg gagcggcgat accgtaaagc acgaggaagc ggtcagccca   3000
```

```
ttcgccgcct caggcaccgg gcttgcgggt catgcaccag gtgcgcggtc cttcgggcac   3060
ctcgacgtcg gcggtgacgg tgaagccgag ccgctcgtag aaggggaggt tgcggggcgc   3120
ggaggtctcc aggaaggcgg gcacccccggc gcgctcggcc gcctccactc cggggagcac   3180
gacggcgctg cccagaccct tgccctggtg gtcgggcgag acgccgacgg tggccaggaa   3240
ccacgcgggc tccttgggcc ggtgcggcgc caggaggcct tccatctgtt gctgcgcggc   3300
cagccgggaa ccgctcaact cggccatgcg cgggccgatc tcggcgaaca ccgcccccgc   3360
ttcgacgctc tccggcgtgg tccagaccgc caccgcggcg ccgtcgtccg cgacccacac   3420
cttgccgatg tcgagcccga cgcgcgtgag gaagagttct tgcagctcgg tgacccgctc   3480
gatgtggcgg tccgggtcga cggtgtggcg cgtggcgggg tagtcggcga acgcggcggc   3540
gagggtgcgt acggcccggg ggacgtcgtc gcgggtggcg aggcgcaccg tgggcttgta   3600
ctcggtcatg gtttagttcc tcaccttgtc gtattatact atgccgatat actatgccga   3660
tgattaattg tcaacacgtg ctgctgcagg tcgaaaggcc cggagatgag gaagaggaga   3720
acagcgcggc agacgtgcgc ttttgaagcg tgcagaatgc cgggcctccg gaggaccttc   3780
gggcgcccgc cccgcccctg agcccgcccc tgagcccgcc cccggaccca ccccttccca   3840
gcctctgagc ccagaaagcg aaggagcaaa gctgctattg gccgctgccc caaaggccta   3900
cccgcttcca ttgctcagcg gtgctgtcca tctgcacgag actagtgaga cgtgctactt   3960
ccatttgtca cgtcctgcac gacgcgagct gcggggcggg ggggaacttc ctgactaggg   4020
gaggagtaga aggtggcgcg aaggggccac caaagaacgg agccggttgg cgcctaccgg   4080
tggatgtgga atgtgtgcga gccagaggcc acttgtgtag cgccaagtgc ccagcggggc   4140
tgctaaagcg catgctccag actgccttgg gaaaagcgcc tcccctaccc ggtagacacc   4200
ccacagtggg tggcctaggg acaggattgc aactccagtc tttcttcttc ttgggcggga   4260
gtcactagtt attaatagta atcaattacg gggtcattag ttcatagccc atatatggag   4320
ttccgcgtta cataacttac ggtaaatggc ccgcctggct gaccgcccaa cgacccccgc   4380
ccattgacgt caataatgac gtatgttccc atagtaacgc caatagggac tttccattga   4440
cgtcaatggg tggactattt acggtaaact gcccacttgg cagtacatca agtgtatcat   4500
atgccaagta cgccccctat tgacgtcaat gacggtaaat ggcccgcctg gcattatgcc   4560
cagtacatga ccttatggga ctttcctact tggcagtaca tctacgtatt agtcatcgct   4620
attaccatgg gtcgaggtga gccccacgtt ctgcttcact ctccccatct cccccccctc   4680
cccaccccca attttgtatt tatttatttt ttaattattt tgtgcagcga tgggggcggg   4740
gggggggggg gcgcgcgcca ggcggggcgg ggcggggcga ggggcggggc ggggcgaggc   4800
ggagaggtgc ggcggcagcc aatcagagcg gcgcgctccg aaagtttcct tttatggcga   4860
ggcggcggcg gcggcggccc tataaaaagc gaagcgcgcg gcgggcggga gtcgctgcgt   4920
tgccttcgcc ccgtgccccg ctccgcgccg cctcgcgccg cccgccccgg ctctgactga   4980
ccgcgttact cccacaggtg agcgggcggg acggcccttc tcctccgggc tgtaattagc   5040
gcttggttta atgacggctc gtttcttttc tgtggctgcg tgaaagcctt aaagggctcc   5100
gggagggccc tttgtgcggg gggagcggc tcggggggtg cgtgcgtgtg tgtgtgcgtg    5160
gggagcgccg cgtgcggccc gcgctgcccg gcggctgtga gcgctgcggg cgcggcgcgg   5220
ggctttgtgc gctccgcgtg tgcgcgaggg gagcgcggcc gggggcggtg ccccgcggtg   5280
cggggggggct gcgaggggaa caaaggctgc gtgcggggtg tgtgcgtggg ggggtgagca  5340
```

-continued gggggtgtgg gcgcggcggt cgggctgtaa cccccccctg caccccccctc cccgagttgc 5400 tgagcacggc ccggcttcgg gtgcggggct ccgtgcgggg cgtggcgcgg ggctcgccgt 5460
gccgggcggg gggtggcggc aggtgggggt gccgggcggg gcggggccgc ctcgggccgg 5520
ggagggctcg gggaggggc gcggcggccc cggagcgccg gcggctgtcg aggcgcggcg 5580
agccgcagcc attgcctttt atggtaatcg tgcgagaggg cgcagggact tcctttgtcc 5640
caaatctggc ggagccgaaa tctgggaggc gccgccgcac cccctctagc gggcgcgggc 5700
gaagcggtgc ggcgccggca ggaaggaaat gggcggggag ggccttcgtg cgtcgccgcg 5760
ccgccgtccc cttctccatc tccagcctcg gggctgccgc agggggacgg ctgccttcgg 5820
gggggacggg gcagggcggg gttcggcttc tggcgtgtga ccggcggctc tagagcctct 5880
gctaaccatg ttcatgcctt cttctttttc ctacagctcc tgggcaacgt gctggttatt 5940
gtgctgtctc atcattttgg caaagaattc gccaccatgg tgcccaagaa gaagaggaaa 6000
gtctctagac tggacaagag caaagtcata aactctgctc tggaattact caatggagtc 6060
ggtatcgaag gcctgacgac aaggaaactc gctcaaaagc tgggagttga gcagcctacc 6120
ctgtactggc acgtgaagaa caagcgggcc ctgctcgatg ccctgccaat cgagatgctg 6180
gacaggcatc atacccactc ctgcccccctg gaaggcgagt catggcaaga ctttctgcgg 6240
aacaacgcca agtcataccg ctgtgctctc ctctcacatc gcgacggggc taaagtgcat 6300
ctcggcaccc gcccaacaga gaaacagtac gaaaccctgg aaaatcagct cgcgttcctg 6360
tgtcagcaag gcttctccct ggagaacgca ctgtacgctc tgtccgccgt gggccacttt 6420
acactgggct gcgtattgga ggaacaggag catcaagtag caaaagagga aagagagaca 6480
cctaccaccg attctatgcc cccacttctg aaacaagcaa ttgagctgtt cgaccggcag 6540
ggagccgaac ctgccttcct tttcggcctg gaactaatca tatgtggcct ggagaaacag 6600
ctaaagtgcg aaagcggcgg gccgaccgac gcccttgacg attttgactt agacatgctc 6660
ccagccgatg cccttgacga ctttgacctt gatatgctgc ctgctgacgc tcttgacgat 6720
tttgaccttg acatgctccc cgggtaaagc ggccgcgact ctagatcata atcagccata 6780
ccacatttgt agaggtttta cttgctttaa aaaacctccc acacctcccc ctgaacctga 6840
aacataaaat gaatgcaatt gttgttgtta acttgtttat tgcagcttat aatggttaca 6900
aataaagcaa tagcatcaca aatttcacaa ataaagcatt tttttcactg cattctagtt 6960
gtggtttgtc caaactcatc aatgtatctt aagggatccc tagagggaca gcccccccccc 7020 aaagccccca gggatgtaat tacgtccctc ccccgctagg ggcagcagcg agccgcccgg 7080
ggctccgctc cggtccggcg ctccccccgc atccccgagc cggcagcgtg cggggacagc 7140
ccgggcacgg ggaaggtggc acgggatcgc tttcctctga acgcttctcg ctgctctttg 7200
agcctgcaga cacctggggg gatacgggga aaaagcttta ggctgaaaga gagatttaga 7260
atgacagaat catagaacgg cctgggttgc aaaggagcac agtgctcatc cagatccaac 7320
cccctgctat gtgcagggtc atcaaccagc agcccaggct gcccagagcc acatccagcc 7380
tggccttgaa tgcctgcagg gatggggcat ccacagcctc cttgggcaac ctgttcagtg 7440
cgtcaccacc ctctggggga aaaactgcct cctcatatcc aacccaaacc tcccctgtct 7500
cagtgtaaag ccattccccc ttgtcctatc aagggggagt ttgctgtgac attgttggtc 7560
tggggtgaca catgtttgcc aattcagtgc atcacggaga ggcagatctt ggggataagg 7620
aagtgcagga cagcatggac gtgggacatg caggtgttga gggctctggg acactctcca 7680
agtcacagcg ttcagaacag ccttaaggat aagaagatag gatagaagga caaagagcaa 7740
gttaaaaccc agcatggaga ggagcacaaa aaggccacag acactgctgg tccctgtgtc 7800
tgagcctgca tgtttgatgg tgtctggatg caagcagaag ggtggaaga gcttgcctgg 7860
agagatacag ctgggtcagt aggactggga caggcagctg gagaattgcc atgtagatgt 7920
tcatacaatc gtcaaatcat gaaggctgga aaagccctcc aagatcccca agaccaaccc 7980
caacccaccc accgtgccca ctggccatgt ccctcagtgc cacatcccca cagttcttca 8040
tcacctccag ggacggtgac ccccccacct ccgtgggcag ctgtgccact gcagcaccgc 8100
tctttggaga aggtaaatct tgctaaatcc agcccgaccc tcccctggca caacgtaagg 8160
ccattatctc tcatccaact ccaggacgga gtcagtgagg atggggctgt cgacctagag 8220
ggacagcccc cccccaaagc ccccagggat gtaattacgt ccctcccccg ctaggggcag 8280
cagcgagccg cccggggctc cgctccggtc cggcgctccc cccgcatccc cgagccggca 8340
gcgtgcgggg acagcccggg cacggggaag gtggcacggg atcgctttcc tctgaacgct 8400
tctcgctgct ctttgagcct gcagacacct ggggggatac ggggaaaaag ctttaggctg 8460
aaagagagat ttagaatgac agaatcatag aacggcctgg gttgcaaagg agcacagtgc 8520
tcatccagat ccaaccccct gctatgtgca gggtcatcaa ccagcagccc aggctgccca 8580
gagccacatc cagcctggcc ttgaatgcct gcagggatgg ggcatccaca gcctccttgg 8640
gcaacctgtt cagtgcgtca ccaccctctg gggaaaaaac tgcctcctca tatccaaccc 8700
aaacctcccc tgtctcagtg taaagccatt ccccccttgtc ctatcaaggg ggagtttgct 8760
gtgacattgt tggtctgggg tgacacatgt ttgccaattc agtgcatcac ggagaggcag 8820
atcttgggga taaggaagtg caggacagca tggacgtggg acatgcaggt gttgagggct 8880
ctgggacact ctccaagtca cagcgttcag aacagcctta aggataagaa gataggatag 8940
aaggacaaag agcaagttaa aacccagcat ggagaggagc acaaaaaggc cacagacact 9000
gctggtccct gtgtctgagc ctgcatgttt gatggtgtct ggatgcaagc agaaggggtg 9060
gaagagcttg cctggagaga tacagctggg tcagtaggac tgggacaggc agctggagaa 9120
ttgccatgta gatgttcata caatcgtcaa atcatgaagg ctggaaaagc cctccaagat 9180
ccccaagacc aaccccaacc cacccaccgt gcccactggc catgtccctc agtgccacat 9240
ccccacagtt cttcatcacc tccagggacg gtgacccccc cacctccgtg ggcagctgtg 9300
ccactgcagc accgctcttt ggagaaggta aatcttgcta aatccagccc gaccctcccc 9360
tggcacaacg taaggccatt atctctcatc caactccagg acggagtcag tgaggatggg 9420
gctcaattgt ttactcccta tcagtgatag agaacgtatg aagagtttac tccctatcag 9480
tgatagagaa cgtatgcaga ctttactccc tatcagtgat agagaacgta taaggagttt 9540
actccctatc agtgatagag aacgtatgac cagtttactc cctatcagtg atagagaacg 9600
tatctacagt ttactcccta tcagtgatag agaacgtata tccagtttac tccctatcag 9660
tgatagagaa cgtataagct ttaggcgtgt acggtgggcg cctataaaag cagagctcgt 9720
ttagtgaacc gtcagatcgc ctggagcaat tccacaacac ttttgtctta taccaacttt 9780
ccgtaccact tcctaccctc gtaaaaagct tgtccaccat gagattcaaa agccacactg 9840
tggaattgag gaggccctgc agcgacatgg agggagctgc tttgctgaga gtctctgtcc 9900
tctgcatctg gatgagtgca cttttccttg gtgtgggagt gagggcagag gaagctggag 9960
cgagggtgca acaaaacgtt ccaagtggga cagatactgg agatcctcaa agtaagcccc 10020
tcggtgactg ggctgctggc accatggacc cagagagcag tatctttatt gaggatgcca 10080

-continued

```
ttaagtattt caaggaaaaa gtgagcacac agaatctgct actcctgctg actgataatg  10140
aggcctggaa cggattcgtg gctgctgctg aactgcccag gaatgaggca gatgagctcc  10200
gtaaagctct ggacaacctt gcaagacaaa tgatcatgaa agacaaaaac tggcacgata  10260
aaggccagca gtacagaaac tggtttctga aagagtttcc tcggttgaaa agtgagcttg  10320
aggataacat aagaaggctc cgtgcccttg cagatggggt tcagaaggtc cacaaaggca  10380
ccaccatcgc caatgtggtg tctggctctc tcagcatttc ctctggcatc ctgaccctcg  10440
tcggcatggg tctggcaccc ttcacagagg gaggcagcct tgtactcttg gaacctggga  10500
tggagttggg aatcacagcc gctttgaccg ggattaccag cagtaccatg gactacggaa  10560
agaagtggtg gacacaagcc caagcccacg acctggtcat caaaagcctt gacaaattga  10620
aggaggtgag ggagtttttg ggtgagaaca tatccaactt tctttcctta gctggcaata  10680
cttaccaact cacacgaggc attgggaagg acatccgtgc cctcagacga gccagagcca  10740
atcttcagtc agtaccgcat gcctcagcct cacgcccacg agtcactgag ccaatctcag  10800
ctgaaagcgg tgaacaggtg gagagggtta atgaacccag catcctggaa atgagcagag  10860
gagtcaagct cacggatgtg gcccctgtaa gcttctttct tgtgctggat gtagtctacc  10920
tcgtgtacga atcaaagcac ttacatgagg gggcaaagtc agagacagct gaggagctga  10980
agaaggtggc tcaggagctg gaggagaagc taaacattct caacaataat tataagattc  11040
tgcaggcgga ccaagaactg tgaaattcta aaatacagca tagcaaaact ttaacctcca  11100
aatcaagcct ctacttgaat ccttttctga gggatgaata aggcataggc atcaggggct  11160
gttgccaatg tgcattagct gtttgcagcc tcaccttctt tcatggagtt taagatatag  11220
tgtattttcc caaggtttga actagctctt catttcttta tgttttaaat gcactgacct  11280
cccacattcc ctttttagta aaatattcag aaataattta aatacatcat tgcaatgaaa  11340
ataaatgttt tttattaggc agaatccaga tgctcaaggc ccttcataat atcccccagt  11400
ttagtagttg gacttaggga acaaaggaac ctttaataga aattggacag caagaaagcg  11460
agcttctagc tcgagatggt ccatatgaat atcctcctta gttcctattc cgctagccta  11520
gagggacagc ccccccccaa agcccccagg gatgtaatta cgtccctccc ccgctagggg  11580
cagcagcgag ccgcccgggg ctccgctccg gtccggcgct ccccccgcat ccccgagccg  11640
gcagcgtgcg gggacagccc gggcacgggg aaggtggcac gggatcgctt tcctctgaac  11700
gcttctcgct gctctttgag cctgcagaca cctgggggga tacggggaaa aagctttagg  11760
ctgaaagaga gatttagaat gacagaatca tagaacggcc tgggttgcaa aggagcacag  11820
tgctcatcca gatccaaccc cctgctatgt gcagggtcat caaccagcag cccaggctgc  11880
ccagagccac atccagcctg gccttgaatg cctgcaggga tggggcatcc acagcctcct  11940
tgggcaacct gttcagtgcg tcaccaccct ctgggggaaa aactgcctcc tcatatccaa  12000
cccaaacctc ccctgtctca gtgtaaagcc attccccctt gtcctatcaa gggggagttt  12060
gctgtgacat tgttggtctg gggtgacaca tgtttgccaa ttcagtgcat cacggagagg  12120
cagatcttgg ggataaggaa gtgcaggaca gcatggacgt gggacatgca ggtgttgagg  12180
gctctgggac actctccaag tcacagcgtt cagaacagcc ttaaggataa gaagatagga  12240
tagaaggaca aagagcaagt taaaacccag catggagagg agcacaaaaa ggccacagac  12300
actgctggtc cctgtgtctg agcctgcatg tttgatggtg tctggatgca agcagaaggg  12360
gtggaagagc ttgcctggag agatacagct gggtcagtag gactgggaca ggcagctgga  12420
gaattgccat gtagatgttc atacaatcgt caaatcatga aggctggaaa agccctccaa  12480
```

gatccccaag accaacccca acccacccac cgtgcccact ggccatgtcc ctcagtgcca 12540
catccccaca gttcttcatc acctccaggg acggtgaccc ccccacctcc gtgggcagct 12600
gtgccactgc agcaccgctc tttggagaag gtaaatcttg ctaaatccag cccgaccctc 12660
ccctggcaca acgtaaggcc attatctctc atccaactcc aggacggagt cagtgaggat 12720
ggggctggat ccgaagcagc tccagcctac acaatcgctc aagacgtgta atgcttttat 12780
tatatattag tcacgatatc tataacaaga aaatatatat ataataagtt atcacgtaag 12840
tagaacatga aataacaata taattatcgt atgagttaaa tcttaaaagt cacgtaaaag 12900
ataatcatgc gtcattttga ctcacgcggt cgttatagtt caaaatcagt gacacttacc 12960
gcattgacaa gcacgcctca cgggagctcc aagcggcgac tgagatgtcc taaatgcaca 13020
gcgacggatt cgcgctattt agaaagagag agcaatattt caagaatgca tgcgtcaatt 13080
ttacgcagac tatctttcta gggttaaaaa agatttgcgc tttactcgac ctaaacttta 13140
aacacgtcat agaatcttcg tttgacaaaa accacattgt ggggtaccga gctcttaatt 13200
aaggcgcgcc ggggaggttc cctttagtga gggttaattg cgggtcgccc tatagtgagt 13260
cgtattacaa ttcactggcc gtcgttttac aacgtcgtga ctgggaaaac cctggcgtta 13320
cccaacttaa tcgccttgca gcacatcccc ctttcgccag ctggcgtaat agcgaagagg 13380
cccgcaccga tcgcccttcc caacagttgc gcagcctgaa tggcgaatgg caaattgtaa 13440
gcgttaatat tttgttaaaa ttcgcgttaa atttttgtta aatcagctca ttttttaacc 13500
aataggccga aatcggcaaa atcccttata aatcaaaaga atagaccgag atagggttga 13560
gtgttgttcc agtttggaac aagagtccac tattaaagaa cgtggactcc aacgtcaaag 13620
ggcgaaaaac cgtctatcag ggcgatggcc cactacgtga accatcaccc taatcaagtt 13680
ttttggggtc gaggtgccgt aaagcactaa atcggaaccc taaagggagc ccccgattta 13740
gagcttgacg gggaaagccg gcgaacgtgg cgagaaagga agggaagaaa gcgaaaggag 13800
cgggcgctag ggcgctggca agtgtagcgg tcacgctgcg cgtaaccacc acacccgccg 13860
cgcttaatgc gccgctacag ggcgcgtcag 13890

<210> SEQ ID NO 13
<211> LENGTH: 17331
<212> TYPE: DNA
<213> ORGANISM: Artificial Sequence
<220> FEATURE:
<223> OTHER INFORMATION: Synthetic Polynucleotide

<400> SEQUENCE: 13
gtggcacttt tcggggaaat gtgcgcggaa cccctatttg tttatttttc taaatacatt 60
caaatatgta tccgctcatg agacaataac cctgataaat gcttcaataa tattgaaaaa 120
ggaagagtat gagtattcaa catttccgtg tcgcccttat tccctttttt gcggcatttt 180
gccttcctgt ttttgctcac ccagaaacgc tggtgaaagt aaaagatgct gaagatcagt 240
tgggtgcacg agtgggttac atcgaactgg atctcaacag cggtaagatc cttgagagtt 300
ttcgccccga agaacgtttt ccaatgatga gcacttttaa agttctgcta tgtggcgcgg 360
tattatcccg tattgacgcc gggcaagagc aactcggtcg ccgcatacac tattctcaga 420
atgacttggt tgagtactca ccagtcacag aaaagcatct tacggatggc atgacagtaa 480
gagaattatg cagtgctgcc ataaccatga gtgataacac tgcggccaac ttacttctga 540
caacgatcgg aggaccgaag gagctaaccg cttttttgca caacatgggg gatcatgtaa 600

-continued

```
ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc ctttttgata   1080
atctcatgac caaaatccct taacgtgagt tttcgttcca ctgagcgtca gaccccgtag   1140
aaaagatcaa aggatcttct tgagatcctt tttttctgcg cgtaatctgc tgcttgcaaa   1200
caaaaaaacc accgctacca gcggtggttt gtttgccgga tcaagagcta ccaactcttt   1260
ttccgaaggt aactggcttc agcagagcgc agataccaaa tactgttctt ctagtgtagc   1320
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag gcgcagcggt cgggctgaac ggggggttcg tgcacacagc   1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740
tatggaaaaa cgccagcaac gcggcctttt tacggttcct ggccttttgc tggccttttg   1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacctcccct agcttaatta accctagaaa   2220
gataatcata ttgtgacgta cgttaaagat aatcatgcgt aaaattgacg catgtgtttt   2280
atcgatctgt atatcgaggt ttatttatta atttgaatag atattaagtt ttattatatt   2340
tacacttaca tactaataat aaattcaaca aacaatttat ttatgtttat ttatttatta   2400
aaaaaaaaca aaaactcaaa atttcttcta taaagtaaca aaacttttaa acattctctc   2460
ttttacaaaa ataaacttat tttgtacttt aaaaacagtc atgttgtatt ataaaataag   2520
taattagctt aacttataca taatagaaac aaattatact tattaatcgc attgattatt   2580
gactagtcac aatatgatta tctttctagg gttaattaag atatctgaag ttcctatact   2640
ttctagagaa taggaacttc ggaataggaa cttcaaagca agctagagac cattaagggt   2700
tccggatcag cttgattcga gccccagctg gttctttccg cctcagaagc catagagccc   2760
accgcatccc cagcatgcct gctattgtct tcccaatcct ccccccttgct gtcctgcccc   2820
accccacccc ccagaataga atgacaccta ctcagacaat gcgatgcaat ttcctcattt   2880
tattaggaaa ggacagtggg agtggcacct tccagggtca aggaaggcac gggggagggg   2940
caaacaacag atggctggca actagaaggc acagtcgagg ctgatcagcg agctctagag   3000
```

aattgatccc ctcagaagaa ctcgtcaaga aggcgataga aggcgatgcg ctgcgaatcg 3060
ggagcggcga taccgtaaag cacgaggaag cggtcagccc attcgccgcc aagctcttca 3120
gcaatatcac gggtagccaa cgctatgtcc tgatagcggt ccgccacacc cagccggcca 3180
cagtcgatga atccagaaaa gcggccattt tccaccatga tattcggcaa gcaggcatcg 3240
ccatgggtca cgacgagatc ctcgccgtcg ggcatgcgcg ccttgagcct ggcgaacagt 3300
tcggctggcg cgagcccctg atgctcttcg tccagatcat cctgatcgac aagaccggct 3360
tccatccgag tacgtgctcg ctcgatgcga tgtttcgctt ggtggtcgaa tgggcaggta 3420
gccggatcaa gcgtatgcag ccgccgcatt gcatcagcca tgatggatac tttctcggca 3480
ggagcaaggt gagatgacag gagatcctgc cccggcactt cgcccaatag cagccagtcc 3540
cttcccgctt cagtgacaac gtcgagcaca gctgcgcaag gaacgcccgt cgtggccagc 3600
cacgatagcc gcgctgcctc gtcctgcagt tcattcaggg caccggacag gtcggtcttg 3660
acaaaaagaa ccgggcgccc ctgcgctgac agccggaaca cggcggcatc agagcagccg 3720
attgtctgtt gtgcccagtc atagccgaat agcctctcca cccaagcggc cggagaacct 3780
gcgtgcaatc catcttgttc aatggccgat cccatggcgg tatcgataag ctagcttggg 3840
ctgcaggtcg agggacctaa ttaagggttc cggatccact agttctagag cggcctcgac 3900
tctacgatac cgtcgatccc cactggaaag accgcgaaga gtttgtcctc aaccgcgagc 3960
tgtggaaaaa aaagggacag gataagtatg acatcatcaa ggaaaccctg gactactgcg 4020
ccctacagat ccctgaagtt cctatacttt ctagagaata ggaacttcgg aataggaact 4080
tcaaagatgc aactccagtc tttcttcttc ttgggcggga gtctactagt tattaatagt 4140
aatcaattac ggggtcatta gttcatagcc catatatgga gttccgcgtt acataactta 4200
cggtaaatgg cccgcctggc tgaccgccca acgacccccg cccattgacg tcaataatga 4260
cgtatgttcc catagtaacg ccaataggga ctttccattg acgtcaatgg gtggactatt 4320
tacggtaaac tgcccacttg gcagtacatc aagtgtatca tatgccaagt acgcccccta 4380
ttgacgtcaa tgacggtaaa tggcccgcct ggcattatgc ccagtacatg accttatggg 4440
actttcctac ttggcagtac atctacgtat tagtcatcgc tattaccatg ggtcgaggtg 4500
agccccacgt tctgcttcac tctccccatc tcccccccct ccccaccccc aattttgtat 4560
ttatttattt tttaattatt ttgtgcagcg atgggggcgg gggggggggg ggcgcgcgcc 4620
aggcggggcg gggcggggcg aggggcgggg cggggcgagg cggagaggtg cggcggcagc 4680
caatcagagc ggcgcgctcc gaaagtttcc ttttatggcg aggcggcggc ggcggcggcc 4740
ctataaaaag cgaagcgcgc ggcgggcggg agtcgctgcg ttgccttcgc cccgtgcccc 4800
gctccgcgcc gcctcgcgcc gcccgccccg gctctgactg accgcgttac tcccacaggt 4860
gagcgggcgg gacggccctt ctcctccggg ctgtaattag cgcttggttt aatgacggct 4920
cgtttctttt ctgtggctgc gtgaaagcct taaagggctc cgggagggcc ctttgtgcgg 4980
gggggagcgg ctcggggggt gcgtgcgtgt gtgtgtgcgt ggggagcgcc gcgtgcggcc 5040
cgcgctgccc ggcggctgtg agcgctgcgg gcgcggcgcg gggctttgtg cgctccgcgt 5100
gtgcgcgagg ggagcgcggc cgggggcggt gccccgcggt gcgggggggc tgcgagggga 5160
acaaaggctg cgtgcggggt gtgtgcgtgg gggggtgagc agggggtgtg ggcgcggcgg 5220
tcgggctgta acccccccct gcacccccct ccccgagttg ctgagcacgg cccggcttcg 5280
ggtgcggggc tccgtgcggg gcgtggcgcg gggctcgccg tgccgggcgg ggggtggcgg 5340
caggtggggg tgccgggcgg ggcggggccg cctcgggccg gggagggctc gggggagggg 5400
cgcggcggcc ccggagcgcc ggcggctgtc gaggcgcggc gagccgcagc cattgccttt 5460
tatggtaatc gtgcgagagg gcgcagggac ttcctttgtc ccaaatctgg cggagccgaa 5520
atctgggagg cgccgccgca ccccctctag cgggcgcggg cgaagcggtg cggcgccggc 5580
aggaaggaaa tgggcgggga gggccttcgt gcgtcgccgc gccgccgtcc ccttctccat 5640
ctccagcctc ggggctgccg caggggggacg gctgccttcg ggggggacgg ggcagggcgg 5700
ggttcggctt ctggcgtgtg accggcggct ctagagcctc tgctaaccat gttcatgcct 5760
tcttcttttt cctacagctc ctgggcaacg tgctggttat tgtgctgtct catcattttg 5820
gcaaagaatt cgccaccatg gtgcccaaga agaagaggaa agtctctaga ctggacaaga 5880
gcaaagtcat aaactctgct ctggaattac tcaatggagt cggtatcgaa ggcctgacga 5940
caaggaaact cgctcaaaag ctgggagttg agcagcctac cctgtactgg cacgtgaaga 6000
acaagcgggc cctgctcgat gccctgccaa tcgagatgct ggacaggcat catacccact 6060
cctgcccccct ggaaggcgag tcatggcaag actttctgcg gaacaacgcc aagtcatacc 6120
gctgtgctct cctctcacat cgcgacgggg ctaaagtgca tctcggcacc cgcccaacag 6180
agaaacagta cgaaaccctg gaaaatcagc tcgcgttcct gtgtcagcaa ggcttctccc 6240
tggagaacgc actgtacgct ctgtccgccg tgggccactt tacactgggc tgcgtattgg 6300
aggaacagga gcatcaagta gcaaaagagg aaagagagac acctaccacc gattctatgc 6360
ccccacttct gaaacaagca attgagctgt tcgaccggca gggagccgaa cctgccttcc 6420
ttttcggcct ggaactaatc atatgtggcc tggagaaaca gctaaagtgc gaaagcggcg 6480
ggccgaccga cgcccttgac gattttgact tagacatgct cccagccgat gcccttgacg 6540
actttgacct tgatatgctg cctgctgacg ctcttgacga ttttgacctt gacatgctcc 6600
ccgggtaaag cggccgcgac tctagatcat aatcagccat accacatttg tagaggtttt 6660
acttgcttta aaaaacctcc cacacctccc cctgaacctg aaacataaaa tgaatgcaat 6720
tgttgttgtt aacttgttta ttgcagctta taatggttac aaataaagca atagcatcac 6780
aaatttcaca aataaagcat ttttttcact gcattctagt tgtggtttgt ccaaactcat 6840
caatgtatct taagggatcc ctagagggac agccccccc caaagccccc agggatgtaa 6900
ttacgtccct cccccgctag ggcagcagcg gagccgcccg gggctccgct ccggtccggc 6960
gctccccccg catccccgag ccggcagcgt gcggggacag cccgggcacg gggaaggtgg 7020
cacgggatcg ctttcctctg aacgcttctc gctgctcttt gagcctgcag acacctgggg 7080
ggatacgggg aaaaagcttt aggctgaaag agagatttag aatgacagaa tcatagaacg 7140
gcctgggttg caaaggagca cagtgctcat ccagatccaa ccccctgcta tgtgcagggt 7200
catcaaccag cagcccaggc tgcccagagc cacatccagc ctggccttga atgcctgcag 7260
ggatggggca tccacagcct ccttgggcaa cctgttcagt gcgtcaccac cctctggggg 7320
aaaaactgcc tcctcatatc caacccaaac ctcccctgtc tcagtgtaaa gccattcccc 7380
cttgtcctat caagggggag tttgctgtga cattgttggt ctggggtgac acatgtttgc 7440
caattcagtg catcacggag aggcagatct tggggataag gaagtgcagg acagcatgga 7500
cgtgggacat gcaggtgttg agggctctgg gacactctcc aagtcacagc gttcagaaca 7560
gccttaagga taagaagata ggatagaagg acaaagagca agttaaaacc cagcatggag 7620
aggagcacaa aaaggccaca gacactgctg gtccctgtgt ctgagcctgc atgtttgatg 7680
gtgtctggat gcaagcagaa ggggtggaag agcttgcctg gagagataca gctgggtcag 7740

```
taggactggg acaggcagct ggagaattgc catgtagatg ttcatacaat cgtcaaatca   7800
tgaaggctgg aaaagccctc caagatcccc aagaccaacc ccaacccacc caccgtgccc   7860
actggccatg tccctcagtg ccacatcccc acagttcttc atcacctcca gggacggtga   7920
cccccccacc tccgtgggca gctgtgccac tgcagcaccg ctctttggag aaggtaaatc   7980
ttgctaaatc cagcccgacc ctcccctggc acaacgtaag gccattatct ctcatccaac   8040
tccaggacgg agtcagtgag gatggggctg tcgacctaga gggacagccc ccccccaaag   8100
cccccaggga tgtaattacg tccctccccc gctaggggca gcagcgagcc gcccggggct   8160
ccgctccggt ccggcgctcc ccccgcatcc ccgagccggc agcgtgcggg gacagcccgg   8220
gcacggggaa ggtggcacgg gatcgctttc ctctgaacgc ttctcgctgc tctttgagcc   8280
tgcagacacc tggggggata cggggaaaaa gctttaggct gaaagagaga tttagaatga   8340
cagaatcata gaacggcctg ggttgcaaag gagcacagtg ctcatccaga tccaaccccc   8400
tgctatgtgc agggtcatca accagcagcc caggctgccc agagccacat ccagcctggc   8460
cttgaatgcc tgcagggatg gggcatccac agcctccttg ggcaacctgt tcagtgcgtc   8520
accaccctct gggggaaaaa ctgcctcctc atatccaacc caaacctccc ctgtctcagt   8580
gtaaagccat tccccttgt cctatcaagg gggagtttgc tgtgacattg ttggtctggg   8640
gtgacacatg tttgccaatt cagtgcatca cggagaggca gatcttgggg ataaggaagt   8700
gcaggacagc atggacgtgg gacatgcagg tgttgagggc tctgggacac tctccaagtc   8760
acagcgttca gaacagcctt aaggataaga agataggata gaaggacaaa gagcaagtta   8820
aaacccagca tggagaggag cacaaaaagg ccacagacac tgctggtccc tgtgtctgag   8880
cctgcatgtt tgatggtgtc tggatgcaag cagaaggggt ggaagagctt gcctggagag   8940
atacagctgg gtcagtagga ctgggacagg cagctggaga attgccatgt agatgttcat   9000
acaatcgtca aatcatgaag gctggaaaag ccctccaaga tccccaagac caaccccaac   9060
ccacccaccg tgcccactgg ccatgtccct cagtgccaca tccccacagt tcttcatcac   9120
ctccagggac ggtgaccccc ccacctccgt gggcagctgt gccactgcag caccgctctt   9180
tggagaaggt aaatcttgct aaatccagcc cgaccctccc ctggcacaac gtaaggccat   9240
tatctctcat ccaactccag gacggagtca gtgaggatgg ggctcaattg tttactccct   9300
atcagtgata gagaacgtat gaagagttta ctccctatca gtgatagaga acgtatgcag   9360
actttactcc ctatcagtga tagagaacgt ataaggagtt tactccctat cagtgataga   9420
gaacgtatga ccagtttact ccctatcagt gatagagaac gtatctacag tttactccct   9480
atcagtgata gagaacgtat atccagttta ctccctatca gtgatagaga acgtataagc   9540
tttaggcgtg tacggtgggc gcctataaaa gcagagctcg tttagtgaac cgtcagatcg   9600
cctggagcaa ttccacaaca cttttgtctt ataccaactt tccgtaccac ttcctaccct   9660
cgtaaaaagc ttgtccacca tggctcctaa gaaaaagcgg aaggtggaca agaaatactc   9720
aatcgggctg gacatcggaa ctaactcagt ggggtgggca gtcattactg acgagtacaa   9780
agtgccaagc aagaaattta aggtcctggg caacaccgat aggcactcca tcaagaaaaa   9840
tctgattggg gccctgctgt tcgactctgg agagacagct gaagcaacta gactgaaaag   9900
gactgctaga aggcgctata cccggcgaaa gaatcgcatc tgctacctgc aggagatttt   9960
ctctaacgaa atggccaagg tggacgatag tttctttcat cggctggagg aatcattcct  10020
ggtcgaggaa gataagaaac acgagagaca tcctatcttt ggaaacattg tggacgaggt  10080
```

cgcttatcac gaaaaatacc ccaccatcta tcatctgcgc aagaaactgg tggactctac 10140
agataaagca gacctgcggc tgatctatct ggccctggct cacatgatta agttcagagg 10200
ccattttctg atcgagggag atctgaaccc agacaatagc gatgtggaca agctgttcat 10260
ccagctggtc cagacataca atcagctgtt tgaggaaaac cctattaatg catctggcgt 10320
ggacgcaaaa gccatcctga gtgccaggct gtctaagagt agaaggctgg agaacctgat 10380
cgctcagctg ccaggcgaaa agaaaaacgg cctgtttgga aatctgattg cactgtcact 10440
gggactgaca cctaacttca agagcaattt tgatctggcc gaggacgcta aactgcagct 10500
gagcaaggac acttatgacg atgacctgga taacctgctg gctcagatcg gagatcagta 10560
cgcagacctg ttcctggccg ctaagaatct gtctgacgct atcctgctga gtgatattct 10620
gcgggtgaac accgagatta caaaagcccc tctgtcagct agcatgatca agagatatga 10680
cgagcaccat caggatctga ccctgctgaa ggcactggtg cgccagcagc tgcccgagaa 10740
gtacaaggaa atcttctttg atcagagtaa gaacgggtac gccggttata ttgacggcgg 10800
agcttcacag gaggaattct acaagtttat caaacctatt ctggagaaga tggacggcac 10860
cgaggaactg ctggtgaaac tgaatcgcga ggacctgctg cgcaagcagc ggacatttga 10920
taacggctcc atcccccacc agattcatct gggagagctg cacgcaatcc tgcgacgaca 10980
ggaagacttc tacccatttc tgaaggataa ccgcgagaag atcgaaaaaa ttctgacctt 11040
ccggatccct tactatgtgg ggcccctggc aaggggtaat tcccgctttg cctggatgac 11100
acggaaatct gaggaaacaa tcactccttg gaacttcgag gaagtggtcg ataagggagc 11160
ttccgcacag tctttcatcg agagaatgac aaacttcgac aaaaacctgc caaatgagaa 11220
agtgctgcct aagcacagtc tgctgtacga gtatttcaca gtctataacg aactgactaa 11280
ggtgaaatac gtcaccgagg ggatgaggaa gcccgccttc ctgagcggtg aacagaagaa 11340
agctatcgtg gacctgctgt ttaaaaccaa tcgcaaggtg acagtcaagc agctgaagga 11400
ggactacttc aagaaaattg aatgtttcga ttctgtggag atcagtggcg tcgaagacag 11460
atttaacgct tctctgggaa cctaccacga tctgctgaag atcattaagg ataaagactt 11520
cctggacaac gaggaaaatg aggatatcct ggaagacatt gtgctgaccc tgacactgtt 11580
tgaggatcgc gaaatgatcg aggaacggct gaaaacttat gcccatctgt tcgatgacaa 11640
ggtgatgaaa cagctgaagc gaagaaggta caccggctgg ggacgactga gcagaaagct 11700
gatcaacggc attcgggaca aacagagtgg aaagactatc ctggactttc tgaaatcaga 11760
tggcttcgct aacagaaatt ttatgcagct gattcacgat gacagcctga ccttcaaaga 11820
ggatatccag aaggcacagg tgtccgggca gggtgactct ctgcacgagc atatcgcaaa 11880
cctggccggg tcccccgcca tcaagaaagg tattctgcag accgtgaagg tggtcgatga 11940
gctggtgaaa gtcatgggca ggcataagcc agaaaacatc gtgattgaga tggcccgcga 12000
aaatcagacc acacagaaag gacagaagaa cagccgcgag cggatgaaaa ggatcgagga 12060
aggcattaag gaactgggat cccagatcct gaaagagcac cctgtggaaa acactcagct 12120
gcagaatgag aagctgtatc tgtactatct gcagaatggg cgggatatgt acgtggacca 12180
ggagctggat attaaccgac tgtctgatta cgacgtggat catatcgtcc cacagtcatt 12240
cctgaaagat gacagcattg acaataaggt gctgacccgg agtgacaaaa accgaggaaa 12300
gagtgataat gtcccttcag aggaagtggt caagaaaatg aagaactact ggagacagct 12360
gctgaatgcc aaactgatca cacagcgaaa gtttgataac ctgactaaag ctgagagagg 12420
gggtctgtca gaactggaca aagcaggctt catcaagcga cagctggtgg agaccagaca 12480

```
gatcacaaag cacgtcgctc agattctgga tagcaggatg aacacaaagt acgatgagaa  12540
tgacaaactg atccgcgaag tgaaggtcat tactctgaag tcaaaacttg tgagcgactt  12600
cagaaaggat ttccagttct acaaagtcag ggagatcaac aattatcacc atgctcatga  12660
cgcatacctg aacgcagtgg tcgggaccgc cctgattaag aaatacccca aactggagag  12720
cgaattcgtg tacggtgact ataaggtgta cgatgtcaga aaaatgatcg ccaagagtga  12780
gcaggaaatt ggaaaagcca ccgctaagta tttcttttac tcaaacatca tgaatttctt  12840
taagactgag atcaccctgg caaatgggga aatccgaaag agaccactga ttgagactaa  12900
cggcgagacc ggagaaatcg tgtgggacaa gggtagggat tttgccacag tgcgcaaggt  12960
cctgtccatg cctcaagtga atattgtcaa gaaaacagag gtgcagactg gcggattcag  13020
taaggaatca attctgccca aacggaactc tgataagctg atcgcccgaa agaaagactg  13080
ggatcccaag aaatatgggg gtttcgactc cccaacagtg gcttactctg tcctggtggt  13140
cgcaaaggtg gagaagggga aaagcaagaa actgaaatcc gtcaaggagc tgctgggtat  13200
cactattatg gagaggagct ccttcgagaa gaaccccatc gattttctgg aggctaaagg  13260
ctataaggaa gtgaagaaag acctgatcat taaactgcca aagtacagcc tgtttgagct  13320
ggaaaacgga aggaagcgaa tgctggcatc cgcaggagag ctgcagaagg gtaatgaact  13380
ggccctgcct tctaagtacg tgaacttcct gtatctggct agccactacg agaagctgaa  13440
aggctccccc gaggataacg aacagaaaca gctgtttgtg gagcagcaca agcattatct  13500
ggacgagatc attgaacaga ttagcgagtt ctccaaaaga gtgatcctgg ctgacgcaaa  13560
tctggataag gtcctgagcg catacaacaa acacagagat aagccaatca gggagcaggc  13620
cgaaaatatc attcatctgt tcactctgac caacctggga gcccctgcag ccttcaagta  13680
ttttgacact accatcgatc ggaaacgata cacatccact aaggaggtgc tggacgctac  13740
cctgattcac cagagcatta ccggcctgta tgaaacaagg attgacctgt ctcagctggg  13800
gggcgacctc gagggaagcg gagagggcag aggaagtctg ctaacatgcg gtgacgtcga  13860
ggagaatcct ggcccagcac cgggatccat ggtgagcaag ggcgaggagc tgttcaccgg  13920
ggtggtgccc atcctggtcg agctggacgg cgacgtaaac ggccacaagt tcagcgtgtc  13980
cggcgagggc gagggcgatg ccacctacgg caagctgacc ctgaagttca tctgcaccac  14040
cggcaagctg cccgtgccct ggcccaccct cgtgaccacc ttcacctacg gcgtgcagtg  14100
cttcgcccgc taccccgacc acatgaagca gcacgacttc ttcaagtccg ccatgcccga  14160
aggctacgtc caggagcgca ccatcttctt caaggacgac ggcaactaca agacccgcgc  14220
cgaggtgaag ttcgagggcg acaccctggt gaaccgcatc gagctgaagg gcatcgactt  14280
caaggaggac ggcaacatcc tggggcacaa gctggagtac aactacaaca gccacaaggt  14340
ctatatcacc gccgacaagc agaagaacgg catcaaggtg aacttcaaga cccgccacaa  14400
catcgaggac ggcagcgtgc agctcgccga ccactaccag cagaacaccc ccatcggcga  14460
cggccccgtg ctgctgcccg acaaccacta cctgagcacc cagtccgccc tgagcaaaga  14520
ccccaacgag aagcgcgatc acatggtcct gctggagttc gtgaccgccg ccgggatcac  14580
tctcggcatg gacgagctgt acaagtaaac ctaatctagc agctcgctga tcagcctcga  14640
ctgtgccttc tagttgccag ccatctgttg tttgcccctc ccccgtgcct tccttgaccc  14700
tggaaggtgc cactcccact gtcctttcct aataaaatga ggaaattgca tcgcattgtc  14760
tgagtaggtg tcattctatt ctggggggtg gggtggggca ggacagcaag ggggaggatt  14820
```

gggaagacaa tagcaggcat gctggggatg cggtgggctc tatggcttct gaggcggaaa 14880
gaaccagctg gggctcgatc ctctagttgg cgcgtcatgg tccatatgaa tatcctcctt 14940
agttcctatt ccgctagcct agagggacag cccccccccca aagcccccag ggatgtaatt 15000
acgtccctcc cccgctaggg gcagcagcga gccgcccggg gctccgctcc ggtccggcgc 15060
tccccccgca tccccgagcc ggcagcgtgc ggggacagcc cgggcacggg gaaggtggca 15120
cgggatcgct ttcctctgaa cgcttctcgc tgctctttga gcctgcagac acctgggggg 15180
atacggggaa aaagctttag gctgaaagag agatttagaa tgacagaatc atagaacggc 15240
ctgggttgca aaggagcaca gtgctcatcc agatccaacc ccctgctatg tgcagggtca 15300
tcaaccagca gcccaggctg cccagagcca catccagcct ggccttgaat gcctgcaggg 15360
atggggcatc cacagcctcc ttgggcaacc tgttcagtgc gtcaccaccc tctgggggaa 15420
aaactgcctc ctcatatcca acccaaacct cccctgtctc agtgtaaagc cattcccccct 15480
tgtcctatca agggggagtt tgctgtgaca ttgttggtct ggggtgacac atgtttgcca 15540
attcagtgca tcacggagag gcagatcttg gggataagga agtgcaggac agcatggacg 15600
tgggacatgc aggtgttgag ggctctggga cactctccaa gtcacagcgt tcagaacagc 15660
cttaaggata agaagatagg atagaaggac aaagagcaag ttaaaaccca gcatggagag 15720
gagcacaaaa aggccacaga cactgctggt ccctgtgtct gagcctgcat gtttgatggt 15780
gtctggatgc aagcagaagg ggtggaagag cttgcctgga gagatacagc tgggtcagta 15840
ggactgggac aggcagctgg agaattgcca tgtagatgtt catacaatcg tcaaatcatg 15900
aaggctggaa aagccctcca agatccccaa gaccaacccc aacccaccca ccgtgcccac 15960
tggccatgtc cctcagtgcc acatccccac agttcttcat cacctccagg gacggtgacc 16020
cccccacctc cgtgggcagc tgtgccactg cagcaccgct ctttggagaa ggtaaatctt 16080
gctaaatcca gcccgaccct cccctggcac aacgtaaggc cattatctct catccaactc 16140
caggacggag tcagtgagga tggggctgga tccgaagcag ctccagccta cacaatcgct 16200
caagacgtgt aatgctttta ttatatatta gtcacgatat ctataacaag aaaatatata 16260
tataataagt tatcacgtaa gtagaacatg aaataacaat ataattatcg tatgagttaa 16320
atcttaaaag tcacgtaaaa gataatcatg cgtcattttg actcacgcgg tcgttatagt 16380
tcaaaatcag tgacacttac cgcattgaca agcacgcctc acgggagctc caagcggcga 16440
ctgagatgtc ctaaatgcac agcgacggat tcgcgctatt tagaaagaga gagcaatatt 16500
tcaagaatgc atgcgtcaat tttacgcaga ctatctttct agggttaaaa aagatttgcg 16560
ctttactcga cctaaacttt aaacacgtca tagaatcttc gtttgacaaa aaccacattg 16620
tggggtaccg agctcttaat taaggcgcgc cggggaggtt ccctttagtg agggttaatt 16680
gcgggtcgcc ctatagtgag tcgtattaca attcactggc cgtcgtttta caacgtcgtg 16740
actgggaaaa ccctggcgtt acccaactta atcgccttgc agcacatccc cctttcgcca 16800
gctggcgtaa tagcgaagag gcccgcaccg atcgcccttc ccaacagttg cgcagcctga 16860
atggcgaatg gcaaattgta agcgttaata ttttgttaaa attcgcgtta aatttttgtt 16920
aaatcagctc attttttaac caataggccg aaatcggcaa aatcccttat aaatcaaaag 16980
aatagaccga gatagggttg agtgttgttc cagtttggaa caagagtcca ctattaaaga 17040
acgtggactc caacgtcaaa gggcgaaaaa ccgtctatca gggcgatggc ccactacgtg 17100
aaccatcacc ctaatcaagt tttttggggt cgaggtgccg taaagcacta aatcggaacc 17160
ctaaagggag cccccgattt agagcttgac ggggaaagcc ggcgaacgtg gcgagaaagg 17220
aagggaagaa agcgaaagga gcgggcgcta gggcgctggc aagtgtagcg gtcacgctgc 17280
gcgtaaccac cacacccgcc gcgcttaatg cgccgctaca gggcgcgtca g 17331

<210> SEQ ID NO 14
<211> LENGTH: 17575
<212> TYPE: DNA
<213> ORGANISM: Artificial Sequence
<220> FEATURE:
<223> OTHER INFORMATION: Synthetic Polynucleotide

<400> SEQUENCE: 14
gtggcacttt tcggggaaat gtgcgcggaa cccctatttg tttatttttc taaatacatt 60
caaatatgta tccgctcatg agacaataac cctgataaat gcttcaataa tattgaaaaa 120
ggaagagtat gagtattcaa catttccgtg tcgcccttat tccctttttt gcggcatttt 180
gccttcctgt ttttgctcac ccagaaacgc tggtgaaagt aaaagatgct gaagatcagt 240
tgggtgcacg agtgggttac atcgaactgg atctcaacag cggtaagatc cttgagagtt 300
ttcgccccga agaacgtttt ccaatgatga gcacttttaa agttctgcta tgtggcgcgg 360
tattatcccg tattgacgcc gggcaagagc aactcggtcg ccgcatacac tattctcaga 420
atgacttggt tgagtactca ccagtcacag aaaagcatct tacggatggc atgacagtaa 480
gagaattatg cagtgctgcc ataaccatga gtgataacac tgcggccaac ttacttctga 540
caacgatcgg aggaccgaag gagctaaccg cttttttgca caacatgggg gatcatgtaa 600
ctcgccttga tcgttgggaa ccggagctga atgaagccat accaaacgac gagcgtgaca 660
ccacgatgcc tgtagcaatg gcaacaacgt tgcgcaaact attaactggc gaactactta 720
ctctagcttc ccggcaacaa ttaatagact ggatggaggc ggataaagtt gcaggaccac 780
ttctgcgctc ggcccttccg gctggctggt ttattgctga taaatctgga gccggtgagc 840
gtgggtctcg cggtatcatt gcagcactgg ggccagatgg taagccctcc cgtatcgtag 900
ttatctacac gacggggagt caggcaacta tggatgaacg aaatagacag atcgctgaga 960
taggtgcctc actgattaag cattggtaac tgtcagacca agtttactca tatatacttt 1020
agattgattt aaaacttcat ttttaattta aaaggatcta ggtgaagatc ctttttgata 1080
atctcatgac caaaatccct taacgtgagt tttcgttcca ctgagcgtca gaccccgtag 1140
aaaagatcaa aggatcttct tgagatcctt tttttctgcg cgtaatctgc tgcttgcaaa 1200
caaaaaaacc accgctacca gcggtggttt gtttgccgga tcaagagcta ccaactcttt 1260
ttccgaaggt aactggcttc agcagagcgc agataccaaa tactgttctt ctagtgtagc 1320
cgtagttagg ccaccacttc aagaactctg tagcaccgcc tacatacctc gctctgctaa 1380
tcctgttacc agtggctgct gccagtggcg ataagtcgtg tcttaccggg ttggactcaa 1440
gacgatagtt accggataag gcgcagcggt cgggctgaac ggggggttcg tgcacacagc 1500
ccagcttgga gcgaacgacc tacaccgaac tgagatacct acagcgtgag ctatgagaaa 1560
gcgccacgct tcccgaaggg agaaaggcgg acaggtatcc ggtaagcggc agggtcggaa 1620
caggagagcg cacgagggag cttccagggg gaaacgcctg gtatctttat agtcctgtcg 1680
ggtttcgcca cctctgactt gagcgtcgat ttttgtgatg ctcgtcaggg gggcggagcc 1740
tatggaaaaa cgccagcaac gcggcctttt tacggttcct ggccttttgc tggccttttg 1800
ctcacatgtt ctttcctgcg ttatcccctg attctgtgga taaccgtatt accgcctttg 1860
agtgagctga taccgctcgc cgcagccgaa cgaccgagcg cagcgagtca gtgagcgagg 1920

-continued aagcggaaga gcgcccaata cgcaaaccgc ctctccccgc gcgttggccg attcattaat 1980
gcagctggca cgacaggttt cccgactgga aagcgggcag tgagcgcaac gcaattaatg 2040
tgagttagct cactcattag gcaccccagg ctttacactt tatgcttccg gctcgtatgt 2100
tgtgtggaat tgtgagcgga taacaatttc acacaggaaa cagctatgac catgattacg 2160
ccaagcgcgc aattaaccct cactaaaggg aacctcccct agcttaatta accctagaaa 2220
gataatcata ttgtgacgta cgttaaagat aatcatgcgt aaaattgacg catgtgtttt 2280
atcgatctgt atatcgaggt ttatttatta atttgaatag atattaagtt ttattatatt 2340
tacacttaca tactaataat aaattcaaca aacaatttat ttatgtttat ttatttatta 2400
aaaaaaaaca aaaactcaaa atttcttcta taaagtaaca aaacttttaa acattctctc 2460
ttttacaaaa ataaacttat tttgtacttt aaaaacagtc atgttgtatt ataaaataag 2520
taattagctt aacttataca taatagaaac aaattatact tattaatcgc attgattatt 2580
gactagtcgt attaagggtt ccggatcagc ttgattcgag ccccagctgg ttctttccgc 2640
ctcagaagcc atagagccca ccgcatcccc agcatgcctg ctattgtctt cccaatcctc 2700
ccccttgctg tcctgcccca ccccaccccc cagaatagaa tgacacctac tcagacaatg 2760
cgatgcaatt tcctcatttt attaggaaag gacagtggga gtggcacctt ccagggtcaa 2820
ggaaggcacg ggggaggggc aaacaacaga tggctggcaa ctagaaggca cagtcgaggc 2880
tgatcagcga gctctagaga attgatcccc tcagaagaac tcgtcaagaa ggcgatagaa 2940
ggcgatgcgc tgcgaatcgg gagcggcgat accgtaaagc acgaggaagc ggtcagccca 3000
ttcgccgcca agctcttcag caatatcacg ggtagccaac gctatgtcct gatagcggtc 3060
cgccacaccc agccggccac agtcgatgaa tccagaaaag cggccatttt ccaccatgat 3120
attcggcaag caggcatcgc catgggtcac gacgagatcc tcgccgtcgg gcatgcgcgc 3180
cttgagcctg gcgaacagtt cggctggcgc gagcccctga tgctcttcgt ccagatcatc 3240
ctgatcgaca agaccggctt ccatccgagt acgtgctcgc tcgatgcgat gtttcgcttg 3300
gtggtcgaat gggcaggtag ccggatcaag cgtatgcagc cgccgcattg catcagccat 3360
gatggatact ttctcggcag gagcaaggtg agatgacagg agatcctgcc ccggcacttc 3420
gcccaatagc agccagtccc ttcccgcttc agtgacaacg tcgagcacag ctgcgcaagg 3480
aacgcccgtc gtggccagcc acgatagccg cgctgcctcg tcctgcagtt cattcagggc 3540
accggacagg tcggtcttga caaaaagaac cgggcgcccc tgcgctgaca gccggaacac 3600
ggcggcatca gagcagccga ttgtctgttg tgcccagtca tagccgaata gcctctccac 3660
ccaagcggcc ggagaacctg cgtgcaatcc atcttgttca atggccgatc ccatggttta 3720
gttcctcacc ttgtcgtatt atactatgcc gatatactat gccgatgatt aattgtcaac 3780
acgtgctgct gcaggtcgaa aggcccggag atgaggaaga ggagaacagc gcggcagacg 3840
tgcgcttttg aagcgtgcag aatgccgggc ctccggagga ccttcgggcg cccgccccgc 3900
ccctgagccc gcccctgagc ccgcccccgg acccacccct tcccagcctc tgagcccaga 3960
aagcgaagga gcaaagctgc tattggccgc tgccccaaag gcctacccgc ttccattgct 4020
cagcggtgct gtccatctgc acgagactag tgagacgtgc tacttccatt tgtcacgtcc 4080
tgcacgacgc gagctgcggg gcggggggga acttcctgac taggggagga gtagaaggtg 4140
gcgcgaaggg gccaccaaag aacggagccg gttggcgcct accggtggat gtggaatgtg 4200
tgcgagccag aggccacttg tgtagcgcca agtgcccagc ggggctgcta aagcgcatgc 4260
tccagactgc cttgggaaaa gcgcctcccc tacccggtag acaccccaca gtgggtggcc 4320

-continued

```
tagggacagg attgcaactc cagtctttct tcttcttggg cgggagtcac tagttattaa   4380
tagtaatcaa ttacggggtc attagttcat agcccatata tggagttccg cgttacataa   4440
cttacggtaa atggcccgcc tggctgaccg cccaacgacc cccgcccatt gacgtcaata   4500
atgacgtatg ttcccatagt aacgccaata gggactttcc attgacgtca atgggtggac   4560
tatttacggt aaactgccca cttggcagta catcaagtgt atcatatgcc aagtacgccc   4620
cctattgacg tcaatgacgg taaatggccc gcctggcatt atgcccagta catgacctta   4680
tgggactttc ctacttggca gtacatctac gtattagtca tcgctattac catgggtcga   4740
ggtgagcccc acgttctgct tcactctccc catctccccc ccctccccac ccccaatttt   4800
gtatttattt atttttaat tattttgtgc agcgatgggg gcgggggggg gggggggcgcg   4860
cgccaggcgg ggcggggcgg ggcgaggggc ggggcggggc gaggcggaga ggtgcggcgg   4920
cagccaatca gagcggcgcg ctccgaaagt ttccttttat ggcgaggcgg cggcggcggc   4980
ggccctataa aaagcgaagc gcgcggcggg cgggagtcgc tgcgttgcct tcgccccgtg   5040
ccccgctccg cgccgcctcg cgccgcccgc cccggctctg actgaccgcg ttactcccac   5100
aggtgagcgg gcgggacggc ccttctcctc cgggctgtaa ttagcgcttg gtttaatgac   5160
ggctcgtttc ttttctgtgg ctgcgtgaaa gccttaaagg gctccgggag ggccctttgt   5220
gcgggggggga gcggctcggg gggtgcgtgc gtgtgtgtgt gcgtggggag cgccgcgtgc   5280
ggcccgcgct gcccggcggc tgtgagcgct gcgggcgcgg cgcggggctt tgtgcgctcc   5340
gcgtgtgcgc gaggggagcg cggccggggg cggtgccccg cggtgcgggg gggctgcgag   5400
gggaacaaag gctgcgtgcg gggtgtgtgc gtgggggggt gagcaggggg tgtgggcgcg   5460
gcggtcgggc tgtaaccccc ccctgcaccc ccctccccga gttgctgagc acggcccggc   5520
ttcgggtgcg gggctccgtg cggggcgtgg cgcggggctc gccgtgccgg gcggggggtg   5580
gcggcaggtg ggggtgccgg gcggggcggg gccgcctcgg gccggggagg gctcggggga   5640
ggggcgcggc ggcccccgag cgccggcggc tgtcgaggcg cggcgagccg cagccattgc   5700
cttttatggt aatcgtgcga gagggcgcag ggacttcctt tgtcccaaat ctggcggagc   5760
cgaaatctgg gaggcgccgc cgcacccccct ctagcgggcg cgggcgaagc ggtgcggcgc   5820
cggcaggaag gaaatgggcg gggagggcct tcgtgcgtcg ccgcgccgcc gtccccttct   5880
ccatctccag cctcggggct gccgcagggg gacggctgcc ttcggggggg acggggcagg   5940
gcggggttcg gcttctggcg tgtgaccggc ggctctagag cctctgctaa ccatgttcat   6000
gccttcttct ttttcctaca gctcctgggc aacgtgctgg ttattgtgct gtctcatcat   6060
tttggcaaag aattcgccac catggtgccc aagaagaaga ggaaagtctc tagactggac   6120
aagagcaaag tcataaactc tgctctggaa ttactcaatg gagtcggtat cgaaggcctg   6180
acgacaagga aactcgctca aaagctggga gttgagcagc ctaccctgta ctggcacgtg   6240
aagaacaagc gggccctgct cgatgccctg ccaatcgaga tgctggacag gcatcatacc   6300
cactcctgcc ccctggaagg cgagtcatgg caagactttc tgcggaacaa cgccaagtca   6360
taccgctgtg ctctcctctc acatcgcgac ggggctaaag tgcatctcgg cacccgccca   6420
acagagaaac agtacgaaac cctggaaaat cagctcgcgt tcctgtgtca gcaaggcttc   6480
tccctggaga acgcactgta cgctctgtcc gccgtgggcc actttacact gggctgcgta   6540
ttggaggaac aggagcatca agtagcaaaa gaggaaagag agacacctac caccgattct   6600
atgcccccac ttctgaaaca agcaattgag ctgttcgacc ggcagggagc cgaacctgcc   6660
```

-continued

```
ttccttttcg gcctggaact aatcatatgt ggcctggaga aacagctaaa gtgcgaaagc   6720
ggcgggccga ccgacgccct tgacgatttt gacttagaca tgctcccagc cgatgccctt   6780
gacgactttg accttgatat gctgcctgct gacgctcttg acgattttga ccttgacatg   6840
ctccccgggt aaagcggccg cgactctaga tcataatcag ccataccaca tttgtagagg   6900
ttttacttgc tttaaaaaac ctcccacacc tcccccctgaa cctgaaacat aaaatgaatg   6960
caattgttgt tgttaacttg tttattgcag cttataatgg ttacaaataa agcaatagca   7020
tcacaaattt cacaaataaa gcattttttt cactgcattc tagttgtggt ttgtccaaac   7080
tcatcaatgt atcttaaggg atccctagag ggacagcccc cccccaaagc ccccagggat   7140
gtaattacgt ccctcccccg ctaggggcag cagcgagccg cccggggctc cgctccggtc   7200
cggcgctccc cccgcatccc cgagccggca gcgtgcgggg acagcccggg cacggggaag   7260
gtggcacggg atcgctttcc tctgaacgct tctcgctgct ctttgagcct gcagacacct   7320
ggggggatac ggggaaaaag ctttaggctg aaagagagat ttagaatgac agaatcatag   7380
aacggcctgg gttgcaaagg agcacagtgc tcatccagat ccaacccccct gctatgtgca   7440
gggtcatcaa ccagcagccc aggctgccca gagccacatc cagcctggcc ttgaatgcct   7500
gcagggatgg ggcatccaca gcctccttgg gcaacctgtt cagtgcgtca ccaccctctg   7560
ggggaaaaac tgcctcctca tatccaaccc aaacctcccc tgtctcagtg taaagccatt   7620
ccccccttgtc ctatcaaggg ggagtttgct gtgacattgt tggtctgggg tgacacatgt   7680
ttgccaattc agtgcatcac ggagaggcag atcttgggga taaggaagtg caggacagca   7740
tggacgtggg acatgcaggt gttgagggct ctgggacact ctccaagtca cagcgttcag   7800
aacagcctta aggataagaa gataggatag aaggacaaag agcaagttaa aacccagcat   7860
ggagaggagc acaaaaaggc cacagacact gctggtccct gtgtctgagc ctgcatgttt   7920
gatggtgtct ggatgcaagc agaaggggtg gaagagcttg cctggagaga tacagctggg   7980
tcagtaggac tgggacaggc agctggagaa ttgccatgta gatgttcata caatcgtcaa   8040
atcatgaagg ctggaaaagc cctccaagat ccccaagacc aaccccaacc cacccaccgt   8100
gcccactggc catgtccctc agtgccacat ccccacagtt cttcatcacc tccagggacg   8160
gtgacccccc cacctccgtg ggcagctgtg ccactgcagc accgctcttt ggagaaggta   8220
aatcttgcta aatccagccc gaccctcccc tggcacaacg taaggccatt atctctcatc   8280
caactccagg acggagtcag tgaggatggg gctgtcgacc tagagggaca gccccccccc   8340
aaagccccca gggatgtaat tacgtccctc ccccgctagg ggcagcagcg agccgcccgg   8400
ggctccgctc cggtccggcg ctcccccccgc atccccgagc cggcagcgtg cggggacagc   8460
ccgggcacgg ggaaggtggc acgggatcgc tttcctctga acgcttctcg ctgctctttg   8520
agcctgcaga cacctggggg gatacgggga aaaagcttta ggctgaaaga gagatttaga   8580
atgacagaat catagaacgg cctgggttgc aaaggagcac agtgctcatc cagatccaac   8640
cccctgctat gtgcagggtc atcaaccagc agcccaggct gcccagagcc acatccagcc   8700
tggccttgaa tgcctgcagg gatggggcat ccacagcctc cttgggcaac ctgttcagtg   8760
cgtcaccacc ctctgggggga aaaactgcct cctcatatcc aacccaaacc tcccctgtct   8820
cagtgtaaag ccattccccc ttgtcctatc aagggggagt ttgctgtgac attgttggtc   8880
tggggtgaca catgtttgcc aattcagtgc atcacggaga ggcagatctt ggggataagg   8940
aagtgcagga cagcatggac gtgggacatg caggtgttga gggctctggg acactctcca   9000
agtcacagcg ttcagaacag ccttaaggat aagaagatag gatagaagga caaagagcaa   9060
```

```
gttaaaaccc agcatggaga ggagcacaaa aaggccacag acactgctgg tccctgtgtc   9120
tgagcctgca tgtttgatgg tgtctggatg caagcagaag ggtggaaga gcttgcctgg   9180
agagatacag ctgggtcagt aggactggga caggcagctg gagaattgcc atgtagatgt   9240
tcatacaatc gtcaaatcat gaaggctgga aaagccctcc aagatcccca agaccaaccc   9300
caacccaccc accgtgccca ctggccatgt ccctcagtgc cacatcccca cagttcttca   9360
tcacctccag ggacggtgac ccccccacct ccgtgggcag ctgtgccact gcagcaccgc   9420
tctttggaga aggtaaatct tgctaaatcc agcccgaccc tcccctggca caacgtaagg   9480
ccattatctc tcatccaact ccaggacgga gtcagtgagg atggggctca attgtttact   9540
ccctatcagt gatagagaac gtatgaagag tttactccct atcagtgata gagaacgtat   9600
gcagacttta ctccctatca gtgatagaga acgtataagg agtttactcc ctatcagtga   9660
tagagaacgt atgaccagtt tactccctat cagtgataga gaacgtatct acagtttact   9720
ccctatcagt gatagagaac gtatatccag tttactccct atcagtgata gagaacgtat   9780
aagctttagg cgtgtacggt gggcgcctat aaaagcagag ctcgtttagt gaaccgtcag   9840
atcgcctgga gcaattccac aacacttttg tcttatacca actttccgta ccacttccta   9900
ccctcgtaaa aagcttgtcc accatggctc ctaagaaaaa gcggaaggtg gacaagaaat   9960
actcaatcgg gctggccatc ggaactaact cagtggggtg ggcagtcatt actgacgagt  10020
acaaagtgcc aagcaagaaa tttaaggtcc tgggcaacac cgataggcac tccatcaaga  10080
aaaatctgat tggggccctg ctgttcgact ctggagagac agctgaagca actagactga  10140
aaaggactgc tagaaggcgc tatacccggc gaaagaatcg catctgctac ctgcaggaga  10200
ttttctctaa cgaaatggcc aaggtggacg atagtttctt tcatcggctg gaggaatcat  10260
tcctggtcga ggaagataag aaacacgaga gacatcctat ctttggaaac attgtggacg  10320
aggtcgctta tcacgaaaaa taccccacca tctatcatct gcgcaagaaa ctggtggact  10380
ctacagataa agcagacctg cggctgatct atctggccct ggctcacatg attaagttca  10440
gaggccattt tctgatcgag ggagatctga acccagacaa tagcgatgtg gacaagctgt  10500
tcatccagct ggtccagaca tacaatcagc tgtttgagga aaaccctatt aatgcatctg  10560
gcgtggacgc aaaagccatc ctgagtgcca ggctgtctaa gagtagaagg ctggagaacc  10620
tgatcgctca gctgccaggc gaaaagaaaa acggcctgtt tggaaatctg attgcactgt  10680
cactgggact gacacctaac ttcaagagca attttgatct ggccgaggac gctaaactgc  10740
agctgagcaa ggacacttat gacgatgacc tggataacct gctggctcag atcggagatc  10800
agtacgcaga cctgttcctg gccgctaaga atctgtctga cgctatcctg ctgagtgata  10860
ttctgcgggt gaacaccgag attacaaaag cccctctgtc agctagcatg atcaagagat  10920
atgacgagca ccatcaggat ctgaccctgc tgaaggcact ggtgcgccag cagctgcccg  10980
agaagtacaa ggaaatcttc tttgatcaga gtaagaacgg gtacgccggt tatattgacg  11040
gcggagcttc acaggaggaa ttctacaagt ttatcaaacc tattctggag aagatggacg  11100
gcaccgagga actgctggtg aaactgaatc gcgaggacct gctgcgcaag cagcggacat  11160
ttgataacgg ctccatcccc caccagattc atctgggaga gctgcacgca atcctgcgac  11220
gacaggaaga cttctaccca tttctgaagg ataaccgcga gaagatcgaa aaaattctga  11280
ccttccggat cccttactat gtggggcccc tggcaagggg taattcccgc tttgcctgga  11340
tgacacggaa atctgaggaa acaatcactc cttggaactt cgaggaagtg gtcgataagg  11400
```

```
gagcttccgc acagtctttc atcgagagaa tgacaaactt cgacaaaaac ctgccaaatg  11460
agaaagtgct gcctaagcac agtctgctgt acgagtattt cacagtctat aacgaactga  11520
ctaaggtgaa atacgtcacc gaggggatga ggaagcccgc cttcctgagc ggtgaacaga  11580
agaaagctat cgtggacctg ctgtttaaaa ccaatcgcaa ggtgacagtc aagcagctga  11640
aggaggacta cttcaagaaa attgaatgtt tcgattctgt ggagatcagt ggcgtcgaag  11700
acagatttaa cgcttctctg ggaacctacc acgatctgct gaagatcatt aaggataaag  11760
acttcctgga caacgaggaa aatgaggata tcctggaaga cattgtgctg accctgacac  11820
tgtttgagga tcgcgaaatg atcgaggaac ggctgaaaac ttatgcccat ctgttcgatg  11880
acaaggtgat gaaacagctg aagcgaagaa ggtacaccgg ctggggacga ctgagcagaa  11940
agctgatcaa cggcattcgg gacaaacaga gtggaaagac tatcctggac tttctgaaat  12000
cagatggctt cgctaacaga aattttatgc agctgattca cgatgacagc ctgaccttca  12060
aagaggatat ccagaaggca caggtgtccg ggcagggtga ctctctgcac gagcatatcg  12120
caaacctggc cgggtccccc gccatcaaga aaggtattct gcagaccgtg aaggtggtcg  12180
atgagctggt gaaagtcatg ggcaggcata agccagaaaa catcgtgatt gagatggccc  12240
gcgaaaatca gaccacacag aaaggacaga agaacagccg cgagcggatg aaaaggatcg  12300
aggaaggcat taaggaactg ggatcccaga tcctgaaaga gcaccctgtg gaaaacactc  12360
agctgcagaa tgagaagctg tatctgtact atctgcagaa tgggcgggat atgtacgtgg  12420
accaggagct ggatattaac cgactgtctg attacgacgt ggatgccatc gtcccacagt  12480
cattcctgaa agatgacagc attgacaata aggtgctgac ccggagtgac aaaaaccgag  12540
gaaagagtga taatgtccct tcagaggaag tggtcaagaa aatgaagaac tactggagac  12600
agctgctgaa tgccaaactg atcacacagc gaaagtttga taacctgact aaagctgaga  12660
gagggggtct gtcagaactg gacaaagcag gcttcatcaa gcgacagctg gtggagacca  12720
gacagatcac aaagcacgtc gctcagattc tggatagcag gatgaacaca aagtacgatg  12780
agaatgacaa actgatccgc gaagtgaagg tcattactct gaagtcaaaa cttgtgagcg  12840
acttcagaaa ggatttccag ttctacaaag tcagggagat caacaattat caccatgctc  12900
atgacgcata cctgaacgca gtggtcggga ccgccctgat taagaaatac cccaaactgg  12960
agagcgaatt cgtgtacggt gactataagg tgtacgatgt cagaaaaatg atcgccaaga  13020
gtgagcagga aattggaaaa gccaccgcta agtatttctt ttactcaaac atcatgaatt  13080
tctttaagac tgagatcacc ctggcaaatg gggaaatccg aaagagacca ctgattgaga  13140
ctaacggcga gaccggagaa atcgtgtggg acaagggtag ggattttgcc acagtgcgca  13200
aggtcctgtc catgcctcaa gtgaatattg tcaagaaaac agaggtgcag actggcggat  13260
tcagtaagga atcaattctg cccaaacgga actctgataa gctgatcgcc cgaaagaaag  13320
actgggatcc caagaaatat gggggtttcg actccccaac agtggcttac tctgtcctgg  13380
tggtcgcaaa ggtggagaag gggaaaagca agaaactgaa atccgtcaag gagctgctgg  13440
gtatcactat tatggagagg agctccttcg agaagaaccc catcgatttt ctggaggcta  13500
aaggctataa ggaagtgaag aaagacctga tcattaaact gccaaagtac agcctgtttg  13560
agctggaaaa cggaaggaag cgaatgctgg catccgcagg agagctgcag aagggtaatg  13620
aactggccct gccttctaag tacgtgaact tcctgtatct ggctagccac tacgagaagc  13680
tgaaaggctc ccccgaggat aacgaacaga aacagctgtt tgtggagcag cacaagcatt  13740
atctggacga gatcattgaa cagattagcg agttctccaa aagagtgatc ctggctgacg  13800
```

caaatctgga taaggtcctg agcgcataca acaaacacag agataagcca atcagggagc 13860
aggccgaaaa tatcattcat ctgttcactc tgaccaacct gggagcccct gcagccttca 13920
agtattttga cactaccatc gatcggaaac gatacacatc cactaaggag gtgctggacg 13980
ctaccctgat tcaccagagc attaccggcc tgtatgaaac aaggattgac ctgtctcagc 14040 tgggggggcga cctcgaggga agcggagagg gcagaggaag tctgctaaca tgcggtgacg 14100
tcgaggagaa tcctggccca gcaccgggat ccatggtgag caagggcgag gagctgttca 14160
ccggggtggt gcccatcctg gtcgagctgg acggcgacgt aaacggccac aagttcagcg 14220
tgtccggcga gggcgagggc gatgccacct acggcaagct gaccctgaag ttcatctgca 14280
ccaccggcaa gctgcccgtg ccctggccca ccctcgtgac caccttcacc tacggcgtgc 14340
agtgcttcgc ccgctacccc gaccacatga agcagcacga cttcttcaag tccgccatgc 14400
ccgaaggcta cgtccaggag cgcaccatct tcttcaagga cgacggcaac tacaagaccc 14460
gcgccgaggt gaagttcgag ggcgacaccc tggtgaaccg catcgagctg aagggcatcg 14520
acttcaagga ggacggcaac atcctggggc acaagctgga gtacaactac aacagccaca 14580
aggtctatat caccgccgac aagcagaaga acggcatcaa ggtgaacttc aagacccgcc 14640
acaacatcga ggacggcagc gtgcagctcg ccgaccacta ccagcagaac acccccatcg 14700
gcgacggccc cgtgctgctg cccgacaacc actacctgag cacccagtcc gccctgagca 14760
aagaccccaa cgagaagcgc gatcacatgg tcctgctgga gttcgtgacc gccgccggga 14820
tcactctcgg catggacgag ctgtacaagt aaacctaatc tagcagctcg ctgatcagcc 14880
tcgactgtgc cttctagttg ccagccatct gttgtttgcc cctcccccgt gccttccttg 14940
accctggaag gtgccactcc cactgtcctt tcctaataaa atgaggaaat tgcatcgcat 15000
tgtctgagta ggtgtcattc tattctgggg ggtggggtgg ggcaggacag caagggggag 15060
gattgggaag acaatagcag gcatgctggg gatgcggtgg gctctatggc ttctgaggcg 15120
gaaagaacca gctggggctc gatcctctag ttggcgcgtc atggtccata tgaatatcct 15180
ccttagttcc tattccgcta gcctagaggg acagcccccc cccaaagccc ccagggatgt 15240
aattacgtcc ctcccccgct aggggcagca gcgagccgcc cggggctccg ctccggtccg 15300
gcgctccccc cgcatccccg agccggcagc gtgcggggac agcccgggca cggggaaggt 15360
ggcacgggat cgctttcctc tgaacgcttc tcgctgctct ttgagcctgc agacacctgg 15420
ggggatacgg ggaaaaagct ttaggctgaa agagagattt agaatgacag aatcatagaa 15480
cggcctgggt tgcaaaggag cacagtgctc atccagatcc aaccccctgc tatgtgcagg 15540
gtcatcaacc agcagcccag gctgcccaga gccacatcca gcctggcctt gaatgcctgc 15600
agggatgggg catccacagc ctccttgggc aacctgttca gtgcgtcacc accctctggg 15660
ggaaaaactg cctcctcata tccaacccaa acctcccctg tctcagtgta aagccattcc 15720
cccttgtcct atcaaggggg agtttgctgt gacattgttg gtctggggtg acacatgttt 15780
gccaattcag tgcatcacgg agaggcagat cttggggata aggaagtgca ggacagcatg 15840
gacgtgggac atgcaggtgt tgagggctct gggacactct ccaagtcaca gcgttcagaa 15900
cagccttaag gataagaaga taggatagaa ggacaaagag caagttaaaa cccagcatgg 15960
agaggagcac aaaaaggcca cagacactgc tggtccctgt gtctgagcct gcatgtttga 16020
tggtgtctgg atgcaagcag aaggggtgga agagcttgcc tggagagata cagctgggtc 16080
agtaggactg ggacaggcag ctggagaatt gccatgtaga tgttcataca atcgtcaaat 16140

```
catgaaggct ggaaaagccc tccaagatcc ccaagaccaa ccccaaccca cccaccgtgc  16200

ccactggcca tgtccctcag tgccacatcc ccacagttct tcatcacctc cagggacggt  16260

gacccccccca cctccgtggg cagctgtgcc actgcagcac cgctctttgg agaaggtaaa  16320

tcttgctaaa tccagcccga ccctcccctg gcacaacgta aggccattat ctctcatcca  16380

actccaggac ggagtcagtg aggatggggc tggatccgaa gcagctccag cctacacaat  16440

cgctcaagac gtgtaatgct tttattatat attagtcacg atatctataa caagaaaata  16500

tatatataat aagttatcac gtaagtagaa catgaaataa caatataatt atcgtatgag  16560

ttaaatctta aaagtcacgt aaaagataat catgcgtcat tttgactcac gcggtcgtta  16620

tagttcaaaa tcagtgacac ttaccgcatt gacaagcacg cctcacggga gctccaagcg  16680

gcgactgaga tgtcctaaat gcacagcgac ggattcgcgc tatttagaaa gagagagcaa  16740

tatttcaaga atgcatgcgt caattttacg cagactatct ttctagggtt aaaaaagatt  16800

tgcgctttac tcgacctaaa ctttaaacac gtcatagaat cttcgtttga caaaaaccac  16860

attgtggggt accgagctct taattaaggc gcgccgggga ggttcccttt agtgagggtt  16920

aattgcgggt cgccctatag tgagtcgtat tacaattcac tggccgtcgt tttacaacgt  16980

cgtgactggg aaaaccctgg cgttacccaa cttaatcgcc ttgcagcaca tccccctttc  17040

gccagctggc gtaatagcga agaggcccgc accgatcgcc cttcccaaca gttgcgcagc  17100

ctgaatggcg aatggcaaat tgtaagcgtt aatattttgt taaaattcgc gttaaatttt  17160

tgttaaatca gctcattttt taaccaatag gccgaaatcg gcaaaatccc ttataaatca  17220

aaagaataga ccgagatagg gttgagtgtt gttccagttt ggaacaagag tccactatta  17280

aagaacgtgg actccaacgt caaagggcga aaaaccgtct atcagggcga tggcccacta  17340

cgtgaaccat caccctaatc aagttttttg gggtcgaggt gccgtaaagc actaaatcgg  17400

aaccctaaag ggagcccccg atttagagct tgacggggaa agccggcgaa cgtggcgaga  17460

aaggaaggga agaaagcgaa aggagcgggc gctagggcgc tggcaagtgt agcggtcacg  17520

ctgcgcgtaa ccaccacacc cgccgcgctt aatgcgccgc tacagggcgc gtcag       17575
```

<210> SEQ ID NO 15
<211> LENGTH: 17950
<212> TYPE: DNA
<213> ORGANISM: Artificial Sequence
<220> FEATURE:
<223> OTHER INFORMATION: Synthetic Polynucleotide

<400> SEQUENCE: 15

```
gtggcacttt tcggggaaat gtgcgcggaa cccctatttg tttatttttc taaatacatt     60

caaatatgta tccgctcatg agacaataac cctgataaat gcttcaataa tattgaaaaa    120

ggaagagtat gagtattcaa catttccgtg tcgcccttat tccctttttt gcggcatttt    180

gccttcctgt ttttgctcac ccagaaacgc tggtgaaagt aaaagatgct gaagatcagt    240

tgggtgcacg agtgggttac atcgaactgg atctcaacag cggtaagatc cttgagagtt    300

ttcgccccga agaacgtttt ccaatgatga gcacttttaa agttctgcta tgtggcgcgg    360

tattatcccg tattgacgcc gggcaagagc aactcggtcg ccgcatacac tattctcaga    420

atgacttggt tgagtactca ccagtcacag aaaagcatct tacggatggc atgacagtaa    480

gagaattatg cagtgctgcc ataaccatga gtgataacac tgcggccaac ttacttctga    540

caacgatcgg aggaccgaag gagctaaccg cttttttgca caacatgggg gatcatgtaa    600

ctcgccttga tcgttgggaa ccggagctga atgaagccat accaaacgac gagcgtgaca    660
```

-continued

```
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc ctttttgata   1080
atctcatgac caaaatccct taacgtgagt tttcgttcca ctgagcgtca gaccccgtag   1140
aaaagatcaa aggatcttct tgagatcctt tttttctgcg cgtaatctgc tgcttgcaaa   1200
caaaaaaacc accgctacca gcggtggttt gtttgccgga tcaagagcta ccaactcttt   1260
ttccgaaggt aactggcttc agcagagcgc agataccaaa tactgttctt ctagtgtagc   1320
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag gcgcagcggt cgggctgaac ggggggttcg tgcacacagc   1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740
tatggaaaaa cgccagcaac gcggcctttt tacggttcct ggccttttgc tggccttttg   1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacctcccct agcttaatta accctagaaa   2220
gataatcata ttgtgacgta cgttaaagat aatcatgcgt aaaattgacg catgtgtttt   2280
atcgatctgt atatcgaggt ttatttatta atttgaatag atattaagtt ttattatatt   2340
tacacttaca tactaataat aaattcaaca aacaatttat ttatgtttat ttatttatta   2400
aaaaaaaaca aaaactcaaa atttcttcta taaagtaaca aaacttttaa acattctctc   2460
ttttacaaaa ataaacttat tttgtacttt aaaaacagtc atgttgtatt ataaaataag   2520
taattagctt aacttataca taatagaaac aaattatact tattaatcgc attgattatt   2580
gactagtcgt attaagggtt ccggatcagc ttgattcgag ccccagctgg ttctttccgc   2640
ctcagaagcc atagagccca ccgcatcccc agcatgcctg ctattgtctt cccaatcctc   2700
ccccttgctg tcctgcccca ccccaccccc cagaatagaa tgacacctac tcagacaatg   2760
cgatgcaatt tcctcatttt attaggaaag gacagtggga gtggcacctt ccagggtcaa   2820
ggaaggcacg ggggaggggc aaacaacaga tggctggcaa ctagaaggca cagtcgaggc   2880
tgatcagcga gctctagaga attgatcccc tcagaagaac tcgtcaagaa ggcgatagaa   2940
ggcgatgcgc tgcgaatcgg gagcggcgat accgtaaagc acgaggaagc ggtcagccca   3000
```

-continued ttcgccgcca agctcttcag caatatcacg ggtagccaac gctatgtcct gatagcggtc 3060
cgccacaccc agccggccac agtcgatgaa tccagaaaag cggccatttt ccaccatgat 3120
attcggcaag caggcatcgc catgggtcac gacgagatcc tcgccgtcgg gcatgcgcgc 3180
cttgagcctg gcgaacagtt cggctggcgc gagcccctga tgctcttcgt ccagatcatc 3240
ctgatcgaca agaccggctt ccatccgagt acgtgctcgc tcgatgcgat gtttcgcttg 3300
gtggtcgaat gggcaggtag ccggatcaag cgtatgcagc cgccgcattg catcagccat 3360
gatggatact ttctcggcag gagcaaggtg agatgacagg agatcctgcc ccggcacttc 3420
gcccaatagc agccagtccc ttcccgcttc agtgacaacg tcgagcacag ctgcgcaagg 3480
aacgcccgtc gtggccagcc acgatagccg cgctgcctcg tcctgcagtt cattcagggc 3540
accggacagg tcggtcttga caaaaagaac cgggcgcccc tgcgctgaca gccggaacac 3600
ggcggcatca gagcagccga ttgtctgttg tgcccagtca tagccgaata gcctctccac 3660
ccaagcggcc ggagaacctg cgtgcaatcc atcttgttca atggccgatc ccatggttta 3720
gttcctcacc ttgtcgtatt atactatgcc gatatactat gccgatgatt aattgtcaac 3780
acgtgctgct gcaggtcgaa aggcccggag atgaggaaga ggagaacagc gcggcagacg 3840
tgcgcttttg aagcgtgcag aatgccgggc ctccggagga ccttcgggcg cccgccccgc 3900
ccctgagccc gcccctgagc ccgcccccgg acccacccct tcccagcctc tgagcccaga 3960
aagcgaagga gcaaagctgc tattggccgc tgccccaaag gcctacccgc ttccattgct 4020
cagcggtgct gtccatctgc acgagactag tgagacgtgc tacttccatt tgtcacgtcc 4080
tgcacgacgc gagctgcggg gcggggggga acttcctgac taggggagga gtagaaggtg 4140
gcgcgaaggg gccaccaaag aacggagccg gttggcgcct accggtggat gtggaatgtg 4200
tgcgagccag aggccacttg tgtagcgcca agtgcccagc ggggctgcta aagcgcatgc 4260
tccagactgc cttgggaaaa gcgcctcccc tacccggtag acaccccaca gtgggtggcc 4320
tagggacagg attgcaactc cagtctttct tcttcttggg cgggagtcac tagttattaa 4380
tagtaatcaa ttacggggtc attagttcat agcccatata tggagttccg cgttacataa 4440
cttacggtaa atggcccgcc tggctgaccg cccaacgacc cccgcccatt gacgtcaata 4500
atgacgtatg ttcccatagt aacgccaata gggactttcc attgacgtca atgggtggac 4560
tatttacggt aaactgccca cttggcagta catcaagtgt atcatatgcc aagtacgccc 4620
cctattgacg tcaatgacgg taaatggccc gcctggcatt atgcccagta catgacctta 4680
tgggactttc ctacttggca gtacatctac gtattagtca tcgctattac catgggtcga 4740
ggtgagcccc acgttctgct tcactctccc catctccccc ccctccccac ccccaatttt 4800
gtatttattt atttttaat tattttgtgc agcgatgggg gcgggggggg ggggggcgcg 4860
cgccaggcgg ggcggggcgg ggcgaggggc ggggcggggc gaggcggaga ggtgcggcgg 4920
cagccaatca gagcggcgcg ctccgaaagt ttccttttat ggcgaggcgg cggcggcggc 4980
ggccctataa aaagcgaagc gcgcggcggg cgggagtcgc tgcgttgcct tcgccccgtg 5040
ccccgctccg cgccgcctcg cgccgcccgc cccggctctg actgaccgcg ttactcccac 5100
aggtgagcgg gcgggacggc ccttctcctc cgggctgtaa ttagcgcttg gtttaatgac 5160
ggctcgtttc ttttctgtgg ctgcgtgaaa gccttaaagg gctccgggag ggccctttgt 5220
gcgggggga gcggctcggg gggtgcgtgc gtgtgtgtgt gcgtggggag cgccgcgtgc 5280
ggcccgcgct gcccggcggc tgtgagcgct gcgggcgcgg cgcggggctt tgtgcgctcc 5340
gcgtgtgcgc gaggggagcg cggccggggg cggtgccccg cggtgcgggg gggctgcgag 5400

```
gggaacaaag gctgcgtgcg gggtgtgtgc gtgggggggt gagcaggggg tgtgggcgcg   5460
gcggtcgggc tgtaaccccc ccctgcaccc ccctccccga gttgctgagc acggcccggc   5520
ttcgggtgcg gggctccgtg cggggcgtgg cgcggggctc gccgtgccgg gcggggggtg   5580
gcggcaggtg gggtgccggg gcggggcggg gccgcctcgg gccggggagg gctcggggga   5640
ggggcgcggc ggcccccggag cgccggcggc tgtcgaggcg cggcgagccg cagccattgc   5700
cttttatggt aatcgtgcga gagggcgcag ggacttcctt tgtcccaaat ctggcggagc   5760
cgaaatctgg gaggcgccgc cgcacccccct ctagcgggcg cgggcgaagc ggtgcggcgc   5820
cggcaggaag gaaatgggcg gggagggcct tcgtgcgtcg ccgcgccgcc gtccccttct   5880
ccatctccag cctcggggct gccgcagggg gacggctgcc ttcggggggg acggggcagg   5940
gcggggttcg gcttctggcg tgtgaccggc ggctctagag cctctgctaa ccatgttcat   6000
gccttcttct ttttcctaca gctcctgggc aacgtgctgg ttattgtgct gtctcatcat   6060
tttggcaaag aattcgccac catggtgccc aagaagaaga ggaaagtctc tagactggac   6120
aagagcaaag tcataaactc tgctctggaa ttactcaatg gagtcggtat cgaaggcctg   6180
acgacaagga aactcgctca aaagctggga gttgagcagc ctaccctgta ctggcacgtg   6240
aagaacaagc gggccctgct cgatgccctg ccaatcgaga tgctggacag gcatcatacc   6300
cactcctgcc ccctggaagg cgagtcatgg caagactttc tgcggaacaa cgccaagtca   6360
taccgctgtg ctctcctctc acatcgcgac ggggctaaag tgcatctcgg cacccgccca   6420
acagagaaac agtacgaaac cctggaaaat cagctcgcgt tcctgtgtca gcaaggcttc   6480
tccctggaga acgcactgta cgctctgtcc gccgtgggcc actttacact gggctgcgta   6540
ttggaggaac aggagcatca agtagcaaaa gaggaaagag agacacctac caccgattct   6600
atgcccccac ttctgaaaca agcaattgag ctgttcgacc ggcagggagc cgaacctgcc   6660
ttccttttcg gcctggaact aatcatatgt ggcctggaga aacagctaaa gtgcgaaagc   6720
ggcgggccga ccgacgccct tgacgatttt gacttagaca tgctcccagc cgatgccctt   6780
gacgactttg accttgatat gctgcctgct gacgctcttg acgattttga ccttgacatg   6840
ctccccgggt aaagcggccg cgactctaga tcataatcag ccataccaca tttgtagagg   6900
ttttacttgc tttaaaaaac ctcccacacc tcccccctgaa cctgaaacat aaaatgaatg   6960
caattgttgt tgttaacttg tttattgcag cttataatgg ttacaaataa agcaatagca   7020
tcacaaattt cacaaataaa gcattttttt cactgcattc tagttgtggt ttgtccaaac   7080
tcatcaatgt atcttaaggg atccctagag ggacagcccc cccccaaagc ccccagggat   7140
gtaattacgt ccctcccccg ctaggggcag cagcgagccg cccggggctc cgctccggtc   7200
cggcgctccc cccgcatccc cgagccggca gcgtgcgggg acagcccggg cacggggaag   7260
gtggcacggg atcgctttcc tctgaacgct tctcgctgct ctttgagcct gcagacacct   7320
ggggggatac ggggaaaaag ctttaggctg aaagagagat ttagaatgac agaatcatag   7380
aacggcctgg gttgcaaagg agcacagtgc tcatccagat ccaacccccct gctatgtgca   7440
gggtcatcaa ccagcagccc aggctgccca gagccacatc cagcctggcc ttgaatgcct   7500
gcagggatgg ggcatccaca gcctccttgg gcaacctgtt cagtgcgtca ccaccctctg   7560
ggggaaaaac tgcctcctca tatccaaccc aaacctcccc tgtctcagtg taaagccatt   7620
ccccccttgtc ctatcaaggg ggagtttgct gtgacattgt tggtctgggg tgacacatgt   7680
ttgccaattc agtgcatcac ggagaggcag atcttgggga taaggaagtg caggacagca   7740
```

tggacgtggg acatgcaggt gttgagggct ctgggacact ctccaagtca cagcgttcag 7800
aacagcctta aggataagaa gataggatag aaggacaaag agcaagttaa aacccagcat 7860
ggagaggagc acaaaaaggc cacagacact gctggtccct gtgtctgagc ctgcatgttt 7920
gatggtgtct ggatgcaagc agaaggggtg gaagagcttg cctggagaga tacagctggg 7980
tcagtaggac tgggacaggc agctggagaa ttgccatgta gatgttcata caatcgtcaa 8040
atcatgaagg ctggaaaagc cctccaagat ccccaagacc aaccccaacc cacccaccgt 8100
gcccactggc catgtccctc agtgccacat ccccacagtt cttcatcacc tccagggacg 8160
gtgacccccc cacctccgtg ggcagctgtg ccactgcagc accgctcttt ggagaaggta 8220
aatcttgcta aatccagccc gaccctcccc tggcacaacg taaggccatt atctctcatc 8280
caactccagg acggagtcag tgaggatggg gctgtcgacc tagagggaca gcccccccc 8340
aaagccccca gggatgtaat tacgtccctc cccgctagg ggcagcagcg agccgcccgg 8400
ggctccgctc cggtccggcg ctccccccgc atccccgagc cggcagcgtg cggggacagc 8460
ccgggcacgg ggaaggtggc acgggatcgc tttcctctga acgcttctcg ctgctctttg 8520
agcctgcaga cacctggggg gatacgggga aaaagcttta ggctgaaaga gagatttaga 8580
atgacagaat catagaacgg cctgggttgc aaaggagcac agtgctcatc cagatccaac 8640
cccctgctat gtgcagggtc atcaaccagc agcccaggct gcccagagcc acatccagcc 8700
tggccttgaa tgcctgcagg gatggggcat ccacagcctc cttgggcaac ctgttcagtg 8760
cgtcaccacc ctctgggga aaaactgcct cctcatatcc aacccaaacc tcccctgtct 8820
cagtgtaaag ccattccccc ttgtcctatc aagggggagt ttgctgtgac attgttggtc 8880
tggggtgaca catgtttgcc aattcagtgc atcacggaga ggcagatctt ggggataagg 8940
aagtgcagga cagcatggac gtgggacatg caggtgttga gggctctggg acactctcca 9000
agtcacagcg ttcagaacag ccttaaggat aagaagatag gatagaagga caaagagcaa 9060
gttaaaaccc agcatggaga ggagcacaaa aaggccacag acactgctgg tccctgtgtc 9120
tgagcctgca tgtttgatgg tgtctggatg caagcagaag ggtggaaga gcttgcctgg 9180
agagatacag ctgggtcagt aggactggga caggcagctg gagaattgcc atgtagatgt 9240
tcatacaatc gtcaaatcat gaaggctgga aaagccctcc aagatcccca agaccaaccc 9300
caacccaccc accgtgccca ctggccatgt ccctcagtgc cacatcccca cagttcttca 9360
tcacctccag ggacggtgac ccccccacct ccgtgggcag ctgtgccact gcagcaccgc 9420
tctttggaga aggtaaatct tgctaaatcc agcccgaccc tcccctggca caacgtaagg 9480
ccattatctc tcatccaact ccaggacgga gtcagtgagg atggggctca attgtttact 9540
ccctatcagt gatagagaac gtatgaagag tttactccct atcagtgata gagaacgtat 9600
gcagacttta ctccctatca gtgatagaga acgtataagg agtttactcc ctatcagtga 9660
tagagaacgt atgaccagtt tactccctat cagtgataga gaacgtatct acagtttact 9720
ccctatcagt gatagagaac gtatatccag tttactccct atcagtgata gagaacgtat 9780
aagctttagg cgtgtacggt gggcgcctat aaaagcagag ctcgtttagt gaaccgtcag 9840
atcgcctgga gcaattccac aacacttttg tcttatacca actttccgta ccacttccta 9900
ccctcgtaaa aagcttgtcc accatggctc ctaagaaaaa gcggaaggtg gacaagaaat 9960
actcaatcgg gctggacatc ggaactaact cagtggggtg ggcagtcatt actgacgagt 10020
acaaagtgcc aagcaagaaa tttaaggtcc tgggcaacac cgataggcac tccatcaaga 10080
aaaatctgat tggggccctg ctgttcgact ctggagagac agctgaagca actagactga 10140
aaaggactgc tagaaggcgc tatacccggc gaaagaatcg catctgctac ctgcaggaga 10200
ttttctctaa cgaaatggcc aaggtggacg atagtttctt tcatcggctg gaggaatcat 10260
tcctggtcga ggaagataag aaacacgaga gacatcctat ctttggaaac attgtggacg 10320
aggtcgctta tcacgaaaaa taccccacca tctatcatct gcgcaagaaa ctggtggact 10380
ctacagataa agcagacctg cggctgatct atctggccct ggctcacatg attaagttca 10440
gaggccattt tctgatcgag ggagatctga acccagacaa tagcgatgtg gacaagctgt 10500
tcatccagct ggtccagaca tacaatcagc tgtttgagga aaaccctatt aatgcatctg 10560
gcgtggacgc aaaagccatc ctgagtgcca ggctgtctaa gagtagaagg ctggagaacc 10620
tgatcgctca gctgccaggc gaaaagaaaa acggcctgtt tggaaatctg attgcactgt 10680
cactgggact gacacctaac ttcaagagca attttgatct ggccgaggac gctaaactgc 10740
agctgagcaa ggacacttat gacgatgacc tggataacct gctggctcag atcggagatc 10800
agtacgcaga cctgttcctg gccgctaaga atctgtctga cgctatcctg ctgagtgata 10860
ttctgcgggt gaacaccgag attacaaaag cccctctgtc agctagcatg atcaagagat 10920
atgacgagca ccatcaggat ctgaccctgc tgaaggcact ggtgcgccag cagctgcccg 10980
agaagtacaa ggaaatcttc tttgatcaga gtaagaacgg gtacgccggt tatattgacg 11040
gcggagcttc acaggaggaa ttctacaagt ttatcaaacc tattctggag aagatggacg 11100
gcaccgagga actgctggtg aaactgaatc gcgaggacct gctgcgcaag cagcggacat 11160
ttgataacgg ctccatcccc caccagattc atctgggaga gctgcacgca atcctgcgac 11220
gacaggaaga cttctaccca tttctgaagg ataaccgcga gaagatcgaa aaaattctga 11280
ccttccggat cccttactat gtggggcccc tggcaagggg taattcccgc tttgcctgga 11340
tgacacggaa atctgaggaa acaatcactc cttggaactt cgaggaagtg gtcgataagg 11400
gagcttccgc acagtctttc atcgagagaa tgacaaactt cgacaaaaac ctgccaaatg 11460
agaaagtgct gcctaagcac agtctgctgt acgagtattt cacagtctat aacgaactga 11520
ctaaggtgaa atacgtcacc gaggggatga ggaagcccgc cttcctgagc ggtgaacaga 11580
agaaagctat cgtggacctg ctgtttaaaa ccaatcgcaa ggtgacagtc aagcagctga 11640
aggaggacta cttcaagaaa attgaatgtt tcgattctgt ggagatcagt ggcgtcgaag 11700
acagatttaa cgcttctctg ggaacctacc acgatctgct gaagatcatt aaggataaag 11760
acttcctgga caacgaggaa aatgaggata tcctggaaga cattgtgctg accctgacac 11820
tgtttgagga tcgcgaaatg atcgaggaac ggctgaaaac ttatgcccat ctgttcgatg 11880
acaaggtgat gaaacagctg aagcgaagaa ggtacaccgg ctggggacga ctgagcagaa 11940
agctgatcaa cggcattcgg gacaaacaga gtggaaagac tatcctggac tttctgaaat 12000
cagatggctt cgctaacaga aattttatgc agctgattca cgatgacagc ctgaccttca 12060
aagaggatat ccagaaggca caggtgtccg ggcagggtga ctctctgcac gagcatatcg 12120
caaacctggc cgggtccccc gccatcaaga aaggtattct gcagaccgtg aaggtggtcg 12180
atgagctggt gaaagtcatg ggcaggcata agccagaaaa catcgtgatt gagatggccc 12240
gcgaaaatca gaccacacag aaaggacaga agaacagccg cgagcggatg aaaaggatcg 12300
aggaaggcat taaggaactg ggatcccaga tcctgaaaga gcaccctgtg gaaaacactc 12360
agctgcagaa tgagaagctg tatctgtact atctgcagaa tgggcgggat atgtacgtgg 12420
accaggagct ggatattaac cgactgtctg attacgacgt ggatcatatc gtcccacagt 12480

```
cattcctgaa agatgacagc attgacaata aggtgctgac ccggagtgac aaaaaccgag  12540
gaaagagtga taatgtccct tcagaggaag tggtcaagaa aatgaagaac tactggagac  12600
agctgctgaa tgccaaactg atcacacagc gaaagtttga taacctgact aaagctgaga  12660
gagggggtct gtcagaactg gacaaagcag gcttcatcaa gcgacagctg gtggagacca  12720
gacagatcac aaagcacgtc gctcagattc tggatagcag gatgaacaca aagtacgatg  12780
agaatgacaa actgatccgc gaagtgaagg tcattactct gaagtcaaaa cttgtgagcg  12840
acttcagaaa ggatttccag ttctacaaag tcagggagat caacaattat caccatgctc  12900
atgacgcata cctgaacgca gtggtcggga ccgccctgat taagaaatac cccaaactgg  12960
agagcgaatt cgtgtacggt gactataagg tgtacgatgt cagaaaaatg atcgccaaga  13020
gtgagcagga aattggaaaa gccaccgcta agtatttctt ttactcaaac atcatgaatt  13080
tctttaagac tgagatcacc ctggcaaatg gggaaatccg aaagagacca ctgattgaga  13140
ctaacggcga gaccggagaa atcgtgtggg acaagggtag ggattttgcc acagtgcgca  13200
aggtcctgtc catgcctcaa gtgaatattg tcaagaaaac agaggtgcag actggcggat  13260
tcagtaagga atcaattctg cccaaacgga actctgataa gctgatcgcc cgaaagaaag  13320
actgggatcc caagaaatat ggggggtttcg actccccaac agtggcttac tctgtcctgg  13380
tggtcgcaaa ggtggagaag ggaaaaagca agaaactgaa atccgtcaag gagctgctgg  13440
gtatcactat tatggagagg agctccttcg agaagaaccc catcgatttt ctggaggcta  13500
aaggctataa ggaagtgaag aaagacctga tcattaaact gccaaagtac agcctgtttg  13560
agctggaaaa cggaaggaag cgaatgctgg catccgcagg agagctgcag aagggtaatg  13620
aactggccct gccttctaag tacgtgaact tcctgtatct ggctagccac tacgagaagc  13680
tgaaaggctc cccgaggat aacgaacaga aacagctgtt tgtggagcag cacaagcatt  13740
atctggacga gatcattgaa cagattagcg agttctccaa aagagtgatc ctggctgacg  13800
caaatctgga taaggtcctg agcgcataca acaaacacag agataagcca atcagggagc  13860
aggccgaaaa tatcattcat ctgttcactc tgaccaacct gggagcccct gcagccttca  13920
agtattttga cactaccatc gatcggaaac gatacacatc cactaaggag gtgctggacg  13980
ctaccctgat tcaccagagc attaccggcc tgtatgaaac aaggattgac ctgtctcagc  14040
tggggggcga cctcgaggat ggcggtggcg cgctgtcccc gcagcactcc gccgtgaccc  14100
aggggagtat aatcaaaaac aaagagggca tggatgctaa gagccttacc gcctggtccc  14160
gaacactggt cacgtttaag gatgtgttcg tcgattttac ccgggaggag tggaaactgc  14220
tcgacaccgc gcagcagatc gtgtaccgga atgtcatgct cgaaaattac aaaaacttgg  14280
tcagcctcgg gtaccaattg accaaaccag atgtcatact gcgactggaa aaaggagagg  14340
aaccctggct cgtcgagcgc gaaattcatc aagaaacaca cccggattct gaaaccgcct  14400
tcgagattaa gagcagtgtg cctaggctcg agggaagcgg agagggcaga ggaagtctgc  14460
taacatgcgg tgacgtcgag gagaatcctg gcccagcacc gggatccatg gtgagcaagg  14520
gcgaggagct gttcaccggg gtggtgccca tcctggtcga gctggacggc gacgtaaacg  14580
gccacaagtt cagcgtgtcc ggcgagggcg agggcgatgc cacctacggc aagctgaccc  14640
tgaagttcat ctgcaccacc ggcaagctgc ccgtgccctg gcccaccctc gtgaccacct  14700
tcacctacgg cgtgcagtgc ttcgcccgct accccgacca catgaagcag cacgacttct  14760
tcaagtccgc catgcccgaa ggctacgtcc aggagcgcac catcttcttc aaggacgacg  14820
gcaactacaa gacccgcgcc gaggtgaagt tcgagggcga caccctggtg aaccgcatcg  14880
```

agctgaaggg catcgacttc aaggaggacg gcaacatcct ggggcacaag ctggagtaca 14940
actacaacag ccacaaggtc tatatcaccg ccgacaagca gaagaacggc atcaaggtga 15000
acttcaagac ccgccacaac atcgaggacg gcagcgtgca gctcgccgac cactaccagc 15060
agaacacccc catcggcgac ggccccgtgc tgctgcccga caaccactac ctgagcaccc 15120
agtccgccct gagcaaagac cccaacgaga agcgcgatca catggtcctg ctggagttcg 15180
tgaccgccgc cgggatcact ctcggcatgg acgagctgta caagtaaacc taatctagca 15240
gctcgctgat cagcctcgac tgtgccttct agttgccagc catctgttgt ttgcccctcc 15300
cccgtgcctt ccttgaccct ggaaggtgcc actcccactg tcctttccta ataaaatgag 15360
gaaattgcat cgcattgtct gagtaggtgt cattctattc tggggggtgg ggtggggcag 15420
gacagcaagg gggaggattg ggaagacaat agcaggcatg ctggggatgc ggtgggctct 15480
atggcttctg aggcggaaag aaccagctgg ggctcgatcc tctagttggc gcgtcatggt 15540
ccatatgaat atcctcctta gttcctattc cgctagccta gagggacagc ccccccccaa 15600
agcccccagg gatgtaatta cgtccctccc ccgctagggg cagcagcgag ccgcccgggg 15660
ctccgctccg gtccggcgct ccccccgcat ccccgagccg gcagcgtgcg gggacagccc 15720
gggcacgggg aaggtggcac gggatcgctt tcctctgaac gcttctcgct gctctttgag 15780
cctgcagaca cctgggggga tacggggaaa aagctttagg ctgaaagaga gatttagaat 15840
gacagaatca tagaacggcc tgggttgcaa aggagcacag tgctcatcca gatccaaccc 15900
cctgctatgt gcagggtcat caaccagcag cccaggctgc ccagagccac atccagcctg 15960
gccttgaatg cctgcaggga tggggcatcc acagcctcct tgggcaacct gttcagtgcg 16020
tcaccaccct ctgggggaaa aactgcctcc tcatatccaa cccaaacctc ccctgtctca 16080
gtgtaaagcc attcccctt gtcctatcaa gggggagttt gctgtgacat tgttggtctg 16140
gggtgacaca tgtttgccaa ttcagtgcat cacggagagg cagatcttgg ggataaggaa 16200
gtgcaggaca gcatggacgt gggacatgca ggtgttgagg gctctgggac actctccaag 16260
tcacagcgtt cagaacagcc ttaaggataa gaagatagga tagaaggaca aagagcaagt 16320
taaaacccag catggagagg agcacaaaaa ggccacagac actgctggtc cctgtgtctg 16380
agcctgcatg tttgatggtg tctggatgca agcagaaggg gtggaagagc ttgcctggag 16440
agatacagct gggtcagtag gactgggaca ggcagctgga gaattgccat gtagatgttc 16500
atacaatcgt caaatcatga aggctggaaa agccctccaa gatccccaag accaacccca 16560
acccacccac cgtgcccact ggccatgtcc ctcagtgcca catccccaca gttcttcatc 16620
acctccaggg acggtgaccc ccccacctcc gtgggcagct gtgccactgc agcaccgctc 16680
tttggagaag gtaaatcttg ctaaatccag cccgaccctc ccctggcaca acgtaaggcc 16740
attatctctc atccaactcc aggacggagt cagtgaggat ggggctggat ccgaagcagc 16800
tccagcctac acaatcgctc aagacgtgta atgcttttat tatatattag tcacgatatc 16860
tataacaaga aaatatatat ataataagtt atcacgtaag tagaacatga aataacaata 16920
taattatcgt atgagttaaa tcttaaaagt cacgtaaaag ataatcatgc gtcattttga 16980
ctcacgcggt cgttatagtt caaaatcagt gacacttacc gcattgacaa gcacgcctca 17040
cgggagctcc aagcggcgac tgagatgtcc taaatgcaca gcgacggatt cgcgctattt 17100
agaaagagag agcaatattt caagaatgca tgcgtcaatt ttacgcagac tatctttcta 17160
gggttaaaaa agatttgcgc tttactcgac ctaaacttta aacacgtcat agaatcttcg 17220
tttgacaaaa accacattgt ggggtaccga gctcttaatt aaggcgcgcc ggggaggttc 17280
cctttagtga gggttaattg cgggtcgccc tatagtgagt cgtattacaa ttcactggcc 17340
gtcgttttac aacgtcgtga ctgggaaaac cctggcgtta cccaacttaa tcgccttgca 17400
gcacatcccc ctttcgccag ctggcgtaat agcgaagagg cccgcaccga tcgcccttcc 17460
caacagttgc gcagcctgaa tggcgaatgg caaattgtaa gcgttaatat tttgttaaaa 17520
ttcgcgttaa atttttgtta aatcagctca ttttttaacc aataggccga aatcggcaaa 17580
atcccttata aatcaaaaga atagaccgag atagggttga gtgttgttcc agtttggaac 17640
aagagtccac tattaaagaa cgtggactcc aacgtcaaag ggcgaaaaac cgtctatcag 17700
ggcgatggcc cactacgtga accatcaccc taatcaagtt ttttggggtc gaggtgccgt 17760
aaagcactaa atcggaaccc taaagggagc ccccgattta gagcttgacg gggaaagccg 17820
gcgaacgtgg cgagaaagga agggaagaaa gcgaaaggag cgggcgctag ggcgctggca 17880
agtgtagcgg tcacgctgcg cgtaaccacc acacccgccg cgcttaatgc gccgctacag 17940
ggcgcgtcag 17950

<210> SEQ ID NO 16
<211> LENGTH: 17451
<212> TYPE: DNA
<213> ORGANISM: Artificial Sequence
<220> FEATURE:
<223> OTHER INFORMATION: Synthetic Polynucleotide

<400> SEQUENCE: 16
gtggcacttt tcggggaaat gtgcgcggaa cccctatttg tttatttttc taaatacatt 60
caaatatgta tccgctcatg agacaataac cctgataaat gcttcaataa tattgaaaaa 120
ggaagagtat gagtattcaa catttccgtg tcgcccttat tccctttttt gcggcatttt 180
gccttcctgt ttttgctcac ccagaaacgc tggtgaaagt aaaagatgct gaagatcagt 240
tgggtgcacg agtgggttac atcgaactgg atctcaacag cggtaagatc cttgagagtt 300
ttcgccccga agaacgtttt ccaatgatga gcacttttaa agttctgcta tgtggcgcgg 360
tattatcccg tattgacgcc gggcaagagc aactcggtcg ccgcatacac tattctcaga 420
atgacttggt tgagtactca ccagtcacag aaaagcatct tacggatggc atgacagtaa 480
gagaattatg cagtgctgcc ataaccatga gtgataacac tgcggccaac ttacttctga 540
caacgatcgg aggaccgaag gagctaaccg cttttttgca caacatgggg gatcatgtaa 600
ctcgccttga tcgttgggaa ccggagctga atgaagccat accaaacgac gagcgtgaca 660
ccacgatgcc tgtagcaatg gcaacaacgt tgcgcaaact attaactggc gaactactta 720
ctctagcttc ccggcaacaa ttaatagact ggatggaggc ggataaagtt gcaggaccac 780
ttctgcgctc ggcccttccg gctggctggt ttattgctga taaatctgga gccggtgagc 840
gtgggtctcg cggtatcatt gcagcactgg ggccagatgg taagccctcc cgtatcgtag 900
ttatctacac gacggggagt caggcaacta tggatgaacg aaatagacag atcgctgaga 960
taggtgcctc actgattaag cattggtaac tgtcagacca agtttactca tatatacttt 1020
agattgattt aaaacttcat ttttaattta aaaggatcta ggtgaagatc ctttttgata 1080
atctcatgac caaaatccct taacgtgagt tttcgttcca ctgagcgtca gaccccgtag 1140
aaaagatcaa aggatcttct tgagatcctt tttttctgcg cgtaatctgc tgcttgcaaa 1200
caaaaaaacc accgctacca gcggtggttt gtttgccgga tcaagagcta ccaactcttt 1260
ttccgaaggt aactggcttc agcagagcgc agataccaaa tactgttctt ctagtgtagc 1320

```
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag gcgcagcggt cgggctgaac ggggggttcg tgcacacagc   1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740
tatggaaaaa cgccagcaac gcggcctttt tacggttcct ggccttttgc tggccttttg   1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacctcccct agcttaatta accctagaaa   2220
gataatcata ttgtgacgta cgttaaagat aatcatgcgt aaaattgacg catgtgtttt   2280
atcgatctgt atatcgaggt ttatttatta atttgaatag atattaagtt ttattatatt   2340
tacacttaca tactaataat aaattcaaca aacaatttat ttatgtttat ttatttatta   2400
aaaaaaaaca aaaactcaaa atttcttcta taaagtaaca aaacttttaa acattctctc   2460
ttttacaaaa ataaacttat tttgtacttt aaaaacagtc atgttgtatt ataaaataag   2520
taattagctt aacttataca taatagaaac aaattatact tattaatcgc attgattatt   2580
gactagtcgt attaagggtt ccggatcagc ttgattcgag ccccagctgg ttctttccgc   2640
ctcagaagcc atagagccca ccgcatcccc agcatgcctg ctattgtctt cccaatcctc   2700
ccccttgctg tcctgcccca ccccaccccc cagaatagaa tgacacctac tcagacaatg   2760
cgatgcaatt tcctcatttt attaggaaag gacagtggga gtggcacctt ccagggtcaa   2820
ggaaggcacg gggggagggc aaacaacaga tggctggcaa ctagaaggca cagtcgaggc   2880
tgatcagcga gctctagaga attgatcccc tcagaagaac tcgtcaagaa ggcgatagaa   2940
ggcgatgcgc tgcgaatcgg gagcggcgat accgtaaagc acgaggaagc ggtcagccca   3000
ttcgccgcca agctcttcag caatatcacg ggtagccaac gctatgtcct gatagcggtc   3060
cgccacaccc agccggccac agtcgatgaa tccagaaaag cggccatttt ccaccatgat   3120
attcggcaag caggcatcgc catgggtcac gacgagatcc tcgccgtcgg gcatgcgcgc   3180
cttgagcctg gcgaacagtt cggctggcgc gagcccctga tgctcttcgt ccagatcatc   3240
ctgatcgaca agaccggctt ccatccgagt acgtgctcgc tcgatgcgat gtttcgcttg   3300
gtggtcgaat gggcaggtag ccggatcaag cgtatgcagc cgccgcattg catcagccat   3360
gatggatact ttctcggcag gagcaaggtg agatgacagg agatcctgcc ccggcacttc   3420
gcccaatagc agccagtccc ttcccgcttc agtgacaacg tcgagcacag ctgcgcaagg   3480
aacgcccgtc gtggccagcc acgatagccg cgctgcctcg tcctgcagtt cattcagggc   3540
accggacagg tcggtcttga caaaaagaac cgggcgcccc tgcgctgaca gccggaacac   3600
ggcggcatca gagcagccga ttgtctgttg tgcccagtca tagccgaata gcctctccac   3660
```

-continued ccaagcggcc ggagaacctg cgtgcaatcc atcttgttca atggccgatc ccatggcggt 3720
atcgataagc tagcttgggc tgcaggtcga gggacctaat taagggttcc ggatccacta 3780
gttctagagc ggcctcgact ctacgatacc gtcgatcccc actggaaaga ccgcgaagag 3840
tttgtcctca accgcgagct gtggaaaaaa aagggacagg ataagtatga catcatcaag 3900
gaaaccctgg actactgcgc cctacagatc cctgaagttc ctatactttc tagagaatag 3960
gaacttcgga ataggaactt caaagaacgc gtaccccaca gtgggtggcc tagggacagg 4020
attgcaactc cagtctttct tcttcttggg cgggagtcac tagttattaa tagtaatcaa 4080
ttacggggtc attagttcat agcccatata tggagttccg cgttacataa cttacggtaa 4140
atggcccgcc tggctgaccg cccaacgacc cccgcccatt gacgtcaata atgacgtatg 4200
ttcccatagt aacgccaata gggactttcc attgacgtca atgggtggac tatttacggt 4260
aaactgccca cttggcagta catcaagtgt atcatatgcc aagtacgccc cctattgacg 4320
tcaatgacgg taaatggccc gcctggcatt atgcccagta catgacctta tgggactttc 4380
ctacttggca gtacatctac gtattagtca tcgctattac catgggtcga ggtgagcccc 4440
acgttctgct tcactctccc catctccccc ccctccccac ccccaatttt gtatttattt 4500 atttttaat tattttgtgc agcgatgggg gcgggggggg ggggggcgcg cgccaggcgg 4560
ggcggggcgg ggcgaggggc ggggcggggc gaggcggaga ggtgcggcgg cagccaatca 4620
gagcggcgcg ctccgaaagt ttccttttat ggcgaggcgg cggcggcggc ggccctataa 4680
aaagcgaagc gcgcggcggg cgggagtcgc tgcgttgcct tcgccccgtg ccccgctccg 4740
cgccgcctcg cgccgcccgc cccggctctg actgaccgcg ttactcccac aggtgagcgg 4800
gcgggacggc ccttctcctc cgggctgtaa ttagcgcttg gtttaatgac ggctcgtttc 4860
ttttctgtgg ctgcgtgaaa gccttaaagg gctccgggag ggccctttgt gcggggggga 4920
gcggctcggg gggtgcgtgc gtgtgtgtgt gcgtggggag cgccgcgtgc ggcccgcgct 4980
gcccggcggc tgtgagcgct gcgggcgcgg cgcggggctt tgtgcgctcc gcgtgtgcgc 5040
gaggggagcg cggccggggg cggtgccccg cggtgcgggg gggctgcgag gggaacaaag 5100
gctgcgtgcg ggtgtgtgc gtgggggggt gagcaggggg tgtgggcgcg gcggtcgggc 5160
tgtaaccccc ccctgcaccc ccctccccga gttgctgagc acggcccggc ttcgggtgcg 5220
gggctccgtg cggggcgtgg cgcggggctc gccgtgccgg gcgggggtg gcggcaggtg 5280 ggggtgccgg gcggggcggg gccgcctcgg gccggggagg gctcggggga ggggcgcggc 5340
ggccccggag cgccggcggc tgtcgaggcg cggcgagccg cagccattgc cttttatggt 5400
aatcgtgcga gagggcgcag ggacttcctt tgtcccaaat ctggcggagc cgaaatctgg 5460
gaggcgccgc cgcacccct ctagcgggcg cgggcgaagc ggtgcggcgc cggcaggaag 5520
gaaatgggcg gggagggcct tcgtgcgtcg ccgcgccgcc gtccccttct ccatctccag 5580
cctcggggct gccgcagggg gacggctgcc ttcggggggg acggggcagg gcggggttcg 5640
gcttctggcg tgtgaccggc ggctctagag cctctgctaa ccatgttcat gccttcttct 5700
ttttcctaca gctcctgggc aacgtgctgg ttattgtgct gtctcatcat tttggcaaag 5760
aattcgccac catggtgccc aagaagaaga ggaaagtctc tagactggac aagagcaaag 5820
tcataaactc tgctctggaa ttactcaatg gagtcggtat cgaaggcctg acgacaagga 5880
aactcgctca aaagctggga gttgagcagc ctaccctgta ctggcacgtg aagaacaagc 5940
gggccctgct cgatgccctg ccaatcgaga tgctggacag gcatcatacc cactcctgcc 6000
ccctggaagg cgagtcatgg caagactttc tgcggaacaa cgccaagtca taccgctgtg 6060
ctctcctctc acatcgcgac ggggctaaag tgcatctcgg cacccgccca acagagaaac 6120
agtacgaaac cctggaaaat cagctcgcgt tcctgtgtca gcaaggcttc tccctggaga 6180
acgcactgta cgctctgtcc gccgtgggcc actttacact gggctgcgta ttggaggaac 6240
aggagcatca agtagcaaaa gaggaaagag agacacctac caccgattct atgcccccac 6300
ttctgaaaca agcaattgag ctgttcgacc ggcagggagc cgaacctgcc ttcctttttcg 6360
gcctggaact aatcatatgt ggcctggaga aacagctaaa gtgcgaaagc ggcgggccga 6420
ccgacgccct tgacgatttt gacttagaca tgctcccagc cgatgccctt gacgactttg 6480
accttgatat gctgcctgct gacgctcttg acgattttga ccttgacatg ctccccgggt 6540
aaagcggccg cgactctaga tcataatcag ccataccaca tttgtagagg ttttacttgc 6600
tttaaaaaac ctcccacacc tcccccctgaa cctgaaacat aaaatgaatg caattgttgt 6660
tgttaacttg tttattgcag cttataatgg ttacaaataa agcaatagca tcacaaattt 6720
cacaaataaa gcattttttt cactgcattc tagttgtggt ttgtccaaac tcatcaatgt 6780
atcttaaggg atccctagag ggacagcccc cccccaaagc ccccagggat gtaattacgt 6840
ccctcccccg ctaggggcag cagcgagccg cccggggctc cgctccggtc cggcgctccc 6900
cccgcatccc cgagccggca gcgtgcgggg acagcccggg cacggggaag gtggcacggg 6960
atcgctttcc tctgaacgct tctcgctgct ctttgagcct gcagacacct gggggggatac 7020
ggggaaaaag ctttaggctg aaagagagat ttagaatgac agaatcatag aacggcctgg 7080
gttgcaaagg agcacagtgc tcatccagat ccaacccccct gctatgtgca gggtcatcaa 7140
ccagcagccc aggctgccca gagccacatc cagcctggcc ttgaatgcct gcagggatgg 7200
ggcatccaca gcctccttgg gcaacctgtt cagtgcgtca ccaccctctg gggggaaaac 7260
tgcctcctca tatccaaccc aaacctcccc tgtctcagtg taaagccatt ccccccttgtc 7320
ctatcaaggg ggagtttgct gtgacattgt tggtctgggg tgacacatgt ttgccaattc 7380
agtgcatcac ggagaggcag atcttgggga taaggaagtg caggacagca tggacgtggg 7440
acatgcaggt gttgagggct ctgggacact ctccaagtca cagcgttcag aacagcctta 7500
aggataagaa gataggatag aaggacaaag agcaagttaa aacccagcat ggagaggagc 7560
acaaaaaggc cacagacact gctggtccct gtgtctgagc ctgcatgttt gatggtgtct 7620
ggatgcaagc agaaggggtg gaagagcttg cctggagaga tacagctggg tcagtaggac 7680
tgggacaggc agctggagaa ttgccatgta gatgttcata caatcgtcaa atcatgaagg 7740
ctggaaaagc cctccaagat ccccaagacc aaccccaacc cacccaccgt gcccactggc 7800
catgtccctc agtgccacat ccccacagtt cttcatcacc tccagggacg gtgacccccc 7860
cacctccgtg ggcagctgtg ccactgcagc accgctcttt ggagaaggta aatcttgcta 7920
aatccagccc gaccctcccc tggcacaacg taaggccatt atctctcatc caactccagg 7980
acggagtcag tgaggatggg gctgtcgacc tagagggaca gcccccccccc aaagcccccca 8040
gggatgtaat tacgtccctc ccccgctagg ggcagcagcg agccgcccgg ggctccgctc 8100
cggtccggcg ctcccccccgc atccccgagc cggcagcgtg cggggacagc ccgggcacgg 8160
ggaaggtggc acgggatcgc tttcctctga acgcttctcg ctgctctttg agcctgcaga 8220
cacctggggg gatacgggga aaaagcttta ggctgaaaga gagatttaga atgacagaat 8280
catagaacgg cctgggttgc aaaggagcac agtgctcatc cagatccaac cccctgctat 8340
gtgcagggtc atcaaccagc agcccaggct gcccagagcc acatccagcc tggccttgaa 8400

```
tgcctgcagg gatggggcat ccacagcctc cttgggcaac ctgttcagtg cgtcaccacc   8460
ctctggggga aaaactgcct cctcatatcc aacccaaacc tcccctgtct cagtgtaaag   8520
ccattccccc ttgtcctatc aagggggagt ttgctgtgac attgttggtc tggggtgaca   8580
catgtttgcc aattcagtgc atcacggaga ggcagatctt ggggataagg aagtgcagga   8640
cagcatggac gtgggacatg caggtgttga gggctctggg acactctcca agtcacagcg   8700
ttcagaacag ccttaaggat aagaagatag gatagaagga caaagagcaa gttaaaaccc   8760
agcatggaga ggagcacaaa aaggccacag acactgctgg tccctgtgtc tgagcctgca   8820
tgtttgatgg tgtctggatg caagcagaag ggtggaaga gcttgcctgg agagatacag    8880
ctgggtcagt aggactggga caggcagctg gagaattgcc atgtagatgt tcatacaatc   8940
gtcaaatcat gaaggctgga aaagccctcc aagatcccca agaccaaccc caacccaccc   9000
accgtgccca ctggccatgt ccctcagtgc cacatcccca cagttcttca tcacctccag   9060
ggacggtgac ccccccacct ccgtgggcag ctgtgccact gcagcaccgc tctttggaga   9120
aggtaaatct tgctaaatcc agcccgaccc tcccctggca caacgtaagg ccattatctc   9180
tcatccaact ccaggacgga gtcagtgagg atggggctca attgtttact ccctatcagt   9240
gatagagaac gtatgaagag tttactccct atcagtgata gagaacgtat gcagacttta   9300
ctccctatca gtgatagaga acgtataagg agtttactcc ctatcagtga tagagaacgt   9360
atgaccagtt tactccctat cagtgataga gaacgtatct acagtttact ccctatcagt   9420
gatagagaac gtatatccag tttactccct atcagtgata gagaacgtat aagctttagg   9480
cgtgtacggt gggcgcctat aaaagcagag ctcgtttagt gaaccgtcag atcgcctgga   9540
gcaattccac aacacttttg tcttatacca actttccgta ccacttccta ccctcgtaaa   9600
aagcttgtcc accatggctc ctaagaaaaa gcggaaggtg gacaagaaat actcaatcgg   9660
gctggccatc ggaactaact cagtggggtg ggcagtcatt actgacgagt acaaagtgcc   9720
aagcaagaaa tttaaggtcc tgggcaacac cgataggcac tccatcaaga aaaatctgat   9780
tggggccctg ctgttcgact ctggagagac agctgaagca actagactga aaaggactgc   9840
tagaaggcgc tatacccggc gaaagaatcg catctgctac ctgcaggaga ttttctctaa   9900
cgaaatggcc aaggtggacg atagtttctt tcatcggctg gaggaatcat tcctggtcga   9960
ggaagataag aaacacgaga gacatcctat ctttggaaac attgtggacg aggtcgctta  10020
tcacgaaaaa taccccacca tctatcatct gcgcaagaaa ctggtggact ctacagataa  10080
agcagacctg cggctgatct atctggccct ggctcacatg attaagttca gaggccattt  10140
tctgatcgag ggagatctga acccagacaa tagcgatgtg gacaagctgt tcatccagct  10200
ggtccagaca tacaatcagc tgtttgagga aaaccctatt aatgcatctg gcgtggacgc  10260
aaaagccatc ctgagtgcca ggctgtctaa gagtagaagg ctggagaacc tgatcgctca  10320
gctgccaggc gaaaagaaaa acggcctgtt tggaaatctg attgcactgt cactgggact  10380
gacacctaac ttcaagagca attttgatct ggccgaggac gctaaactgc agctgagcaa  10440
ggacacttat gacgatgacc tggataacct gctggctcag atcggagatc agtacgcaga  10500
cctgttcctg gccgctaaga atctgtctga cgctatcctg ctgagtgata ttctgcgggt  10560
gaacaccgag attacaaaag cccctctgtc agctagcatg atcaagagat atgacgagca  10620
ccatcaggat ctgaccctgc tgaaggcact ggtgcgccag cagctgcccg agaagtacaa  10680
ggaaatcttc tttgatcaga gtaagaacgg gtacgccggt tatattgacg gcggagcttc  10740
acaggaggaa ttctacaagt ttatcaaacc tattctggag aagatggacg gcaccgagga  10800
```

actgctggtg aaactgaatc gcgaggacct gctgcgcaag cagcggacat ttgataacgg 10860
ctccatcccc caccagattc atctgggaga gctgcacgca atcctgcgac gacaggaaga 10920
cttctaccca tttctgaagg ataaccgcga gaagatcgaa aaaattctga ccttccggat 10980
cccttactat gtggggcccc tggcaagggg taattcccgc tttgcctgga tgacacggaa 11040
atctgaggaa acaatcactc cttggaactt cgaggaagtg gtcgataagg gagcttccgc 11100
acagtctttc atcgagagaa tgacaaactt cgacaaaaac ctgccaaatg agaaagtgct 11160
gcctaagcac agtctgctgt acgagtattt cacagtctat aacgaactga ctaaggtgaa 11220
atacgtcacc gaggggatga ggaagcccgc cttcctgagc ggtgaacaga agaaagctat 11280
cgtggacctg ctgtttaaaa ccaatcgcaa ggtgacagtc aagcagctga aggaggacta 11340
cttcaagaaa attgaatgtt tcgattctgt ggagatcagt ggcgtcgaag acagatttaa 11400
cgcttctctg ggaacctacc acgatctgct gaagatcatt aaggataaag acttcctgga 11460
caacgaggaa aatgaggata tcctggaaga cattgtgctg accctgacac tgtttgagga 11520
tcgcgaaatg atcgaggaac ggctgaaaac ttatgcccat ctgttcgatg acaaggtgat 11580
gaaacagctg aagcgaagaa ggtacaccgg ctggggacga ctgagcagaa agctgatcaa 11640
cggcattcgg gacaaacaga gtggaaagac tatcctggac tttctgaaat cagatggctt 11700
cgctaacaga aattttatgc agctgattca cgatgacagc ctgaccttca aagaggatat 11760
ccagaaggca caggtgtccg ggcagggtga ctctctgcac gagcatatcg caaacctggc 11820
cgggtccccc gccatcaaga aaggtattct gcagaccgtg aaggtggtcg atgagctggt 11880
gaaagtcatg ggcaggcata agccagaaaa catcgtgatt gagatggccc gcgaaaatca 11940
gaccacacag aaaggacaga agaacagccg cgagcggatg aaaaggatcg aggaaggcat 12000
taaggaactg ggatcccaga tcctgaaaga gcaccctgtg gaaaacactc agctgcagaa 12060
tgagaagctg tatctgtact atctgcagaa tgggcgggat atgtacgtgg accaggagct 12120
ggatattaac cgactgtctg attacgacgt ggatgccatc gtcccacagt cattcctgaa 12180
agatgacagc attgacaata aggtgctgac ccggagtgac aaaaaccgag gaaagagtga 12240
taatgtccct tcagaggaag tggtcaagaa aatgaagaac tactggagac agctgctgaa 12300
tgccaaactg atcacacagc gaaagtttga taacctgact aaagctgaga gagggggtct 12360
gtcagaactg gacaaagcag gcttcatcaa gcgacagctg gtggagacca gacagatcac 12420
aaagcacgtc gctcagattc tggatagcag gatgaacaca aagtacgatg agaatgacaa 12480
actgatccgc gaagtgaagg tcattactct gaagtcaaaa cttgtgagcg acttcagaaa 12540
ggatttccag ttctacaaag tcagggagat caacaattat caccatgctc atgacgcata 12600
cctgaacgca gtggtcggga ccgccctgat taagaaatac cccaaactgg agagcgaatt 12660
cgtgtacggt gactataagg tgtacgatgt cagaaaaatg atcgccaaga gtgagcagga 12720
aattggaaaa gccaccgcta agtatttctt ttactcaaac atcatgaatt tctttaagac 12780
tgagatcacc ctggcaaatg gggaaatccg aaagagacca ctgattgaga ctaacggcga 12840
gaccggagaa atcgtgtggg acaagggtag ggattttgcc acagtgcgca aggtcctgtc 12900
catgcctcaa gtgaatattg tcaagaaaac agaggtgcag actggcggat tcagtaagga 12960
atcaattctg cccaaacgga actctgataa gctgatcgcc cgaaagaaag actgggatcc 13020
caagaaatat gggggtttcg actccccaac agtggcttac tctgtcctgg tggtcgcaaa 13080
ggtggagaag ggaaaaagca agaaactgaa atccgtcaag gagctgctgg gtatcactat 13140

-continued

```
tatggagagg agctccttcg agaagaaccc catcgatttt ctggaggcta aaggctataa  13200
ggaagtgaag aaagacctga tcattaaact gccaaagtac agcctgtttg agctggaaaa  13260
cggaaggaag cgaatgctgg catccgcagg agagctgcag aagggtaatg aactggccct  13320
gccttctaag tacgtgaact tcctgtatct ggctagccac tacgagaagc tgaaaggctc  13380
ccccgaggat aacgaacaga aacagctgtt tgtggagcag cacaagcatt atctggacga  13440
gatcattgaa cagattagcg agttctccaa aagagtgatc ctggctgacg caaatctgga  13500
taaggtcctg agcgcataca acaaacacag agataagcca atcagggagc aggccgaaaa  13560
tatcattcat ctgttcactc tgaccaacct gggagcccct gcagccttca agtattttga  13620
cactaccatc gatcggaaac gatacacatc cactaaggag gtgctggacg ctaccctgat  13680
tcaccagagc attaccggcc tgtatgaaac aaggattgac ctgtctcagc tgggggggcga  13740
cctcgagccg aaaaagaaac gcaaagttgg gcgcgccgac gcgctggacg atttcgatct  13800
cgacatgctg ggcagcgacg ccctggatga cttcgacctg gatatgctgg gctctgatgc  13860
cctggacgac tttgacttgg acatgttggg atccgacgct ctcgatgatt ttgaccttga  13920
catgctgatc aacggcagcg gcgagggcag aggcagcctg ctaacatgcg gtgacgtcga  13980
ggagaatcct ggcccagcac cgggatccat ggtgagcaag ggcgaggagc tgttcaccgg  14040
ggtggtgccc atcctggtcg agctggacgg cgacgtaaac ggccacaagt tcagcgtgtc  14100
cggcgagggc gagggcgatg ccacctacgg caagctgacc ctgaagttca tctgcaccac  14160
cggcaagctg cccgtgccct ggcccaccct cgtgaccacc ttcacctacg gcgtgcagtg  14220
cttcgcccgc taccccgacc acatgaagca gcacgacttc ttcaagtccg ccatgcccga  14280
aggctacgtc caggagcgca ccatcttctt caaggacgac ggcaactaca agacccgcgc  14340
cgaggtgaag ttcgagggcg acaccctggt gaaccgcatc gagctgaagg gcatcgactt  14400
caaggaggac ggcaacatcc tggggcacaa gctggagtac aactacaaca gccacaaggt  14460
ctatatcacc gccgacaagc agaagaacgg catcaaggtg aacttcaaga cccgccacaa  14520
catcgaggac ggcagcgtgc agctcgccga ccactaccag cagaacaccc ccatcggcga  14580
cggccccgtg ctgctgcccg acaaccacta cctgagcacc cagtccgccc tgagcaaaga  14640
ccccaacgag aagcgcgatc acatggtcct gctggagttc gtgaccgccg ccgggatcac  14700
tctcggcatg gacgagctgt acaagtaaac ctaatctagc agctcgctga tcagcctcga  14760
ctgtgccttc tagttgccag ccatctgttg tttgcccctc ccccgtgcct tccttgaccc  14820
tggaaggtgc cactcccact gtcctttcct aataaaatga ggaaattgca tcgcattgtc  14880
tgagtaggtg tcattctatt ctggggggtg gggtggggca ggacagcaag ggggaggatt  14940
gggaagacaa tagcaggcat gctggggatg cggtgggctc tatggcttct gaggcggaaa  15000
gaaccagctg gggctcgatc ctctagttgg cgcgtcatgg tccatatgaa tatcctcctt  15060
agttcctatt ccgctagcct agagggacag cccccccccca aagcccccag ggatgtaatt  15120
acgtccctcc cccgctaggg gcagcagcga gccgcccggg gctccgctcc ggtccggcgc  15180
tccccccgca tccccgagcc ggcagcgtgc ggggacagcc cgggcacggg gaaggtggca  15240
cgggatcgct ttcctctgaa cgcttctcgc tgctctttga gcctgcagac acctgggggg  15300
atacggggaa aaagctttag gctgaaagag agatttagaa tgacagaatc atagaacggc  15360
ctgggttgca aaggagcaca gtgctcatcc agatccaacc ccctgctatg tgcagggtca  15420
tcaaccagca gcccaggctg cccagagcca catccagcct ggccttgaat gcctgcaggg  15480
atggggcatc cacagcctcc ttgggcaacc tgttcagtgc gtcaccaccc tctgggggaa  15540
```

aaactgcctc ctcatatcca acccaaacct cccctgtctc agtgtaaagc cattccccct 15600
tgtcctatca agggggagtt tgctgtgaca ttgttggtct ggggtgacac atgtttgcca 15660
attcagtgca tcacggagag gcagatcttg ggataagga agtgcaggac agcatggacg 15720
tgggacatgc aggtgttgag ggctctggga cactctccaa gtcacagcgt tcagaacagc 15780
cttaaggata agaagatagg atagaaggac aaagagcaag ttaaaaccca gcatggagag 15840
gagcacaaaa aggccacaga cactgctggt ccctgtgtct gagcctgcat gtttgatggt 15900
gtctggatgc aagcagaagg ggtggaagag cttgcctgga gagatacagc tgggtcagta 15960
ggactgggac aggcagctgg agaattgcca tgtagatgtt catacaatcg tcaaatcatg 16020
aaggctggaa aagccctcca agatccccaa gaccaacccc aacccaccca ccgtgcccac 16080
tggccatgtc cctcagtgcc acatccccac agttcttcat cacctccagg gacggtgacc 16140
cccccacctc cgtgggcagc tgtgccactg cagcaccgct ctttggagaa ggtaaatctt 16200
gctaaatcca gcccgaccct cccctggcac aacgtaaggc cattatctct catccaactc 16260
caggacggag tcagtgagga tggggctgga tccgaagcag ctccagccta cacaatcgct 16320
caagacgtgt aatgctttta ttatatatta gtcacgatat ctataacaag aaaatatata 16380
tataataagt tatcacgtaa gtagaacatg aaataacaat ataattatcg tatgagttaa 16440
atcttaaaag tcacgtaaaa gataatcatg cgtcattttg actcacgcgg tcgttatagt 16500
tcaaaatcag tgacacttac cgcattgaca agcacgcctc acgggagctc caagcggcga 16560
ctgagatgtc ctaaatgcac agcgacggat tcgcgctatt tagaaagaga gagcaatatt 16620
tcaagaatgc atgcgtcaat tttacgcaga ctatctttct agggttaaaa aagatttgcg 16680
ctttactcga cctaaacttt aaacacgtca tagaatcttc gtttgacaaa aaccacattg 16740
tggggtaccg agctcttaat taaggcgcgc cggggaggtt ccctttagtg agggttaatt 16800
gcgggtcgcc ctatagtgag tcgtattaca attcactggc cgtcgtttta caacgtcgtg 16860
actgggaaaa ccctggcgtt acccaactta atcgccttgc agcacatccc cctttcgcca 16920
gctggcgtaa tagcgaagag gcccgcaccg atcgcccttc ccaacagttg cgcagcctga 16980
atggcgaatg gcaaattgta agcgttaata ttttgttaaa attcgcgtta aatttttgtt 17040
aaatcagctc attttttaac caataggccg aaatcggcaa aatcccttat aaatcaaaag 17100
aatagaccga gatagggttg agtgttgttc cagtttggaa caagagtcca ctattaaaga 17160
acgtggactc caacgtcaaa gggcgaaaaa ccgtctatca gggcgatggc ccactacgtg 17220
aaccatcacc ctaatcaagt tttttggggt cgaggtgccg taaagcacta aatcggaacc 17280
ctaaagggag cccccgattt agagcttgac ggggaaagcc ggcgaacgtg gcgagaaagg 17340
aagggaagaa agcgaaagga gcgggcgcta gggcgctggc aagtgtagcg gtcacgctgc 17400
gcgtaaccac cacacccgcc gcgcttaatg cgccgctaca gggcgcgtca g 17451

<210> SEQ ID NO 17
<211> LENGTH: 18381
<212> TYPE: DNA
<213> ORGANISM: Artificial Sequence
<220> FEATURE:
<223> OTHER INFORMATION: Synthetic Polynucleotide

<400> SEQUENCE: 17
gtggcacttt tcggggaaat gtgcgcggaa cccctatttg tttatttttc taaatacatt 60
caaatatgta tccgctcatg agacaataac cctgataaat gcttcaataa tattgaaaaa 120

```
ggaagagtat gagtattcaa catttccgtg tcgcccttat tccctttttt gcggcatttt    180
gccttcctgt ttttgctcac ccagaaacgc tggtgaaagt aaaagatgct gaagatcagt    240
tgggtgcacg agtgggttac atcgaactgg atctcaacag cggtaagatc cttgagagtt    300
ttcgccccga agaacgtttt ccaatgatga gcacttttaa agttctgcta tgtggcgcgg    360
tattatcccg tattgacgcc gggcaagagc aactcggtcg ccgcatacac tattctcaga    420
atgacttggt tgagtactca ccagtcacag aaaagcatct tacggatggc atgacagtaa    480
gagaattatg cagtgctgcc ataaccatga gtgataacac tgcggccaac ttacttctga    540
caacgatcgg aggaccgaag gagctaaccg cttttttgca caacatgggg gatcatgtaa    600
ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc ctttttgata   1080
atctcatgac caaaatccct taacgtgagt tttcgttcca ctgagcgtca gaccccgtag   1140
aaaagatcaa aggatcttct tgagatcctt tttttctgcg cgtaatctgc tgcttgcaaa   1200
caaaaaaacc accgctacca gcggtggttt gtttgccgga tcaagagcta ccaactcttt   1260
ttccgaaggt aactggcttc agcagagcgc agataccaaa tactgttctt ctagtgtagc   1320
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag gcgcagcggt cgggctgaac ggggggttcg tgcacacagc   1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740
tatggaaaaa cgccagcaac gcggcctttt tacggttcct ggccttttgc tggccttttg   1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacctcccct agcttaatta accctagaaa   2220
gataatcata ttgtgacgta cgttaaagat aatcatgcgt aaaattgacg catgtgtttt   2280
atcgatctgt atatcgaggt ttatttatta atttgaatag atattaagtt ttattatatt   2340
tacacttaca tactaataat aaattcaaca aacaatttat ttatgtttat ttatttatta   2400
aaaaaaaaca aaaactcaaa atttcttcta taaagtaaca aaacttttaa acattctctc   2460
ttttacaaaa ataaacttat tttgtacttt aaaaacagtc atgttgtatt ataaaataag   2520
```

```
taattagctt aacttataca taatagaaac aaattatact tattaatcgc attgattatt   2580
gactagtcgt attaagggtt ccggatcagc ttgattcgag ccccagctgg ttctttccgc   2640
ctcagaagcc atagagccca ccgcatcccc agcatgcctg ctattgtctt cccaatcctc   2700
ccccttgctg tcctgcccca ccccaccccc cagaatagaa tgacacctac tcagacaatg   2760
cgatgcaatt tcctcatttt attaggaaag gacagtggga gtggcacctt ccagggtcaa   2820
ggaaggcacg gggggagggc aaacaacaga tggctggcaa ctagaaggca cagtcgaggc   2880
tgatcagcga gctctagaga attgatcccc tcagaagaac tcgtcaagaa ggcgatagaa   2940
ggcgatgcgc tgcgaatcgg gagcggcgat accgtaaagc acgaggaagc ggtcagccca   3000
ttcgccgcca agctcttcag caatatcacg ggtagccaac gctatgtcct gatagcggtc   3060
cgccacaccc agccggccac agtcgatgaa tccagaaaag cggccatttt ccaccatgat   3120
attcggcaag caggcatcgc catgggtcac gacgagatcc tcgccgtcgg gcatgcgcgc   3180
cttgagcctg gcgaacagtt cggctggcgc gagcccctga tgctcttcgt ccagatcatc   3240
ctgatcgaca agaccggctt ccatccgagt acgtgctcgc tcgatgcgat gtttcgcttg   3300
gtggtcgaat gggcaggtag ccggatcaag cgtatgcagc cgccgcattg catcagccat   3360
gatggatact ttctcggcag gagcaaggtg agatgacagg agatcctgcc ccggcacttc   3420
gcccaatagc agccagtccc ttcccgcttc agtgacaacg tcgagcacag ctgcgcaagg   3480
aacgcccgtc gtggccagcc acgatagccg cgctgcctcg tcctgcagtt cattcagggc   3540
accggacagg tcggtcttga caaaaagaac cgggcgcccc tgcgctgaca gccggaacac   3600
ggcggcatca gagcagccga ttgtctgttg tgcccagtca tagccgaata gcctctccac   3660
ccaagcggcc ggagaacctg cgtgcaatcc atcttgttca atggccgatc ccatggttta   3720
gttcctcacc ttgtcgtatt atactatgcc gatatactat gccgatgatt aattgtcaac   3780
acgtgctgct gcaggtcgaa aggcccggag atgaggaaga ggagaacagc gcggcagacg   3840
tgcgcttttg aagcgtgcag aatgccgggc ctccggagga ccttcgggcg cccgccccgc   3900
ccctgagccc gcccctgagc ccgcccccgg acccacccct tcccagcctc tgagcccaga   3960
aagcgaagga gcaaagctgc tattggccgc tgccccaaag gcctacccgc ttccattgct   4020
cagcggtgct gtccatctgc acgagactag tgagacgtgc tacttccatt tgtcacgtcc   4080
tgcacgacgc gagctgcggg gcggggggga acttcctgac taggggagga gtagaaggtg   4140
gcgcgaaggg gccaccaaag aacggagccg gttggcgcct accggtggat gtggaatgtg   4200
tgcgagccag aggccacttg tgtagcgcca agtgcccagc ggggctgcta aagcgcatgc   4260
tccagactgc cttgggaaaa gcgcctcccc tacccggtag acaccccaca gtgggtggcc   4320
tagggacagg attgcaactc cagtctttct tcttcttggg cgggagtcac tagttattaa   4380
tagtaatcaa ttacggggtc attagttcat agcccatata tggagttccg cgttacataa   4440
cttacggtaa atggcccgcc tggctgaccg cccaacgacc cccgcccatt gacgtcaata   4500
atgacgtatg ttcccatagt aacgccaata gggactttcc attgacgtca atgggtggac   4560
tatttacggt aaactgccca cttggcagta catcaagtgt atcatatgcc aagtacgccc   4620
cctattgacg tcaatgacgg taaatggccc gcctggcatt atgcccagta catgacctta   4680
tgggactttc ctacttggca gtacatctac gtattagtca tcgctattac catgggtcga   4740
ggtgagcccc acgttctgct tcactctccc catctccccc ccctccccac ccccaatttt   4800
gtatttattt atttttaat tattttgtgc agcgatgggg gcgggggggg ggggggcgcg   4860
```

-continued

```
cgccaggcgg ggcggggcgg ggcgaggggc ggggcggggc gaggcggaga ggtgcggcgg   4920
cagccaatca gagcggcgcg ctccgaaagt ttccttttat ggcgaggcgg cggcggcggc   4980
ggccctataa aaagcgaagc gcgcggcggg cgggagtcgc tgcgttgcct tcgccccgtg   5040
ccccgctccg cgccgcctcg cgccgcccgc cccggctctg actgaccgcg ttactcccac   5100
aggtgagcgg gcgggacggc ccttctcctc cgggctgtaa ttagcgcttg gtttaatgac   5160
ggctcgtttc ttttctgtgg ctgcgtgaaa gccttaaagg gctccgggag ggccctttgt   5220
gcggggggga gcggctcggg gggtgcgtgc gtgtgtgtgt gcgtggggag cgccgcgtgc   5280
ggcccgcgct gcccggcggc tgtgagcgct gcgggcgcgg cgcggggctt tgtgcgctcc   5340
gcgtgtgcgc gaggggagcg cggccggggg cggtgccccg cggtgcgggg gggctgcgag   5400
gggaacaaag gctgcgtgcg gggtgtgtgc gtgggggggt gagcaggggg tgtgggcgcg   5460
gcggtcgggc tgtaaccccc ccctgcaccc ccctccccga gttgctgagc acggcccggc   5520
ttcgggtgcg gggctccgtg cggggcgtgg cgcggggctc gccgtgccgg gcggggggtg   5580
gcggcaggtg ggggtgccgg gcggggcggg gccgcctcgg gccggggagg gctcggggga   5640
ggggcgcggc ggccccggag cgccggcggc tgtcgaggcg cggcgagccg cagccattgc   5700
cttttatggt aatcgtgcga gagggcgcag ggacttcctt tgtcccaaat ctggcggagc   5760
cgaaatctgg gaggcgccgc cgcacccccct ctagcgggcg cgggcgaagc ggtgcggcgc   5820
cggcaggaag gaaatgggcg gggagggcct tcgtgcgtcg ccgcgccgcc gtccccttct   5880
ccatctccag cctcggggct gccgcagggg gacggctgcc ttcggggggg acggggcagg   5940
gcggggttcg gcttctggcg tgtgaccggc ggctctagag cctctgctaa ccatgttcat   6000
gccttcttct ttttcctaca gctcctgggc aacgtgctgg ttattgtgct gtctcatcat   6060
tttggcaaag aattcgccac catggtgccc aagaagaaga ggaaagtctc tagactggac   6120
aagagcaaag tcataaactc tgctctggaa ttactcaatg gagtcggtat cgaaggcctg   6180
acgacaagga aactcgctca aaagctggga gttgagcagc ctaccctgta ctggcacgtg   6240
aagaacaagc gggccctgct cgatgccctg ccaatcgaga tgctggacag gcatcatacc   6300
cactcctgcc ccctggaagg cgagtcatgg caagactttc tgcggaacaa cgccaagtca   6360
taccgctgtg ctctcctctc acatcgcgac ggggctaaag tgcatctcgg cacccgccca   6420
acagagaaac agtacgaaac cctggaaaat cagctcgcgt tcctgtgtca gcaaggcttc   6480
tccctggaga acgcactgta cgctctgtcc gccgtgggcc actttacact gggctgcgta   6540
ttggaggaac aggagcatca agtagcaaaa gaggaaagag agacacctac caccgattct   6600
atgcccccac ttctgaaaca agcaattgag ctgttcgacc ggcagggagc cgaacctgcc   6660
ttccttttcg gcctggaact aatcatatgt ggcctggaga aacagctaaa gtgcgaaagc   6720
ggcgggccga ccgacgccct tgacgatttt gacttagaca tgctcccagc cgatgccctt   6780
gacgactttg accttgatat gctgcctgct gacgctcttg acgattttga ccttgacatg   6840
ctccccgggt aaagcggccg cgactctaga tcataatcag ccataccaca tttgtagagg   6900
ttttacttgc tttaaaaaac ctcccacacc tcccccctgaa cctgaaacat aaaatgaatg   6960
caattgttgt tgttaacttg tttattgcag cttataatgg ttacaaataa agcaatagca   7020
tcacaaattt cacaaataaa gcattttttt cactgcattc tagttgtggt ttgtccaaac   7080
tcatcaatgt atcttaaggg atccctagag ggacagcccc cccccaaagc ccccagggat   7140
gtaattacgt ccctcccccg ctaggggcag cagcgagccg cccggggctc cgctccggtc   7200
cggcgctccc cccgcatccc cgagccggca gcgtgcgggg acagcccggg cacggggaag   7260
```

gtggcacggg atcgctttcc tctgaacgct tctcgctgct ctttgagcct gcagacacct 7320
ggggggatac ggggaaaaag ctttaggctg aaagagagat ttagaatgac agaatcatag 7380
aacggcctgg gttgcaaagg agcacagtgc tcatccagat ccaaccccct gctatgtgca 7440
gggtcatcaa ccagcagccc aggctgccca gagccacatc cagcctggcc ttgaatgcct 7500
gcagggatgg ggcatccaca gcctccttgg gcaacctgtt cagtgcgtca ccaccctctg 7560
ggggaaaaac tgcctcctca tatccaaccc aaacctcccc tgtctcagtg taaagccatt 7620
cccccttgtc ctatcaaggg ggagtttgct gtgacattgt tggtctgggg tgacacatgt 7680
ttgccaattc agtgcatcac ggagaggcag atcttgggga taaggaagtg caggacagca 7740
tggacgtggg acatgcaggt gttgagggct ctgggacact ctccaagtca cagcgttcag 7800
aacagcctta aggataagaa gataggatag aaggacaaag agcaagttaa aacccagcat 7860
ggagaggagc acaaaaaggc cacagacact gctggtccct gtgtctgagc ctgcatgttt 7920
gatggtgtct ggatgcaagc agaaggggtg gaagagcttg cctggagaga tacagctggg 7980
tcagtaggac tgggacaggc agctggagaa ttgccatgta gatgttcata caatcgtcaa 8040
atcatgaagg ctggaaaagc cctccaagat ccccaagacc aaccccaacc cacccaccgt 8100
gcccactggc catgtccctc agtgccacat ccccacagtt cttcatcacc tccagggacg 8160
gtgacccccc cacctccgtg ggcagctgtg ccactgcagc accgctcttt ggagaaggta 8220
aatcttgcta aatccagccc gaccctcccc tggcacaacg taaggccatt atctctcatc 8280
caactccagg acggagtcag tgaggatggg gctgtcgacc tagagggaca gccccccccc 8340
aaagccccca gggatgtaat tacgtccctc ccccgctagg ggcagcagcg agccgcccgg 8400
ggctccgctc cggtccggcg ctccccccgc atccccgagc cggcagcgtg cggggacagc 8460
ccgggcacgg ggaaggtggc acgggatcgc tttcctctga acgcttctcg ctgctctttg 8520
agcctgcaga cacctggggg gatacgggga aaaagcttta ggctgaaaga gagatttaga 8580
atgacagaat catagaacgg cctgggttgc aaaggagcac agtgctcatc cagatccaac 8640
cccctgctat gtgcagggtc atcaaccagc agcccaggct gcccagagcc acatccagcc 8700
tggccttgaa tgcctgcagg gatggggcat ccacagcctc cttgggcaac ctgttcagtg 8760
cgtcaccacc ctctggggga aaaactgcct cctcatatcc aacccaaacc tcccctgtct 8820
cagtgtaaag ccattccccc ttgtcctatc aagggggagt ttgctgtgac attgttggtc 8880
tggggtgaca catgtttgcc aattcagtgc atcacggaga ggcagatctt ggggataagg 8940
aagtgcagga cagcatggac gtgggacatg caggtgttga gggctctggg acactctcca 9000
agtcacagcg ttcagaacag ccttaaggat aagaagatag gatagaagga caaagagcaa 9060
gttaaaaccc agcatggaga ggagcacaaa aaggccacag acactgctgg tccctgtgtc 9120
tgagcctgca tgtttgatgg tgtctggatg caagcagaag ggtggaaga gcttgcctgg 9180
agagatacag ctgggtcagt aggactggga caggcagctg gagaattgcc atgtagatgt 9240
tcatacaatc gtcaaatcat gaaggctgga aaagccctcc aagatcccca agaccaaccc 9300
caacccaccc accgtgccca ctggccatgt ccctcagtgc cacatcccca cagttcttca 9360
tcacctccag ggacggtgac ccccccacct ccgtgggcag ctgtgccact gcagcaccgc 9420
tctttggaga aggtaaatct tgctaaatcc agcccgaccc tcccctggca caacgtaagg 9480
ccattatctc tcatccaact ccaggacgga gtcagtgagg atggggctca attgtttact 9540
ccctatcagt gatagagaac gtatgaagag tttactccct atcagtgata gagaacgtat 9600
gcagacttta ctccctatca gtgatagaga acgtataagg agtttactcc ctatcagtga 9660
tagagaacgt atgaccagtt tactccctat cagtgataga gaacgtatct acagtttact 9720
ccctatcagt gatagagaac gtatatccag tttactccct atcagtgata gagaacgtat 9780
aagctttagg cgtgtacggt gggcgcctat aaaagcagag ctcgtttagt gaaccgtcag 9840
atcgcctgga gcaattccac aacacttttg tcttatacca actttccgta ccacttccta 9900
ccctcgtaaa aagcttgtcc actcgagatt ctctagacat cattaattcc taatttttgt 9960
tgacactcta tcattgatag agttatttta ccactcccta tcagtgatag agaaaagtga 10020
aatggccaag cctttgtctc aagaagaatc caccctcatt gaaagagcaa cggctacaat 10080
caacagcatc cccatctctg aagactacag cgtcgccagc gcagctctct ctagcgacgg 10140
ccgcatcttc actggtgtca atgtatatca ttttactggg ggaccttgtg cagaactcgt 10200
ggtgctgggc actgctgctg ctgcggcagc tggcaacctg acttgtatcg tcgcgatcgg 10260
aaatgagaac aggggcatct tgagcccctg cggacggtgt cgacaggtgc ttctcgatct 10320
gcatcctggg atcaaagcga tagtgaagga cagtgatgga cagccgacgg cagttgggat 10380
tcgtgaattg ctgccctctg gttatgtgtg ggagggctaa ctcgagatga gctcagagac 10440
tggcccagtg gctgtggacc ccacattgag acggcggatc gagccccatg agtttgaggt 10500
attcttcgat ccgagagagc tccgcaagga gacctgcctg ctttacgaaa ttaattgggg 10560
gggccggcac tccatttggc gacatacatc acagaacact aacaagcacg tcgaagtcaa 10620
cttcatcgag aagttcacga cagaaagata tttctgtccg aacacaaggt gcagcattac 10680
ctggtttctc agctggagcc catgcggcga atgtagtagg gccatcactg aattcctgtc 10740
aaggtatccc cacgtcactc tgtttattta catcgcaagg ctgtaccacc acgctgaccc 10800
ccgcaatcga caaggcctgc gggatttgat ctcttcaggt gtgactatcc aaattatgac 10860
tgagcaggag tcaggatact gctggagaaa ctttgtgaat tatagcccga gtaatgaagc 10920
ccactggcct aggtatcccc atctgtgggt acgactgtac gttcttgaac tgtactgcat 10980
catactgggc ctgcctcctt gtctcaacat tctgagaagg aagcagccac agctgacatt 11040
ctttaccatc gctcttcagt cttgtcatta ccagcgactg cccccacaca ttctctgggc 11100
caccgggttg aaaagcggca gcgagactcc cgggacctca gagtccgcca cacccgaaag 11160
tgataaaaag tattctattg gtttagccat cggcactaat tccgttggat gggctgtcat 11220
aaccgatgaa tacaaagtac cttcaaagaa atttaaggtg ttggggaaca cagaccgtca 11280
ttcgattaaa aagaatctta tcggtgccct cctattcgat agtggcgaaa cggcagaggc 11340
gactcgcctg aaacgaaccg ctcggagaag gtatacacgt cgcaagaacc gaatatgtta 11400
cttacaagaa atttttagca atgagatggc caaagttgac gattctttct ttcaccgttt 11460
ggaagagtcc ttccttgtcg aagaggacaa gaaacatgaa cggcacccca tctttggaaa 11520
catagtagat gaggtggcat atcatgaaaa gtacccaacg atttatcacc tcagaaaaaa 11580
gctagttgac tcaactgata aagcggacct gaggttaatc tacttggctc ttgcccatat 11640
gataaagttc cgtgggcact ttctcattga gggtgatcta aatccggaca actcggatgt 11700
cgacaaactg ttcatccagt tagtacaaac ctataatcag ttgtttgaag agaaccctat 11760
aaatgcaagt ggcgtggatg cgaaggctat tcttagcgcc cgcctctcta aatcccgacg 11820
gctagaaaac ctgatcgcac aattacccgg agagaagaaa aatgggttgt tcggtaacct 11880
tatagcgctc tcactaggcc tgacaccaaa ttttaagtcg aacttcgact tagctgaaga 11940
tgccaaattg cagcttagta aggacacgta cgatgacgat ctcgacaatc tactggcaca 12000
aattggagat cagtatgcgg acttattttt ggctgccaaa aaccttagcg atgcaatcct 12060
cctatctgac atactgagag ttaatactga gattaccaag gcgccgttat ccgcttcaat 12120
gatcaaaagg tacgatgaac atcaccaaga cttgacactt ctcaaggccc tagtccgtca 12180
gcaactgcct gagaaatata aggaaatatt ctttgatcag tcgaaaaacg ggtacgcagg 12240
ttatattgac ggcggagcga gtcaagagga attctacaag tttatcaaac ccatattaga 12300
gaagatggat gggacggaag agttgcttgt aaaactcaat cgcgaagatc tactgcgaaa 12360
gcagcggact ttcgacaacg gtagcattcc acatcaaatc cacttaggcg aattgcatgc 12420
tatacttaga aggcaggagg atttttatcc gttcctcaaa gacaatcgtg aaaagattga 12480
gaaaatccta acctttcgca taccttacta tgtgggaccc ctggcccgag ggaactctcg 12540
gttcgcatgg atgacaagaa agtccgaaga aacgattact ccatggaatt ttgaggaagt 12600
tgtcgataaa ggtgcgtcag ctcaatcgtt catcgagagg atgaccaact ttgacaagaa 12660
tttaccgaac gaaaaagtat tgcctaagca cagtttactt tacgagtatt tcacagtgta 12720
caatgaactc acgaaagtta agtatgtcac tgagggcatg cgtaaacccg cctttctaag 12780
cggagaacag aagaaagcaa tagtagatct gttattcaag accaaccgca aagtgacagt 12840
taagcaattg aaagaggact actttaagaa aattgaatgc ttcgattctg tcgagatctc 12900
cggggtagaa gatcgattta atgcgtcact tggtacgtat catgacctcc taaagataat 12960
taaagataag gacttcctgg ataacgaaga gaatgaagat atcttagaag atatagtgtt 13020
gactcttacc ctctttgaag atcgggaaat gattgaggaa agactaaaaa catacgctca 13080
cctgttcgac gataaggtta tgaaacagtt aaagaggcgt cgctatacgg gctggggacg 13140
attgtcgcgg aaacttatca acgggataag agacaagcaa agtggtaaaa ctattctcga 13200
ttttctaaag agcgacggct tcgccaatag gaactttatg cagctgatcc atgatgactc 13260
tttaaccttc aaagaggata tacaaaaggc acaggtttcc ggacaagggg actcattgca 13320
cgaacatatt gcgaatcttg ctggttcgcc agccatcaaa aagggcatac tccagacagt 13380
caaagtagtg gatgagctag ttaaggtcat gggacgtcac aaaccggaaa acattgtaat 13440
cgagatggca cgcgaaaatc aaacgactca gaaggggcaa aaaaacagtc gagagcggat 13500
gaagagaata gaagagggta ttaaagaact gggcagccag atcttaaagg agcatcctgt 13560
ggaaaatacc caattgcaga acgagaaact ttacctctat tacctacaaa atggaaggga 13620
catgtatgtt gatcaggaac tggacataaa ccgtttatct gattacgacg tcgatcacat 13680
tgtaccccaa tcctttttga aggacgattc aatcgacaat aaagtgctta cacgctcgga 13740
taagaaccga gggaaaagtg acaatgttcc aagcgaggaa gtcgtaaaga aaatgaagaa 13800
ctattggcgg cagctcctaa atgcgaaact gataacgcaa agaaagttcg ataacttaac 13860
taaagctgag aggggtggct tgtctgaact tgacaaggcc ggatttatta aacgtcagct 13920
cgtggaaacc cgccaaatca caaagcatgt tgcacagata ctagattccc gaatgaatac 13980
gaaatacgac gagaacgata agctgattcg ggaagtcaaa gtaatcactt taaagtcaaa 14040
attggtgtcg gacttcagaa aggattttca attctataaa gttagggaga taaataacta 14100
ccaccatgcg cacgacgctt atcttaatgc cgtcgtaggg accgcactca ttaagaaata 14160
cccgaagcta gaaagtgagt ttgtgtatgg tgattacaaa gtttatgacg tccgtaagat 14220
gatcgcgaaa agcgaacagg agataggcaa ggctacagcc aaatacttct tttattctaa 14280
cattatgaat ttctttaaga cggaaatcac tctggcaaac ggagagatac gcaaacgacc 14340
tttaattgaa accaatgggg agacaggtga aatcgtatgg gataagggcc gggacttcgc 14400
gacggtgaga aaagttttgt ccatgcccca agtcaacata gtaaagaaaa ctgaggtgca 14460
gaccggaggg ttttcaaagg aatcgattct tccaaaaagg aatagtgata agctcatcgc 14520
tcgtaaaaag gactgggacc cgaaaaagta cggtggcttc gatagcccta cagttgccta 14580
ttctgtccta gtagtggcaa aagttgagaa gggaaaatcc aagaaactga agtcagtcaa 14640
agaattattg gggataacga ttatggagcg ctcgtctttt gaaaagaacc ccatcgactt 14700
ccttgaggcg aaaggttaca aggaagtaaa aaaggatctc ataattaaac taccaaagta 14760
tagtctgttt gagttagaaa atggccgaaa acggatgttg gctagcgccg gagagcttca 14820
aaaggggaac gaactcgcac taccgtctaa atacgtgaat ttcctgtatt tagcgtccca 14880
ttacgagaag ttgaaaggtt cacctgaaga taacgaacag aagcaacttt ttgttgagca 14940
gcacaaacat tatctcgacg aaatcataga gcaaatttcg gaattcagta agagagtcat 15000
cctagctgat gccaatctgg acaaagtatt aagcgcatac aacaagcaca gggataaacc 15060
catacgtgag caggcggaaa atattatcca tttgtttact cttaccaacc tcggcgctcc 15120
agccgcattc aagtattttg acacaacgat agatcgcaaa cgatacactt ctaccaagga 15180
ggtgctagac gcgacactga ttcaccaatc catcacggga ttatatgaaa ctcggataga 15240
tttgtcacag cttgggggtg actctggtgg ttctactaat ctgtcagata ttattgaaaa 15300
ggagaccggt aagcaactgg ttatccagga atccatcctc atgctcccag aggaggtgga 15360
agaagtcatt gggaacaagc cggaaagcga tatactcgtg cacaccgcct acgacgagag 15420
caccgacgag aatgtcatgc ttctgactag cgacgcccct gaatacaagc cttgggctct 15480
ggtcatacag gatagcaacg gtgagaacaa gattaagatg ctctctggtg gttctcccaa 15540
gaagaagagg aaagtctaaa aattctaaaa tacagcatag caaaacttta acctccaaat 15600
caagcctcta cttgaatcct ttctgaggg atgaataagg cataggcatc aggggctgtt 15660
gccaatgtgc attagctgtt tgcagcctca ccttctttca tggagtttaa gatatagtgt 15720
attttcccaa ggtttgaact agctcttcat ttctttatgt tttaaatgca ctgacctccc 15780
acattccctt tttagtaaaa tattcagaaa taatttaaat acatcattgc aatgaaaata 15840
aatgtttttt attaggcaga atccagatgc tcaaggccct tcataatatc ccccagttta 15900
gtagttggac ttagggaaca aaggaacctt taatagaaat tggacagcaa gaaagcgagc 15960
ttctagatgg tccatatgaa tatcctcctt agttcctatt ccgctagcct agagggacag 16020
ccccccccca aagcccccag ggatgtaatt acgtccctcc cccgctaggg gcagcagcga 16080
gccgcccggg gctccgctcc ggtccggcgc tccccccgca tccccgagcc ggcagcgtgc 16140
ggggacagcc cgggcacggg gaaggtggca cgggatcgct ttcctctgaa cgcttctcgc 16200
tgctctttga gcctgcagac acctgggggg atacggggaa aaagctttag gctgaaagag 16260
agatttagaa tgacagaatc atagaacggc ctgggttgca aaggagcaca gtgctcatcc 16320
agatccaacc ccctgctatg tgcagggtca tcaaccagca gcccaggctg cccagagcca 16380
catccagcct ggccttgaat gcctgcaggg atggggcatc cacagcctcc ttgggcaacc 16440
tgttcagtgc gtcaccaccc tctgggggaa aaactgcctc ctcatatcca acccaaacct 16500
cccctgtctc agtgtaaagc cattccccct tgtcctatca agggggagtt tgctgtgaca 16560
ttgttggtct ggggtgacac atgtttgcca attcagtgca tcacggagag gcagatcttg 16620
gggataagga agtgcaggac agcatggacg tgggacatgc aggtgttgag ggctctggga 16680
cactctccaa gtcacagcgt tcagaacagc cttaaggata agaagatagg atagaaggac 16740
aaagagcaag ttaaaaccca gcatggagag gagcacaaaa aggccacaga cactgctggt 16800
ccctgtgtct gagcctgcat gtttgatggt gtctggatgc aagcagaagg ggtggaagag 16860
cttgcctgga gagatacagc tgggtcagta ggactgggac aggcagctgg agaattgcca 16920
tgtagatgtt catacaatcg tcaaatcatg aaggctggaa aagccctcca agatccccaa 16980
gaccaacccc aacccaccca ccgtgcccac tggccatgtc cctcagtgcc acatccccac 17040
agttcttcat cacctccagg gacggtgacc cccccacctc cgtgggcagc tgtgccactg 17100
cagcaccgct ctttggagaa ggtaaatctt gctaaatcca gcccgaccct cccctggcac 17160
aacgtaaggc cattatctct catccaactc caggacggag tcagtgagga tggggctgga 17220
tccgaagcag ctccagccta cacaatcgct caagacgtgt aatgctttta ttatatatta 17280
gtcacgatat ctataacaag aaaatatata tataataagt tatcacgtaa gtagaacatg 17340
aaataacaat ataattatcg tatgagttaa atcttaaaag tcacgtaaaa gataatcatg 17400
cgtcattttg actcacgcgg tcgttatagt tcaaaatcag tgacacttac cgcattgaca 17460
agcacgcctc acgggagctc caagcggcga ctgagatgtc ctaaatgcac agcgacggat 17520
tcgcgctatt tagaaagaga gagcaatatt tcaagaatgc atgcgtcaat tttacgcaga 17580
ctatctttct agggttaaaa aagatttgcg ctttactcga cctaaacttt aaacacgtca 17640
tagaatcttc gtttgacaaa aaccacattg tggggtaccg agctcttaat taaggcgcgc 17700
cggggaggtt ccctttagtg agggttaatt gcgggtcgcc ctatagtgag tcgtattaca 17760
attcactggc cgtcgtttta caacgtcgtg actgggaaaa ccctggcgtt acccaactta 17820
atcgccttgc agcacatccc cctttcgcca gctggcgtaa tagcgaagag gcccgcaccg 17880
atcgcccttc ccaacagttg cgcagcctga atggcgaatg gcaaattgta agcgttaata 17940
ttttgttaaa attcgcgtta aatttttgtt aaatcagctc attttttaac caataggccg 18000
aaatcggcaa aatcccttat aaatcaaaag aatagaccga gatagggttg agtgttgttc 18060
cagtttggaa caagagtcca ctattaaaga acgtggactc caacgtcaaa gggcgaaaaa 18120
ccgtctatca gggcgatggc ccactacgtg aaccatcacc ctaatcaagt tttttggggt 18180
cgaggtgccg taaagcacta aatcggaacc ctaaagggag cccccgattt agagcttgac 18240
ggggaaagcc ggcgaacgtg gcgagaaagg aagggaagaa agcgaaagga gcgggcgcta 18300
gggcgctggc aagtgtagcg gtcacgctgc gcgtaaccac cacacccgcc gcgcttaatg 18360
cgccgctaca gggcgcgtca g 18381

<210> SEQ ID NO 18
<211> LENGTH: 19822
<212> TYPE: DNA
<213> ORGANISM: Artificial Sequence
<220> FEATURE:
<223> OTHER INFORMATION: Synthetic Polynucleotide

<400> SEQUENCE: 18
gtggcacttt tcggggaaat gtgcgcggaa cccctatttg tttatttttc taaatacatt 60
caaatatgta tccgctcatg agacaataac cctgataaat gcttcaataa tattgaaaaa 120
ggaagagtat gagtattcaa catttccgtg tcgcccttat tccctttttt gcggcatttt 180
gccttcctgt ttttgctcac ccagaaacgc tggtgaaagt aaaagatgct gaagatcagt 240
tgggtgcacg agtgggttac atcgaactgg atctcaacag cggtaagatc cttgagagtt 300
ttcgccccga agaacgtttt ccaatgatga gcacttttaa agttctgcta tgtggcgcgg 360

```
tattatcccg tattgacgcc gggcaagagc aactcggtcg ccgcatacac tattctcaga    420
atgacttggt tgagtactca ccagtcacag aaaagcatct tacggatggc atgacagtaa    480
gagaattatg cagtgctgcc ataaccatga gtgataacac tgcggccaac ttacttctga    540
caacgatcgg aggaccgaag gagctaaccg cttttttgca caacatgggg gatcatgtaa    600
ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc ctttttgata   1080
atctcatgac caaaatccct taacgtgagt tttcgttcca ctgagcgtca gaccccgtag   1140
aaaagatcaa aggatcttct tgagatcctt tttttctgcg cgtaatctgc tgcttgcaaa   1200
caaaaaaacc accgctacca gcggtggttt gtttgccgga tcaagagcta ccaactcttt   1260
ttccgaaggt aactggcttc agcagagcgc agataccaaa tactgttctt ctagtgtagc   1320
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag gcgcagcggt cgggctgaac ggggggttcg tgcacacagc   1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740
tatggaaaaa cgccagcaac gcggcctttt tacggttcct ggccttttgc tggccttttg   1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacctcccct agcttaatta accctagaaa   2220
gataatcata ttgtgacgta cgttaaagat aatcatgcgt aaaattgacg catgtgtttt   2280
atcgatctgt atatcgaggt ttatttatta atttgaatag atattaagtt ttattatatt   2340
tacacttaca tactaataat aaattcaaca aacaatttat ttatgtttat ttatttatta   2400
aaaaaaaaca aaaactcaaa atttcttcta taaagtaaca aaacttttaa acattctctc   2460
ttttacaaaa ataaacttat tttgtacttt aaaaacagtc atgttgtatt ataaaataag   2520
taattagctt aacttataca taatagaaac aaattatact tattaatcgc attgattatt   2580
gactagtcgt attaagggtt ccggatcagc ttgattcgag ccccagctgg ttctttccgc   2640
ctcagaagcc atagagccca ccgcatcccc agcatgcctg ctattgtctt cccaatcctc   2700
ccccttgctg tcctgcccca ccccaccccc cagaatagaa tgacacctac tcagacaatg   2760
```

-continued cgatgcaatt tcctcatttt attaggaaag gacagtggga gtggcacctt ccagggtcaa 2820
ggaaggcacg ggggaggggc aaacaacaga tggctggcaa ctagaaggca cagtcgaggc 2880
tgatcagcga gctctagaga attgatcccc tcagaagaac tcgtcaagaa ggcgatagaa 2940
ggcgatgcgc tgcgaatcgg gagcggcgat accgtaaagc acgaggaagc ggtcagccca 3000
ttcgccgcca agctcttcag caatatcacg ggtagccaac gctatgtcct gatagcggtc 3060
cgccacaccc agccggccac agtcgatgaa tccagaaaag cggccatttt ccaccatgat 3120
attcggcaag caggcatcgc catgggtcac gacgagatcc tcgccgtcgg gcatgcgcgc 3180
cttgagcctg gcgaacagtt cggctggcgc gagcccctga tgctcttcgt ccagatcatc 3240
ctgatcgaca agaccggctt ccatccgagt acgtgctcgc tcgatgcgat gtttcgcttg 3300
gtggtcgaat gggcaggtag ccggatcaag cgtatgcagc cgccgcattg catcagccat 3360
gatggatact ttctcggcag gagcaaggtg agatgacagg agatcctgcc ccggcacttc 3420
gcccaatagc agccagtccc ttcccgcttc agtgacaacg tcgagcacag ctgcgcaagg 3480
aacgcccgtc gtggccagcc acgatagccg cgctgcctcg tcctgcagtt cattcagggc 3540
accggacagg tcggtcttga caaaaagaac cgggcgcccc tgcgctgaca gccggaacac 3600
ggcggcatca gagcagccga ttgtctgttg tgcccagtca tagccgaata gcctctccac 3660
ccaagcggcc ggagaacctg cgtgcaatcc atcttgttca atggccgatc ccatggttta 3720
gttcctcacc ttgtcgtatt atactatgcc gatatactat gccgatgatt aattgtcaac 3780
acgtgctgct gcaggtcgaa aggcccggag atgaggaaga ggagaacagc gcggcagacg 3840
tgcgcttttg aagcgtgcag aatgccgggc ctccggagga ccttcgggcg cccgccccgc 3900
ccctgagccc gcccctgagc ccgcccccgg acccacccct tcccagcctc tgagcccaga 3960
aagcgaagga gcaaagctgc tattggccgc tgccccaaag gcctacccgc ttccattgct 4020
cagcggtgct gtccatctgc acgagactag tgagacgtgc tacttccatt tgtcacgtcc 4080
tgcacgacgc gagctgcggg gcggggggga acttcctgac taggggagga gtagaaggtg 4140
gcgcgaaggg gccaccaaag aacggagccg gttggcgcct accggtggat gtggaatgtg 4200
tgcgagccag aggccacttg tgtagcgcca agtgcccagc ggggctgcta aagcgcatgc 4260
tccagactgc cttgggaaaa gcgcctcccc tacccggtag acaccccaca gtgggtggcc 4320
tagggacagg attgcaactc cagtctttct tcttcttggg cgggagtcac tagttattaa 4380
tagtaatcaa ttacggggtc attagttcat agcccatata tggagttccg cgttacataa 4440
cttacggtaa atggcccgcc tggctgaccg cccaacgacc cccgcccatt gacgtcaata 4500
atgacgtatg ttcccatagt aacgccaata gggactttcc attgacgtca atgggtggac 4560
tatttacggt aaactgccca cttggcagta catcaagtgt atcatatgcc aagtacgccc 4620
cctattgacg tcaatgacgg taaatggccc gcctggcatt atgcccagta catgacctta 4680
tgggactttc ctacttggca gtacatctac gtattagtca tcgctattac catgggtcga 4740
ggtgagcccc acgttctgct tcactctccc catctccccc ccctccccac ccccaatttt 4800
gtatttattt atttttttaat tattttgtgc agcgatgggg gcgggggggg ggggggcgcg 4860
cgccaggcgg ggcggggcgg ggcgaggggc ggggcggggc gaggcggaga ggtgcggcgg 4920
cagccaatca gagcggcgcg ctccgaaagt ttccttttat ggcgaggcgg cggcggcggc 4980
ggccctataa aaagcgaagc gcgcggcggg cgggagtcgc tgcgttgcct tcgccccgtg 5040
ccccgctccg cgccgcctcg cgccgcccgc cccggctctg actgaccgcg ttactcccac 5100

-continued

```
aggtgagcgg gcgggacggc ccttctcctc cgggctgtaa ttagcgcttg gtttaatgac   5160
ggctcgtttc ttttctgtgg ctgcgtgaaa gccttaaagg gctccgggag ggccctttgt   5220
gcggggggga gcggctcggg gggtgcgtgc gtgtgtgtgt gcgtggggag cgccgcgtgc   5280
ggcccgcgct gcccggcggc tgtgagcgct gcgggcgcgg cgcggggctt tgtgcgctcc   5340
gcgtgtgcgc gaggggagcg cggccggggg cggtgccccg cggtgcgggg gggctgcgag   5400
gggaacaaag gctgcgtgcg gggtgtgtgc gtgggggggt gagcaggggg tgtgggcgcg   5460
gcggtcgggc tgtaaccccc ccctgcaccc ccctccccga gttgctgagc acggcccggc   5520
ttcgggtgcg gggctccgtg cggggcgtgg cgcggggctc gccgtgccgg gcgggggggtg   5580
gcggcaggtg gggggtgccgg gcggggcggg gccgcctcgg gccggggagg gctcgggggga   5640
ggggcgcggc ggccccggag cgccggcggc tgtcgaggcg cggcgagccg cagccattgc   5700
cttttatggt aatcgtgcga gagggcgcag ggacttcctt tgtcccaaat ctggcggagc   5760
cgaaatctgg gaggcgccgc cgcacccccct ctagcgggcg cgggcgaagc ggtgcggcgc   5820
cggcaggaag gaaatgggcg gggagggcct tcgtgcgtcg ccgcgccgcc gtccccttct   5880
ccatctccag cctcggggct gccgcagggg gacggctgcc ttcggggggg acggggcagg   5940
gcggggttcg gcttctggcg tgtgaccggc ggctctagag cctctgctaa ccatgttcat   6000
gccttcttct ttttcctaca gctcctgggc aacgtgctgg ttattgtgct gtctcatcat   6060
tttggcaaag aattcgccac catggtgccc aagaagaaga ggaaagtctc tagactggac   6120
aagagcaaag tcataaactc tgctctggaa ttactcaatg gagtcggtat cgaaggcctg   6180
acgacaagga aactcgctca aaagctggga gttgagcagc ctaccctgta ctggcacgtg   6240
aagaacaagc gggccctgct cgatgccctg ccaatcgaga tgctggacag gcatcatacc   6300
cactcctgcc ccctggaagg cgagtcatgg caagactttc tgcggaacaa cgccaagtca   6360
taccgctgtg ctctcctctc acatcgcgac ggggctaaag tgcatctcgg cacccgccca   6420
acagagaaac agtacgaaac cctggaaaat cagctcgcgt tcctgtgtca gcaaggcttc   6480
tccctggaga acgcactgta cgctctgtcc gccgtgggcc actttacact gggctgcgta   6540
ttggaggaac aggagcatca agtagcaaaa gaggaaagag agacacctac caccgattct   6600
atgcccccac ttctgaaaca agcaattgag ctgttcgacc ggcagggagc cgaacctgcc   6660
ttccttttcg gcctggaact aatcatatgt ggcctggaga aacagctaaa gtgcgaaagc   6720
ggcgggccga ccgacgccct tgacgatttt gacttagaca tgctcccagc cgatgccctt   6780
gacgactttg accttgatat gctgcctgct gacgctcttg acgattttga ccttgacatg   6840
ctccccgggt aaagcggccg cgactctaga tcataatcag ccataccaca tttgtagagg   6900
ttttacttgc tttaaaaaac ctcccacacc tccccctgaa cctgaaacat aaaatgaatg   6960
caattgttgt tgttaacttg tttattgcag cttataatgg ttacaaataa agcaatagca   7020
tcacaaattt cacaaataaa gcattttttt cactgcattc tagttgtggt ttgtccaaac   7080
tcatcaatgt atcttaaggg atccctagag ggacagcccc cccccaaagc cccccagggat   7140
gtaattacgt ccctcccccg ctagggggcag cagcgagccg cccggggctc cgctccggtc   7200
cggcgctccc cccgcatccc cgagccggca gcgtgcgggg acagcccggg cacggggaag   7260
gtggcacggg atcgctttcc tctgaacgct tctcgctgct ctttgagcct gcagacacct   7320
ggggggatac ggggaaaaag ctttaggctg aaagagagat ttagaatgac agaatcatag   7380
aacggcctgg gttgcaaagg agcacagtgc tcatccagat ccaacccccct gctatgtgca   7440
gggtcatcaa ccagcagccc aggctgccca gagccacatc cagcctggcc ttgaatgcct   7500
```

```
gcagggatgg ggcatccaca gcctccttgg gcaacctgtt cagtgcgtca ccaccctctg   7560
ggggaaaaac tgcctcctca tatccaaccc aaacctcccc tgtctcagtg taaagccatt   7620
ccccccttgtc ctatcaaggg ggagtttgct gtgacattgt tggtctgggg tgacacatgt   7680
ttgccaattc agtgcatcac ggagaggcag atcttgggga taaggaagtg caggacagca   7740
tggacgtggg acatgcaggt gttgagggct ctgggacact ctccaagtca cagcgttcag   7800
aacagcctta aggataagaa gataggatag aaggacaaag agcaagttaa aacccagcat   7860
ggagaggagc acaaaaaggc cacagacact gctggtccct gtgtctgagc ctgcatgttt   7920
gatggtgtct ggatgcaagc agaaggggtg gaagagcttg cctggagaga tacagctggg   7980
tcagtaggac tgggacaggc agctggagaa ttgccatgta gatgttcata caatcgtcaa   8040
atcatgaagg ctggaaaagc cctccaagat ccccaagacc aaccccaacc cacccaccgt   8100
gcccactggc catgtccctc agtgccacat ccccacagtt cttcatcacc tccagggacg   8160
gtgacccccc cacctccgtg ggcagctgtg ccactgcagc accgctcttt ggagaaggta   8220
aatcttgcta aatccagccc gaccctcccc tggcacaacg taaggccatt atctctcatc   8280
caactccagg acggagtcag tgaggatggg gctgtcgacc tagagggaca gcccccccccc   8340
aaagccccca gggatgtaat tacgtccctc ccccgctagg ggcagcagcg agccgcccgg   8400
ggctccgctc cggtccggcg ctccccccgc atccccgagc cggcagcgtg cggggacagc   8460
ccgggcacgg ggaaggtggc acgggatcgc tttcctctga acgcttctcg ctgctctttg   8520
agcctgcaga cacctggggg gatacgggga aaaagcttta ggctgaaaga gagatttaga   8580
atgacagaat catagaacgg cctgggttgc aaaggagcac agtgctcatc cagatccaac   8640
cccctgctat gtgcagggtc atcaaccagc agcccaggct gcccagagcc acatccagcc   8700
tggccttgaa tgcctgcagg gatggggcat ccacagcctc cttgggcaac ctgttcagtg   8760
cgtcaccacc ctctgggggga aaaactgcct cctcatatcc aacccaaacc tcccctgtct   8820
cagtgtaaag ccattccccc ttgtcctatc aagggggagt ttgctgtgac attgttggtc   8880
tggggtgaca catgtttgcc aattcagtgc atcacggaga ggcagatctt ggggataagg   8940
aagtgcagga cagcatggac gtgggacatg caggtgttga gggctctggg acactctcca   9000
agtcacagcg ttcagaacag ccttaaggat aagaagatag gatagaagga caaagagcaa   9060
gttaaaaccc agcatggaga ggagcacaaa aaggccacag acactgctgg tccctgtgtc   9120
tgagcctgca tgtttgatgg tgtctggatg caagcagaag ggtggaaga gcttgcctgg   9180
agagatacag ctgggtcagt aggactggga caggcagctg gagaattgcc atgtagatgt   9240
tcatacaatc gtcaaatcat gaaggctgga aaagccctcc aagatcccca agaccaaccc   9300
caacccaccc accgtgccca ctggccatgt ccctcagtgc cacatcccca cagttcttca   9360
tcacctccag ggacggtgac ccccccacct ccgtgggcag ctgtgccact gcagcaccgc   9420
tctttggaga aggtaaatct tgctaaatcc agcccgaccc tcccctggca caacgtaagg   9480
ccattatctc tcatccaact ccaggacgga gtcagtgagg atggggctca attgtttact   9540
ccctatcagt gatagagaac gtatgaagag tttactccct atcagtgata gagaacgtat   9600
gcagacttta ctccctatca gtgatagaga acgtataagg agtttactcc ctatcagtga   9660
tagagaacgt atgaccagtt tactccctat cagtgataga gaacgtatct acagtttact   9720
ccctatcagt gatagagaac gtatatccag tttactccct atcagtgata gagaacgtat   9780
aagctttagg cgtgtacggt gggcgcctat aaaagcagag ctcgtttagt gaaccgtcag   9840
```

```
atcgcctgga gcaattccac aacacttttg tcttatacca actttccgta ccacttccta   9900
ccctcgtaaa aagcttgtcc accatggctc ctaagaaaaa gcggaaggtg gacaagaaat   9960
actcaatcgg gctggccatc ggaactaact cagtggggtg ggcagtcatt actgacgagt  10020
acaaagtgcc aagcaagaaa tttaaggtcc tgggcaacac cgataggcac tccatcaaga  10080
aaaatctgat tggggccctg ctgttcgact ctggagagac agctgaagca actagactga  10140
aaaggactgc tagaaggcgc tatacccggc gaaagaatcg catctgctac ctgcaggaga  10200
ttttctctaa cgaaatggcc aaggtggacg atagtttctt tcatcggctg gaggaatcat  10260
tcctggtcga ggaagataag aaacacgaga gacatcctat ctttggaaac attgtggacg  10320
aggtcgctta tcacgaaaaa taccccacca tctatcatct gcgcaagaaa ctggtggact  10380
ctacagataa agcagacctg cggctgatct atctggccct ggctcacatg attaagttca  10440
gaggccattt tctgatcgag ggagatctga acccagacaa tagcgatgtg gacaagctgt  10500
tcatccagct ggtccagaca tacaatcagc tgtttgagga aaaccctatt aatgcatctg  10560
gcgtggacgc aaaagccatc ctgagtgcca ggctgtctaa gagtagaagg ctggagaacc  10620
tgatcgctca gctgccaggc gaaaagaaaa acggcctgtt tggaaatctg attgcactgt  10680
cactgggact gacacctaac ttcaagagca attttgatct ggccgaggac gctaaactgc  10740
agctgagcaa ggacacttat gacgatgacc tggataacct gctggctcag atcggagatc  10800
agtacgcaga cctgttcctg gccgctaaga atctgtctga cgctatcctg ctgagtgata  10860
ttctgcgggt gaacaccgag attacaaaag cccctctgtc agctagcatg atcaagagat  10920
atgacgagca ccatcaggat ctgaccctgc tgaaggcact ggtgcgccag cagctgcccg  10980
agaagtacaa ggaaatcttc tttgatcaga gtaagaacgg gtacgccggt tatattgacg  11040
gcggagcttc acaggaggaa ttctacaagt ttatcaaacc tattctggag aagatggacg  11100
gcaccgagga actgctggtg aaactgaatc gcgaggacct gctgcgcaag cagcggacat  11160
ttgataacgg ctccatcccc caccagattc atctgggaga gctgcacgca atcctgcgac  11220
gacaggaaga cttctaccca tttctgaagg ataaccgcga gaagatcgaa aaaattctga  11280
ccttccggat cccttactat gtggggcccc tggcaagggg taattcccgc tttgcctgga  11340
tgacacggaa atctgaggaa acaatcactc cttggaactt cgaggaagtg gtcgataagg  11400
gagcttccgc acagtctttc atcgagagaa tgacaaactt cgacaaaaac ctgccaaatg  11460
agaaagtgct gcctaagcac agtctgctgt acgagtattt cacagtctat aacgaactga  11520
ctaaggtgaa atacgtcacc gaggggatga ggaagcccgc cttcctgagc ggtgaacaga  11580
agaaagctat cgtggacctg ctgtttaaaa ccaatcgcaa ggtgacagtc aagcagctga  11640
aggaggacta cttcaagaaa attgaatgtt tcgattctgt ggagatcagt ggcgtcgaag  11700
acagatttaa cgcttctctg ggaacctacc acgatctgct gaagatcatt aaggataaag  11760
acttcctgga caacgaggaa aatgaggata tcctggaaga cattgtgctg accctgacac  11820
tgtttgagga tcgcgaaatg atcgaggaac ggctgaaaac ttatgcccat ctgttcgatg  11880
acaaggtgat gaaacagctg aagcgaagaa ggtacaccgg ctggggacga ctgagcagaa  11940
agctgatcaa cggcattcgg gacaaacaga gtggaaagac tatcctggac tttctgaaat  12000
cagatggctt cgctaacaga aattttatgc agctgattca cgatgacagc ctgaccttca  12060
aagaggatat ccagaaggca caggtgtccg ggcagggtga ctctctgcac gagcatatcg  12120
caaacctggc cgggtccccc gccatcaaga aaggtattct gcagaccgtg aaggtggtcg  12180
atgagctggt gaaagtcatg ggcaggcata agccagaaaa catcgtgatt gagatggccc  12240
```

gcgaaaatca gaccacacag aaaggacaga agaacagccg cgagcggatg aaaaggatcg 12300
aggaaggcat taaggaactg ggatcccaga tcctgaaaga gcaccctgtg gaaaacactc 12360
agctgcagaa tgagaagctg tatctgtact atctgcagaa tgggcgggat atgtacgtgg 12420
accaggagct ggatattaac cgactgtctg attacgacgt ggatgccatc gtcccacagt 12480
cattcctgaa agatgacagc attgacaata aggtgctgac ccggagtgac aaaaaccgag 12540
gaaagagtga taatgtccct tcagaggaag tggtcaagaa aatgaagaac tactggagac 12600
agctgctgaa tgccaaactg atcacacagc gaaagtttga taacctgact aaagctgaga 12660
gaggggtct gtcagaactg gacaaagcag gcttcatcaa gcgacagctg gtggagacca 12720
gacagatcac aaagcacgtc gctcagattc tggatagcag gatgaacaca aagtacgatg 12780
agaatgacaa actgatccgc gaagtgaagg tcattactct gaagtcaaaa cttgtgagcg 12840
acttcagaaa ggatttccag ttctacaaag tcagggagat caacaattat caccatgctc 12900
atgacgcata cctgaacgca gtggtcggga ccgccctgat taagaaatac cccaaactgg 12960
agagcgaatt cgtgtacggt gactataagg tgtacgatgt cagaaaaatg atcgccaaga 13020
gtgagcagga aattggaaaa gccaccgcta agtatttctt ttactcaaac atcatgaatt 13080
tctttaagac tgagatcacc ctggcaaatg gggaaatccg aaagagacca ctgattgaga 13140
ctaacggcga gaccggagaa atcgtgtggg acaagggtag ggattttgcc acagtgcgca 13200
aggtcctgtc catgcctcaa gtgaatattg tcaagaaaac agaggtgcag actggcggat 13260
tcagtaagga atcaattctg cccaaacgga actctgataa gctgatcgcc cgaaagaaag 13320
actgggatcc caagaaatat gggggtttcg actccccaac agtggcttac tctgtcctgg 13380
tggtcgcaaa ggtggagaag gggaaaagca agaaactgaa atccgtcaag gagctgctgg 13440
gtatcactat tatggagagg agctccttcg agaagaaccc catcgatttt ctggaggcta 13500
aaggctataa ggaagtgaag aaagacctga tcattaaact gccaaagtac agcctgtttg 13560
agctggaaaa cggaaggaag cgaatgctgg catccgcagg agagctgcag aagggtaatg 13620
aactggccct gccttctaag tacgtgaact tcctgtatct ggctagccac tacgagaagc 13680
tgaaaggctc ccccgaggat aacgaacaga aacagctgtt tgtggagcag cacaagcatt 13740
atctggacga gatcattgaa cagattagcg agttctccaa aagagtgatc ctggctgacg 13800
caaatctgga taaggtcctg agcgcataca acaaacacag agataagcca atcagggagc 13860
aggccgaaaa tatcattcat ctgttcactc tgaccaacct gggagcccct gcagccttca 13920
agtattttga cactaccatc gatcggaaac gatacacatc cactaaggag gtgctggacg 13980
ctaccctgat tcaccagagc attaccggcc tgtatgaaac aaggattgac ctgtctcagc 14040
tgggggggcga cctcgagatg gccaagcccc tgagccaaga ggaaagcacc ctgatcgagc 14100
gggccaccgc caccatcaac agcatcccca tcagcgagga ctacagcgtg gcctctgccg 14160
ccctgagcag cgacggcaga atcttcaccg gcgtgaacgt gtaccacttc acaggcggcc 14220
cttgcgccga gctggtggtg ctgggaacag ctgccgccgc tgccgctggc aacctgacct 14280
gtatcgtggc catcggcaac gagaaccggg gcatcctgag cccctgcggc agatgcagac 14340
aggtgctgct ggacctgcac cccggcatca aggccatcgt gaaggacagc gacggccagc 14400
ccaccgccgt gggcattaga gagctgctgc ccagcggcta cgtgtgggag ggctgactcg 14460
agattttcaa accagaagaa ctacgacagg cactgatgcc caccctggaa gccctgtacc 14520
ggcaggaccc cgagagcctg cccttcagac agcccgtgga tccccagctg ctgggcatcc 14580
ccgactactt cgacatcgtg aagtccccca tggacctgag caccatcaag cggaagctgg 14640
acaccggcca gtaccaagag ccctggcagt acgtggacga catctggctg atgttcaaca 14700
acgcctggct gtacaacaga aagaccagcc gggtgtacaa gtactgcagc aagctgagcg 14760
aggtgttcga gcaagagatc gaccccgtga tgcagagcct gggctactgc tgcggcagaa 14820
agctggaatt cagcccccag accctgtgct gctacggcaa gcagctgtgc accatccccc 14880
gggacgccac ctactacagc taccagaaca gataccactt ctgcgagaag tgcttcaacg 14940
agatccaggg cgagagcgtg tccctgggcg acgaccctag ccagccccag accacaatca 15000
acaaagagca gttcagcaag cggaagaacg acaccctgga ccccgagctg ttcgtggaat 15060
gcaccgagtg cggccggaag atgcaccaga tctgcgtgct gcaccacgag atcatctggc 15120
ctgccggctt cgtgtgcgac ggctgcctga agaagtccgc ccggacccgg aaagagaaca 15180
agttcagcgc caagcggctg ccctctaccc ggctgggcac cttcctggaa aacagagtga 15240
acgacttcct gcggcggcag aaccaccccg agtccggcga agtgacagtg cgggtggtgc 15300
acgccagcga caagaccgtg gaagtgaagc ctggcatgaa ggccagattc gtggacagcg 15360
gcgagatggc cgagagcttc ccctaccgga ccaaggccct gttcgccttc gaagagatcg 15420
atggcgtgga cctgtgcttc ttcggcatgc acgtgcaaga gtacggcagc gactgccccc 15480
cacccaacca gcggcgggtg tacatcagct acctggacag cgtgcacttc ttccggccca 15540
agtgcctgcg gaccgccgtg tatcacgaga tcctgatcgg ctacctggaa tacgtgaaga 15600
agctgggcta caccaccggc cacatctggg cctgtcctcc cagcgagggc gacgactaca 15660
tcttccactg ccaccccccc gaccagaaga tccccaagcc caagagactg caagagtggt 15720
acaagaagat gctggacaag gccgtgtccg agcggatcgt gcacgactac aaggacatct 15780
tcaagcaggc caccgaggac cggctgacca gcgccaaaga gctgccctac ttcgagggcg 15840
acttctggcc caacgtgctg gaagagagca tcaaagagct ggaacaagag gaagaggaac 15900
gcaagcggga agagaacacc agcaacgaga gcaccgacgt gaccaagggc gacagcaaga 15960
acgccaagaa gaagaacaac aagaaaacca gcaagaacaa gagcagcctg agccggggaa 16020
acaagaaaaa gcccggcatg cccaacgtgt ccaacgacct gagccagaaa ctgtacgcca 16080
ccatggaaaa gcacaaagag gtgttcttcg tcatccggct gatcgccgga cctgccgcca 16140
acagcctgcc ccccatcgtg gaccccgacc ccctgatccc ctgcgacctg atggacggca 16200
gggacgcctt cctgaccctg gcccgggaca agcacctgga attctccagc ctgcggagag 16260
cccagtggtc caccatgtgc atgctggtgg aactgcacac ccagagccag gacgagggca 16320
gaggaagtct gctaacatgc ggtgacgtcg aggagaatcc tggcccagca ccgggatcca 16380
tggtgagcaa gggcgaggag ctgttcaccg gggtggtgcc catcctggtc gagctggacg 16440
gcgacgtaaa cggccacaag ttcagcgtgt ccggcgaggg cgagggcgat gccacctacg 16500
gcaagctgac cctgaagttc atctgcacca ccggcaagct gcccgtgccc tggcccaccc 16560
tcgtgaccac cttcacctac ggcgtgcagt gcttcgcccg ctaccccgac cacatgaagc 16620
agcacgactt cttcaagtcc gccatgcccg aaggctacgt ccaggagcgc accatcttct 16680
tcaaggacga cggcaactac aagacccgcg ccgaggtgaa gttcgagggc gacaccctgg 16740
tgaaccgcat cgagctgaag ggcatcgact tcaaggagga cggcaacatc ctggggcaca 16800
agctggagta caactacaac agccacaagg tctatatcac cgccgacaag cagaagaacg 16860
gcatcaaggt gaacttcaag acccgccaca acatcgagga cggcagcgtg cagctcgccg 16920
accactacca gcagaacacc cccatcggcg acggccccgt gctgctgccc gacaaccact 16980
acctgagcac ccagtccgcc ctgagcaaag accccaacga gaagcgcgat cacatggtcc 17040
tgctggagtt cgtgaccgcc gccgggatca ctctcggcat ggacgagctg tacaagtaaa 17100
cctaatctag cagctcgctg atcagcctcg actgtgcctt ctagttgcca gccatctgtt 17160
gtttgcccct cccccgtgcc ttccttgacc ctggaaggtg ccactcccac tgtcctttcc 17220
taataaaatg aggaaattgc atcgcattgt ctgagtaggt gtcattctat tctggggggt 17280
ggggtggggc aggacagcaa gggggaggat tgggaagaca atagcaggca tgctggggat 17340
gcggtgggct ctatggcttc tgaggcggaa agaaccagct ggggctcgat cctctagttg 17400
gcgcgtcatg gtccatatga atatcctcct tagttcctat tccgctagcc tagagggaca 17460
gcccccccc aaagccccca gggatgtaat tacgtccctc ccccgctagg ggcagcagcg 17520
agccgcccgg ggctccgctc cggtccggcg ctcccccgc atccccgagc cggcagcgtg 17580
cggggacagc ccgggcacgg ggaaggtggc acgggatcgc tttcctctga acgcttctcg 17640
ctgctctttg agcctgcaga cacctggggg gatacgggga aaaagcttta ggctgaaaga 17700
gagatttaga atgacagaat catagaacgg cctgggttgc aaaggagcac agtgctcatc 17760
cagatccaac cccctgctat gtgcagggtc atcaaccagc agcccaggct gcccagagcc 17820
acatccagcc tggccttgaa tgcctgcagg gatggggcat ccacagcctc cttgggcaac 17880
ctgttcagtg cgtcaccacc ctctggggga aaaactgcct cctcatatcc aacccaaacc 17940
tcccctgtct cagtgtaaag ccattccccc ttgtcctatc aagggggagt ttgctgtgac 18000
attgttggtc tggggtgaca catgtttgcc aattcagtgc atcacggaga ggcagatctt 18060
ggggataagg aagtgcagga cagcatggac gtgggacatg caggtgttga gggctctggg 18120
acactctcca agtcacagcg ttcagaacag ccttaaggat aagaagatag gatagaagga 18180
caaagagcaa gttaaaaccc agcatggaga ggagcacaaa aaggccacag acactgctgg 18240
tccctgtgtc tgagcctgca tgtttgatgg tgtctggatg caagcagaag ggtggaaga 18300
gcttgcctgg agagatacag ctgggtcagt aggactggga caggcagctg gagaattgcc 18360
atgtagatgt tcatacaatc gtcaaatcat gaaggctgga aaagccctcc aagatcccca 18420
agaccaaccc caacccaccc accgtgccca ctggccatgt ccctcagtgc cacatcccca 18480
cagttcttca tcacctccag ggacggtgac cccccacct ccgtgggcag ctgtgccact 18540
gcagcaccgc tctttggaga aggtaaatct tgctaaatcc agcccgaccc tcccctggca 18600
caacgtaagg ccattatctc tcatccaact ccaggacgga gtcagtgagg atggggctgg 18660
atccgaagca gctccagcct acacaatcgc tcaagacgtg taatgctttt attatatatt 18720
agtcacgata tctataacaa gaaaatatat atataataag ttatcacgta agtagaacat 18780
gaaataacaa tataattatc gtatgagtta aatcttaaaa gtcacgtaaa agataatcat 18840
gcgtcatttt gactcacgcg gtcgttatag ttcaaaatca gtgacactta ccgcattgac 18900
aagcacgcct cacgggagct ccaagcggcg actgagatgt cctaaatgca cagcgacgga 18960
ttcgcgctat ttagaaagag agagcaatat ttcaagaatg catgcgtcaa ttttacgcag 19020
actatctttc tagggttaaa aaagatttgc gctttactcg acctaaactt taaacacgtc 19080
atagaatctt cgtttgacaa aaaccacatt gtggggtacc gagctcttaa ttaaggcgcg 19140
ccggggaggt tccctttagt gagggttaat tgcgggtcgc cctatagtga gtcgtattac 19200
aattcactgg ccgtcgtttt acaacgtcgt gactgggaaa accctggcgt tacccaactt 19260
aatcgccttg cagcacatcc ccctttcgcc agctggcgta atagcgaaga ggcccgcacc 19320
gatcgccctt cccaacagtt gcgcagcctg aatggcgaat ggcaaattgt aagcgttaat 19380
attttgttaa aattcgcgtt aaatttttgt taaatcagct cattttttaa ccaataggcc 19440
gaaatcggca aaatccctta taaatcaaaa gaatagaccg agatagggtt gagtgttgtt 19500
ccagtttgga acaagagtcc actattaaag aacgtggact ccaacgtcaa agggcgaaaa 19560
accgtctatc agggcgatgg cccactacgt gaaccatcac cctaatcaag ttttttgggg 19620
tcgaggtgcc gtaaagcact aaatcggaac cctaaaggga gcccccgatt tagagcttga 19680
cggggaaagc cggcgaacgt ggcgagaaag gaagggaaga aagcgaaagg agcgggcgct 19740
agggcgctgg caagtgtagc ggtcacgctg cgcgtaacca ccacacccgc cgcgcttaat 19800
gcgccgctac agggcgcgtc ag 19822

<210> SEQ ID NO 19
<211> LENGTH: 18492
<212> TYPE: DNA
<213> ORGANISM: Artificial Sequence
<220> FEATURE:
<223> OTHER INFORMATION: Synthetic Polynucleotide

<400> SEQUENCE: 19
gtggcacttt tcggggaaat gtgcgcggaa cccctatttg tttatttttc taaatacatt 60
caaatatgta tccgctcatg agacaataac cctgataaat gcttcaataa tattgaaaaa 120
ggaagagtat gagtattcaa catttccgtg tcgcccttat tccctttttt gcggcatttt 180
gccttcctgt ttttgctcac ccagaaacgc tggtgaaagt aaaagatgct gaagatcagt 240
tgggtgcacg agtgggttac atcgaactgg atctcaacag cggtaagatc cttgagagtt 300
ttcgccccga agaacgtttt ccaatgatga gcacttttaa agttctgcta tgtggcgcgg 360
tattatcccg tattgacgcc gggcaagagc aactcggtcg ccgcatacac tattctcaga 420
atgacttggt tgagtactca ccagtcacag aaaagcatct tacggatggc atgacagtaa 480
gagaattatg cagtgctgcc ataaccatga gtgataacac tgcggccaac ttacttctga 540
caacgatcgg aggaccgaag gagctaaccg cttttttgca caacatgggg gatcatgtaa 600
ctcgccttga tcgttgggaa ccggagctga atgaagccat accaaacgac gagcgtgaca 660
ccacgatgcc tgtagcaatg gcaacaacgt tgcgcaaact attaactggc gaactactta 720
ctctagcttc ccggcaacaa ttaatagact ggatggaggc ggataaagtt gcaggaccac 780
ttctgcgctc ggcccttccg gctggctggt ttattgctga taaatctgga gccggtgagc 840
gtgggtctcg cggtatcatt gcagcactgg ggccagatgg taagccctcc cgtatcgtag 900
ttatctacac gacggggagt caggcaacta tggatgaacg aaatagacag atcgctgaga 960
taggtgcctc actgattaag cattggtaac tgtcagacca agtttactca tatatacttt 1020
agattgattt aaaacttcat ttttaattta aaaggatcta ggtgaagatc ctttttgata 1080
atctcatgac caaaatccct taacgtgagt tttcgttcca ctgagcgtca gaccccgtag 1140
aaaagatcaa aggatcttct tgagatcctt tttttctgcg cgtaatctgc tgcttgcaaa 1200
caaaaaaacc accgctacca gcggtggttt gtttgccgga tcaagagcta ccaactcttt 1260
ttccgaaggt aactggcttc agcagagcgc agataccaaa tactgttctt ctagtgtagc 1320
cgtagttagg ccaccacttc aagaactctg tagcaccgcc tacatacctc gctctgctaa 1380
tcctgttacc agtggctgct gccagtggcg ataagtcgtg tcttaccggg ttggactcaa 1440
gacgatagtt accggataag gcgcagcggt cgggctgaac ggggggttcg tgcacacagc 1500
ccagcttgga gcgaacgacc tacaccgaac tgagatacct acagcgtgag ctatgagaaa 1560
gcgccacgct tcccgaaggg agaaaggcgg acaggtatcc ggtaagcggc agggtcggaa 1620
caggagagcg cacgagggag cttccagggg gaaacgcctg gtatctttat agtcctgtcg 1680
ggtttcgcca cctctgactt gagcgtcgat ttttgtgatg ctcgtcaggg gggcggagcc 1740
tatggaaaaa cgccagcaac gcggcctttt tacggttcct ggccttttgc tggccttttg 1800
ctcacatgtt ctttcctgcg ttatcccctg attctgtgga taaccgtatt accgcctttg 1860
agtgagctga taccgctcgc cgcagccgaa cgaccgagcg cagcgagtca gtgagcgagg 1920
aagcggaaga gcgcccaata cgcaaaccgc ctctccccgc gcgttggccg attcattaat 1980
gcagctggca cgacaggttt cccgactgga aagcgggcag tgagcgcaac gcaattaatg 2040
tgagttagct cactcattag gcaccccagg ctttacactt tatgcttccg gctcgtatgt 2100
tgtgtggaat tgtgagcgga taacaatttc acacaggaaa cagctatgac catgattacg 2160
ccaagcgcgc aattaaccct cactaaaggg aacctcccct agcttaatta accctagaaa 2220
gataatcata ttgtgacgta cgttaaagat aatcatgcgt aaaattgacg catgtgtttt 2280
atcgatctgt atatcgaggt ttatttatta atttgaatag atattaagtt ttattatatt 2340
tacacttaca tactaataat aaattcaaca aacaatttat ttatgtttat ttatttatta 2400
aaaaaaaaca aaaactcaaa atttcttcta taaagtaaca aaacttttaa acattctctc 2460
ttttacaaaa ataaacttat tttgtacttt aaaaacagtc atgttgtatt ataaaataag 2520
taattagctt aacttataca taatagaaac aaattatact tattaatcgc attgattatt 2580
gactagtcgt attaagggtt ccggatcagc ttgattcgag ccccagctgg ttctttccgc 2640
ctcagaagcc atagagccca ccgcatcccc agcatgcctg ctattgtctt cccaatcctc 2700
ccccttgctg tcctgcccca ccccaccccc cagaatagaa tgacacctac tcagacaatg 2760
cgatgcaatt tcctcatttt attaggaaag gacagtggga gtggcacctt ccagggtcaa 2820
ggaaggcacg gggagggggc aaacaacaga tggctggcaa ctagaaggca cagtcgaggc 2880
tgatcagcga gctctagaga attgatcccc tcagaagaac tcgtcaagaa ggcgatagaa 2940
ggcgatgcgc tgcgaatcgg gagcggcgat accgtaaagc acgaggaagc ggtcagccca 3000
ttcgccgcca agctcttcag caatatcacg ggtagccaac gctatgtcct gatagcggtc 3060
cgccacaccc agccggccac agtcgatgaa tccagaaaag cggccatttt ccaccatgat 3120
attcggcaag caggcatcgc catgggtcac gacgagatcc tcgccgtcgg gcatgcgcgc 3180
cttgagcctg gcgaacagtt cggctggcgc gagcccctga tgctcttcgt ccagatcatc 3240
ctgatcgaca agaccggctt ccatccgagt acgtgctcgc tcgatgcgat gtttcgcttg 3300
gtggtcgaat gggcaggtag ccggatcaag cgtatgcagc cgccgcattg catcagccat 3360
gatggatact ttctcggcag gagcaaggtg agatgacagg agatcctgcc ccggcacttc 3420
gcccaatagc agccagtccc ttcccgcttc agtgacaacg tcgagcacag ctgcgcaagg 3480
aacgcccgtc gtggccagcc acgatagccg cgctgcctcg tcctgcagtt cattcagggc 3540
accggacagg tcggtcttga caaaaagaac cgggcgcccc tgcgctgaca gccggaacac 3600
ggcggcatca gagcagccga ttgtctgttg tgcccagtca tagccgaata gcctctccac 3660
ccaagcggcc ggagaacctg cgtgcaatcc atcttgttca atggccgatc ccatggttta 3720
gttcctcacc ttgtcgtatt atactatgcc gatatactat gccgatgatt aattgtcaac 3780
acgtgctgct gcaggtcgaa aggcccggag atgaggaaga ggagaacagc gcggcagacg 3840
tgcgcttttg aagcgtgcag aatgccgggc ctccggagga ccttcgggcg cccgccccgc 3900

```
ccctgagccc gcccctgagc ccgcccccgg acccacccct tcccagcctc tgagcccaga   3960
aagcgaagga gcaaagctgc tattggccgc tgccccaaag gcctacccgc ttccattgct   4020
cagcggtgct gtccatctgc acgagactag tgagacgtgc tacttccatt tgtcacgtcc   4080
tgcacgacgc gagctgcggg gcggggggga acttcctgac taggggagga gtagaaggtg   4140
gcgcgaaggg gccaccaaag aacggagccg gttggcgcct accggtggat gtggaatgtg   4200
tgcgagccag aggccacttg tgtagcgcca agtgcccagc ggggctgcta aagcgcatgc   4260
tccagactgc cttgggaaaa gcgcctcccc tacccggtag acaccccaca gtgggtggcc   4320
tagggacagg attgcaactc cagtctttct tcttcttggg cgggagtcac tagttattaa   4380
tagtaatcaa ttacggggtc attagttcat agcccatata tggagttccg cgttacataa   4440
cttacggtaa atggcccgcc tggctgaccg cccaacgacc cccgcccatt gacgtcaata   4500
atgacgtatg ttcccatagt aacgccaata gggactttcc attgacgtca atgggtggac   4560
tatttacggt aaactgccca cttggcagta catcaagtgt atcatatgcc aagtacgccc   4620
cctattgacg tcaatgacgg taaatggccc gcctggcatt atgcccagta catgacctta   4680
tgggactttc ctacttggca gtacatctac gtattagtca tcgctattac catgggtcga   4740
ggtgagcccc acgttctgct tcactctccc catctccccc ccctccccac ccccaatttt   4800
gtatttattt attttttaat tattttgtgc agcgatgggg gcgggggggg ggggggcgcg   4860
cgccaggcgg ggcggggcgg ggcgaggggc ggggcggggc gaggcggaga ggtgcggcgg   4920
cagccaatca gagcggcgcg ctccgaaagt ttccttttat ggcgaggcgg cggcggcggc   4980
ggccctataa aaagcgaagc gcgcggcggg cgggagtcgc tgcgttgcct tcgccccgtg   5040
ccccgctccg cgccgcctcg cgccgcccgc cccggctctg actgaccgcg ttactcccac   5100
aggtgagcgg gcgggacggc ccttctcctc cgggctgtaa ttagcgcttg gtttaatgac   5160
ggctcgtttc ttttctgtgg ctgcgtgaaa gccttaaagg gctccgggag ggccctttgt   5220
gcggggggga gcggctcggg gggtgcgtgc gtgtgtgtgt gcgtggggag cgccgcgtgc   5280
ggcccgcgct gcccggcggc tgtgagcgct gcgggcgcgg cgcggggctt tgtgcgctcc   5340
gcgtgtgcgc gaggggagcg cggccggggg cggtgccccg cggtgcgggg gggctgcgag   5400
gggaacaaag gctgcgtgcg gggtgtgtgc gtgggggggt gagcaggggg tgtgggcgcg   5460
gcggtcgggc tgtaaccccc ccctgcaccc ccctccccga gttgctgagc acggcccggc   5520
ttcgggtgcg gggctccgtg cggggcgtgg cgcggggctc gccgtgccgg gcgggggtg    5580
gcggcaggtg gggggtgccgg gcggggcggg gccgcctcgg gccggggagg gctcggggga   5640
ggggcgcggc ggccccggag cgccggcggc tgtcgaggcg cggcgagccg cagccattgc   5700
cttttatggt aatcgtgcga gagggcgcag ggacttcctt tgtcccaaat ctggcggagc   5760
cgaaatctgg gaggcgccgc cgcaccccct ctagcgggcg cgggcgaagc ggtgcggcgc   5820
cggcaggaag gaaatgggcg gggagggcct tcgtgcgtcg ccgcgccgcc gtccccttct   5880
ccatctccag cctcggggct gccgcagggg gacggctgcc ttcggggggg acggggcagg   5940
gcggggttcg gcttctggcg tgtgaccggc ggctctagag cctctgctaa ccatgttcat   6000
gccttcttct ttttcctaca gctcctgggc aacgtgctgg ttattgtgct gtctcatcat   6060
tttggcaaag aattcgccac catggtgccc aagaagaaga ggaaagtctc tagactggac   6120
aagagcaaag tcataaactc tgctctggaa ttactcaatg gagtcggtat cgaaggcctg   6180
acgacaagga aactcgctca aaagctggga gttgagcagc ctaccctgta ctggcacgtg   6240
aagaacaagc gggccctgct cgatgccctg ccaatcgaga tgctggacag gcatcatacc   6300
```

-continued

```
cactcctgcc ccctggaagg cgagtcatgg caagactttc tgcggaacaa cgccaagtca   6360
taccgctgtg ctctcctctc acatcgcgac ggggctaaag tgcatctcgg cacccgccca   6420
acagagaaac agtacgaaac cctggaaaat cagctcgcgt tcctgtgtca gcaaggcttc   6480
tccctggaga acgcactgta cgctctgtcc gccgtgggcc actttacact gggctgcgta   6540
ttggaggaac aggagcatca agtagcaaaa gaggaaagag agacacctac caccgattct   6600
atgcccccac ttctgaaaca agcaattgag ctgttcgacc ggcagggagc cgaacctgcc   6660
ttccttttcg gcctggaact aatcatatgt ggcctggaga aacagctaaa gtgcgaaagc   6720
ggcgggccga ccgacgccct tgacgatttt gacttagaca tgctcccagc cgatgccctt   6780
gacgactttg accttgatat gctgcctgct gacgctcttg acgattttga ccttgacatg   6840
ctccccgggt aaagcggccg cgactctaga tcataatcag ccataccaca tttgtagagg   6900
ttttacttgc tttaaaaaac ctcccacacc tcccctgaa cctgaaacat aaaatgaatg   6960
caattgttgt tgttaacttg tttattgcag cttataatgg ttacaaataa agcaatagca   7020
tcacaaattt cacaaataaa gcattttttt cactgcattc tagttgtggt ttgtccaaac   7080
tcatcaatgt atcttaaggg atccctagag ggacagcccc cccccaaagc cccagggat    7140
gtaattacgt ccctcccccg ctaggggcag cagcgagccg cccggggctc cgctccggtc   7200
cggcgctccc cccgcatccc cgagccggca gcgtgcgggg acagcccggg cacggggaag   7260
gtggcacggg atcgctttcc tctgaacgct tctcgctgct ctttgagcct gcagacacct   7320
gggggatac ggggaaaaag ctttaggctg aaagagagat ttagaatgac agaatcatag    7380
aacggcctgg gttgcaaagg agcacagtgc tcatccagat ccaaccccct gctatgtgca   7440
gggtcatcaa ccagcagccc aggctgccca gagccacatc cagcctggcc ttgaatgcct   7500
gcagggatgg ggcatccaca gcctccttgg gcaacctgtt cagtgcgtca ccaccctctg   7560
ggggaaaaac tgcctcctca tatccaaccc aaacctcccc tgtctcagtg taaagccatt   7620
ccccttgtc ctatcaaggg ggagtttgct gtgacattgt tggtctgggg tgacacatgt    7680
ttgccaattc agtgcatcac ggagaggcag atcttgggga taaggaagtg caggacagca   7740
tggacgtggg acatgcaggt gttgagggct ctgggacact ctccaagtca cagcgttcag   7800
aacagcctta aggataagaa gataggatag aaggacaaag agcaagttaa aacccagcat   7860
ggagaggagc acaaaaaggc cacagacact gctggtccct gtgtctgagc ctgcatgttt   7920
gatggtgtct ggatgcaagc agaaggggtg gaagagcttg cctggagaga tacagctggg   7980
tcagtaggac tgggacaggc agctggagaa ttgccatgta gatgttcata caatcgtcaa   8040
atcatgaagg ctggaaaagc cctccaagat ccccaagacc aaccccaacc cacccaccgt   8100
gcccactggc catgtccctc agtgccacat ccccacagtt cttcatcacc tccagggacg   8160
gtgaccccc cacctccgtg ggcagctgtg ccactgcagc accgctcttt ggagaaggta    8220
aatcttgcta aatccagccc gaccctcccc tggcacaacg taaggccatt atctctcatc   8280
caactccagg acggagtcag tgaggatggg gctgtcgacc tagagggaca gcccccccc    8340
aaagccccca gggatgtaat tacgtccctc ccccgctagg ggcagcagcg agccgcccgg   8400
ggctccgctc cggtccggcg ctcccccgc atccccgagc cggcagcgtg cggggacagc    8460
ccgggcacgg ggaaggtggc acgggatcgc tttcctctga acgcttctcg ctgctctttg   8520
agcctgcaga cacctggggg gatacgggga aaaagcttta ggctgaaaga gagatttaga   8580
atgacagaat catagaacgg cctgggttgc aaaggagcac agtgctcatc cagatccaac   8640
```

-continued

```
cccctgctat gtgcagggtc atcaaccagc agcccaggct gcccagagcc acatccagcc   8700
tggccttgaa tgcctgcagg gatggggcat ccacagcctc cttgggcaac ctgttcagtg   8760
cgtcaccacc ctctggggga aaaactgcct cctcatatcc aacccaaacc tcccctgtct   8820
cagtgtaaag ccattccccc ttgtcctatc aagggggagt ttgctgtgac attgttggtc   8880
tggggtgaca catgtttgcc aattcagtgc atcacggaga ggcagatctt ggggataagg   8940
aagtgcagga cagcatggac gtgggacatg caggtgttga gggctctggg acactctcca   9000
agtcacagcg ttcagaacag ccttaaggat aagaagatag gatagaagga caaagagcaa   9060
gttaaaaccc agcatggaga ggagcacaaa aaggccacag acactgctgg tccctgtgtc   9120
tgagcctgca tgtttgatgg tgtctggatg caagcagaag ggtggaaga gcttgcctgg   9180
agagatacag ctgggtcagt aggactggga caggcagctg gagaattgcc atgtagatgt   9240
tcatacaatc gtcaaatcat gaaggctgga aaagccctcc aagatcccca agaccaaccc   9300
caacccaccc accgtgccca ctggccatgt ccctcagtgc cacatcccca cagttcttca   9360
tcacctccag ggacggtgac ccccccacct ccgtgggcag ctgtgccact gcagcaccgc   9420
tctttggaga aggtaaatct tgctaaatcc agcccgaccc tcccctggca caacgtaagg   9480
ccattatctc tcatccaact ccaggacgga gtcagtgagg atggggctca attgtttact   9540
ccctatcagt gatagagaac gtatgaagag tttactccct atcagtgata gagaacgtat   9600
gcagacttta ctccctatca gtgatagaga acgtataagg agtttactcc ctatcagtga   9660
tagagaacgt atgaccagtt tactccctat cagtgataga gaacgtatct acagtttact   9720
ccctatcagt gatagagaac gtatatccag tttactccct atcagtgata gagaacgtat   9780
aagctttagg cgtgtacggt gggcgcctat aaaagcagag ctcgtttagt gaaccgtcag   9840
atcgcctgga gcaattccac aacacttttg tcttatacca actttccgta ccacttccta   9900
ccctcgtaaa aagcttgtcc accatggctc ctaagaaaaa gcggaaggtg gacaagaaat   9960
actcaatcgg gctggacatc ggaactaact cagtggggtg ggcagtcatt actgacgagt  10020
acaaagtgcc aagcaagaaa tttaaggtcc tgggcaacac cgataggcac tccatcaaga  10080
aaaatctgat tggggccctg ctgttcgact ctggagagac agctgaagca actagactga  10140
aaaggactgc tagaaggcgc tatacccggc gaaagaatcg catctgctac ctgcaggaga  10200
ttttctctaa cgaaatggcc aaggtggacg atagtttctt tcatcggctg gaggaatcat  10260
tcctggtcga ggaagataag aaacacgaga gacatcctat ctttggaaac attgtggacg  10320
aggtcgctta tcacgaaaaa taccccacca tctatcatct gcgcaagaaa ctggtggact  10380
ctacagataa agcagacctg cggctgatct atctggccct ggctcacatg attaagttca  10440
gaggccattt tctgatcgag ggagatctga acccagacaa tagcgatgtg gacaagctgt  10500
tcatccagct ggtccagaca tacaatcagc tgtttgagga aaaccctatt aatgcatctg  10560
gcgtggacgc aaaagccatc ctgagtgcca ggctgtctaa gagtagaagg ctggagaacc  10620
tgatcgctca gctgccaggc gaaaagaaaa acggcctgtt tggaaatctg attgcactgt  10680
cactgggact gacacctaac ttcaagagca attttgatct ggccgaggac gctaaactgc  10740
agctgagcaa ggacacttat gacgatgacc tggataacct gctggctcag atcggagatc  10800
agtacgcaga cctgttcctg gccgctaaga atctgtctga cgctatcctg ctgagtgata  10860
ttctgcgggt gaacaccgag attacaaaag cccctctgtc agctagcatg atcaagagat  10920
atgacgagca ccatcaggat ctgaccctgc tgaaggcact ggtgcgccag cagctgcccg  10980
agaagtacaa ggaaatcttc tttgatcaga gtaagaacgg gtacgccggt tatattgacg  11040
```

```
gcggagcttc acaggaggaa ttctacaagt ttatcaaacc tattctggag aagatggacg  11100
gcaccgagga actgctggtg aaactgaatc gcgaggacct gctgcgcaag cagcggacat  11160
ttgataacgg ctccatcccc caccagattc atctgggaga gctgcacgca atcctgcgac  11220
gacaggaaga cttctaccca tttctgaagg ataaccgcga gaagatcgaa aaaattctga  11280
ccttccggat cccttactat gtggggcccc tggcaagggg taattcccgc tttgcctgga  11340
tgacacggaa atctgaggaa acaatcactc cttggaactt cgaggaagtg gtcgataagg  11400
gagcttccgc acagtctttc atcgagagaa tgacaaactt cgacaaaaac ctgccaaatg  11460
agaaagtgct gcctaagcac agtctgctgt acgagtattt cacagtctat aacgaactga  11520
ctaaggtgaa atacgtcacc gaggggatga ggaagcccgc cttcctgagc ggtgaacaga  11580
agaaagctat cgtggacctg ctgtttaaaa ccaatcgcaa ggtgacagtc aagcagctga  11640
aggaggacta cttcaagaaa attgaatgtt tcgattctgt ggagatcagt ggcgtcgaag  11700
acagatttaa cgcttctctg ggaacctacc acgatctgct gaagatcatt aaggataaag  11760
acttcctgga caacgaggaa aatgaggata tcctggaaga cattgtgctg accctgacac  11820
tgtttgagga tcgcgaaatg atcgaggaac ggctgaaaac ttatgcccat ctgttcgatg  11880
acaaggtgat gaaacagctg aagcgaagaa ggtacaccgg ctggggacga ctgagcagaa  11940
agctgatcaa cggcattcgg gacaaacaga gtggaaagac tatcctggac tttctgaaat  12000
cagatggctt cgctaacaga aattttatgc agctgattca cgatgacagc ctgaccttca  12060
aagaggatat ccagaaggca caggtgtccg ggcagggtga ctctctgcac gagcatatcg  12120
caaacctggc cgggtccccc gccatcaaga aaggtattct gcagaccgtg aaggtggtcg  12180
atgagctggt gaaagtcatg ggcaggcata agccagaaaa catcgtgatt gagatggccc  12240
gcgaaaatca gaccacacag aaaggacaga agaacagccg cgagcggatg aaaaggatcg  12300
aggaaggcat taaggaactg ggatcccaga tcctgaaaga gcaccctgtg gaaaacactc  12360
agctgcagaa tgagaagctg tatctgtact atctgcagaa tgggcgggat atgtacgtgg  12420
accaggagct ggatattaac cgactgtctg attacgacgt ggatcatatc gtcccacagt  12480
cattcctgaa agatgacagc attgacaata aggtgctgac ccggagtgac aaaaaccgag  12540
gaaagagtga taatgtccct tcagaggaag tggtcaagaa aatgaagaac tactggagac  12600
agctgctgaa tgccaaactg atcacacagc gaaagtttga taacctgact aaagctgaga  12660
gagggggtct gtcagaactg gacaaagcag gcttcatcaa gcgacagctg gtggagacca  12720
gacagatcac aaagcacgtc gctcagattc tggatagcag gatgaacaca aagtacgatg  12780
agaatgacaa actgatccgc gaagtgaagg tcattactct gaagtcaaaa cttgtgagcg  12840
acttcagaaa ggatttccag ttctacaaag tcagggagat caacaattat caccatgctc  12900
atgacgcata cctgaacgca gtggtcggga ccgccctgat taagaaatac cccaaactgg  12960
agagcgaatt cgtgtacggt gactataagg tgtacgatgt cagaaaaatg atcgccaaga  13020
gtgagcagga aattggaaaa gccaccgcta agtatttctt ttactcaaac atcatgaatt  13080
tctttaagac tgagatcacc ctggcaaatg gggaaatccg aaagagacca ctgattgaga  13140
ctaacggcga gaccggagaa atcgtgtggg acaagggtag ggattttgcc acagtgcgca  13200
aggtcctgtc catgcctcaa gtgaatattg tcaagaaaac agaggtgcag actggcggat  13260
tcagtaagga atcaattctg cccaaacgga actctgataa gctgatcgcc cgaaagaaag  13320
actgggatcc caagaaatat gggggtttcg actccccaac agtggcttac tctgtcctgg  13380
```

```
tggtcgcaaa ggtggagaag gggaaaagca agaaactgaa atccgtcaag gagctgctgg  13440
gtatcactat tatggagagg agctccttcg agaagaaccc catcgatttt ctggaggcta  13500
aaggctataa ggaagtgaag aaagacctga tcattaaact gccaaagtac agcctgtttg  13560
agctggaaaa cggaaggaag cgaatgctgg catccgcagg agagctgcag aagggtaatg  13620
aactggccct gccttctaag tacgtgaact tcctgtatct ggctagccac tacgagaagc  13680
tgaaaggctc ccccgaggat aacgaacaga aacagctgtt tgtggagcag cacaagcatt  13740
atctggacga gatcattgaa cagattagcg agttctccaa aagagtgatc ctggctgacg  13800
caaatctgga taaggtcctg agcgcataca acaaacacag agataagcca atcagggagc  13860
aggccgaaaa tatcattcat ctgttcactc tgaccaacct gggagcccct gcagccttca  13920
agtattttga cactaccatc gatcggaaac gatacacatc cactaaggag gtgctggacg  13980
ctaccctgat tcaccagagc attaccggcc tgtatgaaac aaggattgac ctgtctcagc  14040
tgggggggcga cctcgaggga agcggagagg gcagaggaag tctgctaaca tgcggtgacg  14100
tcgaggagaa tcctggccca gcaccgggat ccatggtgag caagggcgag gagctgttca  14160
ccggggtggt gcccatcctg gtcgagctgg acggcgacgt aaacggccac aagttcagcg  14220
tgtccggcga gggcgagggc gatgccacct acggcaagct gaccctgaag ttcatctgca  14280
ccaccggcaa gctgcccgtg ccctggccca ccctcgtgac caccttcacc tacggcgtgc  14340
agtgcttcgc ccgctacccc gaccacatga agcagcacga cttcttcaag tccgccatgc  14400
ccgaaggcta cgtccaggag cgcaccatct tcttcaagga cgacggcaac tacaagaccc  14460
gcgccgaggt gaagttcgag ggcgacaccc tggtgaaccg catcgagctg aagggcatcg  14520
acttcaagga ggacggcaac atcctggggc acaagctgga gtacaactac aacagccaca  14580
aggtctatat caccgccgac aagcagaaga acggcatcaa ggtgaacttc aagacccgcc  14640
acaacatcga ggacggcagc gtgcagctcg ccgaccacta ccagcagaac acccccatcg  14700
gcgacggccc cgtgctgctg cccgacaacc actacctgag cacccagtcc gccctgagca  14760
aagaccccaa cgagaagcgc gatcacatgg tcctgctgga gttcgtgacc gccgccggga  14820
tcactctcgg catggacgag ctgtacaagt aaacctaatc tagcagctcg ctgatcagcc  14880
tcgactgtgc cttctagttg ccagccatct gttgtttgcc cctcccccgt gccttccttg  14940
accctggaag gtgccactcc cactgtcctt tcctaataaa atgaggaaat tgcatcgcat  15000
tgtctgagta ggtgtcattc tattctgggg ggtggggtgg ggcaggacag caagggggag  15060
gattgggaag acaatagcag gcatgctggg gatgcggtgg gctctatggc ttctgaggcg  15120
gaaagaacca gctggggctc gatcctctag ttggcgcgtc tgtacaaaaa agcaggcttt  15180
aaaggaacca attcagtcga ctggatccgg taccaaggtc gggcaggaag agggcctatt  15240
tcccatgatt ccttcatatt tgcatatacg atacaaggct gttagagaga taattagaat  15300
taatttgact gtaaacacaa agatattagt acaaaatacg tgacgtagaa agtaataatt  15360
tcttgggtag tttgcagttt taaaattatg ttttaaaatg gactatcata tgcttaccgt  15420
aacttgaaag tatttcgatt tcttggcttt atatatcttg tggaaaggac gaaacaccga  15480
gcatagcaag ttaaaataag gctagtccgt tatcaacttg aaaaagtggc accgagtcgg  15540
tgcttttttt ctagacccag ctttcttgta caaagttggc attaattctc tagacatcat  15600
taattcctaa tttttgttga cactctatca ttgatagagt tattttacca ctccctatca  15660
gtgatagaga aaagtgaaat ggccaagcct ttgtctcaag aagaatccac cctcattgaa  15720
agagcaacgg ctacaatcaa cagcatcccc atctctgaag actacagcgt cgccagcgca  15780
```

```
gctctctcta gcgacggccg catcttcact ggtgtcaatg tatatcattt tactggggga  15840
ccttgtgcag aactcgtggt gctgggcact gctgctgctg cggcagctgg caacctgact  15900
tgtatcgtcg cgatcggaaa tgagaacagg ggcatcttga gcccctgcgg acggtgtcga  15960
caggtgcttc tcgatctgca tcctgggatc aaagcgatag tgaaggacag tgatggacag  16020
ccgacggcag ttgggattcg tgaattgctg ccctctggtt atgtgtggga gggctaaatg  16080
gtccatatga atatcctcct tagttcctat tccgctagcc tagagggaca gccccccccc  16140
aaagccccca gggatgtaat tacgtccctc ccccgctagg ggcagcagcg agccgcccgg  16200
ggctccgctc cggtccggcg ctccccccgc atccccgagc cggcagcgtg cggggacagc  16260
ccgggcacgg ggaaggtggc acgggatcgc tttcctctga acgcttctcg ctgctctttg  16320
agcctgcaga cacctggggg gatacgggga aaaagcttta ggctgaaaga gagatttaga  16380
atgacagaat catagaacgg cctgggttgc aaaggagcac agtgctcatc cagatccaac  16440
cccctgctat gtgcagggtc atcaaccagc agcccaggct gcccagagcc acatccagcc  16500
tggccttgaa tgcctgcagg gatggggcat ccacagcctc cttgggcaac ctgttcagtg  16560
cgtcaccacc ctctgggggga aaaactgcct cctcatatcc aacccaaacc tcccctgtct  16620
cagtgtaaag ccattccccc ttgtcctatc aagggggagt ttgctgtgac attgttggtc  16680
tggggtgaca catgtttgcc aattcagtgc atcacggaga ggcagatctt ggggataagg  16740
aagtgcagga cagcatggac gtgggacatg caggtgttga gggctctggg acactctcca  16800
agtcacagcg ttcagaacag ccttaaggat aagaagatag gatagaagga caaagagcaa  16860
gttaaaaccc agcatggaga ggagcacaaa aaggccacag acactgctgg tccctgtgtc  16920
tgagcctgca tgtttgatgg tgtctggatg caagcagaag gggtggaaga gcttgcctgg  16980
agagatacag ctgggtcagt aggactggga caggcagctg gagaattgcc atgtagatgt  17040
tcatacaatc gtcaaatcat gaaggctgga aaagccctcc aagatcccca agaccaaccc  17100
caacccaccc accgtgccca ctggccatgt ccctcagtgc cacatcccca cagttcttca  17160
tcacctccag ggacggtgac ccccccacct ccgtgggcag ctgtgccact gcagcaccgc  17220
tctttggaga aggtaaatct tgctaaatcc agcccgaccc tcccctggca caacgtaagg  17280
ccattatctc tcatccaact ccaggacgga gtcagtgagg atggggctgg atccgaagca  17340
gctccagcct acacaatcgc tcaagacgtg taatgctttt attatatatt agtcacgata  17400
tctataacaa gaaaatatat atataataag ttatcacgta agtagaacat gaaataacaa  17460
tataattatc gtatgagtta aatcttaaaa gtcacgtaaa agataatcat gcgtcatttt  17520
gactcacgcg gtcgttatag ttcaaaatca gtgacactta ccgcattgac aagcacgcct  17580
cacgggagct ccaagcggcg actgagatgt cctaaatgca cagcgacgga ttcgcgctat  17640
ttagaaagag agagcaatat ttcaagaatg catgcgtcaa ttttacgcag actatctttc  17700
tagggttaaa aaagatttgc gctttactcg acctaaactt taaacacgtc atagaatctt  17760
cgtttgacaa aaaccacatt gtggggtacc gagctcttaa ttaaggcgcg ccggggaggt  17820
tccctttagt gagggttaat tgcgggtcgc cctatagtga gtcgtattac aattcactgg  17880
ccgtcgtttt acaacgtcgt gactgggaaa accctggcgt tacccaactt aatcgccttg  17940
cagcacatcc ccctttcgcc agctggcgta atagcgaaga ggcccgcacc gatcgccctt  18000
cccaacagtt gcgcagcctg aatggcgaat ggcaaattgt aagcgttaat attttgttaa  18060
aattcgcgtt aaatttttgt taaatcagct cattttttaa ccaataggcc gaaatcggca  18120
```

```
aaatccctta taaatcaaaa gaatagaccg agatagggtt gagtgttgtt ccagtttgga  18180

acaagagtcc actattaaag aacgtggact ccaacgtcaa agggcgaaaa accgtctatc  18240

agggcgatgg cccactacgt gaaccatcac cctaatcaag ttttttgggg tcgaggtgcc  18300

gtaaagcact aaatcggaac cctaaaggga gcccccgatt tagagcttga cggggaaagc  18360

cggcgaacgt ggcgagaaag gaagggaaga aagcgaaagg agcgggcgct agggcgctgg  18420

caagtgtagc ggtcacgctg cgcgtaacca ccacacccgc cgcgcttaat gcgccgctac  18480

agggcgcgtc ag                                                      18492
```

<210> SEQ ID NO 20
<211> LENGTH: 17575
<212> TYPE: DNA
<213> ORGANISM: Artificial Sequence
<220> FEATURE:
<223> OTHER INFORMATION: Synthetic Polynucleotide

<400> SEQUENCE: 20

```
gtggcacttt tcggggaaat gtgcgcggaa cccctatttg tttatttttc taaatacatt     60

caaatatgta tccgctcatg agacaataac cctgataaat gcttcaataa tattgaaaaa    120

ggaagagtat gagtattcaa catttccgtg tcgcccttat tccctttttt gcggcatttt    180

gccttcctgt ttttgctcac ccagaaacgc tggtgaaagt aaaagatgct gaagatcagt    240

tgggtgcacg agtgggttac atcgaactgg atctcaacag cggtaagatc cttgagagtt    300

ttcgccccga agaacgtttt ccaatgatga gcacttttaa agttctgcta tgtggcgcgg    360

tattatcccg tattgacgcc gggcaagagc aactcggtcg ccgcatacac tattctcaga    420

atgacttggt tgagtactca ccagtcacag aaaagcatct tacggatggc atgacagtaa    480

gagaattatg cagtgctgcc ataaccatga gtgataacac tgcggccaac ttacttctga    540

caacgatcgg aggaccgaag gagctaaccg cttttttgca caacatgggg gatcatgtaa    600

ctcgccttga tcgttgggaa ccggagctga atgaagccat accaaacgac gagcgtgaca    660

ccacgatgcc tgtagcaatg gcaacaacgt tgcgcaaact attaactggc gaactactta    720

ctctagcttc ccggcaacaa ttaatagact ggatggaggc ggataaagtt gcaggaccac    780

ttctgcgctc ggcccttccg gctggctggt ttattgctga taaatctgga gccggtgagc    840

gtgggtctcg cggtatcatt gcagcactgg ggccagatgg taagccctcc cgtatcgtag    900

ttatctacac gacggggagt caggcaacta tggatgaacg aaatagacag atcgctgaga    960

taggtgcctc actgattaag cattggtaac tgtcagacca agtttactca tatatacttt   1020

agattgattt aaaacttcat ttttaattta aaaggatcta ggtgaagatc ctttttgata   1080

atctcatgac caaaatccct taacgtgagt tttcgttcca ctgagcgtca gaccccgtag   1140

aaaagatcaa aggatcttct tgagatcctt tttttctgcg cgtaatctgc tgcttgcaaa   1200

caaaaaaacc accgctacca gcggtggttt gtttgccgga tcaagagcta ccaactcttt   1260

ttccgaaggt aactggcttc agcagagcgc agataccaaa tactgttctt ctagtgtagc   1320

cgtagttagg ccaccacttc aagaactctg tagcaccgcc tacatacctc gctctgctaa   1380

tcctgttacc agtggctgct gccagtggcg ataagtcgtg tcttaccggg ttggactcaa   1440

gacgatagtt accggataag gcgcagcggt cgggctgaac ggggggttcg tgcacacagc   1500

ccagcttgga gcgaacgacc tacaccgaac tgagatacct acagcgtgag ctatgagaaa   1560

gcgccacgct tcccgaaggg agaaaggcgg acaggtatcc ggtaagcggc agggtcggaa   1620

caggagagcg cacgagggag cttccagggg gaaacgcctg gtatctttat agtcctgtcg   1680
```

ggtttcgcca cctctgactt gagcgtcgat ttttgtgatg ctcgtcaggg gggcggagcc 1740
tatggaaaaa cgccagcaac gcggcctttt tacggttcct ggccttttgc tggccttttg 1800
ctcacatgtt ctttcctgcg ttatcccctg attctgtgga taaccgtatt accgcctttg 1860
agtgagctga taccgctcgc cgcagccgaa cgaccgagcg cagcgagtca gtgagcgagg 1920
aagcggaaga gcgcccaata cgcaaaccgc ctctccccgc gcgttggccg attcattaat 1980
gcagctggca cgacaggttt cccgactgga aagcgggcag tgagcgcaac gcaattaatg 2040
tgagttagct cactcattag gcaccccagg ctttacactt tatgcttccg gctcgtatgt 2100
tgtgtggaat tgtgagcgga taacaatttc acacaggaaa cagctatgac catgattacg 2160
ccaagcgcgc aattaaccct cactaaaggg aacctcccct agcttaatta accctagaaa 2220
gataatcata ttgtgacgta cgttaaagat aatcatgcgt aaaattgacg catgtgtttt 2280
atcgatctgt atatcgaggt ttatttatta atttgaatag atattaagtt ttattatatt 2340
tacacttaca tactaataat aaattcaaca aacaatttat ttatgtttat ttatttatta 2400
aaaaaaaaca aaaactcaaa atttcttcta taaagtaaca aaacttttaa acattctctc 2460
ttttacaaaa ataaacttat tttgtacttt aaaaacagtc atgttgtatt ataaaataag 2520
taattagctt aacttataca taatagaaac aaattatact tattaatcgc attgattatt 2580
gactagtcgt attaagggtt ccggatcagc ttgattcgag ccccagctgg ttctttccgc 2640
ctcagaagcc atagagccca ccgcatcccc agcatgcctg ctattgtctt cccaatcctc 2700
ccccttgctg tcctgcccca ccccaccccc cagaatagaa tgacacctac tcagacaatg 2760
cgatgcaatt tcctcatttt attaggaaag gacagtggga gtggcacctt ccagggtcaa 2820
ggaaggcacg gggggagggc aaacaacaga tggctggcaa ctagaaggca cagtcgaggc 2880
tgatcagcga gctctagaga attgatcccc tcagaagaac tcgtcaagaa ggcgatagaa 2940
ggcgatgcgc tgcgaatcgg gagcggcgat accgtaaagc acgaggaagc ggtcagccca 3000
ttcgccgcca agctcttcag caatatcacg ggtagccaac gctatgtcct gatagcggtc 3060
cgccacaccc agccggccac agtcgatgaa tccagaaaag cggccatttt ccaccatgat 3120
attcggcaag caggcatcgc catgggtcac gacgagatcc tcgccgtcgg gcatgcgcgc 3180
cttgagcctg gcgaacagtt cggctggcgc gagcccctga tgctcttcgt ccagatcatc 3240
ctgatcgaca agaccggctt ccatccgagt acgtgctcgc tcgatgcgat gtttcgcttg 3300
gtggtcgaat gggcaggtag ccggatcaag cgtatgcagc cgccgcattg catcagccat 3360
gatggatact ttctcggcag gagcaaggtg agatgacagg agatcctgcc ccggcacttc 3420
gcccaatagc agccagtccc ttcccgcttc agtgacaacg tcgagcacag ctgcgcaagg 3480
aacgcccgtc gtggccagcc acgatagccg cgctgcctcg tcctgcagtt cattcagggc 3540
accggacagg tcggtcttga caaaaagaac cgggcgcccc tgcgctgaca gccggaacac 3600
ggcggcatca gagcagccga ttgtctgttg tgcccagtca tagccgaata gcctctccac 3660
ccaagcggcc ggagaacctg cgtgcaatcc atcttgttca atggccgatc ccatggttta 3720
gttcctcacc ttgtcgtatt atactatgcc gatatactat gccgatgatt aattgtcaac 3780
acgtgctgct gcaggtcgaa aggcccggag atgaggaaga ggagaacagc gcggcagacg 3840
tgcgcttttg aagcgtgcag aatgccgggc ctccggagga ccttcgggcg cccgccccgc 3900
ccctgagccc gcccctgagc ccgcccccgg acccacccct tcccagcctc tgagcccaga 3960
aagcgaagga gcaaagctgc tattggccgc tgccccaaag gcctacccgc ttccattgct 4020

-continued

```
cagcggtgct gtccatctgc acgagactag tgagacgtgc tacttccatt tgtcacgtcc   4080
tgcacgacgc gagctgcggg gcggggggga acttcctgac taggggagga gtagaaggtg   4140
gcgcgaaggg gccaccaaag aacggagccg gttggcgcct accggtggat gtggaatgtg   4200
tgcgagccag aggccacttg tgtagcgcca agtgcccagc ggggctgcta aagcgcatgc   4260
tccagactgc cttgggaaaa gcgcctcccc tacccggtag acaccccaca gtgggtggcc   4320
tagggacagg attgcaactc cagtctttct tcttcttggg cgggagtcac tagttattaa   4380
tagtaatcaa ttacggggtc attagttcat agcccatata tggagttccg cgttacataa   4440
cttacggtaa atggcccgcc tggctgaccg cccaacgacc cccgcccatt gacgtcaata   4500
atgacgtatg ttcccatagt aacgccaata gggactttcc attgacgtca atgggtggac   4560
tatttacggt aaactgccca cttggcagta catcaagtgt atcatatgcc aagtacgccc   4620
cctattgacg tcaatgacgg taaatggccc gcctggcatt atgcccagta catgacctta   4680
tgggactttc ctacttggca gtacatctac gtattagtca tcgctattac catgggtcga   4740
ggtgagcccc acgttctgct tcactctccc catctccccc ccctccccac ccccaatttt   4800
gtatttattt atttttaat tattttgtgc agcgatgggg gcgggggggg ggggggcgcg   4860
cgccaggcgg ggcggggcgg ggcgaggggc ggggcggggc gaggcggaga ggtgcggcgg   4920
cagccaatca gagcggcgcg ctccgaaagt ttccttttat ggcgaggcgg cggcggcggc   4980
ggccctataa aaagcgaagc gcgcggcggg cgggagtcgc tgcgttgcct tcgccccgtg   5040
ccccgctccg cgccgcctcg cgccgcccgc cccggctctg actgaccgcg ttactcccac   5100
aggtgagcgg gcgggacggc ccttctcctc cgggctgtaa ttagcgcttg gtttaatgac   5160
ggctcgtttc ttttctgtgg ctgcgtgaaa gccttaaagg gctccgggag ggccctttgt   5220
gcggggggga gcggctcggg gggtgcgtgc gtgtgtgtgt gcgtggggag cgccgcgtgc   5280
ggcccgcgct gcccggcggc tgtgagcgct gcgggcgcgg cgcggggctt tgtgcgctcc   5340
gcgtgtgcgc gaggggagcg cggccggggg cggtgccccg cggtgcgggg gggctgcgag   5400
gggaacaaag gctgcgtgcg gggtgtgtgc gtgggggggt gagcaggggg tgtgggcgcg   5460
gcggtcgggc tgtaaccccc ccctgcaccc ccctccccga gttgctgagc acggcccggc   5520
ttcgggtgcg gggctccgtg cggggcgtgg cgcggggctc gccgtgccgg gcggggggtg   5580
gcggcaggtg ggggtgccgg gcggggcggg gccgcctcgg gccggggagg gctcggggga   5640
ggggcgcggc ggcccccgag cgccggcggc tgtcgaggcg cggcgagccg cagccattgc   5700
cttttatggt aatcgtgcga gagggcgcag ggacttcctt tgtcccaaat ctggcggagc   5760
cgaaatctgg gaggcgccgc cgcacccccct ctagcgggcg cgggcgaagc ggtgcggcgc   5820
cggcaggaag gaaatgggcg gggagggcct tcgtgcgtcg ccgcgccgcc gtccccttct   5880
ccatctccag cctcggggct gccgcagggg gacggctgcc ttcggggggg acggggcagg   5940
gcggggttcg gcttctggcg tgtgaccggc ggctctagag cctctgctaa ccatgttcat   6000
gccttcttct ttttcctaca gctcctgggc aacgtgctgg ttattgtgct gtctcatcat   6060
tttggcaaag aattcgccac catggtgccc aagaagaaga ggaaagtctc tagactggac   6120
aagagcaaag tcataaactc tgctctggaa ttactcaatg gagtcggtat cgaaggcctg   6180
acgacaagga aactcgctca aaagctggga gttgagcagc ctaccctgta ctggcacgtg   6240
aagaacaagc gggccctgct cgatgccctg ccaatcgaga tgctggacag gcatcatacc   6300
cactcctgcc ccctggaagg cgagtcatgg caagactttc tgcggaacaa cgccaagtca   6360
taccgctgtg ctctcctctc acatcgcgac ggggctaaag tgcatctcgg cacccgccca   6420
```

acagagaaac agtacgaaac cctggaaaat cagctcgcgt tcctgtgtca gcaaggcttc 6480
tccctggaga acgcactgta cgctctgtcc gccgtgggcc actttacact gggctgcgta 6540
ttggaggaac aggagcatca agtagcaaaa gaggaaagag agacacctac caccgattct 6600
atgcccccac ttctgaaaca agcaattgag ctgttcgacc ggcagggagc cgaacctgcc 6660
ttccttttcg gcctggaact aatcatatgt ggcctggaga aacagctaaa gtgcgaaagc 6720
ggcgggccga ccgacgccct tgacgatttt gacttagaca tgctcccagc cgatgccctt 6780
gacgactttg accttgatat gctgcctgct gacgctcttg acgattttga ccttgacatg 6840
ctccccgggt aaagcggccg cgactctaga tcataatcag ccataccaca tttgtagagg 6900
ttttacttgc tttaaaaaac ctcccacacc tcccctgaa cctgaaacat aaaatgaatg 6960
caattgttgt tgttaacttg tttattgcag cttataatgg ttacaaataa agcaatagca 7020
tcacaaattt cacaaataaa gcattttttt cactgcattc tagttgtggt ttgtccaaac 7080
tcatcaatgt atcttaaggg atccctagag ggacagcccc cccccaaagc cccagggat 7140
gtaattacgt ccctcccccg ctaggggcag cagcgagccg cccggggctc cgctccggtc 7200
cggcgctccc cccgcatccc cgagccggca gcgtgcgggg acagcccggg cacggggaag 7260
gtggcacggg atcgctttcc tctgaacgct tctcgctgct ctttgagcct gcagacacct 7320
ggggggatac ggggaaaaag ctttaggctg aaagagagat ttagaatgac agaatcatag 7380
aacggcctgg gttgcaaagg agcacagtgc tcatccagat ccaacccct gctatgtgca 7440
gggtcatcaa ccagcagccc aggctgccca gagccacatc cagcctggcc ttgaatgcct 7500
gcagggatgg ggcatccaca gcctccttgg gcaacctgtt cagtgcgtca ccaccctctg 7560
ggggaaaaac tgcctcctca tatccaaccc aaacctcccc tgtctcagtg taaagccatt 7620
ccccttgtc ctatcaaggg ggagtttgct gtgacattgt tggtctgggg tgacacatgt 7680
ttgccaattc agtgcatcac ggagaggcag atcttgggga taaggaagtg caggacagca 7740
tggacgtggg acatgcaggt gttgagggct ctgggacact ctccaagtca cagcgttcag 7800
aacagcctta aggataagaa gataggatag aaggacaaag agcaagttaa aacccagcat 7860
ggagaggagc acaaaaaggc cacagacact gctggtccct gtgtctgagc ctgcatgttt 7920
gatggtgtct ggatgcaagc agaaggggtg gaagagcttg cctggagaga tacagctggg 7980
tcagtaggac tgggacaggc agctggagaa ttgccatgta gatgttcata caatcgtcaa 8040
atcatgaagg ctggaaaagc cctccaagat ccccaagacc aaccccaacc cacccaccgt 8100
gcccactggc catgtccctc agtgccacat ccccacagtt cttcatcacc tccagggacg 8160
gtgacccccc cacctccgtg ggcagctgtg ccactgcagc accgctcttt ggagaaggta 8220
aatcttgcta aatccagccc gaccctcccc tggcacaacg taaggccatt atctctcatc 8280
caactccagg acggagtcag tgaggatggg gctgtcgacc tagagggaca gcccccccc 8340
aaagccccca gggatgtaat tacgtccctc ccccgctagg ggcagcagcg agccgcccgg 8400
ggctccgctc cggtccggcg ctccccccgc atccccgagc cggcagcgtg cggggacagc 8460
ccgggcacgg ggaaggtggc acgggatcgc tttcctctga acgcttctcg ctgctctttg 8520
agcctgcaga cacctggggg gatacgggga aaaagcttta ggctgaaaga gagatttaga 8580
atgacagaat catagaacgg cctgggttgc aaaggagcac agtgctcatc cagatccaac 8640
cccctgctat gtgcagggtc atcaaccagc agcccaggct gcccagagcc acatccagcc 8700
tggccttgaa tgcctgcagg gatggggcat ccacagcctc cttgggcaac ctgttcagtg 8760

-continued

```
cgtcaccacc ctctggggga aaaactgcct cctcatatcc aacccaaacc tcccctgtct   8820
cagtgtaaag ccattccccc ttgtcctatc aaggggagt ttgctgtgac attgttggtc   8880
tggggtgaca catgtttgcc aattcagtgc atcacggaga ggcagatctt ggggataagg   8940
aagtgcagga cagcatggac gtgggacatg caggtgttga gggctctggg acactctcca   9000
agtcacagcg ttcagaacag ccttaaggat aagaagatag gatagaagga caaagagcaa   9060
gttaaaaccc agcatggaga ggagcacaaa aaggccacag acactgctgg tccctgtgtc   9120
tgagcctgca tgtttgatgg tgtctggatg caagcagaag ggtggaaga gcttgcctgg   9180
agagatacag ctgggtcagt aggactggga caggcagctg gagaattgcc atgtagatgt   9240
tcatacaatc gtcaaatcat gaaggctgga aaagccctcc aagatcccca agaccaaccc   9300
caacccaccc accgtgccca ctggccatgt ccctcagtgc cacatcccca cagttcttca   9360
tcacctccag ggacggtgac ccccccacct ccgtgggcag ctgtgccact gcagcaccgc   9420
tctttggaga aggtaaatct tgctaaatcc agcccgaccc tcccctggca caacgtaagg   9480
ccattatctc tcatccaact ccaggacgga gtcagtgagg atggggctca attgtttact   9540
ccctatcagt gatagagaac gtatgaagag tttactccct atcagtgata gagaacgtat   9600
gcagacttta ctccctatca gtgatagaga acgtataagg agtttactcc ctatcagtga   9660
tagagaacgt atgaccagtt tactccctat cagtgataga gaacgtatct acagtttact   9720
ccctatcagt gatagagaac gtatatccag tttactccct atcagtgata gagaacgtat   9780
aagctttagg cgtgtacggt gggcgcctat aaaagcagag ctcgtttagt gaaccgtcag   9840
atcgcctgga gcaattccac aacacttttg tcttatacca actttccgta ccacttccta   9900
ccctcgtaaa aagcttgtcc accatggctc ctaagaaaaa gcggaaggtg gacaagaaat   9960
actcaatcgg gctggccatc ggaactaact cagtggggtg ggcagtcatt actgacgagt  10020
acaaagtgcc aagcaagaaa tttaaggtcc tgggcaacac cgataggcac tccatcaaga  10080
aaaatctgat tggggccctg ctgttcgact ctggagagac agctgaagca actagactga  10140
aaaggactgc tagaaggcgc tatacccggc gaaagaatcg catctgctac ctgcaggaga  10200
ttttctctaa cgaaatggcc aaggtggacg atagtttctt tcatcggctg gaggaatcat  10260
tcctggtcga ggaagataag aaacacgaga gacatcctat ctttggaaac attgtggacg  10320
aggtcgctta tcacgaaaaa taccccacca tctatcatct gcgcaagaaa ctggtggact  10380
ctacagataa agcagacctg cggctgatct atctggccct ggctcacatg attaagttca  10440
gaggccattt tctgatcgag ggagatctga acccagacaa tagcgatgtg gacaagctgt  10500
tcatccagct ggtccagaca tacaatcagc tgtttgagga aaaccctatt aatgcatctg  10560
gcgtggacgc aaaagccatc ctgagtgcca ggctgtctaa gagtagaagg ctggagaacc  10620
tgatcgctca gctgccaggc gaaaagaaaa acggcctgtt tggaaatctg attgcactgt  10680
cactgggact gacacctaac ttcaagagca attttgatct ggccgaggac gctaaactgc  10740
agctgagcaa ggacacttat gacgatgacc tggataacct gctggctcag atcggagatc  10800
agtacgcaga cctgttcctg gccgctaaga atctgtctga cgctatcctg ctgagtgata  10860
ttctgcgggt gaacaccgag attacaaaag cccctctgtc agctagcatg atcaagagat  10920
atgacgagca ccatcaggat ctgaccctgc tgaaggcact ggtgcgccag cagctgcccg  10980
agaagtacaa ggaaatcttc tttgatcaga gtaagaacgg gtacgccggt tatattgacg  11040
gcggagcttc acaggaggaa ttctacaagt ttatcaaacc tattctggag aagatggacg  11100
gcaccgagga actgctggtg aaactgaatc gcgaggacct gctgcgcaag cagcggacat  11160
```

ttgataacgg ctccatcccc caccagattc atctgggaga gctgcacgca atcctgcgac 11220
gacaggaaga cttctaccca tttctgaagg ataaccgcga gaagatcgaa aaaattctga 11280
ccttccggat cccttactat gtggggcccc tggcaagggg taattcccgc tttgcctgga 11340
tgacacggaa atctgaggaa acaatcactc cttggaactt cgaggaagtg gtcgataagg 11400
gagcttccgc acagtctttc atcgagagaa tgacaaactt cgacaaaaac ctgccaaatg 11460
agaaagtgct gcctaagcac agtctgctgt acgagtattt cacagtctat aacgaactga 11520
ctaaggtgaa atacgtcacc gaggggatga ggaagcccgc cttcctgagc ggtgaacaga 11580
agaaagctat cgtggacctg ctgtttaaaa ccaatcgcaa ggtgacagtc aagcagctga 11640
aggaggacta cttcaagaaa attgaatgtt tcgattctgt ggagatcagt ggcgtcgaag 11700
acagatttaa cgcttctctg ggaacctacc acgatctgct gaagatcatt aaggataaag 11760
acttcctgga caacgaggaa aatgaggata tcctggaaga cattgtgctg accctgacac 11820
tgtttgagga tcgcgaaatg atcgaggaac ggctgaaaac ttatgcccat ctgttcgatg 11880
acaaggtgat gaaacagctg aagcgaagaa ggtacaccgg ctggggacga ctgagcagaa 11940
agctgatcaa cggcattcgg gacaaacaga gtggaaagac tatcctggac tttctgaaat 12000
cagatggctt cgctaacaga aattttatgc agctgattca cgatgacagc ctgaccttca 12060
aagaggatat ccagaaggca caggtgtccg ggcagggtga ctctctgcac gagcatatcg 12120
caaacctggc cgggtccccc gccatcaaga aaggtattct gcagaccgtg aaggtggtcg 12180
atgagctggt gaaagtcatg ggcaggcata agccagaaaa catcgtgatt gagatggccc 12240
gcgaaaatca gaccacacag aaaggacaga agaacagccg cgagcggatg aaaaggatcg 12300
aggaaggcat taaggaactg ggatcccaga tcctgaaaga gcaccctgtg gaaaacactc 12360
agctgcagaa tgagaagctg tatctgtact atctgcagaa tgggcgggat atgtacgtgg 12420
accaggagct ggatattaac cgactgtctg attacgacgt ggatcatatc gtcccacagt 12480
cattcctgaa agatgacagc attgacaata aggtgctgac ccggagtgac aaaaaccgag 12540
gaaagagtga taatgtccct tcagaggaag tggtcaagaa aatgaagaac tactggagac 12600
agctgctgaa tgccaaactg atcacacagc gaaagtttga taacctgact aaagctgaga 12660
gagggggtct gtcagaactg gacaaagcag gcttcatcaa gcgacagctg gtggagacca 12720
gacagatcac aaagcacgtc gctcagattc tggatagcag gatgaacaca aagtacgatg 12780
agaatgacaa actgatccgc gaagtgaagg tcattactct gaagtcaaaa cttgtgagcg 12840
acttcagaaa ggatttccag ttctacaaag tcagggagat caacaattat caccatgctc 12900
atgacgcata cctgaacgca gtggtcggga ccgccctgat taagaaatac cccaaactgg 12960
agagcgaatt cgtgtacggt gactataagg tgtacgatgt cagaaaaatg atcgccaaga 13020
gtgagcagga aattggaaaa gccaccgcta agtatttctt ttactcaaac atcatgaatt 13080
tctttaagac tgagatcacc ctggcaaatg gggaaatccg aaagagacca ctgattgaga 13140
ctaacggcga gaccggagaa atcgtgtggg acaagggtag ggattttgcc acagtgcgca 13200
aggtcctgtc catgcctcaa gtgaatattg tcaagaaaac agaggtgcag actggcggat 13260
tcagtaagga atcaattctg cccaaacgga actctgataa gctgatcgcc cgaaagaaag 13320
actgggatcc caagaaatat gggggtttcg actccccaac agtggcttac tctgtcctgg 13380
tggtcgcaaa ggtggagaag ggaaaaagca agaaactgaa atccgtcaag gagctgctgg 13440
gtatcactat tatggagagg agctccttcg agaagaaccc catcgatttt ctggaggcta 13500
aaggctataa ggaagtgaag aaagacctga tcattaaact gccaaagtac agcctgtttg 13560
agctggaaaa cggaaggaag cgaatgctgg catccgcagg agagctgcag aagggtaatg 13620
aactggccct gccttctaag tacgtgaact tcctgtatct ggctagccac tacgagaagc 13680
tgaaaggctc cccgaggat aacgaacaga aacagctgtt tgtggagcag cacaagcatt 13740
atctggacga gatcattgaa cagattagcg agttctccaa aagagtgatc ctggctgacg 13800
caaatctgga taaggtcctg agcgcataca acaaacacag agataagcca atcagggagc 13860
aggccgaaaa tatcattcat ctgttcactc tgaccaacct gggagcccct gcagccttca 13920
agtattttga cactaccatc gatcggaaac gatacacatc cactaaggag gtgctggacg 13980
ctaccctgat tcaccagagc attaccggcc tgtatgaaac aaggattgac ctgtctcagc 14040
tgggggggcga cctcgaggga agcggagagg gcagaggaag tctgctaaca tgcggtgacg 14100
tcgaggagaa tcctggccca gcaccgggat ccatggtgag caagggcgag gagctgttca 14160
ccggggtggt gcccatcctg gtcgagctgg acggcgacgt aaacggccac aagttcagcg 14220
tgtccggcga gggcgagggc gatgccacct acggcaagct gaccctgaag ttcatctgca 14280
ccaccggcaa gctgcccgtg ccctggccca ccctcgtgac caccttcacc tacggcgtgc 14340
agtgcttcgc ccgctacccc gaccacatga agcagcacga cttcttcaag tccgccatgc 14400
ccgaaggcta cgtccaggag cgcaccatct tcttcaagga cgacggcaac tacaagaccc 14460
gcgccgaggt gaagttcgag ggcgacaccc tggtgaaccg catcgagctg aagggcatcg 14520
acttcaagga ggacggcaac atcctggggc acaagctgga gtacaactac aacagccaca 14580
aggtctatat caccgccgac aagcagaaga acggcatcaa ggtgaacttc aagacccgcc 14640
acaacatcga ggacggcagc gtgcagctcg ccgaccacta ccagcagaac acccccatcg 14700
gcgacggccc cgtgctgctg cccgacaacc actacctgag cacccagtcc gccctgagca 14760
aagaccccaa cgagaagcgc gatcacatgg tcctgctgga gttcgtgacc gccgccggga 14820
tcactctcgg catggacgag ctgtacaagt aaacctaatc tagcagctcg ctgatcagcc 14880
tcgactgtgc cttctagttg ccagccatct gttgtttgcc cctcccccgt gccttccttg 14940
accctggaag gtgccactcc cactgtcctt tcctaataaa atgaggaaat tgcatcgcat 15000
tgtctgagta ggtgtcattc tattctgggg ggtggggtgg ggcaggacag caagggggag 15060
gattgggaag acaatagcag gcatgctggg gatgcggtgg gctctatggc ttctgaggcg 15120
gaaagaacca gctggggctc gatcctctag ttggcgcgtc atggtccata tgaatatcct 15180
ccttagttcc tattccgcta gcctagaggg acagcccccc cccaaagccc ccagggatgt 15240
aattacgtcc ctcccccgct aggggcagca gcgagccgcc cggggctccg ctccggtccg 15300
gcgctccccc cgcatccccg agccggcagc gtgcggggac agcccgggca cggggaaggt 15360
ggcacgggat cgctttcctc tgaacgcttc tcgctgctct ttgagcctgc agacacctgg 15420
ggggatacgg ggaaaaagct ttaggctgaa agagagattt agaatgacag aatcatagaa 15480
cggcctgggt tgcaaaggag cacagtgctc atccagatcc aaccccctgc tatgtgcagg 15540
gtcatcaacc agcagcccag gctgcccaga gccacatcca gcctggcctt gaatgcctgc 15600
agggatgggg catccacagc ctccttgggc aacctgttca gtgcgtcacc accctctggg 15660
ggaaaaactg cctcctcata tccaacccaa acctcccctg tctcagtgta aagccattcc 15720
cccttgtcct atcaaggggg agtttgctgt gacattgttg gtctggggtg acacatgttt 15780
gccaattcag tgcatcacgg agaggcagat cttggggata aggaagtgca ggacagcatg 15840
gacgtgggac atgcaggtgt tgagggctct gggacactct ccaagtcaca gcgttcagaa 15900

-continued

```
cagccttaag gataagaaga taggatagaa ggacaaagag caagttaaaa cccagcatgg  15960
agaggagcac aaaaaggcca cagacactgc tggtccctgt gtctgagcct gcatgtttga  16020
tggtgtctgg atgcaagcag aaggggtgga agagcttgcc tggagagata cagctgggtc  16080
agtaggactg ggacaggcag ctggagaatt gccatgtaga tgttcataca atcgtcaaat  16140
catgaaggct ggaaaagccc tccaagatcc ccaagaccaa ccccaaccca cccaccgtgc  16200
ccactggcca tgtccctcag tgccacatcc ccacagttct tcatcacctc cagggacggt  16260
gacccccccca cctccgtggg cagctgtgcc actgcagcac cgctctttgg agaaggtaaa  16320
tcttgctaaa tccagcccga ccctcccctg gcacaacgta aggccattat ctctcatcca  16380
actccaggac ggagtcagtg aggatggggc tggatccgaa gcagctccag cctacacaat  16440
cgctcaagac gtgtaatgct tttattatat attagtcacg atatctataa caagaaaata  16500
tatatataat aagttatcac gtaagtagaa catgaaataa caatataatt atcgtatgag  16560
ttaaatctta aaagtcacgt aaaagataat catgcgtcat tttgactcac gcggtcgtta  16620
tagttcaaaa tcagtgacac ttaccgcatt gacaagcacg cctcacggga gctccaagcg  16680
gcgactgaga tgtcctaaat gcacagcgac ggattcgcgc tatttagaaa gagagagcaa  16740
tatttcaaga atgcatgcgt caattttacg cagactatct ttctagggtt aaaaaagatt  16800
tgcgctttac tcgacctaaa ctttaaacac gtcatagaat cttcgtttga caaaaaccac  16860
attgtggggt accgagctct taattaaggc gcgccgggga ggttcccttt agtgagggtt  16920
aattgcgggt cgccctatag tgagtcgtat tacaattcac tggccgtcgt tttacaacgt  16980
cgtgactggg aaaaccctgg cgttacccaa cttaatcgcc ttgcagcaca tccccctttc  17040
gccagctggc gtaatagcga agaggcccgc accgatcgcc cttcccaaca gttgcgcagc  17100
ctgaatggcg aatggcaaat tgtaagcgtt aatattttgt taaaattcgc gttaaatttt  17160
tgttaaatca gctcattttt taaccaatag gccgaaatcg gcaaaatccc ttataaatca  17220
aaagaataga ccgagatagg gttgagtgtt gttccagttt ggaacaagag tccactatta  17280
aagaacgtgg actccaacgt caaagggcga aaaaccgtct atcagggcga tggcccacta  17340
cgtgaaccat caccctaatc aagttttttg gggtcgaggt gccgtaaagc actaaatcgg  17400
aaccctaaag ggagcccccg atttagagct tgacggggaa agccggcgaa cgtggcgaga  17460
aaggaaggga agaaagcgaa aggagcgggc gctagggcgc tggcaagtgt agcggtcacg  17520
ctgcgcgtaa ccaccacacc cgccgcgctt aatgcgccgc tacagggcgc gtcag       17575
```